(12) United States Patent (10) Patent No.: US 12,232,850 B2
Frank et al. (45) Date of Patent: Feb. 25, 2025

(54) DOORWAY SYSTEM THAT UTILIZES WEARABLE-BASED HEALTH STATE VERIFICATIONS

(71) Applicant: Facense Ltd., Kiryat Tivon (IL)

(72) Inventors: Ari M Frank, Haifa (IL); Arie Tzvieli, Berkeley, CA (US); Ori Tzvieli, Berkeley, CA (US); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 893 days.

(21) Appl. No.: 17/320,012

(22) Filed: May 13, 2021

(65) Prior Publication Data

US 2021/0259557 A1 Aug. 26, 2021

Related U.S. Application Data

(63) Continuation-in-part of application No. 17/009,655, filed on Sep. 1, 2020, now Pat. No. 11,154,203, and
(Continued)

(51) Int. Cl.
*G01J 5/00* (2022.01)
*A61B 5/00* (2006.01)
(Continued)

(52) U.S. Cl.
CPC ............ *A61B 5/015* (2013.01); *A61B 5/0075* (2013.01); *A61B 5/165* (2013.01); *A61B 5/6803* (2013.01);
(Continued)

(58) Field of Classification Search
CPC ....... A61B 5/015; A61B 5/0075; A61B 5/165; A61B 5/6803; A61B 5/6814;
(Continued)

(56) References Cited

U.S. PATENT DOCUMENTS 7,031,483 B2 4/2006 Boone et al.
7,447,333 B1 11/2008 Masticola et al.
(Continued)

FOREIGN PATENT DOCUMENTS

CN 111641931 A * 9/2020 ............. H04L 67/12
EP 0291592 A1 * 11/1988
(Continued)

OTHER PUBLICATIONS

U.S. Appl. No. 17/320,012, filed Feb. 21, 2024_JP_4459405_B2_H.pdf,Apr. 28, 2010.*
(Continued)

*Primary Examiner* — Gail Kaplan Verbitsky
(74) *Attorney, Agent, or Firm* — Active Knowledge Ltd.

(57) ABSTRACT

Disclosed herein is a doorway that facilitates passage from an inside to an outside, and which includes a barrier that moves between opened and closed positions based on commands sent by a computer. Sensors measure signals indicating whether a first user is on the outside, and whether a second user on the inside. The computer detects that the first user is on the outside and receives, from a device of the first user, an indication indicating the first user is healthy. The computer detects whether the second user is on the inside, and commands the barrier to move to the opened position if: (i) the second user is not on the inside, or (ii) the second user is on the inside and the computer receives, from a device of the second user, an indication indicating the second user is healthy.

19 Claims, 52 Drawing Sheets

Related U.S. Application Data a continuation-in-part of application No. 17/005,259, filed on Aug. 27, 2020, now Pat. No. 11,103,139, which is a continuation-in-part of application No. 16/854,883, filed on Apr. 21, 2020, now Pat. No. 10,813,559, and a continuation-in-part of application No. 16/831,413, filed on Mar. 26, 2020, now Pat. No. 10,791,938, and a continuation-in-part of application No. 16/689,959, filed on Nov. 20, 2019, now Pat. No. 10,799,122, and a continuation-in-part of application No. 16/689,929, filed on Nov. 20, 2019, now Pat. No. 11,064,892, said application No. 16/831,413 is a continuation-in-part of application No. 16/551,654, filed on Aug. 26, 2019, now Pat. No. 10,638,938, which is a continuation-in-part of application No. 16/453,993, filed on Jun. 26, 2019, now Pat. No. 10,667,697, said application No. 16/854,883 is a continuation-in-part of application No. 16/453,993, filed on Jun. 26, 2019, now Pat. No. 10,667,697, which is a continuation-in-part of application No. 16/375,841, filed on Apr. 4, 2019, now Pat. No. 10,376,163, which is a continuation-in-part of application No. 16/156,493, filed on Oct. 10, 2018, now Pat. No. 10,524,667, said application No. 16/689,929 is a continuation-in-part of application No. 16/156,586, filed on Oct. 10, 2018, now Pat. No. 10,524,696, said application No. 16/453,993 is a continuation-in-part of application No. 16/147,695, filed on Sep. 29, 2018, now Pat. No. 10,376,153, said application No. 16/156,586 is a continuation-in-part of application No. 15/859,772, filed on Jan. 2, 2018, now Pat. No. 10,159,411, said application No. 16/156,493 is a continuation-in-part of application No. 15/832,855, filed on Dec. 6, 2017, now Pat. No. 10,130,308, and a continuation-in-part of application No. 15/833,115, filed on Dec. 6, 2017, now Pat. No. 10,130,261, said application No. 16/156,586 is a continuation-in-part of application No. 15/832,815, filed on Dec. 6, 2017, now Pat. No. 10,136,852, said application No. 15/833,115 is a continuation-in-part of application No. 15/722,434, filed on Oct. 2, 2017, now Pat. No. 10,523,852, said application No. 15/832,855 is a continuation-in-part of application No. 15/722,434, filed on Oct. 2, 2017, now Pat. No. 10,523,852, said application No. 15/833,115 is a continuation-in-part of application No. 15/635,178, filed on Jun. 27, 2017, now Pat. No. 10,136,856, said application No. 16/156,493 is a continuation-in-part of application No. 15/635,178, filed on Jun. 27, 2017, now Pat. No. 10,136,856, said application No. 15/832,855 is a continuation-in-part of application No. 15/635,178, filed on Jun. 27, 2017, now Pat. No. 10,136,856, and a continuation-in-part of application No. 15/284,528, filed on Oct. 3, 2016, now Pat. No. 10,113,913, said application No. 15/833,115 is a continuation-in-part of application No. 15/284,528, filed on Oct. 3, 2016, now Pat. No. 10,113,913, said application No. 15/832,855 is a continuation-in-part of application No. 15/231,276, filed on Aug. 8, 2016, now abandoned, said application No. 16/156,493 is a continuation-in-part of application No. 15/231,276, filed on Aug. 8, 2016, now abandoned, said application No. 15/833,115 is a continuation-in-part of application No. 15/231,276, filed on Aug. 8, 2016, now abandoned, said application No. 15/833,115 is a continuation-in-part of application No. 15/182,592, filed on Jun. 14, 2016, now Pat. No. 10,165,949, said application No. 15/832,855 is a continuation-in-part of application No. 15/182,592, filed on Jun. 14, 2016, now Pat. No. 10,165,949, and a continuation-in-part of application No. 15/182,566, filed on Jun. 14, 2016, now Pat. No. 9,867,546, said application No. 16/147,695 is a continuation of application No. 15/182,592, filed on Jun. 14, 2016, now Pat. No. 10,165,949.

(60) Provisional application No. 63/140,453, filed on Jan. 22, 2021, provisional application No. 63/122,961, filed on Dec. 9, 2020, provisional application No. 63/113,846, filed on Nov. 14, 2020, provisional application No. 63/048,638, filed on Jul. 6, 2020, provisional application No. 63/024,471, filed on May 13, 2020, provisional application No. 63/006,827, filed on Apr. 8, 2020, provisional application No. 62/960,913, filed on Jan. 14, 2020, provisional application No. 62/945,141, filed on Dec. 7, 2019, provisional application No. 62/928,726, filed on Oct. 31, 2019, provisional application No. 62/722,655, filed on Aug. 24, 2018, provisional application No. 62/667,453, filed on May 5, 2018, provisional application No. 62/652,348, filed on Apr. 4, 2018, provisional application No. 62/566,572, filed on Oct. 2, 2017, provisional application No. 62/480,496, filed on Apr. 2, 2017, provisional application No. 62/456,105, filed on Feb. 7, 2017, provisional application No. 62/372,063, filed on Aug. 8, 2016, provisional application No. 62/354,833, filed on Jun. 27, 2016, provisional application No. 62/236,868, filed on Oct. 3, 2015, provisional application No. 62/202,808, filed on Aug. 8, 2015, provisional application No. 62/175,319, filed on Jun. 14, 2015.

(51) Int. Cl.
*A61B 5/01* (2006.01)
*A61B 5/16* (2006.01)
*G01J 5/02* (2022.01)
*G01J 5/12* (2006.01)
*G01J 5/48* (2022.01)

(52) U.S. Cl.
CPC .......... *A61B 5/6814* (2013.01); *A61B 5/7282* (2013.01); *A61B 5/748* (2013.01); *G01J 5/0265* (2013.01); *G01J 5/12* (2013.01); *A61B 5/0077* (2013.01); *A61B 2562/0271* (2013.01); *A61B 2562/0276* (2013.01); *A61B 2576/00* (2013.01); *G01J 2005/0077* (2013.01); *G01J 5/485* (2022.01)

(58) Field of Classification Search
CPC ................ A61B 5/7262; A61B 5/0077; A61B 2562/0271; A61B 2576/00; G01J 2005/0077; G01J 5/0265; G01J 5/12; G01J 5/485
See application file for complete search history.

(56) References Cited

U.S. PATENT DOCUMENTS

| | | |
|---|---|---|
| 7,609,842 B2 | 10/2009 | Sipkema et al. |
| 7,817,046 B2 | 10/2010 | Coveley et al. |
| 8,225,380 B2 | 7/2012 | Moshir |
| 8,392,152 B2 | 3/2013 | Rao |
| 8,684,900 B2 | 4/2014 | Tran |
| 9,075,909 B2 | 7/2015 | Almogy et al. |

(56) References Cited

U.S. PATENT DOCUMENTS

| | | | |
|---|---|---|---|
| 9,152,769 | B2 | 10/2015 | Baudino et al. |
| 9,349,235 | B2 | 5/2016 | Agrafioti et al. |
| 9,367,975 | B2 | 6/2016 | Robertson et al. |
| 9,396,643 | B2 | 7/2016 | He et al. |
| 9,460,263 | B2 | 10/2016 | Holmes et al. |
| 9,524,598 | B2 | 12/2016 | Jang |
| 9,558,336 | B2 | 1/2017 | Lee |
| 9,563,998 | B2 | 2/2017 | Hoyos et al. |
| 9,646,261 | B2 | 5/2017 | Agrafioti et al. |
| 9,727,697 | B1 | 8/2017 | Sundar et al. |
| 9,762,581 | B1 | 9/2017 | Wang et al. |
| 9,811,648 | B2 | 11/2017 | Choi et al. |
| 9,905,107 | B2 | 2/2018 | Chong et al. |
| 9,946,942 | B2 | 4/2018 | Wang et al. |
| 9,990,785 | B2 | 6/2018 | God et al. |
| 10,154,818 | B2 | 12/2018 | Zhang et al. |
| 10,178,969 | B2 | 1/2019 | Anwar et al. |
| 10,186,097 | B2 | 1/2019 | Tehranchi et al. |
| 10,475,260 | B2 | 11/2019 | Yoo et al. |
| 10,629,015 | B1 | 4/2020 | Le Burge et al. |
| 10,885,530 | B2 | 1/2021 | Mercury et al. |
| 2005/0283382 | A1* | 12/2005 | Donoghue ............. G16H 40/20 705/2 |
| 2007/0213877 | A1* | 9/2007 | Hart ..................... G07C 9/22 700/282 |
| 2007/0222554 | A1 | 9/2007 | Hart |
| 2011/0112969 | A1 | 5/2011 | Zaid |
| 2015/0072622 | A1* | 3/2015 | Hwang ................ H04M 19/04 455/41.3 |
| 2015/0126824 | A1 | 5/2015 | LeBoeuf et al. |
| 2015/0223705 | A1* | 8/2015 | Sadhu ................. A61B 5/0006 600/595 |
| 2016/0140834 | A1 | 5/2016 | Tran |
| 2016/0224773 | A1 | 8/2016 | Ramaci |
| 2016/0344509 | A1* | 11/2016 | Hayman ................ H04W 4/44 |
| 2017/0000359 | A1 | 1/2017 | Kohli et al. |
| 2017/0038848 | A1 | 2/2017 | Yuen et al. |
| 2017/0103178 | A1 | 4/2017 | Heinrich et al. |
| 2017/0187710 | A1 | 6/2017 | Outwater et al. |
| 2017/0302641 | A1 | 10/2017 | Ramatchandirane et al. |
| 2018/0049675 | A1 | 2/2018 | Kerber |
| 2018/0054710 | A1 | 2/2018 | Gum |
| 2018/0078187 | A1 | 3/2018 | Anwar et al. |
| 2018/0192893 | A1 | 7/2018 | Magi |
| 2018/0247713 | A1 | 8/2018 | Rothman |
| 2018/0276672 | A1 | 9/2018 | Breed et al. |
| 2018/0317846 | A1 | 11/2018 | Moyerman et al. |
| 2018/0325385 | A1 | 11/2018 | Deterding et al. |
| 2019/0029563 | A1 | 1/2019 | Sels et al. |
| 2019/0209022 | A1 | 7/2019 | Sobol et al. |
| 2019/0246902 | A1 | 8/2019 | Chang et al. |
| 2019/0251238 | A1 | 8/2019 | Venkatraman et al. |
| 2020/0185100 | A1 | 6/2020 | Francois |
| 2020/0281518 | A1 | 9/2020 | Salorinne |
| 2020/0302452 | A1 | 9/2020 | Platt et al. |
| 2020/0327755 | A1 | 10/2020 | Burris et al. |
| 2021/0012871 | A1 | 1/2021 | Hagen et al. |

FOREIGN PATENT DOCUMENTS

| | | | | |
|---|---|---|---|---|
| EP | 1750231 | A1 * | 2/2007 | ............ E05G 5/003 |
| EP | 3238612 | A1 | 11/2017 | |
| EP | 3375362 | | 9/2018 | |
| GB | 2052612 | A * | 1/1981 | ............ E05G 5/003 |
| JP | H01102366 | U * | 7/1989 | |
| JP | H08225265 | A * | 9/1996 | |
| JP | H10234080 | A * | 9/1998 | |
| JP | 2004010303 | A * | 1/2004 | |
| JP | 2004251628 | A * | 9/2004 | |
| JP | 4459405 | B2 * | 4/2010 | |
| KR | 20060017960 | A * | 2/2006 | |
| KR | 101742739 | B1 * | 6/2017 | |
| WO | WO-9956262 | A1 * | 11/1999 | ......... G08B 21/0423 |
| WO | WO2004008409 | A1 * | 11/2005 | |
| WO | WO2011005224 | | 1/2011 | |

OTHER PUBLICATIONS

U.S. Appl. No. 17/320,012, filed Feb. 21, 2024_JP_WO2004008409_A1_H.pdf2,005-11-10.*
U.S. Appl. No. 17/320,012, filed Feb. 22, 2024_EP_1750231_A1_H.pdf,Feb. 7, 2007.*
U.S. Appl. No. 17/320,012, filed Feb. 22, 2024_JP_2004010303_A_H.pdf,Jan. 15, 2004.*
U.S. Appl. No. 17/320,012, filed Feb. 22, 2024_JP_H01102366_U_H.pdf,Jul. 11, 1989.*
U.S. Appl. No. 17/320,012, filed Feb. 22, 2024_JP_H08225265_A_H.pdf,Sep. 3, 1996.*
U.S. Appl. No. 17/320,012, filed Feb. 22, 2024_JP_H10234080_A_H.pdf,Sep. 2, 1998.*
U.S. Appl. No. 17/320,012, filed Feb. 23, 2024_WO_9956262_A1_H.pdf,Nov. 4, 1999.*
U.S. Appl. No. 17/320,012, filed Aug. 15, 2024_CN_111641931_A_H.pdf,Sep. 8, 2020.*
U.S. Appl. No. 17/320,012, filed Nov. 20, 2024_JP_2004251628_A_H.pdf,Sep. 9, 2004.*
U.S. Appl. No. 17/320,012, filed Nov. 20, 2024_KR_101742739_B1_H.pdf,Jun. 1, 2017.*
U.S. Appl. No. 17/320,012, filed Nov. 20, 2024_KR_20060017960_A_H.pdf,Feb. 28, 2006.*
U.S. Appl. No. 17/320,012, filed Nov. 20, 2024_EP_0291592_A1_H.pdf,Nov. 23, 1988.*
U.S. Appl. No. 17/320,012, filed Nov. 20, 2024_GB_2052612_A_H.pdf,Jan. 28, 1981.*
Occupational Safety and Health Administration. "Guidance on preparing workplaces for an influenza pandemic." (2007) U.S. Department of Labor Occupational Safety and Health Administration OSHA 3327-02N 2007.
Thieberger, Gil. Facense smartglasses for early detection of COVID-19 disease, Apr. 8, 2020 [online], [retrieved on Aug. 15, 2021]. Retrieved from <https://www.linkedin.com/pulse/facense-smartglasses-early-detection-covid-19-disease-gil-thieberger>. Gil Thieberger Apr. 8, 2020 (Apr. 8, 2020).
International search report, PCT/IB2021/054072, date of mailing Aug. 17, 2021.
Written opinion of the international searching authority, PCT/IB2021/054072, date of mailing Aug. 17, 2021.

* cited by examiner

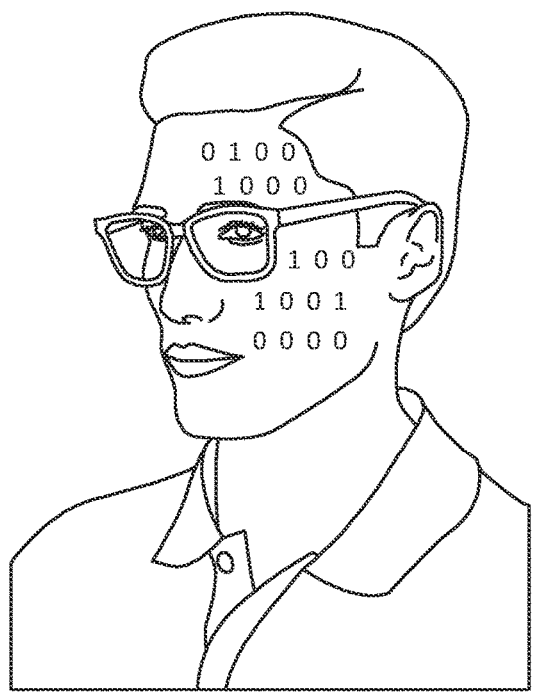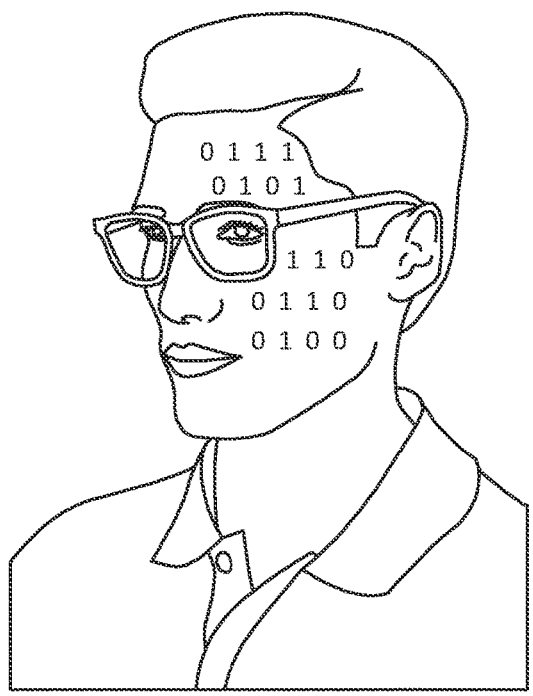
FIG. 14A  FIG. 14B
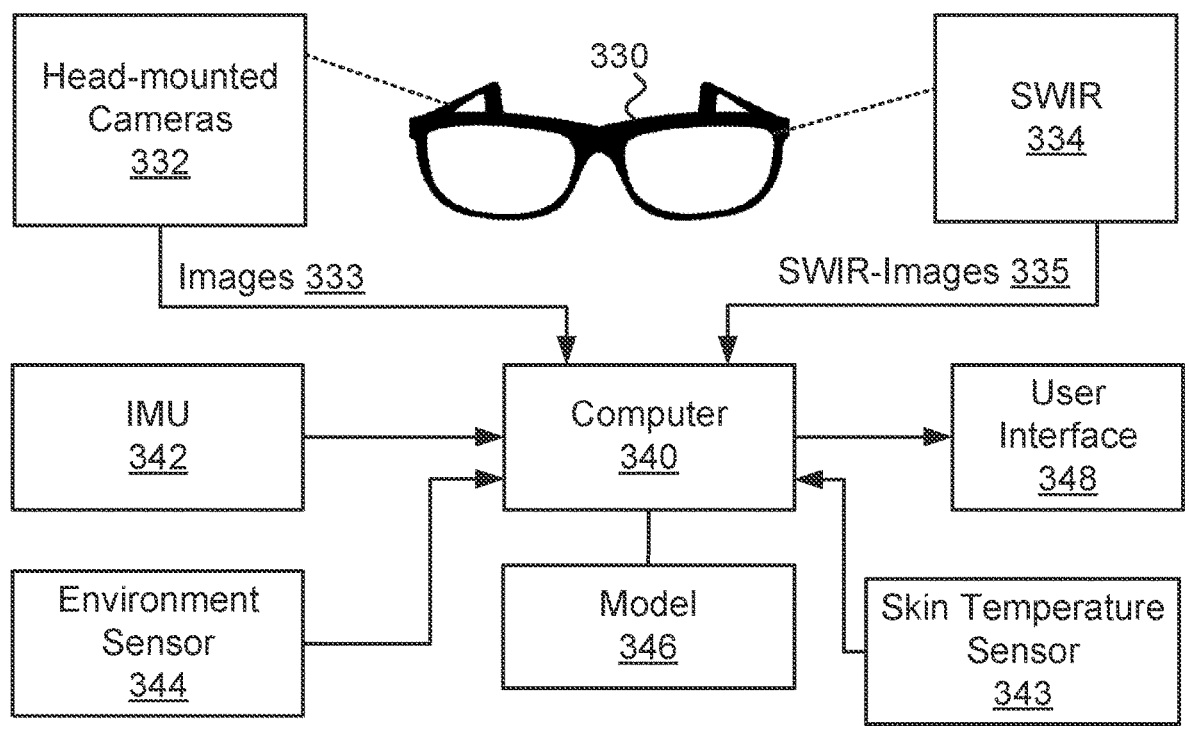
FIG. 14C

FIG. 29A
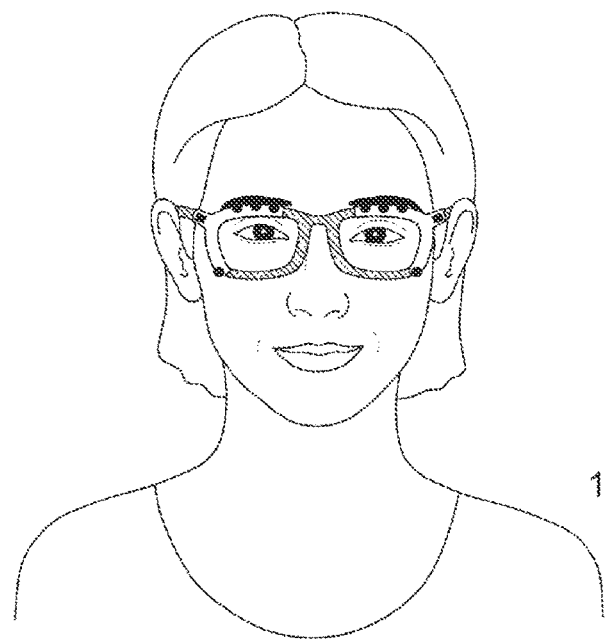
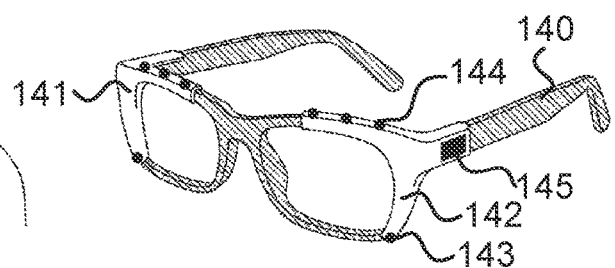
FIG. 29C  FIG. 29B
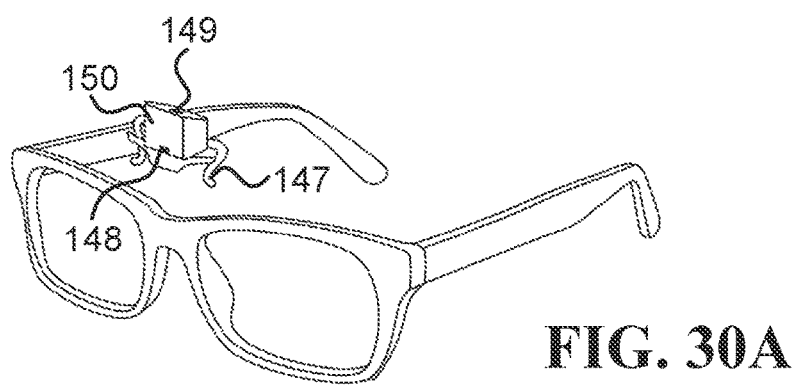
FIG. 30A
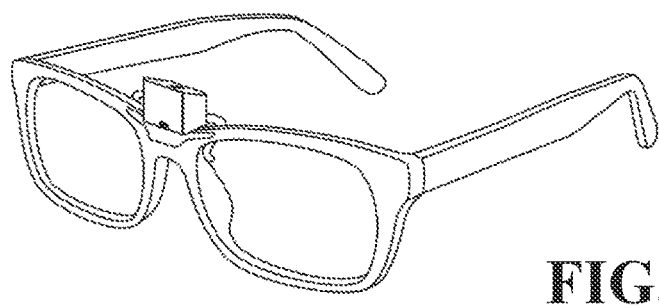
FIG. 30B

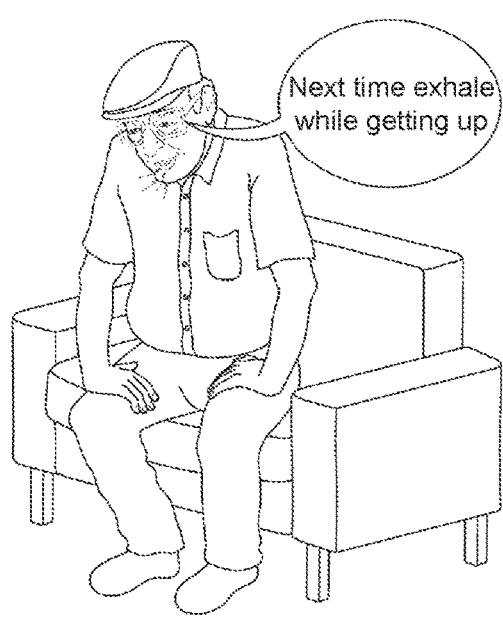 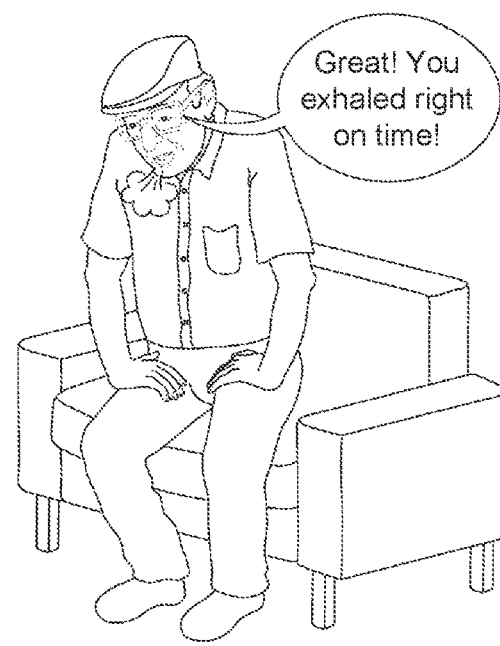
FIG. 39A  FIG. 39B
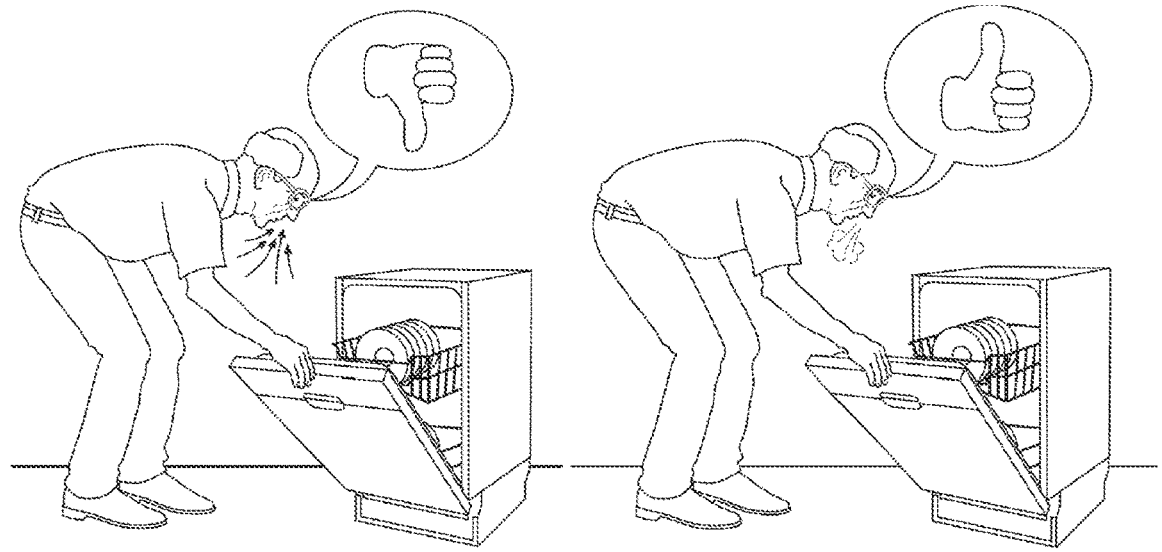
FIG. 40A  FIG. 40B
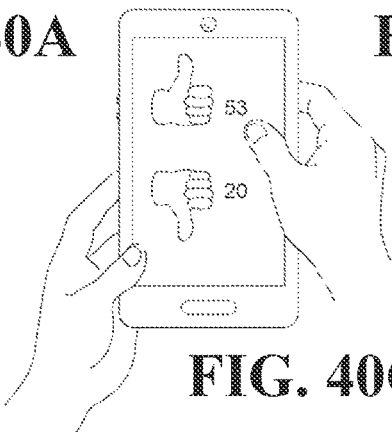
FIG. 40C

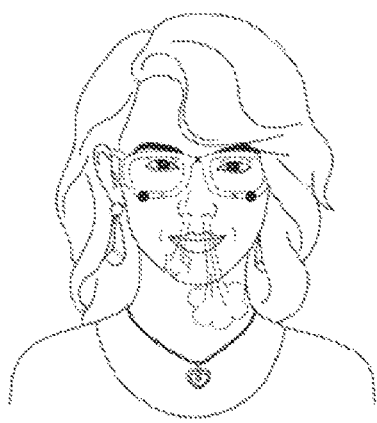 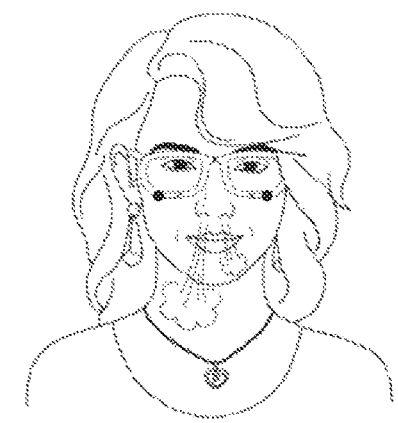 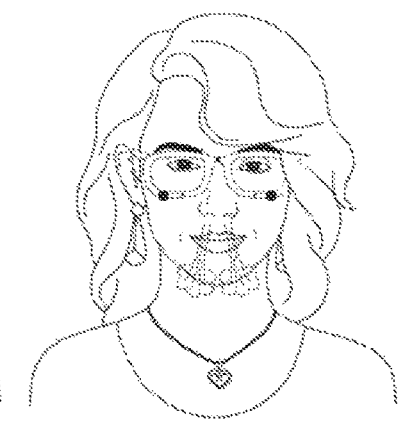
FIG. 47A    FIG. 47B    FIG. 47C
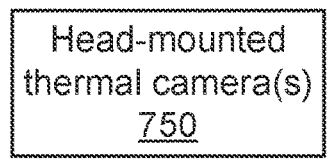 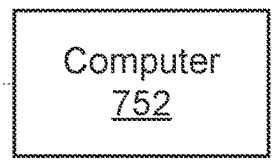 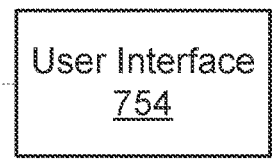
FIG. 48
FIG. 49A
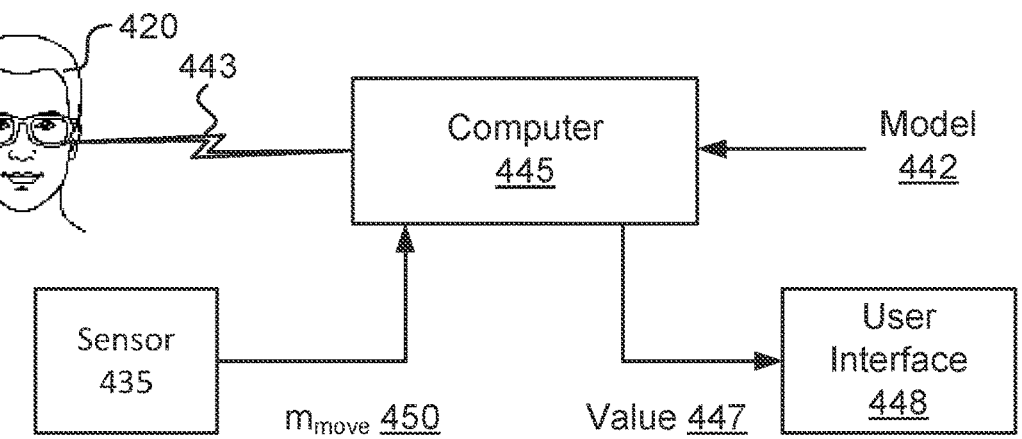
FIG. 49B

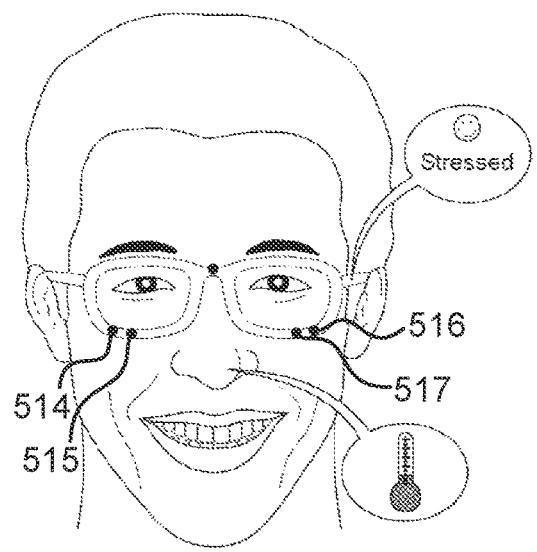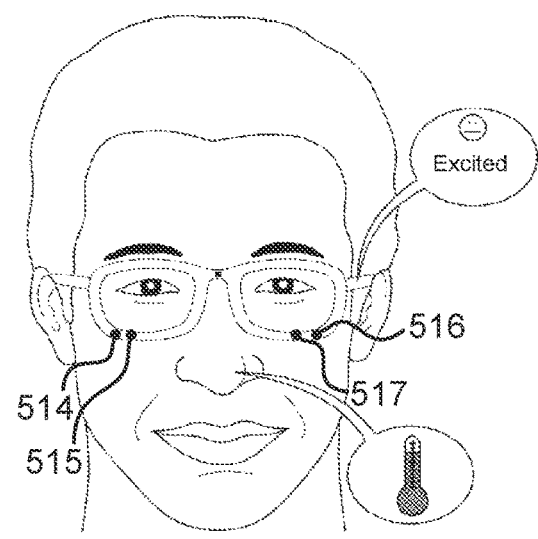
FIG. 57A  FIG. 57B
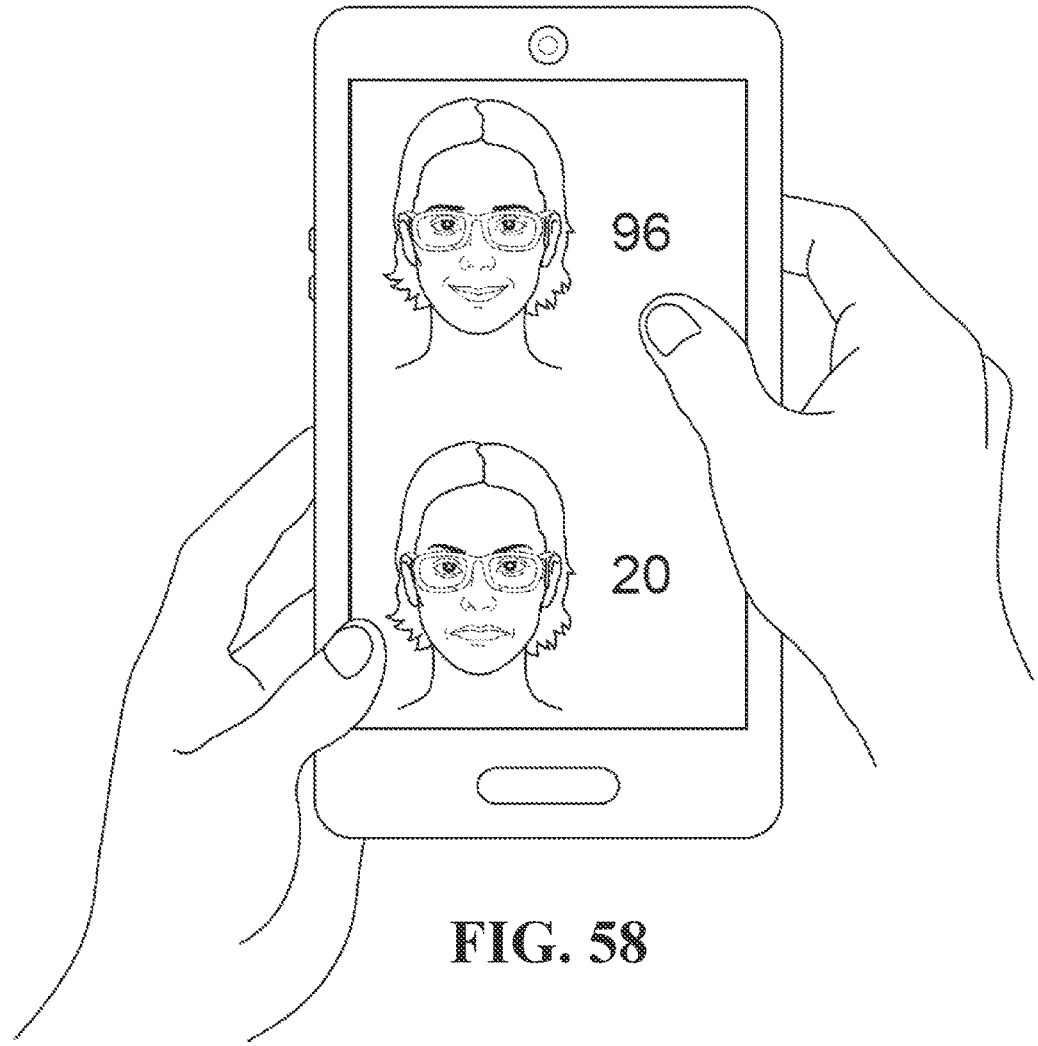
FIG. 58

Two months later
$$$$$$$

DOORWAY SYSTEM THAT UTILIZES WEARABLE-BASED HEALTH STATE VERIFICATIONS

CROSS-REFERENCE TO RELATED APPLICATIONS

This Application claims priority to U.S. Provisional Patent Application No. 63/024,471, filed May 13, 2020, U.S. Provisional Patent Application No. 63/048,638, filed Jul. 6, 2020, U.S. Provisional Patent Application No. 63/113,846, filed Nov. 14, 2020, U.S. Provisional Patent Application No. 63/122,961, filed Dec. 9, 2020, and U.S. Provisional Patent Application No. 63/140,453 filed Jan. 22, 2021.

This Application is a Continuation-In-Part of U.S. application Ser. No. 17/005,259, filed Aug. 27, 2020, which is incorporated herein by reference. U.S. application Ser. No. 17/005,259 claims priority to U.S. Provisional Patent Application No. 62/928,726, filed Oct. 31, 2019, U.S. Provisional Patent Application No. 62/945,141, filed Dec. 7, 2019, U.S. Provisional Patent Application No. 62/960,913, filed Jan. 14, 2020, U.S. Provisional Patent Application No. 63/006,827, filed Apr. 8, 2020, U.S. Provisional Patent Application No. 63/024,471, filed May 13, 2020, and U.S. Provisional Patent Application No. 63/048,638, filed Jul. 6, 2020.

U.S. application Ser. No. 17/005,259 is a Continuation-In-Part of U.S. application Ser. No. 16/689,959, filed Nov. 20, 2019, which claims priority to U.S. Provisional Patent Application No. 62/874,430, filed Jul. 15, 2019.

This Application is also a Continuation-In-Part of U.S. application Ser. No. 16/854,883, filed Apr. 21, 2020, which is a Continuation-In-Part of U.S. application Ser. No. 16/453,993, filed Jun. 26, 2019, now U.S. Pat. No. 10,667,697.

U.S. application Ser. No. 17/005,259 is also a Continuation-In-Part of U.S. application Ser. No. 16/831,413, filed Mar. 26, 2020, which is a Continuation-In-Part of U.S. application Ser. No. 16/551,654, filed Aug. 26, 2019, now U.S. Pat. No. 10,638,938. U.S. Ser. No. 16/551,654 is a Continuation-In-Part of U.S. application Ser. No. 16/453,993, filed Jun. 26, 2019. U.S. Ser. No. 16/453,993 is a Continuation-In-Part of U.S. application Ser. No. 16/375,841, filed Apr. 4, 2019. U.S. Ser. No. 16/375,841 is a Continuation-In-Part of U.S. application Ser. No. 16/156,493, now U.S. Pat. No. 10,524,667, filed Oct. 10, 2018. U.S. Ser. No. 16/156,493, is a Continuation-In-Part of U.S. application Ser. No. 15/635,178, filed Jun. 27, 2017, now U.S. Pat. No. 10,136,856, which claims priority to U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

U.S. Ser. No. 16/156,493 is also a Continuation-In-Part of U.S. application Ser. No. 15/832,855, filed Dec. 6, 2017, now U.S. Pat. No. 10,130,308, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 15/832,855 is a Continuation-In-Part of U.S. application Ser. No. 15/182,592, filed Jun. 14, 2016, now U.S. Pat. No. 10,165,949, a Continuation-In-Part of U.S. application Ser. No. 15/231,276, filed Aug. 8, 2016, a Continuation-In-Part of U.S. application Ser. No. 15/284,528, filed Oct. 3, 2016, now U.S. Pat. No. 10,113,913, a Continuation-In-Part of U.S. application Ser. No. 15/635,178, filed Jun. 27, 2017, now U.S. Pat. No. 10,136,856, and a Continuation-In-Part of U.S. application Ser. No. 15/722,434, filed Oct. 2, 2017.

U.S. Ser. No. 15/832,855 is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/182,592 claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/284,528 claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/833,115, filed Dec. 6, 2017, now U.S. Pat. No. 10,130,261. U.S. Ser. No. 15/833,115 is a Continuation-In-Part of U.S. application Ser. No. 15/182,592, a Continuation-In-Part of U.S. application Ser. No. 15/231,276, filed Aug. 8, 2016, a Continuation-In-Part of U.S. application Ser. No. 15/284,528, a Continuation-In-Part of U.S. application Ser. No. 15/635,178, and a Continuation-In-Part of U.S. application Ser. No. 15/722,434, filed Oct. 2, 2017.

U.S. Ser. No. 16/453,993 is also a Continuation-In-Part of U.S. application Ser. No. 16/147,695, filed Sep. 29, 2018. U.S. Ser. No. 16/147,695 is a Continuation of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

This Application is a Continuation-In-Part of U.S. application Ser. No. 16/689,929, filed Nov. 20, 2019, that is a Continuation-In-Part of U.S. Ser. No. 16/156,586, filed Oct. 10, 2018, that is a Continuation-In-Part of U.S. application Ser. No. 15/832,815, filed Dec. 6, 2017, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 16/156,586 is also a Continuation-In-Part of U.S. application Ser. No. 15/859,772 Jan. 2, 2018, now U.S. Pat. No. 10,159,411.

This Application is a Continuation-In-Part of U.S. application Ser. No. 17/009,655, filed Sep. 1, 2020, which is incorporated herein by reference. U.S. application Ser. No. 17/009,655 claims priority to U.S. Provisional Patent Application No. 62/928,726, filed Oct. 31, 2019, U.S. Provisional Patent Application No. 62/945,141, filed Dec. 7, 2019, U.S. Provisional Patent Application No. 62/960,913, filed Jan. 14, 2020, U.S. Provisional Patent Application No. 63/006,827, filed Apr. 8, 2020, U.S. Provisional Patent Application No. 63/024,471, filed May 13, 2020, and U.S. Provisional Patent Application No. 63/048,638, filed Jul. 6, 2020.

BACKGROUND

Social distancing has emerged as one of the keystone measures put in place to curb the spread of airborne infectious diseases. However, strict social distancing is often difficult to maintain in real life, since people still need to work, commute, and maintain some level of social contact in their daily and professional lives. While people can try and be careful and maintain a certain physical distance from people around them, there are situations in which such contact can accidently occur despite people's vigilance and best intentions. One scenario in which, accidental and unwanted contact can occur with people involves passage through doorways (e.g., building entrances, office doors, etc.) When one approaches a closed door, it is usually not clear if there is someone on the other side and/or whether that person is healthy and/or non-contagious. Thus, in order to avoid such unwanted contacts, especially with people whose health state is unverified, there is a need for a novel type of doorway that can assist in maintaining safe social distancing practices.

SUMMARY

One aspect of this disclosure is a wearable-based system that can help determine in a privacy-preserving manner whether a user is healthy (and thus poses low risk of contagiousness). A health score generated by the wearable device can be used to provide a verified health status for the user, granting the user with greater freedom of movement, e.g., via automatic opening of certain doors that are closed to people who cannot provide furnish such a verified health status.

Some aspects of this disclosure involve utilization of wearable devices with sensors that measure physiological signals of their wearers. An example of such a wearable device are smartglasses with embedded sensors. For example, the smartglasses may include some of the following sensors: a photoplethysmogram (PPG) sensor that measures blood flow and blood oxygen saturation at a region on the face, a thermal sensor that measures temperature at region on the face, an acoustic sensor that takes audio recordings indicative of voice, respiration, and/or coughing, a movement sensor, and more.

One aspect of this disclosure involves utilization of measurements taken by a wearable device worn by a user to calculate a health score for the user. Some examples of physiological signals that may be used to calculate the health score include one or more of the following: heart rate, blood oxygen saturation, respiration rate, skin and/or core body temperature, blood pressure, and extent of coughing. In some embodiments, the health score of a user may be indicative of the extent to which a user is healthy and/or non-contagious. Optionally, a health score may refer to an extent to which a user displays symptoms of a certain disease certain disease (e.g., the flu, COVID-19, or some other communicable disease) and/or is considered contagious with respect to the certain disease. Additionally or alternatively, a health score may refer to an extent to which a user is considered healthy according to general wellness considerations that involve one or more of the user's vital signs (e.g., whether the core body temperature is elevated, blood oxygen saturation is in a normal range, etc.)

In some embodiments described herein, health scores for users are calculated based on differences between current measurements of users (which in some examples are measurements up to 3 hours old) and baseline measurements of the users (which in some examples are at least 10 hours old, or even several days old). Differences between the current measurements and the baseline measurements are used to detect deviation from a baseline state that may be indicative of a change in the health state of the user. For example, a rise in estimated core body temperature compared to a baseline estimated core body temperature and a drop in blood oxygen saturation ($SpO_2$) compared to a baseline $SpO_2$ may be indications that the user is becoming ill.

Another aspect of this disclosure involves utilization of measurements taken by a wearable device worn by a user to authenticate the user and/or determine whether current measurements and baseline measurements are of the same user. In some embodiments, this involves detecting biometric similarities between patterns in the current measurements and the baseline measurements. For example, this similarities may be ascertained by calculating an extent of similarity between characteristics of a PPG signal in the current measurements and characteristics of a PPG signal in the baseline measurements. Optionally, additional physiological signals such as characteristics of gait and/or spectral properties of voice.

Similarities between current measurements and baseline measurements may be used to establish, with a certain degree of certainty, that the baseline measurements and the current measurements are of the same person. This form of biometric identification/verification can help reduce the likelihood of mistakes and/or deceptive behavior when the wearable device is used for various applications related to granting access or privilege based on a wearable-based health state. For example, this can help reduce occurrence of cases that involve measuring a first user (who is healthy) and then providing the wearable device to a second user, who poses as the first user, in order to trick the system.

One aspect of this disclosure involves utilization of wearable devices to facilitate a smart doorway that helps prevent contact between people whose health state poses a risk or whose health and/or non-contagiousness is not verified.

One aspect of this disclosure is a doorway system. In one embodiment, the system includes a doorway that facilitates passage from an inside to an outside, and/or from the outside to the inside and a barrier, disposed in the doorway, configured to move between an opened position and a closed position based on commands sent by a computer. Optionally, when in the closed position, the barrier restricts passage through the doorway, and when in the opened position, the barrier does not restrict the passage through the doorway. The doorway system also includes one or more sensors configured to measure: a first signal indicative of whether there is a first user on the outside of the doorway, and a second signal indicative of whether there is a second user on the inside of the doorway. The doorway system includes a computer that detects based on the first signal that the first user is on the outside and receives, from a first device carried and/or worn by the first user, a first indication indicating the first user is healthy. Optionally, the first indication does not comprise information identifying the first user. The computer detects based on the second signal whether the second user is on the inside. The computer commands the barrier to move to the opened position and/or remain in the opened position, responsive to: (i) detecting that the second user is not on the inside, or (ii) detecting that the second user is on the inside and receiving, from a second device carried and/or worn by the second user, a second indication indicating the second user is healthy. Optionally, the second indication does not comprise information identifying the second user. Optionally, the computer commands the barrier to move to the closed position and/or remain in the closed position, responsive to: (i) detecting based on the first signal that the first user is on the outside, detecting based on the second signal that the second user is not on the inside, and not receiving the first indication indicating the first user is healthy, or (ii) detecting based on the first signal that the first user is on the outside, detecting based on the second signal that the second user is on the inside, and not receiving at least one of the first indication indicating the first user is healthy and the second indication indicating the second user is healthy, respectively.

In one embodiment, the computer commands the barrier to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

In another embodiment, the computer commands the barrier to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

In one example, the barrier is a door that belongs to a vehicle, and commanding the barrier to move to the opened position and/or remain in the opened position comprises commanding the door to unlock and/or move to a position that enables the first user to enter a passenger cabin of the vehicle.

In another example, the barrier is an entrance door to a room and/or building, and commanding the barrier to move to the opened position and/or remain in the opened position comprises commanding the door to unlock and/or move to a position that enables the first user to enter the interior of the room and/or building.

In yet another example, the barrier is a turnstile or a revolving door belonging to a gate, and commanding the barrier to move to the opened position and/or remain in the opened position comprises enabling the turnstile or the revolving door to revolve and/or revolving the turnstile or the revolving door, enabling the first user to pass through the gate.

In one embodiment, the computer transmits a request for the first indication indicating the first user is healthy, responsive to detecting that the first user is on the outside and/or to transmit a request for the second indication indicating the second user is healthy, responsive to detecting that the second user is on the inside.

In one example, the one or more sensors comprise a camera aimed to the outside, the first signal comprises images of the outside, and detecting the first user is outside comprises identifying presence of a person in the images.

In another example, the one or more sensors comprise a thermal sensor aimed to the outside, the first signal comprises thermal measurements of the outside, and detecting the first user is outside comprises identifying a thermal signature corresponding to a person in the thermal measurements.

In yet another example, the one or more sensors comprise a pressure sensor disposed in a surface on the outside, the first signal comprises values indicative of pressure applied to the pressure sensor, and detecting the first user is outside comprises identifying the values reflect application of a pressure corresponding to a weight of a person.

Another aspect of this disclosure is a method for controlling a doorway. In one embodiment, the method includes the following steps:
receiving a first signal indicative of whether there is a first user on an outside of a doorway. Optionally, the doorway facilitates passage from an inside to the outside, and/or from the outside to the inside and the doorway comprises a barrier configured to move between an opened position and a closed position, and when in the closed position, the barrier restricts passage through the doorway, and when in the opened position, the barrier does not restrict passage through the doorway;
detecting based on the first signal that the first user is on the outside;
receiving, from a first device carried and/or worn by the first user, a first indication indicating the first user is healthy;
receiving a second signal indicative of whether there is a second user on the inside of the doorway;
detecting based on the second signal whether the second user is on the inside; and
commanding the barrier to move to the opened position and/or remain in the opened position, responsive to: (i) detecting that the second user is not on the inside, or (ii) detecting that the second user is on the inside and receiving, from a second device carried and/or worn by the second user, a second indication indicating the second user is healthy.

In one embodiment, the method optionally includes a step of commanding the barrier to move to the closed position and/or remain in the closed position, responsive to: (i) detecting based on the first signal that the first user is on the outside, detecting based on the second signal that the second user is not on the inside, and not receiving the first indication indicating the first user is healthy, or (ii) detecting based on the first signal that the first user is on the outside, detecting based on the second signal that the second user is on the inside, and not receiving at least one of the first indication indicating the first user is healthy and the second indication indicating the second user is healthy, respectively.

In one embodiment, the method optionally includes a step of commanding the barrier to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

In one embodiment, the method optionally includes a step of commanding the barrier to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

In one embodiment, the method optionally includes a step of transmitting a request for the first indication indicating the first user is healthy, responsive to detecting that the first user is on the outside.

Yet another aspect of this disclosure is a non-transitory computer readable medium storing one or more computer programs configured to cause a processor based system to execute steps of the aforementioned method.

Managing physical access to locations (e.g., work places, public spaces) can be especially challenging when precautions need to be taken in order to curb the spread of diseases such as the flu or COVID-19. Some embodiments described herein use authenticated wearable-based health state verifications in order to authorize access to such locations, which can help curb the spread of these diseases.

One aspect of this disclosure is a system configured to authorize physical access to a location based on an authenticated health score. In one embodiment, the system includes a wearable device and a computer. The wearable device includes a first sensor configured to measure a signal indicative of a photoplethysmogram signal (PPG signal) of a user, and a second sensor configured to measure a temperature of the user. The computer receives current measurements of the user taken with the wearable device, and baseline measurements of the user taken with the wearable device during one or more earlier days. The computer calculates a health score based on a difference between the baseline measurements and the current measurements, and an authentication score based on a similarity between characteristics of a PPG signal in the current measurements and characteristics of a PPG signal in the baseline measurements. And responsive to the health score reaching a first threshold and the authentication score reaching a second threshold, the computer grants the user a privilege to access the location.

In one embodiment, the computer revokes the privilege of the user to access the location, responsive to the health score not reaching the first threshold and/or the authentication score not reaching the second threshold. Optionally, the computer increases the first threshold responsive to receiving a certain indication indicative of number of people, who are ill and who accessed the location in a preceding period of time, reaches a third threshold; whereby increasing the first threshold reduces tendency to deny and/or revoke privileges to access the location.

In one embodiment, calculation of the health score by the computer comprises: calculating, based on the baseline measurements, an expected value of a physiological signal of the user; calculating, based on the current measurements, a current value of the physiological signal; and calculating the health score based on a difference between the expected value and the current value. In one example, the physiological signal is body temperature, and the calculating of the health score utilizes a function that returns a value that is below the first threshold when a current body temperature is greater than an expected body temperature by at least a certain margin. Optionally, the certain margin is at least 0.4° C. In another example, calculating the current value of the physiological signal by the computer comprises: generating feature values based on the current measurements, and utilizing a model to calculate, based on the feature values, the current value of the physiological signal. Optionally, the model was generated from training data comprising: previous measurements of the user taken with the wearable device, and values of the physiological signal obtained utilizing a sensor that is not part of the wearable device.

In one embodiment, the computer determines, based on measurements taken with the wearable device, whether the wearable device was removed from the user's body while the current measurements were taken or after the current measurements were taken, and responsive to making a determination that the wearable device has been removed, revokes the privilege of the user to access the location. Optionally, the computer performs the following steps responsive to making the determination that the wearable device was removed: receive additional measurements of the user, taken with the wearable device at most three hours after the current measurements were taken; calculate an additional similarity between the characteristics of the PPG signal in the current measurements and characteristics of a PPG signal in the additional measurements; and grant the user a privilege to access the location responsive to the health score reaching the first threshold and the additional similarity reaching the second threshold; whereby the additional similarity reaching the second threshold is indicative of a probability that the current measurements and the additional measurements are of the same person is above a predetermined threshold.

In one embodiment, the computer provides an indication that the user is healthy responsive to the health score reaching the first threshold and the authentication score reaching the second threshold.

In another embodiment, the computer provides an indication that the user is ill responsive to the health score not reaching the first threshold and the authentication score reaching the second threshold.

In one embodiment, the computer generates feature values based on data comprising the current measurements and the baseline measurements, and utilizes a model to calculate, based on the feature values, the health score. Optionally, the model is generated based on training data comprising a first set of training measurements of a plurality of users taken while the plurality of users healthy and a second set of training measurements of the plurality of users taken while the plurality of users were not healthy.

Another aspect of this disclosure is a method for managing authorization of access to a location based on authenticated health scores. In one embodiment, the method includes the following steps: receiving current measurements of a user taken with a wearable device that comprises: a first sensor configured to measure a signal indicative of a photoplethysmogram signal (PPG signal) of a user, and a second sensor configured to measure a temperature of the user; receiving baseline measurements of the user taken with the wearable device during one or more earlier days; calculating a health score based on a difference between the baseline measurements and the current measurements; calculating an authentication score based on a similarity between characteristics of a PPG signal in the current measurements and characteristics of a PPG signal in the baseline measurements; and responsive to the health score reaching a first threshold and the authentication score reaching a second threshold, granting the user a privilege to access the location.

In one embodiment, the method optionally includes a step of revoking the privilege of the user to access the location, responsive to the health score not reaching the first threshold and/or the authentication score not reaching the second threshold. Optionally, the method includes a step of increasing the first threshold responsive to receiving a certain indication indicative of number of people, who are ill and who accessed the location in a preceding period of time, reaches a third threshold; whereby increasing the first threshold reduces tendency to revoke privileges to access the location.

In another embodiment, the method optionally includes a step of providing an indication that the user is ill responsive to the health score not reaching the first threshold and the authentication score reaching the second threshold.

In one embodiment, the method optionally includes the following steps: generating feature values based on data comprising the current measurements and the baseline measurements, and utilizing a model to calculate, based on the feature values, the health score. Optionally, the model is generated based on training data comprising a first set of training measurements of a plurality of users taken while the plurality of users healthy and a second set of training measurements of the plurality of users taken while the plurality of users were not healthy.

Yet another aspect of this disclosure is a non-transitory computer readable medium storing one or more computer programs configured to cause a processor based system to execute steps of the aforementioned method.

BRIEF DESCRIPTION OF THE DRAWINGS

The embodiments are herein described by way of example only, with reference to the following drawings:

FIG. 14A illustrates an example of a hemoglobin concentration pattern of a sober person;

FIG. 14B illustrates an example of the hemoglobin concentration pattern of the same person when intoxicated;

FIG. 14C is a schematic illustration of components of a system configured to detect fever and/or intoxication;

FIG. 29A, FIG. 29B, and FIG. 29C illustrate embodiments of two right and left clip-on devices that are configured to attached/detached from an eyeglasses frame;

FIG. 30A and FIG. 30B illustrate an embodiment of a clip-on device that includes inward-facing head-mounted cameras pointed at the lower part of the face and the forehead;

FIG. 39A, FIG. 39B, FIG. 40A, FIG. 40B and FIG. 40C illustrate how embodiments described herein may help train an elderly user to exhale during effort;

FIG. 47A is a schematic illustration of a left dominant nostril;

FIG. 47B is a schematic illustration of a right dominant nostril;

FIG. 47C is a schematic illustration of balanced breathing;

FIG. 48 is a schematic illustration of an embodiment of a system that identifies the dominant nostril;

FIG. 49A illustrates an embodiment of a system that suggests activities according to the dominant nostril;

FIG. 49B illustrates an embodiment of a system for calculating a respiratory parameter;

FIG. 57A and FIG. 57B illustrate the making of different detections of emotional response based on thermal measurements compared to the emotional response that is visible in a facial expression;

FIG. 58 illustrates an embodiment of a smartphone app that provides a user with feedback about how he/she looks to others;

DETAILED DESCRIPTION

Figure 1:
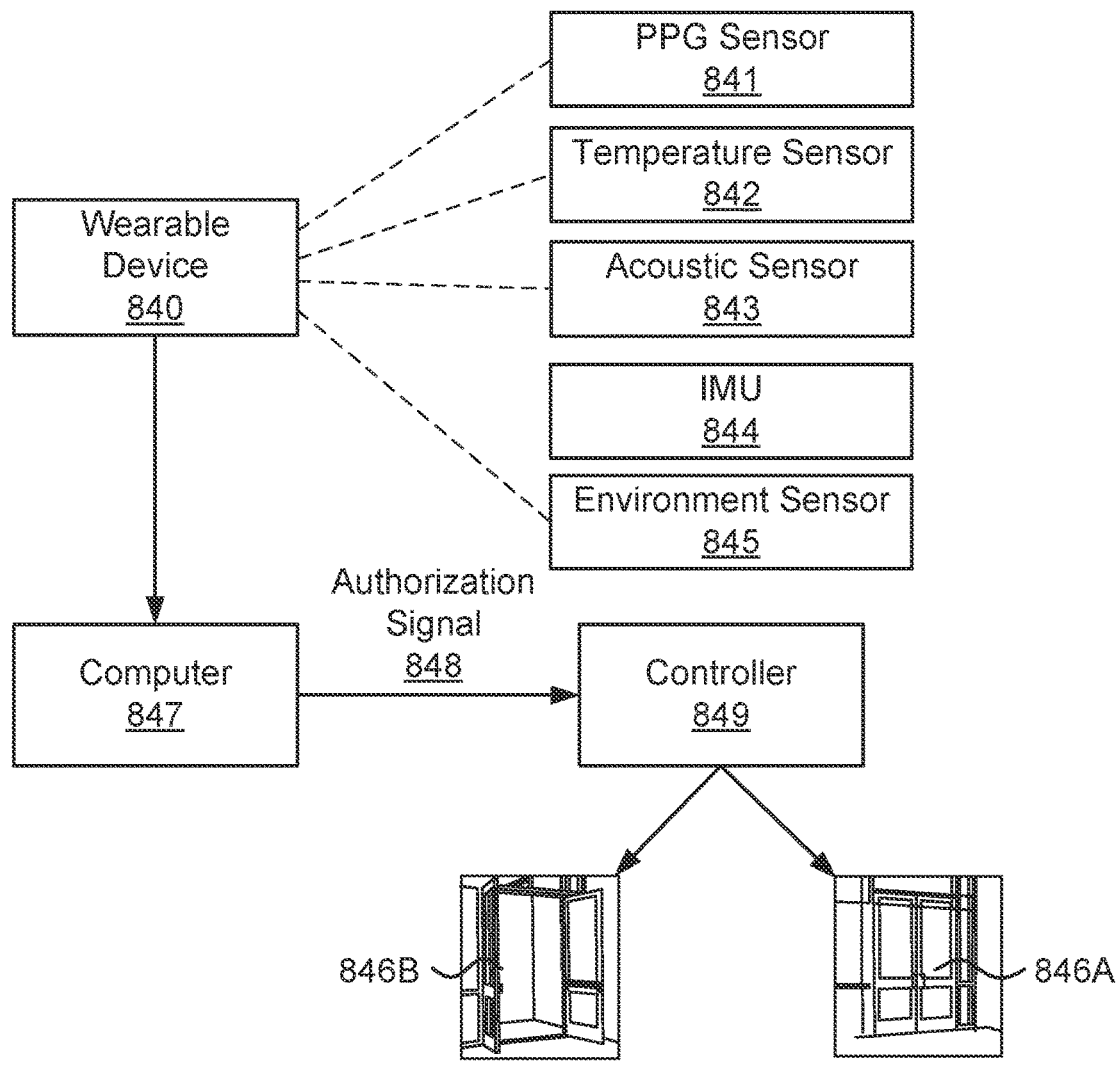
FIG. 1 is a schematic illustration embodiments of a system configured to grant passage through a doorway based on a user's health state.

Herein the terms "photoplethysmogram signal", "photoplethysmographic signal", "photoplethysmography signal", and other similar variations are interchangeable and refer to the same type of signal. A photoplethysmogram signal may be referred to as a "PPG signal", or an "iPPG signal" when specifically referring to a PPG signal obtained from a camera. The terms "photoplethysmography device", "photoplethysmographic device", "photoplethysmogram device", and other similar variations are also interchangeable and refer to the same type of device that measures a signal from which it is possible to extract the photoplethysmogram signal. The photoplethysmography device may be referred to as "PPG device".

Sentences in the form of "a sensor configured to measure a signal indicative of a photoplethysmogram signal" refer to at least one of: (i) a contact PPG device, such as a pulse oximeter that illuminates the skin and measures changes in light absorption, where the changes in light absorption are indicative of the PPG signal, and (ii) a non-contact camera that captures images of the skin, where a computer extracts the PPG signal from the images using an imaging photoplethysmography (iPPG) technique. Other names known in the art for iPPG include: remote photoplethysmography (rPPG), remote photoplethysmographic imaging, remote imaging photoplethysmography, remote-PPG, and multi-site photoplethysmography (MPPG).

A PPG signal is often obtained by using a pulse oximeter, which illuminates the skin and measures changes in light absorption. Another possibility for obtaining the PPG signal is using an imaging photoplethysmography (iPPG) device. As opposed to contact PPG devices, iPPG does not require contact with the skin and is obtained by a non-contact sensor, such as a video camera.

A time series of values measured by a PPG device, which is indicative of blood flow changes due to pulse waves, is typically referred to as a waveform (or PPG waveform to indicate it is obtained with a PPG device). It is well known that PPG waveforms show significant gender-related differences, age-related differences, and health-related differences. As a result, the PPG waveforms of different people often display different characteristics (e.g., slightly different shapes and/or amplitudes). In addition, the PPG waveform depends on the site at which it is measured, skin temperature, skin tone, and other parameters.

The analysis of PPG signals usually includes the following steps: filtration of a PPG signal (such as applying bandpass filtering and/or heuristic filtering), extraction of feature values from fiducial points in the PPG signal (and in some cases may also include extraction of feature values from non-fiducial points in the PPG signal), and analysis of the feature values.

One type of features that is often used when performing calculations involving PPG signals involves fiducial points related to the waveforms of the PPG signal and/or to functions thereof (such as various derivatives of the PPG signal). There are many known techniques to identify the fiducial points in the PPG signal, and to extract the feature values. The following are some non-limiting examples of how to identify fiducial points.

Figure 15A:
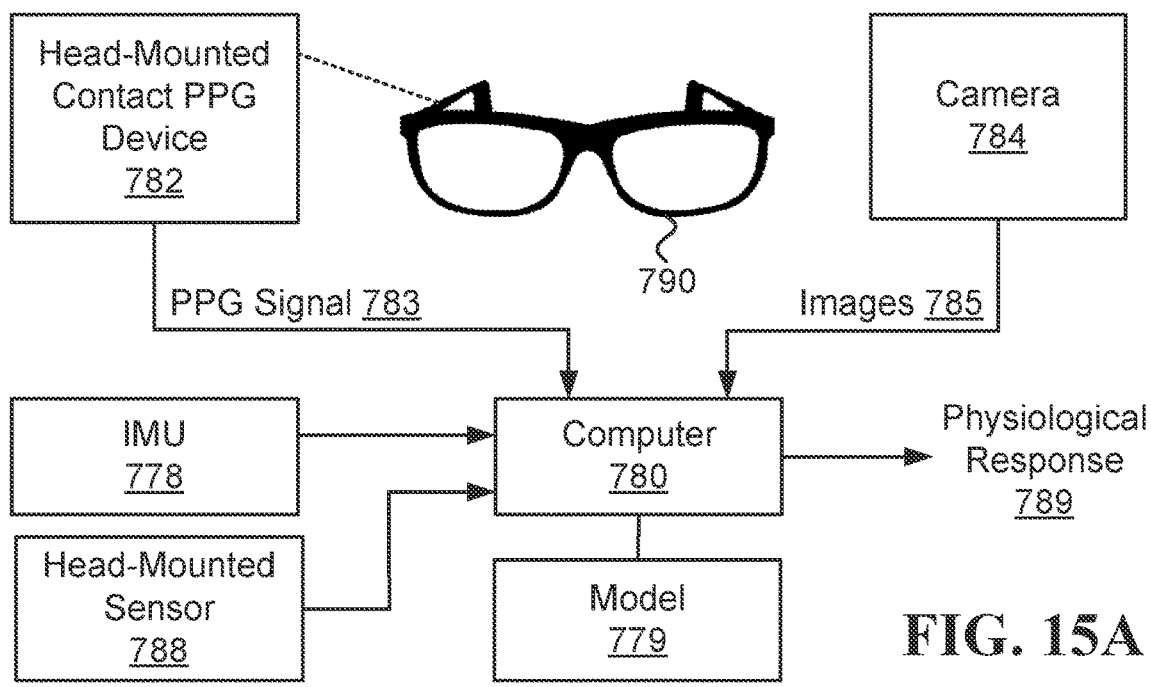
FIG. 15A illustrates an embodiment of a system that utilizes multiple PPG signals, measured using different types of sensors, to detect a physiological response.
Figure 15B:
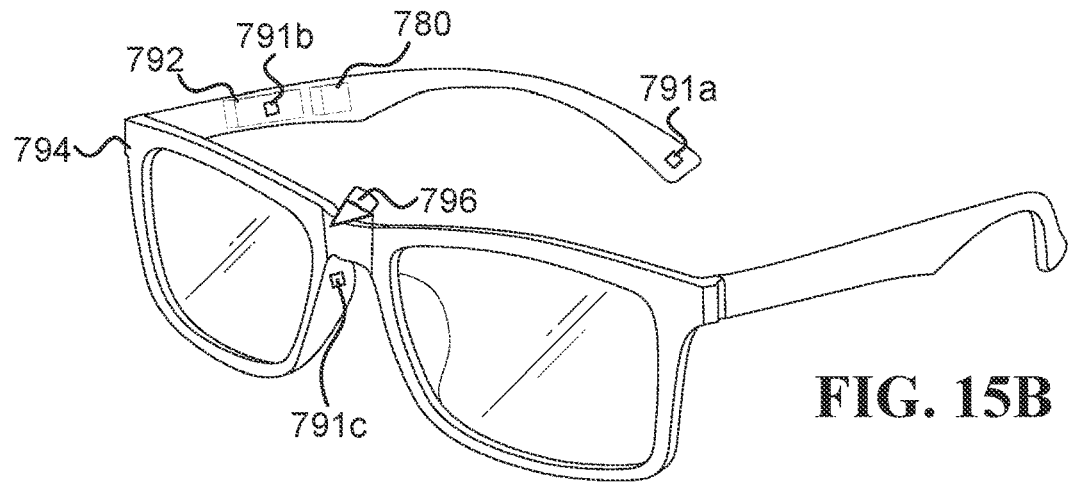
FIG. 15B illustrates smartglasses that include a camera and several contact PPG devices.
Figure 15C:
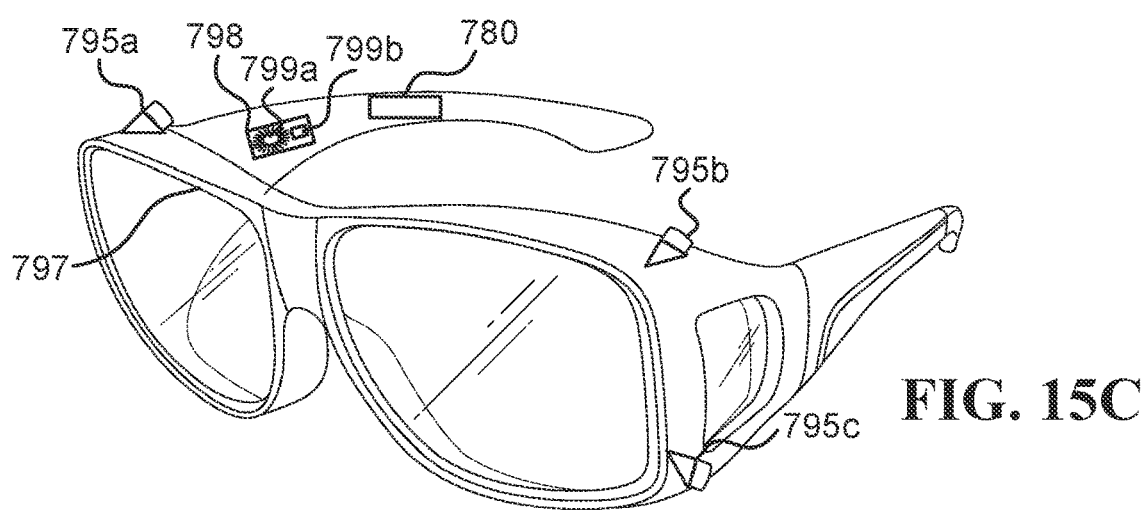
FIG. 15C illustrates smartglasses that include at least first, second, and third inward-facing cameras.
Figure 15D:
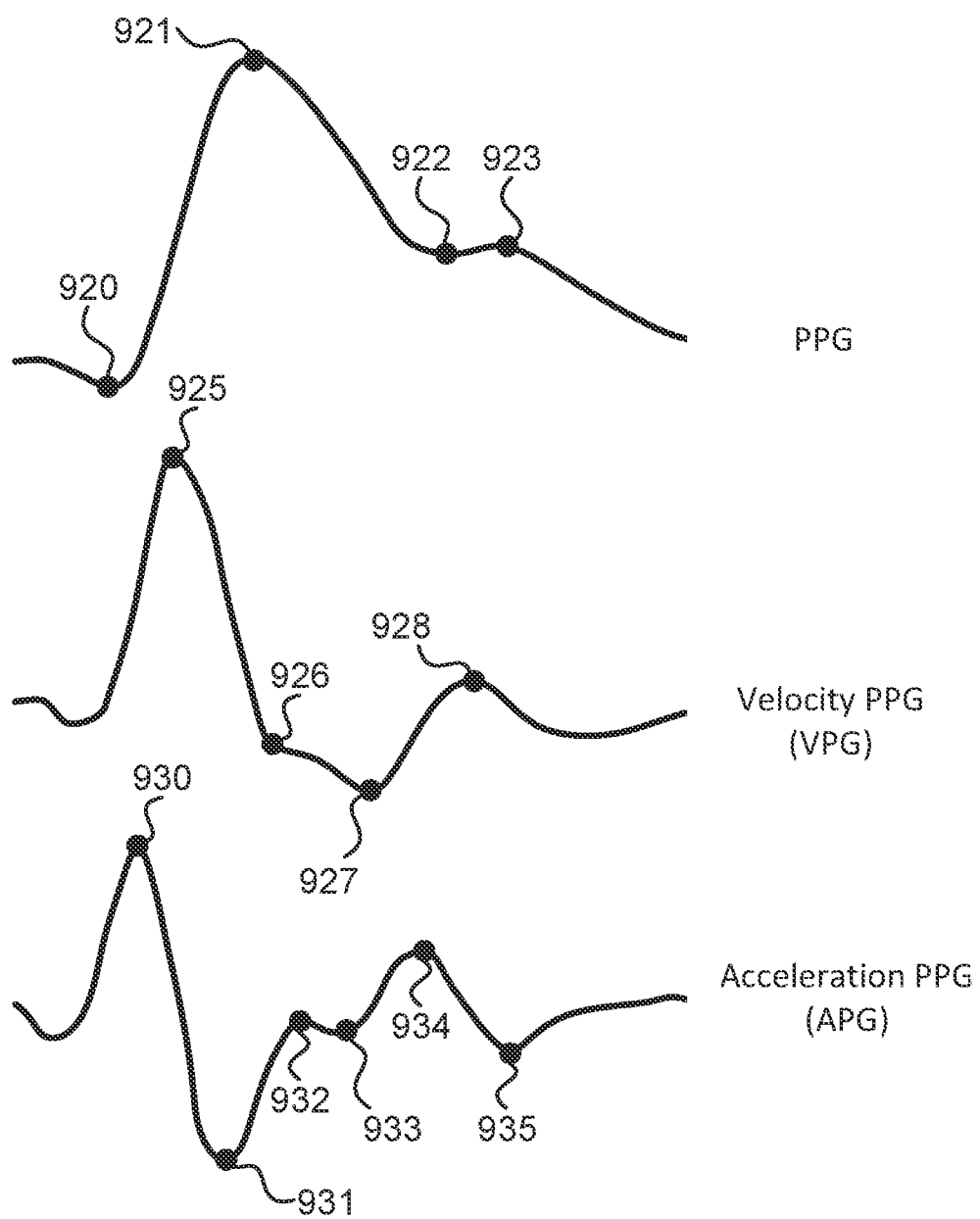
FIG. 15D is a schematic illustration of some of the various fiducial points for PPG signals often used in the art.

FIG. 15D is a schematic illustration of some of the various fiducial points often used in the art (and described below). These examples of fiducial points include fiducial points of the PPG signal, fiducial points in the first derivative of the PPG signal (velocity photoplethysmogram, VPG), and fiducial points in the second derivative of the PPG signal (acceleration photoplethysmogram, APG).

Fiducial points in the PPG signal may include: the systolic notch 920, which is the minimum at the PPG signal onset; the systolic peak 921, which is the maximum of the PPG signal; the dicrotic notch 922, which coincident with e 934 (see below at the second derivative of the PPG signal); and the diastolic peak 923, which is the first local maximum of the PPG signal after the dicrotic notch and before 0.8 of the duration of the cardiac cycle, or if there is no such local maximum, then the first local maximum of the second derivative after e and before 0.8 of the duration of the cardiac cycle.

Fiducial points in the first derivative of the PPG signal (velocity photoplethysmogram, VPG) may include: the maximum slope peak in systolic of VPG 925; the local minima slope in systolic of VPG 926; the global minima slope in systolic of VPG 927; and the maximum slope peak in diastolic of VPG 928.

Fiducial points in the second derivative of the PPG signal (acceleration photoplethysmogram, APG) may include: a 930, which is the maximum of APG prior to the maximum of VPG; b 931, which is the first local minimum of APG following a; c 932, which is the greatest maximum of APG between b and e, or if no maxima then the first of (i) the first maximum of VPG after e, and (ii) the first minimum of APG after e; d 933, which is the lowest minimum of APG after c and before e, or if no minima then coincident with c; e 934, which is the second maximum of APG after maximum of VPG and before 0.6 of the duration of the cardiac cycle, unless the c wave is an inflection point, in which case take the first maximum; and f 935, which is the first local minimum of APG after e and before 0.8 of the duration of the cardiac cycle.

Fiducial points in the third derivative of the PPG signal (PPG''') may include: the first local maximum of PPG''' after b; and the last local minimum of PPG''' before d, unless c=d, in which case take the first local minimum of PPG''' after d, and if there is a local maximum of the PPG signal between this point and the dicrotic notch then use it instead.

Feature values of the PPG signal may also be extracted from relationships in the PPG signal and/or its derivatives. The following are some non-limiting examples such possible feature values: pulse width, peak to peak time, ratio of areas before and after dicrotic notch in a complete cycle, baseline wander (BW), which is the mean of the amplitudes of a beat's peak and trough; amplitude modulation (AM), which is the difference between the amplitudes of each beat's peak and trough; and frequency modulation (FM), which is the time interval between consecutive peaks.

Examples of additional features that can be extracted from the PPG signal, together with schematic illustrations of the feature locations on the PPG signal, can be found in the following three publications: (i) Peltokangas, Mikko, et al. "Parameters extracted from arterial pulse waves as markers of atherosclerotic changes: performance and repeatability." IEEE journal of biomedical and health informatics 22.3 (2017): 750-757; (ii) Ahn, Jae Mok. "New aging index using signal features of both photoplethysmograms and acceleration plethysmograms." Healthcare informatics research 23.1 (2017): 53-59; (iii) Charlton, Peter H., et al. "Assessing mental stress from the photoplethysmogram: a numerical study." Physiological measurement 39.5 (2018): 054001, and (iv) Peralta, Elena, et al. "Optimal fiducial points for pulse rate variability analysis from forehead and finger photoplethysmographic signals." Physiological measurement 40.2 (2019): 025007.

Although the above mentioned references describe manual feature selection, the features may be selected using any appropriate feature engineering technique, including using automated feature engineering tools that help data scientists to reduce data exploration time, and enable non-experts, who may not be familiar with data science and/or PPG characteristics, to quickly extract value from their data with little effort.

Unless there is a specific reference to a specific derivative of the PPG signal, phrases of the form of "based on the PPG signal" refer to the PPG signal and any derivative thereof, including the first derivative of the PPG signal, the second derivative of the PPG signal, and the third derivative of the PPG signal. For example, a sentence in the form of "a computer configured to detect a physiological signal based on the PPG signal" is to be interpreted as "a computer configured to detect a physiological signal based on at least one of: the PPG signal, a first derivative of the PPG signal, a second derivative of the PPG signal, a the third derivative of the PPG signal, and/or any other derivative of the PPG signal".

Algorithms for filtration of the PPG signal, extraction of feature values from fiducial points in the PPG signal, and analysis of the feature values extracted from the PPG signal are well known in the art, and can be found for example in the following references: (i) Allen, John. "Photoplethysmography and its application in clinical physiological measurement." Physiological measurement 28.3 (2007): R1, and also in the thousands of references citing this reference; (ii) Elgendi, Mohamed. "On the analysis of fingertip photoplethysmogram signals." Current cardiology reviews 8.1 (2012): 14-25, and also in the hundreds of references citing this reference; (iii) Holton, Benjamin D, et al. "Signal recovery in imaging photoplethysmography." Physiological measurement 34.11 (2013): 1499, and also in the dozens of references citing this reference, (iv) Sun, Yu, and Nitish Thakor. "Photoplethysmography revisited: from contact to noncontact, from point to imaging." IEEE Transactions on Biomedical Engineering 63.3 (2015): 463-477, and also in the dozens of references citing this reference, (v) Kumar, Mayank, Ashok Veeraraghavan, and Ashutosh Sabharwal. "DistancePPG: Robust non-contact vital signs monitoring using a camera." Biomedical optics express 6.5 (2015): 1565-1588, and also in the dozens of references citing this reference, (vi) Wang, Wenjin, et al. "Algorithmic principles of remote PPG." IEEE Transactions on Biomedical Engineering 64.7 (2016): 1479-1491, and also in the dozens of references citing this reference, and (vii) Rouast, Philipp V., et al. "Remote heart rate measurement using low-cost RGB face video: a technical literature review." Frontiers of Computer Science 12.5 (2018): 858-872, and also in the dozens of references citing this reference.

Various embodiments described herein involve calculations based on machine learning approaches. Herein, the terms "machine learning approach" and/or "machine learning based approaches" refer to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using one or more machine learning approaches. For brevity's sake, at times, a "machine learning-based model" may simply be called a "model". Referring to a model as being "machine learning-based" is intended to indicate that the model is trained using one or more machine learning approaches (otherwise, "model" may also refer to a model generated by methods other than machine learning).

Herein, "feature values" (also known as feature vector, feature data, and numerical features) may be considered input to a computer that utilizes a model to perform the calculation of a value, such as a value indicative of one or more vital signs of a user. It is to be noted that the terms "feature" and "feature value" may be used interchangeably when the context of their use is clear. However, a "feature" typically refers to a certain type of value, and represents a property, while "feature value" is the value of the property with a certain instance (i.e., the value of the feature in a certain sample).

It is to be noted that when it is stated that feature values are generated based on data comprising multiple sources, it means that for each source, there is at least one feature value that is generated based on that source (and possibly other data). For example, stating that feature values are generated from an image capturing first and second regions ($IM_{ROI1}$ and $IM_{ROI2}$, respectively) means that the feature values include at least a first feature value generated based on $IM_{ROI1}$ and a second feature value generated based on $IM_{ROI2}$.

In addition to feature values generated based on measurements taken by sensors mentioned in a specific embodiment, at least some feature values utilized by a computer of the specific embodiment may be generated based on additional sources of data that were not specifically mentioned in the specific embodiment. Some examples of such additional sources of data include: (i) contextual information such as the time of day (e.g., to account for effects of the circadian rhythm), day of month (e.g., to account for effects of the lunar rhythm), day in the year (e.g., to account for seasonal effects), and/or stage in a menstrual cycle; (ii) information about the user being measured such as sex, age, weight, height, body build, genetics, medical records, and/or intake of substances; (iii) measurements of the environment, such as temperature, humidity level, noise level, elevation, air quality, a wind speed, precipitation, and infrared radiation; and/or (iv) values of physiological signals of the user obtained by sensors that are not mentioned in the specific embodiment, such as an electrocardiogram (ECG) sensor, an electroencephalography (EEG) sensor, a galvanic skin response (GSR) sensor, a movement sensor, an acoustic sensor, and/or a temperature sensor.

A machine learning-based model of a specific embodiment may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects that different conditions can have on the measurements, and consequently, be able to achieve better detection of a required parameter in real world day-to-day scenarios.

The machine learning-based model may be personalized for a specific user. For example, after receiving a verified diagnosis of an extent of a physiological condition (such as blood pressure level, extent of a cardiovascular disease, extent of a pulmonary disease, extent of a migraine attack, etc.), the computed can use the verified diagnosis as labels and generate from a physiological measurement (such as the PPG signal, the temperature signal, the movement signal, and/or the audio signal) feature values to train a personalized machine learning-based model for the user. Then the computer can utilize the personalized machine learning-based model for future calculations of the extent of the physiological condition based on feature values.

Sentences in the form of "inward-facing head-mounted camera" refer to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be physically coupled to eyeglasses using a clip-on mechanism (configured to be attached to and detached from the eyeglasses), may be physically coupled to a hat or a helmet, or may be mounted to the user's head using any other known device that keeps the camera in a fixed position relative to the user's head also when the head moves. Sentences in the form of "sensor physically coupled to the frame" mean that the sensor moves with the frame, such as when the sensor is fixed to (or integrated into) the frame, and/or when the sensor is fixed to (or integrated into) an element that is physically coupled to the frame, and/or when the sensor is connected to the frame with a clip-on mechanism.

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frame in Google Glass™ is similar to an eyeglasses frame. Additionally or alternatively, the frame may connect to, be affixed within, and/or be integrated with, a helmet (e.g., a safety helmet, a motorcycle helmet, a combat helmet, a sports helmet, a bicycle helmet, etc.), goggles, and/or a brainwave-measuring headset.

Sentences in the form of "a frame configured to be worn on a user's head in a consistent manner" refer to a frame that is located in the same position relative to the head when worn repeatedly, and thus sensors attached to that frame are most likely to be positioned each time at the same location relative to the head. For example, eyeglasses frames, goggles, and helmets are all included under the definition of a frame that is worn in a consistent manner. However, a flexible headband, or adhesive sensors that are placed manually one by one, are not worn in a consistent manner, because these sensors are most likely to be positioned each time in a different location relative to the head.

The term "smartglasses" refers to any type of a device that reminds eyeglasses, and includes a frame configured to be worn on a user's head in a consistent manner, and includes electronics to operate one or more sensors. The frame may be an integral part of the smartglasses, and/or an element that is connected to the smartglasses. Examples of smartglasses include: any type of eyeglasses with electronics (whether prescription or plano), sunglasses with electronics, safety goggles with electronics, sports goggle with electronics, augmented reality devices, virtual reality devices, and mixed reality devices. In addition, the term "eyeglasses frame" refers to one or more of the following devices, whether with or without electronics: smartglasses, prescription eyeglasses, plano eyeglasses, prescription sunglasses, plano sunglasses, safety goggles, sports goggle, an augmented reality device, virtual reality devices, and a mixed reality device.

The term "smart-helmet" refers to a helmet that includes a frame configured to be worn on a user's head in a consistent manner, and includes electronics to operate one or more sensors. The frame may be an integral part of the smart-helmet, and/or an element that is connected to the smart-helmet. Examples of smart-helmets include: a safety helmet with electronics, a motorcycle helmet with electronics, a combat helmet with electronics, a sports helmet with electronics, and a bicycle helmet with electronics.

Examples of electronics that may be included in smartglasses and/or a smart-helmet include one or more of the following electronic components: a computer, a microcontroller, a processor, a memory, and a communication interface. The electronics of the smartglasses and/or smart-helmets may be integrated in various ways. For example, the electronics may be integrated into the package of one of the sensors, such as a camera housing that is physically coupled to a helmet, where the housing includes the imaging sensor and its processor, memory, power supply and wireless communication unit. In another example, the electronics may be integrated into the frame, such as a microcontroller, power supply and wireless communication unit that are integrated into an eyeglasses frame, and configured to operate a PPG device and a microphone that are physically coupled to the frame.

The term "Visible-light camera" refers to a non-contact device designed to detect at least some of the visible spectrum, such as a video camera with optical lenses and CMOS or CCD sensor. The term "thermal camera" refers to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

A reference to a "camera" herein may relate to various types of devices. In one example, a camera may be a visible-light camera. In another example, a camera may capture light in the ultra-violet range. In another example, a camera may capture near infrared radiation (e.g., wavelengths between 750 and 2000 nm). And in still another example, a camera may be a thermal camera.

When a camera is inward-facing and head-mounted, challenges faced by systems known in the art that are used to acquire images, which include non-head-mounted cameras, may be simplified and even eliminated with some of the embodiments described herein. Some of these challenges may involve dealing with complications caused by movements of the user, image registration, region of interest (ROI) alignment, tracking based on hot spots or markers, and motion compensation.

The term "temperature sensor" refers to a device that measures temperature and/or temperature change. The temperature sensor may be a contact thermometer (such as a thermistor, a thermocouple), and/or a non-contact thermal cameras (such as a thermopile sensor, a microbolometer sensor, a pyroelectric sensor, or a ferroelectric sensor). Some examples of temperature sensors useful to measure skin temperature include: thermistors, thermocouples, thermoelectic effect, thermopiles, microbolometers, and pyroelectric sensors. Some examples of temperature sensors useful to measure environment temperature include: thermistors, resistance temperature detectors, thermocouples; thermopiles, and semiconductor-based sensors.

The term "movement sensor" refers to a sensor comprising one or more of the following components: a 3-axis gyroscope, a 3-axis accelerometer, and a 3-axis magnetometer. The movement sensor may also include a sensor that measures barometric pressure.

The term "acoustic sensor" refers to a device that converts sound waves into an electrical signal. An acoustic sensor can be a microphone, such as a dynamic microphone that works via electromagnetic induction, a piezoelectric microphone that uses the phenomenon of piezoelectricity, a fiber-optic microphone that converts acoustic waves into electrical signals by sensing changes in light intensity, a Micro-Electrical-Mechanical System (MEMS) microphone (such as silicon MEMS and piezoelectric MEMS), and/or other sensors that measure sound waves, such as described in the following examples: (i) Han, Jae Hyun, et al. "Basilar membrane-inspired self-powered acoustic sensor enabled by highly sensitive multi tunable frequency band." Nano Energy 53 (2018): 198-205, describes a self-powered flexible piezoelectric acoustic sensor having high sensitivity, (ii)

Rao, Jihong, et al. "Recent Progress in Self-Powered Skin Sensors." Sensors 19.12 (2019): 2763. describes various self-powered acoustic skin sensors, such as an integrated triboelectric nanogenerator (TENG) with a polymer tube that can pick up and recover human throat voice even in an extremely noisy or windy environment, and (iii) Scanlon, Michael V. Acoustic sensor for voice with embedded physiology. Army Research Lab Adelphi Md., 1999, describes a gel-coupled acoustic sensor able to collect information related to the function of the heart, lungs, and changes in voice patterns.

Herein, the term "blood pressure" is indicative of one or more of the following: the systolic blood pressure of the user, the diastolic blood pressure of the user, and the mean arterial pressure (MAP) of the user. It is specifically noted that the term "blood pressure" is not limited to the systolic and diastolic blood pressure pair.

The terms "substance intake" or "intake of substances" refer to any type of food, beverage, medications, drugs, smoking/inhaling, and any combination thereof.

Some embodiments of systems, methods, and/or computer products for managing access by controlling passage through a doorway are described below. An aspect of these embodiments is utilization of wearable devices, worn by users, in order to determine whether their physiological signals indicates they are healthy, and thus should be allowed through the doorway. Physiological signals may also be used to determine that a person wearing the wearable device, and seeking to pass through the doorway, is the same person determined to be in a healthy state.

FIG. 1 is a schematic illustration embodiments of a system configured to grant passage through a doorway based on a user's health state. In one embodiment, the system includes at least a wearable device 840 and a computer 847. The computer 847 utilizes measurements of the user, taken with the wearable device 840, both on that day, and on earlier days, to determine if the user's health state permits passage through the doorway, and also to determine whether the user wearing the wearable device 840 is the person who wore the wearable device 840 when the earlier measurements were taken. Some embodiments of the system may optionally include additional elements such as a controller 849, which is configured to command an automatic door to open, close, lock and/or unlock, based on signals sent from the computer 847.

The wearable device 840 may include various types of sensors that may be used to measure the user wearing the wearable device and/or the environment that is user is in. In some embodiments, the wearable device includes a photoplethysmogram (PPG) sensor 841 that measures a signal indicative of a photoplethysmogram (PPG) signal of the user wearing the wearable device 840, and a temperature sensor 842 that measures a temperature of the user. Optionally, the PPG sensor 841 and/or the temperature sensor 842 may be head-mounted sensors, such as sensors coupled to, and/or embedded in, frames of smartglasses, such as the smartglasses illustrated in FIG. 2, which is discussed below. Optionally, the wearable device 840 may include additional sensors, such as an acoustic sensor 843, a inertial measurement unit (IMU) 844, and/or an environment sensor 845. These sensors may provide signals that can be utilized by the computer 847 to determine the user's health state, as discussed further below.

In some embodiments, the PPG sensor 841 may be a contact PPG device. Some examples of configurations for the PPG sensor 841, which may be used in different embodiments, include: a contact PPG device embedded in the nosepiece of smartglasses in order to take measurements indicative of blood flow at and/or near the nose, a contact PPG device embedded inside an earbud in order to take measurements indicative of blood flow in the ear, a contact PPG device embedded in a smart band or smartwatch to take measurements indicative of blood flow in the wrist, or a contact PPG device embedded in a patch that may be attached to a portion of the body in order to take measurements of blood flow at the attached region.

The contact PPG device may include one or more light sources configured to illuminate a region on the user's body with which the contact PPG device comes in contact. For example, the one or more light sources may include light emitting diodes (LEDs) that illuminate the region. Optionally, the one or more LEDs include at least two LEDs, where each illuminates the region with light at a different wavelength. In one example, the at least two LEDs include a first LED that illuminates the region with green light and a second LED that illuminates the region with infrared light. The contact PPG device may also include one or more photodetectors configured to detect extents of reflections from the region. In another example, the contact PPG device includes four light sources, which may be monochromatic (such as 625 nm, 740 nm, 850 nm, and 940 nm), and a CMOS or CCD image sensor (without a near-infrared filter, at least until 945 nm).

In other embodiments, the PPG sensor 841 may be a non-contact device. For example, the PPG sensor 841 may be a video camera configured to capture images of a region that includes skin on the user's head (e.g., images that include a region of the forehead, a cheek, and/or a temple). From these images, PPG signals may be extracted utilizing various techniques known in the art at described herein. In one example, the video camera is an inward-facing head-mounted video camera, such as an inward-facing camera coupled to a frame of smartglasses. Additional details about utilizing inward-facing cameras to obtain PPG signals, including possible locations of the cameras, properties of the cameras (e.g., weight, imaging resolution, use of radiation filters for certain spectrum interval, and/or utilization of emitters), as well as various approaches that may be used to process images are provided in in more detail in US Patent Application 2020/0397306, "Detecting fever and intoxication from images and temperatures", which is incorporated herein by reference.

Different types of temperature sensors may be used in embodiments described herein. In some examples, the temperature sensor 842 may be a contact temperature sensor, such as a sensor embedded in a nose piece of smartglasses, embedded in an earbud, or embedded in a patch attached to a region of the user's body. In other examples, the temperature sensor 842 may be a non-contact sensor, such as a thermal camera that takes measurements of a certain region on the user's face. In one example, the thermal camera may be configured to take a measurement of the temperature at a temple of the user. In another example, the thermal camera may be configured to take a measurement of the temperature at a periorbital region of the user. In yet another example, the thermal camera may be configured to take a measurement of the temperature at user's forehead.

The temperature of the user measured by the temperature sensor 842 may refer to different types of values. In one example, "the temperature of the user" is a temperature of the skin of the user at the area measured by the temperature sensor 842. In another example, "the temperature of the user" refers to a value of the user's core body temperature, which is estimated based on a measurement of the temperature sensor 842.

In some embodiments, estimating values based on measurements of the temperature sensor 842, such as estimating the core body temperature may involve utilization of measurements from additional sensors. For example, core body temperature may be estimated utilizing images of the user's face captured with a video camera and/or temperatures of the environment (e.g., obtained by the environment sensor 845). Utilizing these multiple sources of data is discussed in more detail in US Patent Application 2020/0397306, "Detecting fever and intoxication from images and temperatures", which is incorporated herein by reference. Additionally, in some embodiments, the wearable device 840 may include multiple temperature sensors, which may measure temperature at various locations on the user's face. For example, the multiple temperature sensors may be head-mounted sensors, such as temperature sensors embedded in frames of smartglasses, which take measurements of multiple regions on the user's head. Calculation of temperature values by aggregating measurements from multiple regions is discussed in more detail in US Patent Application 2021/0007607, "Monitoring blood sugar level with a comfortable head-mounted device", which is incorporated herein by reference.

The wearable device 840 may optionally include one or more acoustic sensors, such as the acoustic sensor 843, which are configured to take audio recordings of the user. In one example, the one or more acoustic sensors are mounted to a frame worn on the user's head, such as a frame of smartglasses, at fixed positions relative to the head of the user. The audio recordings of the user may include recordings of sounds produced by the user, such as sounds of respiration, coughing, speech, and the like. Indications of the user's respiration and/or extent of coughing may be signals utilized to calculate a health score of a user, as discussed below.

In one embodiment, the wearable device 840 includes the IMU 844. Optionally, the IMU 844 may be head-mounted, such as an IMU embedded in frames of smartglasses. Optionally, the IMU 844 measures a signal indicative of one or more of the following: movements of the user's body (e.g., due to walking, climbing stairs, etc.), movements of the head of user, an orientation of the head of the user with respect to the earth's gravity (i.e., an angle between the head's orientation and the direction in which gravity acts). It is to be noted that various patterns of movements of the user's head may be detected using approaches known in that art to detect activities (e.g., walking or running), as well as whether the user is coughing, talking, or breathing.

In another embodiment, the wearable device 840 includes the environment sensor 845. Optionally, the environment sensor 845 measures the temperature of the environment. Examples of possible embodiments for a sensor that measures the temperature of the environment include: (i) a non-contact temperature sensor, such as a thermopile or a microbolometer sensor, and (ii) a contact temperature sensor, such as a thermistor or a thermocouple. Additionally or alternatively, the environment sensor 845 may be a humidity sensor (hygrometer).

It is to be noted that references to the wearable device 840 being worn by a user may be interpreted as one or more wearable devices worn by said user. When the wearable device 840 refers to more than one wearable device, the aforementioned sensors need not be comprised in a single device. For example, the reference to the wearable device 840 may, in some examples, refer to a first device, e.g., a smartwatch with a contact PPG sensor, and a second device, e.g., a smart shirt with embedded temperature sensors. In other examples, such as the smartglasses illustrated in FIG. 2, various sensors are coupled to a single wearable device.

Figure 2:
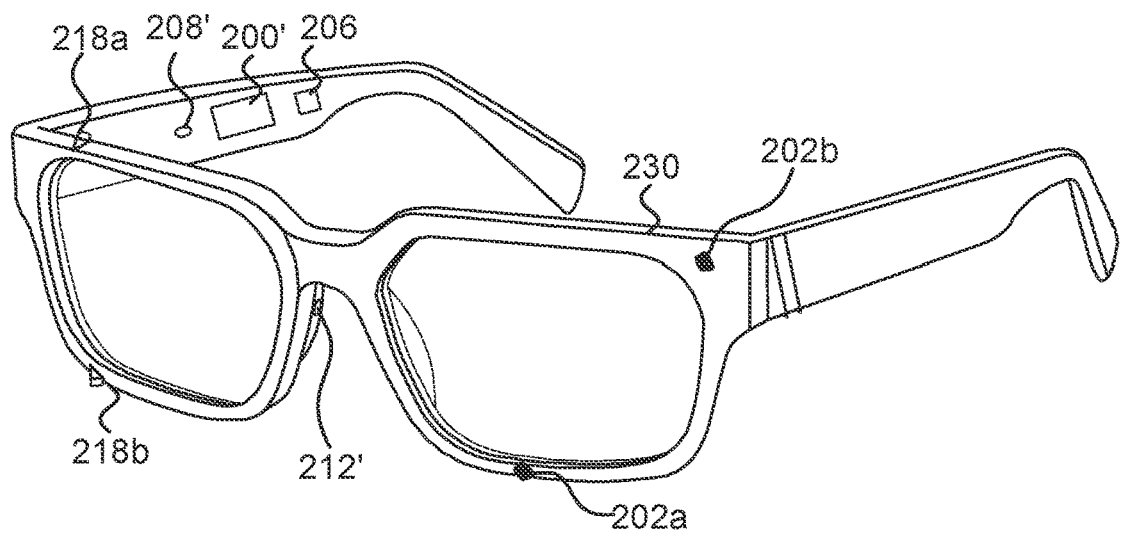
FIG. 2 illustrates an example of smartglasses that may be considered an embodiment of a wearable device that is utilized in some embodiments described herein.

FIG. 2 illustrates an example of smartglasses that may be considered an embodiment of the wearable device 840 that is utilized in some embodiments described herein. FIG. 2 illustrates just one possible embodiment of a combination of some of the components described in FIG. 1. The smartglasses include at least a frame 230, which is configured to be worn on a user's head, and several sensors configured to measure the user and/or the environment. Acoustic sensors 202a and 202b, which may be used to take audio recordings of the user, are mounted at fixed positions on the frame 230 (below and above the left lens, respectively). Contact PPG device 212' is located in the nose piece, and may be utilized to generate a PPG signal of the user, from which the heart rate of the user may be derived, as well as other blood flow-related parameters. Inward-facing cameras 218a and 218b are attached to the frame 230 at locations that are above and below the right lens, respectively. The inward-facing camera 218a is pointed upwards and configured to capture images of a region above the user's eyes (e.g., a portion of the forehead). The inward-facing camera 218b is pointed downwards and configured to capture images of a region below the user's eyes (e.g., a portion of a cheek). A non-contact thermal sensor 208' is coupled to a temple of the smartglasses, which is part of the frame 230, and is configured to measure temperature at a region on the user's face. Additional thermal sensors may be coupled to the frame 230 and be used to measure temperatures at different regions. Environment temperature sensor 210, which may also be a non-contact thermal sensor, is coupled to the frame 230 such that it is pointed away from the user's face in order to measure the temperature of the environment. Movement sensor 206 is also coupled to the frame 230 such that it measures the motion of the user's head. The computer 200' is coupled to the frame 230 and may perform at least some, and in some embodiments, all, of the operations attributed to some of the computers in this disclosure, such as the computer 847.

The computer 847 analyzes measurements taken by the wearable device 840 of the user wearing the wearable device 840, and optionally of the environment the user is in at the time. Optionally, this analysis may involve calculations with measurements taken at different times: (i) "current measurements", which are taken with the wearable device 840 during a period that starts a certain time before the analysis is performed (e.g., a few hours before that time) and/or leading up to when the analysis is performed, and (ii) "baseline measurements" taken with the wearable device 840 on one or more earlier days. Optionally, the current measurements are taken over a duration of at least five minutes. Optionally, the baseline measurements include more than an hour of measurements, taken over a period of several days.

In different embodiments, a reference to "the computer 847", or other computers described in this disclosure, may refer to different components and/or a combination of components. In some embodiments, the computer 847 may include a processor located on the wearable device 840. In some embodiments, at least some of the calculations attributed to the computer 847, and possibly all of those calculations, may be performed on a remote processor that is not on the wearable device 840, such as a processor on the user's smartphone and/or a cloud-based server. Thus, references to calculations being performed by the "computer 847" can also be interpreted as calculations being performed utilizing one or more computers, with some of these one or more computers being in the wearable device 840. Examples of computers that may be utilized to perform the calculations of one or more computers, which may be collectively referred to as "the computer 847", are computer 400 or computer 410, illustrated in FIG. XXA and FIG. XXB, respectively.

In one embodiment, analysis of the current measurements and the baseline measurements, which are taken by the wearable device 840, involves the computer 847 performing the following: calculating a health score based on a difference between the baseline measurements and the current measurements, and calculating an extent of similarity between characteristics of the PPG signal in the current measurements and characteristics of the PPG signal in the baseline measurements. These two values may then be used to determine whether the health of the user of whom the current measurements and baseline measurements were taken, permits passage through the doorway. Herein, characteristics of the PPG signal may be any information that is derived from multiple PPG waveforms in the PPG signal of the user (e.g., relationship between fiducial points), a pulse wave template, and/or other forms of templates of PPG signals known in the art.

The current measurements of a user are measurements that reflect the present state of the user, such as the state of the user during the hours leading up to an intended time of passage through the doorway and/or at that time. As such, the current measurements include measurements of the user taken with the wearable device 840 on that same day, and possibly up to the intended time of passage through the doorway. In one example, the current measurements include measurements taken with the wearable device 840 during a period spanning one hour before the intended time of passage through the doorway and/or the time the health score and the extent of similarity are calculated. In another example, the current measurements include measurements taken with the wearable device 840 sometime during a period spanning between 3 hours before the time the health score and the extent of similarity are calculated and the time these values are calculated.

The baseline measurements include measurements that reflect a typical state of the user on earlier days (i.e., the user's baseline state). As such, the baseline measurements include measurements of the user taken with the wearable device 840 on one or more days before the intended time of passage through the doorway. In one example, the baseline measurements include measurements taken at least a day before the current measurements were taken. In another example, the baseline measurements include measurements that were taken several days, weeks, and even months before the current measurements were taken.

In some embodiments, comparing the current measurements and the baseline measurements serves two purposes. First, differences between the current measurements and the baseline measurements are used to detect deviation from a baseline state that may be indicative of a change in the health state of the user (this is reflected in the calculated health score). Second, similarities between these sets of measurements, and in particular in characteristics of PPG signals in both sets of measurements, may be used to establish, with a certain degree of certainty, that the baseline measurements and the current measurements are of the same person. This form of biometric identification can help reduce the likelihood of mistakes and/or deceptive behavior that involves measuring a first user and then providing the wearable device 840 to a second user, who poses as the first user, in order to trick the system.

In one embodiment, following calculation of the aforementioned health score and the similarity between characteristics of the PPG signal in the current measurements and the characteristics of the PPG signal in the baseline measurements, these values are evaluated in order to determine whether the user should be allowed to pass through the doorway. Optionally, responsive to the health score reaching a first threshold and the extent of the similarity reaching a second threshold, the computer 847 transmits an authorization signal 848 that permits the passage of the user through the doorway. Optionally, the authorization signal 848 indicates that a health state of the user permits passage through the doorway.

It is to be noted that herein reference to a value "reaching a threshold" means the value is at least the threshold's value (i.e., a value that reaches a threshold is equal to the threshold or greater than the threshold).

"Health scores" of users may have different types of values, in different embodiments. However, generally speaking, a value of a health score of a user is indicative of the extent to which a user is healthy and/or non-contagious. Optionally, a health score may refer to an extent to which a user displays symptoms and/or is considered contagious with respect to a certain disease (e.g., the flu, COVID-19, or some other communicable disease). Alternatively, a health score may refer to an extent to which a user is considered healthy according to general wellness considerations that involve one or more of the user's vital signs (e.g., whether the core body temperature is elevated, blood oxygen saturation is in a normal range, etc.) In one example, health scores are binary values (e.g., sick/healthy, or contagious/non-contagious). In another example, a health score of a user may be a numerical value indicative of an extent to which a user is healthy and/or non-contagious (e.g., values on a scale of 1 to 10, where 1 is very sick and 10 is very healthy). In still another example, a health score of a user may a value indicative of a probability a user is healthy and/or non-contagious.

In some embodiments, having a health score that reaches the first threshold may mean that the user is not considered to be in a state that endangers others. For example, if the health score reaches the first threshold, the user may be considered non-contagious. Additionally or alternatively, having a health score that reaches the first threshold may mean that the user is considered healthy. Additional details regarding how the computer 847 may calculate health scores in different embodiments is provided further below.

Setting a value of the first threshold may be done in various ways. In one example, the threshold is set empirically based on health scores calculated for multiple people. The health status at the time measurements of these people were taken and/or their health status on the following day or two may also be known and monitored. The value of the first threshold is then selected to ensure that health scores of a desired proportion of the people who are known to be healthy and/or non-contagious is above the first threshold. Additionally or alternatively, the value of the first threshold may be selected to ensure that health scores of a desired proportion of the people who are known to be sick and/or contagious is below the first threshold.

The extent of similarity between characteristics of the PPG signal in the current measurements and characteristics of the PPG signal in the baseline measurements is indicative, in some embodiments, of a probability that the baseline measurements and the current measurements are measurements of the same person. In some embodiments, the extent of similarity is a value that describes a distance of the current measurements from a template derived from the baseline measurements. In other embodiments, the extent of similarity is a value calculated utilizing a machine learning-based model provided with feature values generated from the current measurements and the baseline measurements, and is indicative of a probability that the current measurements and the baseline measurements are of the same person. Additional details regarding how the computer 847 may calculate the extent of similarity in different embodiments is provided further below.

Having the extent of similarity between characteristics of the PPG signal in the current measurements and characteristics of the PPG signal in the baseline measurements reach the second threshold is indicative, in some embodiments, that a probability the current measurements and baseline measurements are of the same person are at least a certain predetermined probability. For example, the predetermined probability may be greater than 50%, greater than 75%, greater than 90%, greater than 95%, or greater than 99%.

Setting a value of the second threshold may be done in various ways. In one example, the second threshold may be arbitrarily set to a predetermined value (e.g., a certain level of similarity). In other examples, the second threshold may be arbitrarily set according to performance (e.g., values in a confusion matrix). In one example, this may be done by collecting current measurements and baseline measurements of multiple people, and then the extents of similarity are calculated for "matches" (current measurements and baseline measurements of the same person), and "mismatches" (current measurements of one person and baseline measurements of a different person). The value of the second threshold may then selected to ensure that a desired proportion of extents of similarities calculated in cases of matches is above the second threshold. Additionally or alternatively, the value of the second threshold may be selected to ensure that a desired proportion of extents of similarities calculated in cases of mismatches is below the second threshold.

In some embodiments, the baseline measurements used to calculate the health score of the user may be selected from a larger pool of measurements of the user, in such a way so that user was in a condition (while the selected baseline measurements were taken) that is similar to the condition the user is in when the current measurements are taken. Being in "a similar condition" may mean different things in different embodiments.

In one example, the computer 847 selects the baseline measurements such that a difference between the temperature in the environment, measured while the baseline measurements were taken with environment sensor 845, and a temperature in the environment, measured while the current measurements were taken, is below a predetermined threshold. Optionally, the predetermined threshold is below 7° C.

In another example, the computer 847 calculates, based on measurements of the IMU 844 that are part of the current measurements, a current level of physical activity that belongs to a set comprising: being stationary, and walking. The computer 847 selects the baseline measurements that were taken while the user's movements were indicative of a similar level of physical activity.

Transmitting the authorization signal 848 is intended to enable the user wearing the wearable device 840 to pass through the doorway. This may be done in different ways. In one embodiment, transmitting the authorization signal 848 involves sending a message to an access control system that adds an identifier of the user wearing the wearable device 840, and/or an identifier of the wearable device, to a list of users and/or wearable devices that are allowed passage through the doorway. In another embodiment, transmitting the authorization signal 848 causes the doorway to change its state in order to enable the user to enter (some examples of such embodiments involve the controller 849, discussed in more detail below). Optionally, this change in state is temporary and done in response to detecting the presence of the user and/or the wearable device 840 in the vicinity of the doorway.

Certain embodiments described herein limit the type of information that is transmitted in the authorization signal 848, enabling to preserve privacy along with providing an approach to curb the spread of disease. In some embodiments, transmission of the authorization signal 848 does not involve providing an indication of the identity of the user and/or does not involve authentication of said identity. For example, transmission of the authorization signal 848 may not involve sending the user's name, identification number, social security number, credit card number, or any other data that can be used to uniquely identify who the user is. In some embodiments, transmission of the authorization signal 848 does not involve providing an indication of the identity of the wearable device 840, such as a MAC address or a SIM card serial number (ICCID). Thus, in some embodiments, transmission of the authorization signal 848, even on multiple occasions, does not have to involve transmitting information that directly contributes to identification of the user and/or of the wearable device 840 (which can be used to identify a user who purchased the device and/or uses it on a regular basis).

Transmission of the authorization signal 848 may be done in different ways and/or when different conditions are met, in different embodiments. In some embodiments, the authorization signal 848 is transmitted once, which is sufficient to effect changes in the doorway that enable the user wearing the wearable device 840 to pass through the doorway. In other embodiments, the authorization signal 848 is transmitted when the wearable device 840 detects its location is in the vicinity of the doorway (e.g., based on GPS location, triangulation from Wi-Fi or cellular transmissions, and other similar detection methods). In still other embodiments, the authorization signal 848 may be sent in response of receiving a communication, e.g., from the controller 849, indicating a request for the transmission of the authorization signal 848.

Transmission of the authorization signal 848 may cease in response to detecting certain conditions, such as detecting that the wearable device 840 is not in the vicinity of the doorway, that the wearable device 840 has passed through the doorway, and/or that the wearable device 840 might have been removed from the user wearing it.

Encryption and security are important factors of some of the embodiments described herein. This involves protection from eavesdropping and abuse by external parties; for example, parties intending to steal information about the user wearing the wearable device 840 and/or copy an authorization signal and transmit it on another occasion. Encryption and security are also helpful in protecting from abuse by wearers of the wearable device 840, e.g., in order to falsify the health state and/or identity of the wearer of the wearable device 840. There are many approaches, algorithms, and types of hardware known in the art that may be used to secure the wearable device 840, the computer 847, and the integrity of communications between these components (which include the authorization signal 848 and optionally other communications too). The following are some limited examples of approaches that may be used. Various security measures known in the art, which may be utilized in some embodiments (including additional approaches not mentioned below) are described in references mentioned below.

In some embodiments, sensors on the wearable device 840, such as the PPG sensor 841, the temperature sensor 842, and/or other sensors may incorporate a hardware-based layer of security. For example, the data they send to other components of the wearable device 840 and/or the computer 847 involve a method of data masking, such as encryption using a chaotic stream cipher. An example of an implementation of such an approach for sensor-level encryption of temperature measurements is provided in Hedayatipour, et al. "A temperature sensing system with encrypted readout using analog circuits." 2019 *IEEE 62nd International Midwest Symposium on Circuits and Systems (MWSCAS)*. IEEE, 2019.

In some embodiments, when transmitting the authorization signal 848, the computer 847 utilizes one or more cryptographic approaches to encrypt the authorization signal 848 and/or authenticate the wearable device 840. In one example, the computer 847 may utilize a static token, which may be inaccessible to other hardware component unless the conditions for transmitting the authorization signal 848 are met. In another example, synchronous dynamic tokens may be used, e.g., involving a timer to rotate through various combinations produced by a cryptographic algorithm. In this example, both a component receiving the authorization signal 848 and the computer 847 possess synchronized clocks. In another example, asynchronous tokens may be generated by the computer 847 and used for the authorization signal 848 without the need for a synchronized clock, e.g., using an implementation of a one-time pad or a cryptographic algorithm. In yet another example, the authorization signal 848 may be transmitted via a challenge and response scheme. In this example, public key cryptography can be used to prove possession of a private key without revealing that key. An authentication server may encrypt a challenge (typically a random number, or at least data with some random parts) with a public key; the computer 847 proves it possesses a copy of the matching private key by providing the decrypted challenge.

In some embodiments, the computer 847 may utilize A Trusted Platform Module (TPM) to implement one or more of the various security measures described herein. For example, the TPM may include a unique RSA key burned into it, which is used for asymmetric encryption. Additionally, the TPM may be used to generate, store, and protect other keys used in the encryption and decryption process.

More details about measures known in the art that may be implemented in embodiments described herein, via hardware, software, and/or firmware, in order protect the fidelity of the authorization signal 848 and/or secure communications between sensors and the computer 847 and/or the computer 847 and other parties are described in the reference El-Hajj, et al. "A survey of internet of things (IoT) authentication schemes", Sensors 19.5 (2019): 1141, and Alaba, et al. "Internet of Things security: A survey." Journal of Network and Computer Applications 88 (2017): 10-28.

The controller 489 is configured to command an automatic door to open and/or unlock, permitting the passage through the doorway, responsive to receiving the authorization signal 848. The automatic door includes a barrier that restricts the passage through the doorway when the automatic door is in a closed and/or locked position. FIG. 1 illustrates two positions for an automatic door, being closed (846A) and being open (846B), for example, following transmission of the authorization signal 848.

In some embodiments, the controller 849 commands the automatic door to close and/or remain shut, thereby restricting the passage through the doorway, after detecting that the user has passed through the doorway and/or not receiving an additional transmission of the authorization signal 848 within a predetermined time. For example, each transmission of the authorization signal 848 opens the automatic door for a few seconds, and then the controller 849 commands it to shut (unless another authorization signal is transmitted). In some embodiments, the controller 849 may receive a signal indicating that the user has passed through the doorway (e.g., from the wearable device 840 or some other device), which triggers it to command the automatic door to shut and/or remain shut.

In addition to transmitting the authorization signal 848 that leads to opening of the automatic door, in some embodiments the computer 480 may also transmit a second signal responsive to the health score not reaching the first threshold and/or the extent of the similarity not reaching the second threshold. Optionally, upon receiving the second signal, the controller 849 commands the automatic door to close and/or remain shut, thereby restricting the passage through the doorway.

Figure 3:
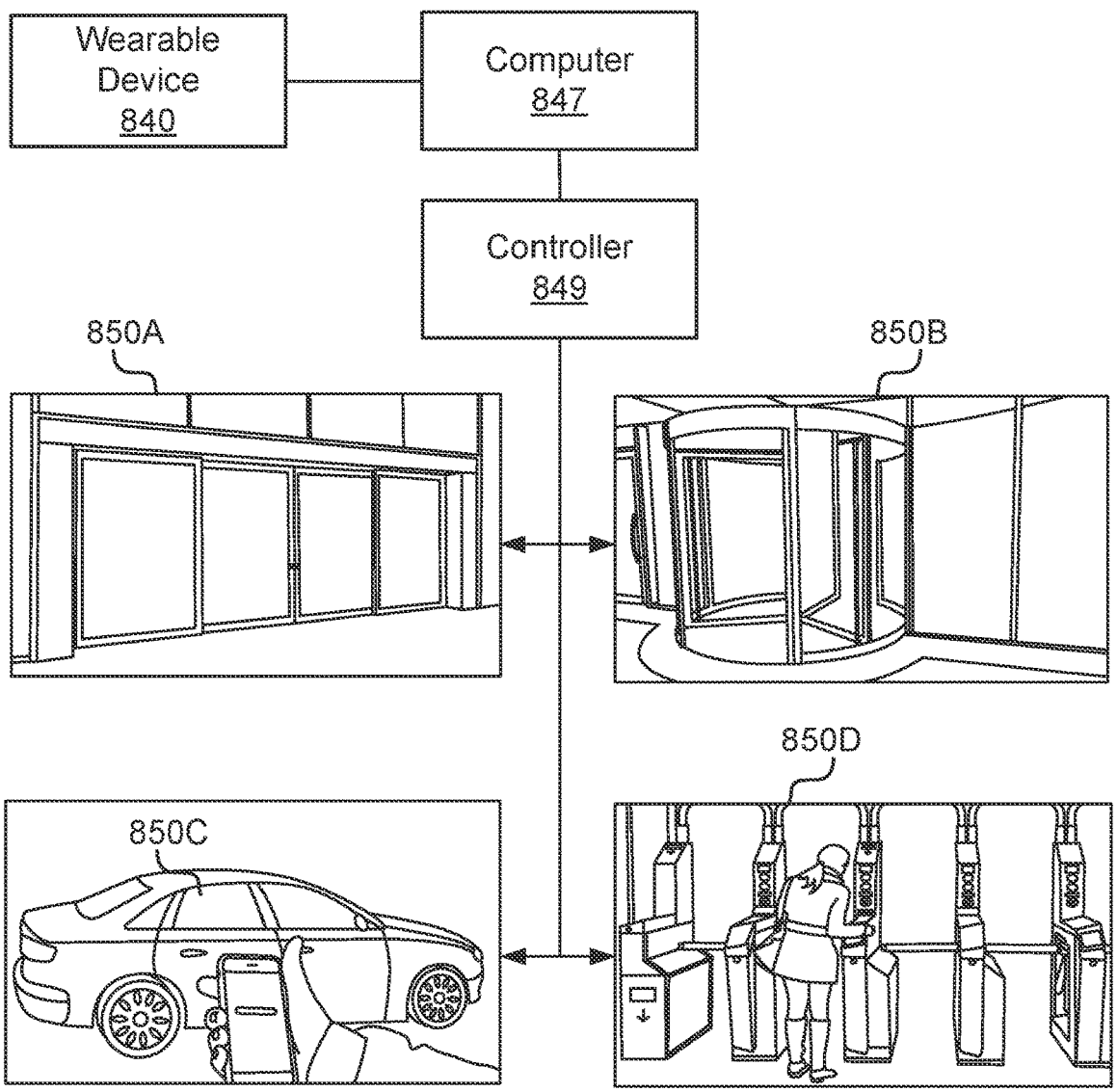
FIG. 3 illustrates examples of automatic doors.

There are various types of automatic doors that may be controlled by embodiments of systems described herein. Some examples of types of automatic doors are illustrated in FIG. 3.

In one embodiment, the automatic door is an entrance door to a room and/or building, and commanding the automatic door to open unlocks the door and/or moves the door to an open position, enabling the user to enter the interior of the room and/or building. For example, FIG. 3 illustrates two types of entrance doors to building that may controlled using embodiments of system described herein. Sliding door 850A may be opened and/or closed based on commands of the controller 849. Turnstile door 850B may commanded by the controller 849 to turn and/or enable the door to revolve when pushed. Similarly the controller 849 may command the turnstile door 850B to stop turning and/or resist effort to force it to revolve (e.g., the door may move to a locked position that can resist force applied in an effort to make the turnstile door 850B revolve).

In another embodiment, the automatic door belongs to a vehicle 850C, and commanding the automatic door to open unlocks the door and/or moves the door to an open position, enabling the user to enter the cabin of the vehicle.

In yet another embodiment, the automatic door is a gate 850D that includes a turnstile, and commanding the automatic door to open enables the turnstile to revolve and/or revolving the turnstile, enabling the user to pass through the gate.

The health score of the user (who is wearing the wearable device 840) may be calculated in different ways by the computer 847. In some embodiments, this calculation involves utilizing differences between the baseline measurements and the current measurements of the user to determine whether there is a deviation from an expected baseline of the user and/or whether the deviation is indicative that the user may be ill and/or contagious and thus, in order to curb the spread of disease, e.g., COVID-19 or the flu, the user should not be permitted to pass through the doorway and put other people at risk.

In some embodiments, calculation of the health score by the computer 847 involves calculating, based on the baseline measurements, an expected value of a physiological signal of the user. For example, the value of the physiological signal may be skin temperature, estimated core body temperature, blood oxygen saturation, heart rate, heart rate variability, extent of coughing, or blood pressure. Additionally, calculation of the health score by the computer 847 may involve calculating, based on the current measurements, a current value of the physiological signal (for which the expected value is calculated). Given these two values, the computer 847 can then set the value of the of the health score based on a difference between the expected value and the current value of the physiological signal.

In one embodiment, the physiological signal is body temperature, and calculating of the health score utilizes a function that returns a value that is below the first threshold when a current body temperature is greater than an expected body temperature by at least a certain margin. Optionally, the certain margin is at least 0.4° C. Thus, for example, if the user is 0.5° C. warmer than expected, the health score that is calculated in this embodiment is such that it falls below the first threshold.

In another embodiment, the physiological signal is blood oxygen saturation ($SpO_2$), and calculating of the health score utilizes a function that returns a value that is below the first threshold when a current $SpO_2$ is lower than an expected $SpO_2$ by at least a certain margin. Optionally, the certain margin is at least 0.03. Thus, for example, if the user's $SpO_2$ is lower by 0.04 than expected, the health score that is calculated in this embodiment is such that it falls below the first threshold. Additionally or alternatively, the health score may depend on a qualitative change in values of $SpO_2$. For example, if it is determined that a user's baseline state is to have an $SpO_2$ level that is always above a certain threshold (e.g., 0.92) and based on the current measurements, the $SpO_2$ falls below the certain threshold, that can lead to assignment of a health score that is below the first threshold.

It is to be noted that calculation of the health score may depend on differences between expected values and current values of more than one physiological signal. Thus, in examples below the calculation of the health score may be based differences between expected and current values of multiple physiological signals. For example, the health score may be a value that depends on a first difference between expected and current values of the user's temperature and a second difference between expected and current values of the user's blood oxygen saturation levels.

Calculation of the health score may be done in different ways, in different embodiments. In some embodiments, current values of one or more physiological signals and baseline values of the one or more of the physiological signals, and/or difference between these current and baseline values, are provided to a predetermined function that calculates the health score. Optionally, the predetermined function may be represented as a lookup table that provides values of health scores determined manually, e.g., by medical experts based on their experience. Optionally, parameters of the predetermined function may be determined by regression that uses outcome variables that are health scores that were manually determined based on medical records of users.

Calculating the baseline values and/or the expected values of physiological signals may involve utilization of machine learning-based approaches. In some embodiments, calculating a current value of the physiological signal may involve generating feature values based on the current measurements, and utilizing a model to calculate the current value of the physiological signal based on the feature values. Similarly, calculating a baseline value of the physiological signal may involve generating additional feature values based on the baseline measurements, and utilizing the model to calculate the baseline value of the physiological signal based on the additional feature values. Optionally, the model is generated from training data that includes: previous measurements of the user taken with the wearable device 840, and values of the physiological signal (considered "labels" or "outcome values") obtained utilizing a sensor that is not part of the wearable device 840. Additionally or alternatively, the model may be generated from training data that includes: previous measurements of other users taken with units of the same type as the wearable device 840, and values of the physiological signal (considered "labels" or "outcome values") obtained utilizing a sensor that is not part of the units of the same type as the wearable device 840.

In some embodiments, at least some feature values utilized to calculate values of one or more physiological signals (e.g., heart rate, heart rate variability, blood pressure, or respiration) are derived from a PPG signal measured utilizing the PPG sensor 841. To this end, various approaches may be employed, which are known in the art, in order to identify landmarks in a cardiac waveform (e.g., systolic peaks, diastolic peaks) may be employed, and/or extract various types of known values that may be derived from the cardiac waveform, as described in the following examples.

In one embodiment, at least some of the feature values generated based on the PPG signal may be indicative of waveform properties that include: systolic-upstroke time, diastolic time, and the time delay between the systolic and diastolic peaks, as described in Samria, Rohan, et al. "Non-invasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the PPG signal may be derived from another analysis approach of PPG waveforms, as described in US Patent Application US20180206733, entitled "Device, method and system for monitoring and management of changes in hemodynamic parameters". This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated, as suggested in the aforementioned publication, include: value of A, value of B, value of C, value of D, value of E, systol area that is the area under ABCE, diastol area that is the area under CDE, and the ratio between BC and DC.

In still another embodiment, various approaches described in Elgendi, M. (2012), "On the analysis of fingertip photoplethysmogram signals", Current cardiology reviews, 8(1), 14-25, may be used in order to generate at least some of the feature values based on the PPG signal.

Additional discussion regarding feature values related to PPG signals that may be extracted from images (e.g., when the PPG sensor 841 is a video camera) and their utilization for machine learning-related calculations, similar to the described above, are provided in U.S. Pat. No. 10,791,938, titled "Smartglasses for detecting congestive heart failure", which is incorporated herein by reference.

In some embodiments, at least some feature values utilized to calculate the values of one or more physiological signals are generated from measurements of the temperature of the user, taken with the temperature sensor 842. Additionally or alternatively, one or more of the feature values may be generated from measurements of the temperature of the environment in which the user was in at the time, as measured for example, by the environment sensor 845. In one embodiment, the feature values include a temperature value itself (e.g., a value measured by the temperature sensor 842 and/or a value measured by the environment sensor 845). Additionally or alternatively, the feature values may include a difference between the temperature and a previously taken temperature (e.g., a temperature taken 10 minutes before or one hour before). Additionally or alternatively, the feature values may include a difference between the temperature and a baseline temperature, which is determined based on the baseline measurement. In one example, the feature values include a value indicative of the difference between a temperature of the user, and the average temperature of the user, as measured by the temperature sensor 842 on multiple previous days. In another example, the feature values include a value indicative of the difference between temperature of the environment, and the average temperature measured in the environment on multiple previous days.

In some embodiments, in which the wearable device 840 includes a movement sensor (e.g., the IMU 844), one or more of the feature values may be generated by the computer 847 from a signal indicative of movements of the user. Optionally, these one or more feature values are indicative of extents of one or more of the following movements: movements of the user's body (e.g., due to walking, climbing stairs, etc.), movements of the head of user, an orientation of the head of the user with respect to the earth's gravity (i.e., an angle between the head's orientation and the direction in which gravity acts).

In some embodiments, in which the wearable device 840 includes one or acoustic sensors, such as the acoustic sensor 843, the computer 847 may generate at least some feature values utilized to calculate the values of one or more physiological signals, based on audio recordings of the user. Optionally, these generated feature values may be "raw" or minimally processed values, such as various acoustic features derived from the audio recordings, as described in are provided in U.S. Pat. No. 10,791,938, titled "Smartglasses for detecting congestive heart failure", which is incorporated herein by reference. Optionally, at least some of the feature values may include higher level, respiration parameters calculated from the audio recordings such as: breathing rate, respiration volume, an indication whether the user is breathing mainly through the mouth or through the nose, exhale (inhale) duration, post-exhale (post-inhale) breathing pause, a dominant nostril, a shape of the exhale stream, smoothness of the exhale stream, and/or temperature of the exhale stream. Various algorithmic approaches may be utilized to extract parameters related to respiration from an acoustic signal. Some examples of possible approaches are provided in (i) Pramono, Renard Xaviero Adhi, Stuart Bowyer, and Esther Rodriguez-Villegas. "Automatic adventitious respiratory sound analysis: A systematic review." PloS one 12.5 (2017): e0177926, and (ii) US patent Application No. 2019/0029563, titled "Methods and apparatus for detecting breathing patterns". Optionally, at least some of the feature values generated based on the audio recordings may be indicative of the extent of behavior such as coughing and wheezing, as described in more detail in U.S. Pat. No. 10,813,559, titled "Detecting respiratory tract infection based on changes in coughing sounds", which is incorporated herein by reference.

In one non-limiting example, feature values generated by the computer 847 in order to calculate values of one or more physiological signals include: intensities of fiducial points (systolic peaks and systolic notches) identified in PPG signals extracted from measurements taken by the PPG sensor 841. Additionally the feature values generated by the computer 847 in order to calculate values of one or more physiological signals include: temperatures of the user measured by the temperature sensor 842 and temperatures of the environment measured by the environment sensor 845. In another non-limiting example, feature values generated by the computer 847 in order to calculate values of one or more physiological signals include values obtained by binning according to filterbank energy coefficients, using MFCC transform on results of FFT of audio recordings recorded by the acoustic sensor 843.

Calculation of the health score by the computer 847 may involve, in some embodiments, utilization of various machine learning methods. In some embodiments, the computer 847 generates feature values based on data comprising the current measurements and the baseline measurements, which are taken by the wearable device 840, as described above. The computer 847 can then utilize a model (also referred herein as the "health score model") to calculate, based on the feature values, the health score. Optionally, the health score model may be generated based on data of multiple users, which is collected under different conditions. In one example, the health score model is generated based on training data comprising a first set of training measurements of a plurality of users taken with wearable devices such as the wearable device 840 while the plurality of users were healthy and a second set of training measurements of the plurality of users, taken with the wearable devices, while the plurality of users were not healthy.

The data collected from the multiple users, which is used to generate the health score model, may include measurements taken at different times, while the multiple users were in various conditions of health. Optionally, for each certain user, from among the multiple users, the training data included certain first and second measurements taken with a wearable device like the wearable device 840, while the certain user had certain first and second known extents of health and/or risks of being contagious, respectively. Thus, the training data reflects measurements in which there is a known change in the state of the health, for the multiple users. Optionally, data of the multiple users is used to create samples, where each sample includes feature values generated based on measurements of a certain user and a label which is indicative of the health score that is to be assigned to the user at the time. For example, labels may be set by a physician who checked the certain user, self-reported by the certain user, and/or derived from medical records of the certain user. Optionally, the samples are generated based on measurements collected in diverse conditions (on different times of day, different locations, different environmental conditions, etc.)

Various computational approaches may be utilized to train the health score model based on the samples described above. In one example, training the model may also involve selecting the first threshold based on the samples. Optionally, a machine learning-based training algorithm known in the art may be utilized to train the model based on the samples. Optionally, the health score model includes parameters of at least one of the following types of models: a regression model, a neural network, a nearest neighbor model, a support vector machine, a support vector machine for regression, a naïve Bayes model, a Bayes network, and a decision tree.

The computer 847 may generate various types of features based on the data it receives from the wearable device 840, such as the current measurements and baseline measurements. Additionally, some of the feature values may be generated based on the additional sources of data, such as additional sensors on the wearable device 840 or sensors that are not on the wearable device 840.

In some embodiments, feature values utilized to calculate the health score include one or more of the following values: a value of a physiological signal of the user calculated based on the current measurements, a value of the physiological signal of the user calculated based on the baseline measurements, and a value indicative of a difference between the value of the physiological signal of the user calculated based on the current measurements and the value of the physiological signal of the user calculated based on the baseline measurements. Optionally, the physiological signal may be a value from among: skin temperature, estimated core body temperature, blood oxygen saturation, heart rate, heart rate variability, respiration rate, extent of coughing, or blood pressure. Optionally, the computer 847 may utilize machine learning-based approaches, as described above, to calculate the values of the physiological signal from the current and/or baseline measurements. In some embodiments, at least some of the feature values utilized to calculate the health score may maybe one or more of the various types of features values described herein (further above) as being utilized to calculate values of physiological signals from measurements taken by the wearable device 840.

Utilizing the various feature values described above can enable representation of changes to the physiological state of the user between a baseline state and the user's current state, which can assist in determining whether the user is healthy and/or non-contagious at the present time In one non-limiting example, feature values generated by the computer 847 based on the current measurements and the baseline measurements in order to calculate the health score of the user include: a baseline temperature of the user, a current temperature of the user, a baseline blood oxygen saturation level, and a current blood oxygen saturation level. Optionally, these values may be calculated using machine-learning based approaches, as already described further above.

In another non-limiting example, feature values generated by the computer 847 based on the current measurements and the baseline measurements in order to calculate the health score of the user include: a baseline extent of coughing and a current extent of coughing. Optionally, these values may be calculated based on recordings of the user with the acoustic sensor 843 and/or measurements of movements of the user, as measured with the IMU 844.

In another non-limiting example, feature values generated by the computer 847 in order to calculate the health score of the user include temperatures in the environment at different times, as measured with the environment sensor 845.

Utilization of PPG signals for biometric authentication is known in the art. In some embodiments, the computer 847 may employ one or more of the techniques described below in order to calculate the extent of the similarity between the characteristics of the PPG signal in the current measurements and the characteristics of the PPG signal in the baseline measurements.

When the similarity between the characteristics of the PPG signal in the current measurements and the characteristics of the PPG signal in the baseline measurements reaches the second threshold, this means that with a least with a certain probability, the current measurements and the baseline measurement are of the same person. This can be considered some form of authentication of the user. This form of authentication does not require providing information identifying who the person is. "Authentication", as the term is typically used in the art in the context of PPG-based biometric authentication, involves comparison with templates of PPG signals in a database. For example, when current measurements are compared to a template in a database that includes multiple users along with their identifiers, this can be considered a form of authentication (since the system then knows which of the users was matched).

Some embodiments described herein do not involve utilization of information that identifies the user being authenticated, and the process of comparing their PPG signals to previous measurements of PPG signals may not be referred to with the specific term "authentication". Nonetheless, various teachings in the art for authenticating users based on PPG signals can be used in embodiments described herein by a simple adaptation. For example, instead of comparing a PPG signal in the current measurements to PPG signals and/or templates stored in a database, the PPG signal in the current measurements can be compared to a previously measured PPG signal from the baseline measurements (which may be stored locally, e.g., on the wearable device 840 and/or in a user's own account). This process may not necessarily involve disclosure of the identity of the user, but nonetheless can utilize the same computational techniques known in the art for authenticating users based on PPG signals.

In one embodiment, the computer 847 may utilize one or more procedures of that are part of an implementation of the teachings provided in Yadav, et al., "Evaluation of PPG biometrics for authentication in different states." 2018 International Conference on Biometrics (ICB). IEEE, 2018, which is incorporated herein by reference. Yadav et al. describe computational procedures in which PPG signals can be used for user authentication by employing a combination of Continuous Wavelet Transform (CWT) and Direct Linear Discriminant Analysis (DLDA), which is demonstrated to have robustness under different conditions involving different emotions (e.g., stress), physical exercise and time-lapse. Optionally, the computer 847 may utilize one or more of the pre-processing techniques described therein (filtering, peak detection, false peak removal, and segmentation). Optionally, the computer 847 may generate a baseline template from the PPG signal in the baseline measurements and a current template from the PPG signal in the current measurements utilizing the template generation approach described therein (CWT-based feature extraction and LDA-based dimensionality reduction). Optionally, calculating the extent of similarity between the characteristics of the PPG signal in the baseline measurements and the characteristics of the PPG signal in the current measurements may then be done by calculating the Pearson distance between vectors generated from the current and baseline templates, as described therein.

In another embodiment, the computer 847 may utilize one or more procedures of that are part of an implementation of the teachings provided in Sancho, et al., "Biometric authentication using the PPG: A long-term feasibility study." Sensors 18.5 (2018): 1525, which is incorporated herein by reference. Sancho et al. perform a comparative study of various computational approaches that may be used for PPG-based biometric authentication. Optionally, the computer 847 may utilize one or more of the pre-processing techniques described therein (filtering, PPG cycle detection, cycle normalization and alignment). Optionally, the computer 847 may generate a baseline template from the PPG signal in the baseline measurements and a current template from the PPG signal in the current measurements utilizing one of the template generation approaches described therein that are based on various feature extraction procedures (Cycles Average, KLT Average, Multi-Cycles, KLT Multi-Cycles). Optionally, calculating the extent of similarity between the characteristics of the PPG signal in the baseline measurements and the characteristics of the PPG signal in the current measurements may then be done utilizing one or more of the matching techniques described therein (e.g., Manhattan distance or Euclidian distance between the templates).

In some embodiments, user authentication based on the current and baseline measurements (or determining that these measurements are of the same person) may done using additional signals measured by sensors on the wearable device 840. In one example, voice analysis of recordings taken by the acoustic sensor 843 may be analyzed to determine that similar acoustic spectral properties appear in both sets of measurements. In another example, gait characteristics of movements measured by the IMU 844 may be compared to determine whether the person wearing the wearable device 840 while the baseline measurements and the current measurements were measured are similar.

In some embodiments, it may be desirable to ensure that following collection of the current measurements and/or transmission of the authorization signal 848, the person wearing the wearable device 840 does not remove it (e.g., in order to let someone else wear it an gain passage through the doorway). This is especially important in embodiments in which the authorization signal 848 does not include information that identifies the person wearing the wearable device 848. In these embodiments, the authorization signal 848 in essence attests that the person wearing the device is healthy and thus should be allowed through the doorway, thus it is important that that assumption still be true during passage through the doorway, otherwise the integrity of the doorway, and its ability to curb the spread of disease may be compromised.

Therefore, in some embodiments, the computer 847 determines, based on measurements taken with the wearable device 840, whether the wearable device was removed from the user's body while the current measurements were taken or after the current measurements were taken, and responsive to making a determination that the wearable device 840 has been removed, the computer 847 refrains from transmitting the authorization signal 848 and/or transmits an additional signal that makes other components (e.g., the controller 489) ignore the authorization signal 848, if it has already been sent.

In one embodiment, the computer 847 identifies when the wearable device 840 has been removed from the user wearing it based on detecting an interference in the amplitude of the PPG signal and/or phase shift of detected reflected light measured by the PPG sensor 841 that exceeds a certain threshold. Large interferences in measured PPG signals often occur when a PPG sensor's contact with the body is weakened or broken (such as when the wearable device 840 is removed). These interferences occur because ambient light and interferences of ambient light are much stronger than the signal detected when the PPG sensor is attached to the body (for contact PPG sensors). Video camera-based PPG sensors (e.g., used for iPPG) will also experience dramatic signal changes when the device is removed because, for a certain period, the images captured by video camera will have completely different color schemes. Thus, virtually any removal of the PPG sensor 841 from the body causes a large interference in the measured PPG signal which is typically not observed when the device housing the PPG sensor is firmly in place.

In another embodiment, the computer 847 identifies when the wearable device 840 is removed from the user wearing it based on detecting a rapid change in temperatures measured by the temperature sensor 842. Physiological body temperature (e.g., core body temperature and skin temperature) typically change at a slow pace, and do not have sudden changes of values such as decreases of several degrees within a few seconds. However, if the wearable device 840 is removed from the body, the temperature sensor 842 is likely to measure the environment and/or other regions of the body, at least for a short period (e.g., until the wearable device 840 is worn again by a person). Nonetheless, such a removal typically generates a spike in temperature that exceeds a predetermined threshold characteristic of temperature changes observed when the wearable device 840 is firmly in place.

Removal of the wearable device 840, whether done intentionally or accidentally, makes the current measurements non-trustworthy, since it is possible that some other person has put on the wearable device 840, in order to take advantage of the health score that has already been calculated with it. In order to be able to transmit the authorization signal 848 again, the computer 847 needs to re-establish that the same person who previously wore the wearable device 840 is wearing it again. Thus, in some embodiments, the computer 847 performs the following steps responsive to making the determination that the wearable device 840 has been removed. The computer 847 receives additional measurements of the user, taken by the wearable device 840 at most three hours after the current measurements were taken. The computer 847 then calculates an additional similarity between characteristics of the PPG signal in the current measurements and characteristics of the PPG signal in the additional measurements. If the additional similarity reaches the second threshold (and the previously calculated health score reaches the first threshold), the computer 847 transmits the authorization signal 848. Optionally, the additional similarity reaching the second threshold is indicative of a probability that the current measurements and the additional measurements are of the same person is above a predetermined threshold. It is to be noted that such a reauthorization may be done, in some embodiments, in a short period and not require extensive collection of additional measurements. In one example, the additional measurements are collected for less than one minute. In another example, the additional measurements are collected for less than 15 seconds.

In some embodiments, the computer 847 may report to the user the calculated health score. Since this is sensitive information, it may be prudent to determine that the person receiving this information is indeed the user. To this ends, the computer 847 may receive additional measurements of the user, taken with the wearable device 840, and then calculate an additional extent of similarity between characteristics of the PPG signal in the additional measurements and characteristics of the PPG signal in the baseline measurements. The computer 847 also calculates an additional health score based on a difference between the baseline measurements and the additional measurements. If the extent of similarity reaches the second threshold, the computer 847 may report the additional health score to the user and/or provide the user with an indication of whether the health state of the user permits passage through the doorway.

Curbing the spread of airborne communicable diseases, such as COVID-19 or the flu, is often done with extreme measures, such as restrictions on peoples' movements, closing places of business, and blanket orders for quarantines. The reason such extreme measures are often used is that it is difficult to determine, on a population-wide scale, who are the symptomatic people who pose a risk of spreading the communicable disease (and limit restrictions to those people). Thus, for practical reasons, often whole populations are treated as if they all pose a risk, and are subject to many restrictions, even though the majority of these people are not symptomatic and cannot spread the disease.

Thus, there is a need for a way to ease restrictions imposed on travel and commerce that will enable healthy and non-symptomatic people the opportunity to congregate or commute in a safe manner that greatly reduces the risk of contracting an airborne communicable disease.

One aspect of this disclosure involves utilization of wearable devices to facilitate the making of reservations for places in spaces shared with other people. (e.g., a reservation at a restaurant, reserving a seat in public transportation, etc.). Since the space is shared by others, it can be very beneficial to make sure that all the people in the shared space are healthy and/or non-contagious in order to curb the spread of disease. In some embodiments described herein, the wearable devices are utilized to determine whether the person making a reservation is likely to be healthy and/or non-contagious, and also whether the person showing up to make use of the reservation is the same person who originally made the reservation.

Wearable-based health state verification, which can be provided by systems such as embodiments illustrated in FIG. 1, can pave the way to novel applications that involve incorporating measures intended to curb the spread of disease into well-established practices. One such scenario involves making reservations that reserve a place for a user in a space that is shared with other users (e.g., a reservation at a restaurant, reserving a seat in public transportation, etc.). Since the space is shared by others, it can be very beneficial to make sure that all the people in the shared space are healthy and/or non-contagious in order to curb the spread of disease. The following embodiments demonstrate how wearable devices can be used to provide health-state verifications in order to make reservations in a safer more efficient way. In some embodiments, the fact the wearable devices can both determine a user's health state and ensure that the user whose health state is verified is the one wearing the wearable device, can be leveraged in order to manage reservations in a manner that does not compromise user privacy.

Figure 4:
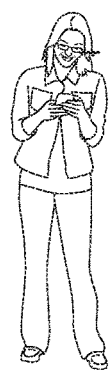
FIG. 4 illustrates components of an embodiment of a system configured to manage access using reservations and wearable-based health state verifications.
Figure 4:
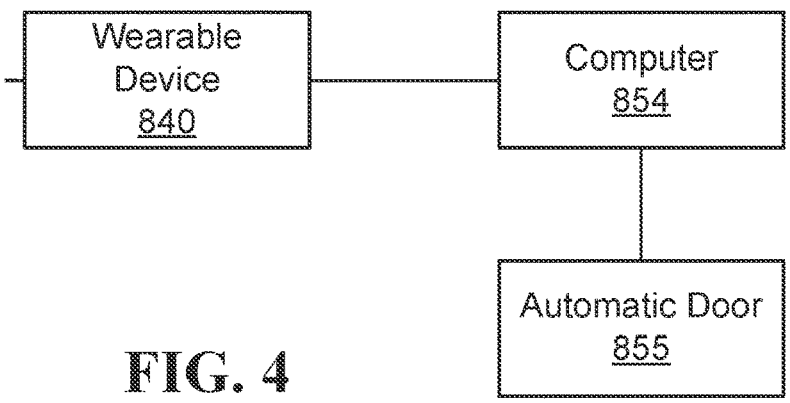
Figure 5:
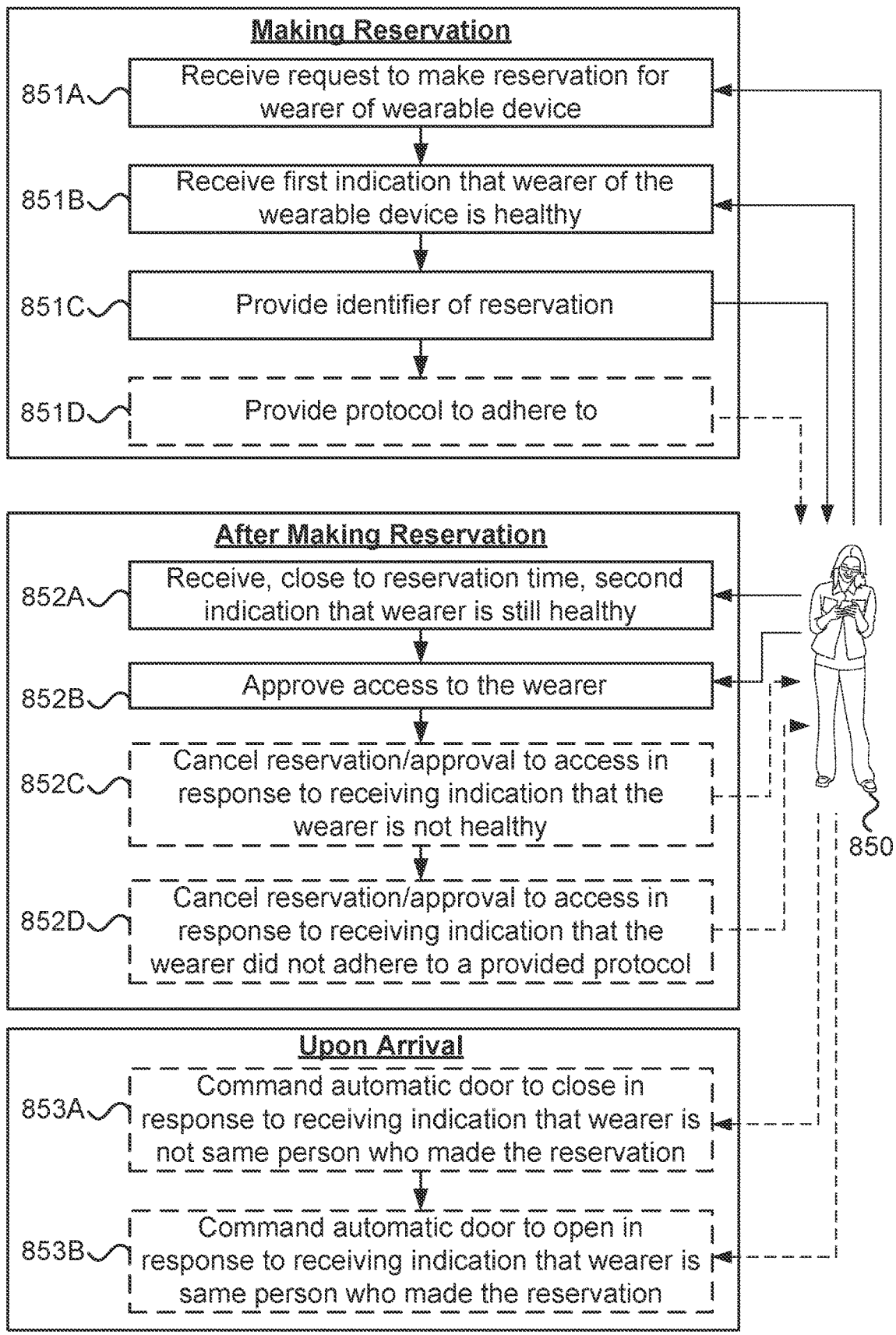
FIG. 5 illustrates steps that may be part of embodiments of a method for managing reservations with wearable-based health state verifications.

FIG. 5 illustrates steps that may be part of embodiments of a method for managing reservations with wearable-based health state verifications. The method may be implemented using embodiments of systems illustrated in FIG. 4, which is discussed further below. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 5 and/or additional steps mentioned below. Conceptually, the steps of the method may be divided into certain steps that are performed while making a reservation, and additional steps that are performed after the reservation is made and/or upon arrival of a user to the venue for which the reservation was made.

Embodiments of the method illustrated in FIG. 5 include several steps involved in making a reservation:

In Step 851A, receiving (e.g., by a computer 854, which is discussed below), a request to make a reservation that involves occupying a place in a space shared with other people. Optionally, the request is made by the wearer of a wearable device that is used to take measurements of a user (e.g., user 850, illustrated in FIG. 4).

In Step 851B, receiving a first indication generated based on first measurements taken during a first period by the wearable device. The first measurements include values of physiological signals of the wearer of the wearable device during the first period, and the first indication indicates said wearer is healthy. Optionally, the first indication does not include information identifying the wearer of the wearable device. Optionally, the first measurements are taken over a duration of at least five minutes. Optionally, the first measurements are taken at least an hour before a time for which the reservation is made. Optionally, the first measurements are taken while the user 850 is not in the vicinity of the space that is to be shared with other people.

In one embodiment, the method includes an optional step of providing an interface through which the request to make the reservation is entered in response to receiving the first indication. This way, reservations are only placed by people who are healthy, which can save time and/or avoid disappointment due to filling out details of a reservation only to shortly thereafter learn that the reservation cannot be made due to there not being a required indication of the state of health.

And In Step 851C, the method includes a step of providing an identifier of the reservation, which reserves the place at a certain time for the wearer of the wearable device during the first period. Optionally, neither the reservation nor the identifier of the reservation include information that identifies the person for whom the reservation is made (i.e., the person wearing the wearable device). For example, the identifier may include a certain code that is not easy to guess or forge, and thus only the maker of the reservation is like to be able to produce the code if requested.

In some embodiments, the first measurements include a signal indicative of a PPG signal of the wearer of the wearable device and a temperature of the wearer of the wearable device. Optionally, the wearable device used to provide the first measurements received in Step 851B is the wearable device 840 that includes PPG sensor 841 and temperature sensor 842, which provide the aforementioned PPG signal and temperature of the wearer of the wearable device.

In some embodiments, the first indication is generated by a certain computer, such as the computer 847, by calculating a value indicative of the health state of the wearer of the wearable device that is based on the first measurements. Optionally, the certain computer may utilize one or more of the approaches described above, with respect to the calculation of the health score of a user by the computer 847. In one example, the value indicative of the health state of the wearer of the wearable device is calculated by a function that evaluates the first measurements and compares them to certain thresholds. For example, if the temperature is below 37.5° C. and the blood oxygen saturation is above 0.92, that person is considered healthy. In another example, the certain computer may utilize one or more the machine learning approaches described with respect to calculation of the health score by the computer 847, such as generating feature values based on the first measurements and utilizing a model to calculate, based on the feature values, a value that indicates whether the wearer of the wearable device is healthy and/or non-contagious (which is used to decide whether to send the first indication).

In other embodiments, the first indication is the authorization signal 848 and/or the first indication is sent based on the same criteria that would lead to sending the authorization signal 848, by the computer 847. Optionally, the first indication is sent by the computer 847 following calculation of a health score for the wearer of the wearable device, which reaches the first threshold and calculation of similarity of PPG signals that reaches the second threshold. In this case, the first measurements may be considered the "current measurements" mentioned with respect to embodiments illustrated in FIG. 1. To calculate the health score and the similarity of PPG signals, the first measurements are compared to baseline measurements, taken at earlier times by the wearable device, as described above in the discussion regarding embodiments illustrated in FIG. 1.

Various types of reservations may be made with the method illustrated in FIG. 5. In one example, the reservation may involve reserving a vehicle, whose cabin space is shared with a driver and/or other vehicles. Optionally, the certain time of the reservation corresponds to an expected arrival time of the vehicle. In another example, the reservation involves reserving a place at the certain time in a building housing an eating establishment and/or entertainment complex, which may be shared by multiple patrons. Optionally, the reservation is indicative of a certain seat reserved for the wearer of the wearable device. In yet another example, the reservation is for a seat in one or more of the following: a public transport vehicle, a passenger train car, an aircraft, and a ferry. Optionally, the reservation is indicative of a certain seat reserved for the wearer of the wearable device.

Embodiments of the method illustrated in FIG. 5 include additional steps that may take place some time after the reservation is made:

In Step 582A, receiving a second indication generated based on second measurements taken by the wearable device during a second period that is after the first period. Optionally, the second measurements include values of physiological signals of the wearer of the wearable device during the second period. Optionally, the second indication indicates: (i) the wearer of the wearable device during the second period is the same person who wore the wearable device during the first period, and (ii) that same person is still healthy. Optionally, the second indication does not include information the identifies the wearer of the wearable device during the first and/or second periods.

And in Step 852B, approving access to the space to the wearer of the wearable device.

Approving the access may be done in various ways. In one example, after receiving the second indication the wearable device may be sent an access code enabling entrance to the space. In another example, after receiving the second indication, the wearable device may transmit information identifying the wearer of the wearable device, which may be utilized to grant the wearer to access to the space. In this example, identifying information of the wearer of the wearable device is only provided if the wearer is healthy and about to make use of the reservation. No identifying information is provided if the wearer of the wearable device does not want to keep the reservation, or if it turns out that the wearer is not healthy.

The second period takes place near the time of the reservation. Thus, the second measurements can reflect the health status of the wearer of the wearable device at the certain time for which the reservation is made. In one example, the second period ends less than three hours before the certain time (to which the reservation corresponds). In another example, the second period ends less than five minutes before the certain time. In yet another example, the second period overlaps with an arrival time of the wearer of the wearable device at a venue of the reservations (i.e., in vicinity of the shared space that is to be shared with other people).

The second indication is similar in its nature to the first indication, and thus, can involve using similar computational approaches used to generate the first indication that is received in Step 851B. For example, determining that the wearer of the wearable device is still healthy can be done by calculating a second value indicative of the health state of the wearer of the wearable device that is based on the second measurements. In the case that the computational approach involves calculation of a health score based on differences between current measurements and baseline measurements, the second measurements may be used as the "current measurements" for the purpose of calculation of the health score.

The second indication also indicates that the wearer of the wearable device during the second period is the same person who wore the wearable device during the first period. Optionally, this fact is determined by calculating an extent of similarity between characteristics of the PPG signal in the second measurements and characteristics of the PPG signal in the first measurements. Optionally, this extent of similarity is compared with the second threshold, and if it reaches it, a determination is made that the first measurements and second measurements are of the same person.

Embodiments of the method illustrated in FIG. 5 may optionally include additional steps that may take place upon arrival to a venue of the reservation (i.e., arrival in the vicinity of the space that is to be shared with others). Optionally, these steps involve operating an automatic door the facilitates access to the space.

In one embodiment, the method optionally includes step 853A, which involves commanding an automatic door that facilitates passage into the space to open and/or remain open, responsive to receiving an indication that the wearable device is in a vicinity of the automatic door and that the wearer of the wearable device at that time is the same person as the wearer of the wearable device during the first period. Optionally, the indication is generated by receiving transmissions from the wearable device that can be detected only when the wearable device is near (e.g., up to 10 meters) from the automatic door. Additionally or alternatively, multiple receivers near the automatic door may be utilized to triangulate transmission of the wearable device and determine its location. Optionally, determining that the wearer of the wearable device at that time is the same person as the wearer of the wearable device during the first period may done by calculating an extent of similarity of characteristics of PPG signal in measurements taken when the wearer is near the automatic door with characteristics of PPG signals in the first measurements, and observing that the extent of similarity reaches the second threshold.

In another embodiment, the method optionally includes step 853B, which involves commanding an automatic door that facilitates passage into the space to close and/or remain shut, thus restricting passage into the space, responsive to receiving an indication indicating that the wearable device is in a vicinity of the automatic door and that the wearer of the wearable device at that time is not the same person as the wearer of the wearable device during the first period.

Optionally, determining that the wearer of the wearable device at that time is not the same person as the wearer of the wearable device during the first period may done by calculating an extent of similarity of characteristics of PPG signals in measurements taken when the wearer is near the automatic door with characteristics of PPG signals in the first measurements, and observing that the extent of similarity does not reach the second threshold.

In some embodiments, the method may optionally include Step 851D that involves providing a description of a protocol for behavior that is to be adhered to (by the wearer of the wearable device and/or the wearable device itself) in order to preserve the reservation. Optionally, the description describes at least one of the following: restrictions involving locations in which to remain, locations to avoid, instructions pertaining to removal of the wearable device (e.g., prohibiting the removal of the wearable device), and instructions pertaining to extent of measurements that need to be provided with the wearable device (e.g., frequency and/or duration of measurements that should be taken using the wearable device). Optionally, the method may include a step that involves canceling the reservation and/or revoking an approval of access to the space given to the wearer of the wearable device during the first period, responsive to receiving an indication indicating that the wearer of the wearable device did not adhere to the protocol. For example, if it is detected from transmissions of the wearable device that the wearer went into a forbidden area and/or that at least a certain extent of measurements were not taken, then the reservation may be canceled.

In some embodiments, the integrity of managing reservations by verifying health states, as described above, relies on the fact that reservations should be kept for users who are healthy and for whom this state is verifiable. If a user is not healthy and/or if this fact cannot be verified, the user's reservation should be canceled. Thus, in some embodiments, the method me optionally include Step 852C, which involves canceling the reservation and/or revoking an approval of access to the space given to the wearer of the wearable device during the first period, responsive to receiving an indication that said wearer is no longer healthy. Optionally, this indication may be sent automatically by the computer 847 as part of a protocol according to which the wearable device and/or the computer 847 are to adhere.

In some embodiments, the integrity of managing reservations by verifying health states, as described above, relies on the fact that reservations should only be honored for users who made them. For example, it is undesirable for it to be possible for one person, who is healthy, to make a reservation and then give the wearable device used to make the reservation to another person, whose health state has not been verified, in order for that person to gain access to shared space. Thus, in some embodiments, the method optionally includes Step 852D, which involves canceling the reservation and/or revoking an approval of access to the space given to the wearer of the wearable device during the first period responsive to receiving an indication indicating the wearable device has been removed from said wearer. Optionally, this indication may be sent automatically by the computer 847.

FIG. 4 illustrates components of an embodiment of a system configured to manage access using reservations and wearable-based health state verifications. The system include the wearable device 840, which includes at least: a first sensor (the PPG sensor 841) that measures a signal indicative of a photoplethysmogram signal (PPG signal) of a wearer of the wearable device 840, and a second sensor (temperature sensor 842) that measures a temperature of said wearer. The system also includes a computer 854, and optionally, an automatic door 855.

The computer 854 manages the process of making and managing reservations, and in this process communicates with the wearable device 840 and/or a computer that sends indications on behalf of the wearable device 840 (and/or on behalf of the wearer of the wearable device 840), such as the computer 847.

In one embodiment, the computer 854 receives a request to make a reservation that involves occupying a place in a space shared with other people. For example, the request may be transmitted from a device used by a user wearing the wearable device 840, a computer that is in communication with the wearable device 840, such as the computer 847 (which may optionally be part of the wearable device 840), or some other computer. Additionally, the computer 854 receives a first indication generated based on first measurements taken during a first period by the wearable device 840. In one example, the first period ends at most three hours before the first indication is generated. Optionally, the first indication is generated by the computer 847 and it indicates that the wearer of the wearable device 840 is healthy. In response to receiving the first indication, the computer 854 provides an identifier of the reservation, which reserves the place at a certain time for the wearer of the wearable device 840 during the first period.

At a later time, which is closes to the certain time of the reservation, the computer 854 receives a second indication generated based on second measurements taken by the wearable device 840 during a second period that is after the first period. Optionally, at least some of the second measurements are taken less than three hours before the certain time, and the second indication indicates: (i) the wearer of the wearable device during the second period is the same person who wore the wearable device during the first period, (ii) that said same person is still healthy, and (iii) that said same person is in the vicinity of an automatic door 855 that facilitates passage into the space. Optionally, the second indication is generated by the computer 847.

In some embodiments, after receiving the second indication, the computer 854 commands the automatic door 855 to open and/or remain open. Optionally, this command is issued following a detection of transmissions of the wearable device 840 indicating that the wearable device is near the automatic door 855.

In other embodiments, the computer 854 commands the automatic door 855 to close and/or remain shut, thus restricting passage into the space, responsive to receiving a third indication, sent after the second indication, indicating that the wearer of the wearable device at that time is not the same person as the wearer of the wearable device during the first period. For example, the computer 847 may send the third indication if an extent of similarity between characteristics of PPG signals in additional measurements taken while the wearable device 840 was near the automatic door 855 and characteristics of PPG signals in the first or second measurements fall below the second threshold.

Figure 6:
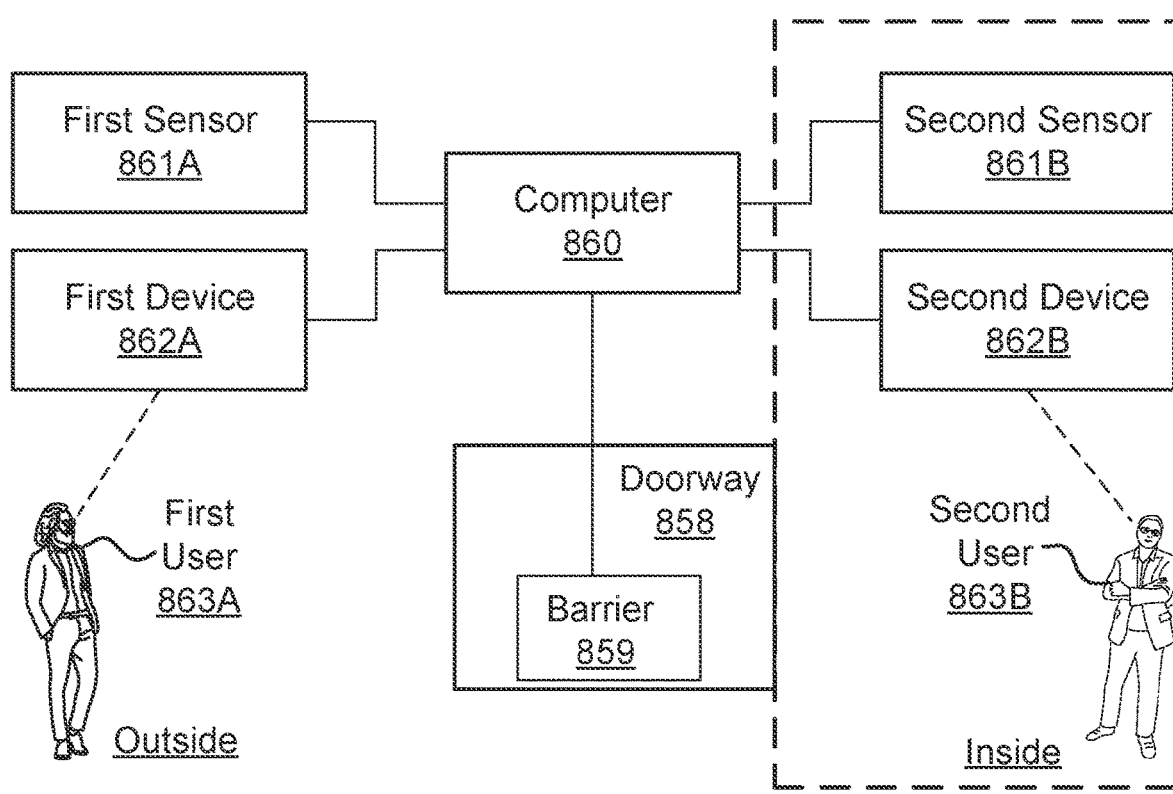
FIG. 6 is a schematic illustration of a doorway system.

FIG. 6 illustrates a doorway system that includes a doorway 858 that facilitates passage from an inside to an outside, and/or from the outside to the inside. The doorway 858 includes a barrier 859, disposed in the doorway 858, that moves between an opened position and a closed position based on commands sent by a computer 860. When in the closed position, the barrier 859 restricts passage through the doorway 858, and when in the opened position, the barrier 859 does not restrict the passage through the doorway.

The doorway system includes one or more sensors that measure: a first signal indicative of whether there is a first user 863A on the outside of the doorway, and a second signal indicative of whether there is a second user 863B on the inside of the doorway. In one example, the doorway system includes at least one of: a first sensor 861A that is capable of detecting whether the first user 863A is outside and a second sensor 861B that is capable of detecting whether the second user 863B is on the inside.

The computer 860 operates the doorway 858 in a manner that helps restrict contact between people that may be dangerous and contribute to the spread of disease. Optionally, this is done by restricting entrance of people who are not healthy through the doorway 858 in to the inside.

Examples of computers that may be utilized to perform the calculations of one or more computers that may be collectively referred to as "the computer 860" are computer 400 or computer 410, illustrated in FIG. XXA and FIG. XXB, respectively.

The computer 860 operates the doorway 858 in a manner that restricts passage through the doorway 858 when the first user 863A is on the outside, the second user 863B is on the inside, and at least one of them is not verified as being healthy and/or non-contagious. In some embodiments, this characteristic of the doorway 858 is implemented by the computer 860 as follows:

The computer 860 determines whether there are users on either side of the doorway 858. This involves detecting based on the first signal whether the first user 863A is on the outside, and detecting based on the second signal whether the second user 863B is on the inside.

If the first user 863A is on the outside, the first user 863A may be admitted if a first indication is received, indicating that the first user 863A is healthy and/or non-contagious. Optionally, the first indication is received from a first device 862A carried and/or worn by the first user 863A. Optionally, the first indication does not include information identifying the first user 863A.

In some embodiments, receiving the first indication is sufficient for the computer 860 to command barrier 859 to move to an open position and/or remain in the opened position (since there is no risk that the first user 863A will put people inside at risk). However, in other embodiments, the computer 860 may restrict the entrance of the first user 863A if that will put the first user 863A at risk because someone else, whose health state is not verified as being healthy and/or non-contagious is on the inside.

In some embodiments, if the computer 860A detects the first user 863A is on the outside and the first indication indicates the first user 863A is healthy, but the computer 860 detects the second user 863B is on the inside, the computer 860 will not allow the first user 863A without verifying the health state of the second user 863B. Thus, in such a situation, the computer 860 commands the barrier 859 to move to an opened position and/or remain in the opened position, responsive to receiving, from a second device 862B carried and/or worn by the second user 863B, a second indication indicating the second user 863B is healthy.

In some embodiments, the first device 862A carried and/or worn by the first user 863A receives measurements of physiological signals of the first user 863A. Optionally, the physiological signals include a PPG signal and a temperature signal (i.e., one or more measurements of the temperature of the first user 863A). Optionally, the physiological signals are sent by the wearable device 840.

In one embodiment, the first indication is sent by the computer 847. Optionally, the first device 862A carried and/or worn by the first user 863A is the wearable device 840.

Similarly, in some embodiments, the second device 862B carried and/or worn by the second user 863B receives measurements of physiological signals of the second user 863B. Optionally, the physiological signals include a PPG signal and a temperature signal (i.e., one or more measurements of the temperature of the second user 863B). Optionally, the physiological signals are sent by the wearable device 840.

In one embodiment, the second indication is sent by the computer 847. Optionally, the second device 862B carried and/or worn by the second user 863B is the wearable device 840. Optionally, the second indication does not include information identifying the second user 863B.

In some embodiments, the computer 860 commands the barrier 859 to move to the closed position and/or remain in the closed position, under certain conditions. One condition that may cause the computer 860 to do so is if it detects, based on the first signal that the first user 863A is on the outside, it detects, based on the second signal that the second user 863B is not on the inside, and does not receive the first indication indicating the first user 863A is healthy. Another condition under which the computer 860 may command the barrier 859 to move to the closed position and/or remain in the closed position is if the computer 860 detects, based on the first signal that the first user 863A is on the outside, it detects, based on the second signal that the second user 863B is on the inside, and does not receive at least one of the first indication indicating the first user 863A is healthy and the second indication indicating the second user 863B is healthy, respectively.

Various examples of doorways that may be controlled by the system illustrated in FIG. 6 are illustrated in FIG. 3.

In one example, the barrier 859 is a door that belongs to a vehicle 850C, and commanding the barrier to move to the opened position and/or remain in the opened position comprises commanding the door to unlock and/or move to a position that enables the first user 863A to enter a passenger cabin of the vehicle 850C.

In another example, the barrier 859 is an entrance door to a room and/or building (e.g., door 850A), and commanding the barrier to move to the opened position and/or remain in the opened position comprises commanding the entrance door to unlock and/or move to a position that enables the first user 863A to enter the interior of the room and/or building.

In yet another example, the barrier 859 is a turnstile or a revolving door belonging to a gate (e.g., door 850B or gate 850D), and commanding the barrier to move to the opened position and/or remain in the opened position comprises enabling the turnstile or the revolving door to revolve and/or revolving the turnstile or the revolving door, which enables the first user 863A to pass through the gate.

A presence of multiple users are on the inside and/or on the outside may require the computer 860 to adjust the operation of the doorway 858 in order to help reduce unwanted contacts with users whose health state is not verified as being healthy and/or non-contagious.

In one embodiment, the computer 860 commands the barrier 859 to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

In another embodiment, when the first user 863A is detected on the outside, the computer 860 may command the barrier 859 to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

The first and/or second indications mentioned above may be transmitted at the request of the computer 860. In one embodiment, the computer 860 transmits a request for the first indication indicating the first user is healthy, responsive to detecting that the first user 863A is on the outside, and/or transmits a request for the second indication indicating the second user 863B is healthy, responsive to detecting that the second user 863B is on the inside.

In some embodiments, the first and second signals may be signals generated by devices worn and/or carried by the first user 863A and the second user 863B, respectively. In these embodiments, the one or more sensors may include a receiver that detects the first and second signals and/or a plurality of receivers that triangulate locations of the devices that sent these signals. In other embodiments, the first and second signals may be signals from which the computer 860 detects the presence of the first user 863A and the second user 863B, respectively.

In one example, the one or more sensors include a camera aimed to the outside, the first signal includes images of the outside, and detecting the first user 863A is outside involves identifying presence of a person in the images.

In another example, the one or more sensors include a thermal sensor aimed to the outside, the first signal includes thermal measurements of the outside, and detecting the first user 863A is outside involves identifying a thermal signature corresponding to a person in the thermal measurements.

In yet another example, the one or more sensors include a pressure sensor disposed in a surface on the outside, the first signal includes values indicative of pressure applied to the pressure sensor, and detecting the first user 863A is outside involves identifying the values reflect application of a pressure corresponding to a weight of a person.

Figure 8:
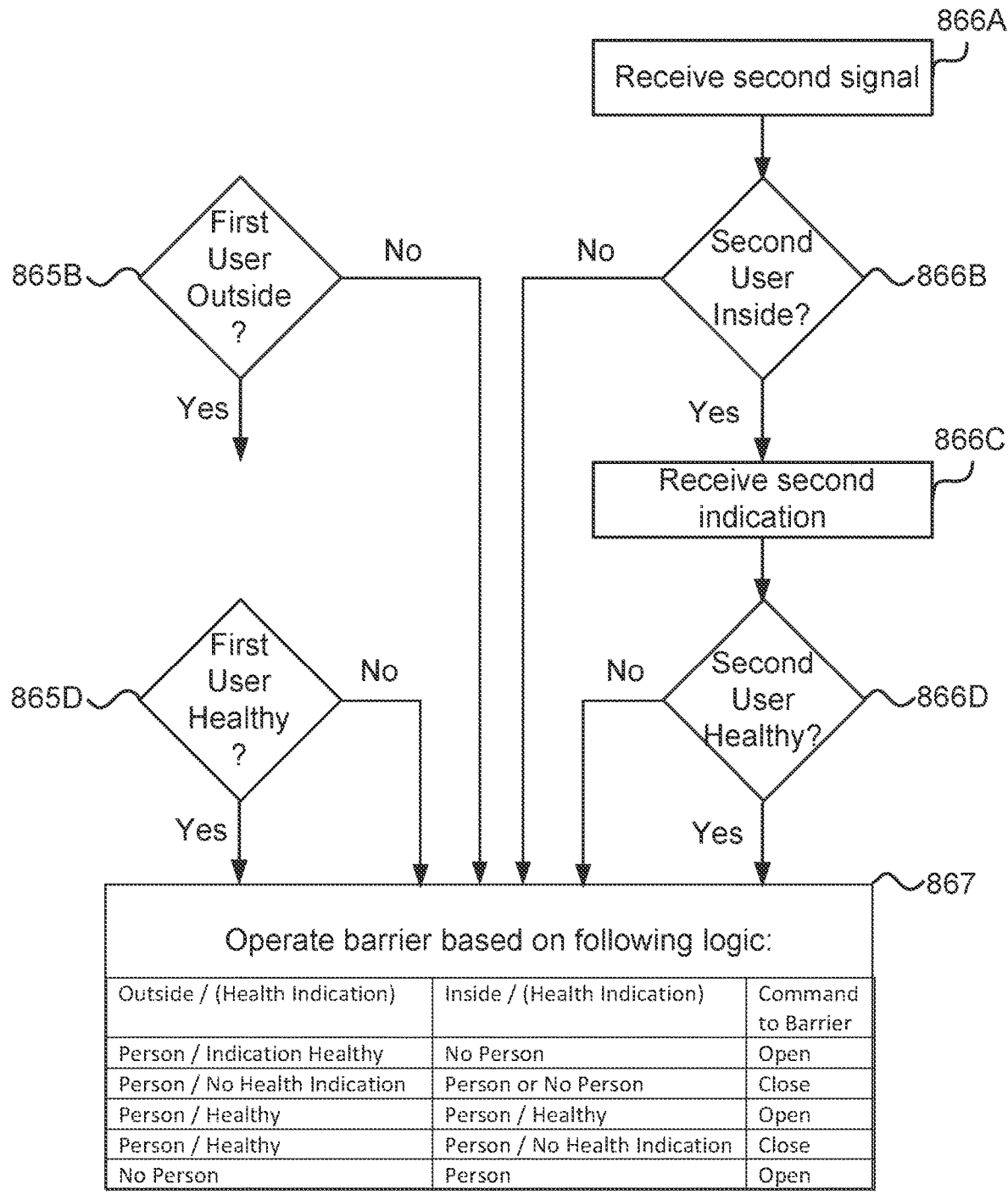
FIG. 8 illustrates a flowchart according to which a computer may operate a barrier disposed in a doorway.

FIG. 8 illustrates a flowchart according to which the computer 860 may command the barrier 859 to open and/or close. Steps 865A and 866A involve receiving the first and second signals, respectively. Steps 865B and 866B involve determining whether the first user 863A is outside and the second user 863B is inside, respectively. Steps 865C and 866C involve receiving the first and second indications, respectively. Steps 865D and 866D involve determining whether the first user 863A is healthy and whether the second user 863B is healthy, respectively. Information determined based on some, or all of the aforementioned steps is provided to the computer 860, which in step 867 operates the barrier according to the logic described in the table included in that the illustration of that step.

The steps illustrated in FIG. 8 may be used to implement a method for controlling the doorway 858. This method may be implemented using an embodiment of a system illustrated in FIG. 6, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps mentioned below.

In one embodiment, the method for controlling the doorway 858 includes the following steps:

In Step 865A, receiving a first signal indicative of whether there is a first user on an outside of the doorway 858.

In Step 865B, detecting based on the first signal that the first user is on the outside.

In Step 865C, receiving, from a first device carried and/or worn by the first user, a first indication indicating the first user is healthy.

In Step 866A, receiving a second signal indicative of whether there is a second user on the inside of the doorway.

In Step 866B, detecting based on the second signal whether the second user is on the inside.

And in Step 867, operating the barrier 859 according to the logic in the table in FIG. 8, which involves commanding the barrier 859 to move to the opened position and/or remain in the opened position, responsive to: (i) detecting that the second user is not on the inside (in Step 866B), or (ii) detecting that the second user is on the inside (in Step 866B) and receiving, from a second device carried and/or worn by the second user, a second indication (in Step 866C), which in Step 866D is determined to indicate the second user is healthy.

In one embodiment, the method for controlling the doorway 858 may optionally include a step of commanding the barrier to move to the closed position and/or remain in the closed position, responsive to: (i) detecting based on the first signal that the first user is on the outside (in Step 865B), detecting based on the second signal that the second user is not on the inside (in Step 866B), and not receiving the first indication indicating the first user is healthy, or (ii) detecting based on the first signal that the first user is on the outside (in Step 865B), detecting based on the second signal that the second user is not on the inside (in Step 866B), and not receiving at least one of the first indication indicating the first user is healthy and the second indication indicating the second user is healthy.

In one embodiment, the method for controlling the doorway 858 may optionally include the following steps: commanding the barrier to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

In one embodiment, the method for controlling the doorway 858 may optionally include the following steps: commanding the barrier to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

In one embodiment, the method for controlling the doorway 858 may optionally include the following step: transmitting a request for the first indication indicating the first user is healthy, responsive to detecting that the first user is on the outside.

Combating the spread of communicable diseases is often done with extreme measures, such as restrictions on peoples' movements and blanket orders for quarantines. The reason such extreme measures are often used is that it is difficult to determine, on a population-wide scale, who are the symptomatic people who pose a risk of spreading the communicable disease (and limit restrictions to those people). Thus, for practical reasons, often whole populations are treated as if they all pose a risk, and are subject to many restrictions, even though the majority of these people are not symptomatic and cannot spread the disease.

Due to the great toll of such measures, which often lead to wide-scale disruption to the economy, they are not sustainable on the long run. However, lifting these restriction prematurely can also have devastating consequences, since it can rekindle the spread of diseases that were on the decline.

The main problem lies in the ability to identify who are the people who pose risk to others (e.g., due to them being symptomatic individuals). While wearable devices with sensors capable of measuring physiological signals of their wearers have been suggested as possible tools that can be used to combat the spread of communicable diseases, so far they have mostly not been adopted in practical applications that go beyond reporting to users their physiological state. Thus, there is a need for ways to utilize wearable devices to loosen blanket restrictions imposed in order to curb the spread of communicable diseases. This can enable more people to go to their work place, school, etc., but needs to be done in a safe manner that does not pose a significant risk of increasing the spread of disease.

Figure 7:
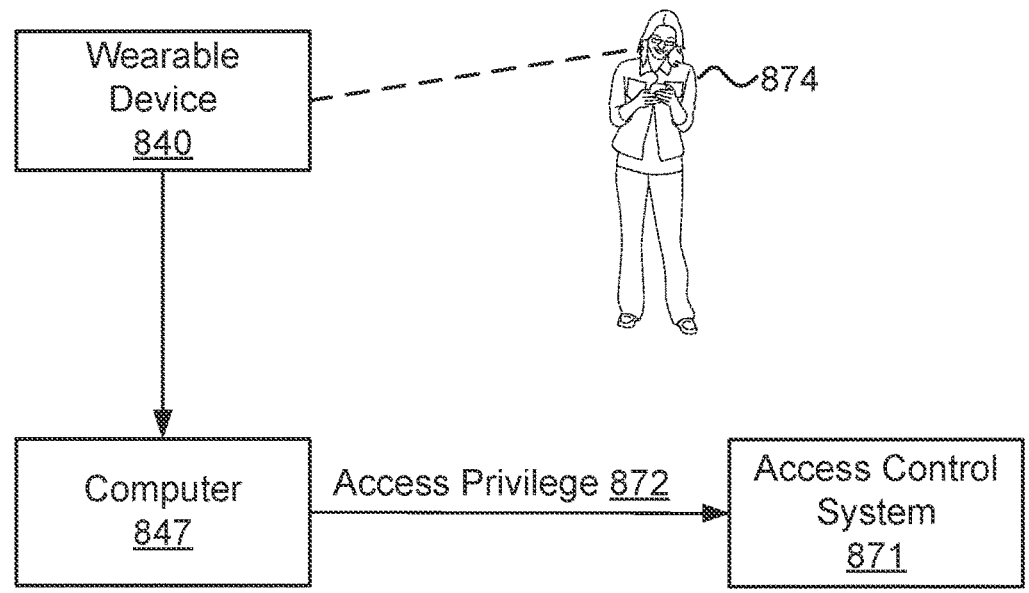
FIG. 7 is a schematic illustration of components of a system configured to authorize physical access to a location based on an authenticated health score.

FIG. 7 is a schematic illustration of components of a system configured to authorize physical access to a location, such as a work place, a public building, etc., based on an authenticated health score. In one embodiment, the system includes at least the wearable device 840 and the computer 847. In this embodiment, the computer 847 utilizes measurements of a user 874 taken with the wearable device 840, that day and on earlier days, to determine both if the user's health state permits access to the location, and also to authenticate the user 874. The system may optionally include additional elements such as an access control system 871, which is configured to allow or deny access to the location based on indications received from the computer 847. Embodiments of the system illustrated in FIG. 7 share many of the components and characteristics of embodiments of the system illustrated in FIG. 1, which is discussed in detail above, possibly with one or more differences. One of the differences involves the computer 847 calculating an authentication score in order to provide or revoke an access privilege 872. This process involves conveying information about the identity of the user being authenticated, which is not aspect that is necessarily present in embodiments of the system illustrated in FIG. 1. Some of the embodiments of the system illustrated in FIG. 1 do not involve providing information that may identify the user wearing the wearable device 840.

In one embodiment, the computer 847 analyzes measurements taken by the wearable device 840 of the user 874 and optionally, of the environment the user 874 is in at the time. This analysis involves calculations involving measurements taken at different times: (i) "current measurements", which are taken with the wearable device 840 during a period that starts a certain time before the analysis is performed (e.g., a few hours before) and/or leading up to when the analysis is performed, and (ii) "baseline measurements" taken with the wearable device 840 on or more earlier days. Optionally, the current measurements are taken over a duration of at least five minutes. Optionally, the baseline measurements include more than an hour of measurements taken over a period of several days.

In some embodiments, the computer 847 calculates a health score for the user 874 based on a difference between the baseline measurements and the current measurements, as explained in detail above (see description of embodiments according to FIG. 1). Additionally, the computer 847 calculates an authentication score based on a similarity between characteristics of a PPG signal in the current measurements and characteristics of a PPG signal in the baseline measurements. Optionally, the authentication score is proportional to the extent of similarity between characteristics of a PPG signal in the current measurements and characteristics of a PPG signal in the baseline measurements. Calculation of the extent of said similarity is explained in detail above (see description of embodiments according to FIG. 1). In some embodiments, the authentication score equals the extent of the similarity between characteristics of a PPG signal in the current measurements and characteristics of a PPG signal in the baseline measurements.

In one embodiment, responsive to the health score reaching a first threshold and the authentication score reaching a second threshold, the computer 847 grants the user 874 the access privilege 872, which enables the user 874 to access the location. Optionally, granting the access privilege 872 involves transmitting an indication to the access control system 871, which may be a system that controls entryways into the location. Optionally, this transmitted indication includes information identifying the user 874 (e.g., a name, an employee number, a national identification number, or some other identifier) and/or information indicating the health state of the user 874. In one example, granting access to the location involves adding an identifier of the user 874 to a list of people permitted to enter the location. In another example, revoking access to the location involves removing an identifier of the user 874 from the list of people permitted to enter the location.

An access privilege previously granted to the user 874 may be revoked under certain conditions, such as it not being clear if it is still safe to let the user 874 enter the location. In one embodiment, the computer 847 revokes the access privilege 872, responsive to the health score not reaching the first threshold and/or the authentication score not reaching the second threshold.

In some embodiments, knowledge about the health state of people who typically access the location can be used to set the first threshold. For example, if many of those people became ill, this may mean that there is an outbreak of an illness associated somehow with the location. In such a case, it may be desirable to increase the first threshold in order to reduce the chance of people who may be beginning to become ill, which may be only slightly symptomatic, of gaining access to the location. In one example, the computer 847 increases the first threshold responsive to receiving a certain indication indicative of number of people, who are ill and who accessed the location in a preceding period of time, reaches a third threshold. Optionally, increasing the first threshold reduces tendency to deny and/or revoke privileges to access the location.

The calculated health score may be utilized to generate a certificate indicative of the health state of the user 874. In one embodiment, the computer 847 may provide an indication the user 874 is healthy, responsive to the health score reaching the first threshold and the authentication score reaching the second threshold. In another embodiment, the computer 847 may provide an indication that the user 874 is ill (a "sick note"), responsive to the health score not reaching the first threshold and the authentication score reaching the second threshold. Optionally, these indications regarding the health state of the user 874 may include information identifying the user 874.

When the health state of the user 874 changes, this can lead to changing the indication about the state of the user 874. For example, when the health of the user 874 improves, a sick note provided to the user 874 may be canceled based on measurements taken with the wearable device 840. In one embodiment, the computer 847 receives additional measurements of the user 874 taken with the wearable device 840 at least four hours after the current measurements were taken. The computer 847 calculates an additional health score based on a difference between the baseline measurements and the additional measurements. The computer 847 also calculates an additional user authentication score based on a similarity between characteristics of the PPG signal in the additional measurements and the characteristics of the PPG signal in the baseline measurements. The computer 847 then provides an indication that the user 874 is no longer ill responsive to the additional health score reaching the first threshold and the additional user authentication score reaching the second threshold.

When the health state of multiple users is tracked using the system illustrated in FIG. 7, this can provide insights into the dynamics of illness, which can be used to predict how long the user 874 may be ill. In one embodiment, the computer 847 generates feature values based on the current measurements and the baseline measurements (e.g., feature values described herein as being generated from that data), and utilizes a model to calculate, based on the feature values, a value indicative of a duration of illness of the user 874. Optionally, the model is generated based on data comprising a first set of training measurements of a plurality of users taken while the plurality of users were not ill, a second set of training measurements of the plurality of users taken during illnesses of the plurality of users, and indications of durations of the illnesses. Optionally, the training measurements were taken using wearable devices, such as the wearable device 840.

Figure 9:
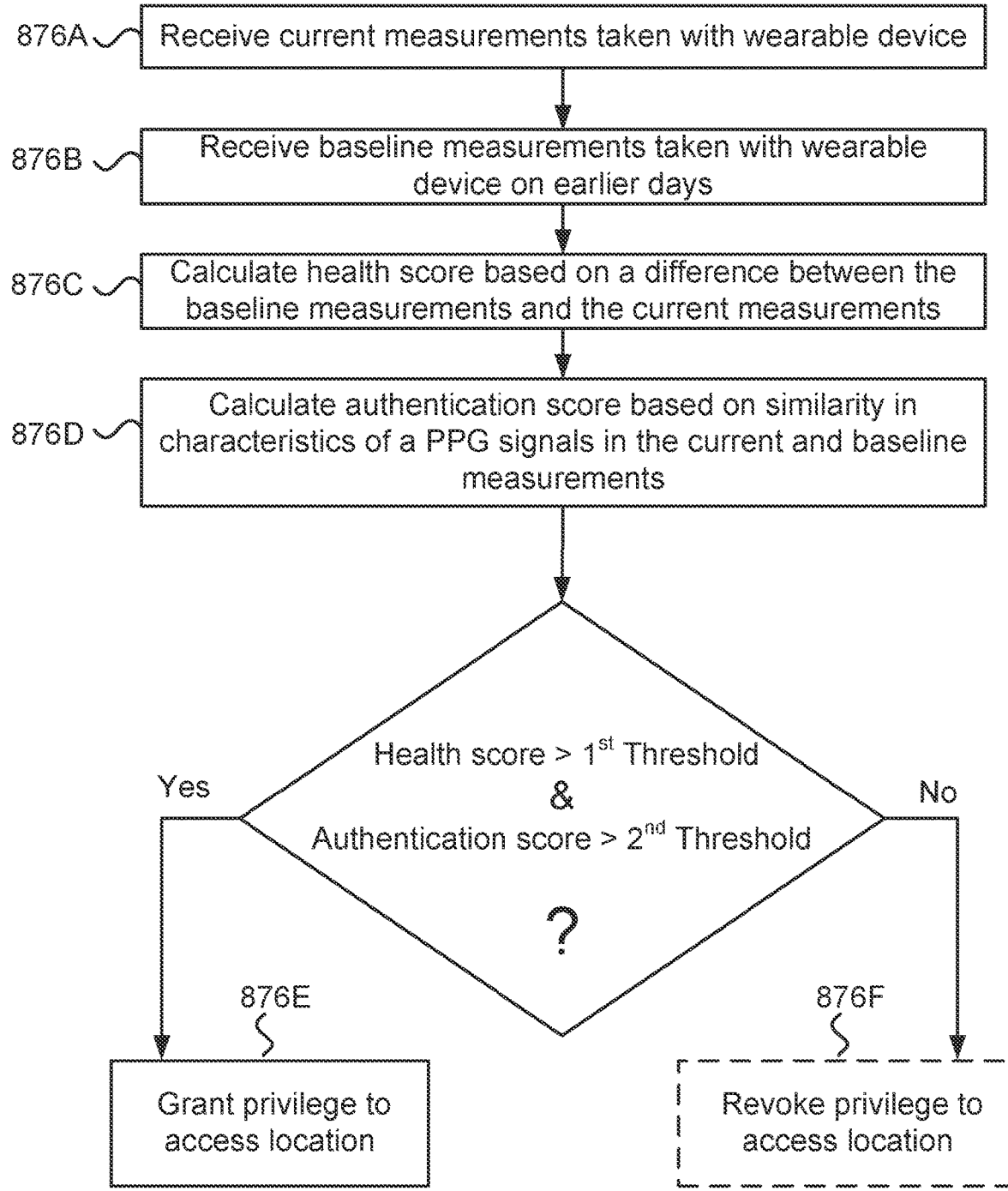
FIG. 9 illustrates steps that may be part of embodiments of a method for managing authorization of access to a location based on authenticated health scores.

FIG. 9 illustrates steps that may be part of embodiments of a method for managing authorization of access to a location based on authenticated health scores. The method may be implemented using embodiments of systems illustrated in FIG. 7, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 9 and/or additional steps mentioned below.

In one embodiment, the method for managing authorization of access to a location based on authenticated health scores includes at least the following steps:

In Step 876A, receiving current measurements of a user taken with a wearable device that includes: a first sensor configured to measure a signal indicative of a photoplethysmogram signal (PPG signal) of a user, and a second sensor configured to measure a temperature of the user. For example, the current measurements may be taken with the wearable device 840.

In Step 876B, receiving baseline measurements of the user taken with the wearable device during one or more earlier days.

In Step 876C, calculating a health score based on a difference between the baseline measurements and the current measurements.

In Step 876D, calculating an authentication score based on a similarity between characteristics of a PPG signal in the current measurements and characteristics of a PPG signal in the baseline measurements.

And in Step 876, responsive to determining the health score reaches a first threshold and the authentication score reaches a second threshold, granting the user a privilege to access the location.

In one embodiment, the method may optionally include Step 876F, which involves revoking the privilege of the user to access the location, responsive to the health score not reaching the first threshold and/or the authentication score not reaching the second threshold.

In one embodiment, the method may optionally include a step involving increasing the first threshold responsive to receiving a certain indication indicative of number of people, who are ill and who accessed the location in a preceding period of time, reaches a third threshold. Optionally, increasing the first threshold reduces tendency to revoke privileges to access the location.

Due to the many interactions that can occur in places of gatherings, such as workplaces, schools, theaters, etc., these locations can be considered dangerous to enter during times of epidemics. It is difficult to keep track of the health state of all the people who entered a location, and thus ascertain if visits to the location pose any risk of contracting a disease. Without knowing the risk from visiting a potentially dangerous location (due to the many people present there), it may be necessary to employ drastic measures to isolate visitors to the location from other people in order to reduce the risk of disease transmission. Thus, there is a need of a way to ascertain the risk of contracting a disease posed by a visit to a location, in order to be able to choose appropriate and proportionate measures to take following the visit.

Some embodiments disclosed herein utilize wearable devices that measure physiological signals of their wearer in order to determine whether people who were at a location were healthy, and thus be able to certify the location as contagion-safe. Being in a contagion-safe location poses little risk of contracting a communicable disease. Therefore, visitors to such a location may not need to take additional measures, such as isolation from other people, which are often required when coming from locations in which there are many people whose health state is unknown.

Figure 10:
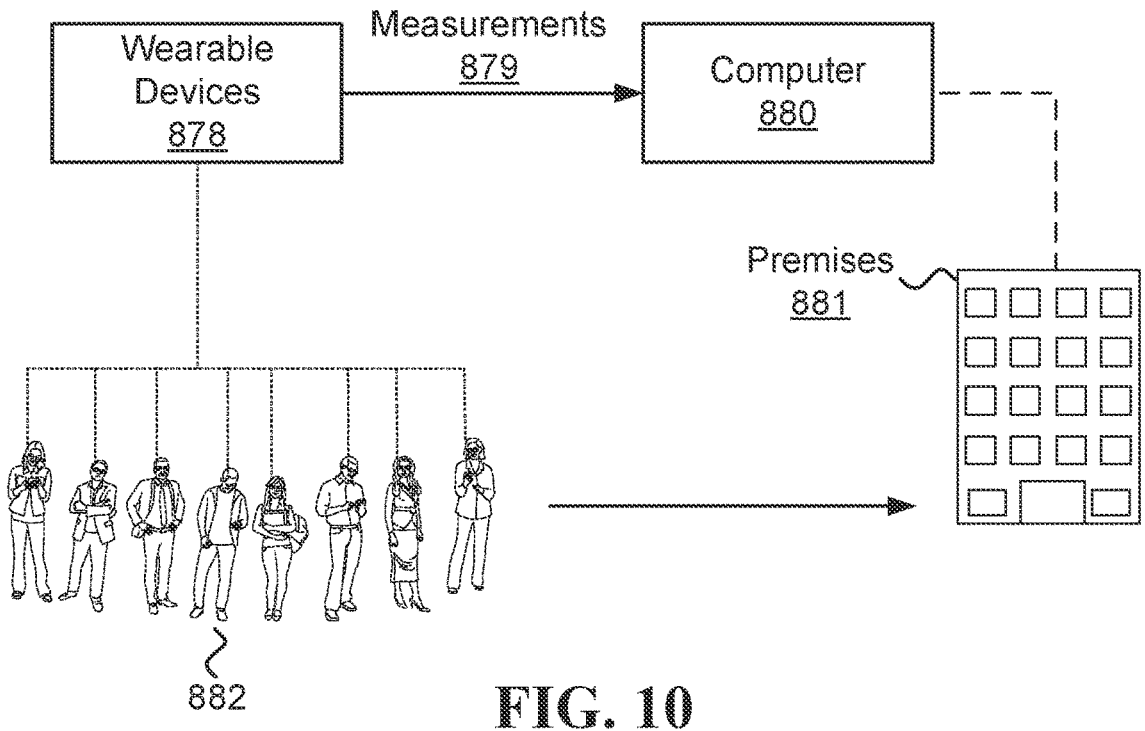
FIG. 10 is a schematic illustration of an embodiment of a system configured to certify a premises as contagion-safe.

FIG. 10 is a schematic illustration of an embodiment of a system configured to certify a premises 881 as contagion-safe. For example, the premises 881 may be a place of work, a school, or a nursing home facility. In some embodiments, the system includes wearable devices 878 that take measurements 879 of users 882 who are wearing the wearable devices 878. Optionally, the measurements 879 include photoplethysmogram signals of the users 882 and temperature signals of the users 882. Optionally, each of the wearable devices 878 is an embodiment of the wearable device 840, described in detail further above. Optionally, at least some of the wearable devices 878 are smartglasses, such as the smartglasses illustrated in FIG. 2.

Embodiments of the system illustrated in FIG. 10 also include a computer 880 which performs several steps in order to determine whether to certify the premises 881 as contagion-safe. In one embodiment, the computer 880 calculates health scores of the users 882 based on measurements 879 of the users 882 taken while the users were not on the premises 881. The computer 880 identifies which of the users 882 are non-symptomatic users based on their health scores reaching a threshold (such as the first threshold mentioned in the context of embodiments illustrated in FIG. 1). The computer 880 also authenticates the identities of the non-symptomatic users based on at least some of the measurements 879 (i.e., at least some of the measurements 879 that are of the non-symptomatic users). Optionally, the predetermined period is set according to characteristics of an epidemic for which the system protects. For example, the predetermined period may be set to a value between one day and ten days, depending on the time it typically takes for symptoms of the epidemic to manifest with infected individuals.

In some embodiments, calculation of the health scores of the users 882 based on the measurements 879 by the computer 880, may be done in the same manner described in embodiments disclosed herein involving the computer 847 calculating health scores based on current and baseline measurements (in which case the measurements 879 include measurements taken over multiple days).

In some embodiments, calculation of the health scores of the users 882 based on the measurements 879 by the computer 880, may be done in the same manner described in embodiments disclosed herein involving the computer 847 calculating health scores by utilizing one or more the machine learning approaches described with respect to calculation of health scores by the computer 847, such as generating feature values based on measurements of a user, from among the measurements 879, and utilizing a model to calculate, based on the feature values, a value that indicates whether that user is healthy and/or non-contagious.

In some embodiments, authenticating the identities of the non-symptomatic users based on at least some of the measurements 879 may be done by the computer 880 in the same manner described in embodiments disclosed herein involving the computer 847. For example, the computer 880 may calculate the extent of similarity of PPG signals of a certain user in measurements from among the measurements 879 with a template generated based on previously measured PPG signals of that certain user. Optionally, if the extent of similarity exceeds a threshold, the certain user may be considered authenticated. Additionally or alternatively, in some embodiments, authenticating the certain user may utilize additional signals from among measurements 879 mentioned herein as useful for authentication, such as acoustic signals and/or movement signals.

Based on the authenticated identities of the non-symptomatic users from among the users 882, the computer 880 determines whether to certify the premises 881 as contagion-safe.

In some embodiments, certifying the premises 881 as contagion-safe means providing an indication to one or more of the users 882, other people, and/or other computer systems, that the premises 881 is contagion-safe. An indication of a certification of the premises 881 as contagion-safe can be used for various applications, such as deciding on quarantine or stay-at-home orders for people who visited the premises 881, assessment of risk these people are ill, and/or assessment of a risk of exposure to people form among the users 882. Optionally, the indication is indicative of the fact that only the non-symptomatic users, whose authentication was successful, entered the premises 881 during the predetermined period. Alternatively, the indication is indicative of the fact that the non-symptomatic users whose authentication was successful comprise at least a certain predetermined proportion of all of the users 882 who visited the premises 881.

In some embodiments, de-certifying the premises 881 as contagion-safe means sending an a second indication canceling the indication sent when certifying the premises 881 as contagion-safe and/or sending an indication to one or more of the users 882, other people, and/or other computer systems, indicating that the premises is not contagion-safe.

In some embodiments, the computer 880 certifies the premises 881 as contagion-safe responsive to determining that, from among the users 882, only non-symptomatic users, whose authentication was successful, entered the premises 881 during a predetermined period.

In other embodiments, the computer 880 certifies the premises 881 as contagion-safe responsive to determining that that the non-symptomatic users whose authentication was successful comprise at least a certain predetermined proportion of all of the users 882 who visited the premises 881. The predetermined proportion may be selected by the operator at the premises 881. For example, the operator may decide that the threshold is 90% of non-symptomatic users in the premises 881, whose authentication was successful, in order to certify the premises 881 as contagion-safe. And if the percent of the non-symptomatic authenticated users falls below 90% then the certification of the premises as contagion-safe is revoked. Additionally or alternatively, the operator may decide that the threshold is density below 0.3 per square meter of non-symptomatic users, density below 0.06 per square meter of users for which symptom status is unknown, and density below 0.03 per square meter of symptomatic users.

In some embodiments, the computer 880 may present, e.g., via a user interface, an indication proportional to at least one of percent and/or density of the following: the non-symptomatic users in the premises 881, symptomatic users in the premises 881, and users for which symptom status is unknown. Optionally, the presented indications support decision of other users whether to visit the premises 881 at that time.

In one embodiment, the computer 880 may receive a location of a certain user at the premises 881, and recommend the certain user use certain personal protection equipment based on the indication proportional to the at least one of the percent and/or the density. This recommendation can help the certain user to decide whether personal protection equipment is required, and to what extent. For example, whether using face mask should be enough, and whether gloves are also needed.

It is to be noted that in different embodiments, a reference to "the computer 880" may refer to different components and/or a combination of components. In some embodiments, the computer 880 may be a server or a collection of servers (e.g., on a computing cloud). In some embodiments, at least some of the functionality attributed to the computer 880, such as calculating the health scores of the users 882 and/or authenticating the non-symptomatic users, may be performed by computers associated with those users, such as cloud-based servers hosting accounts of those users and/or processors on devices of those users (e.g., smartphones) or wearable devices of those users. Thus, references to calculations being performed by the "computer 880", and the like, should be interpreted as calculations being performed utilizing one or more computers, as described in the examples above. Examples of computers that may be utilized to perform the calculations of one or more computers that may be collectively referred to as "the computer 880" are computer 400 or computer 410, illustrated in FIG. XXA and FIG. XXB, respectively.

In some embodiments, the computer 880 may notify certain users, e.g., via user interfaces of devices the carry (e.g., screens of smartphones) or user interfaces of the wearable devices 878, whether they are permitted on the premises 881. In one example, a user interface may be used to notify a non-symptomatic user that said non-symptomatic user is allowed on the premises 881. In another example, the computer 880 may identify some of the users 882 as symptomatic users based on their measurements taken while not on the premises 881. For example, their health scores may be below a threshold. In this example, a user interface may be utilized to notify a symptomatic user, prior that user's arriving to the premises 881, that that user is not allowed on the premises 881.

In some embodiments, the computer 880 receives identities of at least some of the users 882 who arrived at the premises 881 and determines based on the identities, whether a user, who is not among the non-symptomatic users, entered the premises 881. The identities may be received via various systems. In one example, the identities are received from a security system that utilizes video cameras and image recognition to determine who entered the premises 881. In another example, the identities are received from a security system that logs entry to the premises 881 via a key card mechanism. In still another example, the identities may be received via identification of transmissions of the wearable devices 878 and/or other mobile devices carried by the users 882 (e.g., smartphones).

In some embodiments, the computer 880 identifies some of the users 882 as symptomatic users based on their health scores being below the threshold, and decertifies the premises 881 as contagion-safe responsive to detecting that a symptomatic user entered the premises 881 after the predetermined period. Optionally, the computer 880 receives an indication of a time at which the symptomatic user left the premises 881, and re-certifies the premises 881 as contagion-safe after a predetermined duration from that time. Optionally, obtaining the time the symptomatic user left the premises 881 may be done using one of more of the techniques mentioned above (e.g., image processing, access control system or time card system, etc.).

In one embodiment, the computer 880 may identify that a person not wearing one of the wearable devices 878 (a non-cleared person) entered the premises 881 after the predetermined period, and decertify the premises 881 as contagion-safe responsive to detecting that the non-cleared person entered the premises 881.

In one embodiment, the computer 880 may identify, after the predetermined period, that a user on the premises 881 became ill, and decertify the premises 881 as contagion-safe.

In some embodiments, the health scores are calculated with respect to a certain disease, and certification of the premises 881 as contagion-safe is indicative that only non-symptomatic users with respect to the certain disease, whose authentication was successful, entered the premises 881 during the predetermined period. Optionally, the computer 880 may confirm, based on external medical records, immunity of one or more people who had the certain disease and refrain from decertifying the premises 881 due to their entry to the premises 881 during the predetermined period.

Figure 12:
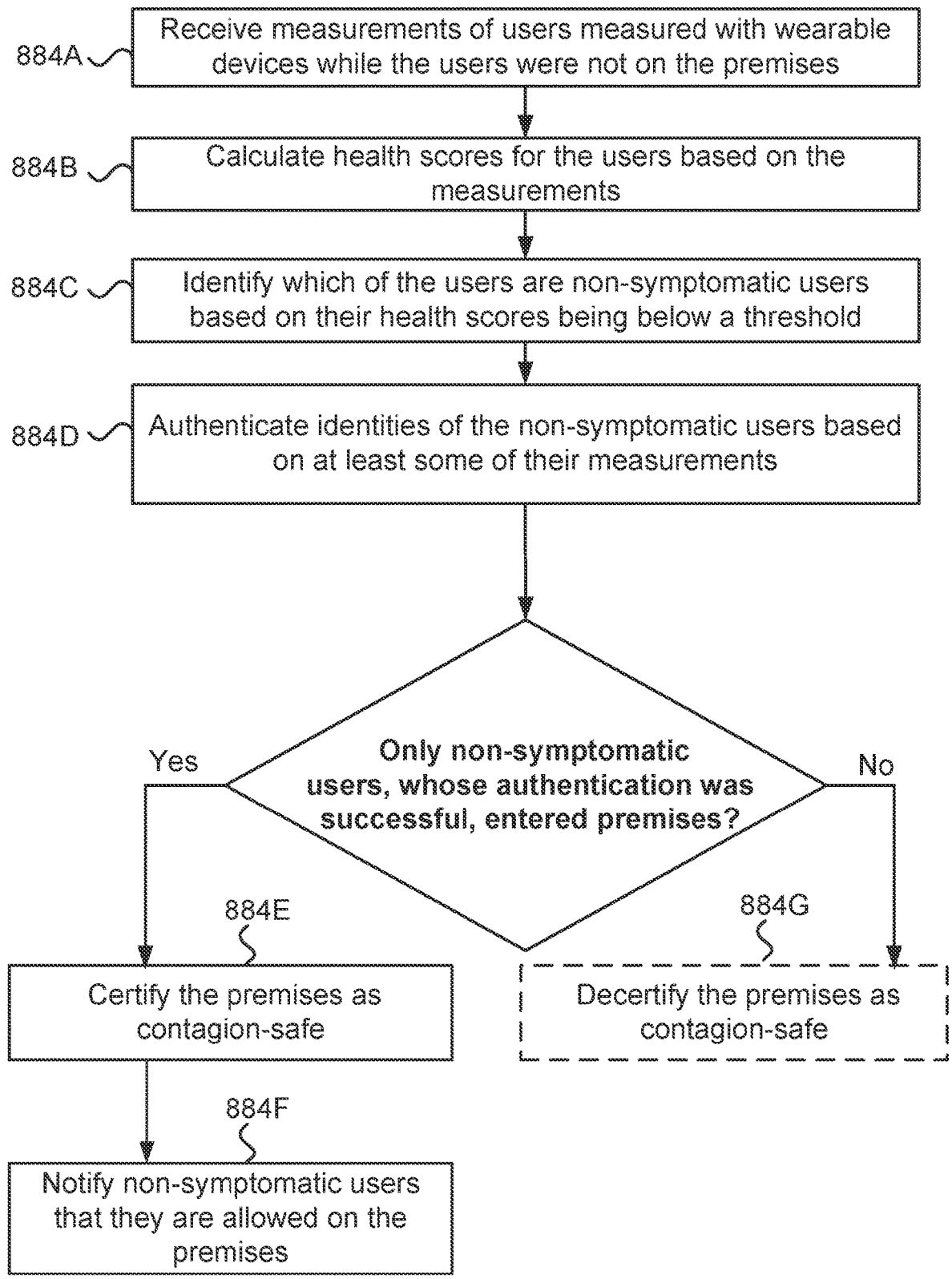
FIG. 12 illustrates steps that may be part of embodiments of a method for certifying a premises as contagion-safe.

FIG. 12 illustrates steps that may be part of embodiments of a method for certifying a premises as contagion-safe. The method may be implemented using embodiments of systems illustrated in FIG. 10, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 12 and/or additional steps mentioned below.

In one embodiment, the method for certifying a premises as contagion-safe includes at least the following steps:
  In Step 884A, receiving measurements of users measured with wearable devices (e.g., units of the wearable device 840), while the users were not on the premises. Optionally, the measurements include photoplethysmogram signals of users and temperature signals of the users.
  In Step 884B, calculating health scores of the users based on the measurements.
  In Step 884C, identifying which of the users are non-symptomatic users based on their health scores being reaching a threshold.
  In Step 884D, authenticating identities of the non-symptomatic users based on at least some of their measurements.
  And in Step 884E certifying the premises as contagion-safe responsive to determining that, from among the users, only non-symptomatic users, whose authentication was successful, entered the premises during a predetermined period.

In one embodiment, the method may optionally include Step 884F involving notifying the non-symptomatic users that they are allowed on the premises. Additionally or alternatively, the method may include optional steps involving: identifying some of the users as symptomatic users based on their measurements measured while not on the premises, and notifying the symptomatic users, prior to their arriving to the premises, that they are not allowed on the premises.

In one embodiment, the method may optionally include Step 884G involving: identifying some of the users as symptomatic users based on their health scores being below the threshold, and decertifying the premises as contagion-safe responsive to detecting that a symptomatic user entered the premises after the predetermined period. Optionally, the method may also include steps involving: receiving an indication of a time when the symptomatic user left the premises, and re-certifying the premises as contagion-safe after a predetermined duration from that time.

In one embodiment, the method may optionally include a step involving: identifying, after the predetermined period, that a user on the premises became ill, and decertifying the premises as contagion-safe.

Due to the many interactions that can occur in places of gathering, such as workplaces, schools, theaters, etc., these locations can be considered dangerous to enter during times of epidemics. It is difficult to keep track of the health state of all the people who entered a location, and thus ascertain if visits to the location posed a substantial risk. One way in which the risk of visiting such a location can be reduced is by ensuring that only healthy people, who are likely to be non-symptomatic and/or non-contagious, may be present at the location. Thus, there needs to be an easy way to make such determinations on a wide scale.

Some embodiments disclosed herein utilize wearable devices that measure physiological signals of users in order to determine whether the users are healthy, and thus should be allowed to enter a location that is assumed to be contagion-sage. In one example, this can be useful for certifying a nursing home is contagion-safe, and then screening new residents prior to their admission in order to keep the nursing home free of disease. In another example, this approach can be used to pre-screen passengers intending to take a flight, in order to keep off the aircraft any passengers who may be symptomatic and spread a disease onboard.

Figure 11:
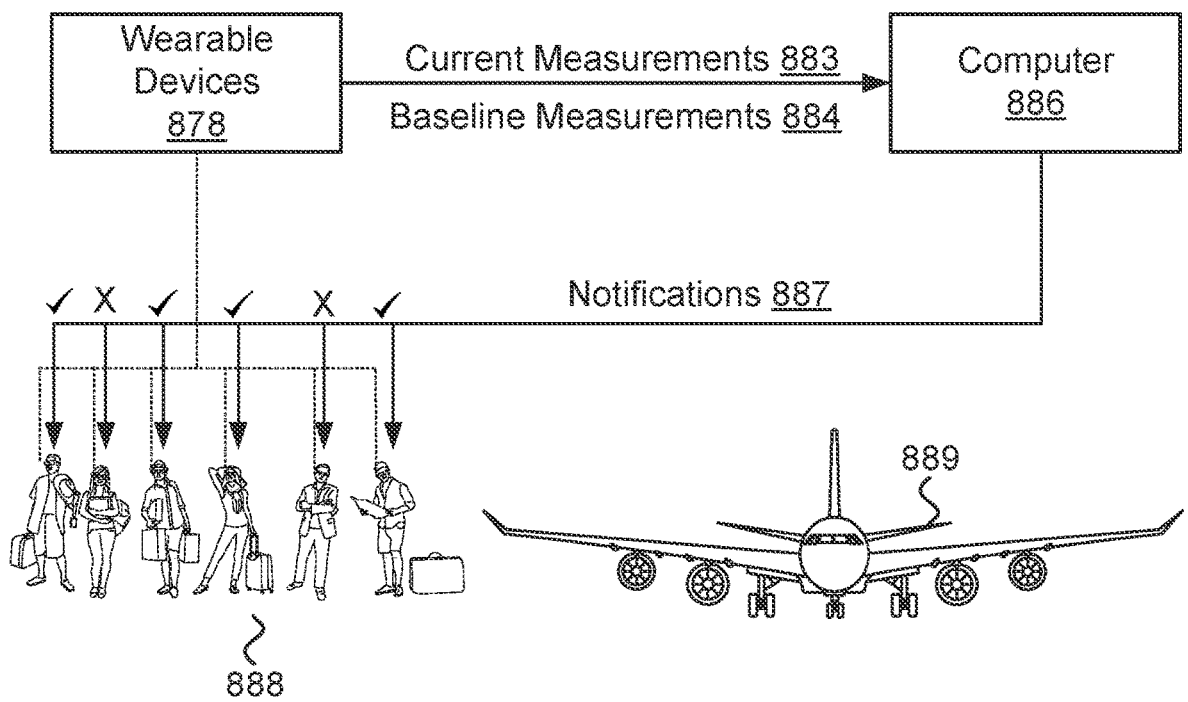
FIG. 11 is a schematic illustration of an embodiment of a system for managing access to a contagion-safe premises.

FIG. 11 a schematic illustration of an embodiment of a system for managing access to a contagion-safe premises. In some embodiments, the system includes wearable devices 878 that take measurements of users 888 who are wearing the wearable devices 878. Additionally, the system includes a computer 886, which performs several steps in order to manage access to the contagion-safe premises.

In some embodiments, the wearable devices 878 take measurements of the users 888 that include photoplethysmogram signals of the users 888 and temperature signals of the users 888. Optionally, each of the wearable devices 878 is an embodiment of the wearable device 840, described in detail further above. Optionally, at least some of the wearable devices 878 are smartglasses, such as the smartglasses illustrated in FIG. 2.

In some embodiments, the measurements of the users 888 taken with the wearable devices 878 include current measurements 883 of the users 888 and baseline measurements 884 of the users 888.

The current measurements 883 include for each user from among the users 888, measurements of the user, taken with a wearable device from among the wearable devices 878, up to 4 hours before an intended arrival time of the user to a premises 889. Optionally, current measurements 883 include measurements that are intended to reflect the state of the user during the hours leading up to an intended time of arriving at the premises 889.

The baseline measurements 884 include for each user from among the users 888, measurements of the user, taken with a wearable device from among the wearable devices 878 at least 10 hours before the intended arrival time of the user (i.e., the baseline measurements are taken 10 hours before the intended arrival or even earlier than 10 hours before the intended arrival). These measurements are intended to reflect a typical state of the user at an earlier time (e.g., the user's baseline state).

The computer 886 calculates health scores of the users 888 based on differences between the current measurements 883 and the baseline measurements 884. Optionally, the health score of each certain user from among the users 888 is calculated based on current measurements of the certain user, from among the current measurements 883, and baseline measurements of the certain user, from among the baseline measurements 884. Calculation of the health score for the certain user may be done in the same manner described herein in which the computer 847 calculates the health score based on differences between the current measurements and baseline measurements in embodiments illustrated in FIG. 1. Optionally, the calculation of the health score of the certain user is performed by a processor on a device of the certain user.

The computer 886 utilizes the health scores of the users 888 in order to identify a subset of the users 888 as non-symptomatic users. Optionally, this identification is done by comparing the health scores of the users 888 to a threshold, and selecting the users whose health score reaches the threshold (e.g., this threshold may be the first threshold mentioned in the context of embodiments illustrated in FIG. 1).

The computer 886 also authenticates identities of the non-symptomatic users based on at least some of their current measurements (i.e., measurements from among the current measurements 883 that are taken from them). Optionally, such an authentication is performed by the computer 886 in the same manner described in embodiments disclosed herein involving the computer 847. For example, the computer 886 may calculate the extent of similarity of PPG signals of a certain user in current measurements from among the current measurements 883 with a template generated based on previously measured PPG signals of that certain user (which may be in a database). Optionally, if the extent of similarity exceeds a threshold, the certain user may be considered authenticated. Additionally or alternatively, in some embodiments, authenticating the certain user may utilize additional signals from among current measurements 883 mentioned herein as useful for authentication, such as acoustic signals and/or movement signals.

The computer 886 may then utilize authentications of non-symptomatic users in order to manage access to the premises 889.

In one embodiment, the computer 886 notifies the non-symptomatic users, prior to their respective intended arrival times, that they are allowed on the premises 889.

In one embodiment, the computer 886 send notifications 887 to the users 888, indicating to each user whether the user will be allowed on the premises 889.

In one embodiment, the computer 886 receives additional measurements of a certain user among the non-symptomatic users, taken with a wearable device from among the wearable devices 878 after the current measurements of the certain user were taken, calculates an additional health score of the certain user based on differences between the additional measurements of the certain user and baseline measurements of the certain user, detects that the additional health score does not reach the threshold, and notifies the certain user that he/she not allowed on the premises 889.

In one embodiment, the computer 886 identifies a second subset of the users 888 as symptomatic users based on their health scores not reaching the threshold, and notifies the symptomatic users, prior to their respective arrival times, that they are not allowed on the premises 889.

In one embodiment, the computer 886 certifies the premises 889 as contagion-safe responsive to receiving an indication that none of the symptomatic users entered the premises 889 during a predetermined period. In one example, the indication that none of the symptomatic users entered the premises is received from a physical access security system that identifies the person at the gate/door/premises, such as: proximity card access system, smart card access system, swipe card access system, multi-technology access system, keypad access system, biometric access system, mobile access system, and/or video intercom access system.

In one embodiment, the premises 889 is an airplane, the intended arrival time is a boarding time to the airplane. Optionally, the computer 886 directs the non-symptomatic users and people who were not identified as non-symptomatic users to different airplanes. Alternatively, the computer 886 places the users 888 in the airplane according to cohorts, such that >75% of the passengers who sit in proximity of up to two rows from people who were not identified as non-symptomatic users are also people who were not identified as non-symptomatic users, and >75% of the passengers who sit in proximity of up to two rows from the non-symptomatic users are non-symptomatic users.

In another embodiment, the premises 889 is a train passenger car, and the computer 886 directs the non-symptomatic users and people who were not identified as non-symptomatic users to different cars.

Figure 13:
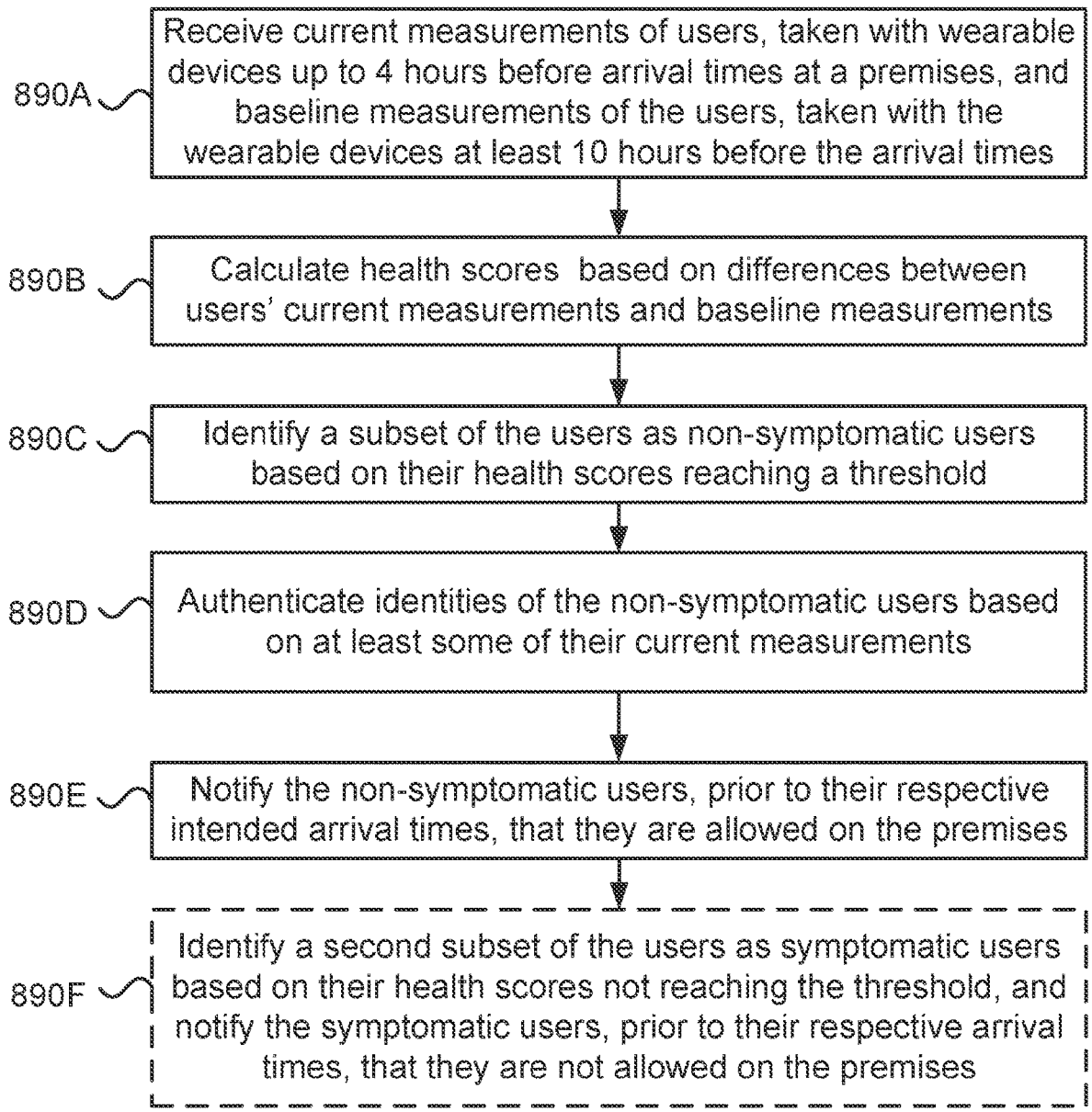
FIG. 13 illustrates steps that may be part of embodiments of a method for managing access to a contagion-safe premises.

FIG. 13B illustrates steps that may be part of embodiments of a method for managing access to a contagion-safe premises. The method may be implemented using embodiments of systems illustrated in FIG. 11, which is discussed above. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform steps from among the steps illustrated in FIG. 13B and/or additional steps mentioned below.

In one embodiment, the method for managing access to a contagion-safe premises includes at least the following steps:

- In Step 890A, receiving measurements of users, measured with wearable devices, comprising photoplethysmogram signals and temperature signals. Optionally, the measurements include, for each users from among the users, current measurements and baseline measurements. Optionally, the current measurements of the user are measured with a wearable device up to 4 hours before an intended arrival time of the user to a premises, and baseline measurements of the user are measured with the wearable device at least 10 hours before the intended arrival time of the user.
- In Step 890B, calculating, for each user from among the users, a health score of the user based on a difference between current measurements of the user and baseline measurements of the user.
- In Step 890C, identifying a subset of the users as non-symptomatic users based on their health scores reaching a threshold.
- In Step 890D, authenticating identities of the non-symptomatic users based on at least some of their current physiological signals.
- And in Step 890E, notifying the non-symptomatic users, prior to their respective intended arrival times, that they are allowed on the premises.

In one embodiment, the method optionally includes Step 890F that involves: identifying a second subset of the users as symptomatic users based on their health scores not reaching the threshold, and notifying the symptomatic users, prior to their respective arrival times, that they are not allowed on the premises.

In one embodiment, the method optionally includes a step of certifying the premises as contagion-safe responsive to receiving an indication that none of the symptomatic users entered the premises during a predetermined period.

In another embodiment, the method optionally includes the following steps: receiving additional measurements of a certain user among the non-symptomatic users, taken after the current measurements of the certain user were taken, calculating an additional health score of the certain user based on differences between the additional measurements of the certain user and baseline measurements of the certain user, detecting that the additional health score does not reach the threshold, and notifying the certain user that he/she not allowed on the premises.

Blood flow in the face can cause certain facial coloration due to concentration of hemoglobin in various vessels such as arterioles, capillaries, and venules. In some embodiments described herein, coloration at a certain facial region, and/or changes thereto (possibly due to varying volume of blood in the certain region at different stages of cardiac pulses), can represent a hemoglobin concentration pattern at the certain region. This pattern can change because of various factors that can affect blood flow and/or vascular dilation, such as the external temperature, core body temperature, the emotional state, consumption of vascular dilating substances, and more. Embodiments described herein utilize analysis of images of the user's face, in which a hemoglobin concentration pattern can be detected, in order to detect various phenomena that may influence facial temperature, such as having a fever, being intoxicated, and/or in order to estimate physiological parameters such as the core body temperature.

In some embodiments, a hemoglobin concentration pattern calculated from images refers to a color mapping of various portions of the area captured in the images (e.g., the mapping provides the colors of different pixels in the images). In one example, the color mapping provides values that are average intensities of one or more colors of the pixels over a period of time during which the images were taken (e.g., values from one or more channels in the images). In another example, the color mapping provides values that are average intensities of one or more colors of the pixels over a period of time during which the images were taken (e.g., values of the maximum of one or more channels in the images). In yet another example, a hemoglobin concentration pattern may be a function of one or more colors (channels) of the pixels over a period of time during which the images were taken.

In other embodiments, a hemoglobin concentration pattern may refer to time series data, such as a sequence of images representing a progression of a pulse wave in the area. Different physiological conditions, such as different skin or core body temperatures or emotional responses, may produce different sequences of representative images, which depend on the structure of the facial blood vessels of the user and their dilation.

In still other embodiments, a hemoglobin concentration pattern may refer to a contour map, representing the extent to which pixels at a certain wavelength (e.g., corresponding to the color red) have at least a certain value. Since the extent of hemoglobin concentration is correlated with an increase in intensity of certain colors (e.g., red), a hemoglobin concentration pattern for more dilated blood vessels will have different contour map than the contour map observed in a hemoglobin concentration pattern for that blood vessels when it is more contracted.

A hemoglobin concentration pattern, such as one of the examples described above, may be calculated, in some embodiments, from images by a computer, such as computer 340 (described below). Optionally, the hemoglobin concentration pattern may be utilized to generate one or more feature values that are used in a machine learning-based approach by the computer for various applications, such as detecting fever, calculating core body temperature, detecting intoxication, and/or other applications described below. In other embodiments, the hemoglobin concentration pattern may be utilized to calculate additional values used to represent the extent of facial blood flow and/or extent of vascular dilation, which may be evaluated, e.g., by comparing the extent of blood flow and/or vascular dilation to thresholds in order to detect whether the user has a fever, estimate core body temperature, detect alcohol intoxication, and/or for other applications described herein.

In one embodiment, a hemoglobin concentration pattern may be converted to a value representing the proportion of the area in which the intensities of pixels reach a threshold. In one example, the intensities being evaluated may be average intensities (e.g., average pixel intensities in the images). In another example, the intensities being evaluated may be maximum intensities corresponding to times of systolic peaks (e.g., as determined by detecting the spread of a pulse wave in the area captured in the images, and/or using a reference signal from a different source such as a PPG sensor that is not the camera that captured the images).

In another embodiment, a hemoglobin concentration pattern may be compared with one or more reference hemoglobin concentration patterns that may correspond to specific physiological conditions (e.g., having a fever, not having a fever, or a specific core body temperature). Optionally, the reference patterns may be based on previously taken images of the user, which were taken at times for which the user's core body temperature was known (e.g., based on a measurement using a thermometer). Optionally, similarity of a hemoglobin concentration pattern to a reference pattern may be utilized to generate one or more feature values utilized in a machine learning approach, as described below. Optionally, the extent of similarity of a hemoglobin concentration pattern to a reference pattern may be utilized to determine whether the user has a certain condition (e.g., fever), as described below.

Various embodiments described herein involve a computer that calculates a hemoglobin concentration pattern. Optionally, values in a hemoglobin concentration pattern may be mapped to specific regions on the face, such that the hemoglobin concentration pattern may be considered a layer or grid that can be mapped onto the face in a predetermined manner.

There are various ways in which a hemoglobin concentration pattern may be calculated in embodiments described herein. Optionally, calculating a hemoglobin concentration pattern involves processing the images, for example, in order to accentuate the color of one or more channels in the images, and/or accentuate the changes to colors of one or more channels in the images (e.g., accentuating color changes caused by blood flow from cardiac pulses). Additionally or alternatively, calculating a hemoglobin pattern may involve calculating a representation of the pattern by assigning values to regions in the images and/or to a representation of regions on the face. Optionally, the values may represent extents of one or more color channels at the different regions. Optionally, the values may represent changes to extents of one or more color channels at the different regions. Optionally, the values may include time series data representing temporal changes to extents of one or more color channels at each of at least some of the different regions.

The following are some examples of processing methods that may be applied to images in order to calculate a hemoglobin concentration pattern based on images. In some embodiments, one or more of the processing methods may be applied by the computer before hemoglobin concentration patterns are used for calculations and/or detections (e.g., prior to detecting fever, intoxication, and/or estimating core body temperature). For example, the images may be processed using one or more of the methods described below, prior to their utilization by the computer to calculate hemoglobin concentration patterns used for the calculations and/or detections. In some embodiments, one or more of the processing methods may be applied by the computer as part of the calculations and/or detections. For example, some layers and/or portions of a deep learning network used by the computer for the calculations and/or detections may implement processing operations of the images (which are involved in calculating the hemoglobin concentration patterns), while other portions of the deep learning network are used to perform the calculations and/or detections on values representing the hemoglobin concentration patterns.

Various preprocessing approaches may be utilized in order to assist in calculating hemoglobin concentration patterns based on images. Some non-limiting examples of the preprocessing approaches that may be used include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081, titled "Estimating cardiac pulse recovery from multi-channel source data via constrained source separation". Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from the images are discussed in Zaunseder et al. (2018), "Cardiovascular assessment by imaging photoplethysmography—a review", Biomedical Engineering 63(5), 617-634. An example of preprocessing that may be used in some embodiments is given in U.S. Pat. No. 9,020,185, titled "Systems and methods for non-contact heart rate sensing", which describes how times-series signals obtained from video of a user can be filtered and processed to separate an underlying pulsing signal by, for example, using an ICA algorithm.

Another approach that may be utilized as part of preprocessing and/or calculation of hemoglobin concentration patterns involves Eulerian video magnification, as described in Wu, Hao-Yu, et al. "Eulerian video magnification for revealing subtle changes in the world." ACM transactions on graphics (TOG) 31.4 (2012): 1-8, and also in the hundreds of references citing this reference. The goal of Eulerian video magnification is to reveal temporal variations in videos that are difficult or impossible to see with the naked eye and display them in an indicative manner. This method takes a standard video sequence as input, and applies spatial decomposition, followed by temporal filtering to the frames. The resulting signal is then amplified to reveal hidden information. This method is successfully applied in many applications in order to visualize the flow of blood as it fills the face and also to amplify and reveal small motions.

In one embodiment, calculating a hemoglobin concentration pattern may involve assigning values to regions on the face and/or in the images that are binary values. FIG. 14A illustrates an example of a hemoglobin concentration pattern of a sober person where certain regions have a value "0" because the color of the red channel in the certain regions is below a certain threshold, and other regions have a value "1" because the color of the red channel in the other regions is above the threshold. FIG. 14B illustrates an example of the hemoglobin concentration pattern of the same person when intoxicated, and as a result the face is redder in certain locations.

In another embodiment, calculating a hemoglobin concentration pattern may involve assigning values to regions on the face and/or in the images, which are continuous. In one example, in a first hemoglobin concentration pattern, the pattern may include values in a two-dimensional grid corresponding to average intensities and/or maximum intensities of colors from one or more channels. In another example, in a second hemoglobin concentration pattern, the pattern may include values obtained after processing the images using techniques described herein for extracting iPPG signals. Thus, the pattern, in this example, may include values representing statistics of PPG signals at different regions on the face (e.g., the pattern may include values that are the average or maximum of the PPG signals at the different regions). In another example, the pattern may include averages of values of certain fiducial points (e.g., systolic peaks and/or dicrotic notches) extracted from PPG signals at different regions using iPPG techniques known in the art.

In yet another embodiment, calculating a hemoglobin concentration pattern may involve assigning values to regions on the face and/or in the images, which are a time series. In one example, in a hemoglobin concentration pattern, the pattern may include values in a two-dimensional grid, where each position in the gird is a time series that represents a shape of a PPG pulse wave at the location on the face corresponding to the position. Optionally, the time series for the position may be extracted from images corresponding to multiple pulse waves (and thus represent a typical PPG shape of a pulse wave at location on the face).

FIG. 14C is a schematic illustration of components of a system configured to detect fever and/or intoxication (e.g., due to alcohol consumption). In one embodiment, the system includes at least first and second head-mounted inward-facing cameras 332 that take images 333 of respective first and second regions on a user's face. Henceforth, for the sake of brevity, "the first and second head-mounted inward-facing cameras 332" will be referred to as "the cameras 332". Optionally, the cameras 332 are physically coupled to a frame of smartglasses 330. The system also includes a computer 340, which may or may not be physically coupled to the frame of the smartglasses 330. The system may include additional elements such as a movement sensor, an inertial measurement unit (IMU) 342, a skin temperature sensor 343, an environment sensor 344 that is configured to measure temperature and/or humidity of the environment, and/or a user interface 348.

In one embodiment, the computer 340 calculates, based on baseline images captured with the cameras 332 while the user did not have a fever, a baseline pattern comprising values indicative of first and second baseline hemoglobin concentrations at the first and second regions on the user's face, respectively. Additionally, the computer 340 calculates, based on a current set of images captured with the cameras 332, a current pattern comprising values indicative of first and second current hemoglobin concentrations at the first and second regions, respectively. In this embodiment, the computer 340 detects whether the user has a fever based on a deviation of the current pattern from the baseline pattern.

In some embodiments, the user is considered to have a fever if the user's body temperature rises above a predetermined extent beyond the baseline ("normal") body temperature for the user. For example, if the user's body temperature rises by 1.5° C. or more above normal, the user is considered to have a fever. In other embodiments, the user is considered to have a fever if the user's body temperature rises above a predetermined threshold (which may or may not be specific to the user, and may or may not depend on the hour of the day because the normal temperature may be a function of the hour of the day). For example, if the user's body temperature rises above 38° C., the user is considered to have a fever.

In another embodiment, the computer 340 calculates, based on baseline images captured with the cameras 332 while the user was sober, a baseline pattern comprising values indicative of first and second baseline hemoglobin concentrations at the first and second regions on the user's face, respectively. Additionally, the computer 340 calculates, based on a current set of images captured with the cameras 332, a current pattern comprising values indicative of first and second current hemoglobin concentrations at the first and second regions, respectively. In this embodiment, the computer 340 detects whether the user is intoxicated based on a deviation of the current pattern from the baseline pattern.

In some embodiments, the user is considered to be intoxicated (from alcohol) if the user's Blood Alcohol Level (BAC) is above a predetermined threshold. For example, the user may be considered intoxicated if the BAC is above 0.05%, 0.08%, or 0.1%. In other embodiments, the user may be considered intoxicated if the user consumed at least a certain amount of alcohol during a preceding window of time. For example, the user may be considered intoxicated if the user consumed at least two standard drinks (e.g., two bottles of beer with 5% alcohol content) during a period of two hours or less. In still other embodiments, the user may be considered intoxicated if the user is assessed to exhibit behavior consistent with intoxication and/or is considered unable to care for the safety of oneself or others.

The smartglasses 330 are configured to be worn on a user's head. Optionally, various sensors and/or cameras that are physically coupled to the smartglasses 330, e.g., by being attached to and/or embedded in the frame of the smartglasses 330, are used to measure the user while the user wears the smartglasses 330. Optionally, at least some of the sensors and/or cameras that are physically coupled to the smartglasses 330 may be utilized to measure the environment in which the user is in. In one example, the smartglasses 330 are eyeglasses with sensors and electronics attached thereto and/or embedded therein. In another example, the smartglasses 330 may be an extended reality device (i.e., an augmented realty device, a virtual reality device, and/or mixed reality device). In some embodiments, the cameras 332 are physically coupled to the frame of the smartglasses 330.

Each camera from among the cameras 332 is located less than 10 cm from the face of the user (to whose head the cameras are mounted). Additionally, the first and second head-mounted inward-facing cameras 332 are configured to capture images of respective first and second regions on the user's face (i.e., the first camera captures images of the first region and the second camera captures images of the second region). The first and second regions do not completely overlap.

Having multiple inward-facing head-mounted cameras close to the face can confer the advantage of covering many regions on the face, while still having an aesthetic head-mounted system (due to the close distances of the cameras from the face) and stable and sharp images (due to the cameras capturing the same regions even when the user makes angular motions). In some embodiments, the cameras 332 may be at closers distances to the face. In one example, each of the cameras 332 is less than 5 cm from the user's face. In another example, each of the cameras 332 is less than 2 cm from the user's face.

The locations, orientations, and/or optical properties of the first and second head-mounted inward-facing cameras 332 can cause them to capture images of different respective first and second regions. Optionally, each of the first and second regions contains an area of at least 1 cm² of skin on the user's face. Optionally, each of the first and second regions contains an area of at least 4 cm² of skin on the user's face.

In some embodiments, the middle of the first region is not at the same location as the middle of the second region. In one example, the middles of the first and second regions are at least 1 cm apart. In another example, the middles of the first and second regions are at least 4 cm apart. In yet another example, the middles of the first and second regions are at least 8 cm apart.

Herein, the middle of a region is the average co-ordinate of points in the region (e.g., when points in the region can be described as residing in a two- or three-dimensional space).

In one example, the first region is located above the user's eyes, and the second region is located below the user's eyes. Optionally, in this example, the first and second regions do not overlap. In another example, the middle of the first region is located less than 4 cm from the vertical symmetric axis of the user's face, and the middle of the second region is located more than 4 cm from the vertical symmetric axis. Optionally, in this example, the first and second regions do overlap.

The first and second head-mounted inward-facing cameras 332 are small and lightweight. In some embodiments, each of the cameras 332 weighs below 10 g and even below 2 g. In one example, each of these cameras is a multi-pixel video camera having a CMOS or a CCD sensor. The video camera may capture images at various rates. In one example, the images 333 include images captured at a frame rate of at least 3 frames per second (fps). In another example, the images 333 include images captured at a frame rate of at least 30 fps. In still another example, the images 333 include images captured at a frame rate of at least 256 fps. Images taken by the cameras 332 may have various resolutions. In one example, the images 333 include images that have a resolution of at least 8×8 pixels. In another example, the images 333 include images that have a resolution of at least 32×32 pixels. In yet another example, the images 333 include images that have a resolution of at least 640×480 pixels.

In some embodiments, at least one of the cameras 332 may capture light in the near infrared spectrum (NIR). Optionally, such a camera may include optics and sensors that capture light rays in at least one of the following NIR spectrum intervals: 700-800 nm, 700-900 nm, 700-1,050 nm. Optionally, the sensors may be CCD sensors designed to be sensitive in the NIR spectrum and/or CMOS sensors designed to be sensitive in the NIR spectrum.

In one example, the cameras 332 are mounted between 5 mm and 50 mm away from the user's head. Examples of camera sensors that are sensitive to wavelengths below 1050 nm include CCD and CMOS sensors, which are sensitive to wavelengths in at least a portion of the range of 350 nm to 1050 nm.

In some embodiments, the system may include an optical emitter configured to direct electromagnetic radiation at the first and/or second regions. Optionally, the optical emitter comprises one or more of the following: a laser diode (LD), a light-emitting diodes (LED), and an organic light-emitting diode (OLED). It is to be noted that when embodiments described in this disclosure utilize optical emitters directed at a region of interest (ROI), such as an area appearing in images 333, the optical emitter may be positioned in various locations relative to the ROI. In some embodiments, the optical emitter may be positioned essentially directly above the ROI, such that electromagnetic radiation is emitted at an angle that is perpendicular (or within 10 degrees from being perpendicular) relative to the ROI. Optionally, a camera may be positioned near the optical emitter in order to capture the reflection of electromagnetic radiation from the ROI. In other embodiments, the optical emitter may be positioned such that it is not perpendicular to the ROI. Optionally, the optical emitter does not occlude the ROI. In one example, the optical emitter may be located at the top of a frame of a pair of eyeglasses, and the ROI may include a portion of the forehead. In another example, optical emitter may be located on an arm of a frame of a pair of eyeglasses and the ROI may be located above the arm or below it.

Due to the position of the cameras 332 relative to the face, in some embodiments, there may be an acute angle between the optical axis of a camera from among these cameras and the area captured by images taken by said camera (e.g., when the camera is fixed to an eyeglasses frame and the area is on, and/or includes a portion of, the forehead or a cheek). In order to improve the sharpness of images captured by said camera, the camera may be configured to operate in a way that takes advantage of the Scheimpflug principle. In one embodiment, a camera from among the cameras 332 includes a sensor and a lens; the sensor plane is tilted by a fixed angle greater than 2° relative to the lens plane according to the Scheimpflug principle in order to capture a sharper image when the smartglasses are worn by the user (where the lens plane refers to a plane that is perpendicular to the optical axis of the lens, which may include one or more lenses). In another embodiment, the camera includes a sensor, a lens, and a motor; the motor tilts the lens relative to the sensor according to the Scheimpflug principle. The tilt improves the sharpness of images when the smartglasses are worn by the user. Additional details regarding the application of the Scheimpflug principle are discussed further below.

In some embodiments, the system may include a short-wave infrared (SWIR 334) inward-facing head-mounted camera that is configured to detect wavelengths in at least a portion of the range of 700 nm to 2500 nm. One example of a SWIR sensor suitable for this embodiment is Indium Gallium Arsenide (inGaAs) sensor. Optionally, the computer 340 is configured to detect whether the user has the fever also based on a deviation of a current SWIR pattern from a baseline SWIR pattern taken while the user did not have a fever. Optionally, the current SWIR pattern is generated based on images taken with the SWIR 334 at a current time, while the baseline SWIR pattern is generated based on SWIR-images 335 taken with the SWIR 334 during one or more previous periods, while the user did not have a fever. In some embodiments, at least some of the feature values, described further below, which are generated based on images from among the images 333 may be generated for the SWIR-images 335. Thus, SWIR-images 335 may be utilized, in some embodiments, as inputs for a detection of whether the user has a fever and/or is intoxicated.

Variations in the reflected ambient light may introduce artifacts into images collected with inward-facing cameras that can add noise to these images and make detections and/or calculations based on these images less accurate. In some embodiments, the system includes an outward-facing camera, which is coupled to the smartglasses, and takes images of the environment. Optionally, this outward-facing camera is located less than 10 cm from the user's face and weighs below 5 g. Optionally, the outward-facing camera may include optics that provide it with a wide field of view.

The computer 340 is configured, in some embodiments, to detect a certain condition (e.g., whether the user has a fever or whether the user is intoxicated) based on a deviation of a current pattern from a baseline pattern.

In different embodiments, a reference to "the computer 340" may refer to different components and/or a combination of components. In some embodiments, the computer 340 may include a processor located on a head-mounted device, such as the smartglasses 330. In other embodiments, at least some of the calculations attributed to the computer 340 may be performed on a remote processor, such as the user's smartphone and/or a cloud-based server. Thus, references to calculations being performed by the "computer 340" should be interpreted as calculations being performed utilizing one or more computers, with some of these one or more computers possibly being of a head-mounted device to which the cameras 332 are coupled.

The current pattern is calculated, by the computer 340, based on current images, from among the images 333, captured by the cameras 332. The current images are taken during some times that fall during a window leading up to a current time. Optionally, the window is at most five second long. Optionally, the window is at most 30 seconds long. Optionally, the window is at most 5 minutes long. Optionally, the window is at most one hour long. The current images taken during the window are utilized by the computer 340 to calculate the current pattern, which is indicative of at least first and second current hemoglobin concentrations at the first and second regions, respectively. It is to be noted that images taken during the window need not be taken continuously throughout the window, rather they may be taken intermittently or sporadically during the window.

As discussed below, extents of reflection and absorption of light through the skin may depend on the wavelength of the light. Thus, in some embodiments, patterns of hemoglobin concentration may include values calculated based on different channels of the same images. Thus, in the detection of fever and/or intoxication, the baseline pattern and/or current pattern may include multiple sets of values derived from multiple different channels.

The baseline pattern is calculated, by the computer 340, based on baseline images from among the images 333, captured by the cameras 332. Optionally, the baseline images were taken previously (prior to when the current images were taken) while the user was not in a state being detected. In one embodiment, in which the computer 340 detects whether the user has a fever, the baseline images were taken while the user did not have a fever. In another embodiment, in which the computer 340 detects whether the user is intoxicated, the baseline images were taken while the user was sober (or assumed to be sober).

Windows during which baseline images were taken may have different lengths, and end prior to the current time. Optionally, windows during which baseline images are taken end before the current window begins. In one example, the baseline images may have been taken at different times during a window spanning several hours. In another example, the baseline images include images taken at different times during a window spanning several days/weeks/months, such that the baseline images include images taken on different days/weeks/months, respectively.

In some embodiments, the computer 340 may receive indications indicative of times in which the user is in a baseline state (e.g., without a fever or not intoxicated). Optionally, at least some of the baseline images are selected based on the indications. For example, images taken by the cameras 332 are included in the baseline images if there is an indication indicating the user was in a baseline state within temporal proximity to when they were taken. In one example, images taken within a window spanning from an hour before to an hour after a time for which there is an indication that the user was in a baseline state, are included in the baseline images. In another example, images taken within a window spanning from five minutes before to five minutes after a time for which there is an indication that the user was in a baseline state, are included in the baseline images. In yet another example, images taken within a window spanning from 30 seconds before to 30 seconds after a time for which there is an indication that the user was in a baseline state, are included in the baseline images.

The indications indicative of the times in which the user is in a baseline state may come from one or more sources. In some embodiments, indications may be self-reported. For example, the user may provide indications indicating when he/she were sober and/or without a fever. In other embodiments, some other person such as a caregiver, physician, supervisor, and/or guardian may provide such indications. In still other embodiments, indications may be received from sensors that measure the user, which are not the cameras 332. In one example, temperature measurements taken by an oral thermometer and/or a non-head-mounted thermal camera are used to determine whether the user has a fever. In another example, analysis of the user's movements (e.g., as measured by the IMU 342) and/or voice patterns (as recorded with microphones) are used to determine whether the user is intoxicated or not (e.g., using machine learning methods known in the art).

In some embodiments, images taken in a certain context are assumed to be taken in a baseline state. In one example, images taken in the daytime at school/work, while the user behaved as expected from a sober/healthy person, are assumed to be taken while the user was not intoxicated and/or without a fever. In another example, all images taken while there is no indication that the user was not in a baseline state, are assumed to be taken in the baseline state. In this example, it may be assumed (for most normative people) that most of the time the user does not have a fever and/or is not intoxicated.

The baseline images are utilized by the computer 340 to calculate the baseline pattern, which is indicative of at least first and second baseline hemoglobin concentrations at the first and second regions, respectively. In one example, the baseline pattern is indicative of first and second baseline hemoglobin concentrations at the first and second regions characteristic of times at which the user does not have a fever, or is not intoxicated.

In addition to a baseline pattern indicating hemoglobin concentrations characteristic of times in which the user is in a baseline state, in some embodiments, the computer 340 may utilize a detected-state pattern indicating hemoglobin concentrations characteristic of times in which the user is in the detected state (e.g., has a fever and/or is intoxicated). Optionally, detection of whether the user is in the detected state is done by a deviation of the current pattern from the detected-state pattern. Optionally, the detected-state pattern is calculated by the computer 340 based on additional images, from among the images 333, taken at times at which there was an indication that the user was in a certain state (e.g., had a fever and/or was intoxicated). Optionally, the indications may be self-reported, provided by another person, and/or a result of analysis of sensor measurements, as described above.

In one embodiment, the computer 340 calculates, based on additional baseline images captured with the cameras 332 while the user had a fever, a fever-baseline pattern comprising values indicative of first and second fever hemoglobin concentrations at the first and second regions, respectively. The computer 340 then bases the detection of whether the user has the fever also on a deviation of the current pattern from the fever-baseline pattern (in addition to the deviation from the baseline pattern).

In one embodiment, the computer 340 calculates, based on additional baseline images captured with the cameras 332 while the user was intoxicated, an intoxication-baseline pattern comprising values indicative of first and second intoxication hemoglobin concentrations at the first and second regions, respectively. The computer 340 then bases the detection of whether the user is intoxicated also based on a deviation of the current pattern from the intoxication baseline pattern in addition to the deviation from the baseline pattern).

Detection of reflections of light at different wavelengths can be used to account for thermal interference by the environment. In some embodiments, accounting for thermal inference relies on the following three observations:
(i) blue and green wavelengths penetrate the skin less deeply compared to red and near-infrared wavelengths, (ii) the capillaries are closer to the skin surface compared to the arterioles, and (iii) the PPG amplitude is proportional to the skin temperature, probably because both blood viscosity and vasoconstriction increase with the increase in skin temperature. Additionally, we will examine the ratio $R_{depth}$, which is defined as follows $$R_{depth} = \frac{\text{reflected light from the capillaries}}{\text{reflected light from the arterioles}}$$

Based on the aforementioned observations, it is to be expected that $R_{depth}$ will be greater for the blue and green wavelengths compared to the red and near-infrared wavelengths. This means that temperature interference from the environment is expected to influence the hemoglobin concentration pattern derived from the blue and green wavelengths more than it influences the hemoglobin concentration pattern derived from the red and near-infrared wavelengths.

In one embodiment, because environment heating increases vasodilation whilst environment cooling decreases blood flow to the skin, and because temperature interference from the environment is expected to influence a hemoglobin concentration pattern derived from the blue and/or green wavelengths more than it influences a hemoglobin concentration pattern derived from the red and/or near-infrared wavelengths, the system can improve its accuracy when estimating temperatures, such as the core body temperature and/or detecting fever based on the level of discrepancy between (i) a hemoglobin concentration pattern derived from a first channel corresponding to wavelengths mostly below 580 nanometers, such as the blue and/or green reflections, and (ii) the hemoglobin concentration pattern derived from a second channel corresponding to wavelengths mostly above 580 nanometers, such as the red and/or near-infrared reflections.

It is noted that most optical filters are not perfect, and the meaning of the sentence "channel corresponding to wavelengths mostly below 580 nanometers" is that the filter suppresses red and near-infrared at least twice as much, compared to blue and/or green. Similarly, the meaning of the sentence "channel corresponding to wavelengths mostly above 580 nanometers" is that the filter suppresses blue and green at least twice as much, compared to red and/or near-infrared.

For example, when a temperature corresponding to hemoglobin concentration pattern derived from the blue and/or green wavelengths is higher than a predetermined threshold compared to a temperature corresponding to the hemoglobin concentration pattern derived from the red and/or near-infrared wavelengths, this may indicate that the user is in a hot environment (such as being close to a heater or in direct sunlight), and/or that the user has just arrived from a hot environment (such as entering a cold building from a hot summer street). In another example, when a temperature corresponding to hemoglobin concentration pattern derived from the blue and/or green wavelengths is lower than a predetermined threshold from the temperature corresponding to the hemoglobin concentration pattern derived from the red and/or near-infrared wavelengths, this may indicate that the user is in a cold environment, and/or that the user is being exposed to a wind that cools the skin.

In one embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. Optionally, the current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Having separate values for different wavelengths enables to account for interference from the environment when detecting whether the user has the fever because temperature interference from the environment is expected to affect the third values more than it affects the fourth values.

In another embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. The current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Optionally, the computer 340 calculates a confidence in a detection of the fever based on the deviation of the current pattern from the baseline pattern, such that the confidence decreases as the difference between the third values and the fourth values increases. For example, the confidence is a value proportional to said deviation. Having separate values for different wavelengths enables to account for interference from the environment when calculating said confidence because temperature interference from the environment is expected to affect the third values more than it affects the fourth values.

In some embodiments, the computer 340 calculates the values indicative of the baseline and current hemoglobin concentrations based on detecting facial flushing patterns in the baseline and current images. In one example, the facial flushing patterns are calculated based on applying decorrelation stretching to the images (such as using a three color space), then applying K-means clustering (such as three clusters corresponding to the three color space), and optionally repeating the decorrelation stretching using a different color space. In another example, the facial flushing patterns are calculated based on applying decorrelation stretching to the images (such as using a three color space), and then applying a linear contrast stretch to further expand the color range.

There are various computational approaches that may be utilized by the computer 340 in order to detect whether the user has a fever, and/or is intoxicated, based on a deviation of a current pattern from a baseline pattern.

In one embodiment, the computer 340 calculates a value indicative of a magnitude of the deviation of the current pattern from the baseline pattern. For example, when both patterns include numerical values, the values in corresponding regions in both patterns may be subtracted from each other. In FIG. 14A and FIG. 14B, this may be interpreted as calculating the difference in the number of "1"s in both patterns. Optionally, if the subtraction of the baseline pattern from the current pattern reaches a certain threshold, the user is assumed to be in a certain state (e.g., has a fever and/or is intoxicated).

In another embodiment, the computer 340 calculates a value indicative of the deviation between the current pattern and the baseline pattern based on vector representations of the patterns. For example, if each of the patterns may be represented as a vector in a multi-dimensional space, the deviation may be calculated using one or more techniques known in the art for calculating distances between vectors, such as a dot product, Euclidean distance, or a distance according to some other norm. Optionally, if the distance has at least a certain value, the user is assumed to be in a certain state (e.g., has a fever and/or is intoxicated).

In yet another embodiment, if the difference between a vector representation of the current pattern and a vector representation of the baseline pattern is in a certain direction, the computer 340 detects the user is in a certain state corresponding to the certain direction. For example, there may be a predetermined direction of change for patterns when the user becomes intoxicated.

In still another embodiment, in which the current pattern and the baseline pattern include time series data, the computer 340 utilizes methods known in the art for comparison of time series, such as dynamic time warping, in order to calculate an extent of deviation of the current pattern from the baseline pattern.

In some embodiments, the computer 340 may utilize the fever-baseline pattern and/or the intoxication-baseline pattern, which are discussed above, in order to detect whether the user has a fever and/or is intoxicated. In one example, if the current pattern is more similar to the fever baseline pattern than it is to the baseline pattern, the computer 340 detect the user has a fever. In another example, if a first difference between the current pattern and the intoxication-baseline pattern is below a first threshold, while a second difference between the current pattern and the baseline pattern is above a second threshold, the computer 340 detects the user is intoxicated.

Detection of whether the user has a fever and/or is intoxicated may involve utilization of machine learning approaches. In some embodiments, baseline images and/or current images may be utilized by the computer 340 to generate feature values that are used in a machine learning-based approach by the computer 340 to detect whether the user has a fever and/or is intoxicated. In some embodiments, the computer 340 calculates the feature values based on data that includes at least some of the images 333 (and possibly other data) and utilizes a model 346 to calculate, based on the feature values, a value indicative of whether the user has a fever and/or a value indicative of whether the user is intoxicated.

In one embodiment, the value calculated by the computer 340 based on the feature values is a binary value. For example, the value is "1" if the user has a fever and "0" if the user does not have a fever. In some embodiments, the value calculated by the computer 340 based on the feature values is a scalar. For example, the calculated value may be an estimation of the user's core body temperature and/or an estimation of the increase of the user's core body temperature. In such embodiments, if the calculated value reaches a threshold, the user is considered to have a fever. In a similar fashion, a binary value may be calculated in the case of intoxication, and detecting intoxication may be done if a calculated value indicative of an intoxication level of the user reaches a predetermined threshold.

Generally, machine learning-based approaches utilized by embodiments described herein involve training a model on samples, with each sample including: feature values generated based on images taken by the cameras 332, and optionally other data, which were taken during a certain period, and a label indicative of an extent of fever and/or intoxication (during the certain period). Optionally, a label may be provided manually by the user and/or other sources described above as providing indications about the state of the user (e.g., indications of a fever level and/or intoxication level, described above). Optionally, a label may be extracted based on analysis of electronic health records of the user, generated while being monitored at a medical facility.

In some embodiments, the model 346 may be personalized for a user by training the model on samples that include: feature values generated based on measurements of the user, and corresponding labels indicative of the extent of fever and/or intoxication of the user while the measurements were taken. In some embodiments, the model 346 may be generated based on measurements of multiple users, in which case, the model 346 may be considered a general model. Optionally, a model generated based on measurements of multiple users may be personalized for a certain user by being retrained on samples generated based on measurements of the certain user.

There are various types of feature values that may be generated by the computer 340 based on input data, which may be utilized to calculate a value indicative of whether the user has a fever and/or is intoxicated. Some examples of feature values include "raw" or minimally processed values based on the input data (i.e., the features are the data itself or applying generic preprocessing functions to the data). Other examples of feature values include feature values that are based on higher-level processing, such a feature values determined based on domain-knowledge. In one example, feature values may include values of the patterns themselves, such as values included in the current pattern, the baseline pattern, the fever-baseline pattern, and/or the intoxication-baseline pattern. In another example, feature values may include values that are functions of patterns, such as values that represent a deviation of the current pattern from the baseline pattern.

In one non-limiting example, feature values generated by the computer 340 include pixel values from the images 333. In another non-limiting example, feature values generated by the computer 340 include timings and intensities corresponding to fiducial points identified in iPPG signals extracted from the images 333. In yet another non-limiting example, feature values generated by the computer 340 include binary values representing the baseline pattern and the current pattern.

The following are some examples of the various types of feature values that may be generated based on images from among the images 333 by the computer 340. In one embodiment, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may derived from multiple images taken at different times, such as volume local binary patterns (VLBP), cuboids, and/or optical strain-based features. In one example, one or more of the feature values may represent a difference between values of pixels at one time t at a certain location on the face and values of pixels at a different location at some other time t+x (which can help detect different arrival times of a pulse wave).

In some embodiments, at least some feature values utilized by the computer 340 describe properties of the cardiac waveform in an iPPG signal derived from images from among the images 333. To this end, the computer 340 may employ various approaches known in the art to identify landmarks in a cardiac waveform (e.g., systolic peaks, diastolic peaks), and/or extract various types of known values that may be derived from the cardiac waveform, as described in the following examples.

In one embodiment, at least some of the feature values generated based on the iPPG signal may be indicative of waveform properties that include: systolic-upstroke time, diastolic time, and the time delay between the systolic and diastolic peaks, as described in Samria, Rohan, et al. "Non-invasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the iPPG signal may be derived from another analysis approach to PPG waveforms, as described in US Patent Application US20180206733, entitled "Device, method and system for monitoring and management of changes in hemodynamic parameters". This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated by the computer 340, which are suggested in the aforementioned publication, include: value of A, value of B, value of C, value of D, value of E, systol area that is the area under ABCE, diastol area that is the area under CDE, and the ratio between BC and DC.

In still another embodiment, the computer 340 may utilize the various approaches described in Elgendi, M. (2012), "On the analysis of fingertip photoplethysmogram signals", Current cardiology reviews, 8(1), 14-25, in order to generate at least some of the feature values bases on the iPPG signal. This reference surveys several preprocessing approaches for PPG signals as well as a variety of feature values that may be utilized. Some of the techniques described therein, which may be utilized by the computer 340, include calculating feature values based on first and second derivatives of PPG signals.

In some embodiments, at least some of the feature values may represent calibration values of a user, which are values of certain parameters such as waveform properties described above when the user had a known state (e.g., while it was known that the user was without a fever and/or sober).

In some embodiments, the computer 340 may utilize one or more feature values indicative of the user's heart rate. Optionally, these feature values may be derived from images from among the images 333, e.g., by performing calculations on iPPG signals extracted from the images. In one example, a time series signal is generated from video images of a subject's exposed skin, and a reference signal is used to perform a constrained source separation (which is a variant of ICA) on the time series signals to obtain the PPG signal; peak-to-peak pulse points are detected in the PPG signal, which may be analyzed to determine parameters such as heart rate, heart rate variability, and/or to obtain peak-to-peak pulse dynamics.

In some embodiments, one or more of the feature values utilized by the computer 340 to calculate a value indicative of whether the user has a fever and/or is intoxicated may be generated based on additional inputs from sources other than the cameras 332.

Stress is a factor that can influence the diameter of the arteries, and thus influence the blood flow and resulting hemoglobin concentration patterns. In one embodiment, the computer 340 is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward-facing head-mounted thermal camera configured to take measurements of a region on the forehead of the user, where the measurements of the region on the forehead of the user are indicative of the stress level of the user. In still another example, the system includes an inward-facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently may affect blood flow and hemoglobin concentration patterns. In one embodiment, the computer 340 is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer 340 as values indicative of the hydration level of the user.

Momentary physical activity can affect the blood flow of the user (e.g., due to the increase in the heart rate that it involves). In order to account for this factor, in some embodiments, the computer 340 may generate one or more feature values representing the extent of the user's movement from measurements of the IMU 342.

The user's skin temperature may affect blood viscosity, thus it may influence facial hemoglobin concentration patterns. Some embodiments may include the skin temperature sensor 343, which may be a head-mounted sensor. The skin temperature sensor 343 measures temperature of a region comprising skin on the user's head ($T_{skin}$). Optionally, the computer 340 generates one or more feature values based on $T_{skin}$, such as feature values indicating average skin temperature or a difference from baseline skin temperature.

The temperature and/or humidity in the environment may also be a factor that is considered in some embodiments. The temperature and/or humidity level in the environment can both impact the user's skin temperature and cause a physiologic response involved in regulating the user's body temperature, which may affect observed hemoglobin concentration patterns. Some embodiments may include the environment sensor 344, which may optionally, be head-mounted (e.g., physically coupled to smartglasses). The environment sensor 344 measures an environmental temperature and/or humidity. In one embodiment, the computer 340 may generate one or more feature values based on the temperature and/or humidity in the environment, such as feature values indicating average environment temperature and/or humidity, maximal environment temperature and/or humidity, or a difference from baseline environment temperature and/or humidity.

Training the model 346 may involve utilization of various training algorithms known in the art (e.g., algorithms for training neural networks, and/or other approaches described herein). After the model 346 is trained, feature values may be generated for certain measurements of the user (e.g., current images and baseline images), for which the value of the corresponding label (e.g., whether the user has a fever and/or whether the user is intoxicated) is unknown. The computer 340 can utilize the model 346 to calculate a value indicative of whether the user has a fever and/or whether the user is intoxicated, based on these feature values.

In some embodiments, the model 346 may be generated based on data that includes measurements of the user (i.e., data that includes images taken by the cameras 332). Additionally or alternatively, in some embodiments, the model 346 may be generated based on data that includes measurements of one or more other users (such as users of different ages, weights, sexes, body masses, and health states). In order to achieve a robust model, which may be useful for detecting fever and/or intoxication in various conditions, in some embodiments, the samples used to train the model 346 may include samples based on measurements taken in different conditions. Optionally, the samples are generated based on measurements taken on different days, while in different locations, and/or while different environmental conditions persisted. In a first example, the model 346 is trained on samples generated from a first set of measurements taken while the user was indoors and not in direct sunlight, and is also trained on other samples generated from a second set of measurements taken while the user was outdoors, in direct sunlight. In a second example, the model 346 is trained on samples generated from a first set of measurements taken during daytime, and is also trained on other samples generated from a second set of measurements taken during nighttime. In a third example, the model 346 is trained on samples generated from a first set of measurements taken while the user was moving, and is also trained on other samples generated from a second set of measurements taken while the user was sitting.

Utilizing the model 346 to detect whether the user has a fever and/or whether the user is intoxicated may involve computer 340 performing various operations, depending on the type of model. The following are some examples of various possibilities for the model 346 and the type of calculations that may be accordingly performed by the computer 340, in some embodiments, in order to detect whether the user has a fever and/or whether the user is intoxicated: (a) the model 346 comprises parameters of a decision tree. Optionally, the computer 340 simulates a traversal along a path in the decision tree, determining which branches to take based on the feature values. A value indicative of whether the user has a fever and/or whether the user is intoxicated may be obtained at the leaf node and/or based on calculations involving values on nodes and/or edges along the path; (b) the model 346 comprises parameters of a regression model (e.g., regression coefficients in a linear regression model or a logistic regression model). Optionally, the computer 340 multiplies the feature values (which may be considered a regressor) with the parameters of the regression model in order to obtain the value indicative of whether the user has a fever and/or whether the user is intoxicated; and/or (c) the model 346 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 340 provides the feature values as inputs to the neural network, computes the values of the various activation functions and propagates values between layers, and obtains an output from the network, which is the value indicative of whether the user has a fever and/or whether the user is intoxicated.

In some embodiments, a machine learning approach that may be applied to calculating a value indicative of whether the user has a fever and/or whether the user is intoxicated based on images may be characterized as "deep learning". In one embodiment, the model 346 may include parameters describing multiple hidden layers of a neural network. Optionally, the model may include a convolution neural network (CNN). In one example, the CNN may be utilized to identify certain patterns in the video images, such as hemoglobin concentration patterns. Due to the fact that calculations are performed on sequences images display a certain pattern of change over time (i.e., across multiple frames), these calculations may involve retaining state information that is based on previous images in the sequence. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In addition to detecting whether the user has a fever and/or whether the user is intoxicated, in some embodiments, the computer 340 may utilize the images 333 to detect additional physiological signals and/or conditions.

In one embodiment, the computer 340 calculates, based on the current set of images, a current heart rate and/or a current respiration rate of the user. For example, the computer 340 may utilize one or more techniques described herein or known in the art for calculating heart rate and/or respiration from iPPG signals. The computer 340 can then utilize the current heart rate and/or the current respiration rate of the user, to detect whether the user has a fever, and other conditions such as hyperthermia or hypothermia, also based on deviations of the current heart rate and/or the current respiration rate from a baseline heart rate and/or baseline respiration rate of the user, respectively. In one example, the computer 340 may utilize a machine learning approach similar to the one described above, but instead of using the model 346, the computer 340 uses a different model trained with labels corresponding to extents of hyperthermia or hypothermia (using feature values similar to the ones described above with respect to the model 346).

In another embodiment, the computer 340 may utilize one or more calibration measurements of the user's core body temperature, taken by a different device (e.g., a thermometer), prior to a certain time, to calculate the user's core body temperature based on a certain set of images that were taken by the cameras 332 after the certain time. For example, the computer 340 may utilize a model trained similarly to the model 346, but also includes feature values describing patterns observed for known core body temperatures. In another example, the calibration measurements can be used to adjust values predicted by the computer 340 when making estimations of the extent of fever using the model 346.

In one embodiment, the computer 340 calculates the user's core body temperature based on the deviation of the current pattern from the baseline pattern. For example, in this embodiment, the model 346 is trained with labels that are indicative of the user's core body temperature.

In yet another embodiment, the computer 340 may detect blushing based on the deviation of the current pattern from the baseline pattern. In one example, the computer 340 may utilize a machine learning approach similar to the one described above, but instead of using the model 346, the computer 340 uses a different model trained with labels corresponding to extents of blushing by the user. In this example, blushing may be identified using image analysis techniques known in the art.

The user interface 348 may be utilized to present values calculated by the computer 340, such as indications whether the user has a fever or whether the user is intoxicated. Optionally, the user interface 348 is a component of a device of the user, such as a smartphone's screen or an augmented reality display.

In one embodiment, the computer 340 detects blushing based on the deviation of the current pattern from the baseline pattern, and presents an alert to the user about the blushing via the user interface 348. In one example, the computer 340 provides a biofeedback for the user to enable the user to learn to control the blushing. Optionally, the biofeedback updates the user about the level of blushing in real time, and by that increases the awareness of the user to the blushing and gradually enables the user to learn to control his/her blushing.

In another embodiment, the computer 340 enables the user to share an intoxication history of the user, upon receiving a permission from the user. For example, the user may be able to decide to share his/her intoxication history with a certain person in order to increase the trust, or not share his/her intoxication history with the certain person if the certain persons does not share in return his/her intoxication history with the user.

The following is an additional embodiment of a system configured to detect alcohol intoxication. This embodiment includes memory, a communication interface, and a processor. The processor is configured to: receive baseline images of a user's face, captured by a video camera while the user was sober; calculate, based on the baseline images, a baseline hemoglobin concentration pattern comprising at least 3 points indicative of hemoglobin concentrations on the user's face; receive current images of the user; calculate, based on the current images, a current hemoglobin concentration pattern comprising the at least 3 points indicative of hemoglobin concentrations on the user's face; and detect whether the user is intoxicated based on a deviation of the current hemoglobin concentration pattern from the baseline hemoglobin concentration pattern. Optionally, the video camera is an inward-facing head-mounted camera (HCAM) that is mounted more than 5 mm away from the user's head and is sensitive to wavelengths below 1050 nanometer.

The following method for detecting fever may be used by systems modeled according to FIG. 14C. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, receiving, from first and second inward-facing head-mounted cameras ($Cam_{1\&2}$) sensitive to wavelengths below 1050 nanometer, images of respective first and second regions on a user's face. Optionally, the middles of the first and second regions are at least 4 cm apart.

In Step 2, calculating, based on baseline images captured with $Cam_{1\&2}$ while the user did not have a fever, a baseline pattern comprising values indicative of first and second baseline hemoglobin concentrations at the first and second regions, respectively.

In Step 3, calculating, based on a current set of images captured with $Cam_{1\&2}$, a current pattern comprising values indicative of first and second current hemoglobin concentrations at the first and second regions, respectively.

And in Step 4, detecting whether the user has a fever based on a deviation of the current pattern from the baseline pattern.

In one embodiment, the method for detecting fever optionally includes the following steps: calculating, based on additional baseline images captured with $Cam_{1\&2}$ while the user had a fever, a fever-baseline pattern comprising values indicative of first and second fever hemoglobin concentrations at the first and second regions, respectively; and basing the detecting of whether the user has the fever also on a deviation of the current pattern from the fever-baseline pattern.

In one embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. The current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Optionally, method for detecting fever includes a step of calculating a confidence in a detection of the fever based on the deviation of the current pattern from the baseline pattern, such that the confidence decreases as the difference between the third values and the fourth values increases.

FIG. 15A illustrates an embodiment of a system that utilizes multiple PPG signals, measured using different types of sensors, to detect a physiological response. In one embodiment, the system includes at least a head-mounted contact PPG device 782, a camera 784, and a computer 780.

In one embodiment, the head-mounted contact PPG device 782 (also referred to as PPG device 782) measures a signal indicative of a PPG signal 783 at a first region of interest ($ROI_1$) on a user's body (also referred to as PPG signal 783). $ROI_1$ includes a region of exposed skin on the user's head, and the PPG device 782 includes one or more light sources configured to illuminate $ROI_1$. For example, the one or more light sources may include light emitting diodes (LEDs) that illuminate $ROI_1$. Optionally, the one or more LEDs include at least two LEDs, wherein each illuminates $ROI_1$ with light at a different wavelength. In one example, the at least two LEDs include a first LED that illuminates $ROI_1$ with green light and a second LED that illuminates $ROI_1$ with an infrared light. Optionally, the PPG device 782 includes one or more photodetectors configured to detect extents of reflections from $ROI_1$.

The camera 784 captures images 785 of a second region of interest ($ROI_2$) on the user's head. The camera is located more than 10 mm away from the user's head. Optionally, the camera is located more than 20 mm away from the user's head. Optionally, the camera 784 is a head-mounted camera. In some embodiments, the camera 784 may utilize a light source to illuminate $ROI_2$. Optionally, the light source is configured to illuminate at least a portion of $ROI_2$, and the camera 784 is located more than 15 cm away from the user's head.

In another embodiment, the system illustrated in FIG. 15A does not include a light source that illuminates $ROI_2$ and the camera 784 may be considered a "passive" camera.

In some embodiments, the camera 784 is not head-mounted. Optionally, the images 785 taken by the non-head mounted camera are synchronized with the PPG signal 783 (e.g., based on synchronizing the clocks of the PPG device 782 and the camera 784, and/or based on time stamps added by the PPG device 782 and time stamps added by the camera 784). Optionally, the system achieves data synchronization that is better than 35 milliseconds between the PPG signal and the iPPG signals. Optionally, the system achieves data synchronization better than 1 millisecond between the PPG signal and the iPPG signals. Examples of cameras that are not head-mounted, which may be synchronized with the head-mounted PPG device 782 include: a smartphone camera, a tablet camera, a laptop camera, and/or webcam.

In some embodiments, references to the camera 784 involve more than one camera. Optionally, the camera 784 may refer to two or more inward-facing head-mounted cameras, and $ROI_2$ includes two or more regions on the user's head that are respectively captured by the two or more inward-facing head-mounted cameras. Optionally, the two or more regions include regions on different sides of the user's head.

Optionally, $ROI_2$ covers a larger area of exposed skin than $ROI_1$. In one example, the area of $ROI_2$ is at least ten times larger than the area of $ROI_1$. In one example, the PPG device 782 does not obstruct the field of view of the camera 784 to $ROI_2$.

In some embodiments, various devices, such as the PPG device 782, the camera 784, and/or the computer 780, may be physically coupled to a frame of smartglasses or to a smart-helmet, which is designed to measure the user in day-to-day activities, over a duration of weeks, months, and/or years. FIG. 15B and FIG. 15C illustrate smartglasses that may be utilized to realize the invention described herein.

FIG. 15B illustrates smartglasses that include camera 796 and several contact PPG devices. The contact PPG devices correspond to the PPG device 782 and are used to measure the PPG signal 783. The contact PPG devices may be coupled at various locations on the frame 794, and thus may come in contact with various regions on the user's head. For example, contact PPG device 791a is located on the right temple tip, which brings it to contact with a region behind the user's ear (when the user wears the smartglasses). Contact PPG device 791b is located on the right temple of the frame 794, which puts it in contact with a region on the user's right temple (when wearing the smartglasses). It is to be noted that in some embodiments, in order to bring the contact PPG device close such that it touches the skin, various apparatuses may be utilized, such as spacers (e.g., made from rubber or plastic), and/or adjustable inserts that can help bridge a possible gap between the frame's temple and the user's face. Such an apparatus is spacer 792 which brings contact PPG device 791b in contact with the user's temple when the user wears the smartglasses. Another possible location for a contact PPG device is the nose bridge, as contact PPG device 791c is illustrated in the figure. It is to be noted the contact PPG device 791c may be embedded in the nose bridge (or one of its components), and/or physically coupled to a part of the nose bridge.

FIG. 15C illustrates smartglasses that include at least first, second, and third inward-facing cameras, each of which may correspond to the camera 784. The figure illustrates a frame 797 to which a first inward-facing camera 795a is coupled above the lens that is in front of the right eye, and a second inward-facing camera 795b that is coupled to the frame 797 above the lens that is in front of the left eye. The figure also illustrates a third inward facing camera 795c that is on the left side of the frame 797 and configured to capture images of lower portions of the user's face (e.g., portions of the left cheek).

The computer 780 is configured, in some embodiments, to detect a physiological response based on: (i) imaging photoplethysmogram signals (iPPG signals) recognizable in the images 785, and (ii) correlations between the PPG signal 783 and the iPPG signals. Some examples of physiological responses that may be detected include: an allergic reaction, a stroke, a migraine, stress, a certain emotional response, pain, and blood pressure (i.e., calculating the blood pressure value). Optionally, the computer 780 forwards an indication of a detection of the physiological response 789 to a device of the user and/or to another computer system. Examples of computers that may be utilized to perform this detection are computer 400 or computer 410 illustrated in FIG. 88A and FIG. 88B, respectively.

Herein, sentences of the form "iPPG signal is recognizable in images" refer to effects of blood volume changes due to pulse waves that may be extracted from a series of images of the region. These changes may manifest as color changes to certain regions (pixels) in the images, and may be identified and/or utilized by a computer (e.g., in order to generate a signal indicative of the blood volume at the region). However, these changes need not necessarily be recognizable to the naked eye (e.g., because of their subtlety, the short duration in which they occur, or involvement of light outside of the visible spectrum). For example, blood flow may cause facial skin color changes (FSCC) that corresponds to different concentrations of oxidized hemoglobin due to varying volume of blood at a certain region due to different stages of a cardiac pulse, and/or the different magnitudes of cardiac output.

Herein, detecting the physiological response may mean detecting that the user is experiencing the physiological response, and/or that there is an onset of the physiological response. In the case of the physiological response being associated with one or more values (e.g., blood pressure), detecting the physiological response may mean calculating the one or more values.

In some embodiments, detecting the physiological response may involve calculating one or more of the following values: an indication of whether or not the user is experiencing the physiological response (e.g., whether or not the user is having a stroke), a value indicative of an extent to which the user is experiencing the physiological response (e.g., a level of pain or stress felt by the user), a duration since the onset of the physiological response (a duration since a migraine has started), and a duration until an onset of the physiological response.

In some embodiments, the computer 780 detects the physiological response utilizing previously taken PPG signals of the user (taken with the PPG device 782) and/or previously taken images (taken with the camera) in which previous iPPG signals are recognizable. Having such previous values can assist the computer 780 to detect changes to blood flow that may be indicative of certain physiological responses. In some embodiments, previously taken PPG signals and/or images are used to generate baseline values representing baseline properties of the user's blood flow. Optionally, calculating the baseline values may be done based on previously taken PPG signals and/or images that were measured at least an hour before taking the PPG signal 783 and/or the images 785. Optionally, calculating the baseline values may be done based on previously taken PPG signals and/or images that were measured at least a day before the PPG signal 783 and/or the images 785. Some examples of baseline values may include baseline physiological signal values (e.g., baseline heart rate, blood pressure, or heart rate variability). Other examples of baseline values may include typical values of fiducial points in PPG signals (e.g., magnitudes of systolic peaks) and/or typical relationships between different fiducial points (e.g., typical distance between systolic peaks and dicrotic notches, and the like).

A baseline value may be calculated in various ways. In a first example, the baseline is a function of the average measurements of the user (which include previously taken PPG signals and/or iPPG signals recognizable in previously taken images described above). In a second example, the baseline value may be a function of the situation the user is in, such that previous measurements taken during similar situations are weighted higher than previous measurements taken during less similar situations. A PPG signal may show different characteristics in different situations because of the different mental and/or physiological states of the user in the different situations. As a result, a situation-dependent baseline can improve the accuracy of detecting the physiological response. In a third example, the baseline value may be a function of an intake of some substances (such as food, beverage, medications, and/or drugs), such that previous measurements taken after consuming similar substances are weighted higher than previous measurements taken after not consuming the similar substances, and/or after consuming less similar substances. A PPG signal may show different characteristics after the user consumes different substances because of the different mental and/or physiological states the user may enter after consuming the substances, especially when the substances include things such as medications, drugs, alcohol, and/or certain types of food. As a result, a substance-dependent baseline can improve the accuracy of detecting the physiological response.

There are various ways in which the computer 780 may utilize correlations between the PPG signal 783 and the iPPG signals to detect the physiological response. In some embodiments, the computer 780 may rely on the fact that due to the proximity of $ROI_1$ and $ROI_2$ (both being on the head and consequently, close by) the appearances of pulse waves at the different ROIs is highly correlated. This fact may be utilized by the computer 780 to identify fiducial points in the PPG signal 783, which is often a strong signal, and then to identify the corresponding fiducial points in the correlated iPPG signals (that are noisier than the PPG signal). Additionally or alternatively, when a using machine learning-based approach, at least some of the feature values used by the computer 780 may reflect values related to correlations between the PPG signal 783 and the iPPG signals (e.g., values of similarity and/or offsets between the PPG signal 783 and the iPPG signals). Both uses of correlations are elaborated on further below.

It is to be noted that because the PPG device 782 touches and occludes $ROI_1$, while the camera 784 does not occlude $ROI_2$, the PPG signal 783 extracted from the PPG device 782 usually has a much better signal-to-noise (SNR) compared to the iPPG signals extracted from the images 785 of $ROI_2$. In addition, due to the shorter distance between the PPG device 782 and $ROI_1$, and especially in embodiments where the camera 784 is a passive camera (i.e., does not include a light source to illuminate $ROI_2$), the PPG signal 783 will typically suffer much less from illumination changes compared to the iPPG signals.

Furthermore, because both $ROI_1$ and $ROI_2$ are on the user's head, and because the PPG device 782 and the camera 784 measure the user essentially simultaneously, manifestation of the pulse arrival in the PPG signal 783 and the iPPG signals are typically highly correlated (e.g., the signals exhibit highly correlated pulse arrival times). This correlation enables the computer 780 to utilize pulse fiducial points identified in the PPG signal 783 (which is less noisy than the iPPG signals) to extract information from iPPG signals more efficiently and accurately.

In one embodiment, the computer 780 extracts from the PPG signal 783 one or more values that may serve as a basis to correlate between the PPG signal 783 and the iPPG signals. Optionally, the extracted values are indicative of one or more of the following PPG waveform fiducial points: a systolic peak, a dicrotic notch, a diastolic peak. Optionally, the extracted values may be indicative of a timing of a certain fiducial point (i.e., when it manifests in the PPG signal 783), and/or the magnitude of the PPG signal 783 at the time corresponding to the certain fiducial point. Additionally or alternatively, the extracted values may be indicative of other waveform properties such as an interbeat interval, and a systolic-diastolic peak-to-peak time.

Due to the camera 784 not being in contact with $ROI_2$, it is often the case that direct identification of the fiducial points in the iPPG signals may be difficult, e.g., due to the excessive noise in the signal because of movements and ambient light. Knowing an identification of fiducial points in the PPG signal 783, such as times of systolic peaks, dicrotic notches, and diastolic peaks, provides useful information for determining when these events are to be expected to manifest in the iPPG signals. The timings of the occurrences of these fiducial points in the PPG signal 783 can serve as a basis according to which fiducial points can be determined in the iPPG signals.

In one embodiment, times corresponding to fiducial points, as determined based on the PPG signal 783, are also used for fiducial points in the iPPG signals. Thus, the magnitudes of the fiducial points in the iPPG signals are taken essentially at the same times of the fiducial points in the PPG signal 783. Such an approach can be especially accurate when $ROI_1$ and $ROI_2$ are close to each other, thus it is likely that manifestation of pulse waves occurs at very similar times in $ROI_1$ and $ROI_2$, so when, for example, there is a systolic peak in the PPG signal 863, there is also one approximately at the same time in the iPPG signals.

In another embodiment, times corresponding to fiducial points, as determined based on the PPG signal 783, may also be used to determine fiducial points in the iPPG signals, by applying a certain offset to the times. This certain offset may be used to account for the difference between the distances/route blood travels in order to reach $ROI_2$ as opposed to the distance/route blood travels in order to reach $ROI_1$.

In one example, an offset used between when a fiducial point (e.g., a systolic peak) occurs in the PPG signal 783, and when it manifests in each of the iPPG signals may be a fixed offset (e.g., an offset that is a function of the relative location of $ROI_2$ from $ROI_1$). In another example, different sub-regions of $ROI_2$ (e.g., corresponding to different pixels in the images 785) may have different offsets that are calculated empirically relative to the timings of the PPG signal. In still another example, the iPPG signals are extracted from the images based on values of time-segments in which the iPPG signals were expected to appear as a function of the locations of respective regions of the iPPG signals relative to the location of the contact PPG device.

An offset used between when a fiducial point (e.g., a systolic peak) occurs in the PPG signal 783, and when it manifests in in each of the iPPG signals may be adjusted to account for blood velocity. For example, the offset may be inversely proportional to the heart rate and/or blood pressure determined from the PPG signal 783. When the heart rate and/or blood pressure increase, this is usually correlated with a higher velocity of blood flow, which will tend to reduce the difference in manifestations of a pulse wave in $ROI_1$ and $ROI_2$.

It is to be noted that offsets used between times of fiducial points identified in the PPG signal 783 and the iPPG signals may be user-specific and learned overtime. For example, histograms of the offsets between the maxima in the PPG signal 783 and the maxima of each of the iPPG signals, as observed over multiple pulses of the user, can be aggregated. Based on these histograms, the most frequent offset can be used to represent the difference between when systolic peaks occur in the PPG signal 783 and when it manifests in each of the iPPG signals.

In another embodiment, times corresponding to fiducial points, as determined based on the PPG signal 783, may be used to set a range of times during which the same fiducial point is expected to manifest in an iPPG signal (from among the iPPG signals). For example, if a systolic peak is observed at time t in the PPG signal 783, a manifestation of a systolic peak will be extracted from a time that falls in [t+a, t+b], where a<b, and the values of a and b are set to correspond to the minimum and maximum offsets between manifestations of systolic peaks in $ROI_1$ and a sub-region of $ROI_2$ to which the iPPG signal corresponds. As discussed above, the values a and b may also be adjusted according to values such as the heart rate and/or blood pressure, and may also be learned for a specific user.

In some embodiments, the computer 780 may utilize the PPG signal 783 to verify the quality of the iPPG signals. Optionally, the computer 780 may refrain from utilizing iPPG signals in calculations when they exhibit a significant difference from the PPG signal 783. For example, if a heart rate calculated based on the PPG signal 783, during a certain period, is significantly different from a heart rate calculated based on the iPPG signals during that period (e.g., a difference greater than a threshold of ±5 bpm), then that may indicate the iPPG signals during the certain period were noisy and/or unreliable.

Additionally, using the PPG signal 783, as described above, to assess various sub-regions of $ROI_2$, can serve as a quality filter to select which regions of the face should be used to perform detection of physiological responses. If a certain region displays consistently an accurate iPPG signal, it may be more reliable for detection of the physiological response than a region from which an accurate signal cannot be extracted.

Another way to describe the benefit of measuring simultaneously the PPG signal 783 and iPPG signals on the head involves the fact that often the iPPG signals are weak relative to the noise. Therefore, automatic detection of the iPPG signals requires discrimination between true PPG pulses and random fluctuations due to the noise. In one embodiment, an algorithm for the selection of the iPPG pulses is based on the values of time-segments in which the iPPG signals are expected to appear as a function of their location relative to the location of the PPG device 782. Optionally, the detected iPPG signals in these time-segments are identified as iPPG signals if they meet one or more criteria based on (i) the spatial waveform of the iPPG signals relative to the reference PPG signal, (ii) correlation between each iPPG signal in the current time-segment and a predetermined number of neighboring time-segments, and (iii) correlations between iPPG signals extracted from neighboring regions of exposed skin on the head, which are expected to show essentially the same rhythm with a bounded time delay. Optionally, the signals are taken as iPPG signals if minimal values of the criteria are obtained in several time-segments. The minimal values and the number of time-segments can be determined in order to achieve minimal standard deviation of the differences between the values of the heart rate extracted from the noisy iPPG signals and the reference heart rate extracted from the less noisy PPG signal.

In some embodiments, the iPPG signals include multiple values for different sub-regions of $ROI_2$, and the physiological response is detected based on differences between amplitudes of the values recognizable in the different sub-regions of $ROI_2$. For example, each sub-region may be captured by a subset of pixels in the images 785.

In one embodiment, the physiological response is indicative of an allergic reaction, and the sub-regions of $ROI_2$ include portions of at least two of the following areas on the user's face: nose, upper lip, lips, cheeks, temples, periorbital area around the eyes, and the forehead. Optionally, the computer 780 detects the allergic reaction based on changes in blood flow which manifest in iPPG signals corresponding to the at least two areas.

In another embodiment, the physiological response is indicative of a stroke, and the sub-regions of $ROI_2$ include at least one of the following pairs on the user's face: left and right cheeks, left and right temples, left and right sides of the forehead, and left and right sides of the periorbital area around the eyes. Optionally, the computer 780 detects the stroke based on a difference in blood flow on the two sides of the face.

In yet another embodiment, the physiological response is indicative of a migraine, and the sub-regions of $ROI_2$ include at least one of the following pairs on the user's face: left and right sides of the forehead, left and right temples, left and right sides of the periorbital area around the eyes, and left and right cheeks.

In still another embodiment, the physiological response is indicative of a blood pressure value that is calculated based on differences in pulse transit times detectable in the sub-regions of $ROI_2$. Optionally, the sub-regions comprise at least two of the following areas on the user's face: left temple, right temple, left side of the forehead, right side of the forehead, left check, right cheek, nose, periorbital area around the left eye, and periorbital area around the right eye.

And in yet another embodiment, the physiological response is indicative of at least one of stress, emotional response, and pain, which are calculated based on changes to hemoglobin concentrations observable in the iPPG signals relative to previous measurements of hemoglobin concentrations observable in the iPPG signals of the user. Optionally, the sub-regions of $ROI_2$ include at least two of the following areas on the user's face: lips, upper lip, chin, left temple, right temple, left side of the forehead, right side of the forehead, left check, right cheek, left ear lobe, right ear lobe, nose, periorbital area around the left eye, and periorbital area around the right eye.

In one embodiment, the computer 780 is a head-mounted computer. Optionally, detecting the physiological response involves performing at least the following: identifying times at which fiducial points appear in the PPG signal; calculating, based on the times, time-segments in which the fiducial points are expected to appear in imaging photoplethysmogram signals recognizable the images (iPPG signals); and detecting a physiological response based on values of the iPPG signals during the time-segments.

As part of the calculations involved in detecting the physiological response, the computer 780 may perform various filtering and/or processing procedures to the PPG signal 783, the images 785, and/or iPPG signals extracted from the images 785. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081.

In some embodiments, the images 785 may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting iPPG signals from images are discussed in Zaunseder et al. (2018), "Cardiovascular assessment by imaging photoplethysmography—a review", Biomedical Engineering 63(5), 617-634. An example of preprocessing that may be used in some embodiments is given in U.S. Pat. No. 9,020,185, titled "Systems and methods for non-contact heart rate sensing", which describes how a times-series signals obtained from video of a user can be filtered and processed to separate an underlying pulsing signal by, for example, using an ICA algorithm.

In some embodiments, detection of the physiological response may involve calculation of pulse arrival times (PATs) at $ROI_1$ and/or at one or more sub-regions of $ROI_2$. Optionally, a PAT calculated from an PPG signal represents a time at which the value representing blood volume (in the waveform represented in the PPG) begins to rise (signaling the arrival of the pulse). Alternatively, the PAT may be calculated as a different time, with respect to the pulse waveform, such as the time at which a value representing blood volume reaches a maximum or a certain threshold, or the PAT may be the average of the time the blood volume is above a certain threshold. Another approach that may be utilized to calculate a PAT from an iPPG signal is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

Detection of the physiological response may involve the computer utilizing an approach that may be characterized as involving machine learning. In some embodiments, such a detection approach may involve the computer generating feature values based on data that includes the PPG signal 783, the images 785, and/or iPPG signals recognizable in the images 785, and optionally other data. Optionally, at least some of the feature values are based on correlations between the PPG signal 783 and the iPPG signals. The computer 780 then utilizes a previously trained model 779 to calculate one or more values indicative of whether, and/or to what extent, the user is experiencing the physiological response (which may be any one of the examples of values mentioned further above as being calculated by the computer 780 for this purpose).

Feature values generated based on PPG signals (e.g., the PPG signal 783 and/or one or more of the iPPG signals extracted from the images 785) may include various types of values, which may be indicative of dynamics of the blood flow at the respective regions to which the PPG signals correspond. Optionally, these feature values may relate to properties of a pulse waveform, which may be a specific pulse waveform (which corresponds to a certain beat of the heart), or a window of pulse waveforms (e.g., an average property of pulse waveforms in a certain window of time).

Some examples of feature values that may be generated based on a pulse waveform include: the area under the pulse waveform, the amplitude of the pulse waveform, a derivative and/or second derivative of the pulse waveform, a pulse waveform shape, pulse waveform energy, and pulse transit time (to the respective ROI). Optionally, some feature values may be derived from fiducial points identified in the PPG signals; these may include values such as magnitudes of the PPG signal at certain fiducial points, time offsets between different fiducial points, and/or other differences between fiducial points. Some examples of fiducial point-based feature values may include one or more of the following: a magnitude of a systolic peak, a magnitude of a diastolic peak, duration of the systolic phase, and duration of the diastolic phase. Additional examples of feature values may include properties of the cardiac activity, such as the heart rate and heart rate variability (as determined from the PPG signal). Additionally, some feature values may include values of other physiological signals that may be calculated based on PPG signals, such as blood pressure and cardiac output.

The aforementioned feature values may be calculated in various ways. In one example, some feature values are calculated for each PPG signal individually. In another example, some feature values are calculated after normalizing a PPG signal with respect to previous measurements from the corresponding PPG device used to measure the PPG signal. In other examples, at least some of the feature values may be calculated based on an aggregation of multiple PPG signals (e.g., different pixels/regions in images captured by an iPPG device), or by aggregating values from multiple contact PPG devices.

In some embodiments, at least some of the feature values may include values indicative of correlations between the PPG signal 783 and iPPG signals extracted from the images 785. In one example, the feature values may include values indicative of offsets between when certain fiducial points appear in the PPG signal 783, and when they appear in each of the iPPG signals. In another example, the feature values may include values indicative of offsets at which the correlation (e.g., as calculated by a dot-product) between the PPG signal 783 and the iPPG signals is maximized In still another example, the feature values may include values indicative of maximal value of correlation (e.g., as calculated by a dot-product) between the PPG signal 783 and the iPPG signals (when using different offsets).

In some embodiments, at least some of the feature values may represent comparative values, which provide an indication of the difference in blood flow, and/or in some other property that may be derived from a PPG signal, between various regions on the head. Optionally, such feature values may assist in detecting asymmetrical blood flow (and/or changes thereto).

In some embodiments, at least some of the feature values describe properties of pulse waveforms (e.g., various types of feature values mentioned above), which are derived from the previous measurements of the user using the PPG device 782 and/or the camera 784. Optionally, these feature values may include various blood flow baselines for the user, which correspond to a certain situation the user was in when the previous measurements were taken.

In some embodiments, at least some of the feature values may be "raw" or minimally processed measurements of the PPG device 782 and/or the camera 784. Optionally, at least some of the feature values may be pixel values obtained by the camera 864. Optionally, the pixel values may be provided as input to functions in order to generate the feature values that are low-level image-based features. Some examples of low-level features, which may be derived from images, include feature generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may be derived from multiple images taken at different times, such as volume local binary patterns (VLBP), cuboids, and/or optical strain-based features. In one example, one or more of the feature values may represent a difference between values of pixels at one time t and values of other pixels at a different region at some other time t+x (which, for example, can help detect different arrival times of a pulse wave).

In some embodiments, at least some feature values may be generated based on other data sources (in addition to PPG signals). In some examples, at least some feature values may be generated based on other sensors, such as movement sensors (which may be head-mounted, wrist-worn, or carried by the user some other way), head-mounted thermal cameras, or other sensors used to measure the user. In other examples, at least some feature values may be indicative of environmental conditions, such as the temperature, humidity, and/or extent of illumination (e.g., as obtained utilizing an outward-facing head-mounted camera). Additionally, some feature values may be indicative of physical characteristics of the user, such as age, sex, weight, Body Mass Index (BMI), skin tone, and other characteristics and/or situations the user may be in (e.g., level of tiredness, consumptions of various substances, etc.)

Stress is a factor that can influence the diameter of the arteries, and thus influence calculated values that relate to the PPG signals and/or blood flow. In one embodiment, the computer 780 receives a value indicative of a stress level of the user, and generates at least one of the feature values based on the received value. Optionally, the value indicative of the stress level is obtained using a thermal camera. In one example, the system may include an inward-facing head-mounted thermal camera that takes measurements of a periorbital region of the user, where the measurements of a periorbital region of the user are indicative of the stress level of the user. In another example, the system includes an inward-facing head-mounted thermal camera that takes measurements of a region on the forehead of the user, where the measurements of the region on the forehead of the user are indicative of the stress level of the user. In still another example, the system includes an inward-facing head-mounted thermal camera that takes measurements of a region on the nose of the user, where the measurements of the region on the nose of the user are indicative of the stress level of the user.

Hydration is a factor that affects blood viscosity, which can affect the speed at which the blood flows in the body. In one embodiment, the computer 780 receives a value indicative of a hydration level of the user, and generates at least one of the feature values based on the received value. Optionally, the system includes an additional camera that detects intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer as values indicative of the hydration level of the user.

The following are examples of embodiments that utilize additional inputs to generate feature values used to detect the physiological response. In one embodiment, the computer 780 receives a value indicative of a temperature of the user's body, and generates at least one of the feature values based on the received value. In another embodiment, the computer 780 receives a value indicative of a movement of the user's body, and generates at least one of the feature values based on the received value. For example, the computer 780 may receive the input form a head-mounted Inertial Measurement Unit (IMU 778) that includes a combination of accelerometers, gyroscopes, and optionally magnetometers, and/or an IMU in a mobile device carried by the user. In yet another embodiment, the computer 780 receives a value indicative of an orientation of the user's head, and generates at least one of the feature values based on the received value. For example, the computer 780 may receive the values indicative of the head's orientation from an outward-facing head-mounted camera, and/or from a nearby non-wearable video camera. In still another embodiment, the computer 780 receives a value indicative of consumption of a substance by the user, and generates at least one of the feature values based on the received value. Optionally, the substance comprises a vasodilator and/or a vasoconstrictor.

The model 779 utilized to detect the physiological response may be generated, in some embodiments, based on data obtained from one or more users. In the case where the physiological response is a certain medical condition (e.g., an allergic reaction and/or a migraine), at least some of the data used to train the model 779 corresponds to times in which the one or more users were not affected by the physiological response, and additional data used to train the model was obtained while the physiological response occurred and/or following that time. Thus, this training data may reflect PPG signals and/or blood flow both at normal times, and changes to PPG signals and/or blood flow that may ensue due to the physiological response. In the case where the physiological response corresponds to a value of a physiological signal (e.g., blood pressure), data used to train the model 779 may include measurements of the one or more users that are associated with a reference value for the physiological signal (e.g., the reference values may be blood pressure values measured by an external device).

The aforementioned training data may be used to generate samples, each sample including feature values generated based on PPG signals of a certain user, additional optional data (as described above), and a label. The PPG signals include measurements of the certain user (e.g., taken with the PPG device 782 and the camera 784) at a certain time, and optionally previous measurements of the user taken before the certain time. The label is a value related to the physiological response (e.g., an indication of the extent of the physiological response). For example, the label may be indicative of whether the user, at the certain time, experienced a certain physiological response (e.g., an allergic reaction or a stroke). In another example, the label may be indicative of the extent or severity of the physiological response at the certain time. In yet another example, the label may be indicative of the duration until an onset of the physiological response. In still another example, the label may be indicative of the duration that has elapsed since the onset of the physiological response.

In some embodiments, the model 779 used by the computer 780 to detect the physiological response of a specific user may be generated, at least in part, based on data that includes previous measurements of the specific user (and as such, may be considered personalized to some extent for the specific user). Additionally or alternatively, in some embodiments, the model 779 may be generated based on data of other users. Optionally, the data used to train the model 779 may include data obtained from a diverse set of users (e.g., users of different ages, weights, sexes, preexisting medical conditions, etc.). Optionally, the data used to train the model 779 includes data of other users with similar characteristics to the specific user (e.g., similar weight, age, sex, height, and/or preexisting condition).

In order to achieve a robust model, which may be useful for detecting the physiological response for a diverse set of conditions, in some embodiments, the samples used for the training of the model 779 may include samples based on data collected when users were in different conditions. Optionally, the samples are generated based on data collected on different days, while indoors and outdoors, and while different environmental conditions persisted. In one example, the model 779 is trained on samples generated from a first set of training data taken during daytime, and is also trained on other samples generated from a second set of training data taken during nighttime. In a second example, the model 779 is trained on samples generated from a first set of training data taken while users were exercising and moving, and is also trained on other samples generated from a second set of data taken while users were sitting and not exercising.

Utilizing the model 779 to detect the physiological response may involve the computer 780 performing various operations, depending on the type of model. The following are some examples of various possibilities for the model 779 and the type of calculations that may be accordingly performed by the computer 780, in some embodiments, in order to calculate a certain value indicative of an extent of the physiological response experienced by the user: (a) the model 779 comprises parameters of a decision tree. Optionally, the computer 780 simulates a traversal along a path in the decision tree, determining which branches to take based on the feature values. The certain value may be obtained at the leaf node and/or based on calculations involving values on nodes and/or edges along the path; (b) the model 779 comprises parameters of a regression model (e.g., regression coefficients in a linear regression model or a logistic regression model). Optionally, the computer 780 multiplies the feature values (which may be considered a regressor) with the parameters of the regression model in order to obtain the certain value; and/or (c) the model 779 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 780 provides the feature values as inputs to the neural network, computes the values of the various activation functions and propagates values between layers, and obtains an output from the network, which is the certain value In some embodiments, a machine learning approach that may be applied to calculating a value indicative of the extent of the physiological response experienced by the user may be characterized as "deep learning". In one embodiment, the model 779 may include parameters describing multiple hidden layers of a neural network. Optionally, the model 779 may include a convolution neural network (CNN). In one example, the CNN may be utilized to identify certain patterns in the images 785, such as the patterns of corresponding to blood volume effects and ballistocardiographic effects of the cardiac pulse. Due to the fact that calculating the value indicative of the extent of the physiological response may be based on multiple, possibly successive, images that display a certain pattern of change over time (i.e., across multiple frames), these calculations may involve retaining state information that is based on previous images. Optionally, the model 779 may include parameters that describe an architecture that supports such a capability. In one example, the model 779 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In some embodiments, the system illustrated in FIG. 15A may optionally include a head-mounted sensor 788 configured to measure a signal indicative of timing of the user's inhalation phase and/or exhalation phase (respiratory-phase signal). Optionally, the computer 780 may utilize the respiratory-phase signal to detect the physiological response. For example, the computer 780 may utilize correlations between timings of fiducial points of the iPPG signals and the respiratory-phase signal. Optionally, at least some of the feature values generated by the computer 780 (when the detection of the physiological response involves a machine learning-based approach) may be generated based on the respiratory-phase signal. For example, the feature values may include values indicating whether a certain fiducial point occurred while the user was inhaling or exhaling. The head-mounted sensor 788 used to measure the respiratory-phase signal may include one or more of the following sensors: (i) an inward-facing camera configured to take video in which movements of the nostrils and/or lips are indicative of the respiratory-phase signal, (ii) an inward-facing thermal camera configured to measure temperatures of the upper lip and/or the mouth, which are indicative of the respiratory-phase signal, and (iii) an acoustic sensor configured to record sound waves that are indicative of the respiratory-phase signal.

In addition to detecting a physiological response, the system illustrated in FIG. 15A may be utilized to authenticate the user. In one embodiment, the camera 784 is integrated in a non-wearable device (e.g., a smartphone or a tablet computer), and the computer 780 may authenticate the identity of the user and determine that the user is using the non-wearable device by checking whether correlations between the PPG signal and the iPPG signals reaches a predetermined threshold. Optionally, the predetermined threshold indicates, above a predetermined certainty, that the PPG signal 783 and the images 785 (in which the iPPG signals are recognizable) belong to the same person.

The following method for detecting physiological response may be used by systems modeled according to FIG. 15A. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, measuring a signal indicative of a PPG signal at a first region that includes exposed skin on a user's head (referred to as a PPG signal) utilizing a head-mounted contact PPG device. In one example, the head-mounted contact PPG device is the PPG device 782.

In Step 2, capturing images of a second region that includes exposed skin on the user's head utilizing a camera. Optionally, the camera is located more than 10 mm away from the user's head. Optionally, the camera used in this step is the camera 784.

And in Step 3, detecting a physiological response based on: (i) imaging photoplethysmogram signals (iPPG signals) recognizable in the images, and (ii) correlations between the PPG signal and the iPPG signals.

In some embodiments, detecting the physiological response is done utilizing a machine learning-based approach. Optionally, the method includes the following steps: generating feature values based on data that includes: (i) the iPPG signals, and (ii) correlations between the PPG signal and the iPPG signals; and utilizing a model to calculate, based on the feature values, a value indicative of the extent of the physiological response experienced by the user.

In one embodiment, the physiological response is indicative of a value of blood pressure, and is calculated based on differences in pulse transit times detectable in iPPG signals of sub-regions of the second region. Optionally, the sub-regions include at least two of the following areas on the user's face: left temple, right temple, left side of the forehead, right side of the forehead, left check, right cheek, nose, periorbital area around the left eye, and periorbital area around the right eye.

In another embodiment, the physiological response is indicative of at least one of stress, an emotional response, and pain, which are calculated based on changes to hemoglobin concentrations observable in the iPPG signals relative to previous measurements of hemoglobin concentrations observable in the iPPG signals of the user. Optionally, the sub-regions comprise at least two of the following areas on the user's face: lips, upper lip, chin, left temple, right temple, left side of the forehead, right side of the forehead, left check, right cheek, left ear lobe, right ear lobe, nose, periorbital area around the left eye, and periorbital area around the right eye.

In one embodiment, a low-power head-mounted iPPG system includes: (i) a head-mounted contact PPG device configured to measure a signal indicative of a PPG signal at a first region comprising exposed skin on a user's head (PPG signal), (ii) a head-mounted camera configured to capture images of a second region comprising exposed skin on the user's head; wherein the camera is located more than 10 mm away from the user's head; and (iii) a head-mounted computer configured to efficiently extract iPPG signals from the images based on focusing the iPPG calculations around pulse timings extracted from the PPG signal.

In one embodiment, a head-mounted iPPG system includes: (i) a head-mounted contact PPG device configured to measure a signal indicative of PPG signal at a first region comprising exposed skin on a user's head, (ii) a head-mounted camera configured to capture images of a second region comprising exposed skin on the user's head; wherein the camera is located more than 10 mm away from the user's head; and (iii) a head-mounted computer configured to: identify times at which fiducial points appear in the PPG signal; calculate, based on the times, time-segments in which the fiducial points are expected to appear in iPPG signals recognizable the images; and detect a physiological response based on values of the iPPG signals during the time-segments.

The following is description of additional aspects of embodiments of systems configured to detect physiological responses, including embodiments for various systems that may detect physiological responses based on thermal measurements and/or other sources of data.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 22, and FIG. 26. Sentences in the form of "the system/camera occludes the ROI" indicate that some of the ROIs cannot be observed directly by that third person, such as ROIs 19 and 37 that are occluded by the lenses in FIG. 16A, and ROIs 97 and 102 that are occluded by cameras 91 and 96, respectively, in FIG. 24.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor.

The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "$CAM_{out}$" denotes "outward-facing head-mounted thermal camera", the abbreviation "VCAM" denotes "inward-facing head-mounted visible-light camera", and the abbreviation "$VCAM_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration, ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 16A:
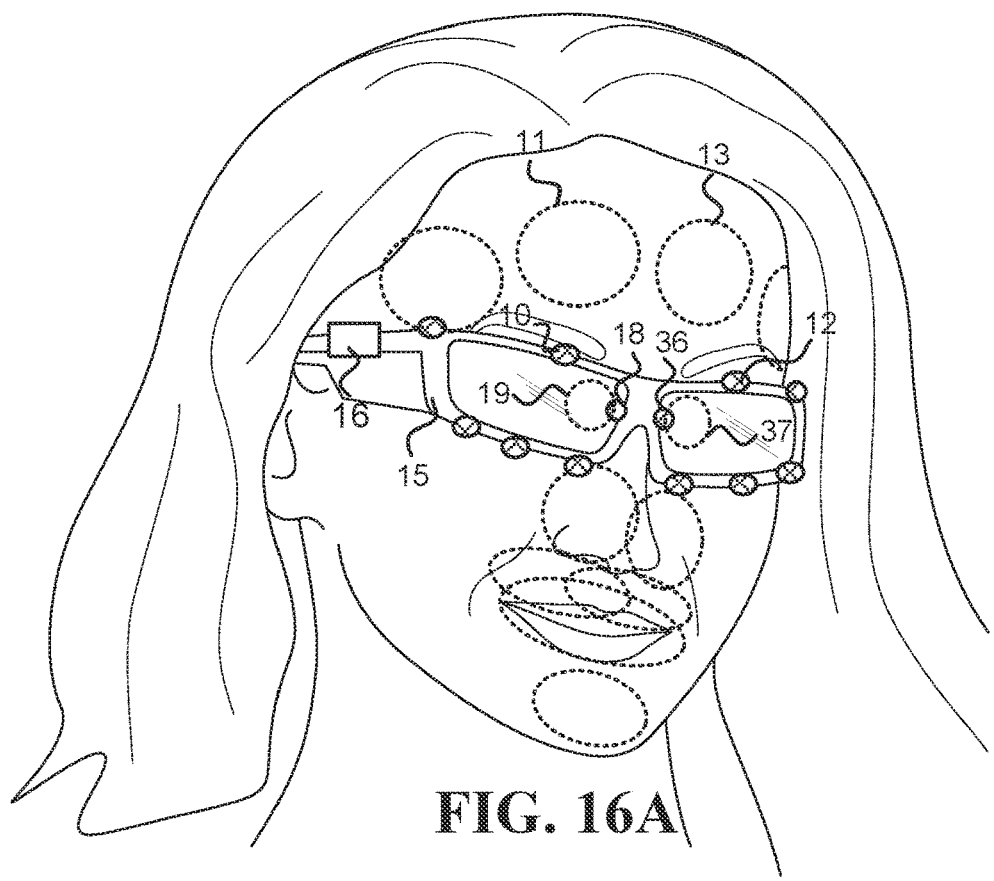
FIG. 16A and FIG. 16B illustrate various inward-facing head-mounted cameras coupled to an eyeglasses frame.
Figure 16B:
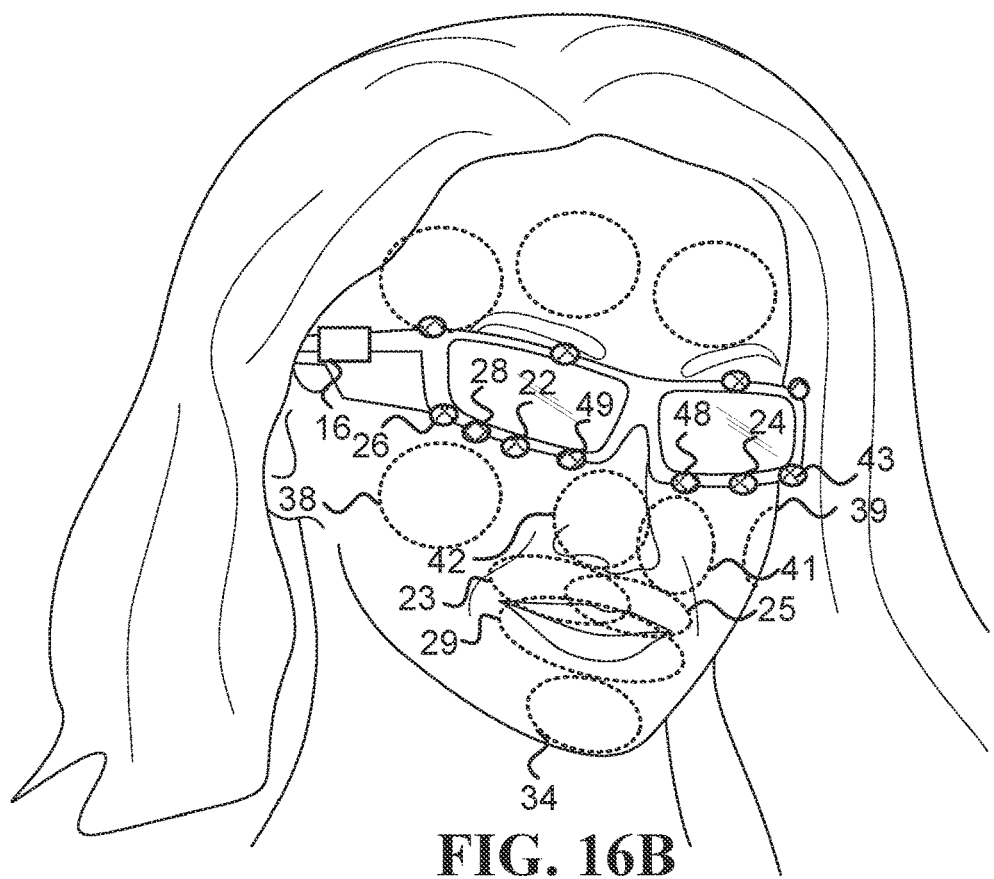

The following figures show various examples of HMSs equipped with head-mounted cameras. FIG. 16A illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 16B illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 17:
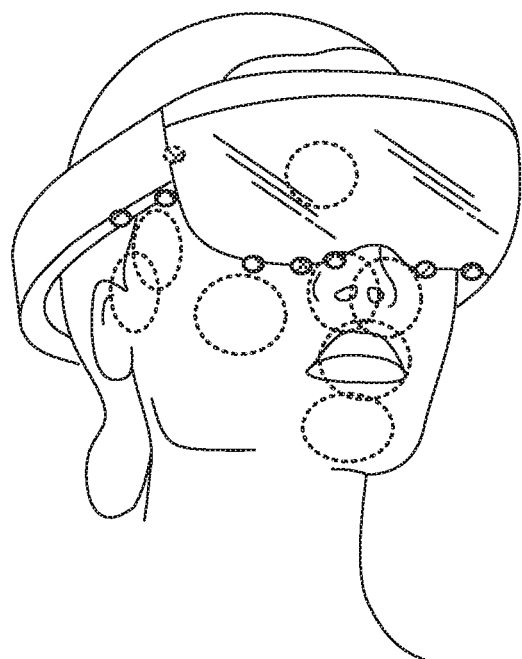
FIG. 17 illustrates inward-facing head-mounted cameras coupled to an augmented reality device.
Figure 18:
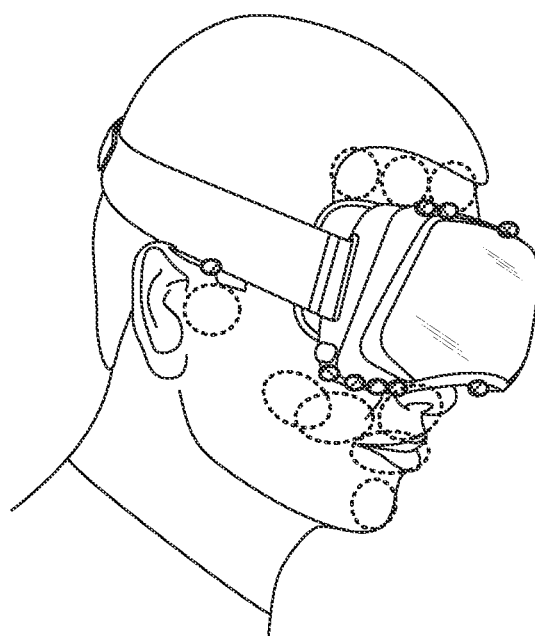
FIG. 18 illustrates head-mounted cameras coupled to a virtual reality device.
Figure 19:
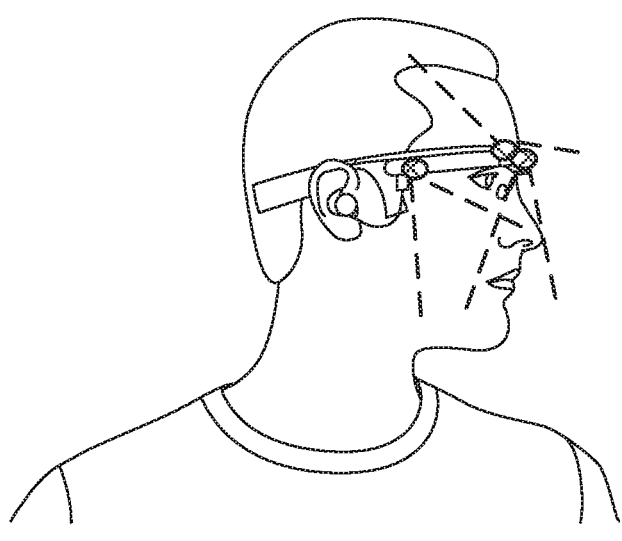
FIG. 19 illustrates a side view of head-mounted cameras coupled to an augmented reality device.
Figure 20:
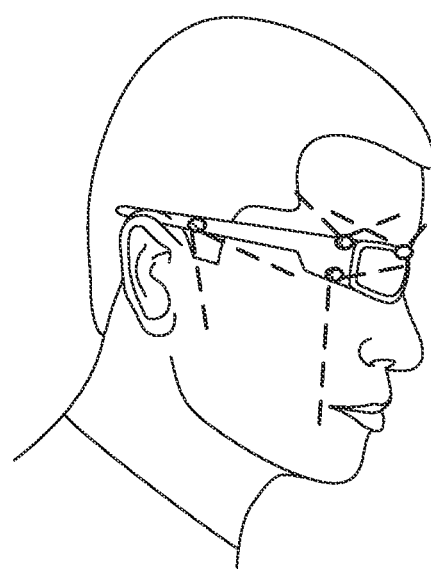
FIG. 20 illustrates a side view of head-mounted cameras coupled to a sunglasses frame.

FIG. 17 illustrates inward-facing head-mounted cameras coupled to an augmented reality device such as Microsoft HoloLens™. FIG. 18 illustrates head-mounted cameras coupled to a virtual reality device such as Facebook's Oculus Rift™. FIG. 19 is a side view illustration of head-mounted cameras coupled to an augmented reality device such as Google Glass™. FIG. 20 is another side view illustration of head-mounted cameras coupled to a sunglasses frame.

Figure 21:
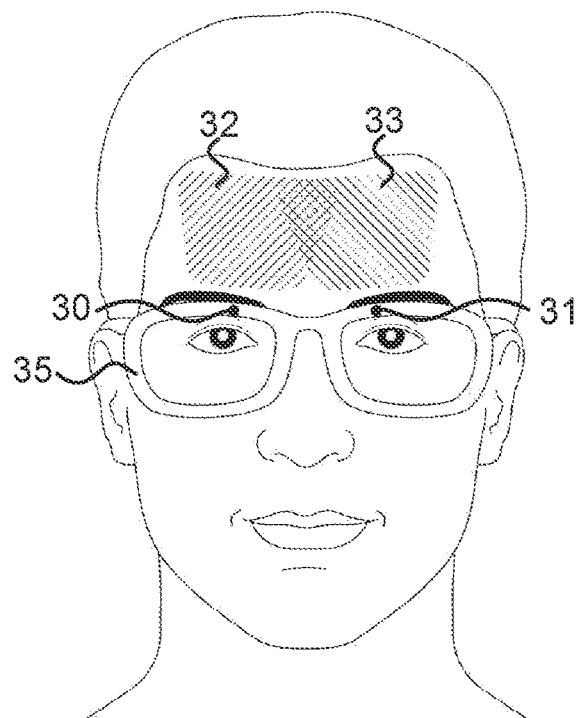
FIG. 21, FIG. 22, FIG. 23 and FIG. 24 illustrate head-mounted systems (HMSs) configured to measure various ROIs relevant to some of the embodiments describes herein.
Figure 22:
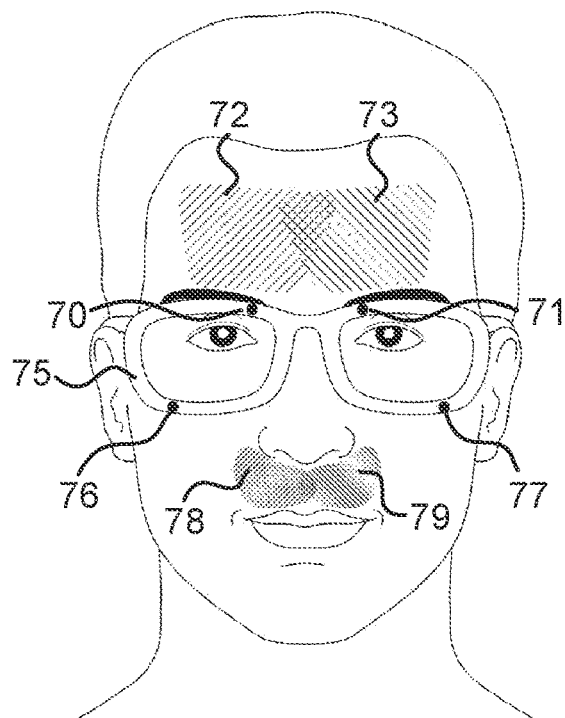
Figure 23:
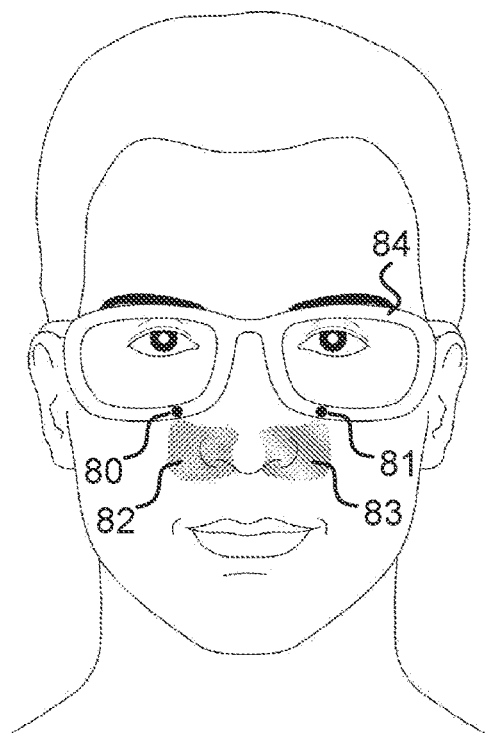
Figure 24:
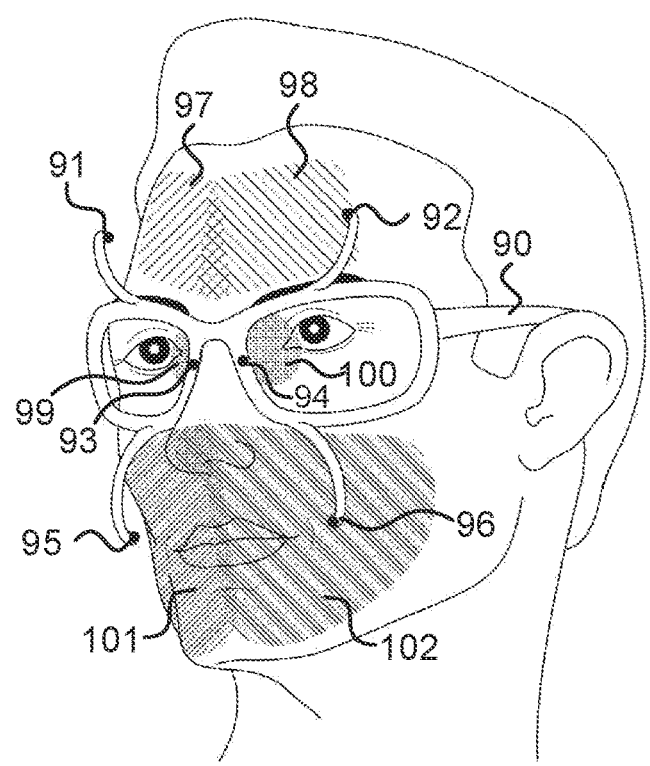

FIG. 21 to FIG. 24 illustrate HMSs configured to measure various ROIs relevant to some of the embodiments describes herein. FIG. 21 illustrates a frame 35 that mounts inward-facing head-mounted cameras 30 and 31 that measure regions 32 and 33 on the forehead, respectively. FIG. 22 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 23 illustrates a frame 84 that mounts inward-facing head-mounted cameras 80 and 81 that measure regions 82 and 83 on the sides of the nose, respectively. And FIG. 24 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 25:
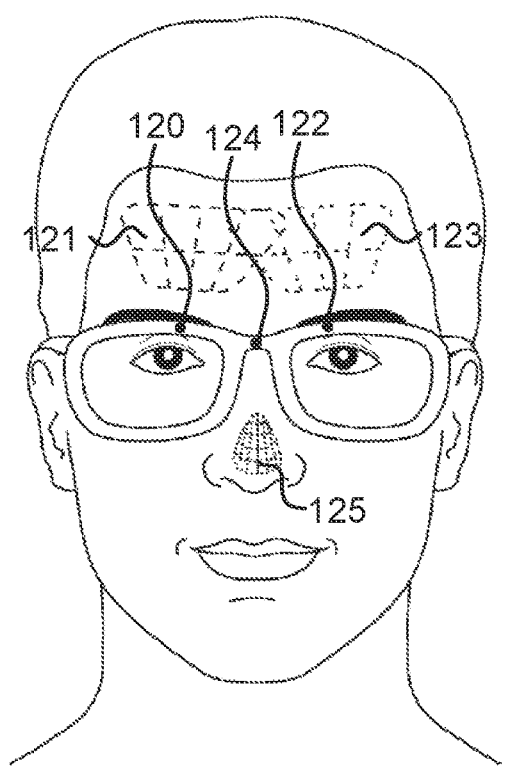
FIG. 25, FIG. 26, FIG. 27 and FIG. 28 illustrate various embodiments of systems that include inward-facing head-mounted cameras having multi-pixel sensors (FPA sensors)
Figure 26:
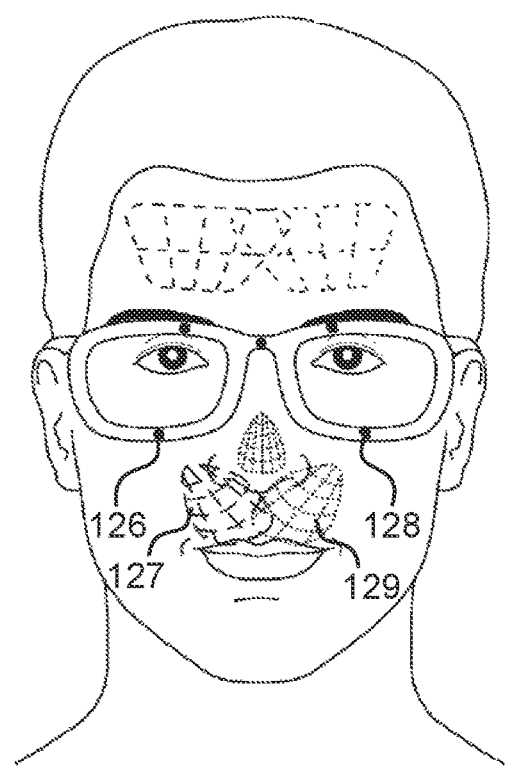
Figure 27:
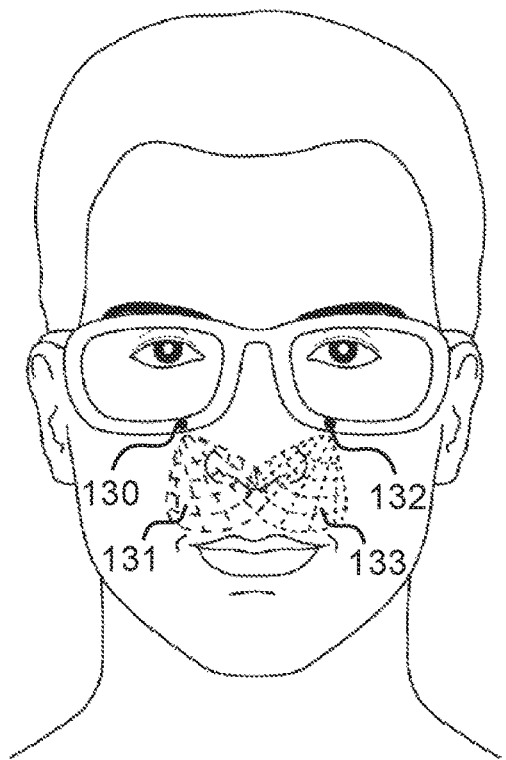
Figure 28:
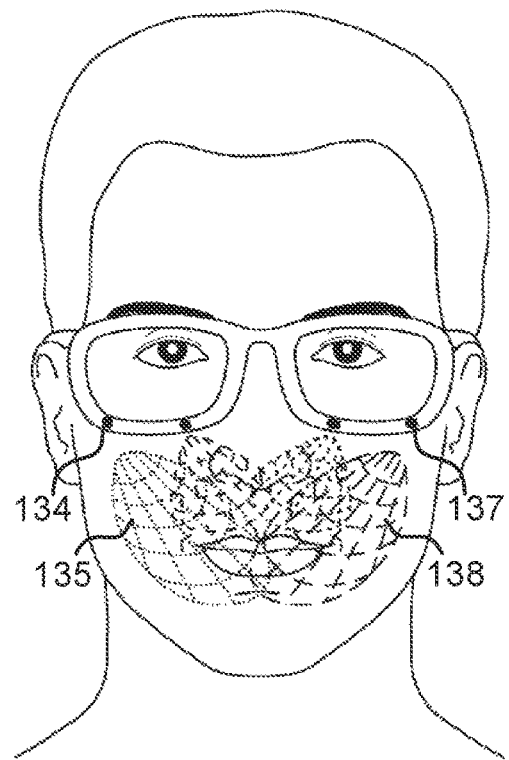

FIG. 25 to FIG. 28 illustrate various inward-facing head-mounted cameras having multi-pixel sensors (FPA sensors), configured to measure various ROIs relevant to some of the embodiments describes herein. FIG. 25 illustrates head-mounted cameras 120 and 122 that measure regions 121 and 123 on the forehead, respectively, and mounts head-mounted camera 124 that measure region 125 on the nose. FIG. 26 illustrates head-mounted cameras 126 and 128 that measure regions 127 and 129 on the upper lip, respectively, in addition to the head-mounted cameras already described in FIG. 25. FIG. 27 illustrates head-mounted cameras 130 and 132 that measure larger regions 131 and 133 on the upper lip and the sides of the nose, respectively. And FIG. 28 illustrates head-mounted cameras 134 and 137 that measure regions 135 and 138 on the right and left cheeks and right and left sides of the mouth, respectively, in addition to the head-mounted cameras already described in FIG. 27.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 29B, FIG. 30B, and FIG. 33), or alternatively, most of the clip-on device may be located behind the frame, as illustrated in FIG. 31B and FIG. 32B.

FIG. 29A, FIG. 29B, and FIG. 29C illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

FIG. 30A and FIG. 30B illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

Figure 31A:
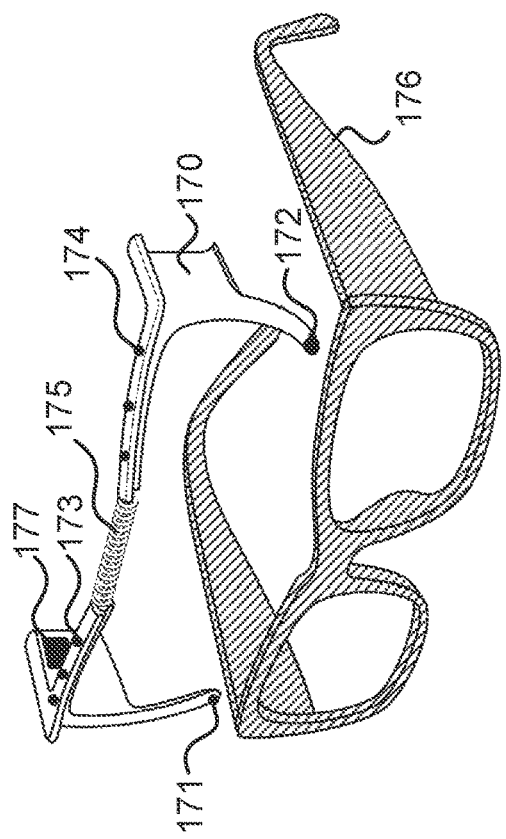
FIG. 31A and FIG. 31B illustrate embodiments of right and left clip-on devices that are configured to be attached behind an eyeglasses frame.
Figure 31B:
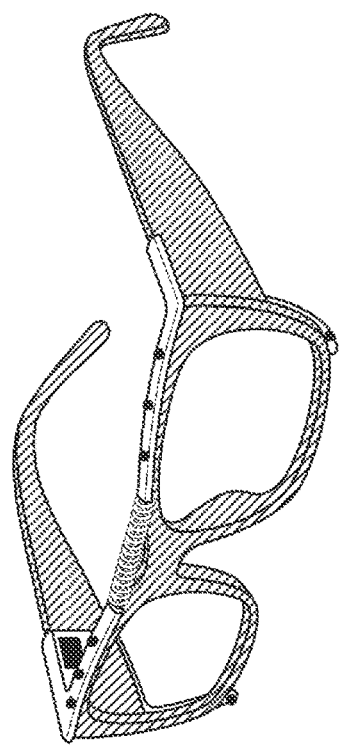

FIG. 31A and FIG. 31B illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

Figure 32A:
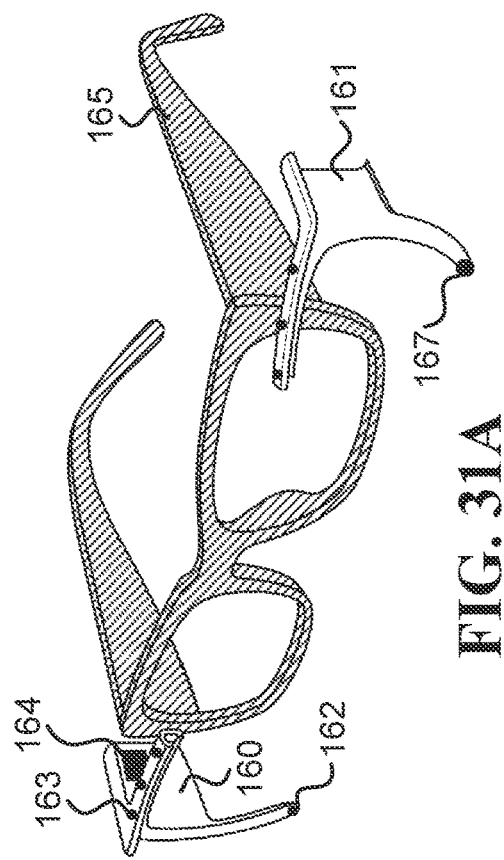
FIG. 32A and FIG. 32B illustrate an embodiment of a single-unit clip-on device that is configured to be attached behind an eyeglasses frame.
Figure 32B:
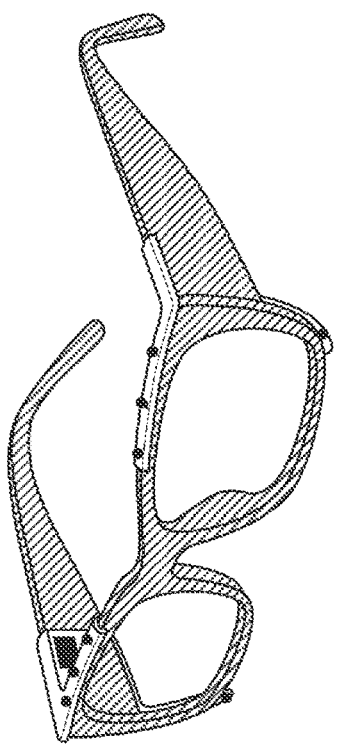
Figure 33:
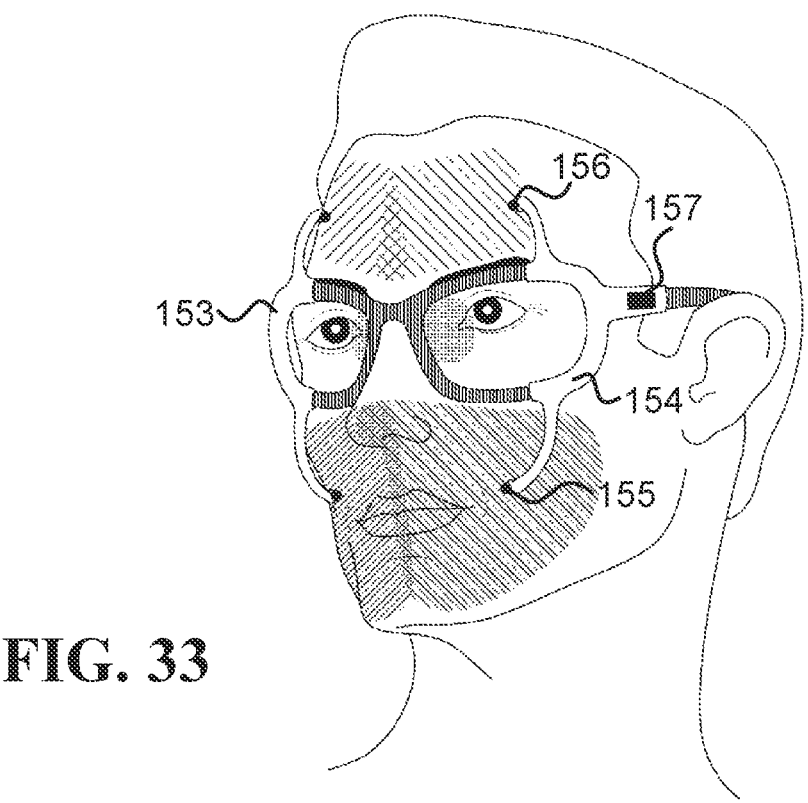
FIG. 33 illustrates embodiments of right and left clip-on devices, which are configured to be attached/detached from an eyeglasses frame, and have protruding arms to hold inward-facing head-mounted cameras.

FIG. 32A and FIG. 32B illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 33 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication, or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorial value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C. in one instance and 37.3° C. in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind; (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

The CAMs can take respiratory-related thermal measurements when their ROIs are on the user's upper lip, the user's mouth, the space where the exhale stream form the user's nose flows, and/or the space where the exhale stream from the user's mouth flows. In some embodiments, one or more of the following respiratory parameters may be calculated based on the respiratory-related thermal measurements taken during a certain period of time:

"Breathing rate" represents the number of breaths per minute the user took during the certain period. The breathing rate may also be formulated as the average time between successive inhales and/or the average between successive exhales.

"Respiration volume" represents the volume of air breathed over a certain duration (usually per minute), the volume of air breathed during a certain breath, tidal volume, and/or the ratio between two or more breaths. For example, the respiration volume may indicate that a first breath was deeper than a second breath, or that breaths during a first minute were shallower than breaths during a second minute.

"Mouth breathing vs nasal breathing" indicates whether during the certain period the user breathed mainly through the mouth (a state characterized as "mouth breathing") or mainly through the nose (a state characterized as "nose breathing" or "nasal breathing"). Optionally, this parameter may represent the ratio between nasal and mouth breathing, such as a proportion of the certain period during which the breathing was more mouth breathing, and/or the relative volume of air exhaled through the nose vs the mouth. In one example, breathing mainly through the mouth refers to inhaling more than 50% of the air through the mouth (and less than 50% of the air through the nose).

"Exhale duration/Inhale duration" represents the exhale(s) duration during the certain period, the inhale(s) duration during the certain period, and/or a ratio of the two aforementioned durations. Optionally, this respiratory parameter may represent one or more of the following: (i) the average duration of the exhales and/or inhales, (ii) a maximum and/or minimum duration of the exhales and/or inhales during the certain period, and (iii) a proportion of times in which the duration of exhaling and/or inhaling reached a certain threshold.

"Post-exhale breathing pause" represents the time that elapses between when the user finishes exhaling and starts inhaling again. "Post-inhale breathing pause" represents the time that elapses between when the user finishes inhaling and when the user starts exhaling after that. The post exhale/inhale breathing pauses may be formulated utilizing various statistics, such as an average post exhale/inhale breathing pause during a certain period, a maximum or minimum duration of post exhale/inhale breathing pause during the certain period, and/or a proportion of times in which the duration of post exhale/inhale breathing pause reached a certain threshold.

"Dominant nostril" is the nostril through which most of the air is exhaled (when exhaling through the nose). Normally the dominant nostril changes during the day, and the exhale is considered balanced when the amount of air exhaled through each nostril is similar. Optionally, the breathing may be considered balanced when the difference between the volumes of air exhaled through the right and left nostrils is below a predetermined threshold, such as 20% or 10%. Additionally or alternatively, the breathing may be considered balanced during a certain duration around the middle of the switching from right to left or left to right nostril dominance. For example, the certain duration of balanced breathing may be about 4 minutes at the middle of the switching between dominant nostrils.

"Temperature of the exhale stream" may be measured based on thermal measurements of the stream that flows from one or both nostrils, and/or the heat pattern generated on the upper lip by the exhale stream from the nose. In one example, it is not necessary to measure the exact temperature of the exhale stream as long as the system is able to differentiate between different temperatures of the exhale stream based on the differences between series of thermal measurements taken at different times. Optionally, the series of thermal measurements that are compared are temperature measurements received from the same pixel(s) of a head-mounted thermal camera.

"Shape of the exhale stream" (also referred to as "SHAPE") represents the three-dimensional (3D) shape of the exhale stream from at least one of the nostrils. The SHAPE changes during the day and may reflect the mental, physiological, and/or energetic state of a user. Usually the temperature of the exhale stream is different from the temperature of the air in the environment; this enables a thermal camera, which captures a portion of the volume through which the exhale stream flows, to take a measurement indicative of the SHAPE, and/or to differentiate between different shapes of the exhale stream (SHAPEs). Additionally, the temperature of the exhale stream is usually different from the temperature of the upper lip, and thus exhale streams having different shapes may generate different thermal patterns on the upper lip. Measuring these different thermal patterns on the upper lip may enable a computer to differentiate between different SHAPEs. In one embodiment, differences between values measured by adjacent thermal pixels of CAM, which measure the exhale stream and/or the upper lip over different time intervals, may correspond to different SHAPEs. In one example, it is not necessary to measure the exact SHAPE as long as it is possible to differentiate between different SHAPEs based on the differences between the values of the adjacent thermal pixels. In another embodiment, differences between average values, measured by the same thermal pixel over different time intervals, may correspond to different SHAPEs. In still another embodiment, the air that is within certain boundaries of a 3D shape that protrudes from the user's nose, which is warmer than the environment air, as measured by CAM, is considered to belong to the exhale stream.

In one embodiment, the SHAPE may be represented by one or more thermal images taken by one or more CAMs. In this embodiment, the shape may correspond to a certain pattern in the one or more images and/or a time series describing a changing pattern in multiple images. In another embodiment, the SHAPE may be represented by at least one of the following parameters: the angle from which the exhale stream blows from a nostril, the width of the exhale stream, the length of the exhale stream, and other parameters that are indicative of the 3D SHAPE. Optionally, the SHAPE may be defined by the shape of a geometric body that confines it, such as a cone or a cylinder, protruding from the user's nose. For example, the SHAPE may be represented by parameters such as the cone's height, the radius of the cone's base, and/or the angle between the cone's altitude axis and the nostril.

"Smoothness of the exhale stream" represents a level of smoothness of the exhale stream from the nose and/or the mouth. In one embodiment, the smoothness of the exhale stream is a value that can be determined based on observing the smoothness of a graph of the respiratory-related thermal measurements. Optionally, it is unnecessary for the system to measure the exact smoothness of the exhale stream as long as it is able to differentiate between smoothness levels of respiratory-related thermal measurements taken at different times. Optionally, the compared thermal measurements taken at different times may be measured by the same pixels and/or by different pixels. As a rule of thumb, the smoother the exhale stream, the lower the stress and the better the physical condition. For example, the exhale stream of a healthy young person is often smoother than the exhale stream of an elderly person, who may even experience short pauses in the act of exhaling.

There are well known mathematical methods to calculate the smoothness of a graph, such as Fourier transform analysis, polynomial fit, differentiability classes, multivariate differentiability classes, parametric continuity, and/or geometric continuity. In one example, the smoothness of $TH_{ROI}$ indicative of the exhale stream is calculated based on a Fourier transform of a series of $TH_{ROI}$. In the case of Fourier transform, the smaller the power of the high-frequencies portion, the smoother the exhale is, and vice versa. Optionally, one or more predetermined thresholds differentiate between the high-frequency and low-frequency portions in the frequency domain In another example, the smoothness of $TH_{ROI}$ indicative of the exhale stream is calculated using a polynomial fit (with a bounded degree) of a series of $TH_{ROI}$. Optionally, the degree of the polynomial used for the fit is proportional (e.g., linear) to the number of exhales in the time series. In the case of polynomial fit, the smoothness may be a measure of the goodness of fit between the series of $TH_{ROI}$ and the polynomial. For example, the lower the squared error, the smoother the graph is considered. In still another embodiment, the smoothness of $TH_{ROI}$ indicative of the exhale stream may be calculated using a machine learning-based model trained with training data comprising reference time series of $TH_{ROI}$ for which the extent of smoothness is known.

In an alternative embodiment, a microphone is used to measure the exhale sounds. The smoothness of the exhale stream may be a value that is proportional to the smoothness of the audio measurement time series taken by the microphone (e.g., as determined based on the power of the high-frequency portion obtained in a Fourier transform of the time series of the audio).

There are various approaches that may be employed in order to calculate values of one or more of the respiratory parameters mentioned above based on respiratory-related thermal measurements. Optionally, calculating the values of one or more of the respiratory parameters may be based on additional inputs, such as statistics about the user (e.g., age, gender, weight, height, and the like), indications about the user's activity level (e.g., input from a pedometer), and/or physiological signals of the user (e.g., heart rate and respiratory rate). Roughly speaking, some approaches may be considered analytical approaches, while other approaches may involve utilization of a machine learning-based model.

In some embodiments, one or more of the respiratory parameters mentioned above may be calculated based on the respiratory-related thermal measurements by observing differences in thermal measurements. In one embodiment, certain pixels that have alternating temperature changes may be identified as corresponding to exhale streams. In this embodiment, the breathing rate may be a calculated frequency of the alternating temperature changes at the certain pixels. In another embodiment, the relative difference in magnitude of temperature changes at different ROIs, such as the alternating temperature changes that correspond to breathing activity, may be used to characterize different types of breathing. For example, if temperature changes at ROI near the nostrils reach a first threshold, while temperature changes at an ROI related to the mouth do not reach a second threshold, then the breathing may be considered nasal breathing; while if the opposite occurs, the breathing may be considered mouth breathing. In another example, if temperature changes at an ROI near the left nostril and/or on the left side of the upper lip are higher than temperature changes at an ROI near the right nostril and/or on the right side of the upper lip, then the left nostril may be considered the dominant nostril at the time the measurements were taken. In still another example, the value of a respiratory parameter may be calculated as a function of one or more input values from among the respiratory-related thermal measurements.

In other embodiments, one or more of the respiratory parameters may be calculated by generating feature values based on the respiratory-related thermal measurements and utilizing a model to calculate, based on the feature values, the value of a certain respiratory parameter from among the parameters mentioned above. The model for the certain respiratory parameter is trained based on samples. Each sample comprises the feature values based on respiratory-related thermal measurements, taken during a certain period of time, and a label indicative of the value of the certain respiratory parameter during the certain period of time. For example, the feature values generated for a sample may include the values of pixels measured by the one or more cameras, statistics of the values of the pixels, and/or functions of differences of values of pixels at different times. Additionally or alternatively, some of the feature values may include various low-level image analysis features, such as feature derived using Gabor filters, local binary patterns and their derivatives, features derived using algorithms such as SIFT, SURF, and/or ORB, image keypoints, HOG descriptors and features derived using PCA or LDA. The labels of the samples may be obtained through various ways. Some examples of approaches for generating the labels include manual reporting (e.g., a user notes the type of his/her breathing), manual analysis of thermal images (e.g., an expert determines a shape of an exhale stream), and/or utilizing sensors (e.g., a chest strap that measures the breathing rate and volume).

Training the model for the certain respiratory parameter based on the samples may involve utilizing one or more machine learning-based training algorithms, such as a training algorithm for a decision tree, a regression model, or a neural network. Once the model is trained, it may be utilized to calculate the value of the certain respiratory parameter based on feature values generated based on respiratory-related thermal measurements taken during a certain period, for which the label (i.e., the value of the certain respiratory parameter) may not be known.

In one embodiment, a system configured to calculate a respiratory parameter includes an inward-facing head-mounted thermal camera (CAM) and a computer. CAM is worn on a user's head and takes thermal measurements of a region below the nostrils ($TH_{ROI}$), where $TH_{ROI}$ are indicative of the exhale stream. The "region below the nostrils", which is indicative of the exhale stream, refers to one or more regions on the upper lip, the mouth, and/or air volume(s) through which the exhale streams from the nose and/or mouth flow. The flowing of the typically warm air of the exhale stream can change the temperature at the one or more regions, and thus thermal measurements of these one or more regions can provide information about properties of the exhale stream. The computer (i) generates feature values based on $TH_{ROI}$, and (ii) utilizes a model to calculate the respiratory parameter based on the feature values. The respiratory parameter may be indicative of the user's breathing rate, and the model may be trained based on previous $TH_{ROI}$ of the user taken during different days. FIG. 49B illustrates one embodiment of a system for calculating a respiratory parameter. The system includes a computer 445 and CAM that is coupled to the eyeglasses frame worn by the user 420 and provides $TH_{ROI}$ 443.

The computer 445 generates feature values based on $TH_{ROI}$ 443, and possibly other sources of data. Then the computer utilizes a model 442 to calculate, based on the feature values, a value 447 of the respiratory parameter. The value 447 may be indicative of at least one of the following: breathing rate, respiration volume, whether the user is breathing mainly through the mouth or through the nose, exhale (inhale) duration, post-exhale (post-inhale) breathing pause, a dominant nostril, a shape of the exhale stream, smoothness of the exhale stream, and/or temperature of the exhale stream. Optionally, the respiratory parameters calculated by the computer 445 may be indicative of the respiration volume. Optionally, the value 447 is stored (e.g., for life-logging purposes) and/or forwarded to a software agent operating on behalf of the user (e.g., in order for the software agent to make a decision regarding the user).

The feature values generated by the computer 445 may include any of the feature values described in this disclosure that are utilized to detect a physiological response. Optionally, the thermal measurements may undergo various forms of filtering and/or normalization. For example, the feature values generated based on $TH_{ROI}$ may include: time series data comprising values measured by CAM, average values of certain pixels of CAM, and/or values measured at certain times by the certain pixels. Additionally, the feature values may include values generated based on additional measurements of the user taken by one or more additional sensors (e.g., measurements of heart rate, heart rate variability, brainwave activity, galvanic skin response, muscle activity, and/or an extent of movement). Additionally or alternatively, at least some of the feature values may include measurements of the environment in which the user is in, and/or confounding factors that may interfere with the detection.

A user interface (UI) 448 may be utilized to present the value 447 of the respiratory parameter and/or present an alert (e.g., to the user 420 and/or to a caregiver). In one example, UI 448 may be used to alert responsive to an indication that the value 447 reaches a threshold (e.g., when the breathing rate exceeds a certain value and/or after the user 420 spent a certain duration mouth breathing instead of nasal breathing). In another example, UI 448 may be used to alert responsive to detecting that the probability of a respiratory-related attack reaches a threshold.

In one embodiment, the value 447 may be indicative of the smoothness of the exhale stream. Optionally, the value 447 may be presented to the user 420 to increase the user's awareness to the smoothness of his/her exhale stream. Optionally, responsive to detecting that the smoothness is below a predetermined threshold, the computer 445 may issue an alert for the user 420 (e.g., via the UI 448) in order to increase the user's awareness to the user's breathing.

The model 442 is trained on data that includes previous $TH_{ROI}$ of the user 420 and possibly other users. Optionally, the previous measurements were taken on different days and/or over a period longer than a week. Training the model 442 typically involves generating samples based on the previous $TH_{ROI}$ and corresponding labels indicative of values of the respiratory parameter. The labels may come from different sources. In one embodiment, one or more of the labels may be generated using a sensor that is not a thermal camera, which may or may not be physically coupled to a frame worn by the user. The sensor's measurements may be analyzed by a human expert and/or a software program in order to generate the labels. In one example, the sensor is part of a smart shirt and/or chest strap that measures various respiratory (and other) parameters, such as Hexoskin™ smart shirt. In another embodiment, one or more of the labels may come from an external source such as an entity that observes the user, which may be a human observer or a software program. In yet another embodiment, one or more of the labels may be provided by the user, for example by indicating whether he/she is breathing through the mouth or nose and/or which nostril is dominant.

The samples used to train the model 442 usually include samples corresponding to different values of the respiratory parameter. In some embodiments, the samples used to train the model 442 include samples generated based on $TH_{ROI}$ taken at different times of the day, while being at different locations, and/or while conducting different activities. In one example, the samples are generated based on $TH_{ROI}$ taken in the morning and $TH_{ROI}$ taken in the evening. In another example, the samples are generated based on $TH_{ROI}$ of a user taken while being indoors, and $TH_{ROI}$ of the user taken while being outdoors. In yet another example, the samples are generated based on $TH_{ROI}$ taken while a user was sitting down, and $TH_{ROI}$ taken while the user was walking, running, and/or engaging in physical exercise (e.g., dancing, biking, etc.).

Additionally or alternatively, the samples used to train the model 442 may be generated based on $TH_{ROI}$ taken while various environmental conditions persisted. For example, the samples include first and second samples generated based on $TH_{ROI}$ taken while the environment had first and second temperatures, with the first temperature being at least 10° C. warmer than the second temperature. In another example, the samples include samples generated based on measurements taken while there were different extents of direct sunlight and/or different extents of wind blowing.

Various computational approaches may be utilized to train the model 442 based on the samples described above. In one example, training the model 442 may involve selecting a threshold based on the samples. Optionally, if a certain feature value reaches the threshold then a certain respiratory condition is detected (e.g., unsmooth breathing). Optionally, the model 442 includes a value describing the threshold. In another example, a machine learning-based training algorithm may be utilized to train the model 442 based on the samples. Optionally, the model 442 includes parameters of at least one of the following types of models: a regression model, a neural network, a nearest neighbor model, a support vector machine, a support vector machine for regression, a naïve Bayes model, a Bayes network, and a decision tree.

In some embodiments, a deep learning algorithm may be used to train the model 442. In one example, the model 442 may include parameters describing multiple hidden layers of a neural network. In one embodiment, when $TH_{ROI}$ include measurements of multiple pixels, the model 442 may include a convolution neural network (CNN). In one example, the CNN may be utilized to identify certain patterns in the thermal images, such as patterns of temperatures in the region of the exhale stream that may be indicative of a respiratory parameter, which involve aspects such as the location, direction, size, and/or shape of an exhale stream from the nose and/or mouth. In another example, calculating a value of a respiratory parameter, such as the breathing rate, may be done based on multiple, possibly successive, thermal measurements. Optionally, calculating values of the respiratory parameter based on thermal measurements may involve retaining state information that is based on previous measurements. Optionally, the model 442 may include parameters that describe an architecture that supports such a capability. In one example, the model 442 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using bidirectional recurrent neural network architecture (BRNN).

The computer 445 may detect a respiratory-related attack (such as an asthma attack, an epileptic attack, an anxiety attack, a panic attack, and a tantrum) based on feature values generated based on $TH_{ROI}$ 443. The computer 445 may further receive additional inputs (such as indications of consuming a substance, a situation of the user, and/or thermal measurements of the forehead), and detect the respiratory-related attack based on the additional inputs. For example, the computer 445 may generate one or more of the feature values used to calculate the value 447 based on the additional inputs.

In a first embodiment, the computer 445 utilizes an indication of consumption of a substance to detect a respiratory-related attack. Optionally, the model 442 is trained based on: a first set of $TH_{ROI}$ taken while the user experienced a respiratory-related attack after consuming the substance, and a second set of $TH_{ROI}$ taken while the user did not experience a respiratory-related attack after consuming the substance. The duration to which "after consuming" refers depends on the substance and may last from minutes to hours. Optionally, the consuming of the substance involves consuming a certain drug and/or consuming a certain food item, and the indication is indicative of the time and/or the amount consumed.

In a second embodiment, the computer 445 utilizes an indication of a situation of the user to detect a respiratory-related attack. Optionally, the model 442 is trained based on: a first set of $TH_{ROI}$ taken while the user was in the situation and experienced a respiratory-related attack, and a second set of $TH_{ROI}$ taken while the user was in the situation and did not experience a respiratory-related attack. Optionally, the situation involves (i) interacting with a certain person, (ii) a type of activity the user is conducting, selected from at least two different types of activities associated with different levels of stress, and/or (iii) a type of activity the user is about to conduct (e.g., within thirty minutes), selected from at least two different types of activities associated with different levels of stress.

In a third embodiment, the system includes another CAM that takes thermal measurements of a region on the forehead ($TH_F$) of the user, and the computer 445 detects a respiratory related attack based on $TH_{ROI}$ and $TH_F$. For example, $TH_{ROI}$ and $TH_F$ may be utilized to generate one or more of the feature values used to calculate the value indicative of the probability that the user is experiencing, or is about to experience, the respiratory-related attack. Optionally, the model 442 was trained based on a first set of $TH_{ROI}$ and $TH_F$ taken while the user experienced a respiratory-related attack, and a second set of $TH_{ROI}$ and $TH_F$ taken while the user did not experience a respiratory-related attack.

The system may optionally include a sensor 435 that takes measurements $m_{move}$ 450 that are indicative of movements of the user 420; the system further detects the physiological response based on $m_{move}$ 450. The sensor 435 may include one or more of the following sensors: a gyroscope and/or an accelerometer, an outward-facing visible-light camera (that feeds an image processing algorithm to detect movement from a series of images), a miniature radar (such as low-power radar operating in the range between 30 GHz and 3,000 GHz), a miniature active electro-optics distance measurement device (such as a miniature Lidar), and/or a triangulation wireless device (such as a GPS receiver). Optionally, the sensor 435 is physically coupled to the frame or belongs to a device carried by the user (e.g., a smartphone or a smartwatch).

In a first embodiment, the computer 445 may detect the respiratory-related attack if the value 447 of the respiratory parameter reaches a first threshold, while $m_{move}$ 450 do not reach a second threshold. In one example, reaching the first threshold indicates a high breathing rate, which may be considered too high for the user. Additionally, in this example, reaching the second threshold may mean that the user is conducting arduous physical activity. Thus, if the user is breathing too fast and this is not because of physical activity, then the computer 445 detects this as an occurrence of a respiratory-related attack (e.g., an asthma attack or a panic attack).

In a second embodiment, the computer 445 may generate feature values based on $m_{move}$ 450 in addition to $TH_{ROI}$ 443, and utilize an extended model to calculate, based on these feature values, a value indicative of the probability that the user is experiencing, or is about to experience, the respiratory related attack. In one example, the feature values used along with the extended model (which may be the model 442 or another model) include one or more of the following: (i) values comprised in $TH_{ROI}$ 443, (ii) values of a respiratory parameter of the user 420, which are generated based on $TH_{ROI}$ 443 (iii) values generated based on additional measurements of the user 420 (e.g., measurements of heart rate, heart rate variability, brainwave activity, galvanic skin response, muscle activity, and an extent of movement), (iv) measurements of the environment in which the user 420 was in while $TH_{ROI}$ 443 were taken, (v) indications of various occurrences which may be considered confounding factors (e.g., touching the face, thermal radiation directed at the face, or airflow directed at the face), and/or (vi) values indicative of movements of the user (which are based on $m_{move}$ 450).

The extended model is trained on samples generated from prior $m_{move}$ and $TH_{ROI}$, and corresponding labels indicating times of having the respiratory-related attack. The labels may come from various sources, such as measurements of the user (e.g., to detect respiratory distress), observations by a human and/or software, and/or the indications may be self-reported by the user. The samples used to train the extended model may be generated based on measurements taken over different days, and encompass measurements taken when the user was in different situations.

Usually the exhaled air warms up the skin below the nostrils, and during inhale the skin below the nostrils cools. This enables the system to identify the exhale based on measuring an increase in the temperature of the skin below the nostrils an inhale, and identify the inhale based on measuring a decrease in the temperature of the skin below the nostrils.

Synchronizing a physical effort with the breathing is highly recommended by therapists and sport instructors. For example, some elderly and/or unfit people can find it difficult to stand up and/or make other physical efforts because many of them do not exhale while making the effort, and/or do not synchronize the physical effort with their breathing. These people can benefit from a system that reminds them to exhale while making the effort, and/or helps them synchronize the physical effort with their breathing. As another example, in many kinds of physical activities it is highly recommended to exhale while making a physical effort and/or exhale during certain movements (such as exhale while bending down in Uttanasana).

In one embodiment, the computer 445 determines based on $m_{move}$ 450 and $TH_{ROI}$ 443 whether the user exhaled while making a physical effort above a predetermined threshold. Optionally, the computer receives a first indication that the user is making or is about to make the physical effort, commands a user interface (UI) to suggest the user to exhale while making the physical effort, and commands the UI to play a positive feedback in response to determining that the user managed to exhale while making the physical effort. Additionally, the computer may further command the UI to play an explanation why the user should try next time to exhale while making the physical effort in response to determining that the user did not exhale while making the physical effort.

FIG. 39A to FIG. 40C illustrate how the system described above may help train an elderly user to exhale during effort. In FIG. 39A the system identifies that the user inhaled rather than exhaled while getting up from a sitting position in a chair; the system alerts the user about this finding and suggests that next time the user should exhale while getting up. In FIG. 39B, the system identifies that the user exhaled at the correct time and commends the user on doing so. Examples of physical efforts include standing up, sitting down, manipulating with the hands an item that requires applying a significant force, defecating, dressing, leaning over, and/or lifting an item.

In FIG. 40A the system identifies that the user inhaled rather than exhaled while bending down to the dishwasher, and presents a thumbs-down signal (e.g., on the user's smartphone). In FIG. 40B the system identifies that the user exhaled while bending down to the dishwasher, and presents a thumbs-up signal. In FIG. 40C illustrates a smartphone app for counting the thumbs-up and thumbs-down signals identified during a day. The app may show various statistics, such as thumbs-up/thumbs-down during the past week, from start training with the app, according to locations the user is, while being with certain people, and/or organized according to types of exercises (such as a first counter for yoga, a second counter for housework, and a third counter for breathing during work time).

Figure 41A:
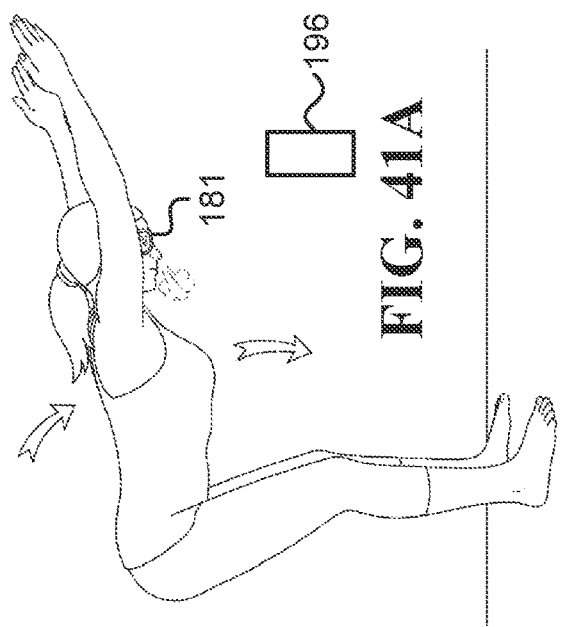
FIG. 41A and FIG. 41B illustrate a fitness app running on smartphone, which instructs the user to exhale while bending down, and to inhale while straightening up.
Figure 41B:
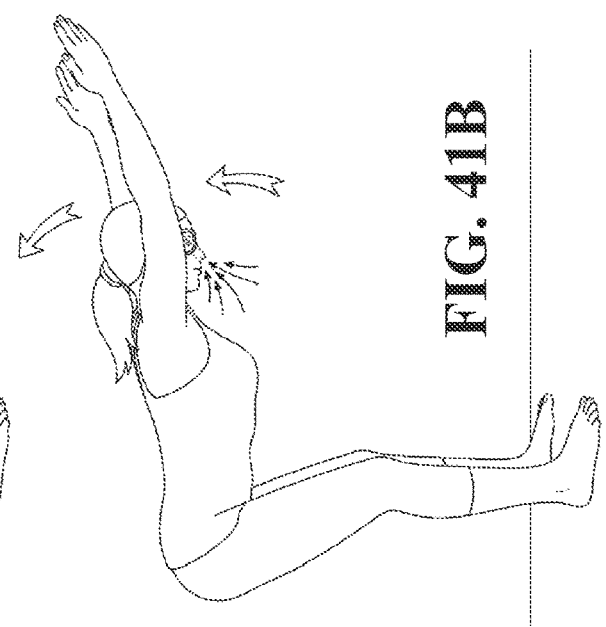

In one embodiment, the computer 445: (i) receives from a fitness app (also known as a personal trainer app) an indication that the user should exhale while making a movement, (ii) determines, based on $m_{move}$, when the user is making the movement, and (iii) determines, based on $TH_{ROI}$, whether the user exhaled while making the movement. Optionally, the computer commands the UI to (i) play a positive feedback in response to determining that the user managed to exhale while making the physical effort, and/or (ii) play an alert and/or an explanation why the user should try next time to exhale while making the physical effort in response to determining that the user did not exhale while making the physical effort. FIG. 41A illustrates a fitness app running on smartphone 196, which instructs the user to exhale while bending down. CAM coupled to eyeglasses frame 181 measures the user breathing and is utilized by the fitness app that helps the user to exhale correctly. FIG. 41B illustrates instructing the user to inhale while straightening up.

Figure 42:
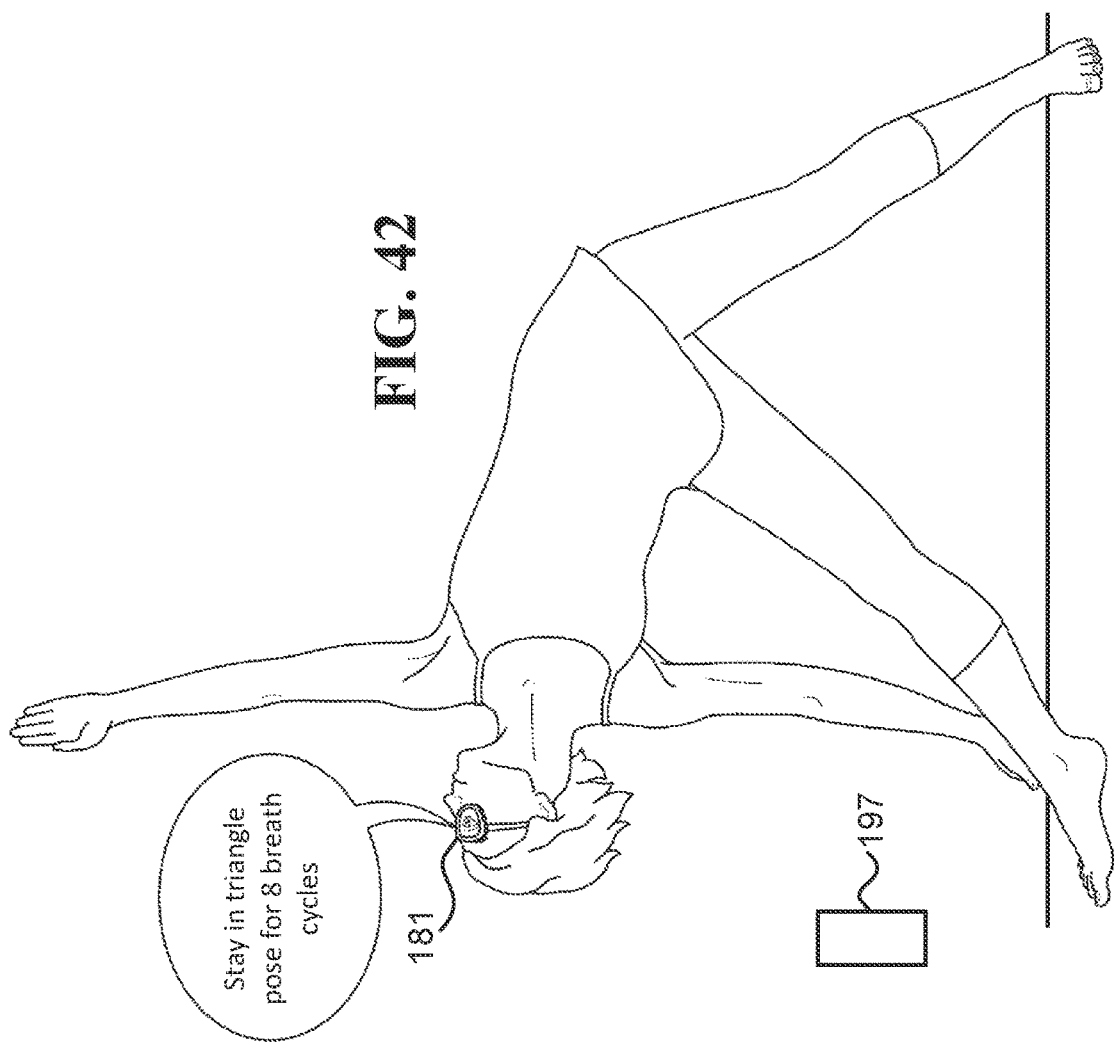
FIG. 42 illustrates a fitness app running on smartphone, which instructs the user to stay in a triangle pose for 8 breath cycles.

In another embodiment, the computer 445: (i) receives from a fitness app a certain number of breath cycles during which the user should perform a physical exercise, such as keeping a static yoga pose for a certain number of breath cycles, or riding a spin bike at a certain speed for a certain number of breath cycles, (ii) determines, based on $m_{move}$, when the user performs the physical exercise, and (iii) counts, based on $TH_{ROI}$, the number of breath cycles the user had while performing the physical exercise. Optionally, the computer commands the UI to play an instruction switch to another physical exercise responsive to detecting that the user performed the physical exercise for the certain number of breath cycles. Additionally or alternatively, the computer commands the UI to play a feedback that refers to the number of counted breath cycles responsive to detecting that the user performed the physical exercise for a number of breath cycles that is lower than the certain number of breath cycles. FIG. 42 illustrates a fitness app running on smartphone 197, which instructs the user to stay in a triangle pose for 8 breath cycles. CAM coupled to eyeglasses frame 181 measures the breathing and is utilized by the fitness app that calculates the breath cycles and counts the time to stay in the triangle pose according to the measured breath cycles.

The duration of exhaling and inhaling (denoted herein $t_{exhale}$ and $t_{inhale}$ respectively) can have various physiological effects. For example, for some users, breathing with prolonged inhales (relative to the exhales) can increase the possibility of suffering an asthma attack. In particular, keeping the duration of exhaling longer than the duration of inhaling (i.e., $t_{exhale}/t_{inhale} > 1$, and preferably $t_{exhale}/t_{inhale} \geq 2$) may provide many benefits, such as having a calming effect and relieving asthma symptoms. In one embodiment, a computer is further configured to calculate, based on $TH_{ROI}$, the ratio between exhale and inhale durations ($t_{exhale}/t_{inhale}$).

Many people are not aware of their breathing most of the time. These people can benefit from a system that is able to calculate $t_{exhale}/t_{inhale}$ and provide them with feedback when it is beneficial to increase the ratio. In one embodiment, a computer suggests the user, via the UI, to increase $t_{exhale}/t_{inhale}$ when it falls below a threshold. Optionally, the computer updates occasionally the calculation of $t_{exhale}/t_{inhale}$, and suggests to progressively increase $t_{exhale}/t_{inhale}$ at least until reaching a ratio of 1.5. Optionally, the computer stops suggesting to the user to increase $t_{exhale}/t_{inhale}$ responsive to identifying that $t_{exhale}/t_{inhale} \geq 2$. In another embodiment, the computer is configured to: (i) receive a first indication that the user's stress level reaches a first threshold, (ii) identify, based on $TH_{ROI}$, that the ratio between exhaling and inhaling durations ($t_{exhale}/t_{inhale}$) is below a second threshold that is below 1.5, and (iii) command the UI to suggest to the user to prolong the exhale until $t_{exhale}/t_{inhale}$ reaches a third threshold that is at least 1.5.

Figure 37:
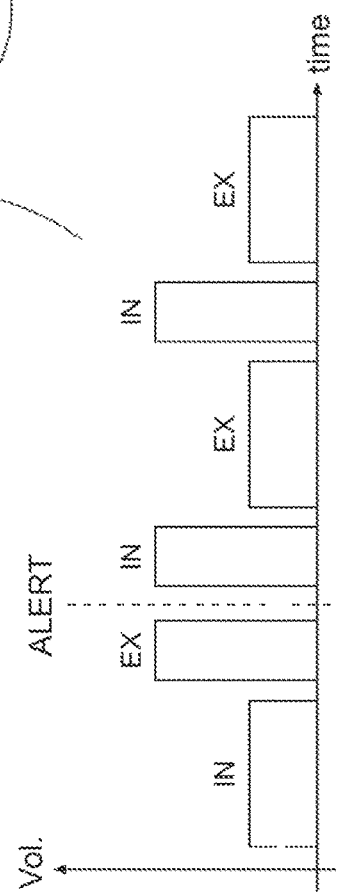
FIG. 37 illustrates a situation in which an alert is issued to a user when it is detected that the ratio the duration of exhaling and inhaling is too low.
Figure 45:
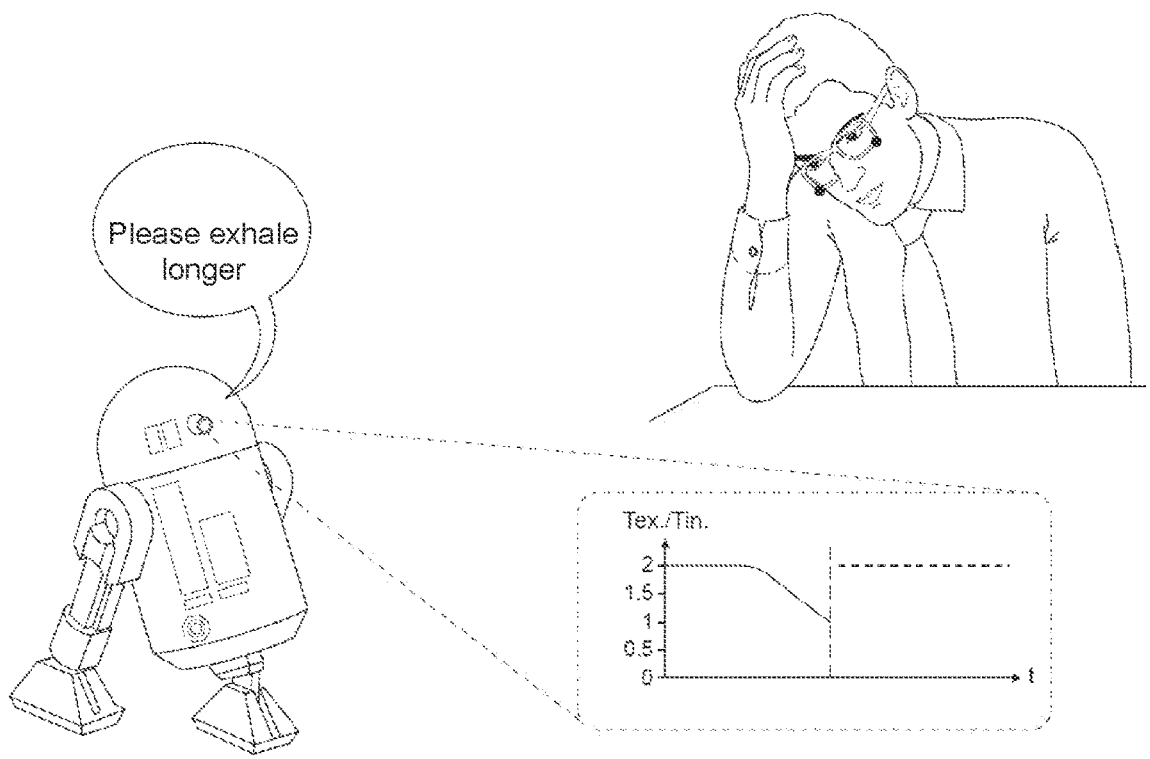
FIG. 45 illustrates a virtual robot that the user sees via augmented reality (AR), which urges the user to increase the ratio between the duration of the user's exhales and inhales.

FIG. 37 illustrates a situation in which an alert is issued to a user when it is detected that the ratio $t_{exhale}/t_{inhale}$ is too low. Another scenario in which such an alert may be issued to a user is illustrated in FIG. 45, which shows a virtual robot that the user sees via augmented reality (AR). The robot urges the user to increase the ratio between the duration of the user's exhales and inhales in order to alleviate the stress that builds up. Monitoring of respiratory parameters, and in particular, the ratio $t_{exhale}/t_{inhale}$ can help a user address a variety of respiratory-related symptoms, as described in the following examples.

Figure 46:
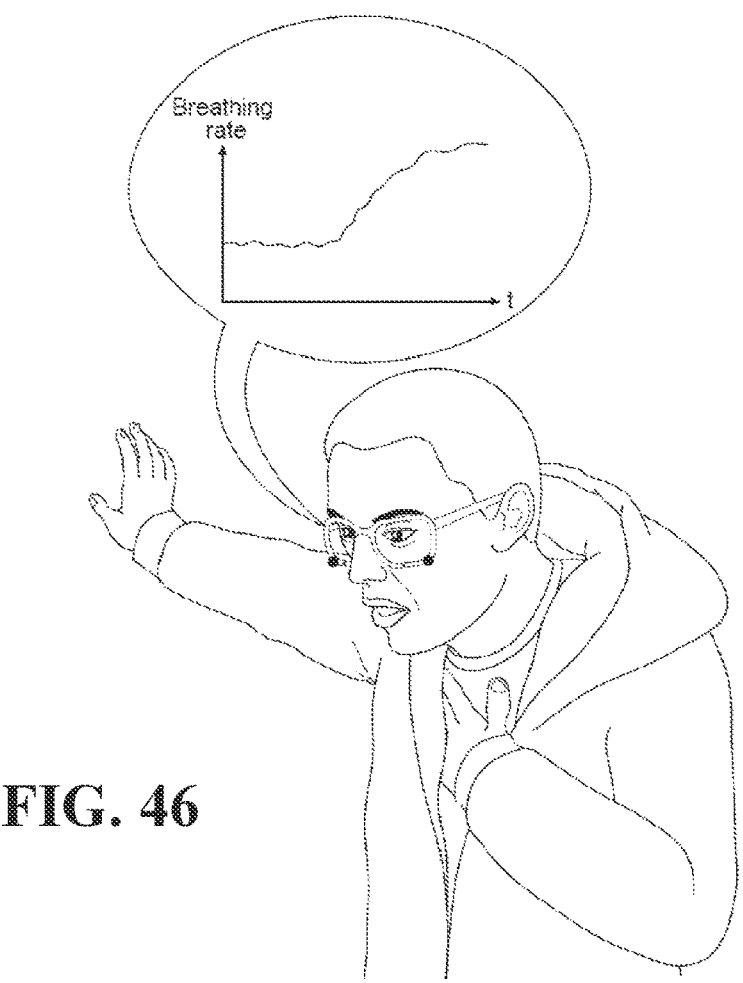
FIG. 46 illustrates an asthmatic patient who receives an alert that his breathing rate increased to an extent that often precedes an asthma attack.

Asthma attacks are related to a person's breathing. Identifying certain changes in respiratory parameters, such as breathing rate above a predetermined threshold, can help a computer to detect an asthma attack based on the thermal measurements. Optionally, the computer utilizes a model, which was trained on previous measurements of the user taken while the user had an asthma attack, to detect the asthma attack based on the thermal measurements. FIG. 46 illustrates an asthmatic patient who receives an alert (e.g., via an augmented reality display) that his breathing rate increased to an extent that often precedes an asthma attack. In addition to the breathing rate, the computer may base its determination that an asthma attack is imminent on additional factors, such as sounds and/or movement analysis as described below.

In a first embodiment, the computer may receive recordings of the user obtained with a microphone. Such recordings may include sounds that can indicate that an asthma attack is imminent; these sounds may include: asthmatic breathing sounds, asthma wheezing, and/or coughing. Optionally, the computer analyzes the recordings to identify occurrences of one or more of the above sounds. Optionally, taking into account the recordings of the user can affect how the computer issues alerts regarding an imminent asthma attack. For example, a first alert provided to the user in response to identifying the increase in the user's breathing rate above the predetermined threshold without identifying at least one of the body sounds may be less intense than a second alert provided to the user in response to identifying both the increase in the user's breathing rate above the predetermined threshold and at least one of the body sounds. Optionally, in the example above, the first alert may not be issued to the user at all.

In a second embodiment, the computer may receive measurements obtained from a movement sensor worn by the user and configured to measure user movements. Some movements that may be measured and may be related to an asthma attack include: spasms, shivering, and/or sagittal plane movements indicative of one or more of asthma wheezing, coughing, and/or chest tightness. Optionally, the computer analyzes the measurements of the movement sensor to identify occurrences of one or more of the above movements. Optionally, considering the measured movements can affect how the computer issues alerts regarding an imminent asthma attack. For example, a first alert provided to the user in response to identifying an increase in the user's breathing rate above a predetermined threshold, without measuring a movement related to an asthma attack, is less intense than a second alert provided to the user in response to identifying the increase in the user's breathing rate above the predetermined threshold while measuring a movement related to an asthma attack.

In some embodiments, a first alert may be considered less intense than a second alert if it is less likely to draw the user's attention. For example, the first alert may not involve a sound effect or involve a low-volume effect, while the second alert may involve a sound effect (which may be louder than the first's). In another example, the first alert may involve a weaker visual cue than the second alert (or no visual cue at all). Examples of visual cues include flashing lights on a device or images brought to the foreground on a display. In still another example, the first alert is not provided to the user and therefore does not draw the user's attention (while the second alert is provided to the user).

In one embodiment, responsive to a determination that an asthma attack is imminent, the UI suggests the user to take a precaution, such as increasing $t_{exhale}/t_{inhale}$, preforming various breathing exercises (e.g., exercises that involve holding the breath), and/or taking medication (e.g., medication administered using an inhaler), in order to decrease or prevent the severity of the imminent asthma attack. Optionally, detecting the signs of an imminent asthma attack includes identifying an increase in the breathing rate above a predetermined threshold.

Stress is also related to a person's breathing. In one embodiment, a computer receives a first indication that the user's stress level reaches a threshold and receives a second indication (i) that the ratio between exhaling and inhaling durations is below 1.5 ($t_{exhale}/t_{inhale} < 1.5$), and/or (ii) that the user's breathing rate reached a predetermined threshold. Then the computer may command a UI to suggest the user to increase $t_{exhale}/t_{inhale}$ to at least 1.5. Optionally, the computer receives the first indication from a wearable device, calculates $t_{exhale}/t_{inhale}$ based on $TH_{ROI}$ (which is indicative of the exhale stream), and commands the UI to provide the user with an auditory and/or visual feedback indicative of the change in $t_{exhale}/t_{inhale}$ in response to the suggestion to increase the ratio. Optionally, the computer may command the UI to update the user about changes in the stress level in response to increasing $t_{exhale}/t_{inhale}$, and may provide positive reinforcement to help the user to maintain the required ratio at least until a certain improvement in the stress level is achieved.

Figure 38:
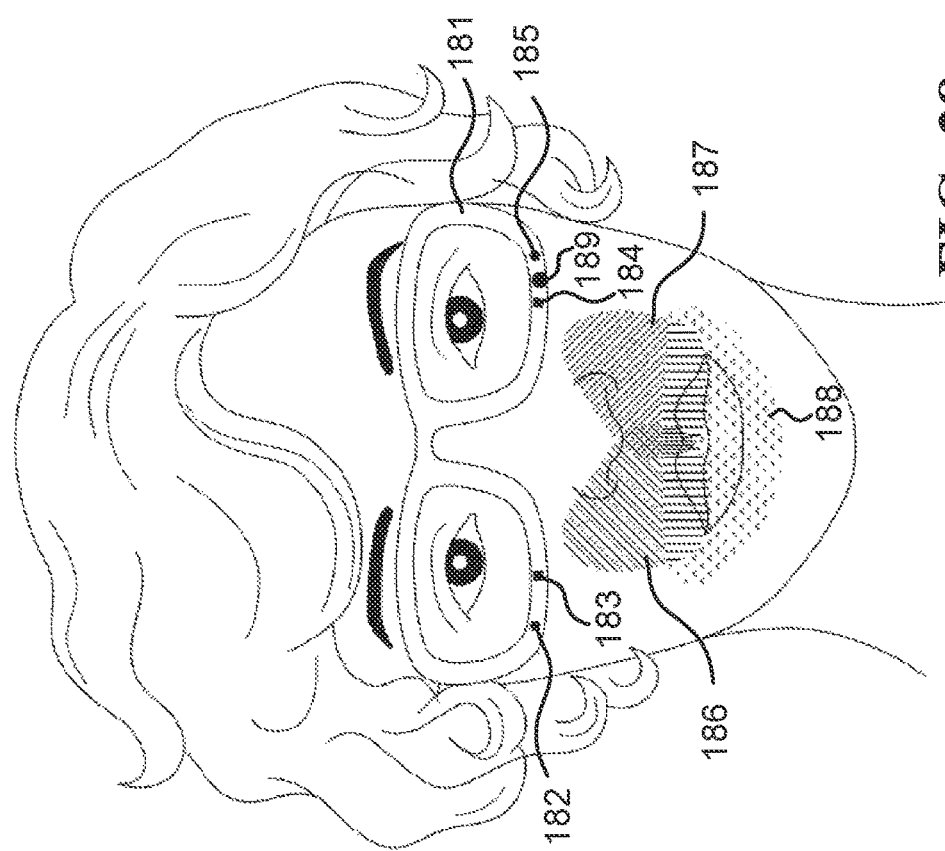
FIG. 38 illustrates an embodiment of a system that collects thermal measurements related to respiration, in which four CAMs are coupled to the bottom of an eyeglasses frame.

FIG. 38 illustrates one embodiment of a system configured to collect thermal measurements related to respiration, in which four inward-facing head-mounted thermal cameras (CAMs) are coupled to the bottom of an eyeglasses frame 181. CAMs 182 and 185 are used to take thermal measurements of regions on the right and left sides of the upper lip (186 and 187, respectively), and CAMs 183 and 184 are used to take thermal measurements of a region on the user's mouth 188 and/or a volume protruding out of the user's mouth. At least some of the ROIs may overlap, which is illustrated as vertical lines in the overlapping areas. Optionally, one or more of the CAMs includes a microbolometer focal-plane array (FPA) sensor or a thermopile FPA sensor.

In one embodiment, a computer detects whether the user is breathing mainly through the mouth or through the nose based on measurements taken by CAMs 182, 183, 184 and 185. Optionally, the system helps the user to prefer breathing through the nose instead of breathing through the mouth by notifying the user when he/she is breathing through the mouth, and/or by notifying the user that the ratio between mouth breathing and nose breathing reaches a predetermined threshold. In one embodiment, the computer detects whether the user is breathing mainly through the right nostril or through the left nostril based on measurements taken by CAMs 182 and 185.

The system may further include an inward-facing head-mounted visible-light camera 189 to take images (IM) of a region on the nose and/or mouth, which are used to calculate a respiratory parameter (e.g., detect whether the user is breathing mainly through the mouth or through the nose, detect the inhale duration, and/or detect the post-inhale pause duration). In one embodiment, one or more feature values may be generated based on IM. The feature values may be generated using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. The one or more feature values may be utilized in the calculation of the respiratory parameter in addition to feature values generated based on the thermal measurements.

Figure 43:
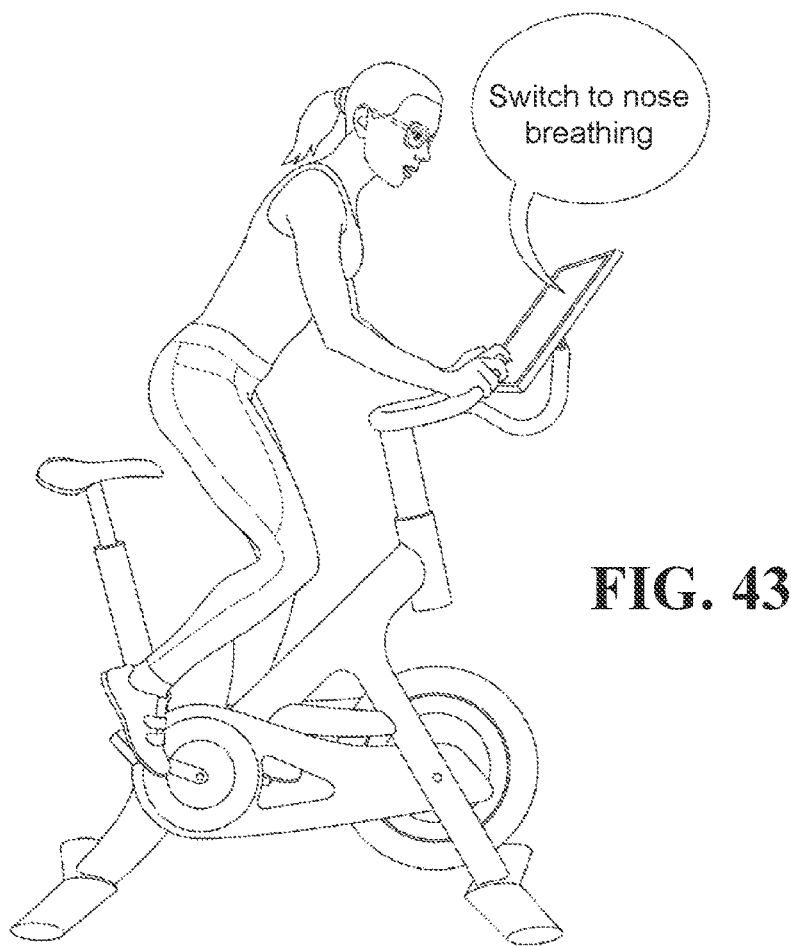
FIG. 43 illustrates notifying a user about mouth breathing and suggesting to breathe through the nose.
Figure 44:
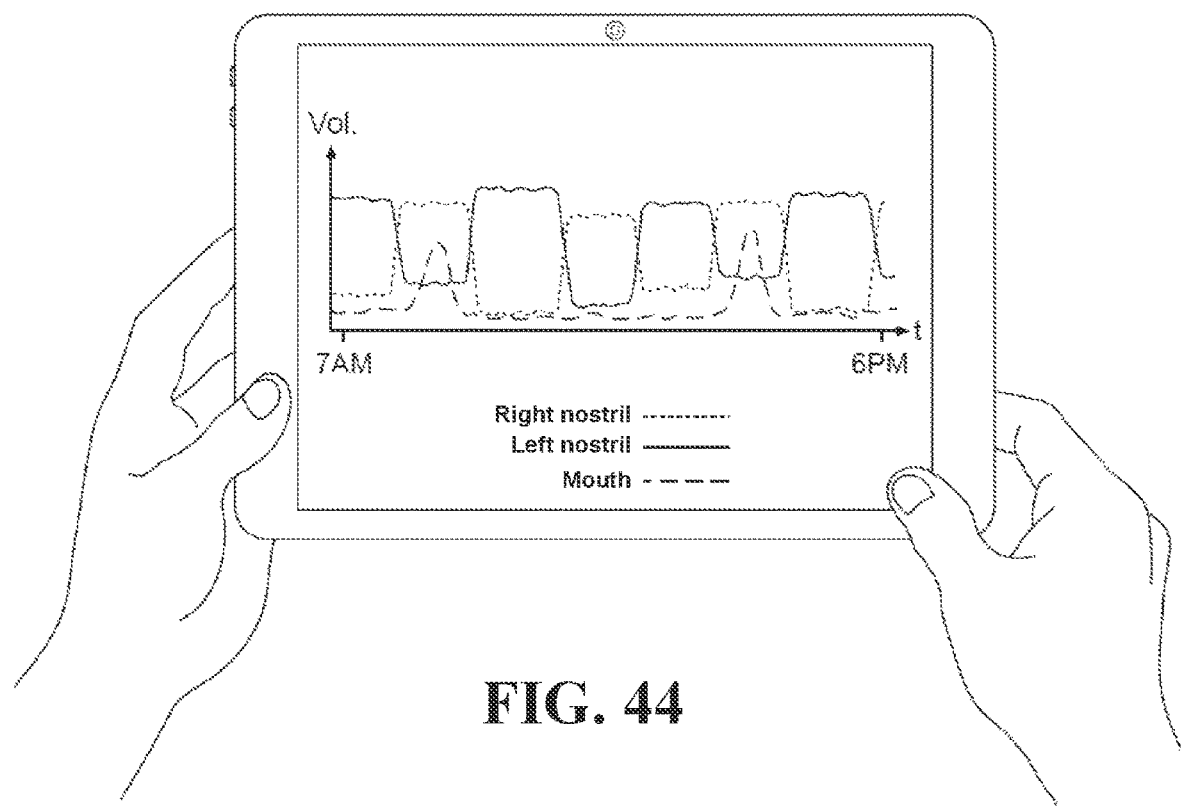
FIG. 44 illustrates an exemplary UI that shows statistics about the dominant nostril and mouth breathing during the day.

In one embodiment, the inward-facing head-mounted visible-light camera 189 takes images of a region on the user's mouth, and IM are indicative of whether the mouth is open or closed. A computer utilizes a model to detect, based on IM and $TH_{ROI}$ (such as the thermal measurements taken by at least one of CAMs 182-185), whether the user is breathing mainly through the mouth or through the nose. Optionally, the model was trained based on: a first set of $TH_{ROI}$ taken while IM was indicative that the mouth is open, and a second set of $TH_{ROI}$ taken while IM was indicative that the mouth is closed. Optionally, the system may help the user to prefer breathing through the nose instead of breathing through the mouth by notifying the user when he/she is breathing through the mouth, and/or by notifying the user that the ratio between mouth breathing and nose breathing reaches a predetermined threshold. FIG. 43 illustrates notifying the user that she breathes mainly through the mouth and should switch to breathing through the nose, while having a physical exercise such as spinning. FIG. 44 illustrates an exemplary UI that shows statistics about the dominant nostril and mouth breathing during the day.

In one embodiment, the inward-facing head-mounted visible-light camera 189 takes images of a region on the nose, and the computer identifies an inhale (and/or differentiates between an inhale and a breathing pause that follows the inhale) based on image processing of IM to detect movements of the nose, especially at the edges of the nostrils, which are indicative of inhaling.

Figure 36:
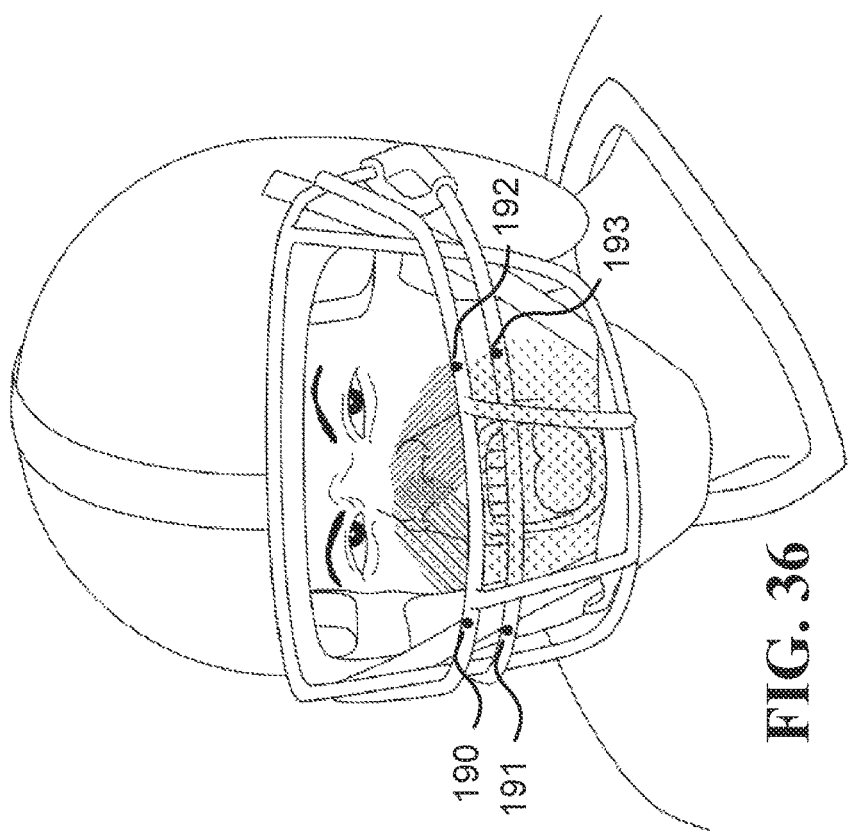
FIG. 36 illustrates an embodiment of a system that collects thermal measurements related to respiration, in which four inward-facing head-mounted thermal cameras (CAMs) are coupled to a football helmet.

FIG. 36 illustrates another embodiment of a system configured to collect thermal measurements related to respiration, in which four CAMs are coupled to a football helmet. CAMs 190 and 191 are used to take thermal measurements of regions on the right and left sides of the upper lip (appear as shaded regions on the users face), and CAMs 192 and 193 are used to take thermal measurements of a region on the user's mouth and/or a volume protruding out of the user's mouth. The illustrated CAMs are located outside of the exhale streams of the mouth and nostrils in order to maintain good measurement accuracy also when using thermal sensors such as thermopiles.

In some embodiments, the system further includes at least one in-the-ear earbud comprising a microphone to measure sounds inside the ear canal. A computer may identify an inhale based on analysis of the recordings from the earbud. Optionally, the inhale sounds measured by the earbud are stronger when the dominant nostril is the nostril closer to the ear in which the earbud is plugged in, compared to the inhale sounds measured by the earbud when the other nostril is the dominant nostril. Optionally, the computer detects whether the user is breathing mainly through the mouth or through the nose based on the thermal measurements and the sounds measured by the earbud. And then the system can help the user to prefer nasal breathing over mouth breathing by alerting the user when he/she breathes mainly through the mouth.

In some embodiments, the dominant nostril at a given time is the nostril through which most of the air is exhaled (with a closed mouth). Optionally, the dominant nostril is the nostril through which at least 70% of the air is exhaled. The different types of nostril dominance are illustrated in FIG. 47A to FIG. 47C. FIG. 47A is a schematic illustration of a left dominant nostril (note the significantly larger exhale stream from the left nostril). FIG. 47B is a schematic illustration of a right dominant nostril. And FIG. 47C is a schematic illustration of a balanced nasal breathing.

FIG. 48 is a schematic illustration of one embodiment of a system configured to identify the dominant nostril. The system includes at least one CAM 750, a computer 752, and an optional UI 754. CAM 750 may be similar to the CAMs in FIG. 38. CAM 750 takes thermal measurements of first and second ROIs below the right and left nostrils ($TH_{ROI1}$ and $TH_{ROI2}$, respectively) of the user. Optionally, each CAM does not occlude any of the user's mouth and nostrils. Optionally, each CAM is located less than 15 cm from the user's face and above the user's upper lip. Optionally, each CAM weighs below 10 g or below 2 g, and utilizes microbolometer or thermopile sensors. Optionally, each CAM includes multiple sensing elements that are configured to take $TH_{ROI1}$ and/or $TH_{ROI2}$. In one example, each CAM includes at least 6 sensing elements, and each of $TH_{ROI1}$ and $TH_{ROI2}$ is based on measurements of at least 3 sensing elements. Optionally, the system includes a frame to which CAM is physically coupled.

In one embodiment, the at least one CAM includes at least first and second thermal cameras (CAM1 and CAM2, respectively) that take $TH_{ROI1}$ and $TH_{ROI2}$, respectively, located less than 15 cm from the user's face. CAM1 is physically coupled to the right half of the frame and captures the exhale stream from the right nostril better than it captures the exhale stream from the left nostril, and CAM2 is physically coupled to the left half of the frame and captures the exhale stream from the left nostril better than it captures the exhale stream from the right nostril.

The at least one CAM may be used to capture thermal measurements of various ROIs. In one embodiment, the first region of interest ($ROI_1$) includes a region on the right side of the user's upper lip, and the second region of interest ($ROI_2$) includes a region on the left side of the user's upper lip. In another embodiment, $ROI_1$ includes a portion of the volume of the air below the right nostril where the exhale stream from the right nostril flows and $ROI_2$ includes a portion of the volume of the air below the left nostril where the exhale stream from the left nostril flows. In yet another embodiment, the at least one CAM may take thermal measurements of a region on the mouth and/or a volume protruding out of the mouth ($TH_{ROI3}$) of the user, which is indicative of the exhale stream from the mouth, and the computer identifies the dominant nostril also based on $TH_{ROI1}$. Optionally, the computer may utilize $TH_{ROI3}$ similarly to how it utilizes $TH_{ROI1}$ and $TH_{ROI2}$ to identify the dominant nostril (e.g., the computer may generate feature values based on $TH_{ROI3}$, as discussed below).

The computer identifies the dominant nostril based on $TH_{ROI1}$ and $TH_{ROI2}$ (and possibly other data such as $TH_{ROI3}$), which were taken during a certain duration. Optionally, the certain duration is longer than at least one of the following durations: a duration of one exhale, a duration of one or more breathing cycles, a half a minute, a minute, and five minutes.

In one embodiment, the computer utilizes a model to identify the dominant nostril. Optionally, the model was trained based on previous $TH_{ROI1}$, $TH_{ROI2}$, and indications indicative of which of the nostrils was dominant while the previous $TH_{ROI1}$ and $TH_{ROI2}$ were taken. In one example, the computer generates feature values based on $TH_{ROI1}$ and $TH_{ROI2}$ (and optionally $TH_{ROI3}$), and utilizes the model to calculate, based on the feature values, a value indicative of which of the nostrils is dominant.

In one embodiment, the computer identifies whether the user's breathing may be considered balanced breathing. Optionally, breathing is considered balanced breathing when the streams through the right and the left nostrils are essentially equal, such as when the extent of air exhaled through the left nostril is 40% to 60% of the total of the air exhaled through the nose. Balanced breathing of a normal healthy human usually lasts 1-4 minutes during the time of switching between the dominant nostrils. Optionally, the computer notifies the user when the user's breathing is balanced. Optionally, the computer suggests to the user, via a UI, to meditate during the balanced breathing The total time the different nostrils remain dominant may be indicative of various medical conditions. In one embodiment, when there is a significant imbalance of the daily total time of left nostril dominance compared to total time of right nostril dominance, and especially if this condition continues for two or more days (and is significantly different from the user's average statistics), it may be an indication of an approaching health problem. For example, when the total time of left nostril dominance is greater than the total time of right nostril dominance, the approaching problem may be more mentally related than physically related; and when the total time of right nostril dominance is greater than the total time of left nostril dominance, the approaching problem may be more physically related than mentally related. In another embodiment, a greater extent of left nostril dominance is related to digestion problems, inner gas, diarrhea, and male impotence; and a greater extent of right nostril dominance may be related to high blood pressure, acid reflux, and ulcers.

In one embodiment, the computer monitors nostril dominance over a certain period, and issues an alert when at least one of the following occurs: (i) a ratio between the total times of the right and left nostril dominance during the certain period reaches a threshold (e.g., the threshold may be below 0.3 or above 0.7) (ii) an average time to switch from right to left nostril dominance reaches a threshold (e.g., a threshold longer than 3 hours), and (iii) an average time to switch from left to right nostril dominance reaches a threshold.

The following are some examples of various applications in which the computer may utilize information about the dominant nostril, which is identified based on $TH_{ROI1}$ and $TH_{ROI2}$, in order to assist the user in various ways.

For some people, a certain dominant nostril may be associated with a higher frequency of having certain health problems, such as an asthma attack or a headache. Making a person aware of which nostril is more associated with the health problem can help the user to alleviate the health problem by switching the dominant nostril. Two examples of ways to switch the dominant nostril include: (i) to plug the current dominant nostril and breathe through the other nostril; and (ii) to lay on the side of the current dominant nostril (i.e., lying on the left side to switch from left to right dominant nostril, and vice versa). In one embodiment, the computer detects that the user is having an asthma attack, notifies the user about the current dominant nostril (which is associated with a higher frequency of asthma attacks), and suggests to switch the dominant nostril (to alleviate the asthma attack). In another embodiment, the computer detects the user has a headache, notifies the user about the current dominant nostril (which is associated with a higher frequency of headaches), and suggests to switch the dominant nostril.

Achieving balanced breathing may be a desired goal at some times. Biofeedback training may help extend the duration and/or increase the frequency at which one has balanced breathing. In one embodiment, the computer provides, via the UI, biofeedback for the user to achieve balanced breathing by playing a feedback. The feedback may be generated according to any suitable known method, such as normally playing the feedback when the breathing becomes more balanced, and stopping, rewinding, and/or dithering the feedback when the breathing becomes less balanced. Examples of feedbacks that may be used include playing a movie, running a video game, and/or playing sounds.

In a similar manner, biofeedback training may help the user to achieve a required breathing pattern, such as making a certain nostril dominant, or learning how to change the nostril from which most of the air is exhaled using thought and optionally without touching the nostrils. In one embodiment, the computer provides, via the UI, biofeedback for the user to achieve the required breathing pattern by playing a feedback. The feedback may be generated according to any suitable known method, such as playing a first sound when the use exhales more air from the right nostril than the left nostril, playing a second sound when the use exhales more air from the left nostril than the right nostril, and playing a third sound when the use exhales essentially the same from the right and left nostrils.

In one embodiment, the length of the exhale stream is considered as the distance from the nose at which the exhale stream can still be detected. For each person, there is a threshold that may change during the day and responsive to different situations. When the length of the exhale stream is below the threshold, it may indicate that the person is calm; and when the length of the exhale stream is longer than the threshold, it may indicate excitement. In general, the shorter the length of the exhale stream the less energy is invested in the breathing process and the less stress the person experiences. An exception may be arduous physical activity (which can increase the length of the exhale stream due to larger volumes of air that are breathed). In one embodiment, $TH_{RO_{f1}}$ and $TH_{RO_{f2}}$ are indicative of the length of the exhale stream, and the computer calculates level of excitement of the user based on the length of the exhale stream. Optionally, the longer the length, the higher the excitement/stress, and vice versa. Additionally, the relationship between the length of the exhale stream and the level of excitement may be a function of parameters such as the time in day, the dominant nostril, the user's mental state, the user's physiological state, the environmental air quality, and/or the temperature of the environment. In one example, the at least one CAM uses multiple sensing elements to take thermal measurements of regions located at different lengths below the nostrils. In this example, the larger the number of the sensing elements that detect the exhale stream, the longer the length of the exhale stream. Optionally, the amplitude of the temperature changes measured by the sensing elements is also used to estimate the length, shape, and/or uniformity of the exhale stream.

Ancient yoga texts teach that learning to extend the duration of the time gaps between inhaling and exhaling, and/or between exhaling and inhaling, increases life span. In one embodiment, the computer assists the user to extend the duration of the time gap between inhaling and exhaling by performing at least one of the following: (i) calculating the average time gap between inhaling and exhaling over a predetermined duration, and providing the calculation to the user via a user interface (UI), (ii) calculating the average time gap between inhaling and exhaling over a first predetermined duration, and reminding the user via the UI to practice extending the duration when the average time gap is shorter than a first predetermined threshold, and (iii) calculating the average time gap between inhaling and exhaling over a second predetermined duration, and encouraging the user via the UI when the average time gap reaches a second predetermined threshold. It is to be noted that to stop breathing after exhaling is considered more beneficial but also more dangerous, therefore the system may enable the user to select different required durations for stopping the breathing after inhaling and for stopping breathing after exhaling.

Typically, the dominant nostril switches sides throughout the day, with the duration between each switch varying, depending on the individual and other factors. Disruption of the typical nasal switching cycle may be indicative of physiological imbalance, emotional imbalance, and/or sickness. For example, slower switching of the dominant nostril may be, in some cases, a precursor of some diseases. In one embodiment, the computer learns the typical sequence of switching between dominant nostrils based on previous measurements of the user taken over more than a week, and issues an alert upon detecting an irregularity in the sequence of changes between the dominant nostrils. In one example, the irregularity involves a switching of the dominant nostril within a period of time that is shorter than a certain period typical for the user, such as shorter than forty minutes. In another example, the irregularity involves a lack of switching of the dominant nostril for a period that is greater than a certain period typical for the user, such as longer than three hours. In yet another example, the cycles of the dominant nostril may be described as a time series (e.g., stating for each minute a value indicative of the dominant nostril). In this example, the computer may have a record of previous time series of the user, acquired when the user was healthy, and the computer may compare the time series to one or more of the previous time series in order to determine whether a sufficiently similar match is found. A lack of such a similar match may be indicative of the irregularity.

The following is a discussion of the role of nostril dominance and other breathing aspects in Asian philosophy. According to Asian philosophy, and specifically the Vedas, all objects are made of the Five Great Elements, also known as the Classical elements, which include earth, water, fire, air, and space. The great elements represent types of energy, but they are related to the physical elements they are called after. During left or right nostril dominance, just one element is typically dominant in the body, and this is reflected in the form of the exhale stream (during balanced breath two elements may share dominance) When dominance in breathing is not forced, each of the five great elements in turn may become dominant and then cedes dominance to the next one. The normal order of dominance according to one text is: air, fire, earth, water, and space. The relative ratios of duration of dominance are: earth—5, water—4, fire—3, air—2, space—1. The dominant element affects breathing in two ways: the length of the exhale and the shape of the exhale stream (SHAPE). The average lengths and shapes of the outbreath are as follows according to one yoga textbook: earth—about 24 cm, straight out of the center of the nostril. Water—about 32 cm length, coming from the bottom of the nostril in a slight downward direction. Fire—8 cm, coming from the top of the nostril with an upward slant. Air—about 16 cm, coming from the external side of the nostril (left for the left nostril and right for the right nostril) with a slant outside. Space—very light and short breath from all parts of the nostril.

In one embodiment, the computer identifies, based on $TH_{RO_{f1}}$ and $TH_{RO_{f2}}$, the dominant element out of the five elements. Optionally, the computer monitors if relative durations and order of elements' dominance is regular, i.e. according to the order and duration ratios specified and optionally with approximate length as prescribed, or there is some irregularity. In one embodiment, irregularity may indicate a potential problem with the associated gland: for earth—ovaries or testes/prostate, water—adrenal, fire—intestines, air—none, space—thyroid and para-thyroid. In another embodiment, irregularity may indicate a potential mental and/or physiological problem(s).

If an element's dominance time (as evident from breathing characteristics) is too long, it may be balanced (reduced) by consuming appropriate food and/or drink. For example, air dominance can be reduced by consuming heavy oily food, fire dominance can be reduced by drinking water or by consuming water-absorbing food like buckwheat, and earth dominance can be reduced by eating light food with a lot of fiber.

If a dominant element is too weak (i.e., judging by breathing characteristics compared to the yardstick for that element, or comparing the SHAPE to a baseline SHAPE), it can be strengthened. For example, air dominance can be strengthened by active physical movement, fire dominance can be strengthened by breath-of-fire (from kundalini yoga), water dominance can be strengthened by drinking, earth can be strengthened by eating proteins and oily food, and space dominance can be strengthened by visualizing a picture that grows and shrinks in size.

As discussed above, the shape of the exhale stream (SHAPE) from the nostrils changes over time. With the at least one CAM it is possible, in some embodiments, to obtain measurements indicative of at least some of the different typical SHAPEs. A non-limiting reason for the system's ability to measure the different SHAPEs is that the exhale stream has a higher temperature than both the typical temperature of the environment and the typical temperature of the upper lip. As a result, the particles of the exhale stream emit at a higher power than both the environment and the upper lip, which enables CAM to measure the SHAPE over time.

As discussed above, different SHAPEs may be characterized by different 3D shape parameters (e.g., the angle from which the exhale stream blows from a nostril, the width of the exhale stream, the length of the exhale stream, and other parameters that are indicative of the 3D SHAPE). Additionally, different SHAPEs may be associated with different states of the user, such as different physiological and/or mental conditions the user may be in. In some embodiments, the computer calculates the SHAPE based on $TH_{ROI1}$ and $TH_{ROI2}$. Optionally, calculating the shape involves calculating values of one or more parameters that characterize the exhale stream's shape (e.g., parameters related to the 3D SHAPE). Optionally, calculating the SHAPE involves generating a reference pattern for the SHAPE. For example, the reference pattern may be a consensus image and/or heat map that is based on $TH_{ROI1}$ and $TH_{ROI2}$ taken over multiple breaths.

In other embodiments, the computer identifies a SHAPE based on $TH_{ROI1}$ and $TH_{ROI2}$. Optionally, the identified SHAPE belongs to a set that includes at least first and second SHAPEs, between which the computer differentiates. Optionally, the first and second SHAPEs are indicative of at least one of the following: two of the five great elements according to the Vedas, two different emotional states of the user, two different moods of the user, two different energetic levels of the user, and a healthy state of the user versus an unhealthy state of the user. In one example, the first SHAPE is indicative of a powerful alert energetic level, while the second SHAPE is indicative of a tired energetic level, and the computer uses this information to improve computerized interactions with the user.

The SHAPE may be related to the dominant nostril at the time. In one embodiment, the first SHAPE occurs more frequently when the right nostril is dominant, and the second SHAPE occurs more frequently when the left nostril is dominant In another embodiment, both the first and the second SHAPEs occur more frequently when the right nostril is dominant.

In one example, differentiating between the first and second SHAPEs means that there are certain first $TH_{ROI1}$ and $TH_{ROI2}$ that the computer identifies as corresponding to the first SAHPE and not as corresponding to the second SHAPE, and there are certain second $TH_{ROI1}$ and $TH_{ROI2}$ that the computer identifies as corresponding to the second SHAPR and as not corresponding to the first SHAPE. In another example, differentiating between first and second SHAPEs means that there are certain third $TH_{ROI1}$ and $TH_{ROI2}$ that the computer identifies as having a higher affinity to the first SHAPE compared to their affinity to the second SHAPE, and there are certain fourth $TH_{ROI1}$ and $TH_{ROI2}$ that the computer identifies as having a higher affinity to the second SHAPE compared to their affinity to the first SHAPE.

In some embodiments, the SHAPE is identified by the computer based on $TH_{ROI1}$, $TH_{ROI2}$, and optionally other sources of data. Since the SHAPE does not typically change between consecutive breaths, detecting the shape of the exhale may be done based on multiple measurements of multiple exhales. Using such multiple measurements can increase the accuracy of the identification of the shape. In one example, the first and second SHAPEs are identified based on first and second sets of $TH_{ROI1}$ and $TH_{ROI2}$ taken during multiple exhales over first and second non-overlapping respective durations, each longer than a minute.

The computer may utilize different approaches to identify the SHAPE. In one embodiment, the computer may compare $TH_{ROI1}$ and $TH_{ROI2}$ to one or more reference patterns to determine whether $TH_{ROI1}$ and $TH_{ROI2}$ are similar to a reference pattern from among the one or more reference patterns. For example, if the similarity to a reference pattern reaches a threshold, the exhale stream measured with $TH_{ROI1}$ and $TH_{ROI2}$ may be identified as having the shape corresponding to the shape of the reference pattern. Determining whether $TH_{ROI1}$ and $TH_{ROI2}$ are similar to a reference pattern may be done using various image similarity functions, such as determining the distance between each pixel in the reference pattern and its counterpart in $TH_{ROI1}$ and $TH_{ROI2}$. One way this can be done is by converting $TH_{ROI1}$ and $TH_{ROI2}$ into a vector of pixel temperatures, and comparing it to a vector of the reference pattern (using some form of vector similarity metric like a dot product or the L2 norm).

The one or more reference patterns may be generated in different ways. In one embodiment, the one or more reference patterns are generated based on previous $TH_{ROI1}$ and $TH_{ROI2}$ of the user taken on different days. Optionally, the SHAPEs were known while previous $TH_{ROI1}$ and $TH_{ROI2}$ of the user taken. In one example, the SHAPE is associated with a state of the user at the time (e.g., relaxed vs. anxious). In another example, the SHAPE may be determined using an external thermal camera (which is not head-mounted). In yet another example, the SHAPE is determined by manual annotation. In one embodiment, the one or more reference patterns are generated based on previous $TH_{ROI1}$ and $TH_{ROI2}$ of one or more other users.

In some embodiments, the SHAPE may be discovered through clustering. Optionally, the computer may cluster sets of previous $TH_{ROI1}$ and $TH_{ROI2}$ of the user into clusters. Where sets of $TH_{ROI1}$ and $TH_{ROI2}$ in the same cluster are similar to each other and the exhale streams they measured are assumed to have the same shape. Thus, each of the clusters may be associated with a certain SHAPE to which it corresponds. In one example, the clusters include at least first and second clusters that correspond to the aforementioned first and second SHAPEs.

The computer may utilize a machine learning-based model to identify the SHAPE. In one embodiment, the computer generates feature values based on $TH_{ROI1}$ and $TH_{ROI2}$, and utilizes a model to classify $TH_{ROI1}$ and $TH_{ROI2}$ to a class corresponding to the SHAPE. Optionally, the class corresponds to the aforementioned first or second shapes.

Optionally, the model is trained based on previous $TH_{ROI1}$ and $TH_{ROI2}$ of the user taken during different days.

In one embodiment, the computer receives an indication of the user's breathing rate, and uses this information along with the SHAPE at that time in order to suggest to the user to perform various activities and/or alert the user. Optionally, the indication of the user's breathing rate is calculated based on $TH_{ROI1}$ and $TH_{ROI2}$. In one example, the SHAPE is correlative with the state of the user, and different states combined with different breathing rates may have different meaning, which cause the computer to suggest different activities. The different activities may vary from different work/learning related activities to different physical activities to different treatments. In one example, the computer suggests to the user, via the UI, to perform a first activity in response to detecting that the breathing rate reached a threshold while identifying the first SHAPE. However, the computer suggest to the user to perform a second activity, which is different from the first activity, in response to detecting that the breathing rate reached the threshold while identifying the second SHAPE. In another example, the computer alerts the user, via the UI, in response to detecting that the breathing rate reached a threshold while identifying the first SHAPE, and the computer does not alert the user in response to detecting that the breathing rate reached the threshold while identifying the second SHAPE. In this example, the SHAPE may be correlated with the state of the user, and different states may be associated with different normal breathing rates. When the difference between the current breathing rate and the normal breathing rate (associated with the current SHAPE) reaches a threshold, the user may be in an abnormal state that warrants an alert.

In another embodiment, the computer configures a software agent that prioritizes activities for the user based on the identified SHAPE, such that a first activity is prioritized over a second activity responsive to identifying the first SHAPE, and the second activity is prioritized over the first activity responsive to identifying the second SHAPE. It is noted that the system may prioritize different activities for different SHAPEs also when the measured breathing rate and respiration volume are the same.

In still another embodiment, the computer learns a flow of typical changes between different SHAPEs based on previous measurements of the user, and issues an alert upon detecting an irregularity related to a flow of changes between the SHAPEs. For example, the irregularity may involve a new SHAPE, more frequent changes between SHAPEs, having certain SHAPEs for more or less time than usual, etc.

In yet another embodiment, the computer receives data about types of foods consumed by the user, stores the data in a memory, and finds correlations between the SHAPEs and the types of foods. These correlations may be used to make suggestions to the user. For example, the computer may suggest the user to eat a first type of food responsive to identifying the first SHAPE, and suggest the user to eat a second type of food responsive to identifying the second SHAPE. According to Ayurveda medicine, it is preferred to eat according to the three doshas and the five great elements. In times when the SHAPE is indicative of the dominant element (out of the five great elements), the computer may guide the user which types of food suit the identified dominant element, and/or may help the user to avoid inappropriate types of foods by identifying the types of food the user eats (and/or is about to eat), and alert the user when the identified food is inappropriate to the current dominant element (that was identified based on the SHAPE).

Data obtained from monitoring the dominant nostril can be utilized to make suggestions of activities for the user. FIG. 49A illustrates one embodiment of a system configured to suggest activities according to the dominant nostril. The system includes a sensor 451 for taking measurements 454 indicative of which of the user's nostrils is dominant at the time the measurements 454 were taken. Optionally, the sensor 451 is one or more thermal cameras, such as the thermal cameras illustrated in FIG. 38, however, as discussed below, other types of sensors may be utilized to take the measurements 454. The system also includes a computer 455 and optionally includes a UI 456.

The computer 455 predicts, based on the measurements 454, which of the user's nostrils will be the dominant nostril at a future time. Optionally, responsive to predicting that the right nostril will be dominant at the future time, the computer 455 suggests having at the future time a first activity, which is more suitable for a right dominant nostril than a second activity. Optionally, responsive to predicting that the left nostril will be dominant at the future time, the computer suggests having at the future time the second activity, which is more suitable for a left dominant nostril than the first activity. Optionally, the computer 455 suggests activities utilizing the UI 456. In one example, the first activity requires more verbal-analytical skills and less spatial skills compared to the second activity. In another example, the first activity requires more logic and/or locomotive skills compared to the second activity, and less empathy and/or imagination. In another example, the second activity requires more creativity and less physical effort compared to the first activity.

The suggestions of activities described above may be based on the premise that the dominant nostril is indicative of which of the user's brain hemispheres is more effective at performing activities that are associated with it. It is typically assumed that the left side of the user's brain is expected to be more effective at performing tasks when the right nostril is dominant (compared to when the left nostril is dominant) Conversely, the right side of the user's brain is expected to be more effective at performing tasks when the left nostril is dominant (compared to when the right nostril is dominant) The right hemisphere is usually believed to be better at expressive and creative tasks. Some of the abilities associated with the right hemisphere include recognizing faces, expressing emotions, music, reading emotions, color, images, intuition, and creativity. The left hemisphere is usually believed to be adept to tasks that involve logic, language, and analytical thinking. The left hemisphere is usually described as being better at language, logic, critical thinking, numbers, and reasoning. Thus, certain activities, which require certain skills that are associated with a certain hemisphere, may be more suitable to perform when one nostril is dominant compared to when the other nostril is dominant.

Additionally or alternatively, the suggestions of activities described above may be based on empirical data of the performances of the user and/or performances of other users. By analyzing the user's performances versus the dominant nostril (and optionally other parameters), and/or using big data analysis of the measured performances of many users versus their dominant nostril (and optionally other parameters), it is possible to identify a first set of activities that are statistically significantly more successfully achieved during right dominant nostril, a second set of activities that are statistically significantly more successfully achieved during left dominant nostril, and a third set of activities that are statistically significantly more successfully achieved during a balanced nasal breathing.

To predict the dominant nostril at the future time, the computer 455 relies on the measurements 454, which were taken prior to a current time, at which the prediction is made. Optionally, the future time may be at least five minutes after the current time, at least thirty minutes after the current time, at least one hour after the current time, at least three hours after the current time, or at least six hours after the current time.

In one embodiment, the computer 455 utilizes the measurements 454 to determine when the dominant nostril last switched (before the current time), and uses this information to predict when it will switch next (possibly multiple times). Thus, the computer can extrapolate, based on the measurements 454, a timeline until the future time, indicating which nostril is dominant at different times until (and including) the future time. Optionally, information useful for determining the time line (such as the time each nostril remains dominant) may be based on the measurements 454 and/or previous measurements of the user taken with the sensor 451 during different days.

In another embodiment, the computer 455 predicts the dominant nostril at the future by generating feature values and utilizing a machine learning-based model to estimate the dominant nostril at the future time (e.g., left nostril dominance, right nostril dominance, or balanced breathing). Optionally, the feature values comprise one or more feature values describing aspects of the future time such as the time to which it corresponds (e.g., how much time ahead the future time is), the location the user is expected to be at the future time, and/or an activity the user is expected to partake at the future time. Optionally, the feature values may include one or more features values corresponding to a state of the user at an earlier time that precedes the future time, such as the user's dominant nostril (e.g., as determine based on the measurements 454), manipulation of the dominant nostril performed by the user recently, previous measurements of the user taken after the user manipulated the dominant nostril and/or practiced pranayama and/or listened to brainwave entrainment, an activity the user had during the earlier time, and/or values of physiological signals of the user at the earlier time. In one embodiment, the machine learning-based model is trained based on samples that include measurements 454 taken at certain earlier times and their corresponding dominant nostrils following certain durations after the certain earlier times.

When a first activity is suggested for the future time (over the second activity), it typically means that the first activity is to be preferred over the second activity. Optionally, to suggest having the first activity at the future time means that the computer schedules the first activity at the future time and does not schedule the second activity at the future time. Additionally or alternatively, to suggest having the first activity at the future time means that the computer 455 ranks the first activity at the future time higher than it ranks the second activity at the future time. Optionally, when the first activity is ranked higher than the second activity it means that the first activity is given a stronger recommendation than the second activity. For example, a stronger recommendation may involve the first activity being suggested by displaying it first on a list of suggested activities. In another example, a stronger recommendation may involve suggesting the first activity with a larger image, a more prominent visual effect, and/or a more noticeable auditory signal than the one used to suggest the second activity.

The computer 455 may utilize a determination of which nostril is dominant at the current time and/or a prediction of which nostril will be dominant at the future in order to assist the user in performing activities at suitable times. In a first embodiment, the computer 455 assists the user to spend more time eating certain types of food when the right nostril is dominant Additionally or alternatively, the computer 455 further assists the user to spend less time eating the certain types of food when the left nostril is dominant In one example, the computer 455 may assist the user by identifying that the user starts looking for food during left nostril dominance, and reminding the user that eating while the left nostril is dominant is probably due to emotional reasons. In another example, the computer 455 may arrange the user's schedule such that at least 60% of the occurrences of lunch and/or dinner are planned to a time when the right nostril is dominant Optionally, the computer 455 recommends to the user to have the main meal of the day while the right nostril is dominant In a second embodiment, the computer 455 assists the user to increase the time spent at the toilet defecating while the right nostril is dominant Optionally, the computer 455 recommends to the user to spend less time at the toilet defecating while the left nostril is dominant. For example, the computer 455 may recommend to go on a bathroom break when the right nostril is dominant Optionally, the computer 455 may assist the user to decrease defecating during times of left nostril dominance by reminding the user that it is preferred to defecate during right nostril dominance, especially when suffering from constipation. In a third embodiment, the activity involves creativity, such as creating art, and the computer 455 assists the user to spend more time on the creative activity when the left nostril is dominant.

It is recommended to perform some activities when the breathing through the nose is balanced. In one embodiment, the computer 455 identifies, based on the measurements 454, times in which the breathing through the nose is balanced, and suggests a third activity for those times. Optionally, the third activity is more suitable for balanced breathing compared to the first and second activities. Optionally, the third activity requires higher self-awareness compared to the first and second activities. For example, the third activity may include a spiritual practice (such as meditating or praying), while the first and second activities do not include spiritual practices.

Various hardware configurations may be utilized in different embodiments of the system configured to suggest activities according to the dominant nostril, in order to take the measurements 454 of the user.

In a first embodiment, the system includes a CAM that takes thermal measurements of a region below the user's nostrils (e.g., CAM 183 or CAM 184). In this embodiment, identifying the dominant nostril and/or whether the breathing is balanced may be done by the computer 455 based on signal processing of the thermal measurements taken by CAM.

In a second embodiment, the sensor 451 includes one or more implanted sensors located around the area of the nostrils. In this embodiment, identification of the dominant nostril and/or whether the breathing is balanced may be done based on signal processing of the measurements of the implanted sensors.

In a third embodiment, the sensor 451 includes right and left in-the-ear earbuds comprising microphones, configured to measure sounds inside the right and left ear canals; the computer 455 identifies the dominant nostril based on analysis of the recordings from the earbuds. For example, the computer 455 may identify the dominant nostril based on the assumption that the inhale sounds measured by the in-the-ear earbud in the dominant side are stronger than the inhale sounds measured by the in-the-ear earbud in the non-dominant side.

In a fourth embodiment, the system includes a frame configured to be worn on the user's head, and the sensor 451 comprises a visible-light camera; the visible-light camera is physically coupled to the frame, and takes images of a region on the user's nose. For example, the computer 455 may identify the dominant nostril based on analyzing the images of the nose by identifying movements of the nose, especially at the edges of the nostrils.

In a fifth embodiment, the sensor 451 includes thermistors that are in contact with the nostrils and/or the upper lip in order to take the measurements. Optionally, the dominant nostril may be identified based on signal processing of the thermistors' measurements.

In a sixth embodiment, the sensor 451 includes anemometers located inside the breathing streams of the nostrils in order to take the measurements. Optionally, the dominant nostril is identified based on signal processing of the anemometers' measurements.

In a seventh embodiment, the sensor 451 includes a non-wearable IR camera pointed to the area around the nostrils in order to take the measurements. Optionally, the dominant nostril is identified based on image processing of the measurements of the non-wearable IR camera.

The suggestions provided by the computer 455 may be done as part of various programs that may benefit the user. Optionally, the computer 455 provides functionality of at least one of the following programs: a virtual assistant (i.e., a software agent), a calendar management program, a priority management program, a project management program, a "to do" list program, a work schedule program, and a self-learning program.

Some embodiments of the system may involve notification of the user about which of the nostrils is dominant at a given time (e.g., via UI 456). Optionally, the notification involves providing a user with an indication (e.g., via sound and/or an image) when the dominant nostril changes and/or every certain period of time (e.g., every hour). Additionally or alternatively, notifying the user about which of the nostrils is dominant may involve utilizing different themes for UI 456. In one example, a first theme for UI 456 is utilized when the right nostril is the dominant nostril, and a second theme for UI 456 is utilized when the left nostril is the dominant nostril. Optionally, the first theme is more logical than the second theme (e.g., presenting data and/or suggestions involves providing more facts and/or detailed explanations), and the second theme is more emotional than the first theme (e.g., presenting data and/or suggestions includes more emotional phrases, abstract images, social-related data, and/or less factual information).

In one embodiment, the computer 455 is programmed to converse with the user according to at least first and second modes. The first mode is perceived by the user as more logical than the second mode, and the second mode is perceived by the user as more emotional than the first mode. The computer 455 uses, on average, the first mode more frequently than the second mode when the right nostril is the dominant nostril, and uses, on average, the second mode more frequently than the first mode when the left nostril is the dominant nostril. Examples of logical speech include sentences built around numbers and facts, while emotional speech includes sentences built around emotions and intuition.

The following is a description of steps involved in one embodiment of a method for suggesting activities according to the dominant nostril. The steps described below may be used by systems modeled according to FIG. 49A, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method.

In one embodiment, the method for alerting about stress includes at least the following steps: In Step 1, taking, utilizing a sensor, measurements of a user, which are indicative of the user's dominant nostril. In Step 2, predicting, based on the measurements, which of the user's nostrils will be the dominant nostril at a future time (that occurs after the measurements in Step 1 were taken). And In Step 3, responsive to predicting that the right nostril will be dominant at the future time, suggesting having at the future time a first activity, which is more suitable for a right dominant nostril than a second activity. Optionally, responsive to predicting that the left nostril will be dominant at the future time, this step involves suggesting having at the future time the second activity, which is more suitable for a left dominant nostril than the first activity. Optionally, the method further includes assisting the user to decrease eating certain types of food during left nostril dominance, and assisting the user to schedule the main meal of the day during right nostril dominance Optionally, the method further includes learning the typical sequence of switching between dominant nostrils based on previous measurements of the user taken over more than a week, and alerting upon detecting an irregularity in the sequence of changes between the dominant nostrils.

In some embodiments, a system is configured to detect a physiological response based on respiratory parameters. Optionally, the physiological response is stress. Optionally, the respiratory parameters include the breathing rate and breathing rate variability (which is discussed further below).

The breathing rate variability (BRV) is a value that is indicative of the physiological phenomenon of variations between consecutive breathes, observed during a certain period of time (e.g., a minute). In a similar fashion to heart rate variability (HRV), which is the physiological phenomenon of variations between consecutive heartbeats, the extent of BRV can be indicative of various physiological phenomena, such as stress and/or physiological state.

In one embodiment, stress is detected based on thermal measurements of ROIs indicative of respiration performances, such as the mouth area, the upper lip area, and/or an air volume below the nostrils where the exhale from the nose flows. Optionally, $TH_{ROI1}$ may be utilized to calculate various respiratory parameters, which include the breathing rate and/or the BRV.

The duration between successive breaths (such as the time between starting successive exhales) and/or breathing irregularity may be calculated using various methods, such as geometric methods, frequency-domain methods, and/or non-linear methods. The computer may calculate the BRV based on $TH_{ROI}$ taken during different periods of time, such as at least one minute long or at least 5 minutes long.

In one embodiment, the breathing rate variability (BRV) and the breathing rate (BR) are utilized by a computer in order to detect when the user is stressed. Optionally, elevated BRV in addition to elevated BR may serve as an indicator of stress. Optionally, elevated BRV, even when the BR is reduced, may serve as an indicator of stress. For example, the computer may calculate $BR_1$ and $BRV_1$ based on $TH_{ROI}$ taken during a first period, calculate $BR_2$ and $BRV_2$ based on $TH_{ROI}$ taken during a second following period, and determine that the user's stress level is higher at the second period relative to the first period because ($BRV_1 < BRV_2$), even though ($BR_1 > BR_2$).

In one embodiment, the computer calculates the stress level based on comparing BR and BRV to various thresholds that correspond to different stress levels. In one example, having a high BRV may lower the threshold on BR that is required in order to detect stress.

In another embodiment, the computer may utilize a machine learning-based model in order to detect the stress level. Optionally, the computer utilizes $TH_{ROI}$ to generate feature values indicative of the BR and/or the BRV, and the model was trained based on samples that each include feature values based on $TH_{ROI}$ and labels indicative of the user's stress level.

Figure 50A:
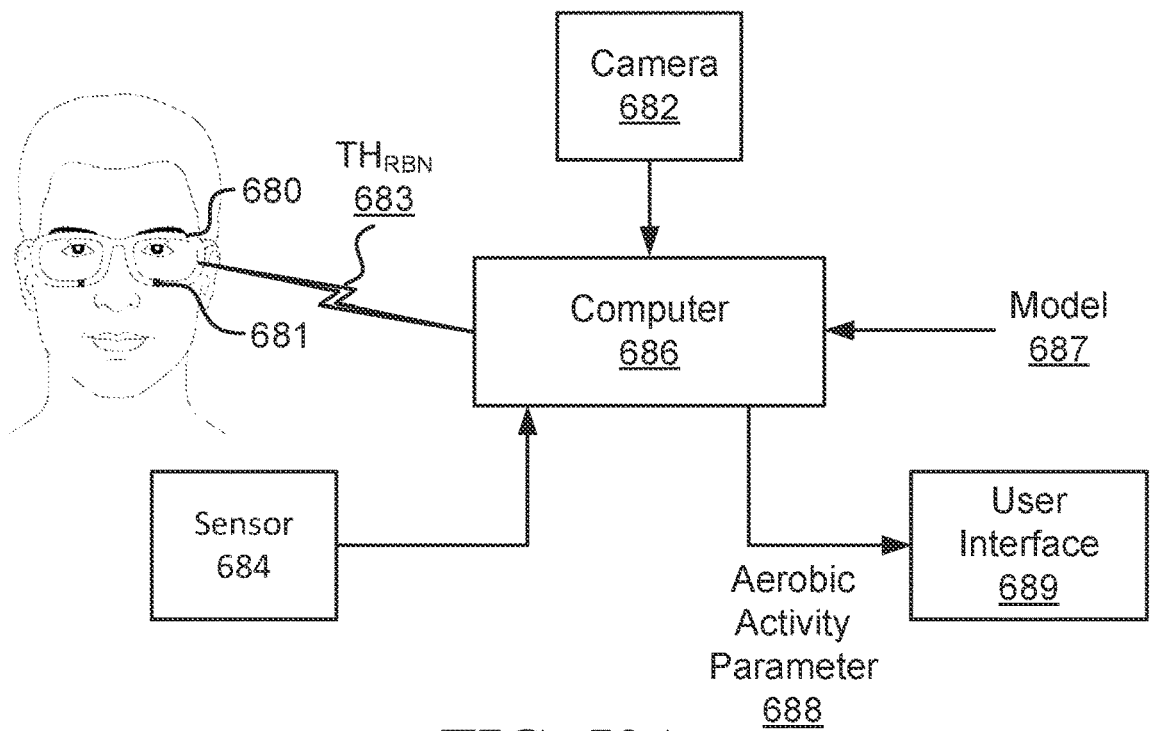
FIG. 50A illustrates an embodiment of a system for estimating an aerobic activity parameter.
Figure 50B:
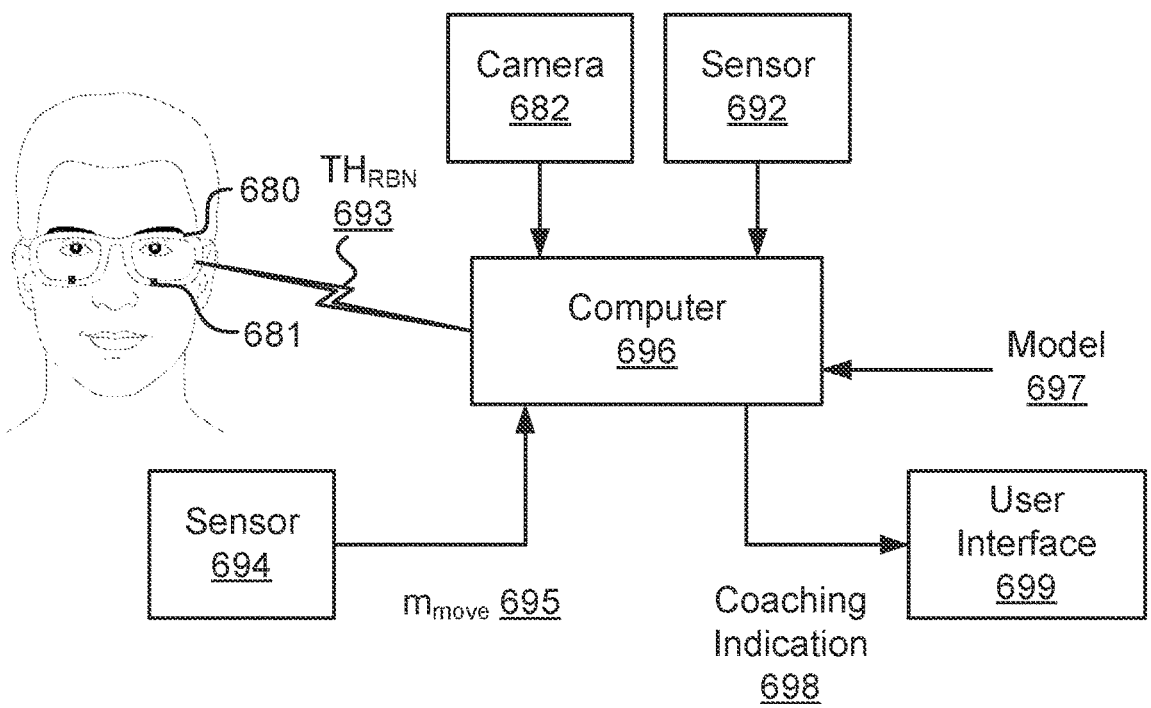
FIG. 50B illustrates an embodiment of an athletic coaching system.

Some embodiments described herein involve utilization of at least one inward-facing head-mounted thermal cameras (such a camera is denoted below CAM) to take thermal measurements of a region below the nostrils (these measurements are denoted below $TH_{RBN}$). $TH_{RBN}$ are indicative of an exhale stream of the user, such as air exhaled from a nostril and/or the mouth of the user. Since exhaled air usually has a different temperature than the environment and/or the human skin, $TH_{RBN}$ can provide indications regarding the user's respiratory activity, such as the breathing rate, whether exhaling is done through the mouth or nose, the respiration volume, and other respiratory parameters described herein. Additionally or alternatively, $TH_{RBN}$ may be used to calculate an aerobic activity parameter (as illustrated in FIG. 50A) and/or a coaching indication (as illustrated in FIG. 50B). The following is a description of embodiments of such systems that utilize $TH_{RBN}$ for such respiratory-related applications. The systems illustrated in FIG. 50A and FIG. 50B include at least one CAM and a computer.

The at least one CAM may include various combinations of one or more CAMs, as described in the various examples given in this disclosure of embodiments that include a single inward-facing head-mounted thermal camera that measures $TH_{RBN}$ (e.g., a single CAM coupled to the bottom of one of the sides of a frame worn by the user) or multiple CAMs (e.g., multiple CAMs coupled to different locations on a frame worn by the user). In one example, the at least one CAM includes CAM 681 illustrated in FIG. 50A. In other examples, the at least one CAM may include one or more of the CAMs described in various figures in this disclosure. For example, FIG. 38 illustrates one embodiment of an HMS that may be used to measure $TH_{RBN}$, in which at least one CAM (four CAMs in this case), is coupled to the bottom of an eyeglasses frame 181. CAMs 182 and 185 are used to take thermal measurements of regions on the right and left sides of the upper lip (186 and 187, respectively), and CAMs 183 and 184 are used to take thermal measurements of a region on the user's mouth 188 and/or a volume protruding out of the user's mouth. At least some of the ROIs may overlap, which is illustrated as vertical lines in the overlapping areas. Optionally, a CAM from among the one or more of the CAMs includes at least one of the following sensors: a thermopile sensor, and a microbolometer sensor. Optionally, a CAM from among the one or more of the CAMs includes a microbolometer focal-plane array (FPA) sensor or a thermopile FPA sensor. Additional examples of systems that include at least one CAM that may be used to take $TH_{RBN}$ are illustrated in FIG. 22 to FIG. 24 as well as FIG. 16B (one or more of the cameras 22, 24, and 28).

In some embodiments, each CAM, from among the at least one CAM, is physically coupled to frame worn on the head of a user (whose measurements are being taken), such as frames of eyeglasses, an augmented reality HMS, a virtual reality HMS, or a mixed reality HMS. In one example, each CAM, from among the at least one CAM, is physically coupled to frame 680. Optionally, each CAM, from among the at least one CAM, is located less than 15 cm from the user's face and weighs less than 10 g. Optionally, the frame holds each CAM, from among the at least one CAM, such that the CAM does not protrude beyond the tip of the user's nose.

In one embodiment, each CAM, from among the at least one CAM, is located above the user's upper lip and less than 15 cm from the user's face, and does not occlude any of the user's mouth and nostrils. Optionally, $TH_{RBN}$ include thermal measurements of at least one of first and second regions below right and left nostrils ($TH_{RBN1}$ and $TH_{RBN2}$, respectively) of the user, which are indicative of exhale streams from the right and left nostrils, respectively. Additionally or alternatively, $TH_{RBN}$ may include thermal measurements of at least one of a region on the mouth and a volume protruding out of the mouth ($TH_{RBN3}$) of the user, indicative of exhale stream from the mouth.

The following is a description of one possible utilization of $TH_{RBN}$, which involves calculation of an aerobic activity parameter of a user. FIG. 50A illustrates an embodiment of a system configured to estimate an aerobic activity parameter 688. The system includes at least one CAM (as described above) that is used to measure $TH_{RBN}$ 683 and a computer 686. Some embodiments of the system may optionally include additional elements, such as the frame 680, a head-mounted inward-facing video camera 682, a sensor 684, and a user interface 689.

The computer 686 is configured, in one embodiment, to calculate, based on $TH_{RBN}$ (taken by the at least one CAM), the aerobic activity parameter 688. Optionally, the aerobic activity parameter 688 is indicative of one or more of the following values: oxygen consumption ($VO_2$), maximal oxygen consumption ($VO_2$ max), and energy expenditure (EE). Optionally, the computer 686 may utilize additional inputs to calculate the aerobic activity parameter such as measurements of the heart rate (HR) of the user, values of the activity level of the user, and/or various statistics about the user (e.g., age, weight, height, gender, etc.).

Herein, $VO_2$ refers to a value indicative of the rate of oxygen consumption. This value typically rises as physical activity becomes more strenuous and the body has a larger demand for oxygen for various metabolic processes. In one example, $VO_2$ is a value expressed in units of mL/(kg·min), or some other units proportional to mL/(kg·min). $VO_2$ max refers to a value indicative of the maximal rate of oxygen consumption; typically, the higher $VO_2$ max, the higher the person's cardiorespiratory fitness and endurance capacity during prolonged exercises. EE may refer to a value indicative of the rate of energy expenditure, and may be expressed in various units such as kcal/h, or some other unit proportional to kcal/h. When the rate of energy expenditure is integrated over a period time, then EE may refer to a value indicative of the total energy expenditure over the period of time, and may be a value expressed in calories or some other unit proportional to calories.

Since direct measurements of aerobic activity parameters such as $VO_2$, $VO_2$ max, and EE are typically cumbersome uncomfortable procedures that need to be performed in controlled settings (e.g., running on a treadmill while wearing a mask that is used to collect and analyze exhaled breath), these values are often estimated based on various values that are correlated to some extent with the aerobic activity parameters. For example, various formulas and/or models were developed to estimate values of aerobic activity parameters from values such as heart rate (and changes from resting heart rate), activity level, and various statistics e.g., age, weight, height, gender, etc.)

Embodiments described herein utilize values indicative of the respiratory activity, such as $TH_{IN}$ 683 and/or values derived from $TH_{RBN}$ 683 (e.g., respiration rate and/or respiration volume) in order to enhance the accuracy of the estimation of aerobic activity parameters. Respiration parameters such as the respiration rate and/or respiration volume are tightly related to parameters such as $VO_2$ and EE and thus provide additional information about these parameters. Additionally, respiration values can help reduce inaccuracies in estimation of aerobic activity parameters due to various artifacts. For example, during changes in body positions (e.g., postural hypotension), there are usually only minor changes in $VO_2$ and respiration but major changes in HR. In another example, a value such as the respiration rate can distinguish between non-metabolic (e.g. mental and non-exercise related physical stress) and metabolic (physical activity induced) increases in HR. Thus, for example, using respiration data in addition to other values (e.g., HR) may provide better estimations of the values of the aerobic activity parameters, compared to estimations that do not involve respiration data.

The computer 686 may utilize various approaches in order to estimate aerobic activity parameters based on data that includes $TH_{RBN}$ 683 and/or values derived from $TH_{RBN}$. In one embodiment, the computer 686 generates feature values based on data comprising $TH_{RBN}$, and utilizes a model 687 to calculate the aerobic activity parameter 688 based on the feature values. Optionally, the model 687 is trained based on data indicative of aerobic activity of multiple users (e.g., data that includes physiological signals such as respiratory rate, heart rate, etc., of the multiple users). Additionally or alternatively, the model 687 is trained based on data that includes previous $TH_{RBN}$ of the multiple users and values of the aerobic activity parameter of the multiple users corresponding to when the previous $TH_{RBN}$ were taken. For example, the training data includes samples, each sample comprising: (i) feature values were generated from certain pervious $TH_{RBN}$ of a certain user taken during certain period of time, and (ii) a label generated based on a measurement of the value of the aerobic activity parameter of the certain user during the certain period of time (i.e., the value of $VO_2$, $VO_2$ max, or EE, as measured during the certain period of time).

The computer 686 may generate various types of feature values that are used to estimate the value of the aerobic activity parameter 688. Optionally, the computer 686 generates one or more feature values, based on $TH_{RBN}$ 683, which may be any of the feature values described in this disclosure that are used to detect a physiological response, and in particular, the one or more feature values may be any of the feature values described in this disclosure as being pertinent to calculation of a respiratory parameter. Additionally or alternatively, feature values generated by the computer 686 may include: time series data comprising values measured by a CAM, average values of certain pixels of a CAM, and/or values measured at certain times by the certain pixels. Additionally or alternatively, at least some of the feature values generated by the computer 686 may include measurements of the environment in which the user is in and/or indications of confounding factors (e.g., indications of use of medication).

In some embodiments, feature values generated by the computer 686 may include values of one or more respiratory parameters calculated based on $TH_{RBN}$ 683. In one example, the feature values generated by the computer 686 include a feature value indicative of a ratio between an extent to which the user breathed via the mouth and an extent to which the user breathed via the nose. In another example, the feature values generated by the computer 686 include a feature value indicative of a ratio between durations of exhales of the user and duration of inhales of the user.

In some embodiment, the feature values generated by the computer 686 may include a feature value indicative of heart rate (HR) of the user while $TH_{RBN}$ 683 were taken. Additionally or alternatively, the feature values generated by the computer 686 include another feature value indicative of cardiac activity such as heart rate variability (HRV). For example, measurements indicative of HR and/or HRV may be obtained by a different sensor, which is not a CAM, such as a photoplethysmogram (PPG) sensor that is head-mounted (e.g., coupled to the temple of eyeglasses worn by the user), coupled to a wearable device such as a smartwatch, or embedded in a garment worn by the user, such as a smart shirt.

In addition to data describing physiological signals mentioned above, in some embodiments, data used to generate at least some of the feature values by the computer 686 may include various values describing the user, such as one or more of the following: age, gender, height, weight, type of body build, and body fat percentage. Additionally or alternatively, data used to generate at least some of the feature values by the computer 686 may include various values describing an activity of the user while $TH_{RBN}$ 683 of the user were taken. Optionally, data describing the activity is obtained by sensor 684. In one example, the sensor 684 comprises at least one of an accelerometer and a gyroscope, and the data describing the activity is indicative of at least one of the following: cadence, stride length, and/or type of movement (e.g., walking, running, rowing, cycling, etc.) In another example, the sensor 684 comprises a GPS receiver and/or some other sensor that may be used to determine the user's location. In this example, the data describing the activity may be indicative of one or more of the following: the speed of the user's movement, the distance of the user's movement, and/or changes in the user's elevation.

A person's baseline physiological signals, such as resting HR, respiration rate, or blood pressure may be indicative of the aerobic fitness of the person, and may provide useful information for calculation of an aerobic activity parameter. Thus, in some embodiments, the computer 686 may generate one or more feature values that are indicative of a baseline physiological signal of the user.

How a person's physiological signals change due to physical activity are indicative of the aerobic fitness of the person. Typically, the more fit an individual, the less dramatic the changes in the physiological signals for a certain type of activity. For example, a fit person's respiration rate will typically increase to a lesser extent after a few minutes of jogging compared to the increase in respiration that occurs to a less fit individual after performing the activity. To capture such aspects that may reflect on fitness, in some embodiments, the feature values generated by the computer 686 may include one or more feature values that reflect a change in the values of a physiological signal, before and after a certain extent of activity. For example, a feature value may be indicative of the change in the respiratory rate, change to the respiration volume, or respiration volume after conducting a certain activity (e.g., five minutes of moderate cycling). In another example, a feature value may be indicative of the change to the heart rate after running at a pace of 12 km/h for five minutes.

In other embodiments, the feature values generated by the computer 686 may include one or more feature values that are indicative of athletic performance of the user. For example, a feature value may be indicative of the time it took the user to complete a certain exercise such as running a mile as fast as the user is capable.

The model 687 is trained on data that includes previous $TH_{RBN}$ of the user and/or other users. Training the model 687 typically involves generating samples based on the previous $TH_{RBN}$ and corresponding labels indicative of values of the aerobic activity parameter when the previous $TH_{RBN}$ were taken. For example, each sample may comprise feature values generated based on at least some of the previous $TH_{RBN}$, and the sample's label represents the value of the aerobic activity parameter corresponding to when the at least some of the previous $TH_{RBN}$ were taken.

In some embodiments, the samples used to train the model 687 include data pertaining to a diverse set of users comprising users of different genders, ages, body builds, and athletic abilities. Optionally, the samples used to train the model 687 include samples generated based on $TH_{RBN}$ taken at different times of the day, while being at different locations, and/or while conducting different activities. In one example, at least some of the samples are generated based on $TH_{RBN}$ taken in the morning and $TH_{RBN}$ taken in the evening. In another example, at least some of the samples are generated based on $TH_{RBN}$ of a user taken while being indoors, and $TH_{RBN}$ of the user taken while being outdoors. In yet another example, at least some of the samples are generated based on $TH_{RBN}$ taken while a user was sitting down, and $TH_{RBN}$ taken while the user was walking, running, and/or engaging in physical exercise (e.g., dancing, biking, etc.). Additionally or alternatively, the samples used to train the model 687 may be generated based on $TH_{RBN}$ taken while various environmental conditions persisted. For example, the samples include first and second samples generated based on $TH_{RBN}$ taken while the environment had first and second temperatures, with the first temperature being at least 10° C. warmer than the second temperature. In another example, the samples include samples generated based on measurements taken while there were different extents of direct sunlight and/or different extents of wind blowing.

Various computational approaches may be utilized to train the model 687 based on the samples described above. In one example, a machine learning-based training algorithm may be utilized to train the model 687 based on the samples. Optionally, the model 687 includes parameters of at least one of the following types of models: a regression model, a neural network, a nearest neighbor model, a support vector machine, a support vector machine for regression, a naïve Bayes model, a Bayes network, and a decision tree.

In some embodiments, a deep learning algorithm may be used to train the model 687. In one example, the model 687 may include parameters describing multiple hidden layers of a neural network. In one embodiment, when $TH_{RBN}$ include measurements of multiple pixels, the model 687 may include a convolution neural network (CNN). In one example, the CNN may be utilized to identify certain patterns in the thermal images, such as patterns of temperatures in the region of the exhale stream that may be indicative of respiratory activity, which involve aspects such as the location, direction, size, and/or shape of an exhale stream from the nose and/or mouth. In another example, calculating a value of an aerobic activity parameter may be done based on multiple, possibly successive, thermal measurements. Optionally, calculating values of the aerobic activity parameter based on thermal measurements may involve retaining state information that is based on previous measurements. Optionally, the model 687 may include parameters that describe an architecture that supports such a capability. In one example, the model 687 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using bidirectional recurrent neural network architecture (BRNN).

Monitoring a user over time can produce many observations indicative of the user's fitness. For example, the extent of increase in the user's respiration rate, change to respiration volume, and/or change in heart rate after moderate running of a few minutes, is indicative of the user's fitness, and can be measured multiple times. These multiple observations can be used to estimate the value of an aerobic activity parameter of the user such as $VO_2$ max (which is also indicative of the user's fitness) as follows. In one embodiment, the computer 686 calculates, based on $TH_{RBN}$ 683, n≥1 values $x_1 \ldots x_n$, of observations of a parameter related to respiration such as the respiration rate, change to respiration rate, respiration volume, change to respiration volume, and the like. For example, $x_i$ may be the increase to the respiration rate observed after moderate running for a period (e.g., five minutes). In another example, $x_i$ may be the change to respiration volume and/or average respiration volume during a half hour of cycling.

The computer 686 may calculate an estimation of a value of the aerobic activity parameter (denoted θ*) utilizing one or more probability functions of the form $P(X=x|\theta)$, which is a conditional probability of a value of the parameter related to respiration given a value of the aerobic activity parameter is equal to θ. Optionally, the computer 686 performs at least one of the following in order to calculate θ* (the estimation value of the aerobic activity parameter): a maximum likelihood (ML) estimation, and a maximum a posteriori probability (MAP) estimation.

The one or more probability functions of the form $P(X=x|\theta)$ may be calculated based on data pertaining to a diverse set users comprising users of different genders, ages, body builds, and athletic abilities. Optionally, the data includes observations of a parameter related to respiration calculated based on $TH_{RBN}$ of the users. In one embodiment, a probability function of the form $P(X=x|\theta)$ may be a table describing the probability of observing different values of x given a certain value of θ. For example, the table may describe an empirically observed probabilities for various increases in respiration (e.g., increases of 2, 4, 6, . . . , 40 breaths per minute) given different values of θ, such as $VO_2$ max=10, 15, 20, . . . , 75, 80 mL/(kg·min). In another embodiment, a probability function of the form $P(X=x|\theta)$ may be described by a model that includes parameters of the distribution, where the parameters may be set using various approaches such as regression and/or maximum entropy approaches. Optionally, the parameters of the probability function describe a continuous exponential distribution.

A user interface 689 may be utilized to present the aerobic activity parameter 688 and/or present an alert related to the aerobic activity parameter 688. In one example, user interface 689 may be used to alert the user responsive to an indication that the aerobic activity parameter has fallen below a threshold (e.g., when the rate of energy expenditure falls below a threshold) or when the aerobic activity parameter reaches a certain threshold (e.g., when the total energy expenditure during a session reaches a certain caloric goal). Optionally, the user interface 689 includes a display, such as the display of a smart phone, a smartwatch, or a head-mounted augmented reality display. Optionally, the user interface 689 includes a speaker, such as a speaker of a smart phone, a smartwatch, or a head-mounted augmented reality display, or a speaker of a pair of headphones or an earbud.

As discussed herein, thermal measurements indicative of an exhale stream may be used by a computer to calculate various respiratory parameters, aerobic activity parameters, and coaching indications. In order to produce a better signal regarding the user's respiratory activity, in some embodiments, the computer 686 (or the computer 696 discussed below) may utilize additional input sources (besides thermal cameras).

In some embodiment, the additional input sources may include one or more visible-light cameras that capture images indicative of respiratory activity. In one example, the additional input sources include at least one inward-facing head-mounted visible-light camera (e.g., the camera 682), which is configured to take images of a region on the mouth ($IM_M$) of the user. In this example, $IM_M$ are indicative of whether the mouth is open or closed. In another example, the additional input sources include at least one inward-facing head-mounted visible-light camera configured to take images of a region on the nose ($IM_N$) of the user; in this example, $IM_N$ are indicative of movement of the nose while the user inhales (in this example, the camera 682 may be configured to take images of the nose in addition to, or instead of, the images of the mouth). Optionally, calculating various values (e.g., breathing rate, an aerobic activity parameters, or a coaching indication) based on $IM_M$ and/or $IM_N$ involves generating feature values based on $IM_M$ and/or $IM_N$ and using them in the calculation of said values (e.g., in addition to feature values generated based on $TH_{RBN}$). For example, feature values generated based on $IM_M$ and/or $IM_N$ involve using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. Optionally, $IM_M$ and/or $IM_N$ may be used to identify different states of the user (e.g., open vs. closed mouth or movement of the nostrils), and the information regarding the different states may be used as input (e.g., feature values) when calculating parameters such as the breathing rate.

In other embodiments, the additional input sources may include one or more microphones configured to record sounds made by the user's respiration. For example, the one or more sensors may include microphones in right and/or left in-the-ear earbuds, and feature values may be generated based on audio signal analysis of the recordings from the earbuds and utilized to calculating parameters such as the breathing rate, to detect inhaling/exhaling events, etc. Optionally, such in-ear measurements are used to calculate the user's breathing rate while the user was walking or running in an environment having ambient noise level above 50 dBA.

Other examples or sensors that may be used as additional input sources include sensors physically that are coupled to a garment worn over the user's torso and comprises at least one of the following: a pressure sensor, a stretch sensor, an electromechanical sensor, and a radio receiver. Optionally, these sensors are configured to measure movements of the chest due to respiration activity of the user, and these measurements are utilized to calculate various parameters such as the breathing rate.

The additional input sources described above may serve, in some embodiments, as complementary data that enhance accuracy of respiratory signals detected based on $TH_{RBN}$. For example, in some embodiments, exhaling air produces a stronger thermal signal than inhaling air. In these embodiments, detection of inhalation events can be assisted by images of the nostrils (which often show distinct movement when inhaling) In another example, there may be conditions in which exhaling may produce a relatively weak thermal signal, e.g., when exercising in warm environments in which the temperature of the exhaled air is close to the temperature in the environment. In such cases, additional data, such as data from sensors embedded in a garment or microphones in earbuds, may help and provide better indications of breathing.

The following is a description of another possible utilization of $TH_{RBN}$, which involves virtual coaching based on respiration data. FIG. 50B illustrates an embodiment of an athletic coaching system. The system includes at least one CAM (as described above) that is used to measure $TH_{RBN}$ 693 and a computer 696. Some embodiments of the system may optionally include additional elements, such as the frame 680, a head-mounted inward-facing video camera 692, a sensor 694, and a user interface 699.

The computer 696 is configured, in some embodiments to: receive measurements of movements ($M_{move}$ 695) involving the user; generate, based on $TH_{RBN}$ 693 and 695, a coaching indication 698; and present, via a $M_{move}$ user interface 699, the coaching indication 698 to the user. Various virtual coaching applications may be realized by analyzing $TH_{RBN}$ 693 and $M_{move}$ 695, and providing the user with insights and/or instructions based on the analysis. These insights and/or instructions may assist to improve the user's athletic performance in various ways.

One type of coaching application built on the system illustrated in FIG. 50B provides insights and/or instructions to a user performing an athletic activity that involves an aerobic exercise with repetitive motions such as running, rowing, or cycling. In one embodiment, the computer 696 generates the coaching indication 698, which is indicative of a change the user should make to one or more of the following: cadence of movements, stride length (if the user is running), breathing rate, breathing type (mouth or nasal), and duration of exhales. Optionally, responsive to a determination that the change is needed, the computer 696 provides, via the user interface 699, an indication to the user of this fact. For example, the user interface 699 may include a speaker (e.g., in earbuds) and the computer 696 generates an audio indication (e.g., a certain sound effect such as beeping at a certain frequency and/or speech conveying the coaching indication 698). In another example, the user interface may include a display and the coaching indication may be provided via visual cues (e.g., text, an image, or a light flashing at a certain frequency). The following are various examples of computations that may be performed by the computer 696 in order to generate the coaching indication 698.

In one embodiment, the computer 696 calculates the breathing rate of the user based on $TH_{RBN}$ 693 and then checks if it is in a desired range. Responsive to the breathing rate being below a first threshold, the computer 696 includes in the coaching indication 698, an instruction to increase the breathing rate. Additionally or alternatively, responsive to the breathing rate being above a second threshold (which is higher than the first threshold), the computer includes in the coaching indication 698 an instruction to decrease the breathing rate. Optionally, the first and/or second thresholds are calculated based on $M_{move}$ 695. For example, the first threshold (minimal desired breathing rate) and/or the second threshold (maximal desired breathing rate) are set according to the level of activity of the user. Optionally, "level of activity" may refer to one or more of the following: the speed of the user (e.g., when running or cycling), the cadence of the user's movement, a value of an aerobic activity parameter of the user (e.g., $VO_2$ or EE).

In another embodiment, the computer 696 calculates a value indicative of the cadence of the user based on $M_{move}$ 695. For example, the computer 696 may identify cyclic signals indicating movement such as pedaling, rowing, or strides. Optionally, the computer 696 utilizes a machine learning model to calculate the cadence based on $M_{move}$ 695, where the model is trained based on $M_{move}$ of other users. Optionally, responsive to the cadence being below a first threshold, the computer 696 includes in the coaching indication 698 an instruction to increase the cadence. Additionally or alternatively, responsive to the cadence being above a second threshold, the computer 696 includes in the coaching indication 698 an instruction to decrease the cadence. Optionally, the first and/or second thresholds are calculated according to $TH_{RBN}$ 693. For example, the first and/or second thresholds may correspond to a desired cadence that is appropriate for the breathing rate of the user, as determined based on $TH_{RBN}$ 693.

In yet another example, the computer 696 calculates a value indicative of exhale durations of the user based on $TH_{RBN}$ 693. Optionally, the computer 696 includes in the coaching indication 698 an instruction to increase the exhale durations responsive to determining that the exhale durations are below a threshold. Optionally, the threshold is calculated based on at least one of $M_{move}$ 695 and $TH_{RBN}$ 693. For example, the threshold may be set according to a predetermined function that assigns a minimal desired duration of exhales based on the cadence or speed of the user (e.g., as determined based on 695) and/or based on the breathing rate of the user (e.g., as $M_{move}$ determined based on $TH_{RBN}$ 693).

In still another embodiment, the computer 696 detects, based on $TH_{RBN}$ 693, whether the user is breathing through the mouth. Responsive to detecting that the user is breathing through the mouth, the computer 696 includes in the coaching indication 698 an instruction to the user to breathe through the nose.

The computer 696 may utilize a machine learning model 697 to generate the coaching indication 698. In some embodiments, the computer generates feature values based on $TH_{RBN}$ 693 and/or 695. For example, the $M_{move}$ feature values may include one or more of the feature values described above which are generated based on $TH_{RBN}$ 683 and/or measurements of the sensor 684 and are used to estimate the aerobic activity parameter 688. Optionally, the computer 696 utilizes the model 697 to calculate, based on the feature values generated based on $TH_{RBN}$ 693 and/or $M_{move}$ 695, a value indicative of whether the change is needed and/or what change in the user's activity should be indicated in the coaching indication 698.

The model 697 may be generated based on data comprising previously taken $TH_{RBN}$ and $M_{move}$ of the user and/or other users and indications of appropriate coaching instructions (and whether coaching needed) corresponding to the time previously taken $TH_{RBN}$ and were taken. For example, the previously taken $TH_{RBN}$ and $M_{move}$ may be used to generate samples; each sample comprising feature values generated based on $TH_{RBN}$ and $M_{move}$ taken during a certain period (the same type of feature values generate by the computer 696, as described above). The indications on appropriate coaching instructions may be used to create labels for the samples. In one example, the coaching instructions are provided by a human annotator (e.g., a human coach) that reviews the data and determines whether changes could be made to improve the athletic performance. In another example, the coaching instructions are provided by an expert system (e.g., a rule based system such as a decision tree), which is designed for this purpose.

In some embodiments, $M_{move}$ 695 are generated by a sensor 694, which may represent herein one or more of various types of sensors. In one embodiment, the sensor 694 is an accelerometer and/or gyroscope in a device carried or worn by the user. For example, the sensor 694 may be a movement sensor in a smartwatch or smart glasses worn by the user or a movement sensor in a smartphone carried by the user. Optionally, analysis of measurements of the sensor 694 provides information about one or more of the following: the types of movements the user is making (e.g., running, cycling, or rowing), the cadence of the user (e.g., number of steps per minute, number of revolutions per minute in cycling, or the number of strokes per minute), and/or the speed of the user. In another embodiment, the sensor 694 is a location identifying sensor, such as a GPS receiver. Optionally, analysis of measurements of the sensor 694 provides information on the speed of the user, the elevation and/or distance traveled, etc. In some embodiments, $M_{move}$ 695 may include information obtained from multiple movement sensors. In one example, information about the speed and/or distance traveled by the user, coupled with information about the cadence, is used in order to determine the length of the user's strides.

Another type of coaching application that may utilize $TH_{RBN}$ 693 and $M_{move}$ 695 provides the user with breathing cues (e.g., a breathing pacer application) in order to assist the user to breathe at a desired pace while conducting athletic activity. In one embodiment, the computer 696 calculates a target breathing rate based on data comprising at least one of $TH_{RBN}$ 693 and $M_{move}$ 695, and includes in the coaching indication breathing cues that correspond to the target breathing rate. Optionally, the computer 696 receives a value indicative of the heart rate (HR) of the user and uses HR to calculate the target breathing rate (in addition to utilizing at least one of $TH_{RBN}$ 693 and $M_{move}$ 695). In one example, $M_{move}$ 695 is utilized to calculate a value indicative of the speed of the user and/or the cadence of the user, and the computer 696 utilizes a predetermined function to select for the user the target breathing rate, based on the speed and/or the cadence. In another example, a current breathing rate of the user, which is calculated based on $TH_{RBN}$ 693, is used to select a target breathing rate that will match the cadence of the user (e.g., which is determined based on $M_{move}$ 695). In still another example, $TH_{RBN}$ 693 and $M_{move}$ 695 are used as input to a function that calculates the target breathing rate. For example, the computer 696 may generate feature values (e.g., as discussed above with respect to the coaching indication regarding an instruction to change an aspect of the user's activity) and utilize a certain model to calculate, based on these feature values, the target breathing rate. Optionally, the certain model is generated based on data comprising previously taken $TH_{RBN}$ and $M_{move}$ of the user and/or other users and indications of the appropriate breathing rate as determined by an expert (e.g., a human or an expert system). The various computational approaches described herein with respect to detecting a physiological response may be employed in order to calculate the target breathing rate (e.g., comparison to threshold, reference time series, and/or machine learning approaches described herein).

In one embodiment, the computer 696 calculates a current breathing rate based on $TH_{RBN}$ 693 and compares the current breathing rate to first and second thresholds, where the first threshold is below the target breathing rate and second threshold is above the target breathing rate. Responsive to the current breathing rate being below the first threshold or above the second threshold, the computer 696 instructs the user interface 699 to start providing the breathing cues or to increase intensity of provided breathing cues. Optionally, responsive to the current breathing rate being above the first threshold and below the second threshold, for at least a certain duration, the computer 696 instructs the user interface 699 to cease from providing the breathing cues or to provide weaker breathing cues.

Figure 50C:
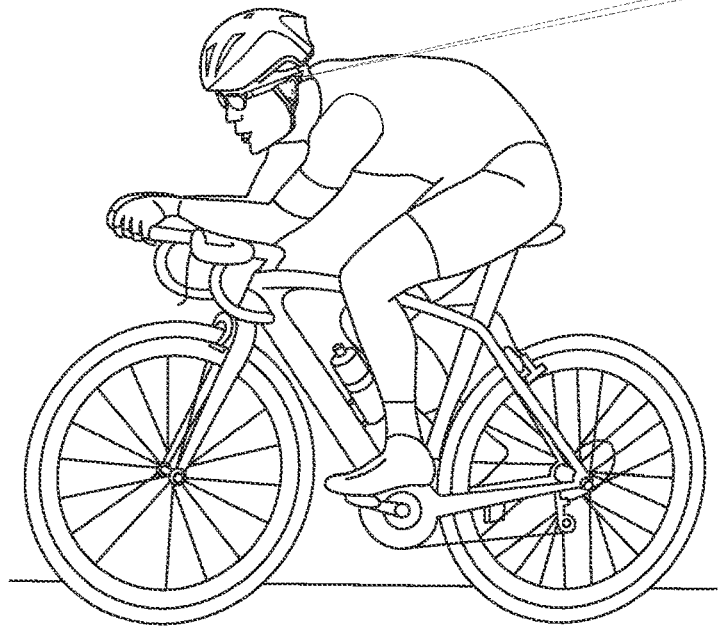
FIG. 50C illustrates a cycler who receives breathing cues via an earbud.

The breathing cues may be provided in various ways. In one example, the user interface 699 includes a speaker (e.g., in an earbud) and the breathing cues comprise auditory cues that have a frequency that corresponds to the target breathing rate (e.g., a beeping sound at the frequency or a music that has an underlying beat at the frequency). FIG. 50C illustrates a cycler who receives breathing cues via an earbud, which correspond to the target breathing rate. In another example, the user interface 699 includes a display (e.g., a display of augmented reality smart glasses, and the breathing cues comprise visual cues that have a frequency that corresponds to the target breathing rate (e.g., a flashing light or icon that changes its size at a frequency that corresponds to the target breathing rate).

Yet another type of coaching application that may utilize $TH_{RBN}$ 693 and $M_{move}$ 695 a coaching indication indicative synchronization of a breathing pattern of the user with a sequence of movements of the user. Optionally, the coaching indication 698 may be indicative of whether the breathing is synchronized with a sequence of movements (i.e., indicate to the user whether the user is breathing correctly when performing the sequence of movements). Additionally or alternatively, the coaching indication 698 may provide cues of the correct breathing pattern corresponding to the sequence of movements (i.e., provide cues that indicate to the user a synchronized breathing pattern). In one embodiment, the computer 696 provides the user, via the user interface 699, an indication indicative of whether the user's breathing is synchronized with the sequence of movements. Additionally or alternatively, the computer 696 determine whether the user did not breathe in an appropriate pattern while performing a sequences of movements. Responsive to determining that the user did not breathe in the appropriate pattern, the computer 696 notifies the user of this fact via a user interface 699.

A "correct" breathing pattern refers to a breathing pattern that is considered appropriate for the sequence of movements, and thus may be considered synchronized with the sequence of movements. Optionally, determining a breathing pattern that is correct for a sequence of movements may be done based on expert knowledge (e.g., coaches, experts in athletics and physiology, etc.) Additionally or alternatively, correct breathing patterns for a sequence of movements may be learned from observations. For example, performance of one or more users may be monitored while they breathe in various patterns while performing a certain sequence of movements, and the optimal breathing pattern (i.e., the breathing pattern that is synchronized with the certain sequence) may be determined based on detecting a breathing pattern for which the performance is maximized (e.g., farthest/most accurate driver hit).

The sequence of movements performed by the user may be, in some embodiments, sequences involved in performing a specific operation, such as swinging a bat, a racket or a golf club, lifting weights, performing a move in yoga, etc. In such cases, various sensors may be utilized in order to obtain $M_{move}$ 695, which provide indications of the type of movements the user is performing and/or how the user is manipulates objects (such as a bat, a racket, a golf club, a barbell, etc.). In some embodiments, the sensor 694 is a camera that takes images of the user, the user's limbs, and/or objects held by the user. In one example, the sensor 694 is an outward-facing head-mounted camera (e.g., a camera pointed outwards that is coupled to a frame worn on the user's head). In another example, the sensor 694 is an external camera, such as a camera in a laptop, smart TV, or a webcam. Optionally, the computer 696 performs image analysis of $M_{move}$ 695 that includes images taken by the sensor 694 in order to identify various movements of the user.

In some embodiments, the sensor 694 may include at least one of LiDAR system and a RADAR system. Optionally, the computer 696 analyzes $M_{move}$ 695 in order to identify movements of the user's limbs, changes to the user's pose, and/or the location of an object held by the user (e.g., a barbell, racket, golf club, etc.)

The following are examples of various sequences of movements and coaching indications that may be generated for them based on $TH_{RBN}$ 693 and $M_{move}$ 695.

In one embodiment, a sequence of movements of the user corresponds to a pressing motion of weights or a barbell, and the coaching indication 698 indicates to inhale in the concentric phase of the press and exhale in the eccentric phase of the press. In one example, the sensor 694 is a movement sensor (e.g., an accelerometer embedded in a garment worn by the user) and the computer 696 analyzes $M_{move}$ 695 to identify different movements involved in the pressing motion. In another example, the sensor 694 is an outward-facing head-mounted camera or a camera external to the user, and $M_{move}$ 695 include images of the user and/or of the weights or barbell. In this example, the computer 696 may utilize image analysis of $M_{move}$ 695 in order to identify different movements involved in the pressing motion. Optionally, the coaching indication 698 is provided to the user while the user performs the sequence of movements, such that when the computer 696 recognizes that the user is about push the weights or barbell, or starts to push (initiating the concentric phase), the user is instructed, in the coaching indication 698, to exhale.

In another embodiment, a sequence of movements of the user corresponds to swinging a racket in order to hit a ball with the racket (e.g., while playing tennis), and the coaching indication 698 indicates to exhale while hitting the ball. In one example, the sensor 694 is a movement sensor (e.g., an accelerometer) on the user's body, and the computer 696 analyzes $M_{move}$ 695 to identify movements that characterize a swinging motion. In another example, the sensor 694 comprises at least one of a LiDAR system and a RADAR system, and the computer 696 analyzes $M_{move}$ 695 to determine the location of the arms and/or the racket relative to the user's body in order to identify the swinging motion. Optionally, the coaching indication 698 is provided to the user while the user performs the sequence of movements, such that when the computer 696 recognizes that the user is about swing the racket, or starts to starts to swing the racket, the user is instructed, in the coaching indication 698, to exhale.

Figure 50D:
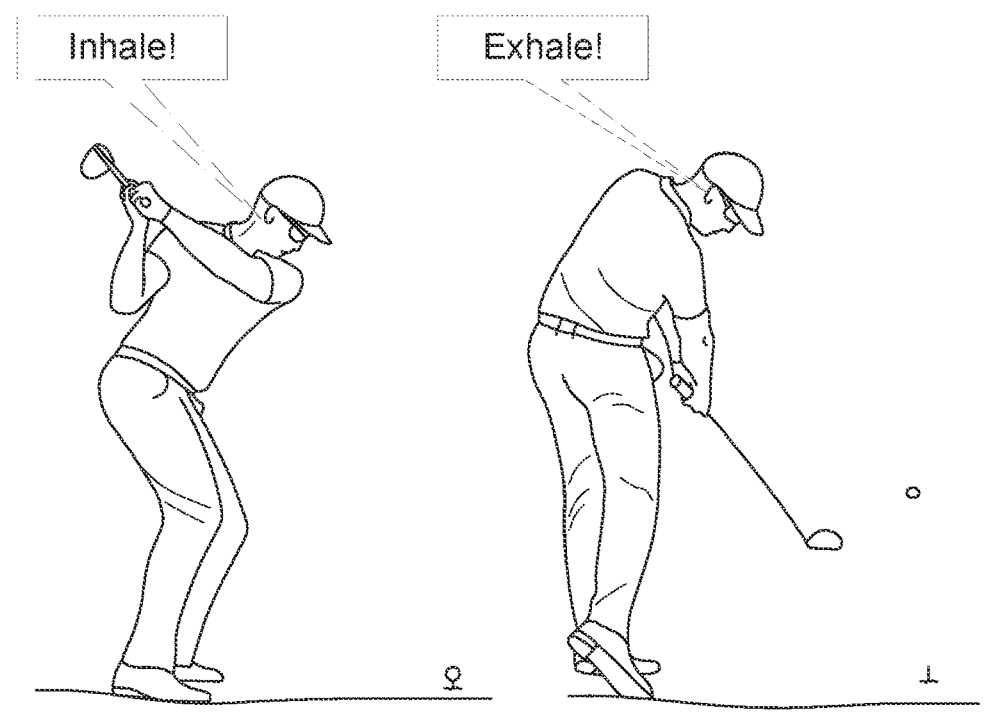
FIG. 50D illustrates a user receiving coaching instructions while hitting a driver in golf.

In yet another embodiment, a sequence of movements of the user corresponds to making a drive shot in golf, and the coaching indication 698 indicates to inhale during the backswing and exhale again on the downswing. Optionally, the coaching indication 698 also indicates to exhale at address. Optionally, the coaching indication 698 is provided to the user while the user performs the sequence of movements, such that when the computer 696 recognizes that the user is about to drive the shot (e.g., based on characteristic movements in the address), or starts the drive shot (e.g., by starting the backswing), the user is instructed, in the coaching indication 698, to exhale. FIG. 50D illustrates a user receiving coaching instructions while hitting a drive in golf; the figure illustrates the user receiving instructions (e.g., via an earbud) to inhale on the backswing and exhale of the downswing.

In still another embodiment, the computer 696: (i) receives from a fitness app (also known as a personal trainer app) an indication that the user should exhale while making a movement, (ii) determines, based on $m_{move}$ 695, when the user is making the movement, and (iii) determines, based on $TH_{RBN}$ 693, whether the user exhaled while making the movement. Optionally, the computer 696 commands the user interface 699 to (i) play a positive feedback in response to determining that the user managed to exhale while making the physical effort, and/or (ii) play an alert and/or an explanation why the user should try next time to exhale while making the physical effort in response to determining that the user did not exhale while making the physical effort. FIG. 41A illustrates a fitness app running on smartphone 196, which instructs the user to exhale while bending down. CAM coupled to eyeglasses frame 181 measures the user breathing and is utilized by the fitness app that helps the user to exhale correctly. FIG. 41B illustrates inhaling while straightening up.

There are various ways in which the computer 696 may generate a coaching indication that is indicative of synchronization of a breathing pattern of the user with a sequence of movements of the user. In some embodiments, generating the coaching indication 698 involves identifying a breathing pattern based on $TH_{RBN}$ 693 and/or the sequence of movements based on 695. Additionally or alternatively, a machine learning model may $M_{move}$ be used to calculate, based on $TH_{RBN}$ 693 and $M_{move}$ 695, a value indicative of an extent to which the breathing pattern of the user is synchronized with the sequence of movements.

In some embodiments, a breathing pattern may refer to a description of characteristics of the user's breathes during a certain period of time. Optionally, the breathing pattern is determined by identifying, based on $TH_{RBN}$ 693, times at which the user inhaled or exhaled and/or by calculating, based on $TH_{RBN}$ 693, one or more of the various respiratory parameters described herein. Optionally, a breathing pattern may describe one or more of the following values: times at which the user inhaled, times at which the user exhaled, durations of inhales, durations of exhales, respiration volume (or changes to the respiration volume), indications of whether the user exhaled and/or inhaled from the mouth, and indications of whether the user exhaled and/or inhaled from the nose. Optionally, the values comprised in a breathing pattern include corresponding temporal values. For example, a breathing pattern may include the following: at time t=0 inhaling, at time t=1.5 exhaling, at time t=3 inhaling, . . . , etc. Additionally or alternatively, a breathing pattern may include qualitative descriptors of respiration (determined based on $TH_{RBN}$ 693). For example, a breathing pattern may include the following descriptors: a regular inhaling followed by a short bursty exhaling (e.g., when hitting a ball).

In some embodiments, a sequence of movements of the user may refer to values describing movement of the user's body (changing location in the 3D space) and/or changes to pose and/or orientation of limbs. Optionally, the sequence of movements may be represented using descriptors that represent specific movements that are identified based on $M_{move}$ 695. For example, the sequence of movements describing a drive shot in golf may include descriptors such as: getting into position (address), a backswing, and a downswing. Optionally, the descriptors of movements in a sequence of movements may have associated temporal values describing properties such as when each of the movements started and/or how long each of the movements lasted.

In one embodiment, identifying a certain movement, from among the sequence of movements, is done using a machine learning-based model. 695 (or a portion thereof, e.g., a segment lasting a second) are $M_{move}$ converted into feature values representing values of $M_{move}$ (e.g., values of an accelerometer, low-level image features, etc.), using approaches described herein and/or approaches known in the art. A model is utilized to calculate, based on the feature values, a value indicative of whether the user performed the certain movement. Optionally, the model is trained on samples of one or more users, each comprising feature values generated based on $M_{move}$ of a user taken while said user performed the certain movement. Optionally, the model is trained on samples of one or more users, each comprising feature values generated based on $M_{move}$ of a user taken while said user did not perform the certain movement.

In one embodiment, identifying a certain movement, from among the sequence of movements, is done using similarity to reference $M_{move}$ taken while a certain user performed the certain movement. $M_{move}$ 695 (or a portion thereof, e.g., a segment lasting a second), is compared to the reference and if the similarity reaches a $M_{move}$ threshold, the user is considered to have performed the certain movement while 695 (or the portion thereof) $M_{move}$ were taken. In one example, the segments of $M_{move}$ being compared are treated as time series data, and one or more of the methods referenced herein with respect to determining similarity of time series are used to determine the similarity. In another example, the segments of being compared may be represented as points in a high $M_{move}$ dimensional space, and a distance function such as the Euclidian distance or some other distance function is used find the distance between the points. The threshold, to which the similarity is compared, may be determined experimentally and selected in order to achieve a desirable balance between specificity and sensitivity of identifications of the certain movement.

In order to determine to what extent the sequence of movements (determined based on $M_{move}$ 695) is synchronized with the breathing pattern (determined based on $TH_{RBN}$ 693) the computer 696 may align the sequence of movements and breathing pattern (e.g., by using temporal information associated with both). This alignment may be done in different ways. In one example, the alignment determines which respiratory actions were performed when different movements of the sequence of movements were performed. In this example, the computer 696 may utilized the alignment to determine whether the respiratory actions correspond to one or more predetermined breathing patterns appropriate for the certain movement sequence.

In another embodiment, feature values are generated based on the sequence of movements and the breathing pattern. For example, some of the feature values may describe which movements were performed, their relative order, and timing. Additionally some feature values may describe which respiratory activities were performed, their order/timing/duration, and other related properties described above. A model is used to calculate, based on the feature values, a value indicative of the extent to the breathing pattern is synchronized with the sequence of movements. Optionally, the model is trained based samples generated from $M_{move}$ and $TH_{RBN}$ of one or more users, which include samples generated based on $M_{move}$ and $TH_{RBN}$ taken while the sequence of movements was performed and a user was breathing in a breathing pattern that was synchronized with the sequence of movements. Additionally, the samples used to train the model may include samples generated based on $M_{move}$ and $TH_{RBN}$ taken while the sequence of movements was performed and a user was not breathing in a breathing pattern that was synchronized with the sequence of movements. Optionally, a breathing pattern is considered not to be synchronized with a sequence of movements if the extent of the synchronization between the two is below a predetermined threshold (and considered synchronized otherwise).

In yet another embodiment, a unified sequence is created from the breathing pattern and the sequence of movements, which describes both movements and respiration activities. For example, the sequence of movements and the breathing pattern may be merged to a single sequence using temporal data. This unified sequence may then be evaluated to determine whether it corresponds to a breathing pattern that is synchronized to a sequence of movements based on similarity to a reference unified sequence and/or a machine learning-based model trained on samples generated based on unified sequences that are generated based on $M_{move}$ and $TH_{RBN}$ taken while the sequence of movements was performed and a user was breathing in a breathing pattern that was synchronized with the sequence of movements.

In some embodiments, determining whether a breathing pattern is synchronized with a sequence of movements of the user is done using a machine learning-based model. The computer 696 generates feature values based on $TH_{RBN}$ 693 (e.g., one or more feature values of types described herein which are used to calculate a respiratory parameter) and/or based on $M_{move}$ 695 (e.g., feature values described above which are used to identify certain movements). The computer 696 utilizes the machine learning-based model to calculate, based on the feature values, a value indicative of whether the breathing pattern was synchronized with the sequence of movements. Optionally, the model was trained based on data comprising: a first set of previous $TH_{RBN}$ and $M_{move}$ of one or more users, taken while performing the sequence of movements and breathing in a pattern that is synchronized with the sequence of movements, and a second set of previous $TH_{RBN}$ and $M_{move}$ of the one or more users taken while performing the sequence of movements and breathing in a pattern that is not synchronized with the sequence of movements.

Figure 51:
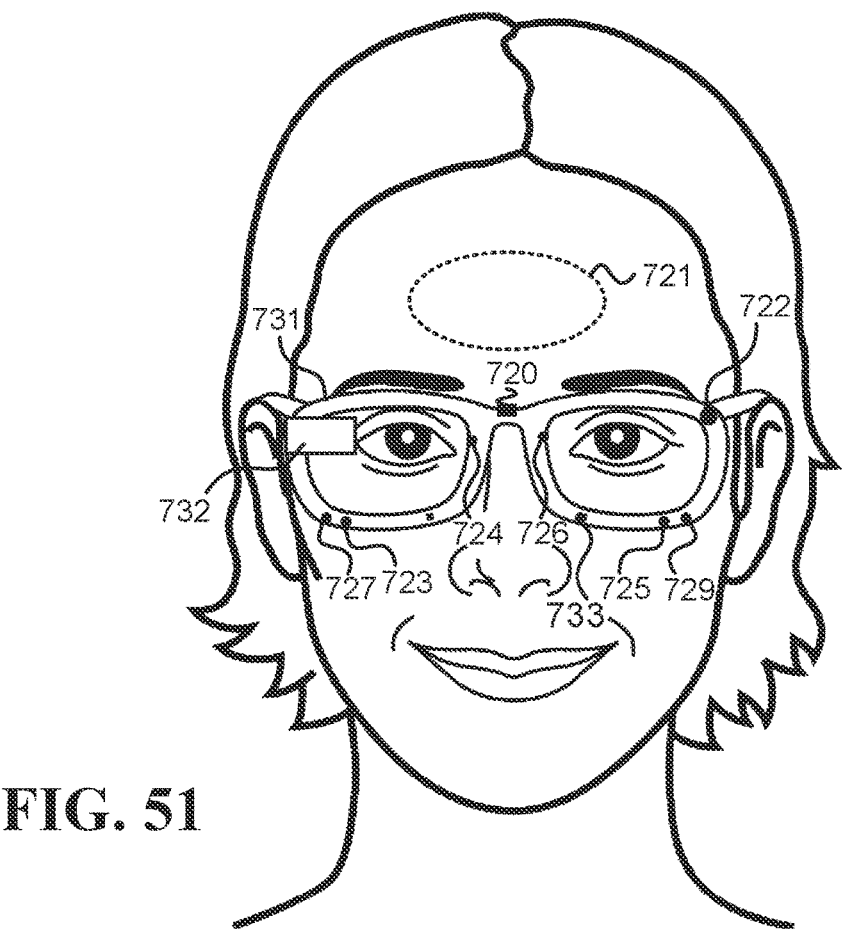
FIG. 51 illustrates an embodiment of a system configured to provide neurofeedback and/or breathing biofeedback.

FIG. 51 illustrates one embodiment of a system configured to provide neurofeedback (based on measurements of thermal camera 720) and/or breathing biofeedback (based on measurements of at least one of thermal cameras 723, 725, 727 and 729). Thermal camera 720 takes thermal measurements of a region on the forehead 721, thermal cameras 723 and 725 take thermal measurements of regions on the right and left sides of the upper lip, respectively, and thermal cameras 727 and 729 take thermal measurements of regions on the user's mouth and/or volumes protruding out of the user's mouth. The thermal cameras are physically coupled to a frame 731 that may be part of an augmented-realty system in which the visual feedback of the breathing biofeedback and/or neurofeedback is presented to the user via UI 732. The system may control the breathing biofeedback and/or neurofeedback session based on measurements taken by additional sensors, such as (i) sensor 722, which may be an outward-facing thermal camera that measures the intensity of infrared radiation directed at the face, and (ii) thermal cameras 724 and 726 that measure regions on the right and left periorbital areas, respectively.

In one embodiment, a system configured to provide a breathing biofeedback session for a user includes at least one inward-facing head-mounted thermal camera (CAM) and a user interface (UI). The at least one CAM takes thermal measurements of a region below the nostrils ($TH_{ROI}$), and $TH_{ROI}$ are indicative of the exhale stream. The UI provides feedback, calculated based on $TH_{ROI}$, as part of a breathing biofeedback session for the user. Optionally, the breathing biofeedback system may include additional elements such as a frame, a computer, additional sensors, and/or thermal cameras as described below.

The at least one CAM may have various configurations. In a first example, each of the at least one CAM is located less than 15 cm from the user's face and above the user's upper lip, and does not occlude any of the user's mouth and nostrils. Optionally, $TH_{ROI}$ include thermal measurements of at least first and second regions below right and left nostrils of the user. Optionally, the at least one CAM consists of a single CAM.

In a second example, the system further includes a frame worn on the user's head. $TH_{ROI}$ include thermal measurements of first and second regions below right and left nostrils ($TH_{ROI1}$ and $TH_{ROI2}$, respectively) of the user. The at least one CAM includes first and second thermal cameras for taking $TH_{ROI1}$ and $TH_{ROI2}$, respectively, which are located less than 15 cm from the user's face and above the nostrils. The first thermal camera is physically coupled to the right half of the frame and captures the exhale stream from the right nostril better than it captures the exhale stream from the left nostril, and the second thermal camera is physically coupled to the left half of the frame and captures the exhale stream from the left nostril better than it captures the exhale stream from the right nostril.

In a third example, $TH_{ROI}$ include thermal measurements of first, second and third regions on the user's face, which are indicative of exhale streams from the right nostril, the left nostril, and the mouth, respectively. The first and second regions are below the right and left nostrils, respectively, and the third region includes the mouth and/or a volume protruding out of the mouth.

The UI provides the feedback for the user during the breathing biofeedback session. The UI may also receive instructions from the user (e.g., verbal commands and/or menu selections) to control the session parameters, such session duration, goal, and type of game to be played. The UI may include different types of hardware in different embodiments. Optionally, the UI includes a display that presents the user with video and/or 3D images, and/or a speaker that plays audio. Optionally, the UI is part of a device carried by the user. Optionally, the UI is part of a HMS to which the at least one CAM is coupled. Some examples of displays that may be used in some embodiments include a screen of a handheld device (e.g., a screen of a smartphone or a smartwatch), a screen of a head-mounted device (e.g., a screen of an augmented reality system or a virtual reality system), and a retinal display. In one embodiment, the UI may provide tactile feedback to the user (e.g., vibrations).

In some embodiments, at least some of the feedback presented to the user via the UI is intended to indicate to the user whether, and optionally to what extent, the user's breathing (as determined based on $TH_{ROI}$) is progressing towards a target pattern. The feedback may be designed to guide the user to breathe at his/her resonant frequency, which maximize amplitude of respiratory sinus arrhythmia and is in the range of 4.5 to 7.0 breaths/min.

The feedback may indicate the user's progress towards the target in different ways, which may involve visual indications, audio indications, and/or tactile indications. In one embodiment, the user is provided with a visual cue indicating the extent of the user's progress. For example, an object may change states and/or locations based on how close the user is to the target, such as an image of a car that moves forward as the user advances towards the target, and backwards if the user regresses. In one example, the feedback may include an audio-visual video of a fish that swims to the left when the exhale becomes smoother and stops swimming or even swims to the right when the exhale becomes less smooth. In another embodiment, the user is provided with an audio cue indicating the extent of the user's progress. For example, music played to the user may change its volume, tune, tone, and/or tempo based on whether the user is advancing towards the target or regressing from it, and/or different music pieces may be played when the user is at different rates of progression. In still another embodiment, the user is provided with a tactile cue indicating the extent of the user's progress. For example, a device worn and/or carried by the user may vibrate at different frequencies and/or at different strengths based on how far the user is from a goal of the session.

Breathing biofeedback requires closing the feedback loop on a signal that changes fast enough. Smoothness of the exhale stream, the shape, and/or the BRV have components that change at frequency above 2 Hz, which may be fast enough to act as the parameter on which the breathing biofeedback loop is closed. The feedback may be calculated and presented to the user at frequencies higher than 1 Hz, 2 Hz, 5 Hz, 10 Hz, 20 Hz and/or 40 Hz (which are all higher than the user's breathing rate).

The computer calculates, based on $TH_{ROI}$, a characteristic of the user's breathing, and generates the feedback based on the characteristic. Some breathing characteristics may be difficult to control, and often people are not even aware of them. However, breathing biofeedback can help the user achieve awareness and/or gain control over his/her breathing, and as a result improve the user's state.

One characteristic of the breathing, which the computer may take into account when controlling the breathing biofeedback session, is the smoothness of the exhale stream. Optionally, the smoothness of the exhale stream refers to a mathematical property of sets of values that include values of $TH_{ROI}$ taken over a period of time (e.g., values in a window that includes a portion of a breath, or even one or more breaths). The smoothness may be considered a property of graphs of the sets of values, and may represent how much of a variance there is in these values when compared to an average trend line that corresponds to the breathing. As discussed above, the smoothness may be calculated in various ways such as using Fourier transform and/or measuring a fit to a low order polynomial.

In one embodiment, the feedback is indicative of similarity between current smoothness of the exhale stream and target smoothness of the exhale stream. The current smoothness is calculated in real-time based on $TH_{ROI}$, and the target smoothness is calculated based on previous $TH_{ROI}$ of the user taken while the user was in a state considered better than the user's state while starting the breathing biofeedback session. Optionally, the similarity may be formulated as the distance between the current smoothness and the target smoothness.

In one embodiment, the feedback is indicative of at least one of the following: whether the smoothness is above or below a predetermined threshold, and whether the smoothness has increased or decreased since a previous feedback that was indicative of the smoothness. Optionally, the smoothness is calculated at frequency $\geq 4$ Hz, and the delay from detecting a change in the smoothness to updating the feedback provided to the user is $\leq 0.5$ second. As another option, the feedback may be indicative of whether the smoothness is above or below the predetermined threshold, and the user interface may update the feedback provided to the user at a rate $\geq 2$ Hz.

Another characteristic of the breathing, which the computer may take into account when controlling the breathing biofeedback session, is the shape of the exhale stream (SHAPE). Optionally, the SHAPE is described by one or more parameters that represent a 3D shape that bounds the exhale stream that flows from one or both of the nostrils. Optionally, the feedback is indicative of whether the SHAPE matches a predetermined shape, and/or whether the SHAPE has become more similar or less similar to the certain shape since a previous feedback that was indicative of the SHAPE. In one embodiment, the feedback is indicative of similarity between current shape of the exhale stream (SHAPE) and target SHAPE, wherein the current SHAPE is calculated in real-time based on $TH_{ROI}$, and the target SHAPE is calculated based on at least one of the following: (i) previous $TH_{ROI}$ of the user taken while the user was in a state considered better than the user's state while starting the breathing biofeedback session, and (ii) $TH_{ROI}$ of other users taken while the other users were in a state considered better than the user's state while starting the breathing biofeedback session.

Another characteristic of the breathing, which the computer may take into account when controlling the breathing biofeedback session, is the breathing rate variability (BRV), which is indicative of the variations between consecutive breathes. Optionally, the feedback may be indicative of similarity between current breathing rate variability (BRV) and a target BRV, wherein the current BRV is calculated in real-time based on $TH_{ROI}$, and the target BRV is calculated based on previous $TH_{ROI}$ of the user taken while the user was in a state considered better than the user's state while starting the breathing biofeedback session. Additionally or alternatively, the feedback may be indicative of whether the BRV is above or below a predetermined threshold, and/or whether a predetermined component of the BRV has increased or decreased since a previous feedback that was indicative of the BRV.

Similarly to how heart rate variability (HRV) is calculated, there are various computational approaches known in the art that may be used to calculate the BRV based on $TH_{ROI}$. In one embodiment, calculating the BRV involves identifying matching events in consecutive breaths (such as start exhaling, exhale peak, and/or inhale peak), and analyzing the variability between these matching events. In another embodiment, the user's breathing is represented as time series data from which low frequency and high frequency components of the integrated power spectrum within the time series signal are extracted using Fast Fourier Transform (FFT). A ratio of the low and high frequency of the integrated power spectrum within these components is computed and analysis of the dynamics of this ratio over time is used to estimate the BRV. In still another embodiment, the BRV may be determined using a machine learning-based model. The model may be trained on samples, each including feature values generated based on $TH_{ROI}$ taken during a certain period and a label indicative of the BRV during the certain period.

In some embodiments, the computer calculates a value indicative of similarity between a current $TH_{ROI}$ pattern and a previous $TH_{ROI}$ pattern of the user taken while the user was in a target state, and generates the feedback based on the similarity. Examples of $TH_{ROI}$ patterns include at least one of: a spatial pattern (e.g., a pattern in a thermal image received from a FPA sensor), a pattern in the time domain (e.g., a pattern detected in a time series of the thermal measurements), and a pattern in the frequency domain (e.g., a pattern detected in a Fourier transform of the thermal measurements).

Biofeedback sessions may have different target states in different embodiments. Generally, the purpose of a session is to bring the user's state during the biofeedback session (the "present state") to become more similar to a target state. In one embodiment, while the user was in the target state, one or more of the following were true: the user was healthier compared to the present state, the user was more relaxed compared to the present state, a stress level of the user was below a threshold, and the user was more concentrated compared to the present state. Additionally, the computer may receive an indication of a period during which the user was in the target state based on a report made by the user (the previous $TH_{ROI}$ pattern comprises $TH_{ROI}$ taken during the period), measurements of the user with a sensor other than CAM, semantic analysis of text written by the user, and/or analysis of the user's speech.

In another embodiment, the computer calculates a value indicative of similarity between current $TH_{ROI}$ and previous $TH_{ROI}$ of the user taken while the user was in a target state, and generates the feedback based on the similarity. The similarity may be calculated by comparing (i) a current value of a characteristic of the user's breathing, calculated based on $TH_{ROI}$, to (ii) a target value of the characteristic of the user's breathing, calculated based on the previous $TH_{ROI}$. Here, the feedback may be indicative of whether the current value of the characteristic of the user's breathing has become more similar or less similar to the target value of the characteristic of the user's breathing since a previous (related) feedback.

In still another embodiment, the computer compares a current set comprising feature values generated based on $TH_{ROI}$ to a target set comprising feature values generated based on previous $TH_{ROI}$ of the user, where the feature values are indicative of values of respiratory parameter(s).

In some embodiments, the system configured to provide a breathing biofeedback session receives indications of when the user is in the target state. Given such indications, the system may collect $TH_{ROI}$ taken during these times and utilize them in biofeedback sessions to steer the user towards the desired target (these collected $TH_{ROI}$ may be considered as the previous $TH_{ROI}$ mentioned above). There are various sources for the indications of when the user is in the certain target state. In one example, the user may report when he/she is in such a state (e.g., through an "app" or a comment made to a software agent). In another example, measurements of the user with one or more sensors other than CAM may provide indications that the user is in a certain physiological and/or emotional state that corresponds to the certain target state. In still another example, an indication of a period of time in which the user was in a certain target state may be derived from analysis of communications of the user, such as using semantic analysis of text written by the user, and/or analysis of the user's speech.

In some embodiments, the computer may utilize a machine learning-based model to determine whether the session is successful (or is expected to be) and/or to determine the user's progress in the breathing biofeedback session at a given time (e.g., the rate of improvement the user is displaying at that time and/or how close the user is to the session's target). Optionally, the computer generates feature values based on $TH_{ROI}$ (e.g., values of $TH_{ROI}$ and/or statistics of $TH_{ROI}$ taken over different periods during the session), and utilizes the model to calculate a value indicative of the progress and/or session success. Optionally, the model is trained on samples comprising feature values based on previously taken $TH_{ROI}$ and labels indicative of the success of the session and/or progress at the time those $TH_{ROI}$ were taken. Optionally, the samples may be generated based on previously taken $TH_{ROI}$ of the user. Additionally or alternatively, the samples may be generated based on previously taken $TH_{ROI}$ of other users. Optionally, the samples include samples generated based on $TH_{ROI}$ taken on different days, and/or while the measured user was in different situations.

The following method for providing a breathing biofeedback session may be used, in some embodiments, by systems modeled according to FIG. 51. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of a region below the nostrils ($TH_{ROI}$) of a user using at least one CAM worn on the user's head; $TH_{ROI}$ are indicative of the exhale stream. In Step 2, taking target $TH_{ROI}$ (TARGET) when the user is in a desired state, such as relaxed, healthy, happy, energized, and/or in a state of elevated concentration. In Step 3, taking current $TH_{ROI}$ (CURRENT) of the user. And in Step 4, providing the user with real-time feedback indicative of similarity between TARGET and CURRENT.

Generating the feedback may involve various calculations in different embodiments. For example, the method may include one or more of the following steps: (i) calculating target smoothness of the exhale stream based on TARGET and calculating current smoothness of the exhale stream based on CURRENT. Optionally, the feedback is indicative of similarity between the target smoothness and the current smoothness, (ii) calculating target shape of the exhale stream (SHAPE) based on TARGET and calculating current SHAPE based on CURRENT. Optionally, the feedback is indicative of similarity between the current SHAPE and the target SHAPE, and/or (iii) calculating target breathing rate variability (BRV) based on TARGET and calculating current BRV based on CURRENT. Optionally, BRV is indicative of variations between consecutive breathes, and the feedback is indicative of similarity between the current BRV and the target BRV.

In one embodiment, a system configured to select a state of a user includes at least one CAM and a computer. Each of the at least one CAM is worn on the user's head and takes thermal measurements of at least three regions below the nostrils ($TH_S$) of the user; wherein $TH_S$ are indicative of shape of the exhale stream (SHAPE). The computer (i) generates feature values based on $TH_S$, where the feature values are indicative of the SHAPE, and (ii) utilize a model to select the state of the user, from among potential states of the user, based on the feature values. Optionally, the model is utilized to calculate a value based on the feature values. In one example, the calculated value is indicative of which state the user is in, and the computer may calculate probabilities that the user is in each of the potential states, and select the state for which the probability is highest. In another example, the calculated value is an output of a classifier (e.g., a neural network-based classifier), which is indicative of the state the user is in.

In order for $TH_S$ to be indicative of the SHAPE, the at least one CAM needs to capture at least three regions from which the shape can be inferred. In a first example, the sensing elements of the at least one CAM include: (i) at least three vertical sensing elements pointed at different vertical positions below the nostrils where the exhale stream is expected to flow, and/or (ii) at least three horizontal sensing elements pointed at different horizontal positions below the nostrils where the exhale stream is expected to flow. Optionally, the larger the number of the vertical sensing elements that detect the exhale stream, the longer the length of the exhale stream, and the larger the number of the horizontal sensing elements that detect the exhale stream, the wider the exhale stream. Additionally, the amplitude of the temperature changes measured by the sensing elements may also be used to estimate the shape and/or uniformity of the exhale stream. It is noted that when a CAM, from among the at least one CAM, is located above the upper lip and pointed downwards, the vertical sensing elements (from the second example above) also provide data about the width of the exhale stream, and the horizontal sensing elements also provide data about the length of the exhale stream.

In a second example, the at least three regions from which the shape can be inferred are located on (i) at least two vertical positions below the nostrils having a distance above 5 mm between their centers, and (ii) at least two horizontal positions below the nostrils having a distance above 5 mm between their centers. Optionally, the at least three regions represent: (i) parameters of a 3D shape that confines the exhale stream, and $TH_S$ are the parameters' values, (ii) locations indicative of different lengths of the exhale stream (such as 8 cm, 16 cm, 24 cm, and 32 cm), and/or (iii) locations indicative of different angles characteristic of directions of some of the different SHAPES of the exhale stream (such as locations indicative of a difference of as at least 5°, 10°, or 25° between the directions of the different SHAPEs).

The potential states corresponding to the different SHAPEs may include various physiological and/or emotional states, and usually have to be learned and classified for each user because they depend on the user's physiological and emotional composition. Additionally, the potential states may include general states corresponding to either being healthy or being unhealthy. In some embodiments, at least some of the potential states may correspond to being in a state in which a certain physiological response is likely to occur in the near future (e.g., within the next thirty minutes). Thus, identifying that the user is in such a state can be used to alert regarding the certain physiological response which the user is expected to have in order for the user and/or some other party to take action to address it.

The feature values generated by the computer in order to calculate the SHAPE may include some of the various feature values described in this disclosure that are used to detect a physiological response. In particular, one or more of the feature values are generated based on $TH_S$, and may include raw and/or processed values collected by one or more sensing elements of the at least one CAM. Additionally or alternatively, these feature values may include feature values derived from analysis of $TH_S$ in order to determine various characteristics of the user's breathing. The feature values include at least one feature value indicative of the SHAPE. For example, the at least one feature value may describe properties of the thermal patterns of $TH_S$. Optionally, the feature values include additional feature values indicative of the breathing rate, breathing rate variability, and/or smoothness of the exhale stream.

The model used to select the user's state based on $TH_S$ (and optionally other sources of data) may be, in some embodiments, a machine learning-based model. Optionally, the model is trained based on samples comprising feature values generated based on previous on $TH_S$ taken when the user being measured was in a known state. Optionally, the previous $TH_S$ include thermal measurements of one or more other users (who are not the user whose state is selected based on $TH_S$); in this case, the model may be considered a general model. Optionally, the previous $TH_S$ include thermal measurements of the user whose state is selected based on $TH_S$; in this case, the model may be considered personalized for this user. Optionally, the previous $TH_S$ include thermal measurements taken during different days. Optionally, for each state from among the potential states, the samples include one or more samples that are generated based on $TH_s$ taken while the user being measured was in the state. Optionally, the model was trained based on: previous $TH_s$ taken while the user was in a first potential state from among the potential states, and other previous $TH_S$ taken while the user was in a second potential state from among the potential states. Optionally, the model was trained based on: previous $TH_s$ taken from users while the users were in a first potential state from among the potential states, and other previous $TH_S$ taken while the users were in a second potential state from among the potential states. Optionally, for the same breathing rate, respiration volume, and dominant nostril, the computer is configured to select different states when $TH_S$ are indicative of different SHAPEs that correspond to different potential states.

For each state from among the potential states, the samples include one or more samples that have a label corresponding to the state. The labels for the samples may be generated based on indications that may come from various sources. In one embodiment, a user whose $TH_S$ are used to generate a sample may provide indications about his/her state, such as by entering values via an app when having a headache or an anger attack. Additionally or alternatively, an observer of that user, which may be another person or a software agent, may provide indications about the user's state. For example, a parent may determine that certain behavior patterns of a child correspond to displaying symptomatic behavior of a certain state. In another embodiment, indications of the state of a user whose $TH_S$ are used to generate a sample may be determined based on measurements of physiological signals of the user, such as measurements of the heart rate, heart rate variability, galvanic skin response, and/or brain activity (e.g., using EEG).

In some embodiments, characteristics of the user's breathing may be indicative of a future state of the user (e.g., a state to which the user may be transitioning). Thus, certain changes in the characteristics of the user's breathing can be used to predict the future state. In these cases, some samples that include feature values generated based on $TH_S$ taken during a certain period may be assigned a label based on an indication corresponding to a future time (e.g., a label corresponding to the state of the user 15 or 30 minutes after the certain period). A model trained on such data may be used to predict the user's state at the future time and/or calculate a value indicative of the probability that the user will be in a certain state a certain amount of time into the future.

Given a set of samples that includes feature values generated based on $TH_S$ (and optionally the other sources of data) and labels indicative of the state, the model can be trained using various machine learning-based training algorithms. Optionally, the model may include various types of parameters, depending on the type of training algorithm utilized to generate the model. For example, the model may include parameters of one or more of the following: a regression model, a support vector machine, a neural network, a graphical model, a decision tree, a random forest, and other models of other types of machine learning classification and/or prediction approaches.

In some embodiments, a deep learning algorithm may be used to train the model. In one example, the model may include parameters describing multiple hidden layers of a neural network. In one embodiment, when $TH_S$ include measurements of multiple pixels, such as when the at least one CAM includes a FPA, the model may include a convolution neural network (CNN). In one example, a CNN may be utilized to identify certain patterns in the thermal images, such as patterns of temperatures in the region of the exhale stream that may be indicative a respiratory parameter, which involve aspects such as the location, direction, size, and/or shape of an exhale stream from the nose and/or mouth. In another example, determining a state of the user based on one characteristics of the user's breathing (e.g., various respiratory parameters), may be done based on multiple, possibly successive, thermal measurements. Optionally, estimating the state of the user may involve retaining state information about the one or more characteristics that is based on previous measurements. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to generate a model suitable for identifying the state of the user in real-world day-to-day situations, in some embodiments, the samples used to train the model are based on thermal measurements (and optionally the other sources of data) taken while the user was in different situations, locations, and/or conducting different activities. For example, the model may be trained based on some sample based on previous thermal measurements taken while the user was indoors and other samples based on other previous thermal measurements taken while the user was outdoors. In another example, the model may be trained based on some sample based on some previous thermal measurements taken while the user was sitting and other samples based on other previous thermal measurements taken while the user was walking.

In one embodiment, the computer detects the SHAPE based on $TH_S$. Optionally, the detected SHAPE corresponds to a certain state of the user, and the computer bases the selection of the state on the detected SHAPE. Optionally, the computer generates one or more of the feature values used to select the state based on the detected SHAPE. For example, the one or more feature values may be indicative of various parameters of the SHAPE (e.g., parameters of a 3D geometrical body to which the SHAPE corresponds).

To detect the SHAPE the computer may utilize a model that was trained based on previous $TH_S$ of the user. Optionally, the previous $TH_S$ of the user were taken during different days. In one embodiment, the model includes one or more reference patterns generated based on the previous $TH_S$. Optionally, each reference pattern corresponds to a certain SHAPE, and is based on a subset of the previous $TH_S$ for which the certain SHAPE was identified. For example, identifying the certain SHAPE may be done using analysis of thermal images of the exhale stream obtained using an external thermal camera that is not head-mounted and/or by a human expert. In this embodiment, detecting the SHAPE may be done by comparing $TH_S$ to the one or more reference thermal patterns and determining whether there is a sufficiently high similarity between the thermal pattern of $TH_S$ and at least one of the one or more reference thermal patterns.

In another embodiment, the model may be a machine learning-based model that was trained on samples, with each sample comprising feature values generated based on a subset of the previous $TH_S$ (e.g., the subset includes previous $TH_S$ taken during a certain period), and a label representing the SHAPE corresponding to the subset of the previous $TH_S$. In one example, the feature values include values of temperatures of various sensing elements of the at least one CAM. In another example, the feature values may include low-level image properties obtained by applying various image processing techniques to the subset of the previous $TH_S$. In this embodiment, detecting the SHAPE may be done by generating feature values based on $TH_S$ and utilizing the model to calculate, based on the feature values, a value indicative of the SHAPE corresponding $TH_S$.

The SHAPE is a property that may be independent, at least to a certain extent, of other respiratory parameters. Thus, $TH_S$ taken at different times may have different SHAPEs detected, even if some other aspects of the breathing at those times are the same (as determined based on values of certain respiratory parameters). In one example, for the same breathing rate of the user, the computer detects a first SHAPE based on a first $TH_S$, and detects a second SHAPE based on a second $TH_S$. In this example, the first and second $TH_S$ have different thermal patterns, e.g., as determined using a similarity function between vector representations of the first and second $TH_S$ (which gives a similarity below a threshold). In another example, for the same breathing rate, respiration volume and dominant nostril, the computer detects a first SHAPE based on a first $TH_S$, and detects a second SHAPE based on a second $TH_S$ (where the first and second $TH_S$ have different thermal patterns).

In one embodiment, the system includes a frame worn on the user's head. Each of the at least one CAM is located less than 15 cm from the user's face and does not occlude any of the user's mouth and nostrils. The at least one CAM includes at least first and second inward-facing head-mounted thermal cameras (CAM1 and CAM2, respectively) that take $TH_{ROn1}$ and $TH_{ROn2}$, respectively. CAM1 is physically coupled to the right half of the frame and captures the exhale stream from the right nostril better than it captures the exhale stream from the left nostril, and CAM2 is physically coupled to the left half of the frame and captures the exhale stream from the left nostril better than it captures the exhale stream from the right nostril. In another embodiment, the at least three regions below the nostrils include a first region on the right side of the user's upper lip, a second region on the left side of the user's upper lip, and a third region on the mouth of the user, where thermal measurements of the third region are indicative of the exhale stream from the user's mouth. In still another embodiment, the at least three regions below the nostrils include a first region comprising a portion of the volume of the air below the right nostril where the exhale stream from the right nostril flows, a second region comprising a portion of the volume of the air below the left nostril where the exhale stream from the left nostril flows, and a third region comprising a portion of a volume protruding out of the mouth where the exhale stream from the user's mouth flows.

In one embodiment, a system configured to present a user's state based on SHAPE, includes a CAM and a UI. The at least one CAM takes thermal measurements of at least three regions below the nostrils ($TH_S$) of the user, where $TH_S$ are indicative of SHAPE. The UI present the user's state based on $TH_S$. Optionally, for the same breathing rate, the UI presents different states for the user when $TH_S$ are indicative of different SHAPEs that correspond to different potential states. Optionally, each of the at least one CAM does not occlude any of the user's mouth and nostrils. Optionally, the system further includes a computer that generates feature values based on $TH_S$, and utilizes a model to select the state, from among potential states, based on the feature values.

The following method for selecting a state of a user may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of at least three regions below the nostrils ($TH_S$) of the user utilizing an inward-facing head-mounted thermal camera (CAM); wherein $TH_S$ are indicative of SHAPE. In Step 2, generating feature values based on $TH_S$, where the feature values are indicative of the SHAPE. And in Step 3, utilizing a model for selecting the state of the user, from among potential states of the user, based on the feature values.

Optionally, the method further includes selecting different states, for the same breathing rate, when $TH_S$ are indicative of different SHAPEs that correspond to different potential states. Optionally, the method further includes training the model based on: previous $TH_S$ taken while the user was in a first potential state from among the potential states, and other previous $TH_S$ taken while the user was in a second potential state from among the potential states.

Figure 52:
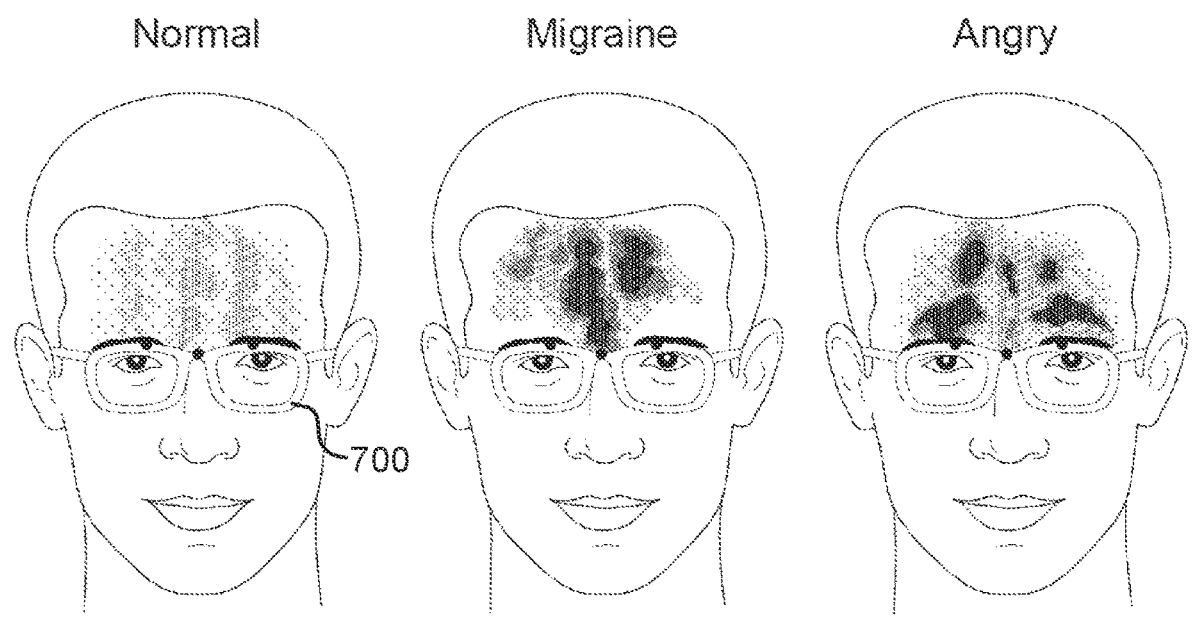
FIG. 52, FIG. 53 and FIG. 54 illustrate an embodiment of eyeglasses with head-mounted thermal cameras, which are able to differentiate between different states of the user based on thermal patterns of the forehead.
Figure 53:
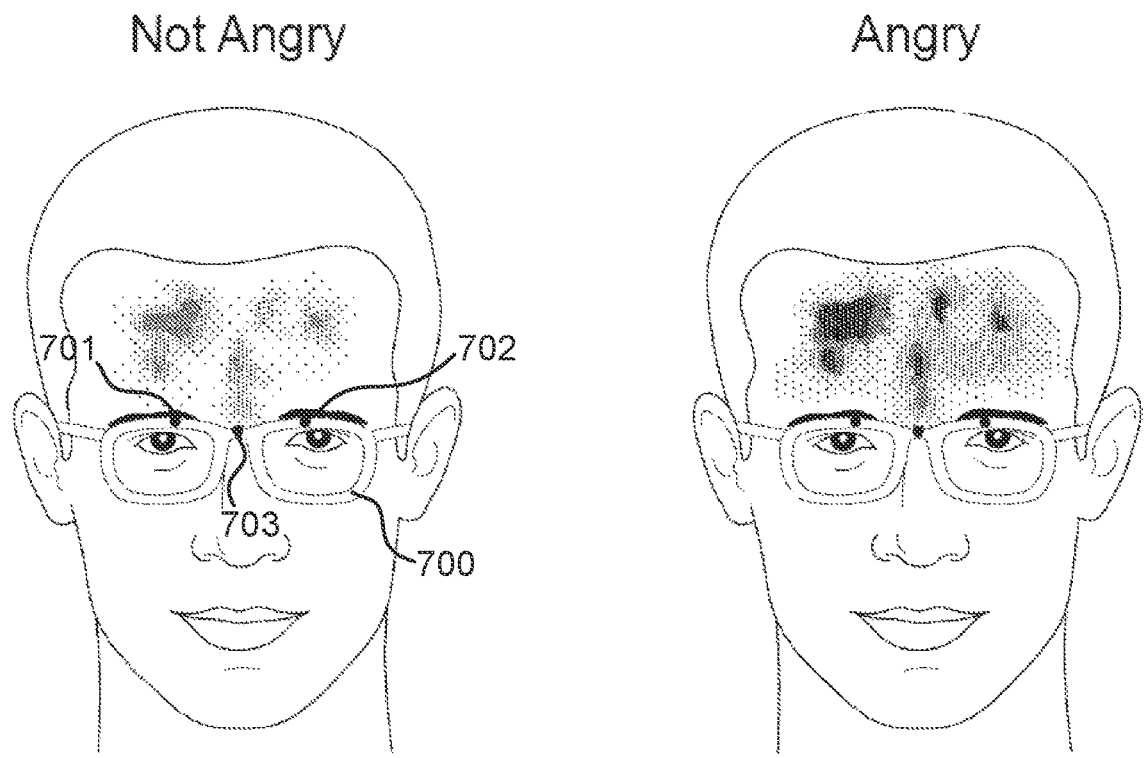
Figure 54:
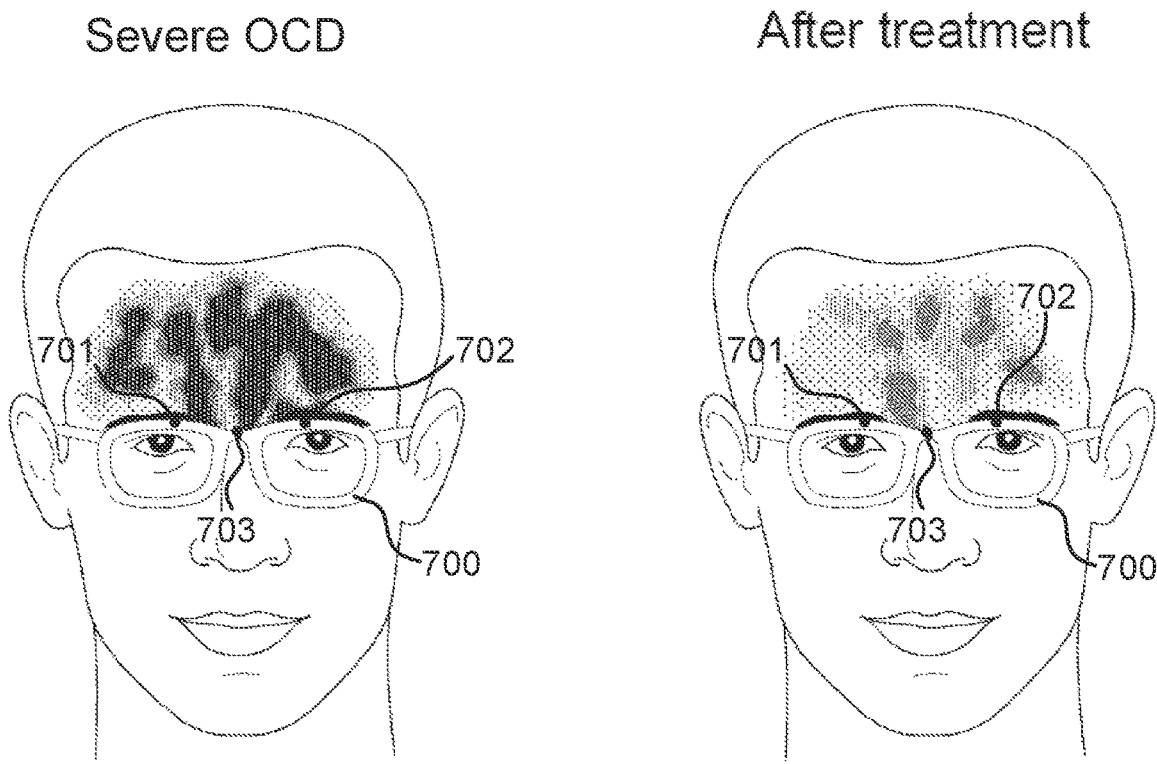

FIG. 52, FIG. 53, and FIG. 54 illustrate one embodiment of eyeglasses 700 with head-mounted thermal cameras, which are able to differentiate between different states of the user based on thermal patterns of the forehead. The illustrated system includes first and second CAMs (701, 702) mounted to the upper right and left portions of the eyeglasses frame, respectively, to take thermal measurements of the forehead. The system further include a sensor 703 mounted to the bridge, which may be utilized to take measurements ($m_{conf}$) indicative of an occurrence of one or more of the various confounding factors described herein. The CAMs forward the thermal measurements to a computer that may differentiate, based on the thermal measurements of the forehead, between normal and abnormal states of a user (which are illustrated as normal vs migraine vs angry in FIG. 52, and not angry vs angry in FIG. 53). The computer may further differentiate between extents of a condition, which is illustrated as severe OCD vs less severe OCD after a treatment in FIG. 54.

In one embodiment, a system configured to differentiate between normal and abnormal states, includes at least one CAM and a computer. The at least one CAM is worn on a user's head and takes thermal measurements of at least first and second regions on the right side of the forehead ($TH_{R1}$ and $TH_{R2}$, respectively) of the user. The at least one CAM further takes thermal measurements of at least third and fourth regions on the left side of the forehead ($TH_{L1}$ and $TH_{L2}$, respectively). The middles of the first and third regions are at least 1 cm above the middles of the second and fourth regions, respectively. Each of the least one CAM is located below the first and third regions, and does not occlude any portion of the first and third regions. Optionally, CAM also does not occlude the second and fourth regions. The computer determines, based on $TH_{R1}$, $TH_{R2}$, $TH_{L1}$, and $TH_{L2}$, whether the user is in a normal state or an abnormal state. Preferably, this embodiment assumes that the user's hair does not occlude the first, second, third and fourth regions on the forehead. Optionally, the at least one CAM includes a CAM that includes a sensor and a lens, and the sensor plane is tilted by more than 2° relative to the lens plane according to the Scheimpflug principle in order to capture sharper images by the CAM, when at least one CAM is worn by the user. Here, the lens plane refers to a plane that is perpendicular to the optical axis of the lens, which may include one or more lenses.

In one embodiment, the at least one CAM includes at least first and second inward-facing head-mounted thermal cameras (CAM1 and CAM2, respectively) located to the right and to the left of the vertical symmetry axis that divides the user's face, respectively (i.e., the axis the goes down the center of the user's forehead and nose). CAM1 is configured to take $TH_{R1}$ and $TH_{R2}$, and CAM2 is configured to take $TH_{L1}$ and $TH_{L2}$. Optionally, CAM1 and CAM2 are located at least 1 cm from each other. In one example, CAM1 and CAM2 are 701 and 702 that are illustrated in FIG. 53. Being able to detect a pattern on the forehead may involve utilization of multiple sensing elements (pixels) by each of CAM1 and CAM2. Optionally, each of CAM1 and CAM2 weighs below 10 g, is located less than 10 cm from the user's face, and includes microbolometer or thermopile sensor with at least 6 sensing elements. Optionally, CAM1 includes at least two multi-pixel thermal cameras, one for taking measurements of the first region, and another one for taking measurements of the second region; CAM2 also includes at least two multi-pixel thermal cameras, one for taking measurements of the third region, and another one for taking measurements of the fourth region.

The computer determines, based on $TH_{R1}$, $TH_{R2}$, $TH_{L1}$, and $TH_{L2}$, whether the user is in a normal state or an abnormal state. In one embodiment, the state of the user is determined by comparing $TH_{L1}$, $TH_{R2}$, $TH_{L1}$, and $TH_{L2}$ to reference thermal patterns of the forehead that include at least one reference thermal pattern that corresponds to the normal state and at least one reference thermal pattern that corresponds to the abnormal state. Optionally, a reference thermal pattern is determined from previous $TH_{L1}$, $TH_{R2}$, $TH_{L1}$, and $TH_{L2}$ of the user, taken while the user was in a certain state corresponding to the reference thermal pattern (e.g., normal or abnormal states). Determining whether $TH_{L1}$, $TH_{R2}$, $TH_{L1}$, and $TH_{L2}$, are similar to a reference thermal pattern may be done using various image similarity functions, such as determining the distance between each pixel in the reference thermal pattern and its counterpart in $TH_{L1}$, $TH_{R2}$, $TH_{L1}$, or $TH_{L2}$. One way this can be done is by converting $TH_{L1}$, $TH_{R2}$, $TH_{L1}$, or $TH_{L2}$ into a vector of pixel temperatures, and comparing it to a vector of the reference thermal pattern (using some form of vector similarity metric like a dot product or the L2 norm). Optionally, if the similarity reaches a threshold, the user is considered to be in the state to which the reference thermal pattern corresponds.

In another embodiment, the computer determines that the user is in a certain state (e.g., normal or abnormal) by utilizing a model to calculate, based on feature values generated from $TH_{L1}$, $TH_{R2}$, $TH_{L1}$, and $TH_{L2}$, a value indicative of the extent to which the user is in the certain state. Optionally, the model is trained based on samples, each comprising feature values generated based on previous $TH_{L1}$, $TH_{R2}$, $TH_{L1}$, and $TH_{L2}$ of the user, taken while the user was in the certain state. In some embodiments, determining whether the user is in a certain state involves determining that $TH_{L1}$, $TH_{R2}$, $TH_{L1}$, and $TH_{L2}$ taken during at least a certain period of time (e.g., at least ten seconds, at least one minute, or at least ten minutes) are similar to a reference thermal pattern that corresponds to the certain state.

Being in a normal/abnormal state may correspond to different behavioral and/or physiological responses. In one embodiment, the abnormal state involves the user displaying symptoms of one or more of the following: an anger attack, Attention Deficit Disorder (ADD), and Attention Deficit Hyperactivity Disorder (ADHD). In this embodiment, being in the normal state refers to usual behavior of the user that does not involve displaying said symptoms. In another embodiment, when the user is in the abnormal state, the user will display within a predetermined duration (e.g., shorter than an hour), with a probability above a predetermined threshold, symptoms of one or more of the following: anger, ADD, and ADHD. In this embodiment, when the user is in the normal state, the user will display the symptoms within the predetermined duration with a probability below the predetermined threshold. In yet another embodiment, when the user is in the abnormal state the user suffers from a headache, and when the user is in the normal state, the user does not suffer from a headache. In still another embodiment, the abnormal state refers to times in which the user has a higher level of concentration compared to the normal state that refers to time in which the user has a usual level of concentration. Although the thermal patterns of the forehead are usually specific to the user, they are usually repetitive, and thus the system may able to learn some thermal patterns of the user that correspond to various states.

Touching the forehead can change the forehead's thermal pattern, even though the user's state did not actually change. Optionally, the system further includes a sensor configured to provide an indication indicative of whether the user touches the forehead. Although the touch is expected to influence thermal readings from the touched area, the computer may continue to operate, for a predetermined duration, according to a state identified shortly (e.g., 1-20 sec) before receiving the indication, even if it identifies a different state shortly (e.g., less than 10, 20, 30, or 60 sec) after receiving the indication. In one example, the sensor is a visible-light camera, and the computer uses image processing to determine whether the user touched the forehead and/or for how long.

The computer may alert the user responsive to identifying an irregularity in $TH_{R1}$, $TH_{R2}$, $TH_{L1}$, and $TH_{L2}$, which does not result from interference, such as touching the forehead. For example, the irregularity may involve a previously unobserved thermal pattern of the forehead. Optionally, the user may be questioned in order to determine if there is a medical reason for the irregularity, such as a stroke or dehydration, in which case medical assistance may be offered, e.g., by summoning medical personnel to the user's location. Optionally, the computer alerts the user when identifying that the user is in an abnormal state associated with antisocial behavior (e.g., an anger attack).

Additional thermal cameras may be utilized to take thermal measurements that may be used to detect the user's state. For example, the system may include at least one additional CAM for taking thermal measurements of regions on the nose and below the nostrils ($TH_{ROI3}$ and $TH_{R}om$, respectively) of the user. Optionally, the additional CAM weighs below 10 g, is physically coupled to a frame worn on the user's head, and is located less than 15 cm from the face. Optionally, the computer determines the user's state also based on $TH_{ROI3}$ and $TH_{ROI4}$. Optionally, the computer (i) generates feature values based on $TH_{R1}$, $TH_{R2}$, $TH_{L1}$, $TH_{L2}$, $TH_{ROI3}$, and $TH_{ROI4}$, and (ii) utilizes a model to determine the user's state based on the feature values. Optionally, the model was trained based on a first set of previous $TH_{R1}$, $TH_{R2}$, $TH_{R1}$, $TH_{L2}$, $TH_{ROI3}$, and $TH_{ROI4}$ taken while the user was in the normal state and a second set of previous $TH_{R1}$, $TH_{R2}$, $TH_{L1}$, $TH_{L2}$, $TH_{ROI3}$, and $TH_{ROI4}$ taken while the user was in the abnormal state.

In another example, the system may include another CAM for taking thermal measurements of a region on the periorbital area ($TH_{ROI3}$) of the user. Optionally, the computer determines the state of the user also based on $TH_{ROI3}$. Optionally, the computer is further configured to: (i) generate feature values based on $TH_{R1}$, $TH_{R2}$, $TH_{L1}$, $TH_{L2}$, and $TH_{ROI3}$, and (ii) utilize a model to determine the user's state based on the feature values. Optionally, the model is trained based on a first set of previous $TH_{R1}$, $TH_{R2}$, $TH_{L1}$, $TH_{L2}$, and $TH_{ROI3}$ taken while the user was in the normal state and a second set of previous $TH_{R1}$, $TH_{R2}$, $TH_{L1}$, $TH_{L2}$, and $TH_{ROI3}$ taken while the user was in the abnormal state.

Determining the user's state based on $TH_{R1}$, $TH_{R2}$, $TH_{L1}$, and $TH_{L2}$ (and optionally other sources of data) may be done using a machine learning-based model. Optionally, the model is trained based on samples comprising feature values generated based on previous $TH_{R1}$, $TH_{R2}$, $TH_{L1}$, and $TH_{L2}$ taken when the user was in a known state (e.g., for different times it was known whether the user was in the normal or abnormal state). Optionally, the user may provide indications about his/her state, such as by entering values via an app when having a headache or an anger attack. Additionally or alternatively, an observer of the user, which may be another person or a software agent, may provide the indications about the user's state. For example, a parent may determine that certain behavior patterns of a child correspond to displaying symptomatic behavior of ADHD. In another example, indications of the state of the user may be determined based on measurements of physiological signals of the user, such as measurements of the heart rate, heart rate variability, breathing rate, galvanic skin response, and/or brain activity (e.g., using EEG).

In some embodiments, one or more of the feature values in the samples may be based on other sources of data (different from $TH_{L1}$, $TH_{R2}$, $TH_{L1}$, and $TH_{L2}$). These may include additional thermal cameras, additional physiological measurements of the user, and/or measurements of the environment in which the user was while the measurements were taken. In one example, at least some of the feature values used in samples include additional physiological measurements indicative of one or more of the following signals of the user: heart rate, heart rate variability, brainwave activity, galvanic skin response, muscle activity, and extent of movement. In another example, at least some of the feature values used in samples include measurements of the environment that are indicative of one or more of the following values of the environment in which the user was in: temperature, humidity level, noise level, air quality, wind speed, and infrared radiation level.

Given a set of samples comprising feature values generated based on $TH_{L1}$, $TH_{R2}$, $TH_{L1}$, and $TH_{L2}$ (and optionally the other sources of data) and labels generated based on the indications, the model can be trained using various machine learning-based training algorithms. Optionally, the model is utilized by a classifier that classifies the user's state (e.g., normal/abnormal) based on feature values generated based on $TH_{L1}$, $TH_{R2}$, $TH_{L1}$, and $TH_{L2}$ (and optionally the other sources). Optionally, the model may include various types of parameters, depending on the type of training algorithm utilized to generate the model. For example, the model may include parameters of one or more of the following: a regression model, a support vector machine, a neural network, a graphical model, a decision tree, a random forest, and other models of other types of machine learning classification and/or prediction approaches.

In some embodiments, the model is trained utilizing deep learning algorithms. Optionally, the model includes parameters describing multiple hidden layers of a neural network. Optionally, the model includes a convolution neural network (CNN), which is useful for identifying certain patterns in the thermal images, such as patterns of temperatures on the forehead. Optionally, the model may be utilized to identify a progression of a state of the user (e.g., a gradual forming of a certain thermal pattern on the forehead). In such cases, the model may include parameters that describe an architecture that supports a capability of retaining state information. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to generate a model suitable for identifying the state of the user in real-world day-to-day situations, in some embodiments, the samples used to train the model are based on thermal measurements (and optionally the other sources of data) taken while the user was in different situations, locations, and/or conducting different activities. In a first example, the model may be trained based on a first set of previous thermal measurements taken while the user was indoors and in the normal state, a second set of previous thermal measurements taken while the user was indoors and in the abnormal state, a third set of previous thermal measurements taken while the user was outdoors and in the normal state, and a fourth set of previous thermal measurements taken while the user was outdoors and in the abnormal state. In a second example, the model may be trained based on a first set of previous thermal measurements taken while the user was sitting and in the normal state, a second set of previous thermal measurements taken while the user was sitting and in the abnormal state, a third set of previous thermal measurements taken while the user was standing and/or moving around and in the normal state, and a fourth set of previous thermal measurements taken while the user was standing and/or moving around and in the abnormal state. Usually the movements while standing and/or moving around, and especially when walking or running, are greater compared to the movement while sitting; therefore, a model trained on samples taken during both sitting and standing and/or moving around is expected to perform better compared to a model trained on samples taken only while sitting.

Having the ability to determine the state of the user can be advantageous when it comes to scheduling tasks for the user and/or making recommendations for the user, which suits the user's state. In one embodiment, responsive to determining that the user is in the normal state, the computer prioritizes a first activity over a second activity, and responsive to determining that the user is in the abnormal state, the computer prioritizes the second activity over the first activity. Optionally, accomplishing each of the first and second activities requires at least a minute of the user's attention, and the second activity is more suitable for the abnormal state than the first activity. Optionally, and the first activity is more suitable for the normal state than the second activity. Optionally, prioritizing the first and second activities is performed by a calendar management program, a project management program, and/or a "to do" list program. Optionally, prioritizing a certain activity over another means one or more of the following: suggesting the certain activity before suggesting the other activity, suggesting the certain activity more frequently than the other activity (in the context of the specific state), allotting more time for the certain activity than for the other activity, and giving a more prominent reminder for the certain activity than for the other activity (e.g., an auditory indication vs. a mention in a calendar program that is visible only if the calendar program is opened).

Such state-dependent prioritization may be implemented in various scenarios. In one example, the normal state refers to a normal concentration level, the abnormal state refers to a lower than normal concentration level, and the first activity requires a high attention level from the user compared to the second activity. For instance, the first and second activities may relate to different topics of a self-learning program for school; when identifying that the user is in the normal concentration state, a math class is prioritized higher than a sports lesson; and when identifying that the user is in the lower concentration state, the math class is prioritized lower than the sports lesson. In another example, the normal state refers to a normal anger level, the abnormal state refers to a higher than normal anger level, and the first activity involves more interactions of the user with other humans compared to the second activity. In still another example, the normal state refers to a normal fear level, the abnormal state refers to a panic attack, and the second activity is expected to have a more relaxing effect on the user compared to the first activity.

In one embodiment, a system configured to alert about an abnormal state includes at least one CAM and a user interface (UI). The at least one CAM takes thermal measurements of at least first and second regions on the right side of the forehead ($TH_{R1}$ and $TH_{R2}$, respectively) of the user, and takes thermal measurements of at least third and fourth regions on the left side of the forehead ($TH_{L1}$ and $TH_{L2}$, respectively). The middles of the first and third regions are at least 1 cm above the middles of the second and fourth regions, respectively. Each of the at least one CAM is located below the first and third regions, and does not occlude any portion of the first and third regions. The UI provides an alert about an abnormal state of the user, where the abnormal state is determined based on $TH_{R1}$, $TH_{R2}$, $TH_{L1}$, and $TH_{L2}$. Optionally, the system includes a transmitter that may be used to transmit $TH_{R1}$, $TH_{R2}$, $TH_{R1}$, and $TH_{L2}$ to a computer that determines, based on $TH_{R1}$, $TH_{R2}$, $TH_{L1}$, and $TH_{L2}$, whether the user is in the normal state or the abnormal state. The computer may include a wearable computer, a computer belonging to a smartphone or a smartwatch carried by the user, and/or cloud-based server. Optionally, responsive to determining that the user is in an abnormal state, the computer commands the UI to provide the alert. For example, the computer may send a signal to a smartphone app, and/or to a software agent that has control of the UI, to provide the alert. In another example, the computer may send an instruction to the UI to provide the alert. Optionally, the alert is provided as text, image, sound, and/or haptic feedback.

The following method for alerting about an abnormal state may be used, in some embodiments, by the system configured to alert about the abnormal state (described above). The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of at least first and second regions on the right side of the forehead ($TH_{L1}$, $TH_{R2}$) of a user, and thermal measurements of at least third and fourth regions on the left side of the forehead ($TH_{L1}$, $TH_{L2}$) of the user. The middles of the first and third regions are at least 1 cm above the middles of the second and fourth regions, respectively.

In Step 2, generating feature values based on $TH_{L1}$, $TH_{R2}$, $TH_{L1}$, and $TH_{L2}$.

In Step 3, utilizing a model for detecting a state of the user based on the feature values. The model was trained based on (i) previous feature values taken while the user was in a normal state, and (ii) other previous feature values taken while the user was in the abnormal state.

And in Step 4, responsive to detecting the abnormal state in Step 3, alerting about the abnormal state. In one example, the alerting may involve providing text, image, sound, and/or haptic feedback via the user interface.

Neurofeedback sessions can assist in treating various brain function-related conditions and/or disorders. In order to maximize their effectives, it may be advantageous to have neurofeedback treatments while a person suffers and/or exhibits the symptoms of a brain function-related condition and/or disorder. The following are descriptions of embodiments of a wearable system that may be utilized for this purpose. Some embodiments of a neurofeedback system described below involve a wearable, lightweight device that is aesthetically acceptable, and may be utilized as needed in day-to-day situations.

Some examples of disorders that may be treated with some embodiments of the neurofeedback system described herein include disorders related to (i) frontal lobe dysfunction, such as ADHD, headaches, anger, anxiety, and depression, (ii) paroxysmal disorders, such as headaches, seizures, rage reactions, and panic attacks, (iii) chronic pain, and (iv) stress. It is noted that the term "neurofeedback" also covers biofeedback and other similar feedback-based treatments.

FIG. 51 (already discussed above) illustrates one embodiment of a system configured to provide neurofeedback (based on measurements of CAM 720) and/or breathing biofeedback (based on measurements of at least some of thermal cameras 723, 725, 727 and 729). The system illustrated in FIG. 54, which uses two inward-facing head-mounted thermal cameras (701 and 702) to measure the forehead, may be used for neurofeedback together with a UI (not illustrated). Other embodiments of neurofeedback HMSs may involve more than two inward-facing head-mounted thermal cameras to measure the forehead. Some embodiments of neurofeedback HMSs may include one or more sensors such as the sensor 722, which are used to take $m_{conf}$ as discussed below.

Figure 56:
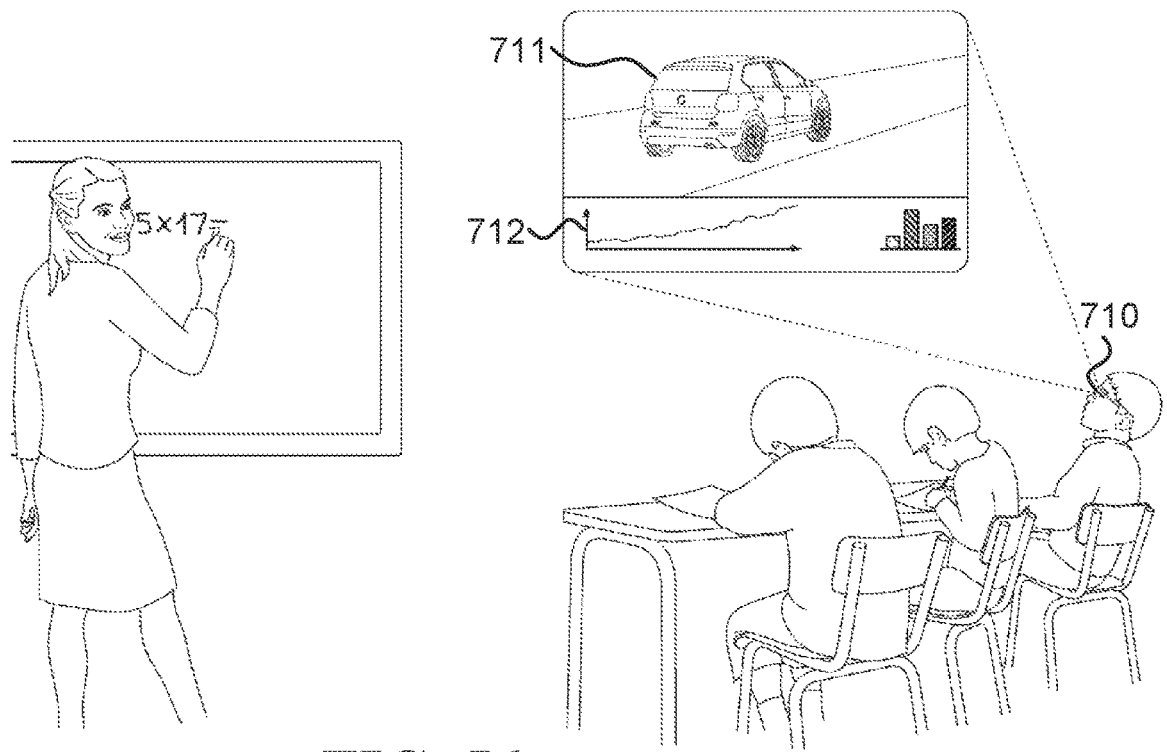
FIG. 56 illustrates a scenario in which a user has neurofeedback session during a day-to-day activity.

FIG. 56 illustrates a scenario in which a user has neurofeedback session during a day-to-day activity, such as during school time. For example, the session may be initiated because the user felt that he was losing concentration and/or the system might have determined that the user was exhibiting symptoms of ADHD and/or was in an undesirable state. The user wears an Augmented Reality device (AR), which includes user interface 710 that includes a display to present the augmented images. The AR includes one or more inward-facing head-mounted thermal cameras, which may be similar to the system illustrated in FIG. 51. The neurofeedback session involves attempting to control brain activity by causing the augmented reality video of the car 711 to drive forwards. For example, the car 711 drives forwards when the temperature at certain regions of the forehead 712 increases, and drives backwards when the temperature at the certain regions of the forehead 712 decreases.

In one embodiment, a neurofeedback system includes at least an inward-facing head-mounted thermal camera (CAM) and a user interface (UI). Optionally, the neurofeedback system may include additional elements such as a frame, a computer, and/or additional sensors and/or thermal cameras, as described below.

CAM is worn on a user's head and takes thermal measurements of a region on the forehead ($TH_F$) of the user. CAM is positioned such that when the user is upright, CAM is located below the middle of the region on the user's forehead. Optionally, CAM does not occlude the center of the forehead, and as such, may be more aesthetically pleasing than systems that have elements that occlude the center of the forehead. Optionally, CAM is located close to the forehead, at a distance below 15 cm, 10 cm, or 5 cm from the user's face. Optionally, CAM may use a single pixel sensor (e.g., discrete thermophile sensor) or a multiple pixel sensor (e.g., microbolometer FPA).

In one embodiment, $TH_F$ measured by CAM includes the area known in the field of electroencephalography as the "Fpz point", which is typically located at a point that is between 5% and 15% the distance from the nasion to the Inion (e.g., approximately at around 10% the distance). Optionally, in this embodiment, $TH_F$ may be indicative of temperature changes at the Fpz point. Additionally or alternatively, the region on the forehead measured by CAM may include the center of the forehead, and $TH_F$ may optionally be indicative of temperature changes at the center of the forehead.

In another embodiment, CAM may measure at least four areas on the user's forehead covering regions on the upper right side of the forehead, lower right side of the forehead, upper left side of the forehead, and lower left side of the forehead, respectively. Optionally, in this embodiment, $TH_F$ may be indicative of a thermal pattern of the user's forehead. Optionally, in this embodiment, "CAM" refers to multiple inward-facing thermal cameras, which include at least first and second inward-facing head-mounted thermal cameras (CAM1 and CAM2, respectively). CAM1 takes the measurements of the upper right side of the forehead and the lower right side of the forehead, and CAM2 takes the measurements of the upper left side of the forehead and the lower left side of the forehead. Optionally, $TH_F$ may include measurements of at least six areas on the user's forehead. Optionally, the at least four areas and the at least six areas each include at least one area that covers the Fpz point.

Due to the proximity of CAM to the face, in some embodiments, there may be an acute angle between the optical axis of CAM and the forehead. In order to improve the sharpness of thermal images of the forehead, in some embodiments, CAM may include a sensor and a lens, which are configured such that the sensor plane is tilted by more than 2° relative to the lens plane according to the Scheimpflug principle, which may enable the capture of sharper images of the forehead when CAM is close to the face.

The UI provides a feedback to the user during the neurofeedback session, which is determined based on $TH_F$ and optionally $m_{conf}$ (that is indicative of confounding factors). Optionally, providing the session for the user involves receiving instructions from the user (e.g., verbal commands and/or menu selections), which may affect the type of feedback the user receives (e.g., what type of session or "game" will be played in the session, how long the session should last, etc.).

In some embodiments, at least some of the feedback presented to the user via the UI is intended to indicate to the user whether, and optionally to what extent, the user's brain activity (as determined based on $TH_F$) is progressing towards a target. Optionally, the target may correspond to a state of brain activity that causes $TH_F$ to have a certain value. Optionally, the target may correspond to a typical $TH_F$ pattern of the user. Optionally, typical $TH_F$ pattern of the user is a pattern of temperatures on different points on the forehead, which determined based on previous $TH_F$ that are measured when the user was in a typical, normal state, and not exhibiting symptoms of anger, ADHD, a headache, etc. In one example, the user may be considered to make progress in the neurofeedback session if the temperature of the forehead (or a certain region on the forehead) becomes closer to a target temperature. In another example, the user may be considered to make progress in the neurofeedback session if the variability of temperatures across certain regions of the forehead reduces. In yet another example, the user may be considered to make progress in the neurofeedback session if asymmetry of temperatures of the forehead reduces. And in still another example, the user may be considered to make progress in the neurofeedback session if $TH_F$ pattern measured during the session becomes more similar to a certain target thermal pattern. Optionally, the user may receive feedback indicative of decreasing positive progress (or negative progress) when the $TH_F$ pattern measured during the session becomes less similar to the typical $TH_F$ pattern.

In one embodiment, video played as part of the feedback is played according to a protocol suitable for a passive infrared hemoencephalography (pIR HEG) session, which is a form of biofeedback for the brain that measures and displays information on the thermal output of the frontal lobe. In one configuration, pIR HEG involves increasing the forehead temperature by watching a movie that provides the feedback. The movie plays when the measured forehead temperature rises and stops when the temperature drops. The system may increase the threshold as the user learns how to raise the forehead temperature, and the user is instructed to calmly concentrate on making the movie continue to play.

The computer controls the neurofeedback session based on $TH_F$ and optionally $m_{conf}$. In one embodiment, the computer compares $TH_F$ to a target temperature. Optionally, different pixels of CAM may be compared to different target temperatures, or the target temperature may refer to an average temperature of the forehead. In another embodiment, the computer may calculate changes to temperature of the forehead ($\Delta T_F$) based on $TH_F$, and utilizes $\Delta T_F$ to control the neurofeedback session. In yet another embodiment, the computer may compare $TH_F$ to a target thermal pattern of the forehead, and the progress of the user in the neurofeedback session is evaluated based on a similarity between $TH_F$ and the target thermal pattern, and/or a change in extent of similarity between $TH_F$ and the target thermal pattern.

In one embodiment, $TH_F$ includes measurements of at least four non-collinear regions on the forehead (e.g., all the four regions do not lie on the same straight line), and the computer controls the neurofeedback session by providing the user a feedback via the user interface. The computer calculates a value indicative of similarity between a current $TH_F$ pattern and a previous $TH_F$ pattern of the user taken while the user was in a target state, and generates, based on the similarity, the feedback provided to the user as part of the neurofeedback session. The $TH_F$ pattern may refer to a spatial pattern of the at least four non-collinear regions on the forehead (e.g., a pattern in a thermal image received from a FPA sensor), and/or to a pattern in the time domain of the at least four non-collinear regions on the forehead (e.g., a pattern detected in a time series of the thermal measurements).

Neurofeedback sessions may have different target states in different embodiments. Generally, the purpose of a session is to bring the user's state during the neurofeedback session (the "present state") to become more similar to a target state. In one embodiment, while the user was in the target state, one or more of the following were true: the user was healthier compared to the present state, the user was more relaxed compared to the present state, a stress level of the user was below a threshold, the user's pain level was below a threshold, the user had no headache, the user did not suffer from depression, and the user was more concentrated compared to the present state. Additionally, the computer may receive an indication of a period during which the user was in the target state based on a report made by the user (the previous $TH_F$ pattern comprises $TH_F$ taken during the period), measurements of the user with a sensor other than CAM, semantic analysis of text written by the user, and/or analysis of the user's speech.

In some embodiments, the computer may utilize a machine learning-based model to determine whether the session is successful (or is expected to be) and/or to determine the user's progress in the neurofeedback session at a given time. Optionally, the computer generates feature values based on $TH_F$, and utilizes the model to calculate a value indicative of the progress and/or session success. Optionally, the model is trained on samples comprising feature values based on previously taken $TH_F$ and labels indicative of the success of the session and/or progress at the time those $TH_F$ were taken. Optionally, the samples may be generated based on previously taken $TH_F$ of the user and/or of other users. Optionally, the samples include samples generated based on $TH_F$ of the user taken on different days, and/or while the user was in different situations.

At a given time, temperatures measured at different areas of the forehead may be different. A value, which is a function of the temperatures at the different areas and is indicative of their variability, may be referred to herein as the "temperature variability" of the measurements. In one example, the function of the temperatures is the statistical variance of the temperatures. Having high temperature variability can be a sign that the user is suffering from various conditions, such as anger, a headache, depression, and/or anxiety. Optionally, a target of the neurofeedback session may be to lower the temperature variability of $TH_F$. Optionally, progress of the neurofeedback session may be evaluated based on a value of the temperature variability of $TH_F$, an extent that the temperature variability of $TH_F$ has decreased, and/or a rate at which the temperature variability of $TH_F$ has decreased.

Various brain function-related conditions may be manifested via asymmetrical thermal patterns on the forehead. Optionally, a target of a neurofeedback session in such cases may be to decrease the asymmetry of the thermal patterns. In one embodiment, CAM is located to the right of the vertical symmetry axis that divides the user's face (e.g. 701), and the region is on the right side of the forehead. The neurofeedback system may include a second inward-facing head-mounted thermal camera (e.g. 702), located to the left of the vertical symmetry axis, which takes thermal measurements of a second region on the left side of the forehead ($TH_{F2}$). Optionally, the computer provides to the user a feedback that becomes more positive as the temperature asymmetry between $TH_F$ and $TH_{F2}$ decreases.

Different regions on the forehead may be associated with different importance, with respect to various physiological responses and/or conditions that may be treated with neurofeedback sessions. In one embodiment, regions that are more important are associated with higher weights compared to weights associated with regions that are less important. Optionally, these weights may be utilized by the computer to calculate various values such as an average temperature of the forehead, which with the weights may be considered a "weighted average temperature". Similarly, a temperature variability of $TH_F$ that is calculated while taking into account the weights associated with the various areas may be a "weighted temperature variability", and temperature asymmetry between $TH_F$ and $TH_{F2}$, which is calculated while taking into account the weights associated with the various areas may be a "weighted temperature asymmetry". In some embodiments, providing feedback to the user based on one or more of the above "weighted" values may increase the efficacy of the neurofeedback session.

The temperature variability may be an indicator for the success or failure of the neurofeedback session. A session that causes a decreasing of the temperature variability below a certain first threshold may be considered a successful session that can be terminated, while a session that causes an increase of the temperature variability above a certain second threshold may be considered a failed session that should be terminated in order to prevent worsening the symptoms.

In one embodiment, the computer terminates the neurofeedback session when $TH_F$ are indicative of the temperature variability decreasing below the certain first threshold. Additionally or alternatively, the computer may terminate the neurofeedback session when $TH_F$ are indicative of the temperature variability increasing above the certain second threshold.

In a similar fashion, the temperature asymmetry may be an indicator for the success or failure of the neurofeedback session for certain disorders. In one embodiment, the computer terminates the neurofeedback session when THF are indicative of the temperature asymmetry decreasing below a certain first threshold. Additionally or alternatively, the computer may terminate the neurofeedback session when $TH_F$ are indicative of the temperature asymmetry increasing above a certain second threshold.

Having neurofeedback sessions, in a real world, day-to-day situations can involve conditions that are less sterile and not as controlled as the conditions that typically encountered when conducting such sessions at a clinic or a laboratory. In particular, thermal measurements of the forehead may be affected by various factors that are unrelated to the type of brain activity the user is conducting, as part of the session; these factors may often be absent and/or less extreme in controlled settings and/or may be noticed and accounted for by a practitioner (who for example, may tell the user not to touch the forehead). Such factors may be referred to herein as confounding factors. Some examples of confounding factors include touching the forehead (e.g., with one's fingers), thermal radiation directed at the forehead (e.g., direct sunlight), and direct airflow on the forehead (e.g., from an air conditioner). Each of these factors can cause changes in $TH_F$ that are not due to brain activity. In order to account for one or more of these confounding factors, in some embodiments, the neurofeedback includes a wearable sensor that takes measurements (denoted $m_{conf}$) indicative of at least one of the following confounding factors: touching the forehead, thermal radiation directed at the forehead, and direct airflow on the forehead. Optionally, the wearable sensor is coupled to a frame worn on the user's head. The following are some examples of types of sensors that the wearable sensor may involve in some embodiments of the neurofeedback system.

In one embodiment, the wearable sensor is an outward-facing head-mounted thermal camera ($CAM_{out}$) that takes thermal measurements of the environment ($TH_{ENV}$). Optionally, the angle between the optical axes of CAM and $CAM_{out}$ is at least one or more of the following angles: 45°, 90°, 130°, 170°, and 180°. In another embodiment, the wearable sensor provides measurements indicative of times at which the user touches the forehead. Optionally, the wearable sensor includes a visible-light camera, a miniature radar (such as low-power radar operating in the range between 30 GHz and 3,000 GHz), an active electro-optics distance measurement device (such as a miniature Lidar), and/or an ultrasound sensor. In yet another embodiment, the sensor may be an anemometer that is physically coupled to a frame worn on the user's head, is located less than 15 cm from the face, and provides a value indicative of a speed of air directed at the face.

There are various way in which the computer may utilize $m_{conf}$ to account for occurrences of a confounding factor during the neurofeedback session. In one embodiment, an occurrence of the confounding factor may prompt the computer to alert the user about the occurrence. In one example, the computer may identify, based on $m_{conf}$, that the extent of a confounding factor reached a threshold, and command the user interface to alert the user that the neurofeedback session is less accurate due to the confounding factor. In another example, upon identifying that the extent of a confounding factor reached the threshold, the computer may refrain from updating the feedback provided to the user as part of the neurofeedback session for at least a certain duration. The certain duration may be a fixed period (e.g., 0.2 seconds from reaching the threshold), and/or may last until $m_{conf}$ indicate that the extent of the confounding factor is below the threshold.

In one embodiment, the computer may adjust the values of $TH_F$ based on the values of $m_{conf}$ according to a certain function and/or transformation. For example, $TH_F$ may be normalized with respect to the intensity of thermal radiation directed at the face and/or the speed of wind directed at the face. In another embodiment, in which the computer utilizes the machine learning-based model to calculate a value indicative of the progress and/or success of the session, the computer may utilize $m_{conf}$ to generate at least some of the feature values that are utilized to calculate the value indicative of the progress and/or success. Optionally, the model is trained based on samples that include at least some samples that are based on $TH_F$ and $m_{conf}$ that were taken while a confounding factor affected $TH_F$.

Another approach that may be utilized by the computer, in some embodiments, is to learn to differentiate between changes to $TH_F$ due to brain activity and changes to $TH_F$ due to various confounding factors (which may have different characteristics). In one embodiment, the computer may generate feature values based on sets of $TH_F$ and $m_{conf}$ and utilize a second machine learning-based model to detect, based on the feature values, whether a change in $TH_F$ occurred responsive to brain activity or a confounding factor. Optionally, the second model may be trained on samples generated based on measurements taken at times that a confounding factor affected $TH_F$ and on other samples based on measurements taken at times that the confounding factor did not affect $TH_F$.

It is to be noted that since in real-world scenarios confounding factors can affect $TH_F$, utilizing one or more of the various measures described above may assist the computer to provide better neurofeedback sessions. Thus, in some embodiments, on average, neurofeedback sessions based on $TH_F$ and $m_{conf}$ provide better results than neurofeedback sessions based on $TH_F$ without $M_{conf}$.

In addition to confounding factors of which $m_{conf}$ may be indicative, in some embodiments, the computer may take into account in a similar way, other cofounding factors. In one embodiment, the neurofeedback system may include an additional wearable and/or head-mounted sensor used to detect a movement of the frame relative to the head while the frame is still worn, a change in the user's position, and/or a change in the user's body temperature. In another embodiment, the neurofeedback system may include a humidity sensor and/or an environmental temperature sensor, which may be coupled to the user.

Consumption of various substances may also be considered confounding factors. In one embodiment, the computer may receive an indication of whether the user took medication before the neurofeedback session (e.g., the type of medication and dosage), whether the user smoked, consumed alcohol, etc. Each of these factors may affect $TH_F$ in certain ways that may not necessarily be because of the user's brain activity. In a similar way to how the computer handles confounding factors in the description above, the computer may warn about the session being ineffective (e.g., after consuming alcohol or drugs) and/or perform various normalizations and/or computations to address these confounding factors (e.g., by generating feature values indicating the consumption of the substances).

Figure 55:
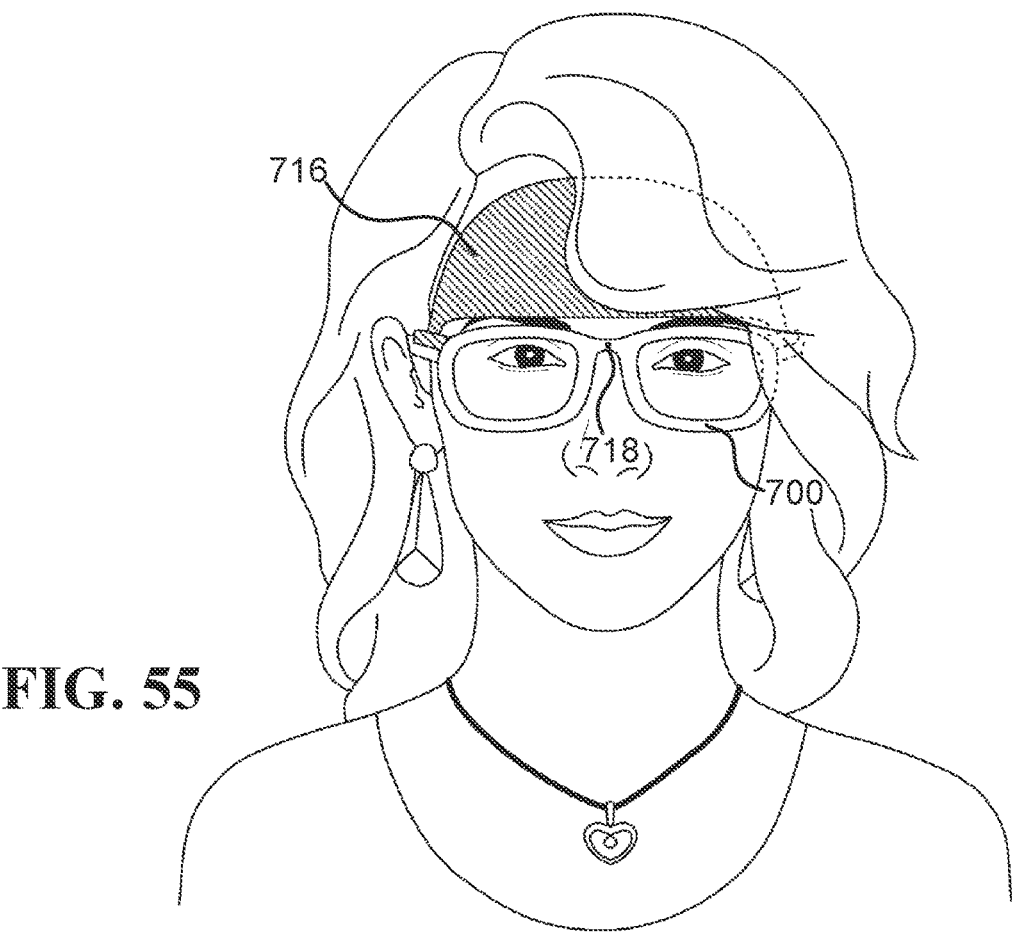
FIG. 55 illustrates an embodiment of a clip-on device configured to be attached and detached from a frame of eyeglasses multiple times.

Another way in which some confounding factors may be addressed, involves providing better insolation for the forehead region from the environment while the neurofeedback session is being conducted. To this end, one embodiment involves utilization of a clip-on structure designed to be attached and detached from the frame multiple times (e.g., it may be attached before a neurofeedback session starts and detached after the session terminates). Optionally, the clip-on includes a cover that occludes (when attached to the frame) the forehead region measured by CAM, which drives the neurofeedback. The clip-on may protect the region against environmental radiation, wind, and touching the region. FIG. 55 illustrates a clip-on 716 configured to be attached and detached from the frame 700 multiple times. The clip-on 716 includes a cover configured to occlude the region on the user's forehead (when the clip-on is attached to the frame) and a mechanism that holds the clip-on to the frame.

This selective use of the clip-on 716 can enable CAM 718 to provide different types of measurements. For example, $TH_F$ taken while the clip-on is attached may be less noisy then measurements taken when the clip-on is not attached. In some embodiments, measurements obtained without the clip-on may be too noisy for an effective neurofeedback session due to environmental confounding factors. Thus, in one embodiment, CAM may be used to detect that the user needs a neurofeedback session while the clip-on does not cover the region on the forehead (e.g., based on a thermal pattern of the forehead that indicates that the user is in an abnormal state). Optionally, the user is prompted to attach the clip-on and commence with the neurofeedback session. After the clip-on is attached, CAM takes $TH_F$ that are used effectively for the neurofeedback session (and may be of better quality than $TH_F$ taken when the clip-on is not attached).

The neurofeedback system may include, in some embodiments, one or more additional CAMs to measure physiological signals indicative of respiration, stress, and other relevant parameters. Optionally, a target of the neurofeedback session may include bringing these physiological signals to a certain value in addition to a target that is related to $TH_F$.

In one example, the neurofeedback system may include a second inward-facing head-mounted thermal camera (CAM2) that takes thermal measurements of a region below the nostrils ($TH_N$), which is indicative of the user's breathing. Optionally, the computer may control the neurofeedback session also based on $TH_N$. Optionally, $TH_N$ is utilized to calculate values of one or more respiratory parameters, such as breathing rate, exhale duration, and/or smoothness of the exhale stream. Optionally, a target state for the neurofeedback session involves having certain values of the one or more respiratory parameters fall in certain ranges. In one example, CAM2 may be the thermal camera 727 or the thermal camera 729, which are illustrated in FIG. 51. Optionally, the computer calculates the user's breathing rate based on $TH_N$, and guides the user to breathe at his/her resonant frequency, which maximizes the amplitude of respiratory sinus arrhythmia and is in the range of 4.5 to 7.0 breaths/min.

In another example, the neurofeedback system may include second and third inward-facing head-mounted thermal cameras (CAM2 and CAM3, respectively), which take thermal measurements of regions on the periorbital area and the nose ($TH_{ROI3}$ and THROB, respectively). Optionally, the computer may control the neurofeedback session also based on $TH_{ROI3}$ and $TH_{ROI3}$. For example, the computer may calculate a stress level of the user based on $TH_{ROI3}$ and/or $TH_{ROI3}$, and a target state of the neurofeedback session may correspond to a certain stress level the user is supposed to have. Optionally, $TH_{ROI2}$ and $TH_{ROI3}$ may be utilized to calculate a stress level of the user. For example, CAM2 may be the thermal camera 724 or 726, and CAM3 may be the thermal camera 733, which are illustrated in FIG. 51.

The following method for conducting a neurofeedback session may be used, in some embodiments, by systems modeled according to FIG. 51. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of a region on a forehead ($TH_F$) of the user, from a location below the middle of the region on the user's forehead and less than 10 cm from the user's forehead.

In Step 2, taking measurements ($m_{conf}$) indicative of at least one of the following confounding factors: touching the forehead, thermal radiation directed at the forehead, and direct airflow on the forehead.

And in Step 3, conducting a neurofeedback session for the user based on $TH_F$ and $m_{conf}$. Optionally, the neurofeedback session is controlled by a computer, as described above. Optionally, the method further includes generating feature values based on $TH_F$ and $m_{conf}$, and utilizing a model to control the neurofeedback session based on the feature values. Optionally, the model was trained on samples generated based on (i) previous $TH_F$ and $m_{conf}$ of the user, and/or (ii) previous $TH_F$ and $m_{conf}$ of other users.

Various physiological responses may be detected based on thermal measurements and images of various regions of the face. In one embodiment, a system configured to detect a physiological response includes an inward-facing head-mounted thermal camera (CAM), an inward-facing head-mounted visible-light camera (VCAM), and a computer. The system may optionally include additional elements such as a frame and additional cameras.

CAM is worn on a user's head and takes thermal measurements of a first ROI ($TH_{ROI2}$) on the user's face. Optionally, CAM weighs below 10 g. Optionally, CAM is located less than 15 cm from the user's face. Optionally, CAM utilizes a microbolometer or a thermopile sensor. In one embodiment, CAM includes a focal-plane array (FPA) sensor and an infrared lens, and the FPA plane is tilted by more than 2° relative to the infrared lens plane according to the Scheimpflug principle in order to improve the sharpness of the image of $ROI_1$ (where the lens plane refers to a plane that is perpendicular to the optical axis of the lens, which may include one or more lenses).

VCAM is worn on the user's head and takes images of a second ROI ($IM_{ROI2}$) on the user's face. Optionally, VCAM weighs below 10 g and is located less than 15 cm from the face. Optionally, $ROI_1$ and $ROI_2$ overlap (which means extend over so as to cover at least partly). For example, $ROI_2$ may cover at least half of the area covered by $ROI_1$. In one embodiment, VCAM includes a multi-pixel sensor and a lens, and the sensor plane is tilted by more than 2° relative to the lens plane according to the Scheimpflug principle in order to improve the sharpness of the image of $ROI_2$.

It is to be noted that in some embodiments the system may be constructed in a way that none of the system's components (including the frame and cameras) occludes $ROI_1$ and/or $ROI_2$. In alternative embodiments, the system may be constructed in a way that at least some of the system components (e.g., the frame and/or CAM) may occlude $ROI_1$ and/or $ROI_2$.

The computer detects the physiological response based on $TH_{ROI1}$, $IM_{ROI2}$, and a model. Optionally, the model includes one or more thresholds to which $TH_{ROI1}$ and/or $IM_{ROI2}$ may be compared in order to detect the physiological response. Optionally, the model includes one or more reference time series to which $TH_{ROI1}$ and/or $IM_{ROI2}$ may be compared in order to detect the physiological response. Optionally, the computer detects the physiological response by generating feature values based on $TH_{ROI1}$ and $IM_{ROI2}$, and utilizing the model to calculate, based on the feature values, a value indicative of the extent of the physiological response. In this case, the model may be referred to as a "machine learning-based model". Optionally, at least some of the feature values, which are generated based on $IM_{ROI2}$ may be used to identify, and/or account for, various confounding factors that can alter $TH_{ROI1}$ without being directly related to the physiological response. Thus, on average, detections of the physiological responses based on $TH_{ROI1}$ and $IM_{ROI2}$ are more accurate than detections of the physiological responses based on $TH_{ROI1}$ without $IM_{ROI2}$.

In one example, the physiological response is indicative of an occurrence of at least one of the following emotional states of the user: joy, fear, sadness, and anger. In another example, the physiological response is indicative of an occurrence of one or more of the following: stress, mental workload, an allergic reaction, a headache, dehydration, intoxication, and a stroke. The physiological response may be a physiological signal of the user. In one example, the physiological response is a heart rate of the user, and in this example, $ROI_1$ is on the skin above at least one of the superficial temporal artery and the frontal superficial temporal artery. In another example, the physiological response is frontal lobe brain activity of the user, and in this example, $ROI_1$ is on the forehead. In still another example, the physiological signal is a breathing rate of the user, and $ROI_1$ is on the nasal area.

A machine learning-based model used to detect a physiological response is typically trained on samples, where each sample includes feature values generated based on $TH_{ROI1}$ and $IM_{ROI2}$ taken during a certain period, and a label indicative of the physiological response of the user during the certain period. Optionally, the model is trained on samples generated based on measurements of the user (in which case the model may be considered a personalized model of the user). Optionally, the model is trained on samples generated based on measurements of one or more other users. Optionally, the samples are generated based on measurements taken while the user being measured was in different situations. Optionally, the samples are generated based on measurements taken on different days.

In some embodiments, images such as $IM_{ROI2}$ may be utilized to generate various types of feature values, which may be utilized to detect the physiological response and/or detect an occurrence of a confounding factor. Some of the feature values generated based on images may include high-level facial-related feature values and their derivatives, such as location and dimensions of facial features and/or landmarks, identification of action units (AUs) in sequences of images, and/or blendshape weights. Other examples of features include various low-level features such as features generated using Gabor filters, local binary patterns (LBP) and their derivatives, algorithms such as SIFT and/or SURF (and their derivatives), image keypoints, histograms of oriented gradients (HOG) descriptors, and statistical procedures such independent component analysis (ICA), principal component analysis (PCA), or linear discriminant analysis (LDA). Yet other examples of feature values may include features derived from multiple images taken at different times, such as volume local binary patterns (VLBP), cuboids, and/or optical strain-based features. Additionally, some of the feature values may be based on other data, such as feature values generated based audio processing of data received from a head-mounted microphone. The audio processing may detect noises associated with talking, eating, and drinking, and convert it to feature values to be provided to the machine learning-based model.

Using both $TH_{ROI1}$ and $IM_{ROI2}$ to detect the physiological response may confer some advantages in some embodiments. For example, there may be times when $TH_{ROI1}$ and $IM_{ROI2}$ provide complementing signals of a physiological response (e.g., due to their ability to measure manifestations of different physiological processes related to the physiological response). This can increase the accuracy of the detections. In one embodiment, in which the physiological response being detected is an emotional response, the computer may identify facial expressions from $IM_{ROI2}$, and detect the emotional response of the user based on $TH_{ROI1}$ and the identified facial expressions. For example, at least some of the feature values generated based on $IM_{ROI2}$, which are used to detect the emotional response, are indicative of the facial expressions. Optionally, on average, detections of emotional responses based on both $TH_{ROI1}$ and the identified facial expressions are more accurate than detections of the emotional responses based on either $TH_{ROI1}$ or the identified facial expressions.

The following are some specific examples how $IM_{ROI2}$ may be utilized to help make detections of a physiological response more accurate. In one example, $ROI_1$ and $ROI_2$ are on the mouth, and $IM_{ROI2}$ are indicative of a change in a facial expression during a certain period that involves a transition from a facial expression in which the lips are in contact to a facial expression with an open mouth. Optionally, by utilizing $IM_{ROI2}$ to detect the physiological response based on $TH_{ROI1}$ taken during the certain period, the computer may be able attribute a change in $TH_{ROI1}$ to opening the mouth rather than a change in the temperature of the lips.

In another example, $ROI_1$ and $ROI_2$ are on the nose and upper lip, and $IM_{ROI2}$ are indicative of a change in a facial expression during a certain period that involves a transition from a neutral facial expression to a facial expression of disgust. Optionally, by utilizing $IM_{ROI2}$ to detect the physiological response based on $TH_{ROI1}$ taken during the certain period, the computer may be able attribute a change in $TH_{ROI1}$ to a raised upper lip and wrinkled nose instead of a change in the temperature of the nose and upper lip.

In yet another example, $ROI_1$ and $ROI_2$ are on the user's forehead located about 1 cm above at least one of the user's eyebrows, and $IM_{ROI2}$ are indicative of a change in a facial expression during a certain period that involves a transition from a neutral expression to a facial expression involving raised and/or lowered eyebrows (including middle-raised or middle-lowered eyebrows). Optionally, by utilizing $IM_{ROI2}$ to detect the physiological response based on $TH_{ROI1}$ taken during the certain period, the computer may be able attribute a change in $TH_{ROI1}$ to raising and/or lowering the eyebrows instead of a change in the temperature of the forehead.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of VCAM to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions." *IEEE transactions on pattern analysis and machine intelligence* 31.1 (2009): 39-58, describes some of the algorithmic approaches that may be used for this task.

In some embodiments, $TH_{ROI1}$ and $IM_{ROI2}$ may provide different and even possibly contradicting indications regarding the physiological response. In particular, facial expressions may not always express how a user truly feels. For example, when in company of other people, a user may conceal his or her true feelings by making non-genuine facial expressions. However, at the same time, thermal measurements of the user's face may reveal the user's true emotions. Thus, a system that relies only on $IM_{ROI2}$ to determine the user's emotional response may be mistaken at times, and using $TH_{ROI1}$ can help make detections more accurate.

In one example, responsive to receiving a first set of $TH_{ROI1}$ and $IM_{ROI2}$ taken during a first period in which the user expressed a certain facial expression, the computer detects a first emotional response of the user. Additionally, responsive to receiving a second set of $TH_{ROI1}$ and $IM_{ROI2}$ taken during a second period in which the user expressed again the certain facial expression, the computer detects a second emotional response of the user, which is not the same as the first emotional response. The computer detected different emotional responses in this example because $TH_{ROI1}$ of the first set are indicative of a first physiological response, while $TH_{ROI1}$ of the second set are indicative of a second physiological response. Following are some more detailed examples of situations in which this may occur.

In one example, the first set includes $IM_{ROI2}$ indicative of a facial expression that is a smile and $TH_{ROI1}$ indicative of stress below a certain threshold, and the first emotional response detected by the computer is happiness. The second set in this example includes $IM_{ROI2}$ indicative of a facial expression that is a smile and $TH_{ROI1}$ indicative of stress above the certain threshold, and the second emotional response detected by the computer is discomfort.

In another example, the first set includes $IM_{ROI2}$ indicative of a facial expression that is a neutral expression and $TH_{ROI1}$ indicative of stress below a certain threshold, and the first emotional response detected by the computer is comfort. The second set includes $IM_{ROI2}$ indicative of a facial expression that is neutral and $TH_{ROI1}$ indicative of stress above the certain threshold, and the second emotional response detected by the computer is concealment.

In yet another example, the first set includes $IM_{ROI2}$ indicative of a facial expression that is an expression of anger and $TH_{ROI1}$ indicative of stress above a certain threshold, and the first emotional response detected by the computer is anger. The second set includes $IM_{ROI2}$ indicative of a facial expression that is an expression of anger and $TH_{ROI1}$ indicative of stress below the certain threshold, and the second emotional response detected by the computer is indicative of pretending to be angry.

The phenomenon of making different detections based on thermal measurements compared to the emotional response that is visible in a facial expression is illustrated in FIG. 57A and FIG. 57B. The illustrated figures include an HMS with CAM 514 and VCAM 515 that may cover portions of a cheek, mouth and/or nose. FIG. 57A illustrates a case in which the user's smiling face may be mistaken for happiness; however, the cold nose indicates that the user is in fact stressed. FIG. 57B illustrates a case in which the facial expression indicates that the user is in a neutral state; however, the warm nose indicates that the user is excited. FIG. 57A and FIG. 57B also illustrate a second CAM 516 and a second VCAM 517, which may be utilized in some embodiments, as described herein.

FIG. 58 illustrates one embodiment of a smartphone app that provides the user a feedback about how he/she looks to others. The illustrated app shows that the user was happy 96 time and angry 20 times. Because the purpose of this app is to measure how the user looks to others, the computer counts the facial expressions based on $IM_{ROI2}$ without correcting the facial expressions according $TH_{ROI1}$.

Figure 59:
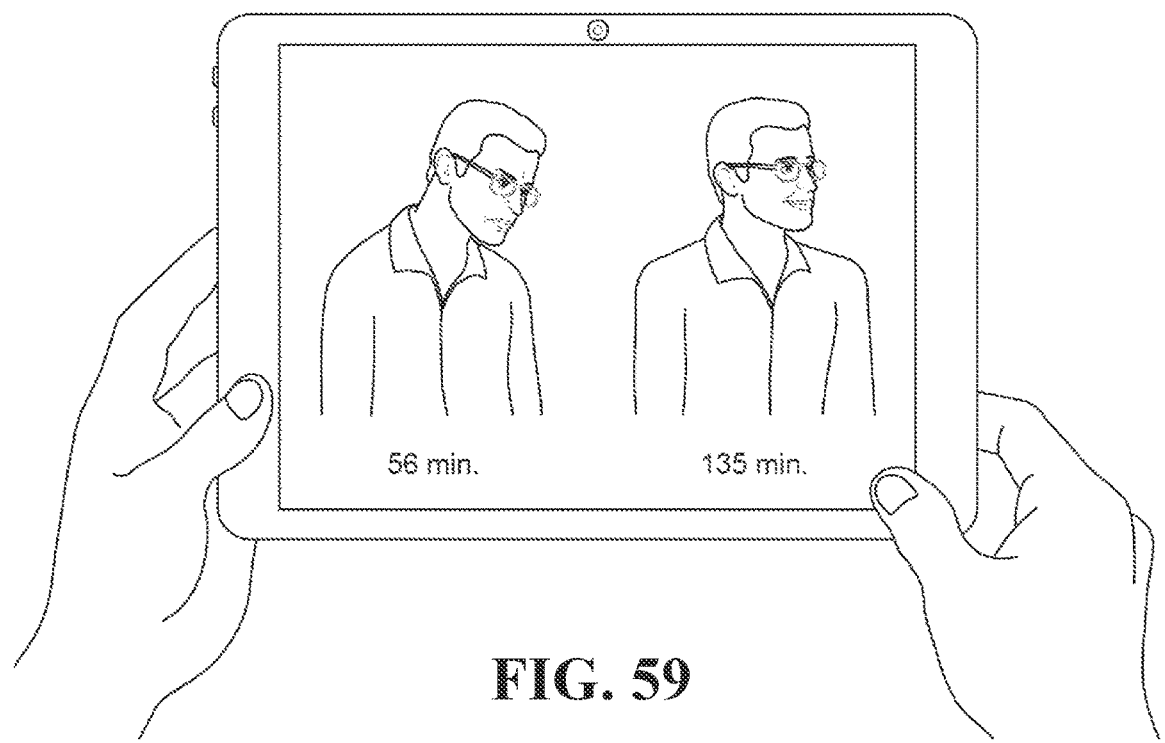
FIG. 59 illustrates one embodiment of a tablet app that provides the user a feedback about how he/she felt during a certain period.

FIG. 59 illustrates one embodiment of a tablet app that provides the user a feedback about how he/she felt during a certain period (e.g., during the day, the week, or while being at a certain location). The illustrated app shows that the user felt sad 56 minutes and happy 135 minutes. Because the purpose of this app is to measure how the user feels (and not just how the user looks to others), the computer determines the user's emotional state based on a combined analysis of $IM_{ROI2}$ and $TH_{ROI1}$, as exemplified above.

In one embodiment, the system may include a second inward-facing head-mounted thermal camera (CAM2) that takes thermal measurements of a third ROI ($TH_{ROI3}$) on the face. Optionally, CAM2 weighs below 10 g and is physically coupled to the frame. Optionally, the center of $ROI_1$ is to the right of the center of the third region of interest ($ROI_3$), and the symmetric overlapping between $ROI_1$ and $ROI_3$ is above 50%. Optionally, to detect the physiological response, the computer accounts for facial thermal asymmetry, based on a difference between $TH_{ROI1}$ and $TH_{ROI3}$.

It is noted that the symmetric overlapping is considered with respect to the vertical symmetry axis that divides the face to the right and left portions. The symmetric overlapping between $ROI_1$ and $ROI_3$ may be observed by comparing the overlap between $ROI_1$ and a mirror image of $ROI_3$, where the mirror image is with respect to a mirror that is perpendicular to the front of the face and whose intersection with the face is along the vertical symmetry axis (which goes through the middle of the forehead and the middle of the nose).

Some examples of calculations that may be performed by the computer to account for thermal asymmetry include: (i) utilizing different thresholds to which $THR_{ROI1}$ and $TH_{ROI3}$ are compared; (ii) utilizing different reference time series to which $TH_{ROI1}$ and $TH_{ROI3}$ are compared; (iii) utilizing a machine learning-based model that provides different results for first and second events that involve the same average change in $TH_{ROI1}$ and $TH_{ROI3}$ with different extents of asymmetry in $TH_{ROI1}$ and $TH_{ROI3}$; and (iv) utilizing the asymmetry for differentiating between (a) temperature changes in $TH_{ROI1}$ and $TH_{ROI3}$ that are related to the physiological response and (b) temperature changes in $TH_{ROI1}$ and $TH_{ROI3}$ that are unrelated to the physiological response.

In one embodiment, the system may include a second inward-facing head-mounted visible-light camera (VCAM2) that takes images of a third ROI ($IM_{ROI3}$) on the face. Optionally, VCAM2 weighs below 10 g and is physically coupled to the frame. Optionally, VCAM and VCAM2 are located at least 0.5 cm to the right and to the left of the vertical symmetry axis that divides the face, respectively, and the symmetric overlapping between $ROI_2$ and $ROI_3$ is above 50%. Optionally, the computer detects the physiological response also based on $IM_{ROI3}$. For example, the computer may generate some feature values based on $IM_{ROI3}$, which may be similar to feature values generated based on $IM_{ROI2}$, and utilizes the some feature values in the detection of the physiological response. In another example, the computer detects the physiological response based on the extent of symmetry between symmetric facial elements extracted from $IM_{ROI2}$ and $IM_{ROI3}$.

In some embodiments, $IM_{ROI2}$ may include recognizable facial skin color changes (FSCC). FSCC are typically a result of changes in the concentration levels of hemoglobin and blood oxygenation under a user's facial skin, and are discussed in more detail elsewhere in this disclosure. In one embodiment, the computer calculates, based on $IM_{ROI2}$, a value indicative of FSCC, and detects an emotional state of the user based on the calculated value. Optionally, on average, detections of the physiological response based on both $TH_{ROI1}$ and FSCC are more accurate than detections of the physiological response based on either $TH_{ROI1}$ or FSCC. In another embodiment, the computer generates feature values that are indicative of FSCC in $IM_{ROI2}$, and utilizes a model to detect the physiological response based on the feature values. Optionally, at least some of the feature values are generated based on $TH_{ROI1}$. Optionally, the model was trained based on samples, with each sample including feature values generated based on corresponding measurements of the user and a label indicative of the physiological response. Optionally, the label may be derived, for example, from analysis of the user's speech/writing, facial expression analysis, speech emotion analysis, and/or emotion extraction from analyzing galvanic skin response (GSR) and heart rate variability (HRV).

$IM_{ROI2}$ may be utilized, in some embodiments, to detect occurrences of confounding factors that can affect the temperature on the face, but are unrelated to the physiological response being detected. Thus, occurrences of confounding factors can reduce the accuracy of detections of the physiological response based on thermal measurements (such as based on $TH_{ROI1}$). Detecting occurrences of the confounding factors described below (cosmetics, sweat, hair, inflammation and touching) may be done utilizing various image-processing and/or image-analysis techniques known in the art. For example, detecting occurrences of at least some of the confounding factors described below may involve a machine learning algorithm trained to detect the confounding factors, and/or comparing $IM_{ROI2}$ to reference images that involve and do not involve the confounding factor (e.g., a first set of reference $IM_{ROI2}$ in which makeup was applied to the face and a second set of reference $IM_{ROI2}$ in which the face was bare of makeup).

The computer may utilize detection of confounding factors in various ways in order to improve the detection of the physiological response based on $TH_{ROI1}$. In one embodiment, the computer may refrain from making a detection of the physiological response responsive to identifying that the extent of a certain confounding factor reaches a threshold. For example, certain physiological responses may not be detected if there is extensive facial hair on the face or extensive skin inflammation. In another embodiment, the model used to detect the physiological response may include a certain feature that corresponds to a certain confounding factor, and the computer may generate a certain feature value indicative of the extent of the certain confounding factor. Optionally, the model in this case may be trained on samples in which the certain feature has different values, such as some of the samples used to train the model are generated based on measurements taken while the certain confounding factor occurred, and other samples used to train the model were generated based on measurements taken while the certain confounding factor did not occur. In yet another embodiment, the computer may weight measurements based on the occurrence of confounding factors, such that measurements taken while certain confounding factors occurred, may be given lower weights than measurements taken while the certain confounding factor did not occur. Optionally, lower weights for measurements mean that they have a smaller influence on the detection of the physiological response than measurements with higher weights. The following are some examples of confounding factors that may be detected, in some embodiments, based on $IM_{ROI2}$.

Some types of cosmetics (e.g., makeup and/or cream) may mask an ROI, affect the ROI's emissivity, and/or affect the ROI's temperature. Thus, taking into account cosmetics as a confounding factor may improve the system's ability to detect the physiological response. In one embodiment, the model was trained on: samples generated based on a first set of $TH_{ROI1}$ and $IM_{ROI2}$ taken after cosmetics were applied to a portion of the overlapping region between $ROI_1$ and $ROI_2$, and other samples generated based on a second set of $TH_{ROI1}$ and $IM_{ROI2}$ taken while the overlapping region was bare of cosmetics. Optionally, utilizing this model may enable the computer to account for presence of cosmetics on a portion of $ROI_2$.

Sweating may affect the ROI's emissivity. Thus, taking into account sweating as a confounding factor may improve the system's ability to detect the physiological response. In one embodiment, the model was trained on: samples generated from a first set of $TH_{ROI1}$ and $IM_{ROI2}$ taken while sweat was detectable on a portion of the overlapping region between ROI1 and ROI2, and additional samples generated from a second set of $TH_{ROI1}$ and $IM_{ROI2}$ taken while sweat was not detectable on the overlapping region. Optionally, utilizing this model may enable the computer to account for sweat on the overlapping region.

Dense hair may affect the ROI's emissivity, which may make the ROI appear, in thermal imaging, colder than it really is. Thus, taking into account hair density and/or hair length (both referred to as hair density) as a confounding factor may improve the system's ability to detect the physiological response. In one embodiment, the model was trained on: samples generated from a first set of $TH_{ROI1}$ and $IM_{ROI2}$ taken while hair density on a portion of the overlapping region between $ROI_1$ and $ROI_2$ was at a first level, and additional samples generated from a second set of $TH_{ROI1}$ and $IM_{ROI2}$ taken while hair density on the portion of the overlapping region between $ROI_1$ and $ROI_2$ was at a second level higher than the first level. Optionally, utilizing a model trained so may enable the computer to account for hair on the overlapping region.

Figure 63A:
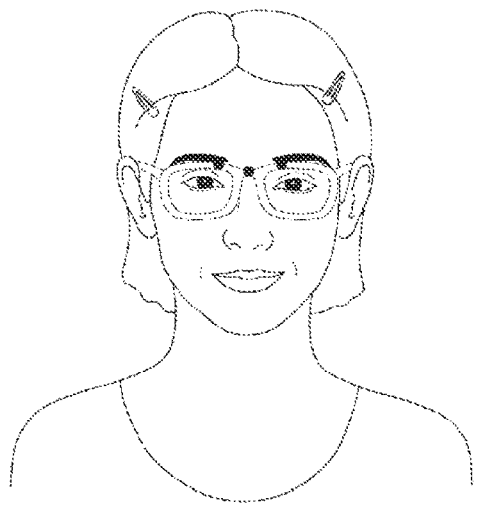
FIG. 63A illustrates a first case where a user's hair does not occlude the forehead.
Figure 63B:
FIG. 63B illustrates a second case where a user's hair occludes the forehead and the system requests the user to move the hair in order to enable correct measurements of the forehead.

In another embodiment, when the hair can be moved the system may request the user to move her hair in order to enable the thermal cameras to take correct measurements. For example, FIG. 63A illustrates a first case where the user's hair does not occlude the forehead. FIG. 63B illustrates a second case where the user's hair does occlude the forehead and thus the system requests the user to move the hair in order to enable correct measurements of the forehead.

Figure 61A:
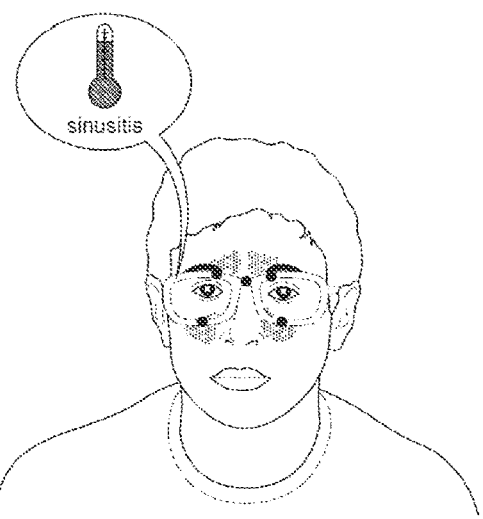
FIG. 61A and FIG. 61B illustrate heating of a ROI for different reasons: sinusitis (which is detected), and acne (which is not detected as sinusitis)
Figure 61B:

Skin inflammations (which may include skin blemishes, acne, and/or inflammatory skin diseases) usually increases ROI temperature in a manner that is unrelated to the physiological response being detected. Thus, taking into account skin inflammation as a confounding factor may improve the system's ability to detect the physiological response. FIG. 61A illustrates heating of the ROI because of sinusitis, for which the system detects the physiological response (sinusitis). On the other hand, FIG. 61B illustrates heating of the same ROI because of acne, for which the system does detect sinusitis. In one embodiment, the model was trained on: samples generated from a first set of $TH_{ROI1}$ and $IM_{ROI2}$ taken while skin inflammation was detectable on a portion of the overlapping region between $ROI_1$ and $ROI_2$, and additional samples generated from a second set of $TH_{ROI1}$ and $IM_{ROI2}$ taken while skin inflammation was not detectable on the overlapping region. Optionally, utilizing a model trained so may enable the computer to account for skin inflammation on the overlapping region.

Touching the ROI may affect $TH_{ROI}$ by increasing or decreasing the temperature at the touched region. Thus, touching the ROI may be considered a confounding factor that can make detections of the physiological response less accurate. In one embodiment, the model was trained on: samples generated from a first set of $TH_{ROI1}$ and $IM_{ROI2}$ taken while detecting that the user touches a portion of the overlapping region between $ROI_1$ and $ROI_2$, and additional samples generated from a second set of $TH_{ROI1}$ and $IM_{ROI2}$ taken while detecting that the user does not touch the overlapping region. Optionally, utilizing a model trained so may enables the computer to account for touching the overlapping region.

Throughout day-to-day activities, a user may make various facial movements that are unrelated to the physiological response being detected, and thus can negatively affect the thermal measurements taken by CAM. This can lead to measurements that may be incorrectly attributed to the physiological response. To address this issue, the computer may identify disruptive activities, such as talking, eating, and drinking, and utilize the identified disruptive activities in order to more accurately detect the physiological response. In one embodiment, the computer utilizes a machine learning-based approach to handle the disruptive activities. This approach may include (i) identifying, based on $IM_{ROI2}$, occurrences of one or more of the disruptive activities, (ii) generating feature values based on the identified disruptive activities, and (iii) utilizing a machine learning-based model to detect the physiological response based on the feature values and feature values generated from $TH_{ROI1}$.

In addition to detecting a physiological response, in some embodiments, the computer may utilize $IM_{ROI2}$ to generate an avatar of the user (e.g., in order to represent the user in a virtual environment). Optionally, the avatar may express emotional responses of the user, which are detected based on $IM_{ROI2}$. Optionally, the computer may modify the avatar to show synthesized facial expressions that are not manifested in the user's actual facial expressions, but the synthesized facial expressions correspond to emotional responses detected based on $TH_{ROI1}$. Some of the various approaches that may be utilized to generate the avatar based on $IM_{ROI2}$ are described in co-pending US patent publication 2016/0360970.

Contraction and relaxation of various facial muscles can cause facial tissue to slightly change its position and/or shape. Thus, facial movements can involve certain movements to ROIs. With thermal cameras that have multiple sensing elements (pixels), this can cause the ROI to move and be covered by various subsets of pixels as the user's face moves (e.g., due to talking/or making facial expressions). For example, smiling can cause the user's cheeks to move upwards. This can cause a thermal camera that covers a cheek to capture an ROI located on a cheek with a first set of pixels (from among the camera's pixels) when the user has a neutral expression, and to capture images of the ROI with a second set of pixels, when the user is smiling. In this example, on average, the pixels in the second set are likely to be located higher in the images than the pixels in the first set. To account for the possible movement of ROIs due to facial expressions, the computer may track locations of one or more facial landmarks in a series of $IM_{ROI2}$, and utilize the locations to adjust $TH_{ROI1}$. Facial landmarks are usually the most salient facial points on the face.

In one embodiment in which CAM comprises multiple sensing elements, which correspond to values of multiple pixels in $TH_{ROI1}$, the computer may assign weights to the multiple pixels based on the locations of the one or more facial landmarks, which are determined based on $IM_{ROI2}$. Assigning weights to pixels based on their location with respect to a facial landmark can be considered a form of selection of the pixels that cover the ROI based on the location of the landmark In one example, the weights are assigned based on a function that takes into account the distance of each pixel from the locations of one or more facial landmarks and/or the relative position of each pixel with respect to the locations.

In another embodiment, the computer may generate certain feature values based on locations of one or more landmarks, which are determined based on analysis of $IM_{ROI2}$. These certain feature values may be utilized in conjunction with other feature values (e.g., feature values generated based on $TH_{ROI1}$) to detect the physiological response using a machine learning-based model.

The following is a description of a method for detecting a physiological response based on measurements from CAM and VCAM. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of a first ROI ($TH_{ROI1}$) on the user's face using an inward-facing head-mounted thermal camera located at most 15 cm from the user's face. In Step 2, taking images of a second ROI ($IM_{ROI2}$) on the user's face with an inward-facing head-mounted visible-light camera located at most 15 cm from the user's face. Optionally, the first ROI ($ROI_1$) and the second ROI ($ROI_2$) overlap. In Step 3, generating feature values based on $TH_{ROI1}$ and $IM_{ROI2}$. And in Step 4, utilizing a model to detect the physiological response based on the feature values. Optionally, the model was trained based on previous $TH_{ROI1}$ and $IM_{ROI2}$ taken on different days.

In one embodiment, the physiological response is an emotional response, and the method optionally includes the following steps: calculating, based on $IM_{ROI2}$, a value indicative of facial skin color changes (FSCC), and utilizing the value indicative of FSCC to generate at least one of the feature values used to detect the physiological response in Step 4.

In another embodiment, generating the feature values in Step 3 involves generating, based on $IM_{ROI2}$, feature values indicative of an occurrence of one or more of the following confounding factors on a portion of the overlapping region between $ROI_1$ and $ROI_2$: a presence of cosmetics, a presence of sweat, a presence of hair, and a presence of skin inflammation.

The following is a description of a system that detects a physiological response based on an inward-facing head-mounted thermal camera ($CAM_{in}$), an outward-facing head-mounted thermal camera ($CAM_{out}$), and a computer. $CAM_{out}$ measures the environment and generates data indicative of confounding factors, such as direct sunlight or air conditioning. Accounting for confounding factors enables the system to more accurately detect the physiological response compared to a system that does not account for these confounding factors. Optionally, $CAM_{in}$ and/or $CAM_{out}$ are physically coupled to a frame worn on a user's head, such as a frame of a pair of eyeglasses or an augmented reality device. Optionally, each of $CAM_{in}$ and $CAM_{out}$ weighs below 5 g and is located less than 15 cm from the user's face.

$CAM_{in}$ takes thermal measurements of an ROI ($TH_{ROI}$) on the user's face. Optionally, $CAM_{in}$ does not occlude the ROI. In one example, the ROI includes a region on the forehead and the physiological response involves stress, a headache, and/or a stroke. In another example, the ROI includes a region on the nose and the physiological response is an allergic reaction.

$CAM_{out}$ takes thermal measurements of the environment ($TH_{ENV}$). Optionally, $CAM_{out}$ does not occlude the ROI. Optionally, the angle between the optical axes of $CAM_{in}$ and $CAM_{out}$ is at least 45°, 90°, 130°, 170°, or 180°. Optionally, the field of view (FOV) of $CAM_{in}$ is larger than the FOV of $CAM_{out}$ and/or the noise equivalent differential temperature (NEDT) of $CAM_{in}$ is lower than NEDT of $CAM_{out}$. In one example, $CAM_{in}$ has a FOV smaller than 80° and $CAM_{out}$ has a FOV larger than 80°. In another example, $CAM_{in}$ has more sensing elements than $CAM_{out}$ (e.g., $CAM_{in}$ has at least double the number of pixels as $CAM_{out}$).

In one embodiment, $CAM_{in}$ and $CAM_{out}$ are based on sensors of the same type with similar operating parameters. Optionally, $CAM_{in}$ and $CAM_{out}$ are located less than 5 cm or 1 cm apart. Having sensors of the same type, which are located near each other, may have an advantage of having both $CAM_{in}$ and $CAM_{out}$ be subject to similar inaccuracies resulting from heat conductance and package temperature. In another embodiment, $CAM_{in}$ and $CAM_{out}$ may be based on sensors of different types, with different operating parameters. For example, $CAM_{in}$ may be based on a microbolometer FPA while $CAM_{out}$ may be based on a thermopile (that may be significantly less expensive than the microbolometer).

Figure 64A:
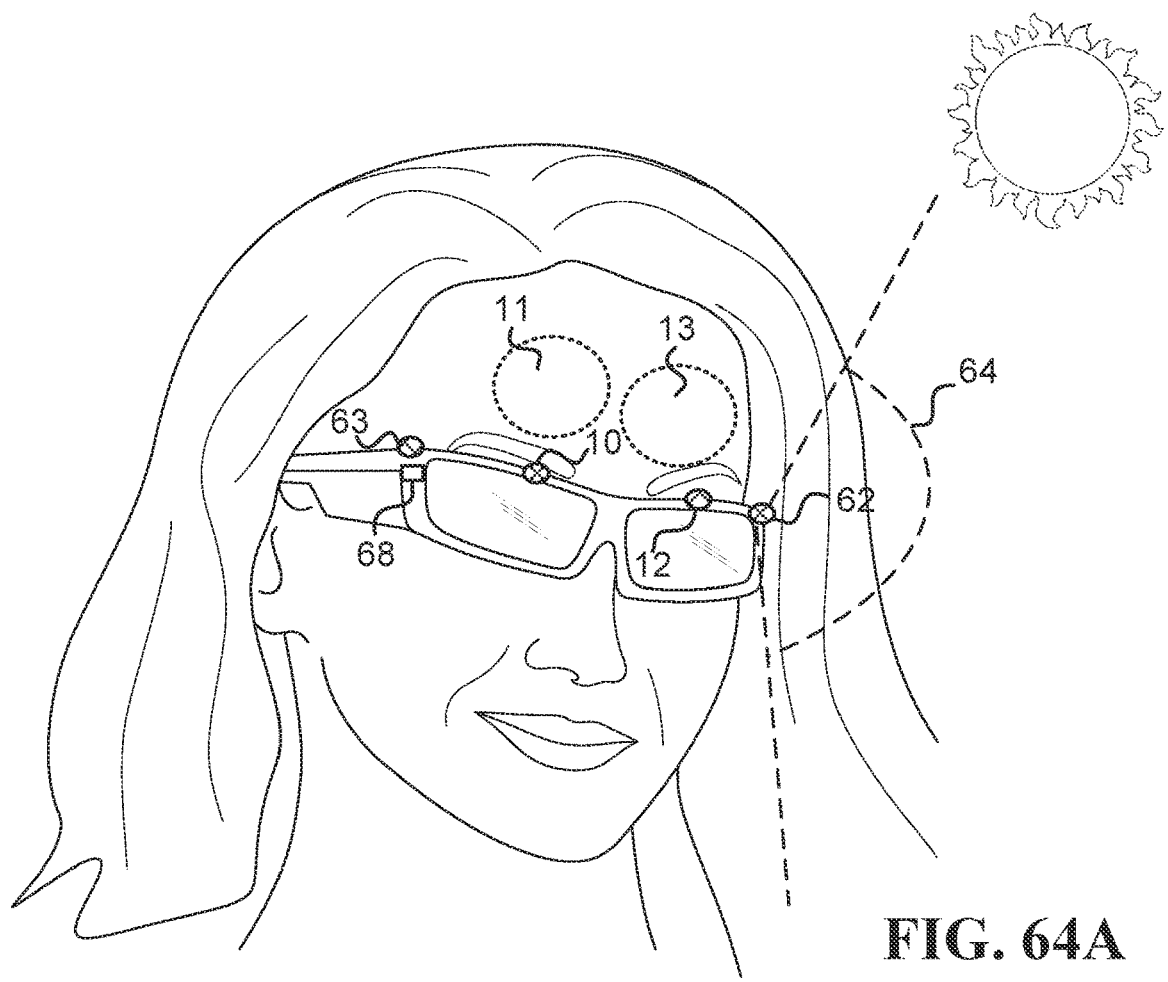
FIG. 64A illustrates an embodiment of a system that detects a physiological response based on measurements taken by an inward-facing head-mounted thermal camera and an outward-facing head-mounted thermal camera.
Figure 64B:
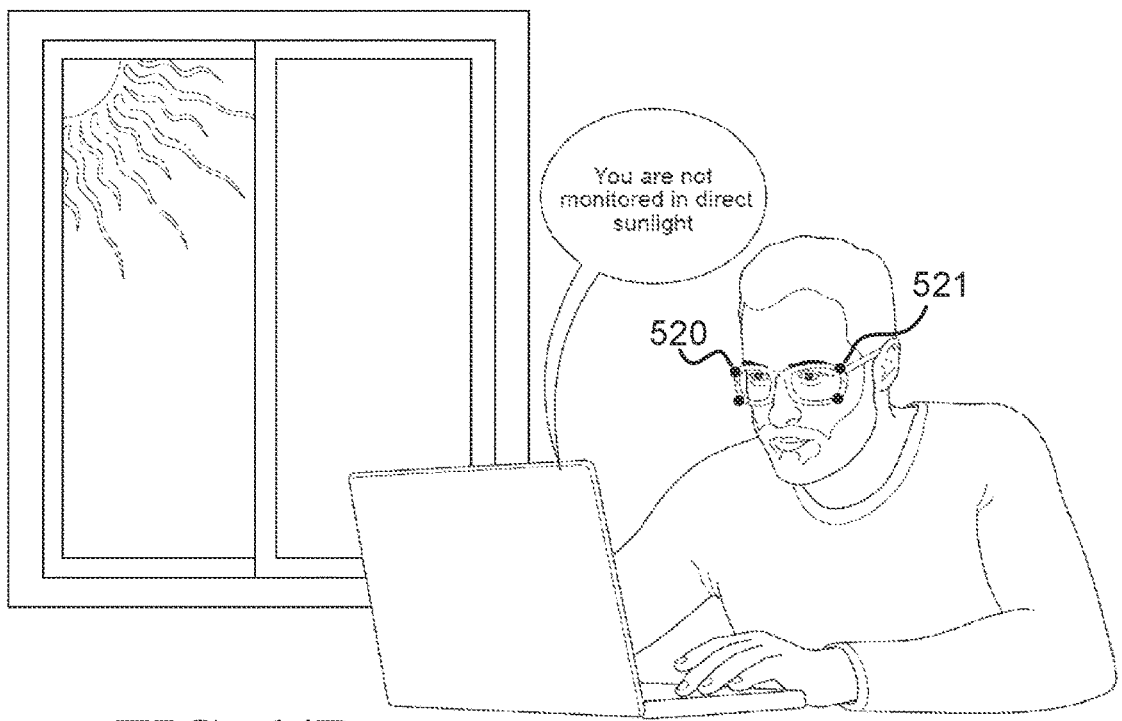
FIG. 64B illustrates a scenario in which a user receives an indication on a GUI that the user is not monitored in direct sunlight.

FIG. 64A illustrates one embodiment of the system that includes inward-facing and outward-facing head-mounted thermal cameras on both sides of the frame. In this illustration, $CAM_{in}$ is the inward-facing thermal camera 12, which takes thermal measurements of ROI 13, and $CAM_{out}$ is the outward-facing thermal camera 62. Arc 64 illustrates the larger FOV of $CAM_{out}$ 62, compared to the FOV of $CAM_{in}$ that covers ROI 13. The illustrated embodiment includes a second head-mounted thermal camera 10 ($CAM_{in2}$) on the right side of the frame, which takes thermal measurements of ROI 11, and a second outward-facing head-mounted thermal camera 63 ($CAM_{out2}$). FIG. 64B illustrates receiving an indication on a GUI (on the illustrated laptop) that the user is not monitored in direct sunlight. Cameras 520 and 521 are the outward-facing head-mounted thermal cameras.

The computer detects a physiological response based on $TH_{ROI}$ and $TH_{ENV}$. Optionally, $TH_{ENV}$ are utilized to account for at least some of the effect of heat transferred from the environment to the ROI (and not due to the user's physiological response). Thus, on average, detections of the physiological response based on $TH_{ROI}$ and $TH_{ENV}$ may be more accurate than detections of the physiological response based on $TH_{ROI}$ without $TH_{ENV}$.

There are various ways in which the computer may utilize $TH_{ENV}$ to increase the accuracy of detecting the physiological response. In one embodiment, the computer generates feature values based on a set of $TH_{ROI}$ and $TH_{ENV}$, and utilizes a machine learning-based model to detect, based on the feature values, the physiological response. By utilizing $TH_{ENV}$ to generate one or more of the feature values, the computer may make different detections of the physiological response based on similar $TH_{ROI}$ that are taken in dissimilar environments. For example, responsive to receiving a first set of measurements in which $TH_{ROI}$ reaches a first threshold while $TH_{ENV}$ does not reach a second threshold, the computer detects the physiological response. However, responsive to receiving a second set of measurements in which $TH_{ROI}$ reaches the first threshold while $TH_{ENV}$ reaches the second threshold, the computer does not detect the physiological response. Optionally, $TH_{ENV}$ reaching the second threshold indicates that the user was exposed to high infrared radiation that is expected to interfere with the detection.

In another embodiment, the computer may utilize $TH_{ENV}$ for the selection of values that are appropriate for the detection of the physiological response. In one example, the computer may select different thresholds (to which $TH_{ROI}$ are compared) for detecting the physiological response. In this example, different $TH_{ENV}$ may cause the computer to use different thresholds. In another example, the computer may utilize $TH_{ENV}$ to select an appropriate reference time series (to which $TH_{ROI}$ may be compared) for detecting the physiological response. In yet another example, the computer may utilize $TH_{ENV}$ to select an appropriate model to utilize to detect the physiological response based on the feature values generated based on $TH_{ROI}$.

In still another embodiment, the computer may normalize $TH_{ROI}$ based on $TH_{ENV}$. In one example, the normalization may involve subtracting a value proportional to $TH_{ENV}$ from $TH_{ROI}$, such that the value of the temperature at the ROI is adjusted based on the temperature of the environment at that time and/or in temporal proximity to that time (e.g., using an average of the environment temperature during the preceding minute). Additionally or alternatively, the computer may adjust weights associated with at least some $TH_{ROI}$ based on $TH_{ENV}$, such that the weight of measurements from among $TH_{ROI}$ that were taken during times the measurements of the environment indicated extreme environmental temperatures is reduced.

In yet another embodiment, responsive to determining that $TH_{ENV}$ represent an extreme temperature (e.g., lower than 5° C., higher than 35° C., or some other ranges deemed inappropriate temperatures), the computer may refrain from performing detection of the physiological response. This way, the computer can avoid making a prediction that is at high risk of being wrong due to the influence of the extreme environmental temperatures. In a similar manner, instead of determining that $TH_{ENV}$ represent an extreme temperature, the computer may determine that the difference between $TH_{ROI}$ and $TH_{ENV}$ are not in an acceptable range (e.g., there is a difference of more than 15° C. between the two), and refrain from making a detection of the physiological response in that event.

The following examples describe ways to use $TH_{ENV}$ to detect the physiological response based on $TH_{ROI}$. In one example, the computer detects the physiological response based on a difference between $TH_{ROI}$ and $TH_{ENV}$, which enables the system to operate well in an uncontrolled environment that does not maintain environmental temperature in a range below ±1° C. and does not maintain humidity in a range below ±3%. In another example, the computer detects the physiological response by performing the following steps: calculating a temperature difference between $TH_{ROI}$ and $TH_{ENV}$ taken at time x ($\Delta T_x$), calculating a temperature difference between $TH_{ROI}$ and $TH_{ENV}$ taken at time y ($\Delta T_y$), and detecting the physiological response based on a difference between $\Delta T_x$ and $\Delta T_y$. Optionally, detecting the physiological response is based on the difference between $\Delta T_x$ and $\Delta T_y$ reaching a predetermined threshold. Optionally, the predetermined threshold is selected from a threshold in the time domain, and/or a threshold in the frequency domain Optionally, the magnitude of the difference between $\Delta T_x$ and $\Delta T_y$ is indicative of an extent of the physiological response. It is noted that sentences such as "calculating a difference between M and N" or "detecting a difference between M and N" are intended to cover any function that is proportional to the difference between M and N.

Because the FOV of $CAM_{out}$ is limited and the responsivity of $CAM_{out}$ decreases when drawing away from the optical axis, it may be beneficial to utilize two or more $CAM_{out}$ pointed at different angles.

In one embodiment, the system may include a second outward-facing head-mounted thermal camera ($CAM_{out2}$), which takes thermal measurements of the environment ($TH_{ENV2}$). Optionally, there is an angle of at least 30° between the optical axes of $CAM_{out}$ and $CAM_{out2}$ Utilizing two or more outward-facing head-mounted thermal cameras such as $CAM_{out}$ and $CAM_{out2}$ can help identify cases in which there is a directional environmental interference (e.g., sunlight coming from a certain direction). In some cases, such a directional interference can lead to refraining from making a detection of the physiological response. For example, responsive to receiving a first set of measurements in which $TH_{ROI}$ reach a first threshold while the difference between $TH_{ENV}$ and $TH_{ENV2}$ does not reach a second threshold, the computer detects the physiological response. However, responsive to receiving a second set of measurements in which $TH_{ROI}$ reach the first threshold while the difference between $TH_{ENV}$ and $TH_{ENV2}$ reaches the second threshold, the computer does not detect the physiological response. Optionally, the computer detects the physiological response based on a difference between $TH_{ROI}$, $TH_{ENV}$, and $TH_{ENV2}$, while taking into account the angle between the optical axes of $CAM_{out}$ and $CAM_{out2}$ and a graph of responsivity as function of the angle from the optical axes of each of $CAM_{out}$ and $CAM_{out2}$.

In another embodiment, $CAM_{in}$ and $CAM_{out}$ are located to the right of the vertical symmetry axis that divides the user's face, and the ROI is on the right side of the face. Optionally, the system includes a second inward-facing head-mounted thermal camera ($CAM_{in2}$) and a second outward-facing head-mounted thermal camera ($CAM_{out2}$) located to the left of the vertical symmetry axis. $CAM_{in2}$ takes thermal measurements of a second ROI ($TH_{ROI2}$) on the left side of the face, and does not occlude the second ROI (ROI$_2$). CAM$_{out2}$ takes thermal measurements of the environment (TH$_{ENV2}$) that is more to the left relative to TH$_{ENV}$. In this embodiment, the computer detects the physiological response also based on TH$_{ROI2}$ and TH$_{ENV2}$.

In still another embodiment, the optical axes of CAM$_{in}$ and CAM$_{out}$ are above the Frankfort horizontal plane, and the system further includes a second inward-facing head-mounted thermal camera (CAM$_{in2}$) and a second outward-facing head-mounted thermal camera (CAM$_{out2}$), located such that their optical axes are below the Frankfort horizontal plane, which take thermal measurements TH$_{ROI2}$ and TH$_{ENV2}$, respectively. In this embodiment, the computer detects the physiological response also based on TH$_{ROI2}$ and TH$_{ENV2}$.

Optionally, the computer detects the physiological response by performing at least one of the following calculations: (i) when the difference between TH$_{ENV}$ and TH$_{ENV2}$ reaches a threshold, the computer normalizes TH$_{ROI}$ and TH$_{ROI2}$ differently against thermal interference from the environment, (ii) when TH$_{ENV}$ does not reach a predetermined threshold for thermal environmental interference, while TH$_{ENV2}$ reaches the predetermined threshold, the computer assigns TH$_{ROI}$ a higher weight than TH$_{ROI2}$ for detecting the physiological response, and (iii) the computer generates feature values based on TH$_{ROI}$, TH$_{ENV}$, TH$_{ENV2}$ and optionally TH$_{ROI2}$ and utilizes a model to detect, based on the feature values, the physiological response. Optionally, the model was trained based on a first set of TH$_{ROI}$, TH$_{ROI2}$, TH$_{ENV}$ and TH$_{ENV2}$ of one or more users taken while the one or more users had the physiological response, and a second set of TH$_{ROI}$, TH$_{ROI2}$, TH$_{ENV}$ and TH$_{ENV2}$ of the one or more users taken while the one or more users did not have the physiological response.

In addition to having one or more CAM$_{out}$, or instead of having the one or more CAM$_{out}$, some embodiments may include a sensor that may be used to address various other confounding factors, such as user movements and wind, which are discussed below. Optionally, the sensor is coupled to a frame worn on the user's head. An example of such a sensor is sensor 68 in FIG. 64A.

In one embodiment, the sensor takes measurements (denoted m$_{conf}$) that are indicative of an extent of the user's activity, an orientation of the user's head, and/or a change in a position of the user's body. For example, the sensor may be (i) a movement sensor that is physically coupled to a frame worn on the user's head, or coupled to a wearable device worn by the user, (ii) a visible-light camera that takes images of the user, and/or (iii) an active 3D tracking device that emits electromagnetic waves and generates 3D images based on received reflections of the emitted electromagnetic waves. Optionally, the computer detects the physiological response also based on m$_{conf}$. In one example, the computer may refrain from detecting the physiological response if m$_{conf}$ reaches a threshold (which may indicate the user was very active which causes an increase in body temperature). In another example, the computer generates feature values based on TH$_{ROI}$, TH$_{ENV}$, and m$_{conf}$ and utilizes a model to detect the physiological response based on the feature values. Optionally, the model was trained based on previous TH$_{ROI}$, TH$_{ENV}$, and M$_{conf}$ taken while the user had different activity levels. For example, the model may be trained based on: a first set of previous TH$_{ROI}$, TH$_{ENV}$, and m$_{conf}$ taken while the user was walking or running, and a second set of previous TH$_{ROI}$, TH$_{ENV}$, and m$_{conf}$ taken while the user was sitting or standing.

Figure 66:
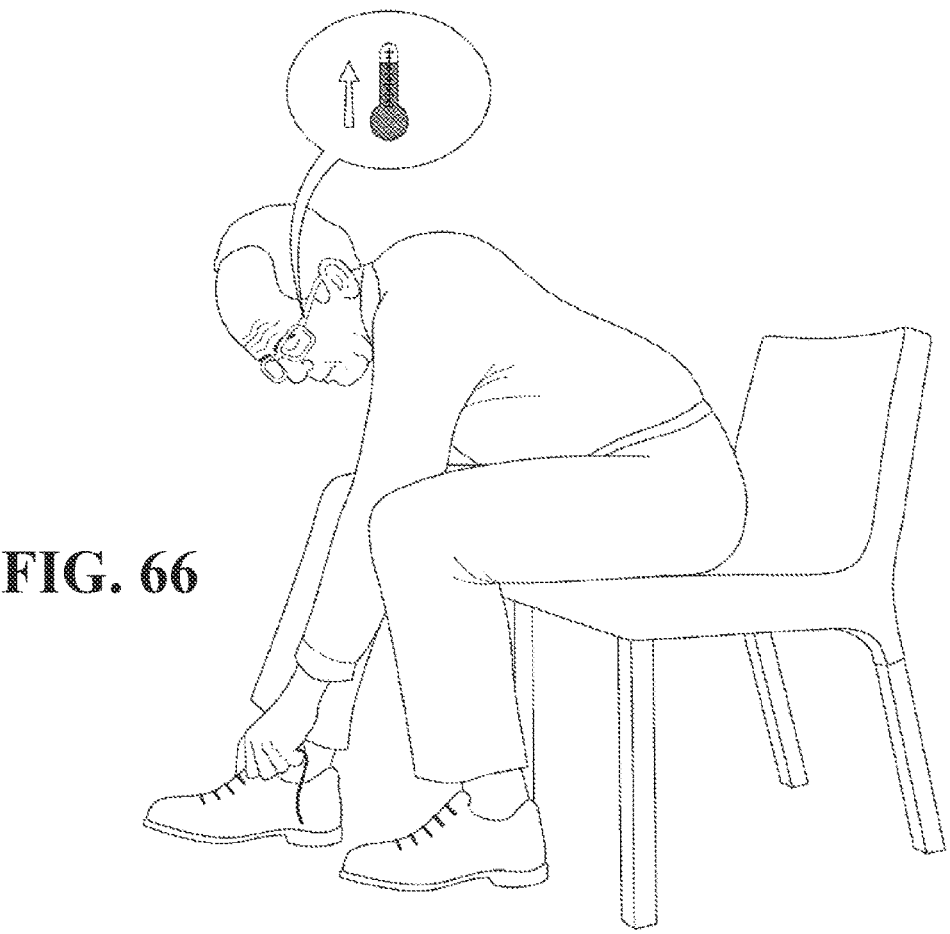
FIG. 66 illustrates an elderly person whose facial temperature increases as a result of bending over.

FIG. 66 illustrates an elderly person whose facial temperature increases as a result of bending the head down towards the floor. In this example, the system receives an indication of the user's action via the sensor (e.g., one or more gyroscopes) and consequently refrains from erroneously detecting certain physiological responses, since the increase in temperature may be attributed to the person being bent over. In one embodiment, a sensor provides indications indicative of bending the head down above a certain degree from the normal to earth, where bending the head down above the certain degree is expected to cause a change in TH$_{ROI}$. The computer generates feature values based on TH$_{ROI}$, TH$_{ENV}$, and m$_{conf}$, and utilizes a model to detect the physiological response based on the feature values. The model was trained based on: a first set of previous TH$_{ROI}$, TH$_{ENV}$, and m$_{conf}$ taken while a user was bending the head down above the certain degree, and a second set of previous TH$_{ROI}$, TH$_{ENV}$, and M$_{conf}$ taken while the user was not bending the head down above the certain degree.

Figure 65:
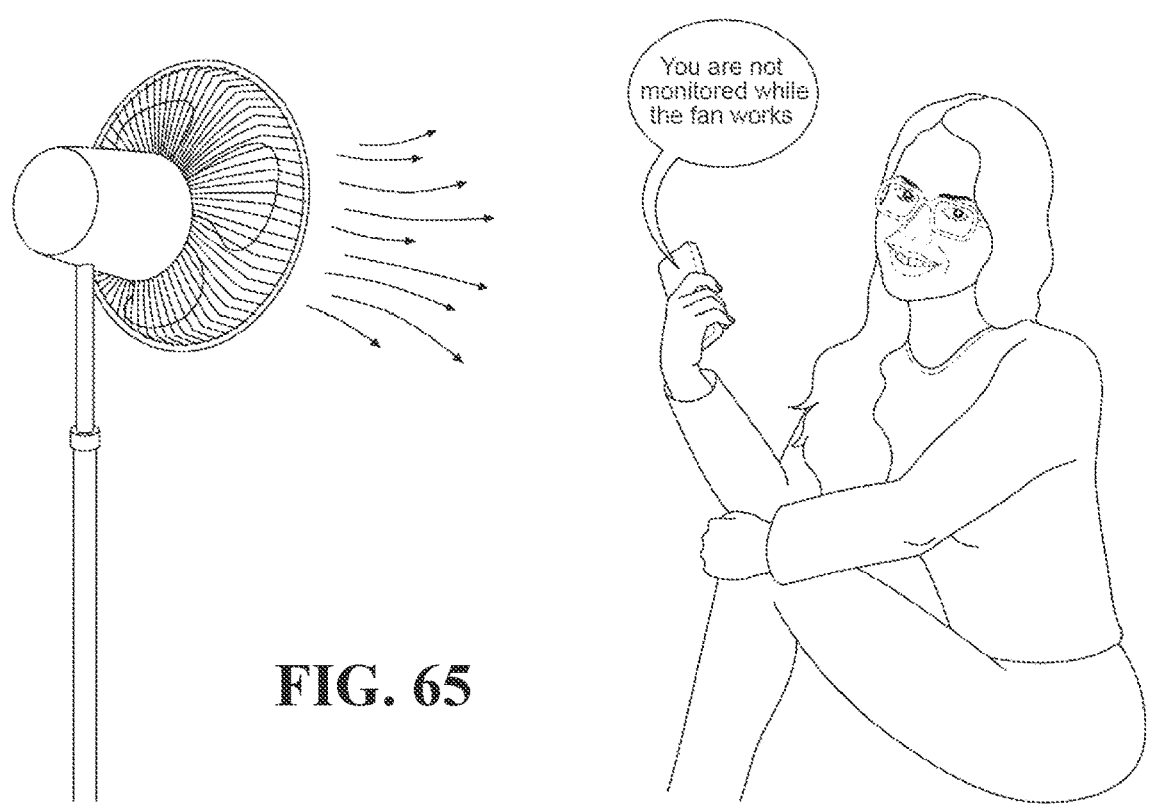
FIG. 65 illustrates a case in which a user receives an indication that she is not being monitored in a windy environment.

In another embodiment, the sensor may be an anemometer that is physically coupled to a frame worn on the user's head, is located less than 15 cm from the face, and provides a value indicative of a speed of air directed at the face (m$_{wind}$). Optionally, the computer detects the physiological response also based on m$_{wind}$. In one example, the computer refrains from detecting the physiological response if m$_{wind}$ reaches a threshold (which may indicate that the user was in an environment with strong wind that may excessively cool regions on the face). In another example, the computer generates feature values based on TH$_{ROI}$, TH$_{ENV}$, and m$_{wind}$ and utilizes a model to detect, based on the feature values, the physiological response. FIG. 65 illustrates a case in which a user receives an indication that she is not being monitored in a windy environment. Optionally, the model was trained based on previous TH$_{ROI}$, TH$_{ENV}$, and m$_{wind}$ taken while a user was in different environments. For example, the model may be trained based on: a first set of previous TH$_{ROI}$, TH$_{ENV}$, and m$_{wind}$ taken while being indoors, and a second set of previous TH$_{ROI}$, TH$_{ENV}$, and m$_{wind}$ taken while being outdoors.

The following is a method for detecting a physiological response while taking into account a confounding factor that involves environmental thermal interferences (e.g., direct sunlight). Having different environmental conditions may cause a system such as the one illustrated in FIG. 64A to behave differently, as shown in the steps below. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of a region of interest (TH$_{ROI}$) on a user's face utilizing an inward-facing head-mounted thermal camera (CAM$_{in}$) worn by the user. In step 2, taking thermal measurements of the environment (TH$_{ENV}$) utilizing an outward-facing head-mounted thermal camera (CAM$_{out}$) worn by the user. In step 3, generating feature values based on TH$_{ROI}$ and TH$_{ENV}$. And in step 4, utilizing a machine learning-based model to detect the physiological response based on the feature values.

The method may optionally further include the following steps: taking a first set of TH$_{ROI}$ (first TH$_{ROI}$), where the first set of TH$_{ROI}$ reach a first threshold; taking a first set of TH$_{ENV}$ (first TH$_{ENV}$), where the first set of TH$_{ENV}$ do not reach a second threshold; detecting, based on the first set of $TH_{ROI}$ and the first set of $TH_{ENV}$, that the user had the physiological response; taking a second set of $TH_{ROI}$, where the second set of $TH_{ROI}$ reach the first threshold; taking a second set of $TH_{ENV}$, where the second set of $TH_{ENV}$ reach the second threshold; and detecting, based on the second set of $TH_{ROI}$ and the second set of $TH_{ENV}$, that the user did not have the physiological response. Optionally, the method further includes: taking a third set of $TH_{ROI}$, where the third set of $TH_{ROI}$ do not reach the first threshold; taking a third set of $TH_{ENV}$, where the third set of $TH_{ENV}$ do not reach the second threshold; and detecting, based on the third set of $TH_{ROI}$ and the third set of $TH_{ENV}$, that the user did not have the physiological response.

The following is a description of a system for detecting a physiological response, which includes a CAM and a sensor. The sensor provides measurements indicative of times at which the user touches the face. Touching the face can warm certain regions of the face, and the system may utilize these measurements in order to account for such cases. Thus, the system may more accurately detect the physiological response compared to systems that do not account for touching of the face.

CAM is worn on the user's head and takes thermal measurements of an ROI ($TH_{ROI}$) on the user's face. Optionally, the system includes a frame to which CAM and the sensor may be physically coupled. Optionally, CAM is located less than 15 cm from the face and/or weighs below 10 g.

The sensor provides measurements (M) indicative of times at which the user touches the ROI. The user may touch the ROI using/with a finger, the palm, a tissue or a towel held by the user, a makeup-related item held by the user, and/or a food item eaten by the user. Touching the ROI may affect $TH_{ROI}$ by increasing or decreasing the temperature at the touched region. Thus, touching the ROI may be considered a confounding factor that can make detections of the physiological response by a computer less accurate. M may include values measured by the sensor and/or results of processing of values measured by the sensor. Various types of sensors may be utilized in different embodiments to generate M, such as: a visible-light camera (where the computer uses image processing to identify touching the ROI), a miniature radar (such as low-power radar operating in the range between 30 GHz and 3,000 GHz, where the computer uses signal processing of the reflections to identify touching the ROI), a miniature active electro-optics distance measurement device, and/or an ultrasound sensor.

In some embodiments, the sensor may be unattached to a frame worn on the user's head. For example, the sensor may include a visible-light camera mounted to an object in the user's environment (e.g., a laptop), and may normally located at a distance greater than 20 cm from the user's face. Optionally, the computer may utilize M to determine when it is likely (but not necessarily certain) that the user touched the face. In one example, the sensor includes a movement-measuring device embedded in a bracelet, and the computer increases the probability for a physical contact with the face when the user's hand is estimated to be at face level and/or close to the face. In another example, the sensor includes an altimeter embedded in a bracelet, and the computer increases the probability for an event of physical contact with the face when the user's hand is estimated to be at face level.

Figure 62A:
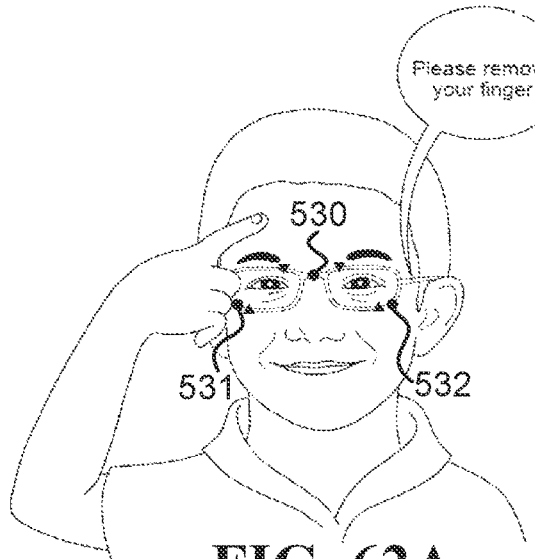
FIG. 62A and FIG. 62B illustrate an embodiment of a system that provides indications when the user touches his/her face.
Figure 62B:
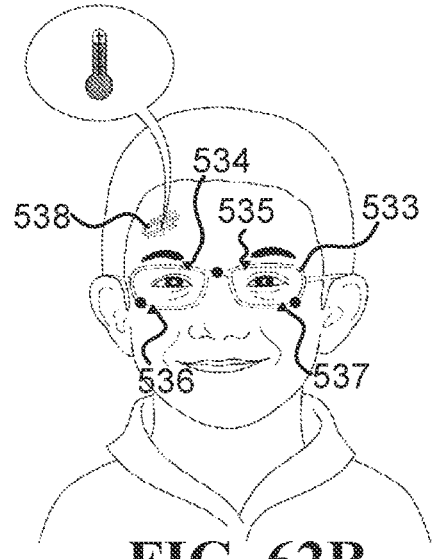

FIG. 62A and FIG. 62B illustrate one embodiment of a system that provides indications when the user touches his/her face. The system includes a frame 533, head-mounted sensors (530, 531, 532) able to detect touching the face, and head-mounted thermal cameras (534, 535, 536, 537). Optionally, the head-mounted sensors are visible-light cameras that take images of the ROIs. Head-mounted sensor 530 captures an ROI above the frame, and head-mounted sensors 531 and 532 capture ROIs below the frame. Hot spot 538, which is measured by the thermal camera 534, was caused by touching the forehead and is unrelated to the physiological response being detected. Upon detecting touching of the ROI, the computer may use the associated thermal measurements differently than it would use had the touching not been detected. Additionally or alternatively, a user interface may provide an indication that touching the ROI hinders the detection of the physiological response.

The computer detects the physiological response based on $TH_{ROI}$ and M. Optionally, since the computer utilizes M to account, at least in part, for the effect of touching the face, on average, detections of the physiological response based on $TH_{ROI}$ and M are more accurate than detections of the physiological response based on $TH_{ROI}$ without M. The computer may utilize $TH_{ROI}$ in various ways in order to detect the physiological response, such as comparing one or more values derived from $TH_{ROI}$ to a threshold and/or comparing $TH_{ROI}$ to a reference time series.

Another approach that may be utilized involves a machine learning-based model. In one embodiment, the computer generates feature values based on $TH_{ROI}$ and M, and utilizes the model to detect, based on the feature values, the physiological response. By utilizing M to generate one or more of the feature values, the computer may make different detections of the physiological response based on similar $TH_{ROI}$ that are taken while there are different extents of touching the ROI. For example, responsive to receiving a first set of measurements in which $TH_{ROI}$ reaches a threshold, while M indicate that there was no touching of the ROI, the computer detects the physiological response. However, responsive to receiving a second set of measurements in which $TH_{ROI}$ reaches the threshold, but M indicate that the user touched the ROI, the computer does not detect the physiological response. Optionally, the model is trained based on samples, each comprising: (i) feature values generated based on $TH_{ROI}$ taken while M indicates touching the ROI, and (ii) a corresponding label indicative of an extent of the physiological response. Optionally, the samples include: a first set of samples with labels corresponding to having the physiological response, which are generated based on M indicating that the ROI was not touched, and a second set of samples with labels corresponding to not having the physiological response, which are generated based on M indicating that the ROI was touched. Optionally, the samples comprise: a third set of samples with labels corresponding to having the physiological response, which are generated based on M indicating that the ROI was touched, and/or a fourth set of samples with labels corresponding to not having the physiological response, which are generated based on M indicating that the ROI was not touched.

M may be utilized by the computer in order to decrease the chance of making incorrect detections of the physiological response. In one embodiment, the computer utilizes, for the detection of the physiological response, $TH_{ROI}$ taken at times in which M are not indicative of touching the ROI. In this embodiment, the computer does not utilize, for the detection of the physiological response, $TH_{ROI}$ taken at times in which M are indicative of touching the ROI. In another embodiment, the computer does not utilize, for the detection of the physiological response, $TH_{ROI}$ taken during at least one of the following intervals starting after M indicate that the user touched the ROI: 0-10 seconds, 0-30 second, 0-60 second, 0-180 seconds, and 0-300 seconds. In yet another embodiment, the computer attributes, for the detection of the physiological response, a smaller weight to $TH_{ROI}$ taken during a certain interval starting after M indicate that the user touched the ROI, compared to a weight attributed to $TH_{ROI}$ taken at times shortly before M indicate that the user touched the ROI. Optionally, the certain interval includes at least one of the following durations: 10-30 second, 30-60 second, 60-120 seconds, and 120-300 seconds. Optionally, the higher the weight attributed to a measurement, the more it influences calculations involved in the detection of the physiological response.

In one embodiment, the system optionally includes a user interface (UI) which notifies the user about touching the ROI. Optionally, this notification is in lieu of notifying extent of the physiological response corresponding to the time the user touched the ROI. The notification may be delivered to the user using a sound, a visual indication on a head-mounted display, and/or a haptic feedback. Optionally, the UI includes a screen of an HMS (e.g., a screen of an augmented reality headset), a screen of a device carried by the user (e.g., a screen of a smartphone or a smartwatch), and/or a speaker (e.g., an earbud or headphones). Optionally, the computer identifies that the duration and/or extent of touching the face reached a threshold, and then commands the UI to alert the user that an accurate detection of the physiological response cannot be made as long as the touching continues.

In one embodiment, the sensor includes a visible-light camera and/or a near-infrared camera, the system is powered by a battery, and the system may operate in a state belonging to a set comprising first and second states. While operating in the first state, the system checks on a regular basis whether the user touches the ROI. While operating in the second state, the system checks whether the user touches the ROI in response to detecting abnormal $TH_{ROI}$. Optionally, the system consumes less power while operating in the second state compared to the power it consumes while operating in the first state.

In one embodiment, the measurements taken by the sensor are further indicative of an angular position of CAM relative to the ROI while the frame is still worn on the head, and the computer detects the physiological response also based on the angular position. Optionally, the measurements of the angular position are utilized to account for instances in which the frame has moved, and consequently CAM captures a region that only overlaps, or does not overlap at all, with the intended ROI. Optionally, the computer is able to detect changes below 5° in the angular position, which may also influence $TH_{ROI}$. Thus, on average, detections of the physiological response based on $TH_{ROI}$ and the angular position are more accurate compared to detections of the physiological responses based on $TH_{ROI}$ without the angular position, while the frame is still worn on the head.

In a first example, responsive to the angular position of CAM relative to the ROI reaching a predetermined threshold, the computer refrains from detecting the physiological response and/or alerts the user.

In a second example, the computer generates feature values based on $TH_{ROI}$ and the angular position, and utilizes a model to detect the physiological response based on the feature values. Optionally, the model was trained based on data comprising $TH_{ROI}$ collected while CAM was at different distances and/or angular positions relative to the ROI. Thus, the model may account, in its parameters, for various effects that the distance and/or orientation of CAM may have on $TH_{RO}$ in order to more accurately detect the physiological response.

In a third example, the sensor includes a visible-light camera that takes images of a region on the user's face, and the computer calculates the angular position of the visible-light camera relative to the face based on analyzing the images, and then calculates the angular position of CAM relative to the ROI based on a predetermined transformation between the angular position of the visible-light camera relative to the face and the angular position of CAM relative to the ROI.

In a fourth example, the sensor includes a transceiver of electromagnetic waves, and the computer calculates the angular position of the transceiver relative to the face based on signal processing of the reflections from the face, and then calculates the angular position of CAM relative to the ROI based on a predetermined transformation between the angular position of the transceiver relative to the face and the angular position of CAM relative to the ROI.

The following method for detecting a physiological response may be used, in some embodiments, by the system described above, which detects a physiological response while taking into account a confounding factor such as touching the face. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, taking thermal measurements of an ROI ($TH_{ROI}$) on a user's face using an inward-facing head-mounted thermal camera. In Step 2, taking, utilizing a sensor, measurements (M) indicative of times at which the user touches the ROI. Touching the ROI may affect $TH_{ROI}$, for example by increasing the temperatures at the ROI (which may increase the values of $TH_{ROI}$). The sensor may be a head-mounted sensor or a sensor that is not head-mounted. And in Step 3, detecting the physiological response based on $TH_{ROI}$ and M. For example, the detection may be performed by the computer, as described above. On average, detections of the physiological response based on $TH_{ROI}$ and M are more accurate compared to detections of the physiological response based on $TH_{ROI}$ without M.

Optionally, the method further includes the following steps: generating feature values based on $TH_{ROI}$ and M, and utilizing a model for detecting the physiological response based on the feature values. Optionally, the model was trained based on samples, each comprising: (i) feature values generated based on previous $TH_{ROI}$ taken while M indicates touching the ROI, and (ii) a corresponding label indicative of an extent of the physiological response. Optionally, the samples include: a first set of samples with labels corresponding to having the physiological response, which are generated based on M indicating that the ROI was not touched, and a second set of samples with labels corresponding to not having the physiological response, which are generated based on M indicating that the ROI was touched.

Optionally, M are further indicative of angular position of CAM relative to the ROI, while the frame is still worn on the head. And the method further includes a step of detecting the physiological response also based on the angular position. On average, detections of the physiological response based on $TH_{ROI}$ and the angular position are more accurate compared to detections of the physiological responses based on $TH_{ROI}$ without the angular position, while the frame is still worn on the head.

The following is a description of a system that detects a physiological response while taking into account a consumption of a confounding substance. When a person consumes a confounding substance, it may affect thermal measurements of an ROI ($TH_{ROI}$) on the person's face. The affect to $TH_{ROI}$ can be attributed to various physiological and/or metabolic processes that may ensue following the consumption of the confounding substance, which can result (amongst possibly other effects) in a raising or decreasing of the temperature at the ROI in a manner that is unrelated to the physiological response being detected. Thus, embodiments of this system utilize indications indicative of consumption of a confounding substance (such as medication, an alcoholic beverage, a caffeinated beverage, and/or a cigarette) to improve the system's detection accuracy. In one embodiment, the system includes a CAM and a computer.

CAM is worn on the user's head and takes thermal measurements of an ROI ($TH_{ROI}$) on the user's face. Optionally, the system includes a frame to which CAM and the device are physically coupled. Optionally, CAM is located less than 15 cm from the face and/or weighs below 10 g.

In different embodiments, the ROI may cover different regions on the face and CAM may be located at different locations on a frame worn on the user's head and/or at different distances from the user's face. In one embodiment, the ROI is on the forehead, and CAM is physically coupled to an eyeglasses frame, located below the ROI, and does not occlude the ROI. Optionally, the physiological response detected in this embodiment is stress, a headache, and/or a stroke. In another embodiment, the ROI is on the periorbital area, and CAM is located less than 10 cm from the ROI. Optionally, the physiological response detected in this embodiment is stress. In yet another embodiment, the ROI is on the nose, and CAM is physically coupled to an eyeglasses frame and is located less than 10 cm from the face. Optionally, the physiological response detected in this embodiment is an allergic reaction. In still another embodiment, the ROI is below the nostrils, and CAM: is physically coupled to an eyeglasses frame, located above the ROI, and does not occlude the ROI. Optionally, the ROI covers one or more areas on the upper lip, the mouth, and/or air volume(s) through which the exhale streams from the nose and/or mouth flow, and the physiological response detected in this embodiment is a respiratory parameter such as the user's breathing rate.

The computer may receive, from a device, an indication indicative of consuming a confounding substance that is expected to affects $TH_{ROI}$, such as an alcoholic beverage, a medication, caffeine, and/or a cigarette. Various types of devices may be utilized in different embodiments in order to identify consumption of various confounding substances.

In one embodiment, the device includes a visible-light camera that takes images of the user and/or the user's environment. Optionally, the visible-light camera is a head-mounted visible-light camera having in its field of view a volume that protrudes out of the user's mouth. Optionally, the computer identifies a consumption of the confounding substance based on analyzing the images. In one example, the visible-light camera may belong to a camera based system such as OrCam (http://www.orcam.com/), which is utilized to identify various objects, products, faces, and/or recognize text. In another example, images captured by the visible-light camera may be utilized to determine the nutritional composition of food a user consumes. Such an approach in which images of meals are utilized to generate estimates of food intake and meal composition, is described in Noronha, et al., "Platemate: crowdsourcing nutritional analysis from food photographs", Proceedings of the 24th annual ACM symposium on User interface software and technology, ACM, 2011. Additional examples of how a visible-light camera may be utilized to identify consumption of various substances is given in U.S. Pat. No. 9,053,483 (Personal audio/visual system providing allergy awareness) and in U.S. Pat. No. 9,189,021 (Wearable food nutrition feedback system).

In another embodiment, the device includes a microphone that records the user, and the computer identifies a consumption of the confounding substance utilizing a sound recognition algorithm operated on a recording of the user. Optionally, the sound recognition algorithm comprises a speech recognition algorithm configured to identify words that are indicative of consuming the confounding substance.

In yet another embodiment, the confounding substance is a medication, and the device includes a pill dispenser that provides an indication indicating that the user took a medication, and/or a sensor-enabled pill that includes an ingestible signal generator coupled to a medication that is configured to generate a body-transmissible signal upon ingestion by a user, such as the sensor-enabled pill described in PCT publication WO/2016/129286. Optionally, the indication indicates the type of medication and/or its dosage.

In still another embodiment, the device is a refrigerator, a pantry, and/or a serving robot. Optionally, the device provides an indication indicative of the user taking an alcoholic beverage and/or a food item.

In yet another embodiment, the device has an internet-of-things (IoT) capability through which the indication is provided to the system. For example, the device may be part of a "smart device" with network connectivity.

And in yet another embodiment, the device belongs to a user interface that receives an indication from the user or/or a third party about the consuming of the confounding substance.

Due to various metabolic and/or other physiological processes, consumption of a confounding substance may affect $TH_{ROI}$. For example, many drugs are known to act on the hypothalamus and other brain centers involved in controlling the body's thermoregulatory system. Herein, stating "the confounding substance affects $TH_{ROI}$" means that consuming the confounding substance leads to a measureable change of the temperature at the ROI, which would likely not have occurred had the confounding substance not been consumed. Similarly, a time in which "confounding substance did not affect $TH_{ROI}$" is a time that occurs after at least a certain duration has elapsed since the confounding substance was last consumed (or was not consumed at all), and the consumption of the confounding substance is no longer expected to have a noticeable effect on the ROI temperature. This certain duration may depend on factors such as the type of substance, the amount consumed, and previous consumption patterns. For example, the certain duration may be at least: 30 minutes, two hours, or a day.

The duration of the effect of a confounding substance may vary between substances, and may depend on various factors such as the amount of substance, sex, weight, genetic characteristics, and the user's state. For example, consumption of alcohol on an empty stomach often has a greater effect on $TH_{ROI}$ than consumption of alcohol with a meal. Some confounding substances may have a long-lasting effect, possibly throughout the period they are taken. For example, hormonal contraceptives can significantly alter daily body temperatures. Other confounding factors, such as caffeine and nicotine, may have shorter lasting effects, typically subsiding within less than an hour or two following their consumption.

The computer detects the physiological response based on $TH_{ROI}$ and the indication indicative of consuming the confounding substance. In one embodiment, the computer refrains from detecting the physiological response within a certain window during which the confounding substance affected the user (e.g., an hour, two hours, or four hours). In another embodiment, the computer utilizes a model, in addition to $TH_{ROI}$ and the indication, to detect whether the user had the physiological response during the time that a consumed confounding substance affected $TH_{ROI}$. Optionally, the computer detects the physiological response by generating feature values based on $TH_{ROI}$ and the indication (and possibly other sources of data), and utilizing the model to calculate, based on the feature values, a value indicative of the extent of the physiological response. Optionally, the feature values include a feature value indicative of one or more of the following: the amount of the consumed confounding substance, the dosage of the consumed confounding substance, the time that has elapsed since the confounding substance had last been consumed, and/or the duration during which the confounding factor has been consumed (e.g., how long the user has been taking a certain medication).

In one embodiment, the model was trained based on data collected from the user and/or other users, which includes $TH_{ROI}$, the indications described above, and values representing the physiological response corresponding to when $TH_{ROI}$ were taken. Optionally, the data is used to generate samples, with each sample comprising feature values and a label. The feature values of each sample are generated based on $TH_{ROI}$ taken during a certain period and an indication indicating whether a confounding substance affected $TH_{ROI}$ taken during the certain period. The label of the sample is generated based on one or more of the values representing the physiological response, and indicates whether (and optionally to what extent) the measured user had the physiological response during the certain period. Optionally, the data used to train the model reflects both being affected and being unaffected by the confounding substance. For example, the data used to train the model may include: a first set of $TH_{ROI}$ taken while the confounding substance affected $TH_{ROI}$, and a second set of $TH_{ROI}$ taken while the confounding substance did not affect $TH_{ROI}$. Optionally, each of the first and second sets comprises at least some $TH_{ROI}$ taken while the measured user had the physiological response and at least some $TH_{ROI}$ taken while the measured user did not have the physiological response.

Using the indications (indicative of the user consuming a confounding substance) may lead to cases where the detection of the physiological response depends on whether the confounding substance was consumed. In one example, in which the physiological response is detected when $TH_{ROI}$ reach a threshold, the computer's detection behavior may be as follows: the computer detects the physiological response based on first $TH_{ROI}$ for which there is no indication indicating that the first $TH_{ROI}$ were affected by a consumption of the confounding substance, and the first $TH_{ROI}$ reach the threshold; the computer does not detect the physiological response based on second $TH_{ROI}$ for which there is an indication indicating that the second $TH_{ROI}$ were affected by a consumption of the confounding substance, and the second $TH_{ROI}$ also reach the threshold; and the computer does not detect the physiological response based on third $TH_{ROI}$ for which there is no indication indicating that the third $TH_{ROI}$ were affected by a consumption the confounding substance, and the third $TH_{ROI}$ do not reach the threshold.

Figure 67:
FIG. 67 illustrates the effect of consuming alcohol on values of thermal measurements.

The following three figures illustrate scenarios where issuing of alerts are dependent on the consumption of confounding substances. FIG. 67 illustrates that the effect of consuming alcohol on a certain $TH_{ROI}$ usually decreases after duration typical to the user (e.g., the duration is based on previous measurements of the user). Thus, when the effect remains high there may be a problem and the system may issue an alert. The figure illustrates an outward-facing visible-light camera 525 that generates the indications indicative of when the user consumes alcoholic beverages.

Figure 68:
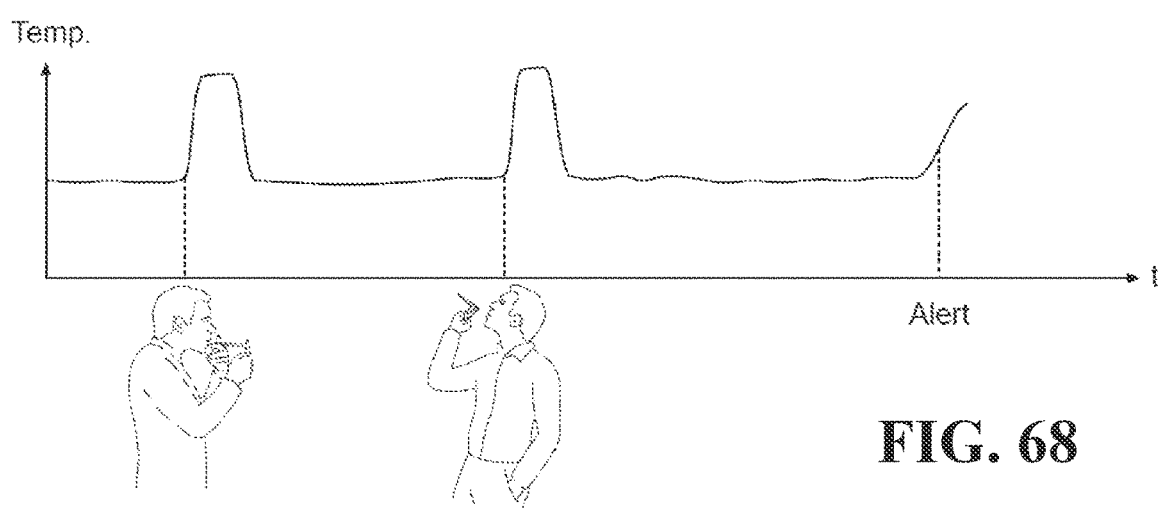
FIG. 68 illustrates an increase in the thermal measurements due to smoking.

FIG. 68 illustrates a usual increase in a certain $TH_{ROI}$ while the user smokes. The system identifies when the user smoked (e.g., based on images taken by the outward-facing visible-light camera 525) and doesn't alert because of an increase in $TH_{ROI}$ caused by the smoking. However, when the temperature rises without the user having smoked for a certain time, then it may be a sign that there is a problem, and the user might need to be alerted.

Figure 69:
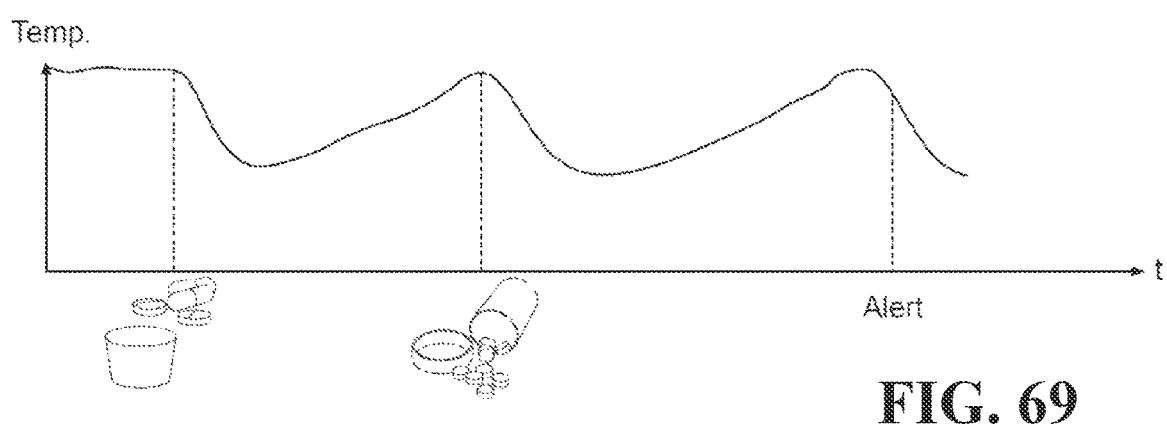
FIG. 69 illustrates a decrease in the thermal measurements due to taking medication.

FIG. 69 illustrates the expected decrease in a certain $TH_{ROI}$ after the user takes medication, based on previous $TH_{ROI}$ of the user. The system identifies when the medication is consumed, and does not generate an alert at those times. However, when $TH_{ROI}$ falls without medication having been taken, it may indicate a physiological response of which the user should be made aware.

The following method for detecting a physiological response while taking into account consumption of a confounding substance may be used, in some embodiments, by the system described above, which detects a physiological response while taking into account a consumption of a confounding substance. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of an ROI ($TH_{ROI}$) on the user's face utilizing an inward-facing head-mounted thermal camera.

In Step 2, receiving an indication indicative of consuming a confounding substance that affects $TH_{ROI}$. Optionally, the indication is received from one or more of the various device described above that provide an indication indicative of consuming a confounding substance. Optionally, the indication is generated based on image processing of images taken by a head-mounted visible-light camera having in its field of a volume that protrudes out of the user's mouth.

And in Step 3, detecting the physiological response, while the consumed confounding substance affects $TH_{ROI}$, based on $TH_{ROI}$, the indication, and a model. Optionally, the model was trained on: a first set of $TH_{ROI}$ taken while the confounding substance affected $TH_{ROI}$, and a second set of $TH_{ROI}$ taken while the confounding substance did not affect $TH_{ROI}$. Optionally, the model is a machine learning-based model, and this step involves: generating feature values based on $TH_{ROI}$ and the indication, and utilizing the machine learning-based model to detect the physiological response based on the feature values.

One way in which a user may wear a head-mounted camera (such as CAM or VCAM) involves attaching a clip-on device that houses the camera onto a frame worn by the user, such as an eyeglasses frame. This may enable the user to be selective regarding when to use the head-mounted camera and take advantage of eyeglasses that he or she owns, which may be comfortable and/or esthetically pleasing.

In some embodiments, the clip-on device includes a body that may be attached and detached, multiple times, from a pair of eyeglasses in order to secure and release the clip-on device from the eyeglasses. The body is a structure that has one or more components fixed to it. For example, the body may have one or more inward-facing camera fixed to it. Additionally, the body may have a wireless communication module fixed to it. Some additional components that may each be optionally fixed to the body include a processor, a battery, and one or more outward-facing cameras.

In one example, "eyeglasses" are limited to prescription eyeglasses, prescription sunglasses, plano sunglasses, and/or augmented reality eyeglasses. This means that "eyeglasses" do not refer to helmets, hats, virtual reality devices, and goggles designed to be worn over eyeglasses. Additionally or alternatively, neither attaching the clip-on device to the eyeglasses nor detaching the clip-on device from the eyeglasses should take more than 10 seconds for an average user. This means that manipulating the clip-on device is not a complicated task. Optionally, the body is configured to be detached from the eyeglasses by the user who wears the eyeglasses, who is not a technician, and without using a tool such as a screwdriver or a knife. Thus, the clip-on device may be attached and detached as needed, e.g., enabling the user to attach the clip-on when there is a need to take measurements, and otherwise have it detached.

In order to be warn comfortably, possibly for long durations, the clip-on device is a lightweight device, weighing less than 40 g (i.e., the total weight of the body and the components fixed to it is less than 40 g). Optionally, the clip-on device weighs below 20 g and/or below 10 g.

The body is a structure to which components (e.g., an inward-facing camera) may be fixed such that the various components do not fall off while the clip-on device is attached to the eyeglasses. Optionally, at least some of the various components that are fixed to the body remain in the same location and/or orientation when the body is attached to the eyeglasses. Herein, stating that a component is "fixed" to the body is intended to indicate that, during normal use (e.g., involving securing/releasing the clip-on device), the components are typically not detached from the body. This is opposed to the body itself, which in normal use is separated from the eyeglasses frame, and as such, is not considered "fixed" to the eyeglasses frame.

In some embodiments, the body is a rigid structure made of a material such as plastic, metal, and/or an alloy (e.g., carbon alloy). Optionally, the rigid structure is shaped such that it fits the contours of at least a portion of the frame of the eyeglasses in order to enable a secure and stable attachment to the eyeglasses. In other embodiments, the body may be made of a flexible material, such as rubber. Optionally, the flexible body is shaped such that it fits the contours of at least a portion of the frame of the eyeglasses in order to enable a secure and stable attachment to the eyeglasses. Additionally or alternatively, the flexible body may assume the shape of a portion of the frame when it is attached to the eyeglasses.

The body may utilize various mechanisms in order to stay attached to the eyeglasses. In one embodiment, the body may include a clip member configured to being clipped on the eyeglasses. In another embodiment, the body may include a magnet configured to attach to a magnet connected to the eyeglasses and/or to a metallic portion of the eyeglasses. In yet another embodiment, the body may include a resting tab configured to secure the clip-on to the eyeglasses. In still another embodiment, the body may include a retention member (e.g., a clasp, buckle, clamp, fastener, hook, or latch) configured to impermanently couple the clip-on to the eyeglasses. For example, clasp 147 is utilized to secure the clip-on device illustrated in FIG. 30A to the frame of the eyeglasses. And in yet another embodiment, the body may include a spring configured to apply force that presses the body towards the eyeglasses. An example of this type of mechanism is illustrated in FIG. 32A where spring 175 is used to apply force that pushes body 170 and secures it in place to frame 176.

Herein, to "impermanently couple" something means to attach in a way that is easily detached without excessive effort. For example, coupling something by clipping it on or closing a latch is considered impermanently coupling it. Coupling by screwing a screw with a screwdriver, gluing, or welding is not considered impermanently coupling. The latter would be examples of what may be considered to "fix" a component to the body.

The inward-facing camera is fixed to the body. It takes images of a region of interest on the face of a user who wears the eyeglasses. Optionally, the inward-facing camera remains pointed at the region of interest even when the user's head makes lateral and/or angular movements. The inward-facing camera may be any of the CAMs and/or VCAMs described in this disclosure. Optionally, the inward-facing camera weighs less than 10 g, 5 g or 1 g. Optionally, the inward-facing camera is a thermal camera based on a thermopile sensor, a pyroelectric sensor, or a microbolometer sensor, which may be a FPA sensor.

In one embodiment, the inward-facing camera includes a multi-pixel sensor and a lens, and the sensor plane is tilted by more than 2° relative to the lens plane according to the Scheimpflug principle in order to capture sharper images when the body is attached to the eyeglasses that are worn by a user.

The clip-one device may include additional components that are fixed to it. In one embodiment, the clip-on device include a wireless communication module fixed to the body which transmits measurements (e.g., images and/or thermal measurements) taken by one or more of the cameras that are fixed to the body. Optionally, the clip-on device may include a battery fixed to the body, which provides power to one or more components fixed to the body. Optionally, the clip-on device may include a processor that controls the operation of one or more of the components fixed to the body and/or processes measurements taken by the camera fixed to the body.

In some embodiments, a computer receives measurements taken by the inward-facing camera (and possibly other cameras fixed to the body), and utilizes the measurements to detect a physiological response. Optionally, the computer is not fixed to the body. For example, the computer may belong to a device of the user (e.g., a smartphone or a smartwatch), or the computer may be a cloud-based server. Optionally, the computer receives, over a wireless channel, the measurements, which are sent by the wireless communication module.

The following are various examples of embodiments using different types of inward- and outward-facing cameras that are fixed to the body, which may be used to take images of various regions of interest on the face of the user who wears the eyeglasses. It is to be noted that while the discussion below generally refers to a single "inward-facing camera" and/or a single "outward-facing camera", embodiments of the clip-on device may include multiple inward- and/or outward-facing cameras.

In some embodiments, the inward-facing camera is a thermal camera. Optionally, when the body is attached to the eyeglasses, the thermal camera is located less than 5 cm from the user's face. Optionally, measurements taken by the thermal camera are transmitted by the wireless communication module and are received by a computer that uses them to detect a physiological response of the user. In one example, when the body is attached to the eyeglasses, the optical axis of the thermal camera is above 20° from the Frankfort horizontal plane, and the thermal camera takes thermal measurements of a region on the user's forehead. In another example, when the body is attached to the eyeglasses, the thermal camera takes thermal measurements of a region on the user's nose. In yet another example, when the body is attached to the eyeglasses, the thermal camera takes thermal measurements of a region on a periorbital area of the user.

In one embodiment, the inward-facing camera is a thermal camera. When the body is attached to the eyeglasses, the thermal camera is located below eye-level of a user who wears the eyeglasses and at least 2 cm from the vertical symmetry axis that divides the user's face (i.e., the axis that goes down the center of the user's forehead and nose). Additionally, when the body is attached to the eyeglasses, the inward-facing thermal camera takes thermal measurements of a region on at least one of the following parts of the user's face: upper lip, lips, and a cheek. Optionally, measurements taken by the thermal camera are transmitted by the wireless communication module and are received by a computer that uses them to detect a physiological response of the user.

In another embodiment, the inward-facing camera is a visible-light camera. Optionally, when the body is attached to the eyeglasses, the visible-light camera is located less than 10 cm from the user's face. Optionally, images taken by the visible-light camera are transmitted by the wireless communication module and are received by a computer that uses them to detect a physiological response of the user. Optionally, the computer detects the physiological response based on facial skin color changes (FSCC) that are recognizable in the images. In one example, when the body is attached to the eyeglasses, the optical axis of the visible-light camera is above 20° from the Frankfort horizontal plane, and the visible-light camera takes images of a region located above the user's eyes. In another example, when the body is attached to the eyeglasses, the visible-light camera takes images of a region on the nose of a user who wears the eyeglasses. In still another example, the computer detects the physiological response based on facial expressions, and when the body is attached to the eyeglasses, the visible-light camera takes images of a region above or below the user's eyes.

In still another embodiment, the inward-facing camera is a visible-light camera, and when the body is attached to the eyeglasses, the visible-light camera takes images of a region on an eye ($IM_E$) of a user who wears the eyeglasses, and is located less than 10 cm from the user's face. Optionally, the images are transmitted by the wireless communication module and are received by a computer that detects a physiological response based in $IM_E$.

In one example, the computer detects the physiological response based on color changes to certain parts of the eye, such as the sclera and/or the iris. Due to the many blood vessels that are close to the surface of the eye, physiological responses that are manifested through changes to the blood flow (e.g., a cardiac pulse and certain emotional responses), may cause recognizable changes to the color of the certain parts of the eye. The various techniques described in this disclosure for detecting a physiological response based on FSCC that is recognizable in images can be applied by one skilled in the art to detect a physiological response based on color changes to the sclera and/or iris; while the sclera and iris are not the same color as a person's skin, they too exhibit blood flow-related color changes that are qualitatively similar to FSCC, and thus may be analyzed using similar techniques to the techniques used to analyze FSCC involving the forehead, nose, and/or cheeks.

In another example, $IM_E$ may be utilized to determine the size of the pupil, which may be utilized by the computer to detect certain emotional responses (such as based on the assumption that the pupil's response reflects emotional arousal associated with increased sympathetic activity).

If needed as part of the computer's detection of the physiological response, identifying which portions of $IM_E$ correspond to certain parts of the eye (e.g., the sclera or iris) can be done utilizing various image processing techniques known in the art. For example, identifying the iris and pupil size may be done using the techniques described in US patent application 20060147094, or in Hayes, Taylor R., and Alexander A. Petrov. "Mapping and correcting the influence of gaze position on pupil size measurements." Behavior Research Methods 48.2 (2016): 510-527. Additionally, due to the distinct color differences between the skin, the iris, and the sclera, identification of the iris and/or the white sclera can be easily done by image processing methods known in the art.

In one embodiment, the inward-facing camera is a visible-light camera; when the body is attached to the eyeglasses, the visible-light camera is located below eye-level of a user who wears the eyeglasses, and at least 2 cm from the vertical symmetry axis that divides the user's face. The visible-light camera takes images ($IM_{ROI}$) of a region on the upper lip, lips, and/or a cheek. Optionally, $IM_{ROI}$ are transmitted by the wireless communication module and are received by a computer that uses them to detect a physiological response. In one example, the physiological response is an emotional response, which is detected based on extracting facial expressions from $IM_{ROI}$. In another example, the physiological response is an emotional response, which is detected based on FSCC recognizable in $IM_{ROI}$. In still another example, the physiological response, which is detected based FSCC recognizable in $IM_{ROI}$, is heart rate and/or breathing rate.

The body may include an outward-facing camera that may be utilized to provide measurements that may be used to account for various environmental interferences that can decrease detections of the physiological response of a user who wears the eyeglasses. Optionally, the outward-facing camera is a head-mounted camera. Optionally, the outward-facing camera is fixed to the body.

In one embodiment, the inward-facing camera is a thermal camera, and when the body is attached to the eyeglasses, the thermal camera is located less than 10 cm from the face of the user who wears the eyeglasses, and takes thermal measurements of a region of interest ($TH_{ROI}$) on the face of the user. In this embodiment, an outward-facing head-mounted thermal camera takes thermal measurements of the environment ($TH_{ENV}$). The wireless communication module transmits $TH_{ROI}$ and $TH_{ENV}$ to a computer that detects a physiological response of the user based on $TH_{ROI}$ and $TH_{ENV}$.

Optionally, the computer utilizes $TH_{ENV}$ to account for thermal interferences from the environment, as discussed elsewhere herein.

In another embodiment, the inward-facing camera is a visible-light camera, and when the body is attached to the eyeglasses, the visible-light camera is located less than 10 cm from the face of the user who wears the eyeglasses and takes images of a region of interest ($IM_{ROI}$) on the face of the user. In this embodiment, an outward-facing head-mounted visible-light camera takes images of the environment ($IM_{ENV}$). The wireless communication module transmits $IM_{ROI}$ and $IM_{ENV}$ to a computer that detects a physiological response of the user based on $IM_{ROI}$ and $IM_{ENV}$. Optionally, the computer detects the physiological response based on FSCC recognizable in $IM_{ROI}$, and utilizes $IM_{ENV}$ to account for variations in ambient light, as discussed elsewhere herein.

Inward-facing cameras attached to the body may be utilized for additional purposes, beyond detection of physiological responses. In one embodiment, the inward-facing camera is a visible-light camera, and the clip-on device includes a second visible-light camera that is also fixed to the body. Optionally, the visible-light camera and/or the second visible-light camera are light field cameras. Optionally, when the body is attached to the eyeglasses, the first and second visible-light cameras are located less than 10 cm from the user's face, and take images of a first region above eye-level and a second region on the upper lip ($IM_{ROI}$ and $IM_{ROI2}$, respectively). Optionally, the wireless communication module transmits $IM_{ROI}$ and $IM_{ROI2}$ to a computer that generates an avatar of the user based on $IM_{ROI}$ and $IM_{ROI2}$. Some of the various approaches that may be utilized to generate the avatar based on $IM_{ROI}$ and $IM_{ROI2}$ are described in co-pending US patent publication 2016/0360970.

Different embodiments of the clip-on device may involve devices of various shapes, sizes, and/or locations of attachment to the eyeglasses. FIG. 29A to FIG. 33 illustrate some examples of clip-on devices. When the body is attached to the eyeglasses, most of the clip-on device may be located in front of the frame of the eyeglasses, as illustrated in FIG. 29B, FIG. 30B, and FIG. 33, or alternatively, most of the clip-on device may be located behind the frame, as illustrated in FIG. 31B and FIG. 32B. Some clip-on devices may include a single unit, such as illustrated in FIG. 30A and FIG. 32A. While other clip-on devices may include multiple units (which each may optionally be considered a separate clip-on device). Examples of multiple units being attached to the frame are illustrated in FIG. 29B, FIG. 31B, and FIG. 33. The following is a more detailed discussion regarding embodiments illustrated in the figures mentioned above.

FIG. 29A, FIG. 29B, and FIG. 29C illustrate two right and left clip-on devices comprising bodies 141 and 142, respectively, which are configured to attached/detached from an eyeglasses frame 140. The body 142 has multiple inward-facing cameras fixed to it, such as camera 143 that points at a region on the lower part of the face (such as the upper lip, mouth, nose, and/or cheek), and camera 144 that points at the forehead. The body 142 may include other electronics 145, such as a processor, a battery, and/or a wireless communication module. The bodies 141 and 142 of the left and right clip-on devices may include additional cameras illustrated in the drawings as black circles.

In one another embodiment, the eyeglasses include left and right lenses, and when the body is attached to the eyeglasses, most of the volume of the clip-on device is located to the left of the left lens or to the right of the right lens. Optionally, the inward-facing camera takes images of at least one of: a region on the nose of a user wearing the eyeglasses, and a region on the mouth of the user. Optionally, a portion of the clip-on device that is located to the left of the left lens or to the right of the right lens does not obstruct the sight of the user when looking forward.

FIG. 30A and FIG. 30B illustrate a clip-on device that includes a body 150, to which two head-mounted cameras are fixed: a head-mounted camera 148 that points at a region on the lower part of the face (such as the nose), and a head-mounted camera 149 that points at the forehead. The other electronics (such as a processor, a battery, and/or a wireless communication module) are located inside the body 150. The clip-on device is attached and detached from the frame of the eyeglasses with the clasp 147.

In one embodiment, when the body is attached to the eyeglasses, most of the volume of the clip-on device is located above the lenses of the eyeglasses, and the inward-facing camera takes images of a region on the forehead of a user who wears the eyeglasses. Optionally, a portion of the clip-on device that is located above the lenses of the eyeglasses does not obstruct the sight of the user when looking forward.

While the clip-on device may often have a design intended to reduce the extent to which it sticks out beyond the frame, in some embodiments, the clip-on device may include various protruding arms. Optionally, these arms may be utilized in order to position one or more cameras in a position suitable for taking images of certain regions of the face. FIG. 33 illustrates right and left clip-on devices that include bodies 153 and 154, respectively, which are configured to attached/detached from an eyeglasses frame. These bodies have protruding arms that hold the head-mounted cameras. Head-mounted camera 155 measures a region on the lower part of the face, head-mounted camera 156 measures regions on the forehead. The left clip-on device also includes other electronics 157 (such as a processor, a battery, and/or a wireless communication module). The clip-on devices illustrated in this figure may include additional cameras illustrated in the drawings as black circles.

In other embodiments, at least a certain portion of the clip-on device is located behind the eyeglasses' frame. Thus, when the clip-on device is attached to the eyeglasses, they may remain aesthetically pleasing, and attaching the clip-on device may cause little or no blocking of the user's vision. FIG. 31B and FIG. 32B illustrate two examples of clip-on devices that are mostly attached behind the frame. The following are some additional examples of embodiments in which a portion of the clip-on device may be located behind the frame.

FIG. 31A and FIG. 31B illustrate two, right and left, clip-on devices with bodies 160 and 161, respectively, configured to be attached behind an eyeglasses frame 165. The body 160 has various components fixed to it which include: an inward-facing head-mounted camera 162 pointed at a region below eye-level (such as the upper lip, mouth, nose, and/or cheek), an inward-facing head-mounted camera 163 pointed at a region above eye-level (such as the forehead), and other electronics 164 (such as a processor, a battery, and/or a wireless communication module). The right and left clip-on devices may include additional cameras illustrated in the drawings as black circles.

FIG. 32A and FIG. 32B illustrate a single-unit clip-on device that includes the body 170, which is configured to be attached behind the eyeglasses frame 176. The body 170 has various cameras fixed to it, such as head-mounted cameras 171 and 172 that are pointed at regions on the lower part of the face (such as the upper lip, mouth, nose, and/or cheek), and head-mounted cameras 173 and 174 that are pointed at the forehead. The spring 175 is configured to apply force that holds the body 170 to the frame 176. Other electronics 177 (such as a processor, a battery, and/or a wireless communication module), may also be fixed to the body 170. The clip-on device may include additional cameras illustrated in the drawings as black circles.

In one embodiment, when the body is attached to the eyeglasses, more than 50% of the out-facing surface of the clip-on device is located behind the eyeglasses frame. Optionally, a portion of the clip-on device that is located behind the eyeglasses frame is occluded from a viewer positioned directly opposite to the eyeglasses, at the same height as the eyeglasses. Thus, a portion of the clip-on device that is behind the frame might not be visible to other people from many angles, which can make the clip-on device less conspicuous and/or more aesthetically pleasing. Optionally, a larger portion of the clip-on device is behind the frame when the body is attached to the eyeglasses, such as more than 75% or 90% of the out-facing surface.

Various physiological responses may be detected based on Facial skin color changes (FSCC) that occur on a user's face. In one embodiment, a system configured to detect a physiological response based on FSCC includes at least an inward-facing head-mounted visible-light camera ($VCAM_{in}$) and a computer. The system may optionally include additional elements such as a frame and additional inward-facing camera(s) and/or outward-facing camera(s).

Figure 60:
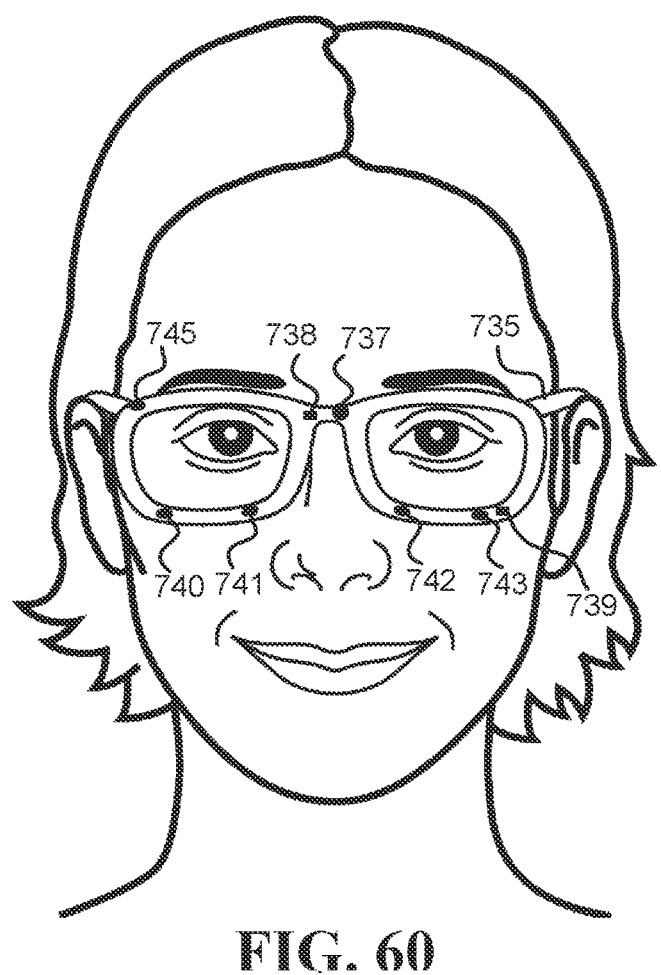
FIG. 60 illustrates an embodiment of the system configured to detect a physiological response based on facial skin color changes (FSCC)

FIG. 60 illustrates one embodiment of the system configured to detect a physiological response based on FSCC. The system includes a frame 735 (e.g., an eyeglasses frame) to which various cameras are physically coupled. These cameras include visible-light cameras 740, 741, 742, and 743, which may each take images of regions on the user's cheeks and/or nose. Each of these cameras may possibly be VCAM, which is discussed in more detail below. Another possibility for $VCAM_{in}$ is camera 745 that takes images of a region on the user's forehead and is coupled to the upper portion of the frame. Visible-light camera 737, which takes images of the environment ($IM_{ENV}$), is an example of $VCAM_{out}$ discussed below, which may optionally be included in some embodiments. Additional cameras that may optionally be included in some embodiments are outward-facing thermal camera 738 (which may be used to take $TH_{ENV}$ mentioned below) and inward-facing thermal camera 739 (which may be used to take $TH_{ROI2}$ mentioned below).

$VCAM_{in}$ is worn on the user's head and takes images of a region of interest ($IM_{ROI}$) on the user's face. Depending on the physiological response being detected, the ROI may cover various regions on the user's face. In one example, the ROI is on a cheek of the user, a region on the user's nose, and/or a region on the user's forehead. Optionally, $VCAM_{in}$ does not occlude the ROI, is located less than 10 cm from the user's face, and weighs below 10 g. The ROI is illuminated by ambient light. Optionally, the system does not occlude the ROI, and the ROI is not illuminated by a head-mounted light source. Alternatively, the ROI may be illuminated by a head-mounted light source that is weaker than the ambient light.

The computer detects the physiological response based on $IM_{ROI}$ by relying on effects of FSCC that are recognizable in $IM_{ROI}$. Herein, sentences of the form "FSCC recognizable in $IM_{ROI}$" refer to effects of FSCC that may be identified and/or utilized by the computer, which are usually not recognized by the naked eye. The FSCC phenomenon may be utilized to detect various types of physiological responses. In one embodiment, the physiological response that is detected may involve an expression of emotional response of the user. For example, the computer may detect whether the user's emotional response is neutral, positive, or negative. In another example, the computer may detect an emotional response that falls into a more specific category such as distress, happiness, anxiousness, sadness, frustration, intrigue, joy, disgust, anger, etc. Optionally, the expression of the emotional response may involve the user making a facial expression and/or a microexpression (whose occurrence may optionally be detected based on $IM_{ROI}$). In another embodiment, detecting the physiological response involves determining one or more physiological signals of the user, such as a heart rate (which may also be referred to as "cardiac pulse"), heart rate variability, and/or a breathing rate.

$IM_{ROI}$ are images generated based on ambient light illumination that is reflected from the user's face. Variations in the reflected ambient light may cause FSCC that are unrelated to the physiological response being detected, and thus possibly lead to errors in the detection of the physiological response. In some embodiments, the system includes an outward-facing head-mounted visible-light camera ($VCAM_{out}$), which is worn on the user's head, and takes images of the environment ($IM_{ENV}$). Optionally, $VCAM_{out}$ is located less than 10 cm from the user's face and weighs below 10 g. Optionally, $VCAM_{out}$ may include optics that provide it with a wide field of view. Optionally, the computer detects the physiological response based on both $IM_{ROI}$ and $IM_{ENV}$. Given that $IM_{ENV}$ is indicative of illumination towards the face and $IM_{ROI}$ is indicative of reflections from the face, utilizing $IM_{ENV}$ in the detection of the physiological response can account, at least in part, for variations in ambient light that, when left unaccounted, may possibly lead to errors in detection of the physiological response.

It is noted that the system may include multiple $VCAM_{in}$ configured to take images of various ROIs on the face, $IM_{ROI}$ may include images taken from the multiple $VCAM_{in}$, and multiple $VCAM_{out}$ located at different locations and/or orientation relative to the face may be used to take images of the environment.

In some embodiments, $VCAM_{in}$ and/or $VCAM_{out}$ are physically coupled to a frame, such as an eyeglasses frame or an augmented realty device frame. Optionally, the angle between the optical axes of $VCAM_{in}$ and $VCAM_{out}$ is known to the computer, and may be utilized in the detection of the physiological response. Optionally, the angle between the optical axes of $VCAM_{in}$ and $VCAM_{out}$ is fixed.

Due to the proximity of $VCAM_{in}$ to the face, in some embodiments, there may be an acute angle between the optical axis of $VCAM_{in}$ and the ROI (e.g., when the ROI includes a region on the forehead). In order to improve the sharpness of $IM_{ROI}$, $VCAM_{in}$ may be configured to operate in a way that takes advantage of the Scheimpflug principle. In one embodiment, $VCAM_{in}$ includes a sensor and a lens; the sensor plane is tilted by a fixed angle greater than 2° relative to the lens plane according to the Scheimpflug principle in order to capture a sharper image when $VCAM_{in}$ is worn by the user (where the lens plane refers to a plane that is perpendicular to the optical axis of the lens, which may include one or more lenses). Optionally, $VCAM_{in}$ does not occlude the ROI. In another embodiment, $VCAM_{in}$ includes a sensor, a lens, and a motor; the motor tilts the lens relative to the sensor according to the Scheimpflug principle. The tilt improves the sharpness of $IM_{ROI}$ when $VCAM_{in}$ is worn by the user.

In addition to capturing images in the visible spectrum, some embodiments may involve capturing light in the near infrared spectrum (NIR). In some embodiments, $VCAM_{in}$ and/or VCAM$_{out}$ may include optics and sensors that capture light rays in at least one of the following NIR spectrum intervals: 700-800 nm, 700-900 nm, 700-1,000 nm. Optionally, the computer may utilize data obtained in a NIR spectrum interval to detect the physiological response (in addition to or instead of data obtained from the visible spectrum). Optionally, the sensors may be CCD sensors designed to be sensitive in the NIR spectrum and/or CMOS sensors designed to be sensitive in the NIR spectrum.

One advantage of having VCAM$_{in}$ coupled to the frame involves the handling of chromatic aberrations. Chromatic aberrations refract different wavelengths of light at different angles, depending on the incident angle. When VCAM$_{in}$ is physically coupled to the frame, the angle between VCAM$_{in}$ and the ROI is known, and thus the computer may be able to select certain subsets of pixels, which are expected to measure light of certain wavelengths from the ROI. In one embodiment, VCAM$_{in}$ includes a lens and a sensor comprising pixels; the lens generates chromatic aberrations that refract red and blue light rays in different angles; the computer selects, based on the angle between the camera and the ROI (when the user wears the frame), a first subset of pixels to measure the blue light rays reflected from the ROI, and a second subset of pixels to measure the red light rays reflected from the ROI. Optionally, the first and second subsets are not the same. Optionally, VCAM$_{in}$ may include a sensor that captures light rays also in a portion of the NIR spectrum, and the computer selects, based on the angle between VCAM$_{in}$ and the ROI, a third subset of pixels to measure the NIR light rays reflected from the ROI. Optionally, the second and third subsets are not the same.

The computer may utilize various approaches in order to detect the physiological response based on IM$_{ROI}$. Some examples of how such a detection may be implemented are provided in the prior art references mentioned above, which rely on FSCC to detect the physiological response. It is to be noted that while the prior art approaches involve analysis of video obtained from cameras that are not head-mounted, are typically more distant from the ROI than VCAM$_{in}$, and are possibly at different orientations relative to the ROI, the computational approaches described in the prior art used to detect physiological responses can be readily adapted by one skilled in the art to handle IM$_{ROI}$. In some cases, embodiments described herein may provide video in which a desired signal is more easily detectable compared to some of the prior art approaches. For example, given the short distance from VCAM$_{in}$ to the ROI, the ROI is expected to cover a larger portion of the images in IM$_{ROI}$ compared to images obtained by video cameras in some of the prior art references. Additionally, due to the proximity of VCAM$_{in}$ to the ROI, additional illumination that is required in some prior art approaches, such as illuminating the skin for a pulse oximeter to obtain a photoplethysmographic (PPG) signal, may not be needed. Furthermore, given VCAM$_{in}$'s fixed location and orientation relative to the ROI (even when the user makes lateral and/or angular movements), many preprocessing steps that need to be implemented by the prior art approaches, such as image registration and/or face tracking, are extremely simplified in embodiments described herein, or may be foregone altogether.

IM$_{ROI}$ may undergo various preprocessing steps prior to being used by the computer to detect the physiological response and/or as part of the process of the detection of the physiological response. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081. Additionally or alternatively, some embodiments may involve generating feature values based on a single image or a sequence of images. In some examples, generation of feature values from one or more images may involve utilization of some of the various approaches described in this disclosure for generation of high-level and/or low-level image-based features.

The following is a discussion of some approaches that may be utilized by the computer to detect the physiological response based on IM$_{ROI}$. Additionally, implementation-related details may be found in the provided references and the references cited therein. Optionally, IM$_{ENV}$ may also be utilized by the computer to detect the physiological response (in addition to IM$_{ROI}$), as explained in more detail below.

In some embodiments, the physiological response may be detected using signal processing and/or analytical approaches. Optionally, these approaches may be used for detecting repetitive physiological signals (e.g., a heart rate, heart rate variability, or a breathing rate) in IM$_{ROI}$ taken during a certain period. Optionally, the detected physiological response represents the value of the physiological signal of the user during the certain period.

In one example, U.S. Pat. No. 8,768,438, titled "Determining cardiac arrhythmia from a video of a subject being monitored for cardiac function", describes how a heart rate may be determined based on FSCC, which are represented in a PPG signal obtained from video of the user. In this example, a time series signal is generated from video images of a subject's exposed skin, and a reference signal is used to perform a constrained source separation (which is a variant of ICA) on the time series signals to obtain the PPG signal. Peak-to-peak pulse points are detected in the PPG signal, which may be analyzed to determine parameters such as heart rate, heart rate variability, and/or to obtain peak-to-peak pulse dynamics that can be indicative of conditions such as cardiac arrhythmia.

In another example, U.S. Pat. No. 8,977,347, titled "Video-based estimation of heart rate variability", describes how a times-series signal similar to the one described above may be subjected to a different type of analysis to detect the heart rate variability. In this example, the time series data are de-trended to remove slow non-stationary trends from the signal and filtered (e.g., using bandpass filtering). Following that, low frequency and high frequency components of the integrated power spectrum within the time series signal are extracted using Fast Fourier Transform (FFT). A ratio of the low and high frequency of the integrated power spectrum within these components is computed. And analysis of the dynamics of this ratio over time is used to estimate heart rate variability.

In yet another example, U.S. Pat. No. 9,020,185, titled "Systems and methods for non-contact heart rate sensing", describes how a times-series signals obtained from video of a user can be filtered and processed to separate an underlying pulsing signal by, for example, using an ICA algorithm. The separated pulsing signal from the algorithm can be transformed into frequency spacing data using FFT, in which the heart rate can be extracted or estimated.

In some embodiments, the physiological response may be detected using machine learning-based methods. Optionally, these approaches may be used for detecting expressions of emotions and/or values of physiological signals.

Generally, machine learning-based approaches involve training a model on samples, with each sample including: feature values generated based on IM$_{ROI}$ taken during a certain period, and a label indicative of the physiological response during the certain period. Optionally, the model may be personalized for a user by training the model on samples including: feature values generated based on $IM_{ROI}$ of the user, and corresponding labels indicative of the user's respective physiological responses. Some of the feature values in a sample may be generated based on other sources of data (besides $IM_{ROI}$), such as measurements of the user generated using thermal cameras, movement sensors, and/or other physiological sensors, and/or measurements of the environment. Optionally, $IM_{ROI}$ of the user taken during an earlier period may serve as a baseline to which to compare. Optionally, some of the feature values may include indications of confounding factors, which may affect FSCC, but are unrelated to the physiological response being detected. Some examples of confounding factors include touching the face, thermal radiation directed at the face, and consuming certain substances such as a medication, alcohol, caffeine, or nicotine.

Training the model may involve utilization of various training algorithms known in the art (e.g., algorithms for training neural networks and/or other approaches described herein). After the model is trained, feature values may be generated for $IM_{ROI}$ for which the label (physiological response) is unknown, and the computer can utilize the model to detect the physiological response based on these feature values.

It is to be noted that in some embodiments, the model is trained based on data that includes measurements of the user, in which case it may be considered a personalized model of the user. In other embodiments, the model is trained based on data that includes measurements of one or more other users, in which case it may be considered a general model.

In order to achieve a robust model, which may be useful for detecting the physiological response in various conditions, in some embodiments, the samples used in the training may include samples based on $IM_{ROI}$ taken in different conditions and include samples with various labels (e.g., expressing or not expressing certain emotions, or different values of physiological signals). Optionally, the samples are generated based on $IM_{ROI}$ taken on different days.

The following are four examples of different compositions of samples that may be used when training the model in different embodiments. The "measured user" in the four examples below may be "the user" who is mentioned above (e.g., when the model is a personalized model that was trained on data that includes measurements of the user), or a user from among one or more other users (e.g., when the model is a general model that was trained on data that includes measurements of the other users). In a first example, the system does not occlude the ROI, and the model is trained on samples generated from a first set of $IM_{ROI}$ taken while the measured user was indoors and not in direct sunlight, and is also trained on other samples generated from a second set of $IM_{ROI}$ taken while the measured user was outdoors, in direct sunlight. In a second example, the model is trained on samples generated from a first set of $IM_{ROI}$ taken during daytime, and is also trained on other samples generated from a second set of $IM_{ROI}$ taken during nighttime. In a third example, the model is trained on samples generated from a first set of $IM_{ROI}$ taken while the measured user was exercising and moving, and is also trained on other samples generated from a second set of $IM_{ROI}$ taken while the measured user was sitting and not exercising. And a fourth example, the model is trained on samples generated from a first set of $IM_{ROI}$ taken less than 30 minutes after the measured user had an alcoholic beverage, and is also trained on other samples generated from a second set of $IM_{ROI}$ taken on a day in which the measured user did not have an alcoholic beverage.

Labels for the samples may be obtained from various sources. In one embodiment, the labels may be obtained utilizing one or more sensors that are not $VCAM_{in}$. In one example, a heart rate and/or heart rate variability may be measured using an ECG sensor. In another example, the breathing rate may be determined using a smart shirt with sensors attached to the chest (e.g., a smart shirt by Hexoskin®). In yet another example, a type emotional response of the user may be determined based on analysis of a facial expression made by the user, analysis of the user's voice, analysis of thermal measurements of regions of the face of the user, and/or analysis of one or more of the following sensor-measured physiological signals of the user: a heart rate, heart rate variability, breathing rate, and galvanic skin response.

In another embodiment, a label describing an emotional response of the user may be inferred. In one example, the label may be based on semantic analysis of a communication of the user, which is indicative of the user's emotional state at the time $IM_{ROI}$ were taken. In another example, the label may be generated in a process in which the user is exposed to certain content, and a label is determined based on an expected emotional response corresponding to the certain content (e.g., happiness is an expected response to a nice image while distress is an expected response to a disturbing image).

Due to the nature of the physiological responses being detected and the type of data (video images), a machine learning approach that may be applied in some embodiments is "deep learning". In one embodiment, the model may include parameters describing multiple hidden layers of a neural network. Optionally, the model may include a convolution neural network (CNN). In one example, the CNN may be utilized to identify certain patterns in the video images, such as the patterns of the reflected FSCC due to the physiological response. Optionally, detecting the physiological response may be done based on multiple, possibly successive, images that display a certain pattern of change over time (i.e., across multiple frames), which characterizes the physiological response being detected. Thus, detecting the physiological response may involve retaining state information that is based on previous images. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

Some of the prior art references mentioned herein provide additional detailed examples of machine learning-based approaches that may be utilized to detect the physiological response (especially in the case in which it corresponds to an emotional response). In one example, Ramirez, et al. ("Color analysis of facial skin: Detection of emotional state") describe detection of an emotional state using various machine learning algorithms including decision trees, multinomial logistic regression, and latent-dynamic conditional random fields. In another example, Wang, et al. ("Microexpression recognition using color spaces") describe various feature extraction methods and pixel color value transformations, which are used to generate inputs for a support vector machine (SVM) classifier trained to identify microexpressions.

As mentioned above, in some embodiments, $IM_{ENV}$ may be utilized in the detection of the physiological response to account, at least in part, for illumination interferences that may lead to errors in the detection of the physiological response. There are different ways in which $IM_{ENV}$ may be utilized for this purpose.

In one embodiment, when variations in $IM_{ENV}$ reach a certain threshold (e.g., which may correspond to ambient light variations above a certain extent), the computer may refrain from detecting the physiological response.

In another embodiment, $IM_{ENV}$ may be utilized to normalize $IM_{ROI}$ with respect to the ambient light. For example, the intensity of pixels in $IM_{ROI}$ may be adjusted based on the intensity of pixels in $IM_{ENV}$ when $IM_{ROI}$ were taken. US patent application number 20130215244 describes a method of normalization in which values of pixels from a region that does not contain a signal (e.g., background regions that include a different body part of the user or an object behind the user) are subtracted from regions of the image that contain the signal of the physiological response. While the computational approach described therein may be applied to embodiments in this disclosure, the exact setup described therein may not work well in some cases due to the close proximity of $VCAM_{in}$ to the face and the fact that $VCAM_{in}$ is head-mounted. Thus, it may be advantageous to subtract a signal from the environment ($IM_{ENV}$) that is obtained from $VCAM_{out}$, which may more accurately represent the ambient light illuminating the face.

It is to be noted that training data that includes a ground-truth signal (i.e., values of the true physiological response corresponding to $IM_{ROI}$ and $IM_{ENV}$) may be utilized to optimize the normalization procedure used to correct $IM_{ROI}$ with respect to the ambient light measured in $IM_{ENV}$. For example, such optimization may be used to determine parameter values of a function that performs the subtraction above, which lead to the most accurate detections of the physiological response.

In still another embodiment, $IM_{ENV}$ may be utilized to generate feature values in addition to $IM_{ROI}$. Optionally, at least some of the same types of feature values generated based on $IM_{ROI}$ may also be generated based on $IM_{ENV}$. Optionally, at least some of the feature values generated based on $IM_{ENV}$ may relate to portions of images, such as average intensity of patches of pixels in $IM_{ENV}$.

By utilizing $IM_{ENV}$ as inputs used for the detection of the physiological response, a machine learning-based model may be trained to be robust, and less susceptible, to environmental interferences such as ambient light variations. For example, if the training data used to train the model includes samples in which no physiological response was present (e.g., no measured emotional response or microexpression was made), but some ambient light variations might have introduced some FSCC-related signal, the model will be trained such that feature values based on $IM_{ENV}$ are used to account for such cases. This can enable the computer to negate, at least in part, the effects of such environmental interferences, and possibly make more accurate detections of the physiological response.

In one embodiment, the computer receives an indication indicative of the user consuming a confounding substance that is expected to affect FSCC (e.g., alcohol, drugs, certain medications, and/or cigarettes). The computer detects the physiological response, while the consumed confounding substance affects FSCC, based on: $IM_{ROI}$, the indication, and a model that was trained on: a first set of $IM_{ROI}$ taken while the confounding substance affected FSCC, and a second set of $IM_{ROI}$ taken while the confounding substance did not affect FSCC.

Prior art FSCC systems are sensitive to user movements and do not operate well while the user is running. This is because state-of-the-art FSCC systems use hardware and automatic image trackers that are not accurate enough to crop correctly the ROI from the entire image while running, and the large errors in cropping the ROI are detrimental to the performances of the FSCC algorithms. Contrary to the prior art FSCC systems, the disclosed $VCAM_{in}$ remains pointed at its ROI also when the user's head makes angular and lateral movements, and thus the complicated challenges related to image registration and ROI tracking are much simplified or even eliminated Therefore, systems based on $VCAM_{in}$ (such as the one illustrated in FIG. 60) may detect the physiological response (based on FSCC) also while the user is running.

$VCAM_{in}$ may be pointed at different regions on the face. In a first embodiment, the ROI is on the forehead, $VCAM_{in}$ is located less than 10 cm from the user's face, and optionally the optical axis of $VCAM_{in}$ is above 20° from the Frankfort horizontal plane. In a second embodiment, the ROI is on the nose, and $VCAM_{in}$ is located less than 10 cm from the user's face. Because $VCAM_{in}$ is located close to the face, it is possible to calculate the FSCC based on a small ROI, which is irrelevant to the non-head-mounted prior arts that are limited by the accuracy of their automatic image tracker. In a third embodiment, $VCAM_{in}$ is pointed at an eye of the user. The computer selects the sclera as the ROI and detects the physiological response based on color changes recognizable in $IM_{ROI}$ of the sclera. In a fourth embodiment, $VCAM_{in}$ is pointed at an eye of the user. The computer selects the iris as the ROI and detects the physiological response based on color changes recognizable in $IM_{ROI}$ of the iris. Optionally, the computer further calculates changes to the pupil diameter based on the $IM_{ROI}$ of the iris, and detects an emotional response of the user based on the changes to the pupil diameter.

In order to improve the detection accuracy, and in some cases in order to better account for interferences, the computer may utilize measurements of one or more head-mounted thermal cameras in the detection of the physiological response. In one embodiment, the system may include an inward-facing head-mounted thermal camera that takes thermal measurements of a second ROI ($TH_{ROI2}$) on the user's face. Optionally, ROI and $ROI_2$ overlap, and the computer utilizes $TH_{ROI2}$ to detect the physiological response. Optionally, on average, detecting the physiological response based on both FSCC recognizable in $IM_{ROI}$ and $TH_{ROI2}$ is more accurate than detecting the physiological response based on the FSCC without $TH_{ROI3}$. Optionally, the computer utilizes $TH_{ROI3}$ to account, at least in part, for temperature changes, which may occur due to physical activity and/or consumption of certain medications that affect the blood flow. Optionally, the computer utilizes $TH_{ROI3}$ by generating feature values based on $TH_{ROI2}$, and utilizing a model that was trained on data comprising $TH_{ROI2}$ in order to detect the physiological response.

In another embodiment, the system may include an outward-facing head-mounted thermal camera that takes thermal measurements of the environment ($TH_{ENV}$). Optionally, the computer may utilize $TH_{ENV}$ to detect the physiological response (e.g., by generating feature values based on $TH_{ENV}$ and utilizing a model trained on data comprising $TH_{ENV}$).

Optionally, on average, detecting the physiological response based on both FSCC recognizable in $IM_{ROI}$ and $TH_{ENV}$ is more accurate than detecting the physiological response based on the FSCC without $TH_{ENV}$. Optionally, the computer utilizes $TH_{ENV}$ to account, at least in part, for thermal interferences from the environment, such as direct sunlight and/or a nearby heater.

In addition to detecting a physiological response, in some embodiments, the computer may utilize $IM_{ROI}$ to generate an avatar of the user (e.g., in order to represent the user in a virtual environment). Optionally, the avatar may express emotional responses of the user, which are detected based on $IM_{ROI}$. Optionally, the computer may modify the avatar of the user to show synthesized facial expressions that are not manifested in the user's actual facial expressions. In one embodiment, the synthesized facial expressions correspond to emotional responses detected based on FSCC that are recognizable in $IM_{ROI}$. In another embodiment, the synthesized facial expressions correspond to emotional responses detected based on thermal measurements taken by CAM. Some of the various approaches that may be utilized to generate the avatar based on $IM_{ROI}$ are described in co-pending US patent publication 2016/0360970.

The following method for detecting a physiological response based on facial skin color changes (FSCC) may be used by systems modeled according to FIG. 60. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking images of a region of interest ($IM_{ROI}$) on a user's face utilizing an inward-facing head-mounted visible-light camera ($VCAM_{in}$). The ROI is illuminated by ambient light.

And in Step 2, detecting the physiological response based on FSCC recognizable in $IM_{ROI}$. Optionally, detecting the physiological response involves generating feature values based on $IM_{ROI}$ and utilizing a model to calculate, based on the feature values, a value indicative of an extent of the physiological response. Optionally, the model was trained based on $IM_{ROI}$ of the user taken during different days.

In one embodiment, the method may optionally include a step of taking images of the environment ($IM_{ENV}$) utilizing an outward-facing head-mounted visible-light camera ($VCAM_{out}$). Optionally, detecting the physiological response is also based on $IM_{ENV}$.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 34:
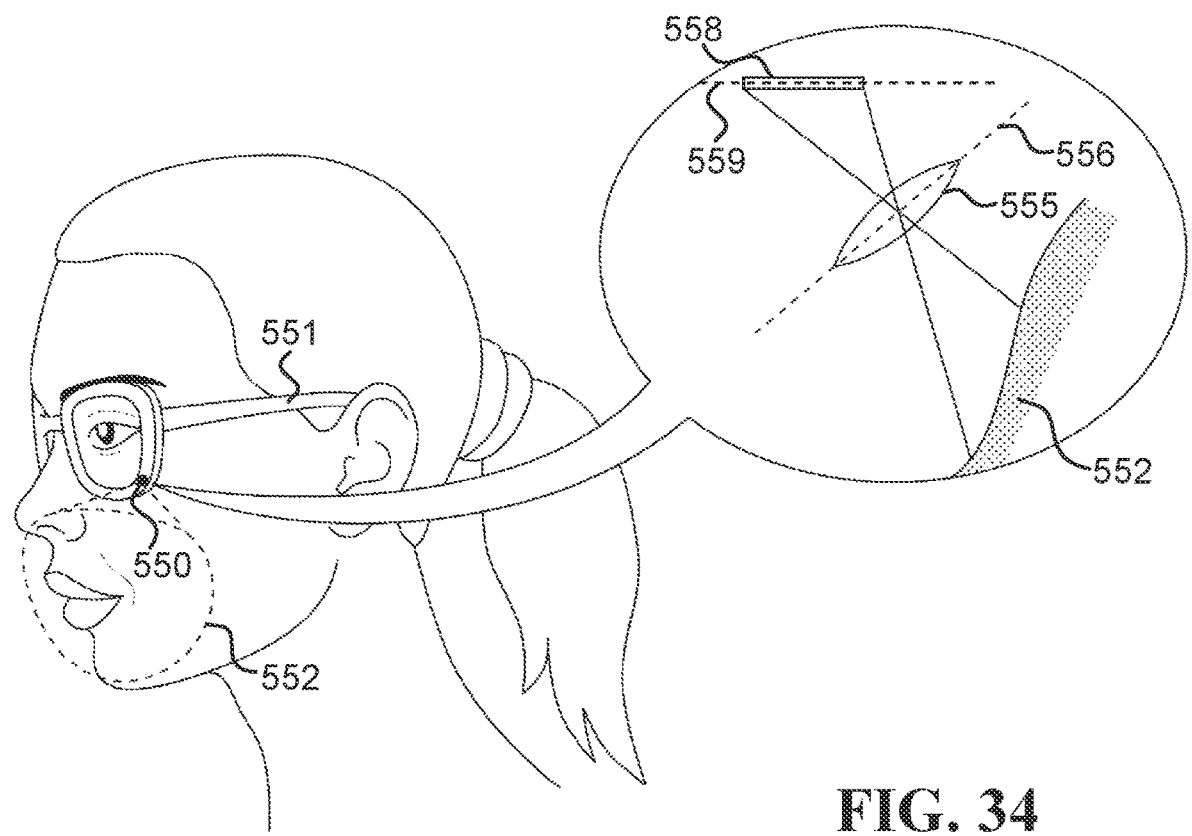
FIG. 34 is a schematic illustration of an inward-facing head-mounted camera embedded in an eyeglasses frame, which utilizes the Scheimpflug principle.

FIG. 34 is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 35:
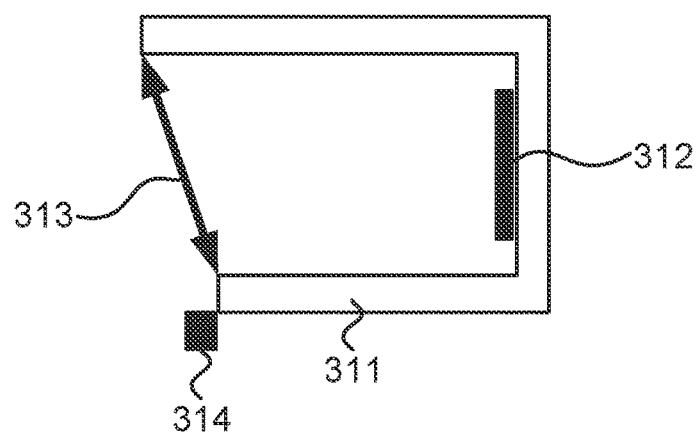
FIG. 35 is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 35 is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological response (which may be the user's emotional response in some cases). In one embodiment, the ROI covers first and second areas, where the first area includes finer details and/or is more important for detecting the physiological response than the second area. Therefore, the tilt between the lens and sensor planes is adjusted such that the image of the first area is shaper than the image of the second area.

In another embodiment, the ROI covers both a first area on the upper lip and a second area on a cheek, and the tilt is adjusted such that the image of the first area is shaper than the image of the second area, possibly because the upper lip usually provides more information and has more details relative to the cheek.

In still another embodiment, the ROI covers both a first area on the upper lip and a second area on the nose, and the tilt is adjusted such that the image of the first area is shaper than the image of the second area, possibly because the upper lip usually provides more information relative to the nose.

In still another embodiment, the ROI covers a first area on the cheek straight above the upper lip, a second area on the cheek from the edge of the upper lip towards the ear, and a third area on the nose. And the tilt between the lens plane and the sensor plane is adjusted such that the image of the first area is shaper than both the images of the second and third areas.

In still another embodiment, the ROI covers both a first area on the lips and a second area on the chin, and the tilt is adjusted such that the image of the first area is shaper than the image of the second area, possibly because the lips usually provides more information than the chin.

In still another embodiment, the camera is a visible-light camera, and the ROI covers both a first area on the lower forehead (including an eyebrow) and a second area on the upper forehead, and the tilt is adjusted such that the image of the first area is shaper than the image of the second area, possibly because the eyebrow provides more information about the user's emotional response than the upper forehead.

In still another embodiment, the camera is a thermal camera, and the ROI covers an area on the forehead, and the tilt is adjusted such that the image of a portion of the middle and upper part of the forehead (below the hair line) is shaper than the image of a portion of the lower part of the forehead, possibly because the middle and upper parts of the forehead are more indicative of prefrontal cortex activity than the lower part of the forehead, and movements of the eyebrows disturb the thermal measurements of the lower part of the forehead.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle; (ii) a device that changes the angle of the lens relative to the sensor; and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various types of cameras may be utilized in different embodiments described herein. In one embodiment, the camera is a thermal camera that takes thermal measurements of the ROI with a focal plane array thermal sensor having an angle above 2° between the lens and sensor planes. Optionally, the thermal camera weighs below 10 g, is located less than 10 cm from the user's face, and the tilt of the lens plane relative to the sensor plane is fixed. The fixed tilt is selected according to an expected orientation between the camera and the ROI when the user wears the frame. Optionally, the system includes a computer to detect a physiological response based on the thermal measurements. Optionally, the computer processes time series measurements of each sensing element individually to detect the physiological response.

In another embodiment, the camera is a visible-light camera that takes visible-light images of the ROI, and a computer generates an avatar for the user based on the visible-light images. Some of the various approaches that may be utilized to generate the avatar based on the visible-light images are described in co-pending US patent publication 2016/0360970. Additionally or alternatively, the computer may detect an emotional response of the user based on (i) facial expressions in the visible-light images utilizing image processing, and/or (ii) facial skin color changes (FSCC), which result from concentration changes of hemoglobin and/or oxygenation.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of the visible-light cameras to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions" IEEE transactions on pattern analysis and machine intelligence 31.1 (2009): 39-58, describes some of the algorithmic approaches that may be used for this task. The following references discuss detection of emotional responses based on FSCC: (i) Ramirez, Geovany A., et al. "Color analysis of facial skin: Detection of emotional state" in Proceedings of the IEEE Conference on Computer Vision and Pattern Recognition Workshops, 2014; and (ii) Wang, Su-Jing, et al. "Micro-expression recognition using color spaces", in IEEE Transactions on Image Processing 24.12 (2015): 6034-6047.

In still another embodiment, the camera is a light field camera that implements a predetermined blurring at a certain Scheimpflug angle, and decodes the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug adjustment gets better, and vice versa. Additionally or alternatively, the autofocusing may use the variance of the neighborhood around each pixel as a measure of sharpness, where a proper Scheimpflug adjustment should increase the variance.

Thermal and/or FSCC patterns corresponding to physiological responses may show high variability between different users due to variability of the their brains, blood vessel locations, skin properties, hair, physical conditions, and face shapes and sizes. Thus, patterns and/or various extractable features from one user's thermal and/or FSCC data may not be easily transferable to another user, or even to the same user under different physiological and/or mental conditions. Therefore, some of the embodiments described herein involve training personalized models involving thermal and/or FSCC patterns that are predictive of various user-defined categories of experiencing and/or perceiving certain events. Personalized models can overcome some of the possible disadvantages of using normed physiological statistics, which paves the way for personalized training, detection, and therapies, which are able to account for arbitrary user-defined physiological and/or mental states corresponding to a wide variety of individual needs. Leveraging machine learning algorithms can enable assignment of arbitrary user-defined physiological and/or mental states to recorded thermal and/or FSCC data during day-to-day activities, which are later used as basis for automatic detection and/or therapies for the user, optionally without involving a clinician.

The personalized model does not need to correspond to a standard universally applicable pattern, and thus the user may be free to define his/her arbitrary user-defined physiological and/or mental states. In other words, in addition to (or instead of) detecting a state that corresponds to some arbitrary population average, the personalized model allows a personalized detection of a user-defined state.

One embodiment in which a personalized model is utilized involves a training phase and an operation phase. In the training phase, the system identifies desired and/or undesired physiological and/or mental states of the user using active methods (e.g., the user presses a button) and/or passive methods (e.g., applying semantic analysis to the user's speech and typing). The system may also continue to update the personalized model to accommodate for changes over time, to supports increased efficacy, and to identify new personalized states beyond those represented by population average. Instead of relying on a model trained based on data obtained from a wide population, the personalized model may decouple commonly coupled ROIs and/or putative physiological responses from the applications, allowing the user to train the system to detect arbitrary personalized thermal and/or FSCC patterns that may not suite the wide population. Training the personalized model may be based on known machine learning methods such as neural networks, supervised machine learning, pattern recognition, pattern matching, etc. The system may detect, predict, and train for the arbitrary user-defined physiological and/or mental states, identified by personalized thermal and/or FSCC patterns, not limited to averages obtained from a wide population.

In the operation phase, the system alerts, predicts, and/or treats the user based on the personalized model. The system may alert when the user is in the desired/undesired state, predict when the user is going to be in that state, and treat the user to get into a desired state or avoid an undesired state by providing a feedback. The operation phase may include known biofeedback/neurofeedback interactive sessions tuned to guide the user towards the user-defined personalized physiological and/or mental states. For example, the personalized model may be trained to guide the user towards flow, creativity, curiosity, compassion, and/or happiness states, as defined and experienced by the user, and to alert against anger, aggression, boredom, and/or sadness, also as defined and experienced by the user, without these necessarily being suitable for the wide population.

One embodiment of a method for personalized thermal and/or FSCC detection includes a timestamping step, a machine learning step, a refinement step, an optional detection step, and an optional biofeedback step (where biofeedback refers also to neurofeedback).

In the timestamping step, an HMS records arbitrary user-defined physiological and/or mental states for personal use. The user may provide, via a user interface, timestamped markers on the recorded data used as labels by machine learning approaches for detecting target user-defined physiological and/or mental states (which may be desired or undesired states). When the user engages in a certain task, and as the user enters a target state, the user may (via a user interface) manual provide a timestamp to mark the time of entering into the target state, and/or the computer may set an automated timestamp based on inferring the entering into the target state from the user's performance and/or activities (for example, using predetermined limits of performance that once reached automatically trigger timestamping the recorded data as entering into the target state). Upon leaving the target state, the user may provide a timestamp to mark the leaving of the target state, and/or the computer may set an automated timestamp based on inferring the leaving of the target state from the user's performance and/or activities. Several iterations involving timestamping of entering and leaving the target state may complete the timestamping step.

In the machine learning step, the computer extracts and selects features from the thermal and/or FSCC measurements, labels the extracted and selected features according to the timestamps, and tries one or more machine learning algorithms to train a classifier, while treating the measurements as the training and testing sets. Optionally, for unique personalized states, the machine learning algorithm may be optimized for cross-validation by splitting the training set into a first part used for training and a second part used for testing. In addition, testing sets comprising data of other users may be used to measure the classifier's generality. The following examples illustrate various ways to label the HMS measurements based on the timestamps.

In a first example, the computer may (i) label as "not desired" $TH_{ROI}$ taken before receiving from the user a first timestamp marking the entering into a desired state, (ii) label as "desired" $TH_{ROI}$ taken after receiving the first timestamp and before receiving a second timestamp marking the leaving of the desired state, and (iii) label as "not desired" $TH_{ROI}$ taken after receiving the second timestamp. Optionally, the computer may label as "unknown" $TH_{ROI}$ taken sufficiently before receiving the first timestamp and $TH_{ROI}$ taken sufficiently after receiving the second timestamp.

In a second example, the computer may (i) label as "leading to headache" $TH_{ROI}$ taken during a first window of time before receiving from the user a first timestamp marking occurrence of a headache, (ii) label as "headache" $TH_{ROI}$ taken after receiving the first timestamp and until a second window before receiving from the user a second timestamp marking "no headache", (iii) label as "headache leaving" $TH_{ROI}$ taken during the second window, and (iv) label as "no headache" $TH_{ROI}$ taken after receiving the second timestamp.

In a third example, the computer may (i) label as "leading to asthma attack" $TH_{breath}$ indicative of the user's breathing pattern (such as thermal measurements of a region on the upper lip) taken during a first window before identifying that the user uses a first inhaler, (ii) label as "first inhaler immediate effect" $TH_{breath}$ taken during a second window after using the first inhaler, (iii) label as "first inhaler long effect" $TH_{breath}$ taken during a third window following the second window, and (iv) label as "second inhaler immediate effect" $TH_{breath}$ taken during a fourth window after identifying that the user uses a second inhaler Optionally, the computer may use the automated labeling for assessing the user's reaction to using the first inhaler vs using the second inhaler.

In a fourth example, the computer may (i) label as "building concentration" $TH_{breath}$ indicative of the user's breathing pattern and $TH_{forehead}$ indicative of a thermal pattern on the user's forehead taken while the user's software agent indicates that the user does not check distracting websites (such as social networks, news and email) but the user's gaze is not essentially continuously focused on the screen, (ii) label as "concentrated" $TH_{breath}$ and $TH_{forehead}$ taken while the software agent indicates that the user's gaze is continuously focused on the screen and until a certain duration before the user lost concentration, and (iii) label as "start losing concentration" $TH_{breath}$ and $TH_{forehead}$ taken during the certain duration.

In a fifth example, the computer may (i) label as "possibly happy" $TH_{ROI}$ and FSCC taken during a first window before a speech analysis module provides a timestamp that the user is happy, (ii) label as "happy" $TH_{ROI}$ and FSCC taken during a second window after receiving the timestamp, and (iii) label as "angry" $TH_{ROI}$ and FSCC taken during a third window after the speech analysis module provides a timestamp that the user is angry.

In the refinement step, the computer starts guessing the physiological and/or mental states, and asks the user to confirm correct, incorrect, or inapplicable status of the guesses. The refinement step increases fidelity the more it is performed.

In the optional detection step, the computer analyzes in real time feature values generated based on the thermal and/or FSCC measurements in order to alert the user about entering and/or leaving a target state. For example, the computer permits administration of pain medication to the user after the classifier determines that the user experiences pain above a threshold previously determined by the user during the timestamping step. This may reduce addiction by reducing unnecessary administrations of higher dose pain medication. Additionally, the user may be trained to control his/her pain perception during the biofeedback step, which may be more effective after a personalized model has been applied.

In the optional biofeedback step, the computer generates a feedback for the user based on the personalized target state. The biofeedback step may use a standard biofeedback protocol, but instead of training the user towards achieving externally derived thermal and/or FSCC target patterns that suit the wide population, the user is trained to achieve personalized thermal and/or FSCC target patterns that most closely resemble the thermal and/or FSCC patterns found to be predictive during the timestamping and refinement steps.

In one embodiment, the user labels during the timestamping step pairs of undesired and desired states (such as pain vs no pain, migraine vs no migraine, angry vs calmed, stressed vs calmed, concentrated vs not concentrated, sad vs happy, self-focused vs compassionate). Then the biofeedback step trains the user to move out of the undesired state by (i) encouraging changes that bring the current measured thermal and/or FSCC pattern closer to the desired personalized thermal and/or FSCC pattern found to be predictive during the timestamping and refinement steps, and (ii) discouraging changes that bring the current measured thermal and/or FSCC pattern closer to the undesired personalized thermal and/or FSCC pattern found to be predictive during the timestamping and refinement steps.

The following is one example of the information flow in an HMS that includes a head-mounted thermal camera and a computer. In the timestamping step, the head-mounted thermal camera takes thermal measurements, and the user (or computer) adds manual (or automated) timestamps for entering and/or leaving a target state. The timestamping step feeds the machine learning step, in which a machine learning-based training algorithm is used to train a personalized model that is evaluated against user measurements in known states. The machine learning step feeds the refinement step with processed data and questions, and in the refinement step the user answers whether the machine learning algorithm has correctly detected the user's state. Both the machine learning step and the refinement step may provide data to the optional detection and biofeedback steps (which may communicate with each other).

Big data analysis may be performed to identify trends and detect new correlations over users and populations, together with other sources of information, such as other wearable devices (e.g., smart watches, smart shirts, EEG headsets, smart earphones), mobile devices (e.g., smartphone, laptop), and other sources of information (e.g., social networks, search engines, bots, software agents, medical records, IoT devices).

Various embodiments described herein involve an HMS that may be connected, using wires and/or wirelessly, with a device carried by the user and/or a non-wearable device. The HMS may include a battery, a computer, sensors, and a transceiver.

Figure 70A:
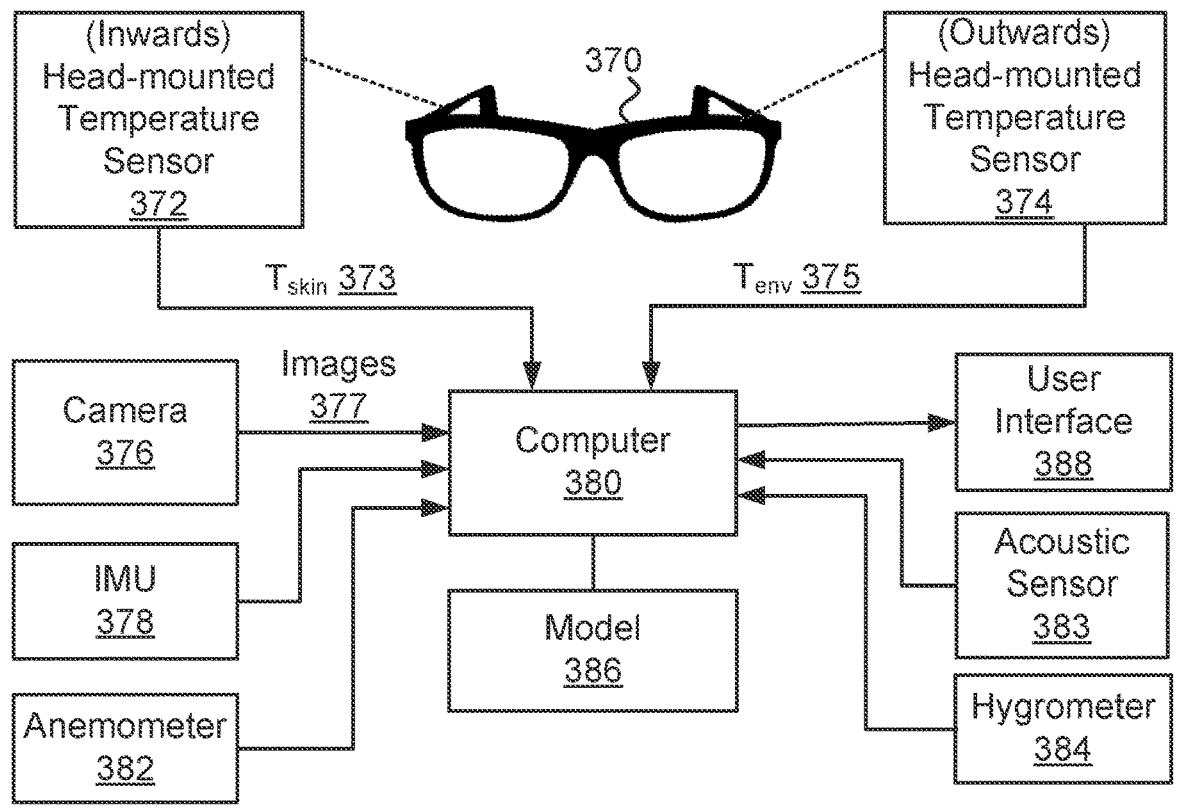
FIG. 70A is a schematic illustration of components of additional embodiments of a system to detect fever and/or intoxication.

FIG. 70A is a schematic illustration of components of additional embodiments of a system configured to detect fever and/or intoxication (e.g., due to alcohol consumption). In one embodiment, a system that detects fever includes at least a first head-mounted temperature sensor 372 that is configured to measure skin temperature ($T_{skin}$ 373) at a first region on a user's head, and a second head-mounted temperature sensor 374 that is configured to measure a temperature of the environment ($T_{env}$ 375). Optionally, the first region covers a portion of skin that is not located above a portion of a branch of the external carotid artery. Optionally, these temperature sensors are physically coupled to a frame of smartglasses 370. The system also includes a computer 380, which may or may not be physically coupled to the frame of the smartglasses 370. The system may include additional elements such as a movement sensor (e.g., inertial measurement unit (IMU) 378), a camera 376 that is sensitive to wavelengths below 1050 nanometer, an anemometer 382, an acoustic sensor 383, a hygrometer 384, and/or a user interface 388.

In one embodiment, the computer 380, receives images 377 of a second region on the user's face, captured by the camera 376, and calculates, based on the images 377, values indicative of hemoglobin concentrations at three or more regions on the user's face. The computer 380 then detects whether the user has a fever based on $T_{skin}$ 373, $T_{env}$ 375, and the values. Additionally or alternatively, the computer 380 may detect whether the user was sober, based on $T_{skin}$ 373, $T_{env}$ 375, and the values.

Various configurations of sensors may be utilized in embodiments described herein to measure various regions on the user's face. In one embodiment, the first region at which $T_{skin}$ 373 are measured, covers a portion of skin that is not located above a portion of a branch of the external carotid artery. In another embodiment, the second head-mounted temperature sensor 374 is an outward-facing thermal camera configured to measure levels of radiation directed at the user's head.

In still another embodiment, the first head-mounted temperature sensor 372 is a contact temperature sensor (e.g., a thermistor), the second region is larger than 3 cm², and the camera 376 is not head-mounted. Optionally, in this embodiment, the camera 376 captures images 377 from a distance that is farther than 5 cm from the user's head. Some examples of cameras that are not head-mounted that may be used in this embodiment include a smartphone camera, a laptop camera, a webcam, and a security camera.

In yet another embodiment, the first head-mounted temperature sensor 372 may include an inward-facing thermal camera located more than 2 mm away from the user's head, the second region is larger than 2 cm², and the camera 376 is an inward-facing head-mounted camera that captures the images 377 from a distance between 5 mm and 5 cm from the user's head.

In one example, the first head-mounted temperature sensor 372 is physically coupled to the frame of the smartglasses 370, and the first region is located on the user's nose or temple. In another example, the first head-mounted temperature sensor 372 is physically coupled to a helmet or goggles, and the first region is located on the user's forehead, cheekbone, and/or temple.

The temperature of the environment may be measured by a head-mounted sensor and/or by a sensor that is not head-mounted. In some cases, the region that includes skin on the user's head may have a different temperature from another region that includes skin below the user's head. For example, when sitting nearby a window where the head is exposed to direct sunlight while the hands are not exposed to the direct sunlight, or when sitting nearby a heater where the head and certain lower parts of the body absorb different amounts of directed infrared radiation. In such cases, utilizing a head-mounted temperature sensor to measure the temperature of the environment is preferred over a non-head mounted temperature sensor to measure the temperature of the environment.

Examples of possible embodiments for a sensor that measures the temperature of the environment include: (i) a head-mounted non-contact temperature sensor, such as a thermopile or a microbolometer sensor, (ii) a head-mounted contact temperature sensor, such as a thermistor or a thermocouple, (iii) a wearable sensor that is not head-mounted, which may utilize a contact and/or a non-contact sensor, and/or (iv) a non-wearable sensor which may utilize a contact and/or a non-contact sensor.

In some embodiments, in which the camera 376 is an inward-facing head-mounted camera, the camera 376 may have the same properties as other inward-facing head-mounted cameras described herein, such as the cameras 332. In some embodiments, the images 377 may have various properties that are attributed herein to images taken with visible-light cameras, such as the properties attributed to the images 333. Optionally, the images 377 may be processed in various ways described herein for image processing. For example, the computer 380 may utilize one or more of the techniques described with regards to processing the images 333, in order to assist in calculating hemoglobin concentration patterns.

In some embodiments, various processing procedures known in the art, such as face tracking, image recognition, and/or facial landmark discovery may be utilized to process the images 377. Optionally, these procedures are applied when the camera 376 is not a head-mounted camera.

The computer 380 is configured, in some embodiments, to detect a certain condition (e.g., whether the user has a fever or whether the user is intoxicated) based on a $T_{skin}$ 373, $T_{env}$ 375, and the values indicative of hemoglobin concentrations at three or more regions on the user's face, which are calculated based on the images 377.

In different embodiments, a reference to "the computer 380" may refer to different components and/or a combination of components. In some embodiments, the computer 380 may include a processor located on a head-mounted device, such as the smartglasses 370. In other embodiments, at least some of the calculations attributed to the computer 380 may be performed on a remote processor, such as the user's smartphone and/or a cloud-based server. Thus, references to calculations being performed by the "computer 380" should be interpreted as calculations being performed utilizing one or more computers, with some of these one or more computers possibly being attached to a head-mounted device to which the first head-mounted temperature sensor 372 is coupled.

Calculating the values indicative of hemoglobin concentrations at three or more regions on the user's face may be done utilizing the various teachings described herein regarding calculating patterns indicative of hemoglobin concentrations at different regions (e.g., calculations described herein as being performed by the computer 340 on at least some of the images 333 in order to calculate a baseline and/or current pattern). In one example, the middles of the three or more regions are at least 3 mm apart from each other. In another example, the middles of the three or more regions are at least 1 cm apart from each other. In yet another example, the middles of the three or more regions are at least 3 cm apart from each other. Optionally, the values indicative of the hemoglobin concentrations at three or more regions on the user's face may include values calculated based on different channels of the images 377. Optionally, the images 377 used to calculate the values are taken during a window in time, such as a window that is at most five second long. Optionally, the window is at most 30 seconds long. Optionally, the window is at most 5 minutes long. Optionally, the window is at most one hour long.

In one embodiment, the computer 380 may optionally calculate the values indicative of hemoglobin concentrations based on detecting facial flushing patterns in the images. Optionally, the camera 376 in this embodiment may be an inward-facing head-mounted camera that captures the images 377 from a distance between 5 mm and 5 cm from the user's head, and the second region is larger than 2 cm$^2$.

In another embodiment, the computer 380 may optionally calculate the values indicative of hemoglobin concentrations based on detecting imaging photoplethysmogram signals in the images. Optionally, the camera 376 in this embodiment may also be an inward-facing head-mounted camera that captures the images 377 from a distance between 5 mm and 5 cm from the user's head.

As discussed in more detail above in this disclosure, detection of reflections of light at different wavelengths can be used to account for thermal interference by the environment. To this end, in some embodiments, the computer 380 may calculate separate values indicative of hemoglobin concentrations from the images 377, which correspond to different channels in the images 377. In one embodiment, the images 377 include a first channel corresponding to wavelengths that are mostly below 580 nanometers and a second channel corresponding to wavelengths mostly above 580 nanometers. In this embodiment, the computer 380 calculates the values indicative of hemoglobin concentrations, which include the following: (i) first values derived based on the first channel in the images, and (ii) second values derived based on the second channel in the images. Having separate values for different wavelengths enables to account for interference from the environment when detecting whether the user has the fever because temperature interference from the environment is expected to affect the first values more than the second values. Optionally, the computer 380 also calculates a confidence in a detection of the fever, such that the confidence decreases as the difference between the first values and the second values increases.

Detection of whether the user has a fever and/or is intoxicated may involve utilization of machine learning approaches. In some embodiments, the computer 380 generates feature values based on $T_{skin}$ 373, $T_{env}$ 375, and the values indicative of hemoglobin concentrations at three or more regions on the user's face (which are calculated based on the images 377). These feature values are utilized by the computer 380 in a machine learning-based approach to detect whether the user has a fever and/or whether the user is intoxicated. Optionally, the computer 380 utilizes a model 386 to calculate, based on the feature values, a value indicative of whether the user has a fever and/or a value indicative of whether the user is intoxicated.

As discussed above with reference to similar calculations performed by the computer 340, the value calculated by the computer 380 based on the feature values may be a binary value, or some other value, such as a scalar. Additionally, in some embodiments, the model 386 may be trained utilizing training data collected under different conditions (similar to the different conditions under which the data used training for model 346 were collected). Furthermore, in some embodiments, the model 386 may be personalized for a user by training the model on samples that include: feature values generated based on measurements of the user, and corresponding labels indicative of the extent of fever and/or intoxication of the user while the measurements were taken. In some embodiments, the model 386 may be generated based on measurements of multiple users, in which case, the model 386 may be considered a general model.

There are various types of feature values that may be generated by the computer 380 based on input data, which may be utilized to calculate a value indicative of whether the user has a fever and/or whether the user is intoxicated. Some examples of feature values include "raw" or minimally processed values based on the input data (i.e., the features are the data itself or applying generic preprocessing functions to the data). Other examples of feature values include feature values that are based on higher-level processing, such a feature values determined based on domain-knowledge. In one example, feature values may include values of patterns of hemoglobin concentration at the three or more regions on the user's face, which are generated based on the images 377.

As mentioned in more detail above in the discussion about detecting fever and/or intoxication by the computer 340 based on a deviation of a current pattern from a baseline pattern of hemoglobin concentration, generating a baseline pattern of hemoglobin concentration can be done based on images previously taken by the camera 376 (referred to as "baseline images"). Optionally, the baseline images were taken previously (prior to when the images 377 were taken) while the user was not in a state being detected. Optionally, windows during which the baseline images were taken may have different lengths, and end prior to a current time (when the images 377 were taken). Optionally, windows during which baseline images are taken end before the current time. In one example, the baseline images may have been taken at different times during a window spanning several hours. In another example, the baseline images include images taken at different times during a window spanning several days/weeks/months, such that the baseline images include images taken on different days/weeks/months, respectively. Optionally, the computer 380 may receive indications indicative of times in which the user is in a baseline state (e.g., without a fever or not intoxicated), and at least some of the baseline images are selected based on the indications.

In one embodiment, the baseline images are utilized by the computer 380 to calculate the baseline pattern, which is indicative of baseline hemoglobin concentrations at the three or more regions on the user's face. Optionally, the baseline hemoglobin concentrations at three or more regions on the user's face are values characteristic of times in which the user did not have a fever and/or was sober. Additionally or alternatively, the computer 380 may utilize a detected-state pattern indicating hemoglobin concentrations characteristic of times in which the user is in the detected state (e.g., while the user has a fever and/or is intoxicated). Optionally, the detected-state baseline may be utilized by the computer when detecting whether the user has a fever and/or whether the user is intoxicated.

In one embodiment, the computer 380 calculates, based on additional baseline images captured with the cameras 376 while the user had a fever, a fever-baseline pattern comprising additional values indicative of hemoglobin concentrations at the three or more regions on the user's face. The computer 380 then bases the detection of whether the user has the fever also on a deviation of the values indicative of hemoglobin concentration at the three or more regions on the user's face, which are generated based on the images 377 (i.e., the "current pattern") from the aforementioned additional values (the fever-baseline pattern).

In another embodiment, the computer 380 calculates, based on additional baseline images captured with the cameras 376 while the user was intoxicated, an intoxication-baseline pattern comprising additional values indicative of hemoglobin concentrations at the three or more regions on the user's face. The computer 380 then bases the detection of whether the user is intoxicated also based on a deviation on a deviation of the values indicative of hemoglobin concentration at the three or more regions on the user's face, which are generated based on the images 377 (i.e., the "current pattern") from the aforementioned additional value (the intoxication-baseline pattern).

Various types of feature values may be generated based on temperature measurements of a region on the user's face, such as $T_{skin}$ 373, or temperature of the environment, as is the case with $T_{env}$ 375. In one embodiment, the feature values include a temperature value itself (e.g., the value reported in $T_{skin}$ 373). Additionally or alternatively, the feature values may include a difference between the temperature and a previously taken temperature (e.g., a temperature taken 10 minutes prior or one hour prior). Additionally or alternatively, the feature values may include a difference between the temperature and a baseline temperature. In one example, the feature values include a value indicative of the difference between $T_{skin}$ 373, and the average temperature measured at the first region on multiple previous days. In another example, the feature values include a value indicative of the difference between $T_{env}$ 375, and the average temperature measured in the environment on multiple previous days.

The values indicative of hemoglobin concentrations at three or more regions on the user's face may be utilized to generate various types of feature values, in embodiments described herein. In one example, the hemoglobin concentrations at each of the three or more regions are provided as feature values. In another example, a change to the value corresponding to a certain region (e.g., the difference compared to a previous point in time and/or a derivative of the value at the region) is provided as a feature value.

In some embodiments, the values indicative of hemoglobin concentrations at three or more regions on the user's face are treated as a current pattern of hemoglobin concentrations and feature values are generated based on a deviation of the current pattern from one or more reference patterns (e.g., a baseline pattern, a fever-baseline pattern, or an intoxication-baseline pattern). This deviation may be assessed using various methods described above involving calculations by the computer 340 to make a detection based on a deviation of a current pattern from a baseline pattern.

In some embodiments, at least some of the feature values generated by the computer 380 based on the images 377 are feature values described herein as being generated by the computer 340 based on the images 333 (e.g., low-level image features, iPPG signal features, etc.).

In one non-limiting example, feature values generated by the computer 380 include pixel values from the images 377 during a certain window, as well as a value of $T_{skin}$ 373 and a value of $T_{env}$ 375 during the certain window. In another non-limiting example, feature values generated by the computer 380 include timings and intensities corresponding to fiducial points identified in iPPG signals extracted from the images 377 as well as a value of $T_{skin}$ 373 and a value of $T_{env}$ 375. In yet another non-limiting example, feature values generated by the computer 380 include a value of $T_{skin}$ 373, a value of $T_{env}$, and the values indicative of hemoglobin concentrations at three or more regions on the user's face generated based on the images 377.

In some embodiments, one or more of the feature values utilized by the computer 380 to calculate a value indicative of whether the user has a fever and/or is intoxicated may be generated based on additional inputs from sources other than the first head-mounted temperature sensor 372, the second head-mounted temperature sensor 374, and the camera 376. Some examples of such additional inputs include: values indicative of a stress level of the user (e.g., based on measurements of a thermal camera), values indicative of a hydration level of the user (e.g., based on measurements of a thermal camera), values representing the extent of the user's movement (e.g., measurements with IMU 378). Additional details about these inputs are provided above in the discussion of how the computer 340 may utilize these additional inputs to generate feature values.

Training the model 386 may involve utilization of various training algorithms known in the art (e.g., algorithms for training neural networks, and/or other approaches described herein). After the model 386 is trained, feature values may be generated for certain measurements of the user (e.g., $T_{skin}$ 373, $T_{env}$ 375, and images 377), for which the value of the corresponding label (e.g., whether the user has a fever and/or whether the user is intoxicated) is unknown. The computer 380 can utilize the model 386 to calculate a value indicative of whether the user has a fever and/or whether the user is intoxicated based on these feature values.

In some embodiments, the model 386 may be generated based on data that includes measurements of the user. Additionally or alternatively, in some embodiments, the model 386 may be generated based on data that includes measurements of one or more other users (such as users of different ages, weights, sexes, body masses, and health states) Similar to the case with the model 346, in order to achieve a robust model that is useful for detecting fever and/or intoxication in various conditions, in some embodiments, the samples used to train the model 386 may also include samples based on measurements taken in different conditions.

In one embodiment, in which the computer 380 detects whether the user is intoxicated, the model 386 was trained based on previous data sets that include: (i) previously measured $T_{skin}$ and $T_{env}$, and previous values indicative of hemoglobin concentrations captured by the camera 376 while the user was sober, and (ii) additional previously measured $T_{skin}$ and $T_{env}$, and additional previous values indicative of hemoglobin concentrations captured by the camera 376 while the user was intoxicated.

Utilizing the model 386 to detect whether the user has a fever and/or whether the user is intoxicated may involve computer 380 performing various operations, depending on the type of model. Examples of the types of calculations that may be performed by the computer 380 when performing such detections are given in the discussion above about some of the examples of various possibilities for the model 346 and the type of calculations that may be accordingly performed by the computer 340.

Figure 70B:
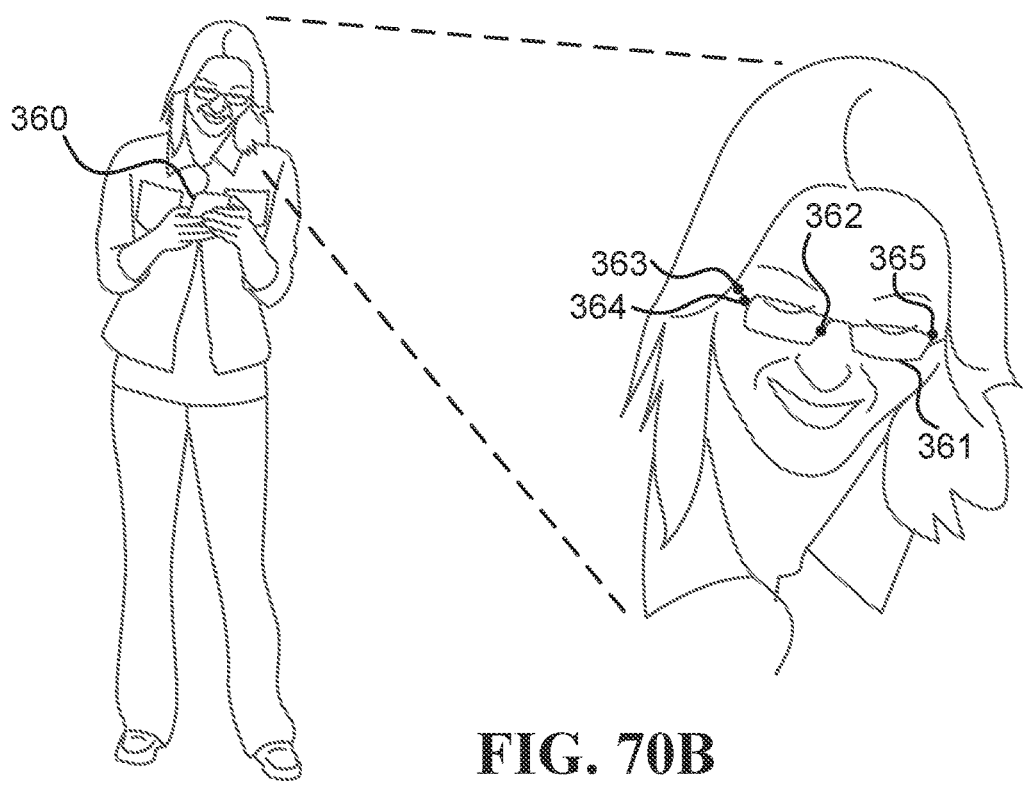
FIG. 70B illustrates one example of a system to detect fever and/or intoxication.

FIG. 70B illustrates one example of a system configured to detect fever and/or intoxication, comprising: (i) a smartphone 360 comprising a camera sensitive to wavelengths below 1050 nanometer, which captures the images, and a computer to detect state of the user (such as whether the user has a fever or is intoxicated), (ii) smartglasses frame 361, (iii) a contact head-mounted temperature sensor 362 (such as a thermistor) to measure skin temperature ($T_{skin}$) of a region on the user's nose, (iv) a non-contact head-mounted thermal camera (such as a thermopile) 363 to measure skin temperature of a region on the user's temple, (v) a head-mounted temperature sensor 364 configured to measure temperature of the environment ($T_{env}$), and (vi) an inward-facing head-mounted camera 365 to capture additional or alternative feed of images of a region on the user's face, from which the values indicative of hemoglobin concentrations can be calculated.

The closer the region, measured by the skin temperature sensor ($S_1$), is to a branch of the external carotid artery (such as the temporal artery), the higher the correlation between $T_{skin}$ and the core body temperature. $S_1$ may be a contact temperature sensor 362 (such as a thermistor or a thermocouple), or a non-contact temperature sensor 363 (such as a thermopile or a microbolometer). When $S_1$ is a contact sensor, the frame to which $S_1$ is coupled to is designed to keep $S_1$ in contact with the first region of skin while wearing the frame. When $S_1$ is a non-contact sensor, the frame is designed to keep $S_1$ in an essentially fixed position relative to the first region of skin while wearing the frame. Optionally, the frame may be an eyeglasses frame, a goggles frame, or a frame embedded in or coupled to a helmet. Additionally or alternatively, the frame may be designed specifically for holding $S_1$ to the user's head.

In one example, the skin region measured by $S_1$ is not located above a portion of a branch of the external carotid artery, which means that the correlation between $T_{skin}$ and the user's core body temperature is expected to be lower compared to the case where the first region is located above a portion of a branch of the external carotid artery. The correlation between $T_{skin}$ and the user's core body temperature is expected to get worse as the thermal interference from the environment becomes more severe. Because the thermal interference affects also the hemoglobin concentrations, the computer can improve the accuracy of estimating the user's core body temperature based on detecting these changes in the hemoglobin concentrations.

In one example, the first region covers a portion of skin located above a portion of a branch of the external carotid artery, and the computer improve the accuracy of estimating the user's core body temperature, when being under thermal interference from the environment, based on detecting the changes in the current hemoglobin concentrations relative to baseline hemoglobin concentrations of the user.

In addition to detecting whether the user has a fever and/or whether the user is intoxicated, in some embodiments, the computer 380 may utilize $T_{skin}$ 373, $T_{env}$ 375, and the values indicative of hemoglobin concentrations calculated based on the images 377 to detect additional physiological signals and/or conditions.

In some embodiments, the computer 380 calculates a value indicative of a level of dehydration of the user based on $T_{skin}$ 373, $T_{env}$ 375, the values indicative of hemoglobin concentrations, and additional measurements of the user. Various types of additional measurements of the user may be used. In one embodiment, the computer 380 receives audio recordings of the user recorded using a head-mounted acoustic sensor 383. In another embodiment, the computer 380 receives a head-movement signal (i.e., values indicative of movements of the user's head) measured with a head-mounted movement sensor (e.g., the IMU 378). Optionally, the head-mounted acoustic sensor 383 and/or the head-mounted movement sensor are coupled to a device to which the head-mounted temperature sensors 372 and 374 are coupled, such as the frame of the smartglasses 370.

In one embodiment, the computer 380 utilizes $T_{skin}$ 373, $T_{env}$ 375, the values indicative of hemoglobin concentrations, the audio recordings, and the head-movement signal, to generate certain feature values and utilizes a certain machine learning-based model to calculate, based on the certain feature values, the value indicative of the level of dehydration of the user. Optionally, at least some of the certain feature values are generated in a similar fashion to the generation of feature values discussed above, which are utilized to detect fever and/or intoxication. Optionally, to generate at least some of the certain feature values that are based on the audio recordings, the computer 380 utilizes some of the various techniques known in the art and/or described in this disclosure for extracting features from audio recordings (e.g., feature values used for detection of coughing and/or respiration, which are described herein). In one example, to generate some of the certain feature values based on the audio recordings, the computer 380 extracts features indicative of the user's respiratory rate and vocal changes. Such features can be beneficial because dehydration is associated with an increase in the respiratory rate and a decrease in the speed quotient at low-pitch phonation. Optionally, to generate at least some of the certain feature values based on the head-movement signal, the computer 380 may utilize various approaches known in the art for extracting values indicative of the extent of movement and smoothness of movement. Such features can be beneficial because dehydration may be associated with both changes to extent of movement and reduction in movement smoothness.

The certain machine learning-based model utilized to calculate the value indicative of the level of dehydration of the user may be trained on data collected from one or more users. Optionally, this data is converted to training samples, each training sample comprising measurements $T_{skin}$, $T_{env}$, the values indicative of hemoglobin concentrations, audio recordings, and a head-movement signal of a certain user taken during a creation period, and a label indicative of the dehydration level of the certain user during the certain period.

In one embodiment, the computer 380 calculates the user's core body temperature based on $T_{skin}$ 373, $T_{env}$ 375, the values indicative of hemoglobin concentrations, and optional additional measurements of the user obtained with one or more sensors. To this end, the computer 380 generates certain feature values based on $T_{skin}$ 373, $T_{env}$ 375, the values indicative of hemoglobin concentrations, and the optional additional measurements and utilizes a certain machine learning machine learning-based model to calculate, based on the certain feature values, the user's core body temperature. Generating at least some of the certain feature values based $T_{skin}$ 373, $T_{env}$ 375, and the values indicative of hemoglobin concentrations may involve one or more of the various procedures mentioned above with respect to generating feature values from such data. Generation of one or more of the certain feature values based on the optional additional measurements is discussed below with respect to different types of optional additional measurements that may be utilized in different embodiments.

The certain machine learning-based model utilized to calculate the core body temperature may be trained on data collected from one or more users. Optionally, the data is converted to training samples, each training sample comprising measurements $T_{skin}$, $T_{env}$, the values indicative of hemoglobin concentrations, and values of the additional measurements of the user taken during a creation period, and a label indicative of the core body temperature of the user during the certain period. Training the machine learning-based model may involve utilizing one or more training algorithms known in the art, such as training procedures for neural networks, linear regression, support vector machines, decision trees, and the like.

The following are examples of embodiments in which different types of sensors may be used in order to measure at least some of the optional additional measurements mentioned above. Optionally, one or more of the different types of sensors described below may be coupled to a device to which the head-mounted temperature sensors 372 and 374 are coupled, such as the frame of the smartglasses 370.

In one embodiment, the computer 380 receives audio recordings of the user taken with the head-mounted acoustic sensor 383. Optionally, the computer 380 generates one or more of the certain feature values, which are used to calculate the core body temperature, based on the audio recordings. Optionally, the computer 380 generates the one or more of the certain feature values utilizing one or more of the computational approaches described herein for analyzing acoustic data in order to obtain parameters related to respiratory activity. In one example, at least one of the one or more of the certain feature values is indicative of the respiration rate of the user.

In another embodiment, the computer 380 receives a signal indicative of movements of the user's head measured using a head-mounted movement sensor, such as the IMU 378. Optionally, to generate at least one or more of the certain feature values based on the signal indicative of movements of the user's head, the computer 380 may utilize various approaches known in the art for extracting values indicative of the extent of movement of the user. In one example, at least one of the one or more of the certain feature values is indicative of the physical activity level of the user.

In still another embodiment, the computer 380 receives a signal indicative of wind speed hitting the user's head (wind signal) and a signal indicative of humidity (humidity signal) and generates one or more of the certain feature values based on the wind signal and/or the humidity signal. Optionally, the wind signal is measured using the head-mounted anemometer 382 and the humidity signal is measured using the head-mounted hygrometer 384.

In yet another embodiment, the computer 380 receives images of an eye of the user, and generates one or more of the certain feature values based on the images of the eye. Optionally, the one or more of the certain feature values is indicative of a level of reflectiveness of the eye, which often increases with the temperature. Optionally, the images of the eye are taken using a head-mounted inward-facing camera.

In some embodiments, the computer 380 may utilize calibration measurements of the user's core body temperature in order to more accurately calculate the user's core body temperature based on $T_{skin}$ 373, $T_{env}$ 375, the values indicative of hemoglobin concentrations, and optionally some of the additional measurements of the user mentioned above. Optionally, the calibration measurements of the user's core body temperature include measurements of the user's core body temperature taken at a certain time with a different device that is not one of the head-mounted temperature sensors 372 and 374 or the camera 376. Additionally, the calibration measurements of the user's core body temperature may have corresponding measurements taken at the certain time with the head-mounted temperature sensors 372 and 374 or the camera 376.

In one embodiment, one or more of the certain feature values described above, which are used to calculate the core body temperature, may reflect values of the calibration measurements and/or a difference between the values of the calibration measurements and values obtained with the head-mounted temperature sensors 372 and 374 and/or the camera 376 at the time the calibration measurements were taken.

In another embodiment, the computer 380 may utilize a model, which may be a formula, for calculating the core body temperature based on $T_{skin}$ 373, $T_{env}$ 375, the values indicative of hemoglobin concentrations. Optionally, the computer 380 may utilize the calibration measurements to calibrate parameters of the model. In one example, calibration measurements are utilized to set an offset between the calculated core body temperature (based on corresponding measurements taken with the head-mounted temperature sensors 372 and 374 or the camera 376) and the measurements taken with the different device. Thus, the offset may be applied to make calculated values of core body temperature more accurate. In another example, three or more calibration measurements are used to perform linear regression that is used to obtain a regression formula that is used by the computer 380 to calculate the core body temperature.

In one embodiment, the computer 380 calculates, based on the images 377, a heart rate and/or a respiration rate of the user. For example, the computer 380 may utilize one or more techniques described herein or known in the art for calculating heart rate and/or respiration from iPPG signals (extracted from the images 377). The computer 380 can then utilize the heart rate and/or the respiration rate of the user, to detect whether the user has a fever, and other conditions such as hyperthermia or hypothermia, based on deviations of the current heart rate and/or the current respiration rate from a baseline heart rate and/or baseline respiration rate of the user, respectively. In one example, the computer 380 may utilize a machine learning approach similar to the one described above (for detecting fever and/or intoxication), but instead of using the model 386, the computer 380 uses a different model trained with labels corresponding to extents of hyperthermia or hypothermia (using feature values similar to the ones described above with respect to the model 386).

The user interface 388 may be utilized to present values calculated by the computer 380, such as indications whether the user has a fever or whether the user is intoxicated. Optionally, the user interface 388 is a component of a device of the user, such as a smartphone's screen or an augmented reality display.

In one embodiment, the computer 380 enables the user to share a fever history of the user, upon receiving a permission from the user. For example, the fever history may include indications of times, durations, and/or extent of fever spells the user had. The user may be able to decide to share his/her fever history with a certain person in order to increase the trust and/or receive help, or not share his/her fever history with the certain person if he/she is not interested in increasing the trust and/or receiving help.

In another embodiment, the computer 380 enables the user to share an intoxication history of the user, upon receiving a permission from the user. For example, the intoxication history may include indications of times and/or durations during which the user was intoxicated. The user may be able to decide to share his/her intoxication history with a certain person in order to increase the trust, or not share his/her intoxication history with the certain person if the certain persons does not share in return his/her intoxication history with the user.

The following method for detecting fever may be used by systems modeled according to FIG. 70A. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, receiving, from a first head-mounted temperature sensor, measurements of skin temperature ($T_{skin}$) at a first region on a user's head. In Step 2, receiving, from a second head-mounted temperature sensor, measurements of temperature of the environment ($T_{env}$). In Step 3, receiving, from a camera sensitive to wavelengths below 1050 nanometer, images of a second region on the user's face. In Step 4, calculating, based on the images, values indicative of hemoglobin concentrations at three or more regions on the user's face. And in Step 5, detecting whether the user has a fever based on $T_{skin}$, $T_{env}$, and the values indicative of hemoglobin concentrations.

In one embodiment, the first region covers a portion of skin that is not located above a portion of a branch of the external carotid artery, and detecting of whether the user has the fever in Step 5 involves (i) generating feature values based on: $T_{skin}$, $T_{env}$, and the values indicative of hemoglobin concentrations, and (ii) utilizing a machine learning-based model to calculate, based on the feature values, a values indicative of whether the user has the fever.

In one embodiment, a system configured to detect alcohol intoxication, comprises: a first head-mounted temperature sensor configured to measure skin temperature ($T_{skin}$) at a first region on a user's head; a second head-mounted temperature sensor configured to measure temperature of the environment ($T_{env}$); and a computer configured to: (i) receive images of a second region on the user's face, captured by a camera sensitive to wavelengths below 1050 nanometer, (ii) calculate, based on the images, values indicative of hemoglobin concentrations at three or more regions on the user's face, and (iii) detect whether the user is intoxicated based on $T_{skin}$, $T_{env}$ and the values.

Optionally, the computer detects whether the user is intoxicated by (i) generating feature values based on: $T_{skin}$, $T_{env}$ and the values indicative of hemoglobin concentrations; and (ii) utilizing a machine learning-based model to calculate, based on the feature values, a values indicative of whether the user is intoxicated. Wherein the machine learning-based model was trained based on previous data sets comprising: (i) $T_{skin}$, $T_{env}$ and previous values indicative of hemoglobin concentrations captured by the camera while the user was sober, and (ii) $T_{skin}$, $T_{env}$ and previous values indicative of hemoglobin concentrations captured by the camera while the user was intoxicated.

Optionally, the second region is larger than 2 cm$^2$, the camera is an inward-facing head-mounted camera configured to capture the images from a distance between 5 mm and 5 cm from the user's head, and the computer calculates the values indicative of hemoglobin concentrations based on detecting facial flushing patterns in the images.

Optionally, the camera is an inward-facing head-mounted camera configured to capture the images from a distance between 5 mm and 5 cm from the user's head, and the computer calculates the values indicative of hemoglobin concentrations based on detecting imaging photoplethysmogram signals in the images.

The following are additional embodiments of system configured to detect fever and/or calculate core body temperature.

In one embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to perform the following: receive images of a second region larger than 2 cm$^2$ on the user's face, captured by a camera sensitive to wavelengths below 1050 nanometer; calculate, based on the images, values indicative of hemoglobin concentrations at three or more regions on the face; generate feature values based on: $T_{skin}$, $T_{env}$, and the values indicative of hemoglobin concentrations; and utilize a machine learning-based model to detect whether the user has a fever based on the feature values.

In another embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The first and second inward-facing head-mounted cameras ($Cam_{1\&2}$), which located less than 5 cm from the face, sensitive to wavelengths below 1050 nanometer, are configured to capture images of respective first and second regions on the face. Optionally, the middles of the first and second regions are at least 4 cm apart. The computer is configured to perform the following: generate feature values based on: $T_{skin}$, $T_{env}$, and values indicative of hemoglobin concentrations at the first and second regions which are recognizable in the images; and utilize a machine learning-based model to detect whether the user has a fever based on the feature values.

In yet another embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to generate baseline values based on: (i) $T_{skin}$ and $T_{env}$, measured during a certain period during which the user's core body temperature was in a normal range, and (ii) images of a second region larger than 1 cm$^2$ on the user's face, captured by a camera sensitive to wavelengths below 1050 nanometer during the certain period, which are indicative of a baseline facial flushing pattern comprising at least 3 points recognizable in the images. Additionally, the computer generates current values based on: (i) $T_{skin}$ and $T_{env}$, measured during a later period, and (ii) current images of the second region, taken during the later period, which are indicative of a current facial flushing pattern comprising the at least 3 points recognizable in the current images. Optionally, the measurements used to calculate the current values are taken at least four hours after the certain period. The computer then detects the fever based on a difference between the baseline values and the current values reaching a threshold.

In still another embodiment, a system configured to calculate core body temperature includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to perform the following: receive images of a second region larger than 2 cm$^2$ on the user's face, captured by a camera sensitive to wavelengths below 1050 nanometer; generate feature values based on: $T_{skin}$, $T_{env}$ and hemoglobin concentration pattern comprising at least 3 points indicative of hemoglobin concentrations recognizable in the images; and utilize a machine learning-based model to calculate the core body temperature based on the feature values.

In yet another embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to: receive images of a second region larger than 1 cm² on the user's face, captured by a camera sensitive to wavelengths below 1050 nanometer; generate feature values based on: $T_{skin}$, $T_{env}$, and facial flushing pattern recognizable in the images; and utilize a machine learning-based model to detect the fever based on the feature values.

Some embodiments of systems for calculating an extent of congestive heart failure (CHF) that a user is suffering from, and/or identify exacerbation of CHF, are described below. These systems rely on measuring signs of CHF that include changes to facial blood flow, respiration, and/or level of activity. Embodiments of these systems include: smartglasses with various sensors and/or cameras coupled thereto, and a computer that is used to calculate the extent of CHF and/or to detect the exacerbation of CHF.

Figure 71A:
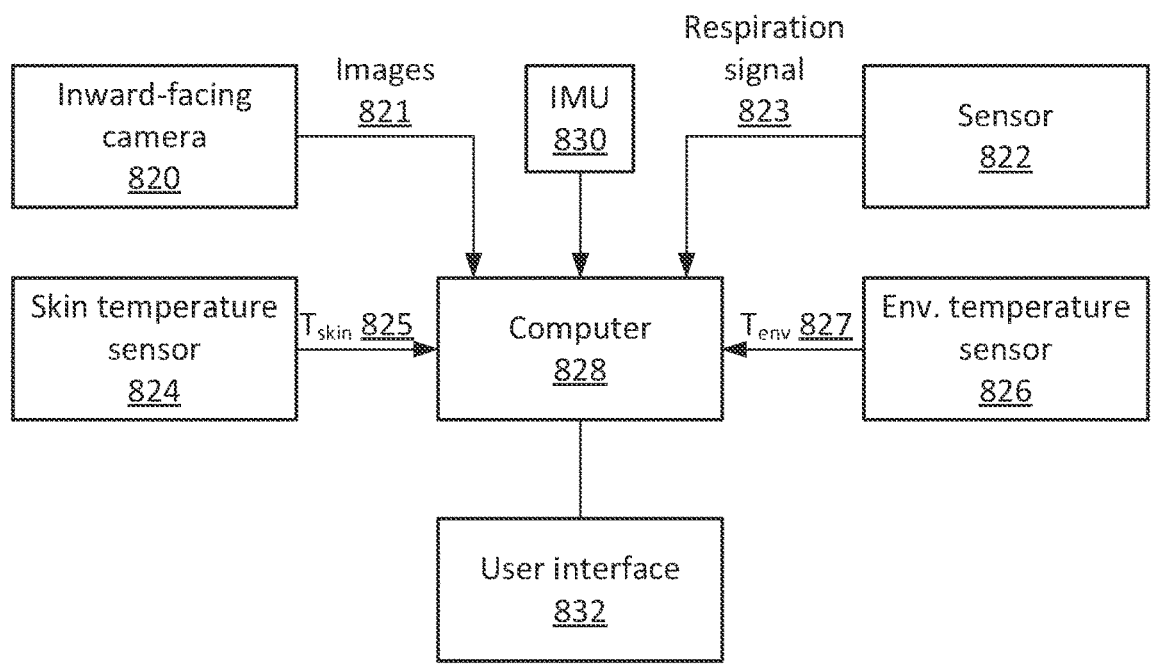
FIG. 71A is a schematic illustration of components of a system to calculate an extent of CHF and/or identify exacerbation of CHF.

FIG. 71A is a schematic illustration of components of a system configured to calculate an extent of CHF and/or identify exacerbation of CHF. In one embodiment, the system includes at least a pair of smartglasses (e.g., smartglasses 800 or smartglasses 805, illustrated in FIG. 71B and FIG. 71C, respectively), and an inward-facing camera 820, such a camera from among cameras 802a, 802b, and 802c illustrated in FIG. 2b, or a camera from among cameras 806a and 806b illustrated in FIG. 71C. The system also includes computer 828. The system may include additional elements such as a sensor 822, which is configured to measure a signal indicative of respiration, a movement sensor, such as inertial measurement unit (IMU) 830, a skin temperature sensor 824, an environment temperature sensor 826, and/or a user interface 832.

The smartglasses are configured to be worn on a user's head. Optionally, various sensors and/or cameras that are physically coupled to the smartglasses, e.g., by being attached to and/or embedded in the frame of the smartglasses, are used to measure the user while the user wears the smartglasses. Optionally, at least some of the sensors and/or cameras that are physically coupled to the smartglasses may be utilized to measure the environment in which the user is in. In one example, the smartglasses are eyeglasses with sensors and electronics attached thereto and/or embedded therein. In another example, the smartglasses may be an extended reality device (i.e., an augmented realty device, a virtual reality device, and/or mixed reality device).

Figure 71B:
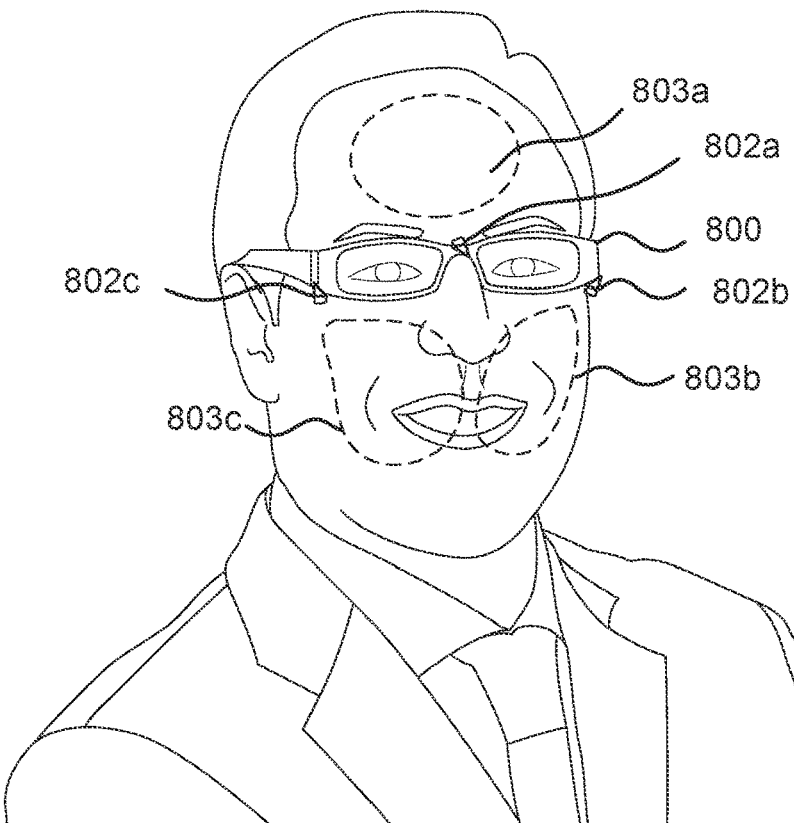
FIG. 71B illustrates various possibilities for positioning one or more inward-facing cameras on smartglasses.
Figure 71C:
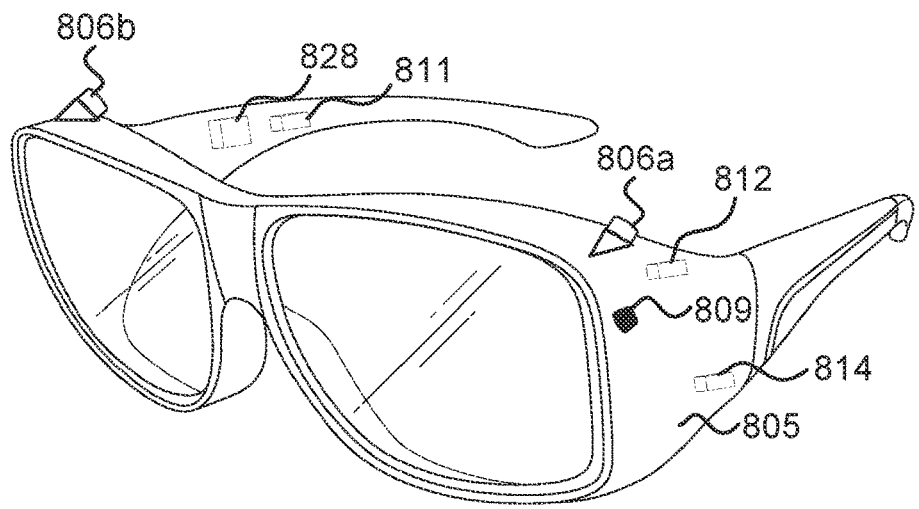
FIG. 71C illustrates an embodiment of smartglasses that are part of a system for calculating an extent of CHF that a user is suffering from, and/or identify exacerbation of CHF.

FIG. 71C illustrates an embodiment of smartglasses that are part of a system for calculating an extent of congestive heart failure (CHF) that a user is suffering from, and/or identify exacerbation of CHF. The system includes smartglasses 805, which have various components coupled thereto. These components include the inward-facing cameras 806a and 806b, which capture images that include portions of the left and right sides of the forehead, respectively. Additionally, the smartglasses 805 may include a microphone 809, which can be used to measure a signal indicative of respiration, a temperature sensor 811 that measures temperature on the user's face, a temperature sensor 812 that measures temperature of the environment, and IMU 814. The smartglasses 805 also include computer 828, which in this embodiment is physically coupled to the frame of the smartglasses 805.

One or more inward-facing cameras, such as the inward-facing camera 820, are physically coupled to the smartglasses. Each of these cameras is configured to capture images of an area comprising skin on the user's head. For example, the inward-facing camera 820 captures images 821 of an area on the user's head. Optionally, the area comprises a portion of the lips of the user. Additional examples of the area are illustrated in FIG. 71B, which describes various possibilities for positioning one or more inward-facing cameras on smartglasses 800. Inward-facing camera 802a is located above the nose bridge and captures images of an area 803a on the user's forehead. Inward-facing cameras 802b and 802c are located on the left and right sides of the smartglasses 800, respectively; they capture images that include areas 803b and 803c on the left and right sides of the user's face, respectively.

Inward-facing cameras, such as the inward-facing camera 820, are optionally mounted more than 5 mm away from the head and/or at least 5 mm away from the area appearing in the images they capture. Optionally, the inward-facing camera 820 is mounted less than 10 cm away from the head (i.e., the frame of the smartglasses holds the camera at a distance that is smaller than 10 cm from the head). Optionally, each area appearing in images captured by an inward-facing camera, such as the inward-facing camera 820, is larger than 4 cm^2. In some embodiments, the area on the user's head appearing in images 821 is not occluded by the inward-facing camera 820.

Cameras utilized in embodiments described herein (including the inward-facing camera 820) are typically small and lightweight. In some embodiments, each camera weighs below 10 g and even below 2 g. In one example, the inward-facing camera 820 camera is a multi-pixel video camera having a CMOS or a CCD sensor. The video camera may capture images at various rates. In one example, the images 821 are captured at a frame rate of at least 30 frames per second (fps). In another example, the images 821 are captured at a frame rate of at least 100 fps. In still another example, the images 821 are captured at a frame rate of at least 256 fps. Images taken by inward-facing cameras may have various resolutions. In one example, the images 821 have a resolution of at least 8×8 pixels. In another example, the images 821 have a resolution of at least 32×32 pixels. In yet another example, the images 821 have a resolution of at least 640×480 pixels.

In some embodiments, at least one of the inward-facing cameras may capture light in the near infrared spectrum (NIR). Optionally, each of the at least one of the inward-facing cameras may include optics and sensors that capture light rays in at least one of the following NIR spectrum intervals: 700-800 nm, 700-900 nm, 700-1,000 nm. Optionally, the sensors may be CCD sensors designed to be sensitive in the NIR spectrum and/or CMOS sensors designed to be sensitive in the NIR spectrum.

In some embodiments, the system may include an optical emitter configured to direct electromagnetic radiation at an area on the user's head that appears in images captured by an inward-facing camera. Optionally, the optical emitter comprises one or more of the following: a laser diode (LD), a light-emitting diodes (LED), and an organic light-emitting diode (OLED).

It is to be noted that when embodiments described in this disclosure utilize optical emitters directed at a region of interest (ROI), such as an area appearing in images captured by an inward-facing camera, the optical emitter may be positioned in various locations relative to the ROI. In some embodiments, the optical emitter may be positioned essentially directly above the ROI, such that electromagnetic radiation is emitted at an angle that is perpendicular (or within 10 degrees from being perpendicular) relative to the ROI. Optionally, an inward-facing camera may be positioned near the optical emitter in order to capture the reflection of electromagnetic radiation from the ROI. In other embodiments, the optical emitter may be positioned such that it is not perpendicular to the ROI. Optionally, the optical emitter does not occlude the ROI. In one example, the optical emitter may be located at the top of a frame of a pair of eyeglasses, and the ROI may include a portion of the forehead. In another example, optical emitter may be located on an arm of a frame of a pair of eyeglasses and the ROI may be located above the arm or below it.

The computer 828 may utilize various preprocessing approaches in order to assist in calculations and/or in extraction of an iPPG signal from the images 821. Optionally, the images 821 may undergo various preprocessing steps prior to being used by the computer 828. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081. Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from the images 821 are discussed in Zaunseder et al. (2018), "Cardiovascular assessment by imaging photoplethysmography—a review", Biomedical Engineering 63(5), 617-634. An example of preprocessing that may be used in some embodiments is given in U.S. Pat. No. 9,020,185, titled "Systems and methods for non-contact heart rate sensing", which describes how times-series signals obtained from video of a user can be filtered and processed to separate an underlying pulsing signal by, for example, using an ICA algorithm.

Due to the proximity of the one or more inward-facing cameras to the face, in some embodiments, there may be an acute angle between the optical axis of an inward-facing camera and the area captured by images taken by said camera (e.g., when the area is on, and/or includes a portion of, the forehead or a cheek). In order to improve the sharpness of images captured by said camera, camera may be configured to operate in a way that takes advantage of the Scheimpflug principle. In one embodiment, camera includes a sensor and a lens; the sensor plane is tilted by a fixed angle greater than 2° relative to the lens plane according to the Scheimpflug principle in order to capture a sharper image when the smartglasses are worn by the user (where the lens plane refers to a plane that is perpendicular to the optical axis of the lens, which may include one or more lenses). In another embodiment, the camera includes a sensor, a lens, and a motor; the motor tilts the lens relative to the sensor according to the Scheimpflug principle. The tilt improves the sharpness of images when the smartglasses are worn by the user. Additional details regarding the application of the Scheimpflug principle are discussed further below.

Variations in the reflected ambient light may introduce artifacts into images collected with inward-facing cameras that can add noise to these images and make detections and/or calculations based on these images less accurate. In some embodiments, the system includes an outward-facing camera, which is coupled to the smartglasses, and takes images of the environment. Optionally, this outward-facing camera is located less than 10 cm from the user's face and weighs below 10 g. Optionally, the outward-facing camera may include optics that provide it with a wide field of view.

Changes in respiration pattern (in particular an increased respiration rate) are often associated with CHF and its exacerbation. In order to incorporate information about respiration into detection of CHF, some embodiments include the sensor 822, which is physically coupled to the smartglasses, and configured to measure a respiration signal 823, which is a signal indicative of the user's respiration rate. Various types of sensors may be utilized for this purpose.

In one embodiment, the sensor 822 may be a microphone from among one or more microphones coupled to the smartglasses. The computer 828 may utilize the microphone to measure audio signal comprising sounds in the user's vicinity, and the respiration signal 823 is derived from the sounds. From this respiration signal, values of respiration parameters may be extracted (such as the respiration rate). Various algorithmic approaches may be utilized to extract parameters related to respiration from an acoustic signal. Some examples of possible approaches are provided in Avalur, D. S. "*Human breath detection using a microphone*", Diss. Faculty of Science and Engineering, 2013. Additional algorithmic approaches that may be utilized, in some embodiments, are described in U.S. Pat. No. 7,850,619, titled "Apparatus and method for breathing pattern determination using a non-contact microphone", and in US patent application No. 2019/0029563, titled "Methods and apparatus for detecting breathing patterns".

In another embodiment, the sensor 822 may be an inward-facing head-mounted thermal camera and the respiration signal 823 may include, and/or be derived from, thermal measurements of a region below the nostrils ($TH_{ROI}$) of a user, where $TH_{ROI}$ are indicative of the exhale stream. Optionally, the computer 828 generates certain feature values based on $TH_{ROI}$, and utilizes a certain model to calculate a respiratory parameter, such as the respiration rate, based on the certain feature values. Optionally, the certain model is trained based on previous $TH_{ROI}$ of the user. Additional details regarding utilization of head-mounted thermal cameras to measure signals indicative of respiratory activity are provided in U.S. Pat. No. 10,130,308, titled "Calculating respiratory parameters from thermal measurements", and U.S. Pat. No. 10,136,856, titled "Wearable respiration measurements system".

The computer 828 is configured, in some embodiments, to calculate the extent of CHF based on facial blood flow patterns recognizable the images 821 taken by the inward-facing camera 820 and optionally additional inward-facing cameras. Optionally, the computer 828 may utilize additional information such as a respiration rate recognizable in the respiration signal 823. Examples of computers that may be utilized to perform this calculation are computer 400 or computer 410 illustrated in FIG. 88A and FIG. 88B, respectively.

In different embodiments, the computer 828 may refer to different components and/or a combination of components. In some embodiments, the computer 828 may include a processor located on the smartglasses (as illustrated in FIG. 71C). In other embodiments, at least some of the calculations attributed to the computer 828 may be performed on a remote processor, such as a cloud-based server. Thus, references to calculations being performed by the "computer 828" should be interpreted as calculations being performed utilizing one or more computers, with some of these one or more computers possibly being remote of the smartglasses. For example, some of the operations attributed to the computer 828 may be performed, in some embodiment's, by a processor in another device of the user (e.g., a processor on a smartphone) or by a cloud based server.

The images 821 may provide values of coloration intensities (i.e., intensities detected at one or more light wavelengths) at different portions of the area on the user's head, which correspond to the different pixels in the images. In some embodiments, the computer 828 may utilize various computational techniques described herein to extract a photoplethysmogram signal (iPPG signal) from the images 821. In some embodiments, the computer 828 may extract from the images 821 coloration values that do not exhibit a temporal variation that corresponds to the user's cardiac pulses (e.g., average color values for various pixels during a period spanning a duration of several seconds, or longer).

The coloration intensities may represent a facial blood flow pattern that is recognizable in the images 821. A facial blood flow pattern represents characteristics of blood flow in the area captured in the images 821, while the images 821 were taken. A "facial blood flow pattern" may refer to various types of patterns, in embodiments described herein. The following are some examples of types of patterns that may be recognizable in the images 821.

In some embodiments, a facial blood flow pattern refers to a color mapping of various portions of the area captured in the images 821 (e.g., the mapping provides the colors of different pixels in the images 821). Optionally, the mapping provides average intensities of one or more colors of the pixels over a period of time during which the images 821 were taken. Since the extent of cutaneous blood flow affects the skin coloration, the colors observed in the images 821 can indicate the extent of blood flow in different portions of the area. For example, increased blood flow can be detected as higher pixel intensities for the color red (due to the flushness accompanying the increase blood flow). In another example, CHF may lead to decreased blood flow, which may cause colors in the area to change towards pallor (an extremely pale or grayish coloring of the face) or change due to cyanosis (having a bluish coloring of the nails, lips and possibly the skin). The occurrence of CHF can lead to slight changes in the colors, which may not be detected by the naked eye. However, the head-mounted system can detect these slight (or distinct) color changes, and track their trend that is indicative of the extent of CHF.

In other embodiments, a facial blood flow pattern may refer to time series data, such as a sequence of images representing a progression of a pulse wave in the area. Different extents of blood flow may produce different sequences of representative images, which depend on the structure of the facial blood vessels of the user. For example, for the same user and area, a stronger blood flow can be represented by a sequence of images with larger color variations than the color variation in a sequence of images representing a weaker blood flow in the area.

In still other embodiments, a facial blood flow pattern may refer to a contour map, representing the extent to which pixels at a certain wavelength (e.g., corresponding to the color red) have at least a certain value. Since the extent of blood flow is correlated with an increase in intensity of certain colors (e.g., red), a facial blood flow pattern for a stronger blood flow will have different contour map than the contour map observed in a facial blood flow pattern that corresponds to a weaker blood flow in the same area. The contour map depends on the structure of the facial blood vessels of the user, and a machine learning model used to determine extent of blood flow can be trained on sets of images corresponding to different levels of blood flows captured from different users.

Herein, sentences of the form "a facial blood flow pattern recognizable in the images (of an area comprising skin on the user's head)" refer to effects of blood volume changes due to pulse waves that may be extracted from one or more images of the area. These changes may be identified and/or utilized by a computer, but need not necessarily be recognizable to the naked eye (e.g., because of their subtlety, the short duration in which they occur, or involvement of light outside of the visible spectrum).

Additionally, sentences of the form "a respiration rate recognizable in the respiration signal" refer to values that may be extracted from the respiration signal, when algorithms known in the art are utilized to calculate the respiration rate from the respiration signal.

It is to be noted that stating that a computer performs a calculation based on a certain value that is recognizable in certain data (e.g., the respiration rate recognizable in the respiration signal) does not necessarily imply that the computer explicitly extracts the value from the data. For example, the computer may perform its calculation without explicitly calculating the respiration rate. Rather, data that reflects the respiration rate (the respiration signal) may be provided as input utilized by a machine learning algorithm. Many machine learning algorithms (e.g., neural networks) can utilize such an input without the need to explicitly calculate the value that is "recognizable".

A facial blood flow pattern, such as one of the examples described above, may be calculated, in some embodiments, from the images 821 by the computer 828. Optionally, the facial blood flow pattern may be utilized to generate one or more feature values that are used in a machine learning-based approach by the computer 828 to calculate the extent of CHF and/or identify an exacerbation of CHF, as described below. In other embodiments, the calculated blood flow pattern may be utilized to calculate additional values used to represent the extent of facial blood flow, which may be evaluated, e.g., by comparing the extent of blood flow to thresholds in order to calculate the extent of CHF and/or identify an exacerbation of CHF.

In one embodiment, a facial blood flow pattern may be converted to a value representing the proportion of the area in which the intensities of pixels reach a threshold. In one example, the intensities being evaluated may be average intensities (e.g., average pixel intensities in the images 821). In another example, the intensities being evaluated may be intensities of systolic peaks (determined by detecting the spread of a pulse wave in the area captured in the images 821).

In another embodiment, a facial blood flow pattern may be compared with one or more reference facial blood flow patterns that may correspond to specific blood flow levels and/or specific levels of CHF. Optionally, the reference patterns may be based on previously taken images of the user, which were taken at times for which the extent of CHF and/or blood flow was determined manually, e.g., by a physician. Optionally, the similarity of the facial blood flow pattern to the reference patterns may be utilized to generate one or more feature values utilized in a machine learning approach, as described below.

The computer 828 may produce different types of results, in embodiments described herein, based on input data that includes the images 821 and optionally other data, such as the respiration signal 823, $T_{skin}$ 825, $T_{env}$ 827, measurements of an IMU 830, and/or additional optional data described herein. Optionally, the results, which may include, for example, an indication of extent of CHF and/or an indication of the exacerbation, are reported via the user interface 832. Optionally, the results may be reported to a caregiver (e.g., a physician).

In some embodiments, the computer 828 is configured to calculate the extent of CHF based on: a facial blood flow patterns recognizable in the images 821, and respiration rate recognizable in the respiration signal 823.

In order to calculate the extent of CHF, in one embodiment, the computer 828 may compare a value calculated based on the facial blood flow pattern (e.g., a similarity to a reference facial blood flow patter) to a first threshold, and compare the respiration rate to a second threshold. Responsive to the value reaching the first threshold, and the respiration rate reaching the second threshold, the computer 828 may determine that the user is experiencing CHF to at least a specified extent.

In another embodiment, calculating the extent of CHF involves generating feature values based on data that includes the facial blood flow pattern and the respiration rate. The computer 828 then utilizes a machine learning model to calculate, based on the feature values, a value indicative of the extent of CHF the user is experiencing. Additional details regarding the machine learning-based approach are provided further below.

Calculating the extent of CHF may involve, in some embodiments, utilization of previous measurements for which a corresponding baseline extent of CHF the user experienced is known. Optionally, the baseline extent of CHF is determined by a physician examining the user. Optionally, one or more feature values utilized to calculate the extent of CHF may be indicative of the baseline value and/or indicative of a difference between the value and a baseline value.

In one embodiment, the computer 828 calculates, based on the images 821, a value indicative of an extent to which skin in the area is blue and/or gray. The computer 828 then utilizes a difference between the value and a baseline value for the extent to which skin in the area is blue and/or gray to calculate the extent of CHF. Optionally, the baseline value was determined while the user experienced a certain baseline extent of CHF.

In another embodiment, the computer 828 calculates, based on the images 821, a value indicative of an extent of color changes to skin in the area due to cardiac pulses. The computer 828 then utilizes a difference between the value and a baseline value for the extent of the color changes to calculate the extent of CHF. Optionally, the baseline value for the extent of the color changes was determined while the user experienced a certain baseline extent of CHF.

The computer 828 may identify, in some embodiments, an exacerbation of the CHF by comparing current measurements of the user, with previous measurements of the user. To this end, in one embodiment, the computer 828 receives: (i) previous images of the area, which are indicative of a previous facial blood flow pattern while the user had a certain extent of CHF, and (ii) a previous respiration rate taken while the user had the certain extent of CHF. Optionally, the certain extent of CHF is provided from manual examination of the user, e.g., by a physician who examined the user at the time. Additionally or alternatively, the certain extent of CHF was calculated by the computer 828 based on data that includes the previous images and the previous respiration signal.

In one embodiment, the computer 828 may identify exacerbation of the CHF based on: a difference above a first predetermined threshold between the first facial blood flow pattern and the previous facial blood flow pattern, and an increase above a second predetermined threshold in the respiration rate compared to the previous respiration rate. Optionally, the first and second thresholds are determined based on previously observed differences in facial blood flow patterns and respiration signals of the user when the user experienced an exacerbation of CHF. Additionally or alternatively, the first and second thresholds may be determined based on differences in facial blood flow patterns and respiration signals of observed when other users experienced an exacerbation of CHF.

In one embodiment, the computer 828 may identify exacerbation of the CHF utilizing a machine learning based approach, in which feature values used to detect an exacerbation of CHF include a feature value is indicative a difference between the first facial blood flow pattern and the previous facial blood flow patter, and another feature value is indicative of an extent of increase in the respiration rate compared to the previous respiration rate.

Identifying an exacerbation of CHF may involve, in some embodiments, monitoring the user over a period of multiple days, weeks, and even months or more. Thus, the images 821 and the images and the respiration signal 823 may be measured over a period spanning multiple days. In these embodiments, the computer 828 may identify the exacerbation of the CHF based on a reduction in average facial blood flow recognizable in the images 821 taken during the period and an increase in the average respiration rate recognizable in measurements of the respiration signal 823 measured during the period.

One sign of CHF is a difficulty in performing physical activity. This leads people who have CHF to be less active. Additionally, when they are physically active, such as walking a certain distance, the physical activity takes a greater than usual toll on their body. This is often manifested as a change in cardio-respiratory activity (such as a smaller increase in blood flow), which takes longer to return to baseline levels from before conducting the physical activity. Thus, in some embodiments, the computer 828 may utilize measurements taken before and after physical activity to calculate an extent of CHF and/or detect exacerbation of CHF.

In order to detect a period in which the user conducted in physical activity, and/or what type of physical activity the user conducted, in some embodiments, the computer 828 may utilize measurements of movements of the user. Optionally, the measurements of movements are obtained utilizing a movement sensor, such as the IMU 830, which is physically coupled to the smartglasses, and configured to measure movements of the user. In one example, the computer 828 may detect when a period of physical activity involves walking for at 20 steps, and compare measurements of the user taken before and after the period to determine the extent of CHF and/or identify exacerbation of CHF, as described below.

In one embodiment, the computer 828 receives a first set of images taken while the user was at rest and prior to a period during which the user performed physical activity. The computer 828 also receives a second set of the images taken within ten minutes after the period. The computer 828 calculates the extent of CHF based on differences in facial blood flow patterns recognizable in the first and second sets of the images. For example, the computer 828 may detect the extent of CHF and/or the exacerbation of CHF based on a determination of whether a difference in parameters of the extent of blood flow which are determined based on the first and second sets of images, reaches a threshold. In another example, the computer 828 may generate one or more feature values utilized by a machine learning approach described herein, which are indicative of differences between extents of blood flow which are determined based on the first and second sets of images.

In one embodiment, the computer 828 calculates a value indicative of skin color at different times based on the second set of images, and calculates the extent of CHF based on a length of a duration following the period, in which the difference between the skin color and a baseline skin color, calculated based on the first set of images, was above a threshold. Optionally, a feature value indicative of the length of the duration may be utilized to calculate the extent of CHF.

In another embodiment, the computer 828 calculates a value indicative of skin color at different times based on the second set of images, and calculates the extent of CHF based on a rate of return of the user's skin color to a baseline skin color calculated based on the first set of images. Optionally, a feature value indicative of the rate of return may be utilized to calculate the extent of CHF.

Dynamics of the user's heart rate following physical activity may also be used to calculate the extent of CHF. In one embodiment, the computer 828 calculates first and second series of heart rate values from portions of iPPG signals extracted from the first and second sets of images, respectively. The computer 828 may calculate the extent of the CHF also based on the extent to which heart rate values in the second series were above heart rate values in the first series. For example, the computer 828 may generate one or more feature values indicative of these differences, and utilize them in the calculation of the extent of the CHF.

In one embodiment, the computer 828 calculates the user's heart rate at different times based on the second sets of images, and calculates the extent of CHF based on a length of a duration following the period, in which the difference between the user's heart rate and a baseline heart rate, calculated based on the first set of images, was above a threshold. Optionally, a feature value indicative of the length of the duration may be utilized to calculate the extent of CHF.

Characteristics of respiration before and after physical activity may also be indicators of the extent of CHF. In one embodiment, the computer 828 receives respiration signal measured while the user was at rest and prior to a period during which the user performed physical activity. The computer 828 also receives a second respiration signal measured within ten minutes after the period. The computer 828 calculates the extent of CHF based on differences respiration rates recognizable in the first and second respiration signals. For example, the computer 828 may detect the extent of CHF, and/or the exacerbation of CHF, based on a determination of whether a difference in respiration rates determined based on the first and second respiration signals, reaches a threshold. In another example, the computer 828 may generate one or more feature values utilized by a machine learning approach described herein, which are indicative of differences between the aforementioned respiration rates.

In one embodiment, the computer 828 calculate the user's respiration rate at different times based on the second respiration signal, and calculate the extent of CHF based on a length of a duration following the period, in which the difference between the user's respiration rate and a baseline respiration rate, calculated based on the first respiration signal, was above a threshold. Optionally, a feature value indicative of the length of the duration may be utilized to calculate the extent of CHF.

The computer 828 may utilize machine learning approaches, in some embodiments, to calculate the extent of CHF and/or identify exacerbation of CHF. In some embodiments, the computer 828 calculates feature values based on data that includes the images 821 (and possibly other data) and utilizes a model to calculate, based on the feature values, a value indicative of the extent of CHF and/or a value indicative of exacerbation of CHF (compared to a previous state of the user). Various examples of feature values that may be generated based on the images 821, the respiration signal 823, and/or measurements of the IMU 830 are provided above in this disclosure.

Generally, machine learning-based approaches utilized by embodiments described herein involve training a model on samples, with each sample including: feature values generated based on images taken by the inward-facing camera 820, and optionally respiration signals measured with the sensor 822, and/or other data, which were taken during a certain period, and a label indicative of the extent of CHF (during the certain period). Optionally, a label may be provided manually by the user and/or by a medical professional who examined the user. Optionally, a label may be extracted based on analysis of electronic health records of the user, generated while being monitored at a medical facility.

In some embodiments, the model may be personalized for a user by training the model on samples that include: feature values generated based on measurements of the user, and corresponding labels indicative of the extent of CHF experienced by the user at the time. In some embodiments, the model may be generated based on measurements of multiple users, in which case, the model may be considered a general model. Optionally, a model generated based on measurements of multiple users may be personalized for a certain user by being retrained on samples generated based on measurements of the certain user.

There are various types of feature values that may be generated by the computer 828 based on input data, which may be utilized to calculate the extent of CHF and/or identify an exacerbation. Some examples of feature values include "raw" or minimally processed values based on the input data (i.e., the features are the data itself or applying generic preprocessing functions to the data). Other examples of feature values include feature values that are based on higher-level processing, such a feature values determined based on domain-knowledge (e.g., feature values describing properties of pulse waveforms) and/or feature values that are based on high-level image-analysis.

The following are some examples of the various types of feature values that may be generated based on the images 821 by the computer 828. In one embodiment, at least some of the feature values may be derived directly from values of pixels in the images 821. Optionally, at least some of the feature values are values of pixels from the images 821. Optionally, one or more of the feature values may be the values of the pixels themselves or some simple function of the pixels, such as the average of pixels at certain regions in each of the images. Optionally, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may derived from multiple images taken at different times, such as volume local binary patterns (VLBP), cuboids, and/or optical strain-based features. In one example, one or more of the feature values may represent a difference between values of pixels at one time t at a certain location on the face and values of pixels at a different location at some other time t+x (which can help detect different arrival times of a pulse wave).

In some embodiments, at least some feature values utilized by the computer 828 to calculate the extent of CHF and/or identify exacerbation of CHF describe properties of the cardiac waveform in an iPPG signal derived from the images 821. To this end, the computer 828 may employ various approaches known in the art to identify landmarks in a cardiac waveform (e.g., systolic peaks, diastolic peaks), and/or extract various types of known values that may be derived from the cardiac waveform, as described in the following examples.

In one embodiment, at least some of the feature values generated based on the iPPG signal may be indicative of waveform properties that include: systolic-upstroke time, diastolic time, and the time delay between the systolic and diastolic peaks, as described in Samria, Rohan, et al. "Non-invasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the iPPG signal may be derived from another analysis approach to PPG waveforms, as described in US Patent Application US20180206733, entitled "Device, method and system for monitoring and management of changes in hemodynamic parameters", which was published on 26 Jul. 2018. This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated by the computer 828, which are suggested in the aforementioned publication, include: value of A, value of B, value of C, value of D, value of E, systol area that is the area under ABCE, diastol area that is the area under CDE, and the ratio between BC and DC.

In still another embodiment, the computer 828 may utilize the various approaches described in Elgendi, M. (2012), "On the analysis of fingertip photoplethysmogram signals", Current cardiology reviews, 8(1), 14-25, in order to generate at least some of the feature values bases on the iPPG signal. This reference surveys several preprocessing approaches for PPG signals as well as a variety of feature values that may be utilized. Some of the techniques described therein, which may be utilized by the computer 828, include calculating feature values based on first and second derivatives of PPG signals.

In some embodiments, at least some of the feature values may represent calibration values of a user, which are values of certain parameters such as waveform properties described above when the user had a known extent of CHF (e.g., as determined based on an evaluation by a physician). Optionally, the computer 828 generates one or more values that are indicative of: (i) a value of the extent of CHF experienced by the user during a certain previous period, and (ii) a value of a property of the pulse waveform (e.g., systolic-upstroke time or diastolic time) during the certain previous period.

One sign of CHF is an increase heart rate. In some embodiments, the computer 828 may utilize one or more feature values indicative of the user's heart rate. Optionally, these feature values may be derived from the images 821, e.g., by performing calculations on iPPG signals extracted from the images 821. In one example, U.S. Pat. No. 8,768,438, titled "Determining cardiac arrhythmia from a video of a subject being monitored for cardiac function", describes how to obtain a PPG signal from video of a user's face. In this example, a time series signal is generated from video images of a subject's exposed skin, and a reference signal is used to perform a constrained source separation (which is a variant of ICA) on the time series signals to obtain the PPG signal. Peak-to-peak pulse points are detected in the PPG signal, which may be analyzed to determine parameters such as heart rate, heart rate variability, and/or to obtain peak-to-peak pulse dynamics that can be indicative of conditions such as cardiac arrhythmia.

In some embodiments, the computer 828 generates at least some feature values utilized to calculate the extent of CHF, and/or identify exacerbation of CHF, based on the respiration signal 823. In some embodiments, these feature values may be "raw" or minimally processed values. In one example, in which the respiration signal 823 includes thermal measurements, the feature values may be values of the measurements themselves and/or various functions and/or statistics of the thermal measurements such as minimum/maximum measurement values and/or average values during certain windows of time. In another example, in which the respiration signal 823 includes audio, the feature values may include various acoustic features derived from the audio. For example, the audio may be represented as a time series of vectors of acoustic features, where each vector corresponds to a short window of the audio. For example, windows may be between 5 ms and 200 ms long. The signal in a window may be processed in various ways to obtain acoustic features. In one example, fast Fourier transform (FFT) is performed on the audio in each window. From the FFT data for each window, various features may be extracted. For example, some acoustic features may be determined by binning according to filterbank energy coefficients, using a Mel-frequency cepstral component (MFCC) transform, using a perceptual linear prediction (PLP) transform, or using other techniques.

In some embodiments, the computer 828 generates at least some feature values utilized to calculate the extent of CHF and/or identify exacerbation of CHF based on values of respiration parameters calculated based on the respiration signal 823 (e.g., the respiration rate and/or other respiration parameters). Some examples of respiration parameters that may be calculated based on thermal measurements include: breathing rate, respiration volume, whether the user is breathing mainly through the mouth or through the nose, exhale (inhale) duration, post-exhale (post-inhale) breathing pause, a dominant nostril, a shape of the exhale stream, smoothness of the exhale stream, and/or temperature of the exhale stream. Additional details regarding calculation of these parameters is provided in U.S. Pat. No. 10,130,308, titled "Calculating respiratory parameters from thermal measurements".

In one non-limiting example, feature values generated by the computer 828 include pixel values from the images 821 and values obtained by binning according to filterbank energy coefficients, using MFCC transform on results of FFT of the respiration signal 823, which includes audio.

In another non-limiting example, feature values generated by the computer 828 include timings and intensities corresponding to fiducial points identified in iPPG signals extracted from the images 821, and values of respiration parameters calculated based on the respiration signal 823.

In some embodiments, one or more of the feature values utilized by the computer 828 to calculate the extent of CHF and/or identify exacerbation of CHF may be generated based on additional inputs from sources other than the inward-facing camera 820 or the sensor 822.

Stress is a factor that can influence the diameter of the arteries, and thus influence the blood flow. In one embodiment, the computer 828 is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward-facing head-mounted thermal camera configured to take measurements of a region on the forehead of the user, where the measurements of the region on the forehead of the user are indicative of the stress level of the user. In still another example, the system includes an inward-facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently may affect blood flow patterns recognizable in the images 821. In one embodiment, the computer 828 is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer 828 as values indicative of the hydration level of the user.

Momentary physical activity can affect the blood flow of the user (e.g., due to the increase in the heart rate that it involves). In order to account for this factor, in some embodiments, the computer 828 may generate one or more feature values representing the extent of the user's movement from measurements of the IMU 830. In addition, the extent of movement of the user may be indicative of the extent of CHF, since users with advanced CHF tend to be less physically active because physical activity becomes more difficult due to their condition. Thus, the extent of physical activity (e.g., how many steps a user walked in a day), which may also be derived from measurements of the IMU 830, may be utilized to generate one or more feature values, in some embodiments.

The user's skin temperature may affect blood viscosity, thus it may influence facial blood flow patterns that are recognizable in images taken by the inward-facing camera 820. Some embodiments may include the skin temperature sensor 824, which may be a head-mounted sensor physically coupled to the smartglasses. The skin temperature sensor 824 measures temperature of a region comprising skin on the user's head ($T_{skin}$ 825). In one embodiments, the computer 828 is configured to utilize $T_{skin}$ 825 to compensate for effects of skin temperature on the facial blood flow pattern. For example, the computer 828 may generate one or more feature values based on $T_{skin}$. 825, such as feature values indicating average skin temperature or a difference from baseline skin temperature, and utilize these one or more feature values to calculate the extent of CHF and/or identify exacerbation of CHF.

The temperature in the environment may also be a factor that is considered in some embodiments. The temperature in the environment can both impact the user's skin temperature and cause a physiologic response involved in regulating the user's body temperature on the facial blood flow pattern. Some embodiments may include the environment temperature sensor 826, which may optionally, be head-mounted (e.g., physically coupled to the smartglasses). The environment temperature sensor 826 measures an environmental temperature ($T_{env}$ 827). In one embodiment, the computer 828 is configured to utilize $T_{env}$ 827 to compensate for effects of physiologic changes related to regulating the user's body temperature on the facial blood flow pattern. For example, the computer 828 may generate one or more feature values based on $T_{env}$ 827, such as feature values indicating average environment temperature, maximal environment temperature, or a difference from baseline environment temperature, and utilize these one or more feature values to calculate the extent of CHF and/or identify exacerbation of CHF.

Training the model utilized to calculate the extent of CHF and/or identify an exacerbation of CHF may involve utilization of various training algorithms known in the art (e.g., algorithms for training neural networks, and/or other approaches described herein). After the model is trained, feature values may be generated for certain measurements of the user (e.g., the images 821, respiration signal 823, etc.), for which the value of the corresponding label (e.g., the extent of CHF and/or indicator of whether there is an exacerbation) is unknown. The computer 828 can utilize the model to calculate the extent of CHF, and/or whether there is an exacerbation of CHF, based on these feature values.

In some embodiments, the model may be generated based on data that includes measurements of the user (i.e., data that includes images taken by the inward-facing camera 820, the sensor 822, and/or other sensors mentioned herein). Additionally or alternatively, in some embodiments, the model may be generated based on data that includes measurements of one or more other users (such as users of different ages, weights, sexes, body masses, and health states). In order to achieve a robust model, which may be useful for calculating the extent of CHF in various conditions, in some embodiments, the samples used to train the model may include samples based on measurements taken in different conditions. Optionally, the samples are generated based on measurements taken on different days, while in different locations, and/or while different environmental conditions persisted. In a first example, the model is trained on samples generated from a first set of measurements taken while the user was indoors and not in direct sunlight, and is also trained on other samples generated from a second set of measurements taken while the user was outdoors, in direct sunlight. In a second example, the model is trained on samples generated from a first set of measurements taken during daytime, and is also trained on other samples generated from a second set of measurements taken during nighttime. In a third example, the model is trained on samples generated from a first set of measurements taken while the user was moving, and is also trained on other samples generated from a second set of measurements taken while the user was sitting.

Utilizing the model to calculate the extent of CHF and/or identify exacerbation of CHF may involve the computer 828 performing various operations, depending on the type of model. The following are some examples of various possibilities for the model and the type of calculations that may be accordingly performed by the computer 828, in some embodiments, in order to calculate extent of CHF and/or identify exacerbation of CHF: (a) the model comprises parameters of a decision tree. Optionally, the computer 828 simulates a traversal along a path in the decision tree, determining which branches to take based on the feature values. A value indicative of the extent of CHF may be obtained at the leaf node and/or based on calculations involving values on nodes and/or edges along the path; (b) the model comprises parameters of a regression model (e.g., regression coefficients in a linear regression model or a logistic regression model). Optionally, the computer 828 multiplies the feature values (which may be considered a regressor) with the parameters of the regression model in order to obtain the value indicative of the extent of CHF; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 828 provides the feature values as inputs to the neural network, computes the values of the various activation functions and propagates values between layers, and obtains an output from the network, which is the value indicative of the extent of the CHF and/or an indicator of whether there was an exacerbation of the CHF.

In some embodiments, a machine learning approach that may be applied to calculating extent of CHF and/or identifying exacerbation of CHF based on images may be characterized as "deep learning". In one embodiment, the model may include parameters describing multiple hidden layers of a neural network. Optionally, the model may include a convolution neural network (CNN). In one example, the CNN may be utilized to identify certain patterns in the video images, such as the facial blood flow patterns involving blood volume effects and ballistocardiographic effects of the cardiac pulse. Due to the fact that calculations are performed on sequences images display a certain pattern of change over time (i.e., across multiple frames), these calculations may involve retaining state information that is based on previous images in the sequence. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

The following is description of additional aspects of embodiments of systems configured to detect an abnormal medical event, as well as additional embodiments for various systems that may detect physiological responses based on sensor measurements and/or other sources of data.

In some embodiments, a system configured to detect an abnormal medical event includes a computer and several head-mounted devices that are used to measure photoplethysmographic signals (PPG signals) indicative of blood flow at various regions on a user's head. Optionally, the system may include additional components, such as additional sensors that may be used to measure the user and/or the environment. Additionally or alternatively, the system may include a frame configured to be worn on the user's head (e.g., a frame of eyeglasses or smartglasses) and to which at least some of the head-mounted devices and sensors are physically coupled. Having sensors, such as the devices that are used to measure photoplethysmographic signals, physically coupled to the frame may convey certain advantages, such as having the sensors remain at the same positions with respect to the head, even when the user's head makes angular movements. Some examples of abnormal medical events that may be detected by embodiments described herein include an ischemic stroke, a migraine, a headache, cellulitis (soft tissue infection), dermatitis (skin infection), and an ear infection.

In one embodiment, the system includes at least one right-side head-mounted device, configured to measure at least two signals indicative of photoplethysmographic signals ($PPG_{SR1}$ and $PPG_{SR2}$, respectively) at first and second regions of interest ($ROI_{R1}$ and $ROI_{R2}$, respectively) on the right side of a user's head. Optionally, $ROI_{R1}$ and $ROI_{R2}$ are located at least 2 cm apart (where cm denotes centimeters). Optionally, each device, from among the at least one right-side head-mounted device(s), is located to the right of the vertical symmetry axis that divides the user's face.

Additionally, the system includes at least one left-side head-mounted device configured to measure at least two signals indicative of photoplethysmographic signals ($PPG_{SL1}$ and $PPG_{SL2}$, respectively) at first and second regions of interest ($ROI_{L1}$ and $ROI_{L2}$, respectively) on the left side of the user's head. Optionally, each device, from among the at least one right-side head-mounted device(s), is located to the left of the vertical symmetry axis that divides the user's face.

In some embodiments, $ROI_{R1}$ and $ROI_{L1}$ may be symmetrical regions on the right and left sides of the head, respectively (with respect to a symmetry axis that splits the face to right and left sides). Additionally or alternatively, $ROI_{R2}$ and $ROI_{L2}$ may be symmetrical regions on the right and left sides of the head, respectively. In other embodiments, $ROI_{R1}$ and $ROI_{L1}$ may not be symmetrical regions on the right and left side of the head, and/or $ROI_{R2}$ and $ROI_{L2}$ may not be symmetrical regions on the right and left side of the head. Optionally, two regions are considered to be in symmetrical locations if one region is within 1 cm of the symmetrical region on the head.

Various types of devices may be utilized in order to obtain $PPG_{SR1}$, $PPG_{SR2}$, $PPG_{SL2}$, and/or $PPG_{SL2}$. In one embodiment, the at least one right-side head-mounted device includes first and second contact photoplethysmographic devices ($PPG_1$, $PPG_2$, respectively). Additionally or alternatively, the at least one left-side head-mounted device may include third and fourth contact photoplethysmographic devices ($PPG_3$, $PPG_4$, respectively). Herein, a "contact photoplethysmographic device" is a photoplethysmographic device that comes in contact with the user's skin, and typically occludes the area being measured. An example of a contact photoplethysmographic device is the well-known pulse oximeter.

In one example, $PPG_1$, $PPG_2$, $PPG_3$, and $PPG_4$ are physically coupled to an eyeglasses frame, $PPG_1$ and $PPG_3$ are in contact with the nose, and $PPG_2$ and $PPG_4$ are in contact with regions in the vicinities of the ears (e.g., within a distance of less than 5 cm from the center of the concha), respectively.

Figure 72A:
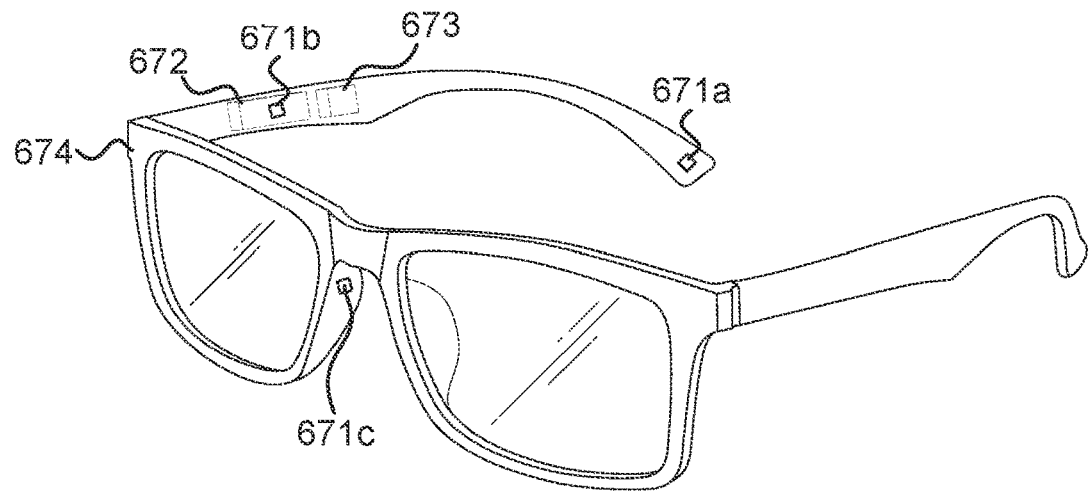
FIG. 72A illustrates smartglasses which include contact photoplethysmographic devices.

FIG. 72A illustrates smartglasses that include contact photoplethysmographic devices that may be used to obtain PPG signals, as described above. The contact PPG devices are coupled to a frame 674. The contact PPG devices may be coupled at various locations on the frame 674 and thus may come in contact with various regions on the user's head. For example, contact PPG device 671a is located on the right temple tip, which brings it to contact with a region behind the user's ear (when the user wears the smartglasses). Contact PPG device 671b is located on the right temple of the frame 674, which puts it in contact with a region on the user's right temple (when wearing the smartglasses). It is to be noted that in some embodiments, in order to bring the contact PPG device close such that it touches the skin, various apparatuses may be utilized, such as spacers (e.g., made from rubber or plastic), and/or adjustable inserts that can help bridge a possible gap between a frame's temple and the user's face. Such an apparatus is spacer 672 which brings contact PPG device 671b in contact with the user's temple when the user wears the smartglasses.

Another possible location for a contact PPG device is the nose bridge, as contact PPG device 671c is illustrated in the figure. It is to be noted the contact PPG device 671c may be embedded in the nose bridge (or one of its components), and/or physically coupled to a part of the nose bridge. The figure also illustrates computer 673, which may be utilized in some embodiments, to perform processing of PPG signals and/or detection of the abnormal medical event, as described further below.

It is to be noted that FIG. 72A illustrates but a few of the possible locations for contact PPG devices on a frame. Any pair of contact PPG devices 671a, 671b, and 671c may be the aforementioned $PPG_1$ and $PPG_2$. Additionally, some embodiments may include additional contact PPG devices on each side of the frames. Furthermore, it is to be noted that while contact PPG devices on the left side were not illustrated in the figure, additional PPG devices may be located in similar locations to the ones of PPG devices 671a to 671c are located, but on the left side of the frame.

In another embodiment, one or more video cameras may be utilized to obtain $PPG_{SR1}$, $PPG_{SR2}$, $PPG_{SL1}$, and/or $PPG_{SL2}$ utilizing imaging photoplethysmography. Using video cameras can be advantageous in some scenarios, such as stroke, where it is unknown in advanced where the physiological response associated with the abnormal medical event will appear on the user's head. Thus, in some embodiments involving these scenarios, using video cameras may provide a great advantage over contact PPG devices, because the video cameras cover larger areas, which increase the chance to capture on time the physiological response associated with the abnormal medical event.

In one embodiment, the at least one right-side head-mounted device includes a first inward-facing camera located more than 0.5 cm away from $ROI_{R1}$ and $ROI_{R2}$, and $PPG_{SR1}$ and $PPG_{SR2}$ are recognizable from color changes in regions in images taken by the first camera. Additionally or alternatively, the at least one left-side head-mounted device may include a second inward-facing camera located more than 0.5 cm away from $ROI_{L1}$ and $ROI_{L2}$, and $PPG_{SL1}$ and $PPG_{SL2}$ are recognizable from color changes in regions in images taken by the second camera. In one embodiment, the system includes both at least one contact PPG device and at least one video camera.

In one embodiment, each of the first and second inward-facing cameras utilizes a sensor having more than 30 pixels, and each of $ROI_{R1}$ and $ROI_{L1}$ covers a skin area greater than 6 cm^2, which is illuminated by ambient light. In another embodiment, each of the first and second inward-facing cameras utilizes a sensor having more than 20 pixels, and each of $ROI_{R1}$ and $ROI_{L1}$ covers a skin area greater than 2 cm^2, which is illuminated by ambient light. In still another embodiment, each of the first and second inward-facing cameras utilizes a sensor comprising at least 3×3 pixels configured to detect electromagnetic radiation having wavelengths in at least a portion of the range of 200 nm to 1200 nm. Optionally, the system includes first and second active light sources configured to illuminate portions of the right side of the face (which include $ROI_{R1}$ and $ROI_{R2}$) and portions of the left side of the face (which include $ROI_{L1}$ and $ROI_{L2}$), respectively. In one example, the first and second active light sources are head-mounted light sources configured to illuminate their respective portions of the face with electromagnetic radiation having wavelengths in at least a portion of the range of 750 nm to 1200 nm.

In one embodiment, due to the angle between the optical axis of a certain inward-facing camera (from among the first and second inward-facing cameras) and its ROI, the Scheimpflug principle may be employed in order to capture sharper images with the certain inward-facing camera. For example, when the user wears a frame to which the certain inward-facing camera is coupled, the certain inward-facing camera may have a certain tilt greater than 2° between its sensor and lens planes, in order to capture the sharper images.

Figure 72B:
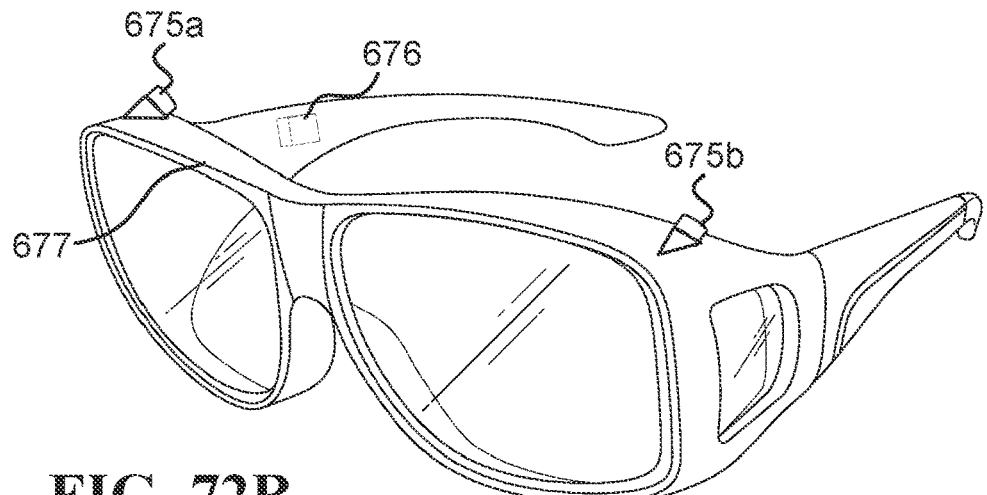
FIG. 72B illustrates smartglasses that include first and second inward-facing cameras.

FIG. 72B illustrates smartglasses that include first and second inward-facing cameras, such as the ones described above. The figure illustrates a frame 677 to which a first inward-facing camera 675a is coupled above the lens that is in front of the right eye, and a second inward-facing camera 675b that is coupled to the frame 677 above the lens that is in front of the left eye. The figure also illustrates a computer 676 that is coupled to the frame 677, and may be utilized to process images obtained by the first inward-facing camera 675a and/or the second inward-facing camera 675b, and/or perform the detection of the abnormal medical event based on PPG signals recognizable in images captured by those cameras.

Various regions on the face may be measured in embodiments that utilize imaging photoplethysmography. In one example, $ROI_{R1}$ and $ROI_{L1}$ are located on the user's right and left cheeks, respectively. In another example, $ROI_{R2}$ and $ROI_{L2}$ are located on the right and left sides of the user's nose, respectively. In yet another example, $ROI_{R1}$ and $ROI_{L1}$ are located on the right and left sides of the user's forehead, respectively. In still another example, $ROI_{R2}$ and $ROI_{L2}$ are located on the user's right and left temples, respectively.

Figure 73:
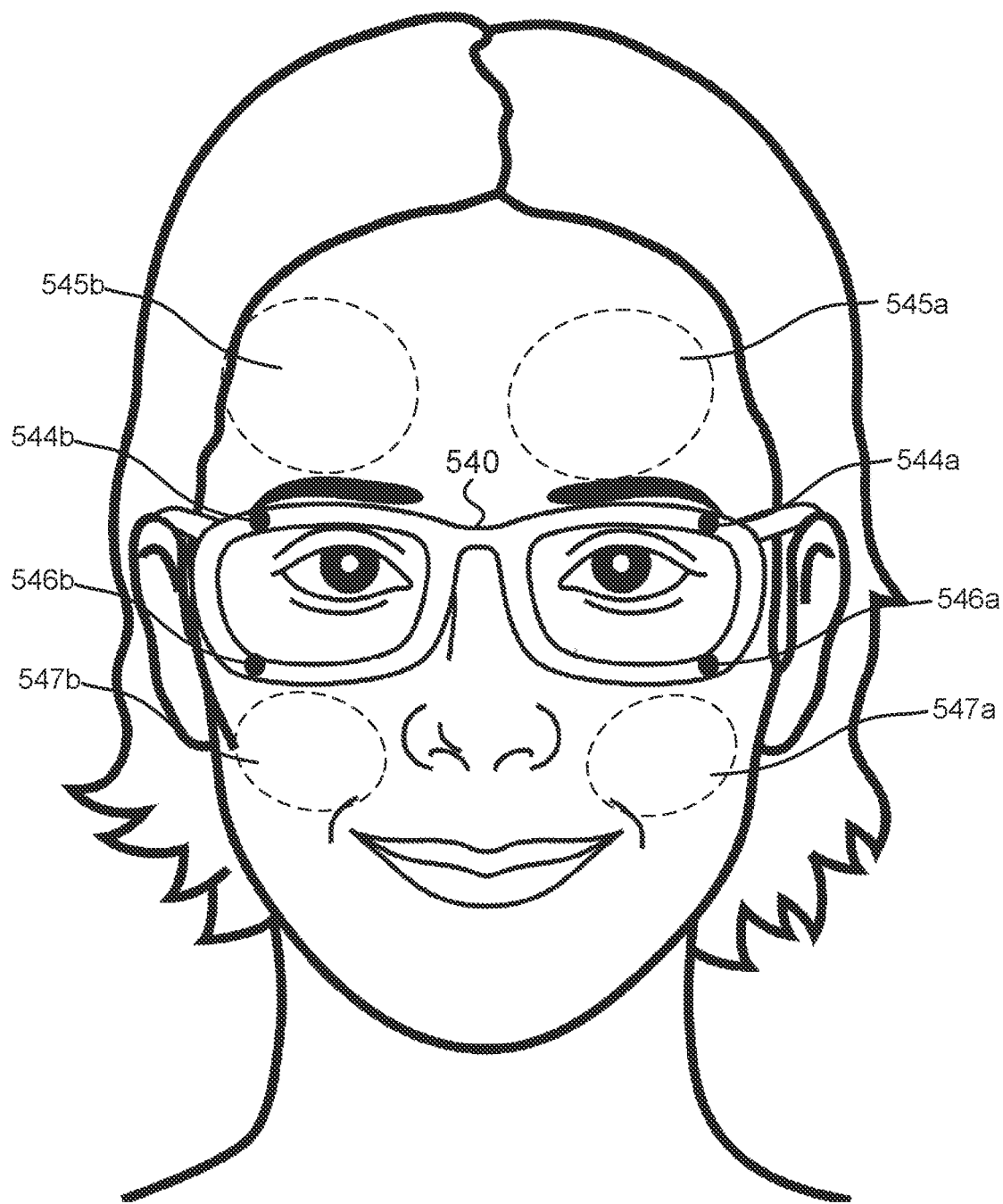
FIG. 73 illustrates smartglasses that include four inward-facing cameras.

A configuration consistent with some of the examples described above is illustrated in FIG. 73. In this figure, four inward-facing cameras are coupled to a frame 540 worn on a user's head: (i) Inward-facing camera 544a is coupled to the top-left side of the frame and captures images of ROI 545a, which is on the left side of the user's forehead; (ii) Inward-facing camera 544b is coupled to the top-right side of the frame and captures images of ROI 545b, which is on the right side of the user's forehead; (iii) Inward-facing camera 546a is coupled to the bottom-left side of the frame and captures images of ROI 547a, which is on the user's left cheek; And (iv) Inward-facing camera 546b is coupled to the bottom-right side of the frame and captures images of ROI 547b, which is on the user's right cheek.

Herein, sentences of the form "a PPG signal is recognizable from color changes in a region in images" refer to effects of blood volume changes due to pulse waves that may be extracted from a series of images of the region. These changes may be identified and/or utilized by a computer (e.g., in order to generate a signal indicative of the blood volume at the region), but need not necessarily be recognizable to the naked eye (e.g., because of their subtlety, the short duration in which they occur, or involvement of light outside of the visible spectrum). For example, blood flow may cause facial skin color changes (FSCC) that corresponds to different concentrations of oxidized hemoglobin due to varying volume of blood at a certain region due to different stages of a cardiac pulse, and/or the different magnitudes of cardiac output Similar blood flow dependent effects may be viewed with other types of signals (e.g., slight changes in cutaneous temperatures due to the flow of blood).

In some embodiments, the system configured to detect the abnormal medical event may further include first and second outward-facing head-mounted cameras for taking images of the environment to the right and to the left of the user's head, respectively. Images taken by these cameras, which are indicative of illumination towards the face, may be utilized to improve the accuracy of detecting the abnormal medical event.

In one example, the first and second outward-facing head-mounted cameras may be thermal cameras that take thermal measurements of the environment. Heat from the environment may affect the surface blood flow, and thus reduce the accuracy of detecting the abnormal medical event. By taking the thermal measurements of the environment into account, the computer is able to detect, and maybe even compensate, for temperature interferences from the environment. Examples of outward-facing head-mounted thermal cameras include thermopile-based and/or microbolometer-based cameras having one or more pixels.

In another example, the first and second outward-facing head-mounted cameras may be visible-light cameras (such as CMOS cameras), and/or light intensity sensors (such as photodiodes, photoresistors, and/or phototransistor). Illumination from the environment may affect the surface blood flow (especially when heating the skin), and/or interfere with the photoplethysmographic signals to be measured, and thus reduce the accuracy of detecting the abnormal medical event. By taking the illumination from the environment into account, the computer is able to detect, and maybe even compensate, for the interferences from the environment.

In one embodiment, the at least one right-side head-mounted device and/or the at least one left-side head-mounted device are coupled to a clip-on, and the clip-on comprises a body configured to be attached and detached, multiple times, from a frame configured to be worn on the user's head. Various embodiments described herein include a computer configured to detect the abnormal medical event based on an asymmetrical change to blood flow recognizable in at least $PPG_{SR1}$, $PPG_{SR2}$, $PPG_{SL1}$, and $PPG_{SL2}$. Optionally, the asymmetrical change to the blood flow corresponds to a deviation of $PPG_{SR1}$, $PPG_{SR2}$, $PPG_{SL1}$, and $PPG_{SL2}$ compared to a baseline based on previous measurements of $PPG_{SR1}$, $PPG_{SR2}$, $PPG_{SL1}$, and $PPG_{SL2}$ of the user, taken before the abnormal medical event (e.g., minutes, hours, and even days before the abnormal medical event). In one example, "a baseline based on the previous measurements" is one or more values that are calculated based on the previous measurements (e.g., one or more values representing a normal, baseline blood flow of the user). In another example, "a baseline based on the previous measurements" may be some, or even all, the previous measurements themselves, which may be provided as an input used in calculations involved in the detection of the abnormal medical event (without necessarily calculating an explicit value that is considered a "baseline" value of the user's blood flow).

Figure 88A:
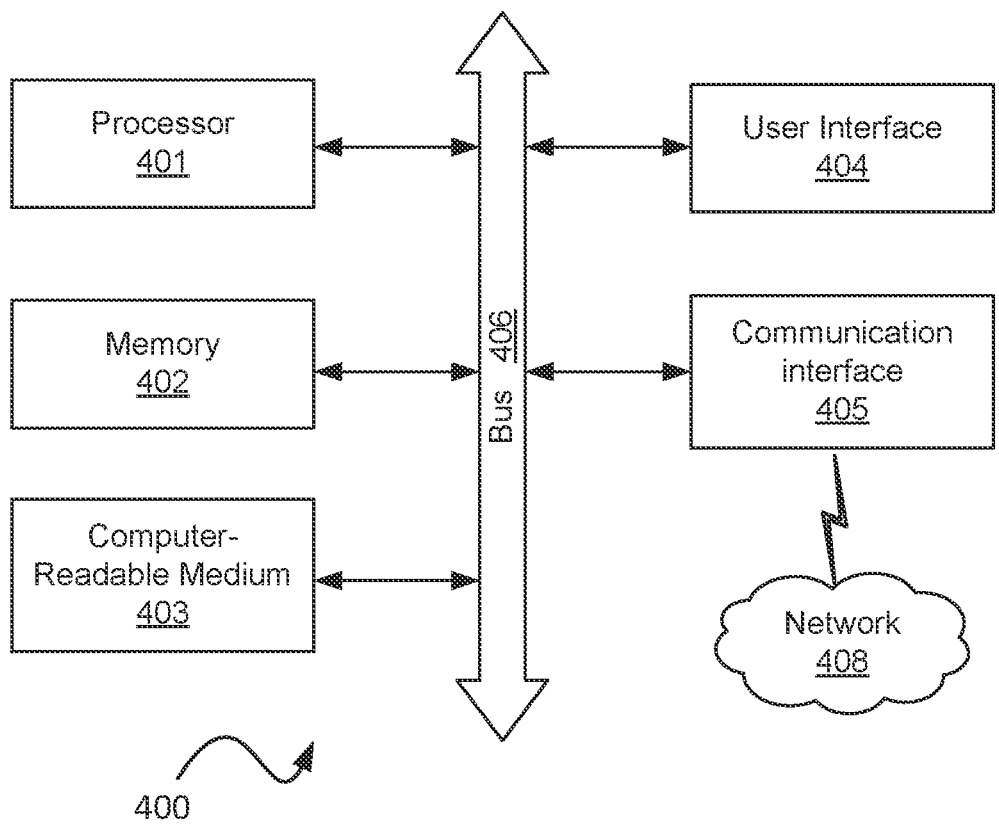
FIG. 88A and FIG. 88B are schematic illustrations of possible embodiments for computers.
Figure 88B:
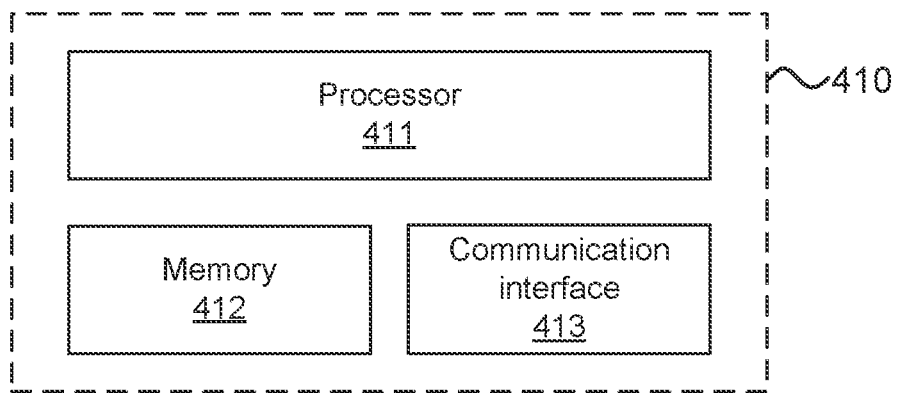

Examples of computers that may be utilized to perform calculations involved in the detection of the abnormal medical event are computers modeled according to computer 400 or computer 410 illustrated in FIG. 88A and FIG. 88B, respectively. Additional examples are the computers 673 and 676 illustrated in FIG. 72A and FIG. 72B, respectively. It is to be noted that the use of the singular term "computer" is intended to imply one or more computers, which jointly perform the functions attributed to "the computer" herein. In particular, in some embodiments, some functions attributed to the computer, such as preprocessing $PPG_{SR1}$, $PPG_{SR2}$, $PPG_{SL1}$, and $PPG_{SL2}$, may be performed by a processor on a wearable device (e.g., smartglasses) and/or a computing device of the user (e.g., smartphone), while other functions, such as the analysis of sensor data and determining whether the user is experiencing the abnormal medical event, may be performed on a remote processor, such as a cloud-based server. In other embodiments, essentially all functions attributed to the computer herein may be performed by a processor on a wearable device (e.g., smartglasses to which the head-mounted devices are coupled) and/or some other device carried by the user, such as a smartwatch or smartphone.

Herein, detecting the abnormal medical event may mean detecting that the user is suffering from the abnormal medical event, and/or that there is an onset of the abnormal medical event. Additionally, an "abnormal" medical event may be a medical event that the user has yet to experience, or does not experience most of the time.

In some embodiments, detecting the abnormal medical event may involve calculating one or more of the following values: an indication of whether or not the user is experiencing the abnormal medical event, a value indicative of an extent to which the user is experiencing the abnormal medical event, a duration since the onset of the abnormal medical event, and a duration until an onset of the abnormal medical event.

When the blood flow on both sides of the head and/or body are monitored, asymmetric changes may be recognized. These changes are typically different from symmetric changes that can be caused by factors such as physical activity (which typically affects the blood flow on both sides in the same way). An asymmetric change to the blood flow can mean that one side has been affected by an event, such as a stroke, which does not influence the other side. In one example, the asymmetric change to blood flow involves a change in blood flow velocity on left side of the head that is at least 10% greater or 10% lower than a change in blood flow velocity on one right side of the head. In another example, the asymmetric change to blood flow involves a change in the volume of blood the flows during a certain period in the left side of the head that is at least 10% greater or 10% lower than the volume of blood that flows during the certain period in the right side of the head. In yet another example, the asymmetric change to blood flow involves a change in the direction of the blood flow on one side of the head (e.g., as a result of a stroke), which is not necessarily observed at the symmetric location on the other side of the head.

Referring to an asymmetrical change to blood flow as being "recognizable in $PPG_{SR1}$, $PPG_{SR2}$, $PPG_R A$, and $PPG_{SL2}$" means that values extracted from $PPG_{SR1}$, $PPG_{SR2}$, $PPG_{SL1}$, and $PPG_{SL2}$ provide an indication that an asymmetric change to the blood flow has occurred. That is, a difference that has emerged in the $PPG_{SR1}$, $PPG_{SR2}$, $PPG_{SL1}$, and $PPG_{SL2}$ may reflect a change in blood flow velocity on one side of the head, a change in blood flow volume, and/or a change in blood flow direction, as described in the examples above. It is to be noted, that the change in blood flow does not need to be directly quantified from the values $PPG_{SR1}$, $PPG_{SR2}$, $PPG_{SL1}$, and $PPG_{SL2}$ in order for it to be "recognizable in $PPG_{SR1}$, $PPG_{SR2}$, $PPG_{SL1}$, and $PPG_{SL2}$". Rather, in some embodiments, feature values generated based on $PPG_{SR1}$, $PPG_{SR2}$, $PPG_{R}A$, and $PPG_{SL2}$ may be used by a machine learning-based predictor to detect a phenomenon, such as the abnormal medical event, which is associated with the asymmetrical change in blood flow.

Having multiple PPG signals, measured at different sides of the head, can assist in detecting an asymmetric change to blood flow in different ways. In one example, an asymmetric change in blood flow may be characterized in an increase in volume at a certain region and/or side of the head, compared to other regions and/or the other side of the head. In this example, the amplitude of the PPG signal at the certain region may show a greater increase compared to increases observed with PPG signals at other regions and/or on the other side of the head. In another example, an asymmetric change in blood flow may be characterized by a decrease in blood velocity at a certain region and/or side of the head, compared to other regions and/or the other side of the head. In this example, a pulse arrival time (PAT) at the certain region may exhibit a larger delay compared to the delay of PATs at other regions and/or at the other side of the head. In still another example, an asymmetric change in blood flow may be characterized by a change in a direction of blood flow at a certain region, compared to other regions and/or the symmetric region on the other side of the head. In this example, an order at which pulse waves arrive at different regions (as evident by PPG signals at the different regions) may be indicative of the direction of blood flow. Thus, a change in the arrival order of pulse waves on one side of the head, which does not occur at regions on the other side of the head, may indicate an asymmetrical change of a direction of blood flow.

In some embodiments, the computer detects the abnormal medical event by utilizing previously taken PPG signals of the user (i.e., previously taken $PPG_{SR1}$, $PPG_{SR2}$, $PPG_{SL1}$, and $PPG_{SL2}$), from a period that precedes the current abnormal medical event being detected at that time. This enables an asymmetrical change to be observed, since it provides a baseline according to which it is possible to compare current $PPG_{SR1}$, $PPG_{SR2}$, $PPG_{SL1}$, and $PPG_{SL2}$, such that it may be determined that a change to blood flow on one side of the head is not the same as a change on the other side of the head. In some embodiments, previously taken $PPG_{SR1}$, $PPG_{SR2}$, $PPG_{SL1}$, and $PPG_{SL2}$ are utilized to calculate a baseline blood flow, such as values representing the extent of blood flow at the different sides of the head, and/or at different regions (e.g., $ROI_{R1}$, $ROI_{R2}$, $ROI_{L1}$, and $ROI_{L2}$). Optionally, calculating the baseline blood flow may be done based on previously taken $PPG_{SR1}$, $PPG_{SR2}$, $PPG_{SL1}$, and $PPG_{SL2}$ that were measured at least an hour before the abnormal medical event is detected. Optionally, the previously taken $PPG_{SR1}$, $PPG_{SR2}$, $PPG_{R}A$, and $PPG_{SL2}$ include PPG signals measured at least a day before the abnormal medical event is detected. Optionally, the previously taken $PPG_{SR1}$, $PPG_{SR2}$, $PPG_{SL1}$, and $PPG_{SL2}$ include PPG signals measured more than a week before the abnormal medical event is detected.

A baseline for the blood flow may be calculated in various ways. In a first example, the baseline is a function of the average measurements of the user (which include previously taken $PPG_{SR1}$, $PPG_{SR2}$, $PPG_{SL1}$, and $PPG_{SL2}$), which were taken before the occurrence of the abnormal medical event. In a second example, the baseline may be a function of the situation the user is in, such that previous measurements taken during similar situations are weighted higher than previous measurements taken during less similar situations. A PPG signal may show different characteristics in different situations because of the different mental and/or physiological states of the user in the different situations. As a result, a situation-dependent baseline can improve the accuracy of detecting the abnormal medical event. In a third example, the baseline may be a function of an intake of some substance, such that previous measurements taken after consuming similar substances are weighted higher than previous measurements taken after not consuming the similar substances and/or after consuming less similar substances. A PPG signal may show different characteristics after the user consumes different substances because of the different mental and/or physiological states the user may be in after consuming the substances, especially when the substances include things such as medications, drugs, alcohol, and/or certain types of food. As a result, a substance-dependent baseline can improve the accuracy of detecting the abnormal medical event.

There are various types of abnormal medical events that may be detected based on PPG signals that reflect an asymmetrical change to blood flow, which is recognizable in $PPG_{SR1}$, $PPG_{SR2}$, $PPG_{SL1}$, and $PPG_{SL2}$ of the user.

In some embodiments, the abnormal medical event may involve the user having a cerebrovascular accident, which is also known as having a stroke. An occurrence of a stroke often has the following effect on a person. A blood clot (in the case of ischemic stroke) or the raptured artery (in the case of a hemorrhagic stroke) changes the blood flow to certain regions of the brain. One or more of several mechanisms may be the cause of changes to blood flow that are observed following an onset of a stroke. Blood flow may change due to a stroke because of flaccid muscles (on one side of the face) that use less oxygen and demand less blood. In such an event, local regulation mechanisms may generate signals to the smooth muscles that decrease the diameter of the arteries (which can reduce blood flow). Additionally or alternatively, blood flow may change due to a stroke because of nerve control changes that occur due to reduced blood flow to the brain (a neurogenic mechanism); the same nerves that control the muscles can also be involved in the control of the constriction/dilation of blood vessels. Another possible cause of changes to blood flow involves obstruction-related passive changes. Blood that flows through the major vessels (in the base of the brain it is either the carotid (front) or vertebral (back) arteries, must flow out through one of the branches. When one pathway is blocked or restricted (due to the stroke), more blood has to go through collateral pathways (which may change the blood flow). Thus, changes to the blood flow in the face (and other areas of the head), especially if they are asymmetric, can be early indicators of a stroke. An event of a stroke may be detected in various ways, some which are described in the following examples.

In one embodiment, the abnormal medical event is an ischemic stroke, and the deviation (of $PPG_{SR1}$, $PPG_{SR2}$, $PPG_{SL1}$, and $PPG_{SL2}$ compared to a baseline based on the previous measurements of $PPG_{SR1}$, $PPG_{SR2}$, $PPG_{SL1}$, and $PPG_{SL2}$ of the user) involves an increase in asymmetry between blood flow on the left side of the head and blood flow on the right side of the head, with respect to a baseline asymmetry level between blood flow on the left side of the head and blood flow on the right side of the head (as determined based on the previous measurements). In some embodiments, the term "ischemic stroke" may also include Transient Ischemic Attack (TIA), known as "mini stroke".

In another embodiment, the abnormal medical event is an ischemic stroke, and the deviation (of $PPG_{SR1}$, $PPG_{SR2}$, $PPG_{SL1}$, and $PPG_{SL2}$ compared to a baseline based on the previous measurements of $PPG_{SR1}$, $PPG_{SR2}$, $PPG_{SL1}$, and $PPG_{SL2}$ of the user) involves a monotonic increase in asymmetry between blood flow at $ROI_{R1}$ and $ROI_{R2}$, with respect to a baseline asymmetry of the user (between blood flow at $ROI_{R1}$ and $ROI_{R2}$) during a period longer than 10 minutes. Optionally, $ROI_{R1}$ is located in proximity of the mastoid process behind the right ear, and $ROI_{R2}$ is located before of the right ear.

In yet another embodiment, the abnormal medical event is an ischemic stroke, and the deviation involves an increase in variation between blood flow at $ROI_{R1}$ and $ROI_{R2}$, with respect to a baseline variation of the user between blood flow at $ROI_{R1}$ and $ROI_{R2}$. Optionally, the computer suggests the user to take images of at least one of the retinas, responsive to detecting the increase in variation. The computer may then compare the images of the retinas with previously taken images of the user's retinas, and utilize such a comparison to improve the accuracy of detecting whether the user has suffered the ischemic stroke. Optionally, the comparison of the images of the retinas may take into account parameters such as the diameter of retinal arteries, swelling of the boundaries of the optic disk, and/or blurring of the boundaries of the optic disk. The images of the retinas may be taken by any known and/or to be invented appropriate device.

In some embodiments, the abnormal medical event may involve the user having a migraine or another form of headache. With migraines and other headaches, vasoconstriction of facial or cranial blood vessels may lead to asymmetric changes in blood flow between the left and right sides of the head. Compensatory mechanisms may change smooth muscle constriction around blood vessels, further exacerbating this asymmetry. This vasoconstriction can lead to differential surface blood flow, muscle contraction, and facial temperature changes, leading to asymmetric blood flow. As each individual's particular patterns of vasoconstriction would be unique to the individual, the asymmetric phenomena may be different for different users. Thus, measuring deviation from the user's baseline blood flow patterns may increase the accuracy of detecting these asymmetric phenomena, in some embodiments. Additionally, the time course of migraine or headache usually involves an occurrence over the course of minutes to hours (from the onset of changes to blood flow), and usually occurs with a characteristic pattern, allowing it to be differentiated from signs of other medical, artificial or external causes, which manifest different patterns of blood flow and/or time courses.

In one embodiment, the abnormal medical event is a migraine attack, and the deviation (of $PPG_{SR1}$, $PPG_{SR2}$, $PPG_{SL1}$, and $PPG_{SL2}$ compared to a baseline based on the previous measurements of $PPG_{SR1}$, $PPG_{SR2}$, $PPG_{SL1}$, and $PPG_{SL2}$ of the user) is indicative of a pattern of a certain change to facial blood flow, which is associated with a pattern of a change to facial blood flow of at least one previous migraine attack, determined based on data comprising previous $PPG_{SR1}$, $PPG_{SR2}$, $PPG_{SL1}$, and $PPG_{SL2}$, which were measured starting from at least 5 minutes before the previous migraine attack. In this embodiment, the time of the beginning of the previous migraine attack corresponds to the time at which the user became aware of the migraine attack.

In another embodiment, the abnormal medical event is headache, and the deviation is indicative of at least one of: a change in directionality of facial blood flow, and an asymmetrical reduction in blood flow to one side of the face (for a period lasting more than one minute). For some people, a migraine attack and/or a headache may cause a change in directionality of facial blood flow because the pulse propagation across the face arrives at one side before it arrives to the other side. In one example, the changes in directionality of facial blood flow are calculated from phase variations between $PPG_{SR1}$, $PPG_{SR2}$, $PPG_{SL1}$, and $PPG_{SL2}$ relative to a baseline for the user. For some people, vasoconstriction caused by a migraine attack and/or a headache may affect the amplitude of the PPG signals, such as decreasing of amplitudes of the PPG signals in a certain region. In one example, the reduction in blood flow to one side of the face is calculated from changes between amplitudes of $PPG_{SR1}$, $PPG_{SR2}$, $PPG_{SL1}$, and $PPG_{SL2}$ relative to the baseline.

In some embodiments, the abnormal medical event may involve the user suffering from an infection. Inflammatory conditions, such as cellulitis, dermatitis and ear infection, originate in infection or inflammation in one particular region of the face, causing vasodilation leading to a facial asymmetry originating from phenomena such as increase in swelling, redness and warmth, which are detectable only in the vicinity of the infection. As each individual's baseline facial blood flow and coloration is different, comparing current measurements with the baseline may allow accurate identification of vasodilation resulting from an inflammatory condition. The time course of such inflammatory conditions would usually occur over the course of hours to days, allowing it to be differentiated from other medical or artificial phenomena, which may have similar signs but over a different time course.

Since inflammation often causes temperatures at the infected region to rise, accuracy of detection of some abnormal medical events may increase by measuring the temperature at different regions on the head. In one embodiment, the system configured to detect an abnormal medical event includes right and left head-mounted thermometers, located at least 2 cm to the right and to the left of a vertical symmetry axis that divides the face, respectively. The head-mounted thermometers may be contact thermometers, such as thermistors, and/or non-contact thermal cameras. Optionally, the head-mounted thermometers measure ROIs on one or more of the following regions: the forehead, the temples, behind the ear, the cheeks, the nose, and the mouth. The right and left head-mounted thermometers take right and left temperature measurements, respectively. Optionally, the computer detects the abnormal medical event also based on a deviation of the right and left temperature measurements from a baseline temperature for the user, where the baseline temperature for the user is calculated based on data comprising previous right and left temperature measurements of the user, taken more than a day before the abnormal medical event. Optionally, the abnormal medical event detected in this embodiment is selected from a set comprising cellulitis and dermatitis.

In one embodiments, the system configured to detect an abnormal medical event may optionally include right and left head-mounted thermometers, located less than 4 cm from the right and left earlobes, respectively, which provide right and left temperature measurements, respectively. Optionally, the computer detects the abnormal medical event also based on a deviation of the right and left temperature measurements from a baseline temperature for the user, where the baseline temperature for the user is calculated based on data comprising previous right and left temperature measurements of the user, taken more than a day before the abnormal medical event. In one example, the abnormal medical event is ear infection. In another example, the abnormal medical event is cerebrovascular accident. In still another example, the abnormal medical event is mastoiditis.

Obtaining the PPG signals $PPG_{SR1}$, $PPG_{SR2}$, $PPG_{SL1}$, and $PPG_{SL2}$ from measurements taken by the at least one right-side head-mounted device and the at least one left-side head-mounted device may involve, in some embodiments, performing various preprocessing operations in order to assist in calculations and/or in extraction of the PPG signals. Optionally, the measurements may undergo various preprocessing steps prior to being used by the computer to detect the abnormal medical event, and/or as part of the process of the detection of the abnormal medical event. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081.

In some embodiments, in which the at least one right-side head-mounted device and/or at least one left-side head-mounted device are cameras, images taken by the cameras may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an PPG signals from images are discussed in Zaunseder et al. (2018), "Cardiovascular assessment by imaging photoplethysmography—a review", Biomedical Engineering 63(5), 617-634. An example of preprocessing that may be used in some embodiments is given in U.S. Pat. No. 9,020,185, titled "Systems and methods for non-contact heart rate sensing", which describes how a times-series signals obtained from video of a user can be filtered and processed to separate an underlying pulsing signal by, for example, using an ICA algorithm.

In some embodiments, detection of the abnormal medical event may involve calculation of pulse arrival times (PATs) at one or more of the regions $ROI_{R1}$, $ROI_{R2}$, $ROI_{L1}$ and $ROI_{L2}$. Optionally, a PAT calculated from an PPG signal represents a time at which the value representing blood volume (in the waveform represented in the PPG) begins to rise (signaling the arrival of the pulse). Alternatively, the PAT may be calculated as a different time, with respect to the pulse waveform, such as the time at which a value representing blood volume reaches a maximum or a certain threshold, or the PAT may be the average of the time the blood volume is above a certain threshold. Another approach that may be utilized to calculate a PAT from an iPPG signal is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

Detection of the abnormal medical event may involve the computer utilizing an approach that may be characterized as involving machine learning. In some embodiments, such a detection approach may involve the computer generating feature values based on data that includes PPG signals (i.e., $PPG_{SR1}$, $PPG_{SR2}$, $PPG_{SL1}$, and $PPG_{SL2}$ of the user) and optionally other data, and then utilizing a previously trained model to calculate one or more values indicative of whether the user is experiencing the abnormal medical event (which may be any one of the examples of values mentioned further above as being calculated by the computer for this purpose). It is to be noted that when the computer calculates a value that is indicative of the user having the abnormal medical event, at least some of the feature values may reflect the fact that an asymmetrical change to blood flow had occurred. Optionally, the additional data used to generate at least some of the feature values includes previous measurements of $PPG_{SR1}$, $PPG_{SR2}$, $PPG_{SL1}$, and $PPG_{SL2}$ of the user, and/or measurements from additional sensors and/or data sources as discussed below.

Feature values generated based on PPG signals may include various types of values, which may be indicative of dynamics of the blood flow at the respective regions to which the PPG signals correspond. Optionally, these feature values may relate to properties of a pulse waveform, which may be a specific pulse waveform (which corresponds to a certain beat of the heart), or a window of pulse waveforms (e.g., an average property of pulse waveforms in a certain window of time). Some examples of feature values that may be generated based on a pulse waveform include: the area under the pulse waveform, the amplitude of the pulse waveform, a derivative and/or second derivative of the pulse waveform, a pulse waveform shape, pulse waveform energy, and pulse transit time (to the respective ROI). Some additional examples of features may be indicative one or more of the following: a magnitude of a systolic peak, a magnitude of a diastolic peak, duration of the systolic phase, and duration of the diastolic phase. Additional examples of feature values may include properties of the cardiac activity, such as the heart rate and heart rate variability (as determined from the PPG signal). Additionally, some feature values may include values of other physiological signals that may be calculated based on PPG signals, such as blood pressure and cardiac output.

It is to be noted that the aforementioned feature values may be calculated in various ways. In one example, some feature values are calculated for each PPG signal individually. In another example, some feature values are calculated after normalizing a PPG signal with respect to previous measurements from the corresponding PPG device used to measure the PPG signal. In other examples, at least some of the feature values may be calculated based on an aggregation of multiple PPG signals (e.g., different pixels/regions in images captured by an iPPG device), or by aggregating values from multiple contact PPG devices.

In some embodiments, at least some of the feature values may represent comparative values, which provide an indication of the difference in blood flow, and/or in some other property that may be derived from a PPG signal, between various regions on the head. Optionally, such feature values may assist in detecting asymmetrical blood flow (and/or changes thereto). In one example, the feature values include a certain feature value indicative of a difference in maximal amplitudes of one or more of the following pairs of PPG signals: (i) $PPG_{SR1}$ and $PPG_{SR2}$, (ii) $PPG_{SR1}$ and $PPG_{SL1}$, and (iii) $PPG_{SR1}$ and $PPG_{SL2}$. In another example, the feature values include a certain feature value indicative of a difference in a pulse arrival time between the following pairs of regions of interest: (i) $ROI_{R1}$ and $ROI_{R2}$, $ROI_{R1}$ and $ROI_{L1}$, and (iii) $ROI_{R1}$ and $ROI_{L2}$.

In some embodiments, at least some of the feature values describe properties of pulse waveforms (e.g., various types of feature values mentioned above), which are derived from the previous measurements of $PPG_{SR1}$, $PPG_{SR2}$, $PPG_{SL1}$, and $PPG_{SL2}$ of the user. Optionally, these feature values may include various blood flow baselines for the user, which correspond to a certain situation the user was in when the previous measurements were taken.

In some embodiments, at least some of the feature values may be "raw" or minimally processed measurements of the at least one right-side head-mounted device and/or at least one left-side head-mounted device. In one example, at least some of the feature values may be values obtained from contact PPG devices. In another example, at least some of the feature values may be pixel values obtained by inward-facing head-mounted cameras. Optionally, the pixel values may be provided as input to functions in order to generate at feature values that are low-level image-based features. Some examples of low-level features, which may be derived from images, include feature generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may be derived from multiple images taken at different times, such as volume local binary patterns (VLBP), cuboids, and/or optical strain-based features. In one example, one or more of the feature values may represent a difference between values of pixels at one time t and values of other pixels at a different region at some other time t+x (which, for example, can help detect different arrival times of a pulse wave).

In some embodiments, at least some feature values may be generated based on other data sources (in addition to PPG signals). In some examples, at least some feature values may be generated based on other sensors, such as movement sensors (which may be head-mounted, wrist-worn, or carried by the user some other way), head-mounted thermal cameras (e.g., as mentioned above), or other sensors used to measure the user. In other examples, at least some feature values may be indicative of environmental conditions, such as the temperature, humidity, and/or extent of illumination (e.g., as obtained utilizing an outward-facing head-mounted camera). Additionally, some feature values may be indicative of physical characteristics of the user, such as age, sex, weight, Body Mass Index (BMI), skin tone, and other characteristics and/or situations the user may be in (e.g., level of tiredness, consumptions of various substances, etc.)

Stress is a factor that can influence the diameter of the arteries, and thus influence calculated values that relate to the PPG signals and/or blood flow. In one embodiment, the computer receives a value indicative of a stress level of the user, and generates at least one of the feature values based on the received value. Optionally, the value indicative of the stress level is obtained using a thermal camera. In one example, the system may include an inward-facing head-mounted thermal camera that takes measurements of a periorbital region of the user, where the measurements of a periorbital region of the user are indicative of the stress level of the user. In another example, the system includes an inward-facing head-mounted thermal camera that takes measurements of a region on the forehead of the user, where the measurements of the region on the forehead of the user are indicative of the stress level of the user. In still another example, the system includes an inward-facing head-mounted thermal camera that takes measurements of a region on the nose of the user, where the measurements of the region on the nose of the user are indicative of the stress level of the user.

Hydration is a factor that affects blood viscosity, which can affect the speed at which the blood flows in the body. In one embodiment, the computer receives a value indicative of a hydration level of the user, and generates at least one of the feature values based on the received value. Optionally, the system includes an additional camera that detects intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer as values indicative of the hydration level of the user.

The following are examples of embodiments that utilize additional inputs to generate feature values used to detect the abnormal medical event. In one embodiment, the computer receives a value indicative of a temperature of the user's body, and generates at least one of the feature values based on the received value. In another embodiment, the computer receives a value indicative of a movement of the user's body, and generates at least one of the feature values based on the received value. For example, the computer may receive the input form a head-mounted Inertial Measurement Unit (IMU) that includes a combination of accelerometers, gyroscopes, and optionally magnetometers, and/or an IMU in a mobile device carried by the user. In yet another embodiment, the computer receives a value indicative of an orientation of the user's head, and generates at least one of the feature values based on the received value. For example, the computer may receive the values indicative of the head's orientation from an outward-facing head-mounted camera, and/or from a nearby non-wearable video camera. In still another embodiment, the computer receives a value indicative of consumption of a substance by the user, and generates at least one of the feature values based on the received value. Optionally, the substance comprises a vasodilator and/or a vasoconstrictor.

The model utilized to detect the abnormal medical event may be generated, in some embodiments, based on data obtained from one or more users, corresponding to times in which the one or more users were not affected by the abnormal medical event, and additional data obtained while the abnormal medical event occurred and/or following that time. Thus, this training data may reflect PPG signals and/or blood flow both at normal times, and changes to PPG signals and/or blood flow that may ensue due to the abnormal medical event. This data may be used to generate samples, each sample including feature values generated based on PPG signals of a user and optionally additional data (as described above), and a label. The PPG signals include $PPG_{SR1}$, $PPG_{SR2}$, $PPG_{SL1}$, and $PPG_{SL2}$ of the user at a certain time, and optionally previous $PPG_{SR1}$, $PPG_{SR2}$, $PPG_{SL1}$, and $PPG_{SL2}$ of the user, taken before the certain time. The label is a value related to the status of the abnormal medical event. For example, the label may be indicative of whether the user, at the certain time, experienced the abnormal medical event. In another example, the label may be indicative of the extent or severity of the abnormal medical event at the certain time. In yet another example, the label may be indicative of the duration until an onset of the abnormal medical event. In still another example, the label may be indicative of the duration that has elapsed since the onset of the abnormal medical event.

In some embodiments, the model used by the computer to detect the abnormal medical event from measurements of a certain user may be generated, at least in part, based on data that includes previous measurements of the certain user (and as such, may be considered personalized to some extent for the certain user). Additionally or alternatively, in some embodiments, the model may be generated based on data of other users. Optionally, the data used to train the model may include data obtained from a diverse set of users (e.g., users of different ages, weights, sexes, preexisting medical conditions, etc.). Optionally, the data used to train the model which is used to detect the abnormal medical event with a certain user includes data of other users with similar characteristics to the certain user (e.g., similar weight, age, sex, height, and/or preexisting condition).

In order to achieve a robust model, which may be useful for detecting the abnormal medical event for a diverse set of conditions, in some embodiments, the samples used for the training of the model may include samples based on data collected when users were in different conditions. Optionally, the samples are generated based on data collected on different days, while indoors and outdoors, and while different environmental conditions persisted. In one example, the model is trained on samples generated from a first set of training data taken during daytime, and is also trained on other samples generated from a second set of training data taken during nighttime. In a second example, the model is trained on samples generated from a first set of training data taken while users were exercising and moving, and is also trained on other samples generated from a second set of data taken while users were sitting and not exercising.

Utilizing the model to detect the abnormal medical event may involve the computer performing various operations, depending on the type of model. The following are some examples of various possibilities for the model and the type of calculations that may be accordingly performed by the computer, in some embodiments, in order to calculate a value indicative of whether the user was experiencing the abnormal medical event: (a) the model comprises parameters of a decision tree. Optionally, the computer simulates a traversal along a path in the decision tree, determining which branches to take based on the feature values. A value indicative of whether the user was experiencing the abnormal medical event may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of whether the user was experiencing the abnormal medical event; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of whether the user was experiencing the abnormal medical event.

In some embodiments, a machine learning approach that may be applied to calculating a value indicative of whether the user is experiencing an abnormal medical event may be characterized as "deep learning". In one embodiment, the model may include parameters describing multiple hidden layers of a neural network. Optionally, the model may include a convolution neural network (CNN). In one example, the CNN may be utilized to identify certain patterns in video images, such as the patterns of corresponding to blood volume effects and ballistocardiographic effects of the cardiac pulse. Due to the fact that calculating a value indicative of whether the user is experiencing the abnormal medical event may be based on multiple, possibly successive, images that display a certain pattern of change over time (i.e., across multiple frames), these calculations may involve retaining state information that is based on previous images. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

The following method for detecting an abnormal medical event may be used by systems modeled according to FIG. 72A or FIG. 72B. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, measuring, utilizing at least one right-side head-mounted device, at least two signals indicative of photoplethysmographic signals ($PPG_{SR1}$ and $PPG_{SR2}$, respectively) at first and second regions of interest ($ROI_{R1}$ and $ROI_{R2}$, respectively) on the right side of a user's head. $ROI_{R1}$ and $ROI_{R2}$ are located at least 2 cm apart.

In Step 2, measuring, utilizing at least one left-side head-mounted device, at least two signals indicative of photoplethysmographic signals ($PPG_{SL1}$ and $PPG_{SL2}$, respectively) at first and second regions of interest ($ROI_{L1}$ and $ROI_{L2}$, respectively) on the left side of the user's head. $ROI_{L1}$ and $ROI_{L2}$ are located at least 2 cm apart.

And in Step 3, detecting the abnormal medical event based on an asymmetrical change to blood flow recognizable in $PPG_{SR1}$, $PPG_{SR2}$, $PPG_{SL1}$, and $PPG_{SL2}$, relative to a baseline based on previous measurements of $PPG_{SR1}$, $PPG_{SR2}$, $PPG_{SL1}$, and $PPG_{SL2}$ of the user, taken before the abnormal medical event.

In some embodiments, detecting the abnormal medical event is done utilizing a machine learning-based approach. Optionally, the method includes the following steps: generating feature values based on data comprising: (i) $PPG_{SR1}$, $PPG_{SR2}$, $PPG_{SL1}$, and $PPG_{SL2}$ of the user, and (ii) the previous measurements of $PPG_{SR1}$, $PPG_{SR2}$, $PPG_{SL1}$, and $PPG_{SL2}$ of the user; and utilizing a model to calculate, based on the feature values, a value indicative of whether the user is experiencing the abnormal medical event.

Various embodiments described herein involve detections of physiological responses based on user measurements. Some examples of physiological responses include stress, an allergic reaction, an asthma attack, a stroke, congestive heart failure, dehydration, intoxication (including drunkenness), a headache (which includes a migraine), and/or fatigue. Other examples of physiological responses include manifestations of fear, startle, sexual arousal, anxiety, joy, pain or guilt. Still other examples of physiological responses include physiological signals such as cardiovascular parameters (such as heart rate, blood pressure, and/or cardiac output), temperature, values of eye-related parameters (such as eye movements and/or pupil diameter), values of speech related parameters (such as frequencies and/or tempo), and/or values of respiratory related parameters (such as respiration rate, tidal volume, and/or exhale duration) of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of measurements taken during multiple of the above-described windows, such as measurements taken during different days. In some embodiments, a computer may receive a stream of measurements, taken while the user wears an HMS with coupled cameras and/or other sensors during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with cameras and/or other sensors, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken over a long period (e.g., measurements taken on "different days") may have an advantage, in some embodiments, of contributing to the generalizability of a trained model. Measurements taken over the long period likely include measurements taken in different environments, and/or measurements taken while the measured user was in various physiological and/or mental states (e.g., before/after meals, and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing measurements to a threshold (when the threshold is reached that may be indicative of an occurrence of the physiological response), comparing measurements to a reference time series, and/or by performing calculations that involve a model trained using machine learning methods. Optionally, the measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minutes, one hour, four hours, one day, or one week. In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline measurement values, most of which were taken when the user was not experiencing the physiological response. Optionally, detecting the physiological response may rely on observing a change to typical measurement value at one or more ROIs (the baseline), where different users might have different typical measurement values at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorical value indicative of the severity/extent of the physiological response, (iv) an expected change in measurements of an ROI, and/or (v) rate of change in measurements of an ROI. Optionally, when the physiological response corresponds to a physiological signal (e.g., a heart rate, a breathing rate, or an extent of frontal lobe brain activity), the extent of the physiological response may be interpreted as the value of the physiological signal.

One approach for detecting a physiological response, which may be utilized in some embodiments, involves comparing measurements of one or more ROIs to a threshold. In these embodiments, the computer may detect the physiological response by comparing the measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to a value (such as temperature or heart rate), the certain change may be positive or negative. Different physiological responses described herein may involve different types of thresholds, which may be an upper threshold (where reaching the threshold means≥the threshold) or a lower threshold (where reaching the threshold means≤the threshold).

Another approach for detecting a physiological response, which may be utilized in some embodiments, may be applicable when the measurements of a user are treated as time series data. In some embodiments, the computer may compare measurements (represented as a time series) to one or more reference time series that correspond to periods of time in which the physiological response occurred. Additionally or alternatively, the computer may compare the measurements to other reference time series corresponding to times in which the physiological response did not occur. Optionally, if the similarity between the measurements and a reference time series corresponding to a physiological response reaches a threshold, this is indicative of the fact that the measurements correspond to a period of time during which the user had the physiological response. Optionally, if the similarity between the measurements and a reference time series that does not correspond to a physiological response reaches another threshold, this is indicative of the fact that the measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

A user interface (UI) may be utilized, in some embodiments, to notify the user and/or some other entity, such as a caregiver, about the physiological response, and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following non-limiting examples: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or blood pressure reaching a predetermined level).

Due to the mostly symmetric nature of the human body, when the face undergoes temperature changes, e.g., due to external factors such as the temperature in the environment or internal factors such as an activity-related rise in body temperature, the changes to the face are generally symmetric. That is, the temperature changes at a region of interest (ROI) on the left side of the face (e.g., the left side of the forehead) are usually similar to the temperature changes at the symmetric ROI on the right side of the face (e.g., the right side of the forehead). However, when the temperature on the face changes in an asymmetric way, this can be indicative of various physiological responses and/or undesirable phenomena. Some examples of phenomena that may be identified by detecting asymmetric thermal patterns ("thermal asymmetry") on a user's face include some types of strokes. In the case of stroke, often the decreased blood flow in certain regions of the head (due to the stroke) can cause a decrease in the cutaneous temperatures near those certain regions.

Some embodiments utilize head-mounted sensors in order to detect stroke signs that involve detectable changes in temperature and/or blood flow due to a stroke event.

In some embodiments, "stroke symptoms" refers to changes to function/sensation reported by the patient. In some embodiments, "stroke signs" refers to objective changes observable by a human individual and/or a sensor. Detecting stroke symptoms and/or stroke signs may also be referred to herein as detecting "whether the user has suffered from a stroke". It is to be noted that a detection that the user has suffered from a stroke may be interpreted, in some cases, as indicating that there is a higher than normal risk that the user has suffered from a stroke, and that certain actions should be taken (such as further investigation of the user's state by other means or seeking medical attention). Thus, in some embodiments, detection by the computer that the user has suffered from a stroke may serve as an initial step that triggers further steps for diagnosing the user's condition and not a definitive final step in diagnosing the user's state.

In some embodiments, a system configured to detect a stroke based on thermal measurements includes at least one inward-facing head-mounted thermal camera (CAM) and computer. The at least one CAM is/are configured to take thermal measurements of at least first and second regions on the right and left sides of the head ($TH_{R1}$ and $TH_{L1}$, respectively) of a user. Optionally, the at least one CAM is located below the first and second regions, and does not occlude the first and second regions. The computer is configured to detect, based on $TH_{R1}$ and $TH_{L1}$, whether the user has suffered a stroke. Optionally, detecting whether the user has suffered from a stroke refers to a recent stroke event, such as an ischemic or hemorrhagic stroke event that started a short while before $TH_{R1}$ and $TH_{L1}$ were taken, where "a short while" may be a period between minutes and several hours before $TH_{R1}$ and $TH_{L1}$ were taken. In this scenario, detection that the user has suffered from a stroke may enable an intervention that can reduce the permanent damage of the stroke. Additionally detecting whether the user has suffered from a stroke may also refer, in some embodiments, to earlier stroke events, which occurred more than six hours before $TH_{R1}$ and $TH_{L1}$ were taken.

The first and second regions of which measurements are taken may include portions of various parts of the head. For example, in different embodiments, the first and second regions may cover a portion of at least one of the following pairs of regions: the right and left sides of the forehead, the right and left temples, the right and left cheeks, the right and left earlobes, behind the right and left ears, periorbital areas around the right and left eyes, the area of the right and left mastoid processes.

In one embodiment, each of the at least one CAM is physically coupled to a frame worn on a user's head, and is located less than 15 cm, 5 cm, or 2 cm from the user's face. In another embodiment, the at least one CAM is physically coupled to a clip-on, and the clip-on comprises a body configured to be attached and detached, multiple times, from a frame configured to be worn on the user's head.

In one embodiment, due to the angle between the optical axis of a certain CAM from among the at least one CAM and the Frankfort horizontal plane, the Scheimpflug principle may be employed in order to capture sharper images with the certain CAM. For example, when the user wears a frame to which the certain CAM is coupled, the certain CAM has a certain tilt greater than 2° between its sensor and lens planes, in order to capture the sharper images. Additional details regarding application of the Scheimpflug are provided herein further below.

Figure 74:
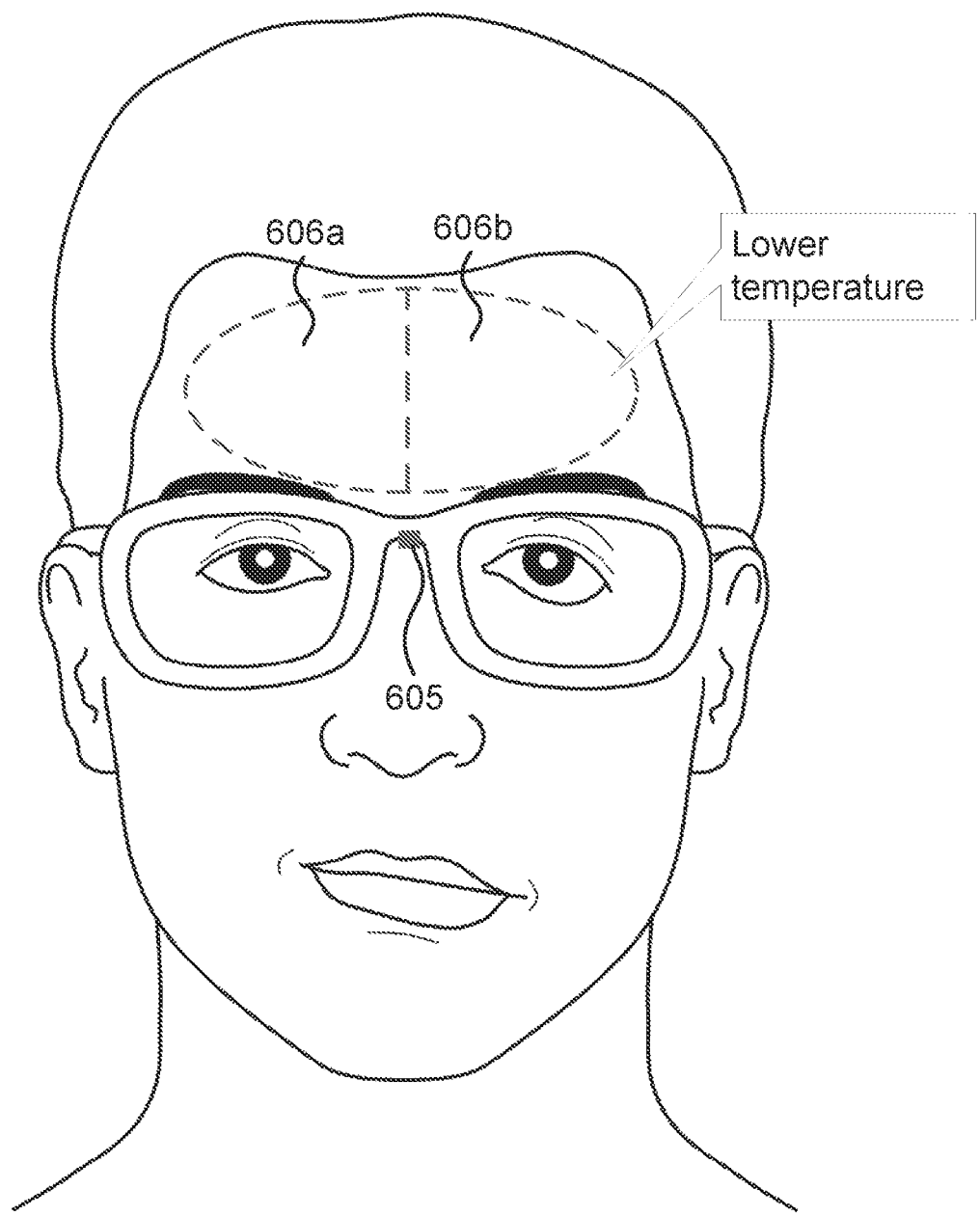
FIG. 74 illustrates an embodiment of a system that includes a single head-mounted thermal camera that may be used to detect a stroke.

The at least one CAM may be a single CAM, in one embodiment, such as a single FPA that captures images that include a portion of both sides of the forehead. In this embodiment, $TH_{R1}$ and $TH_{L1}$ include measurements that cover portions of the left side and right side of user's forehead, respectively. Optionally, $TH_{R1}$ and $TH_{L1}$ may be measured by different subsets of pixels of the FPA. An example of a system that includes a single thermal camera is illustrated in FIG. 74, which illustrates a user wearing glasses with a single thermal sensor 605 that measures ROIs 606a and 606b on the right and left of the forehead, respectively. The user in the figure has already been affected by a stroke, as is evident by the lower temperature detected on the left side of the forehead and the drooping of the left side of the face.

In other embodiments, the at least one CAM may include two or more CAMs. Optionally, the at least one CAM includes two CAMs, denoted CAM1 and CAM2. Optionally, CAM1 and CAM2 are located at least 0.5 cm to the right and to the left of the vertical symmetry axis that divides the face, respectively. Optionally, each of CAM1 and CAM2 weighs below 10 g, 5 g, or 1 g.

Figure 75:
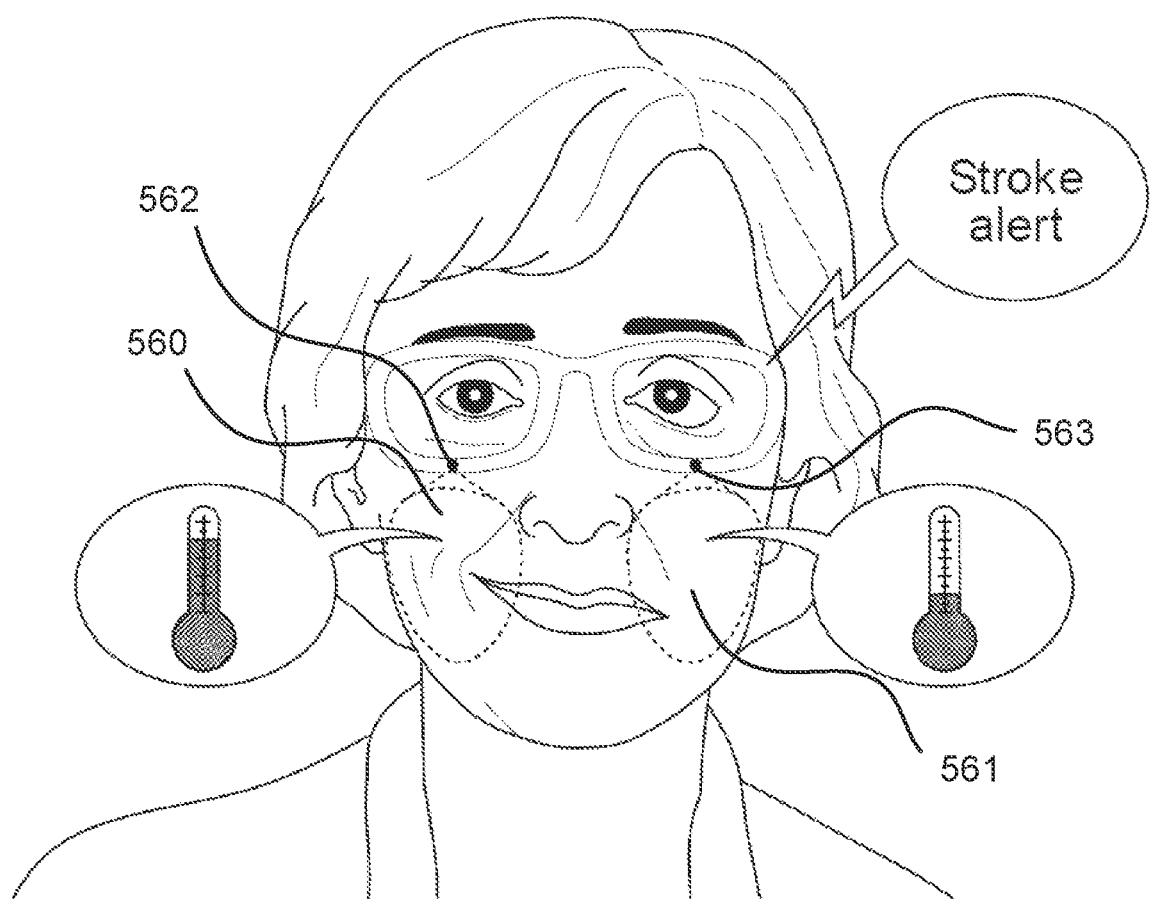
FIG. 75 illustrates a scenario in which an alert regarding a possible stroke is issued.

FIG. 75 illustrates one example of a system for detecting a stroke that includes at least CAM1 and CAM2 described above. The figure illustrates a user wearing a frame with CAM1 and CAM2 (562 and 563, respectively) coupled thereto, which measure ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a video camera provides additional data in the form of images that may help in detecting the stroke.

Depending on the locations the at least first and second regions on the right and left sides of the head, CAM1 and CAM2 mentioned above may be located in specific locations with respect to the face. In one example, CAM1 and CAM2 are located outside the exhale stream of the mouth and/or the exhale streams of the nostrils. In another example, each of CAM1 and CAM2 is located less than 10 cm from the face and there are angles greater than 20° between the Frankfort horizontal plane and the optical axes of CAM1 and CAM2.

Measurements of additional regions on the head may be used to detect whether the user suffered from a stroke. In one embodiment, the at least one CAM is further configured to take thermal measurements of at least third and fourth regions on the right and left sides of the head ($TH_{R2}$ and $TH_{L2}$, respectively), and the computer is further configured to detect whether the user has suffered a stroke also based on $TH_{R2}$ and $TH_{L2}$ (in addition to $TH_{R1}$ and $TH_{L1}$). Optionally, the middles of the first and second regions are at least 1 cm above the middles of the third and fourth regions, respectively. Optionally, the third and fourth regions cover at least a portion of one of the following pairs of regions (which is not covered by the first and second regions): the right and left sides of the forehead, the right and left temples, the right and left cheeks, the right and left earlobes, behind the right and left ears, periorbital areas around the right and left eyes, the area of the right and left mastoid processes.

In one embodiment, the system optionally includes at least one outward-facing head-mounted thermal camera ($CAM_{out}$), which is configured to take thermal measurements of the environment ($TH_{ENV}$). Optionally, the computer is further configured to also utilize $TH_{ENV}$ (in addition to $TH_{R1}$ and $TH_{L1}$) to detect whether the user has suffered a stroke.

There are various approaches that may be used by the computer, in different embodiments, to detect based on $TH_{R1}$ and $TH_{L1}$ whether the user has suffered a stroke. In some embodiments, detecting whether the user has suffered a stroke involves comparing $TH_{R1}$ and $TH_{L1}$ (referred to as current measurements) to previously taken thermal measurements (previous measurements), such as previously taken $TH_{R1}$ and $TH_{L1}$ of the user. Optionally, the previous measurements are taken at least fifteen minutes before the current measurements. Optionally, the previous measurements are taken at least one hour before the current measurements. Optionally, the previous measurements are taken at least one six hours before the current measurements. Optionally, the previous measurements are taken at least one day before the current measurements.

In some embodiments, the previous measurements are taken over a long period and are used to calculate baseline thermal values of regions of the face, and/or used to generate various models, which are used to detect a stroke, as discussed below. It is to be noted that discussion below regarding detection of the stroke based on $TH_{R1}$ and $TH_{L1}$ can be generalized to involve thermal measurements of other regions (such as $TH_{R2}$ and $TH_{L2}$ discussed above).

In one embodiment, the computer calculates a magnitude of thermal asymmetry of the head of the user based on a difference between $TH_{R1}$ and $TH_{L1}$, and compares the magnitude to a threshold. Responsive to the magnitude reaching the threshold, the computer detects that the user has suffered a stroke. Optionally, the difference between $TH_{R1}$ and $TH_{L1}$ needs to have reached the threshold (i.e., equal the threshold value or exceed it) for at least a predetermined minimal duration, such as at least one minute, at least five minutes, at least fifteen minutes, or at least some other period that is greater than 30 minutes. Optionally, the threshold is calculated based on previous magnitudes of thermal asymmetry of the head of the user, which were calculated based on previously taken $TH_{R1}$ and $TH_{L1}$ of the user. Thus, this threshold may be set according to a baseline thermal asymmetry that represents the typical difference in the temperatures of the first and second regions; a stroke may be detected when the thermal asymmetry becomes significantly different from this baseline.

In another embodiment, the computer calculates feature values and utilizes a model to calculate, based on the feature values, a value indicative of whether the user has suffered a stroke. At least some of the feature values are generated based on $TH_{R1}$ and $TH_{L1}$ of the user; examples of feature values that may be generated are given in the discussion regarding feature values that may be generated to detect a physiological response (herein suffering from a stroke is considered a type of physiological response). Optionally, at least some feature values are generated based on additional sources of information (other than the at least one CAM), such as additional thermal cameras, additional sensors that measure physiological signals of the user (e.g., heart rate or galvanic skin response), and/or additional sensors that measure the environment. Optionally, one or more of the feature values are indicative of the extent of difference between $TH_{R1}$ and $TH_{L1}$ of the user and previous $TH_{R1}$ and $TH_{L1}$ of the user, taken at least a certain period earlier (such as at least fifteen minutes earlier, one hour earlier, a day earlier, or more than a day earlier). Thus, these one or more feature values may represent a difference between the current thermal measurements and baseline thermal values for the first and second regions. Optionally, the model is generated based on data that includes previously taken $TH_{R1}$ and $TH_{L1}$ of the user and/or other users. Optionally, when data includes previously taken $TH_{R1}$ and $TH_{L1}$ of other users, at least some of the measurements of the other users were taken while they did not suffer from a stroke, and at least some of the measurements of the other users were taken while they did suffer from a stroke.

In another embodiment, the computer calculates a value indicative of a joint probability of $TH_{R1}$ and $TH_{L1}$ based on a model that includes distribution parameters calculated based on previously taken $TH_{R1}$ and $TH_{L1}$ of the user. Thus, the model describes a typical distribution of thermal measurements on regions of the user's head (when the user did not suffer from a stroke). The computer may compare the value indicative of the joint probability to a threshold, and responsive to the value being below the threshold, the computer detects that the user has suffered a stroke. The threshold may represent an atypical thermal asymmetry, with very low probability to normally occur, which warrants an alert of the possibility that the user has had a stroke.

In some embodiments described herein, detecting whether the user has suffered a stroke may involve calculating a change to thermal asymmetry on the head based on a change between thermal measurements taken at different times. This calculation can be performed in different ways, as described below.

In one embodiment, the computer calculates the change between the thermal measurements as follows: calculate a temperature difference between the first and second regions at time x ($\Delta T_x$) based on [$TH_{R1}$ and $TH_{L1}$] taken at time x, calculate a temperature difference between the first and second regions at time y ($\Delta T_x$) based on [$TH_{R1}$ and $TH_{L1}$] taken at time y, and calculate the output indicative of the change in the thermal asymmetry on the face based on a difference between $\Delta T_x$ and $\Delta T_y$.

The embodiment described above may optionally be implemented using a differential amplifier that receives $TH_{R1}$ and $TH_{L1}$ as inputs, and outputs the temperature difference between the first and second regions. Optionally, the at least one CAM is/are based on thermopile sensors. Alternatively, the at least one CAM is/are based on pyroelectric sensors. In one example, pairs of thermal sensor elements are wired as opposite inputs to a differential amplifier in order for the thermal measurements to cancel each other and thereby remove the average temperature of the field of view from the electrical signal. This allows the at least one CAM to be less prone to providing false indications of temperature changes in the event of being exposed to brief flashes of radiation or field-wide illumination. This embodiment may also minimize common-mode interference, and as a result improve the accuracy of the thermal cameras.

In another embodiment, the computer calculates the change between the thermal measurements as follows: the computer calculates a temperature change between $TH_{R1}$ taken at times $t_1$ and $t_2$ ($\Delta TH_{R1}$), calculates a temperature change between $TH_{L1}$ taken at times $t_1$ and $t_2$ ($\Delta TH_{L1}$), and then calculates the output indicative of the thermal asymmetry on the face based on a difference between $\Delta TH_{R1}$ and $\Delta TH_{L1}$.

It is noted that sentences such as "calculate a difference between X and Y" or "detect a difference between X and Y" may be achieved by any function that is proportional to the difference between X and Y.

The detection of a stroke based on $TH_{R1}$ on $TH_{L1}$, and optionally other inputs, such as additional thermal measurements or additional physiological signals, may be sufficient, in some embodiments, to prompt the computer to take an action such as alerting the user, a caregiver, and/or emergency services. In other embodiments, the detection may be considered an indication that there is a risk that the user has suffered a stroke, and the computer may encourage the user to take a test (e.g., the FAST test described below or portions thereof), in order to validate the detection. Optionally, measurements and/or results taken during the test may be used in addition to $TH_{R1}$ and $TH_{L1}$ and the optional additional inputs, or instead of that data, in order to make a second, more accurate detection of whether the user has suffered from a stroke.

Upon detecting that the user has suffered from a stroke, in some embodiments, the computer may prompt the user to take a test to validate and/or increase the confidence in the detection. This test may involve performing one or more steps of a FAST test. Herein, FAST is an acronym used as a mnemonic to help detect and enhance responsiveness to the needs of a person having a stroke. The acronym stands for Facial drooping, Arm weakness, Speech difficulties and Time to call emergency services. Facial drooping involves a section of the face, usually only on one side, that is drooping and hard to move (often recognized by a crooked smile). Arm weakness typically involves an inability to raise one's arm fully. Speech difficulties typically involve an inability or difficulty to understand or produce speech.

Figure 76:
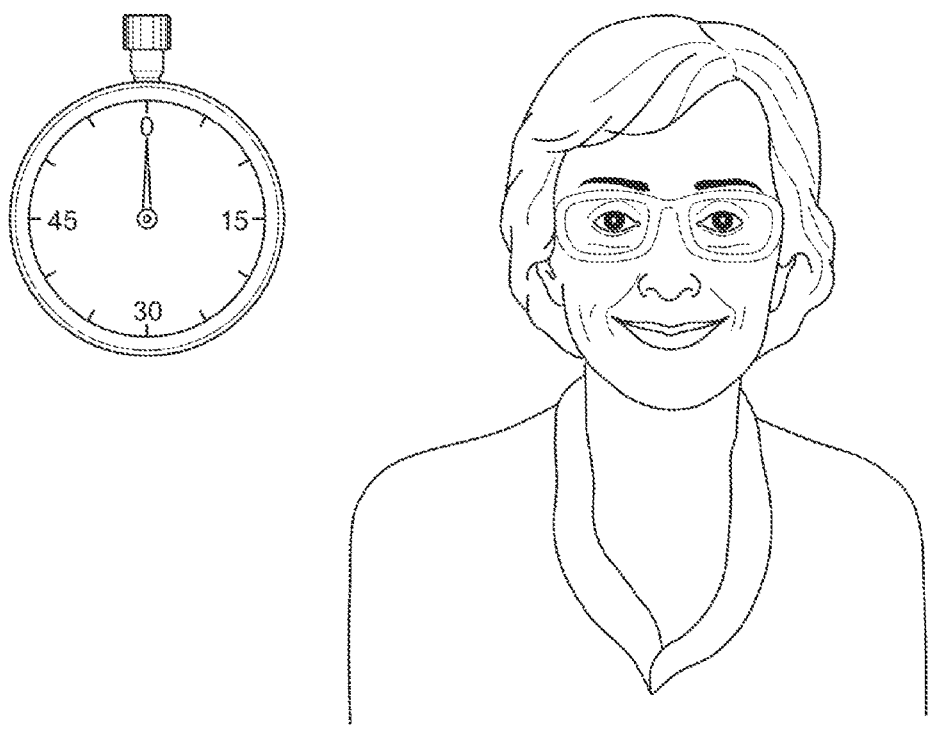
FIG. 76, FIG. 77, FIG. 78, and FIG. 79 illustrate physiological and behavioral changes that may occur following a stroke.
Figure 77:
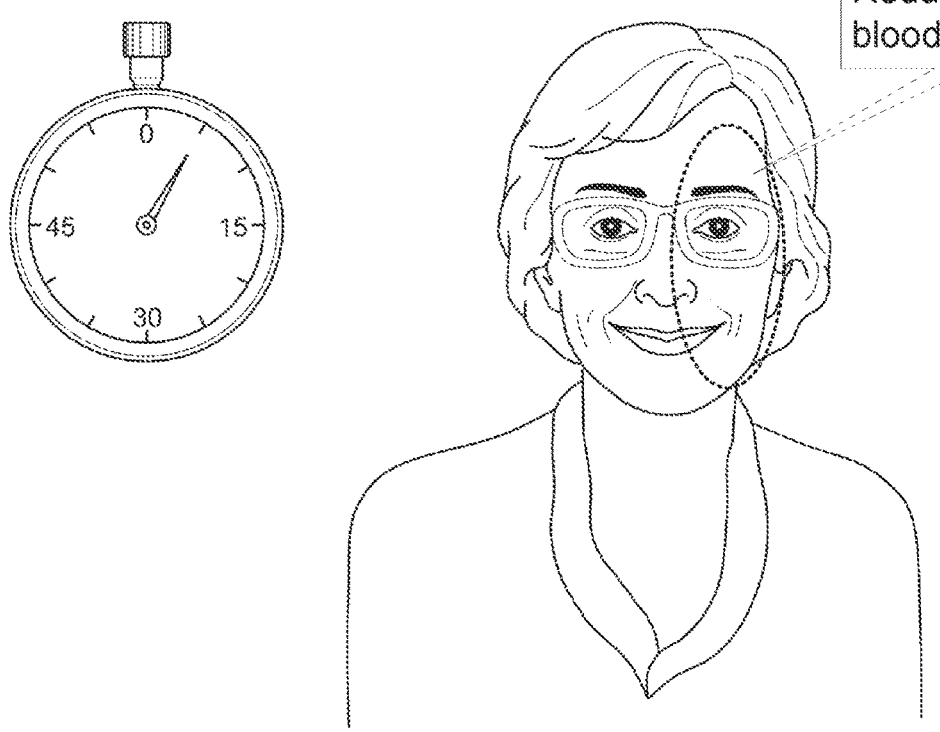
Figure 78:
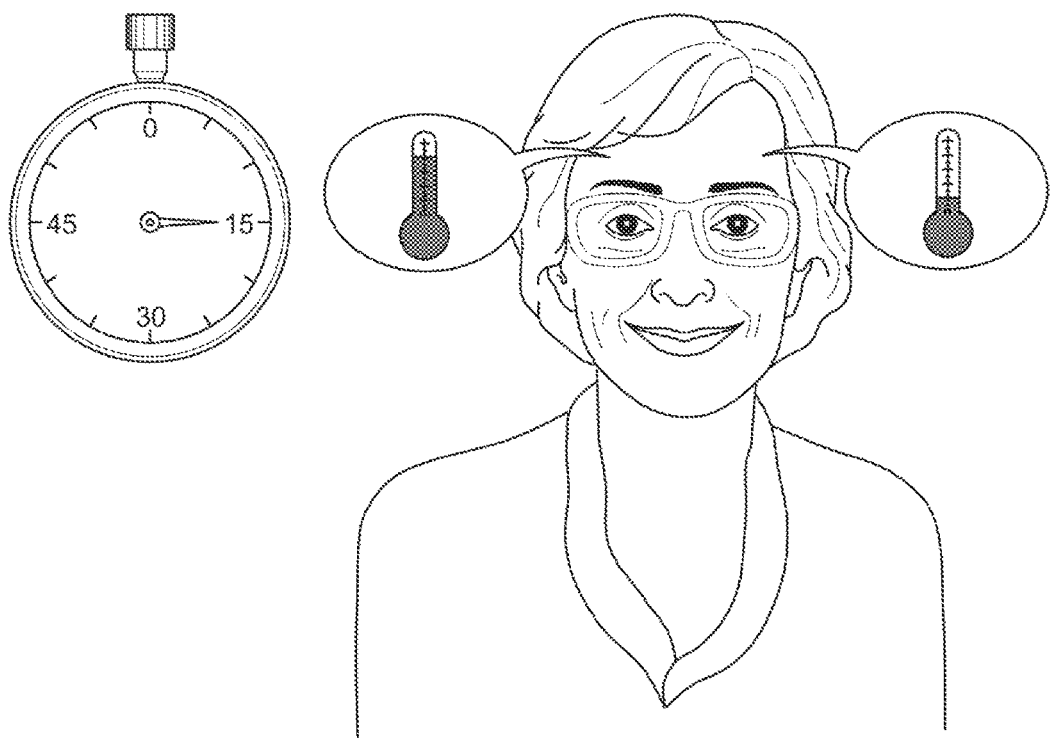
Figure 79:
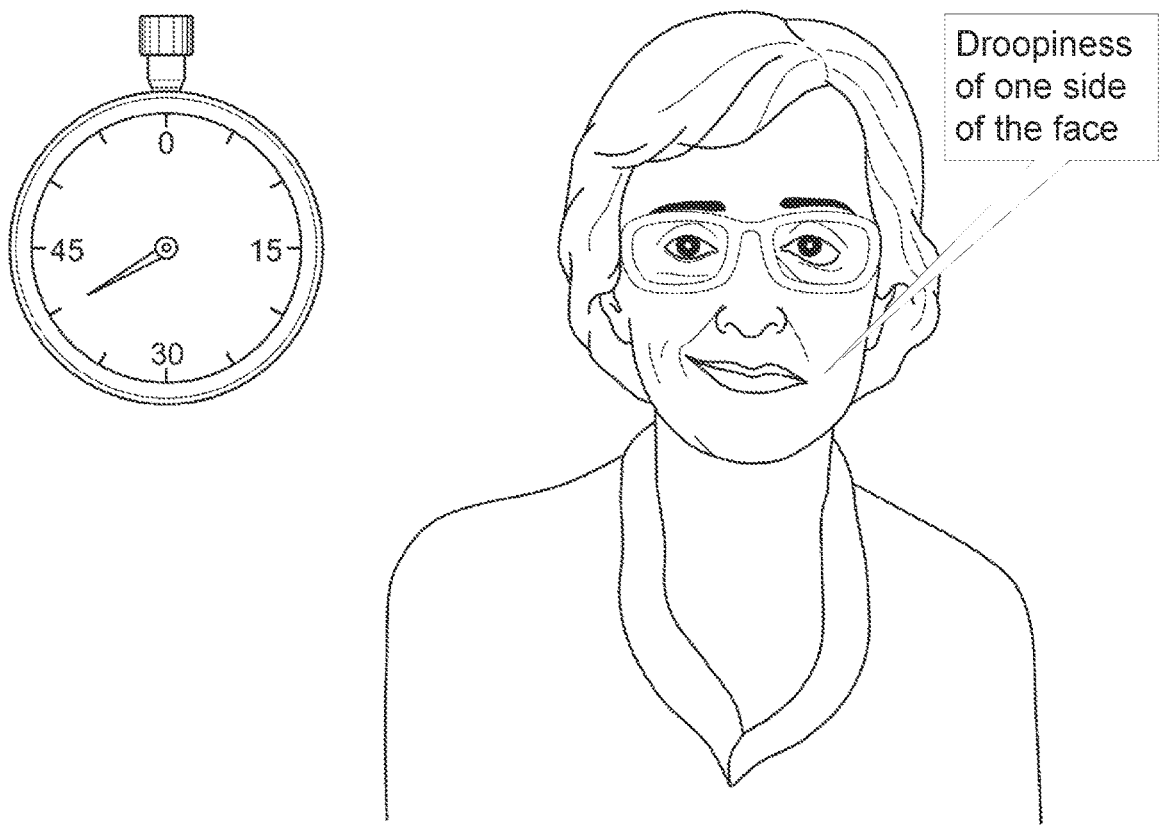

FIG. 76 to FIG. 79 illustrate physiological and behavioral changes that may occur following a stroke, which may be detected using embodiments described herein. FIG. 76 illustrates a person at time zero, at the very beginning of the onset of the stroke. At this time there may be no detectable signs of the stroke. FIG. 77 illustrates the person's state after 5 minutes since the beginning of the stroke. By this time, certain changes to the blood flow in the head, which were caused by the stroke, may be detectable. For example, the blood flow on one side of the face may decrease. FIG. 78 illustrates the person's state 15 minutes after the beginning of the stroke. At this time, temperature changes to regions of the face, which are due to the changes in blood flow, may be detectable. FIG. 79 illustrates the person's state 45 minutes after the beginning of the stroke. At this time, droopiness of one side of the face (e.g., due to reduced blood flow and impaired neurologic control) may be observable.

The following are some examples of steps that may be taken to further diagnose whether the user has suffered from a stroke (e.g., steps from a FAST test). Optionally, results of these steps may be used to further strengthen the computer's detection (e.g., to increase confidence in the detection) or change the detection (e.g., and decide the detection was a false alarm). Optionally, upon determining, based on one or more of the steps, that the user may have a suffered a stroke, the computer performs at least one of the following steps: (i) instruct the user to seek emergency medical assistance, (ii) connect the user through live video chat with a medical specialist, and (iii) automatically alert a predetermined person and/or entity about the user's condition.

Figure 80:
FIG. 80, FIG. 81, FIG. 82, and FIG. 83 illustrates various activities that a person may be requested to perform in order to determine whether the person has suffered from a stroke.
Figure 81:

In one embodiment, a camera (e.g., a cellphone camera or an inward-facing camera coupled to a frame worn by the user) takes images of at least a portion of the user's face. Optionally, the computer is further configured to (i) instruct the user, via a user interface, to smile and/or stick out the tongue, and (ii) detect, based on analysis of the images taken by the camera, whether a portion of one side of the user's face droops and/or whether the user was able to stick out the tongue. Detecting that the portion of the one side of the user's face droops may be done based on a comparison of the images of at least a portion of the user's face to previously taken images of at least the portion of the user's face, which were taken at least one hour before. Optionally, the computer utilizes a machine learning based model to determine whether the comparison indicates that the face droops. In this case, the model may be trained based on sets of images that include before and after images of people who suffered a stroke. Additionally or alternatively, detecting that the portion of the one side of the user's face droops is done using a machine learning-based model trained on examples of images of faces of people with a portion of one side of the face drooping. Optionally, detecting whether the tongue is sticking out may be done using image analysis and/or machine learning approaches (e.g., utilizing a model trained on previous images of the user and/or other users sticking out their tongue). FIG. 80 illustrates a user who is requested by a smartphone app to smile. Images of the user may be taken by the smartphone and analyzed in order to determine whether the user has smiled and/or to what extent the smile is considered "normal". Similarly, FIG. 81 illustrates a user who is requested by a smartphone app to stick out his tongue.

Figure 82:

In another embodiment, a microphone is used to record the user's speech. The computer is configured to (i) instruct the user, via a user interface, to speak (e.g., say a predetermined phrased), and (ii) detect, based on analysis of a recording of the user taken by the microphone, whether the user's speech is slurred, and/or whether a difference between the recording and previous recordings of the user exceeds a threshold that indicates excessively slurred or difficult. Optionally, the computer uses a model trained based on examples of peoples' normal and incoherent speech (e.g., recordings of people before and after they had a stroke). FIG. 82 illustrates a user who is requested by a smartphone app to say a sentence. The user's speech can be recorded by the smartphone and analyzed to detect slurry and/or uncharacteristic speech.

Figure 83:

In yet another embodiment, a sensor is used to take measurements indicative of at least one of movement and position, of at least one of the user's arms. Optionally, the computer is further configured to (i) instruct the user, via a user interface, to raise at least one the arms, and (ii) detect, based on analysis of the measurements taken by the sensor, whether an arm of the user drifts downward. In one example, the sensor is in a cellphone held by the user. In another example, the sensor is in a smartwatch or bracelet on the user's wrist. In still another example, the sensor is embedded in a garment worn by the user. FIG. 83 illustrates a user who is requested by a smartphone app to raise his arms. The user's movements can be detected by the smartphone in order to determine whether one arm falls. In the illustrated example, the user may be requested to raise the arms at least twice, each time holding the phone in a different hand Such measurements can serve as a baseline to compare the rate of ascent and descent of each of the arms.

In still another embodiment, a sensor is used to take measurements indicative of how the user walks. Optionally, the computer is further configured to (i) instruct the user, via a user interface, to walk, and (ii) detect, based on analysis of the measurements taken by the sensor, whether a difference between the measurements taken by the sensor and previous measurements of the user taken by the sensor exceeds a threshold. Optionally, exceeding the threshold is indicative of a sudden loss of balance or coordination In one example, the sensor is coupled to a frame worn on the user's head (e.g., a glasses frame). In another example, the sensor is in a cellphone, smartwatch, bracelet, garment, or shoe worn by the user.

Figure 84:
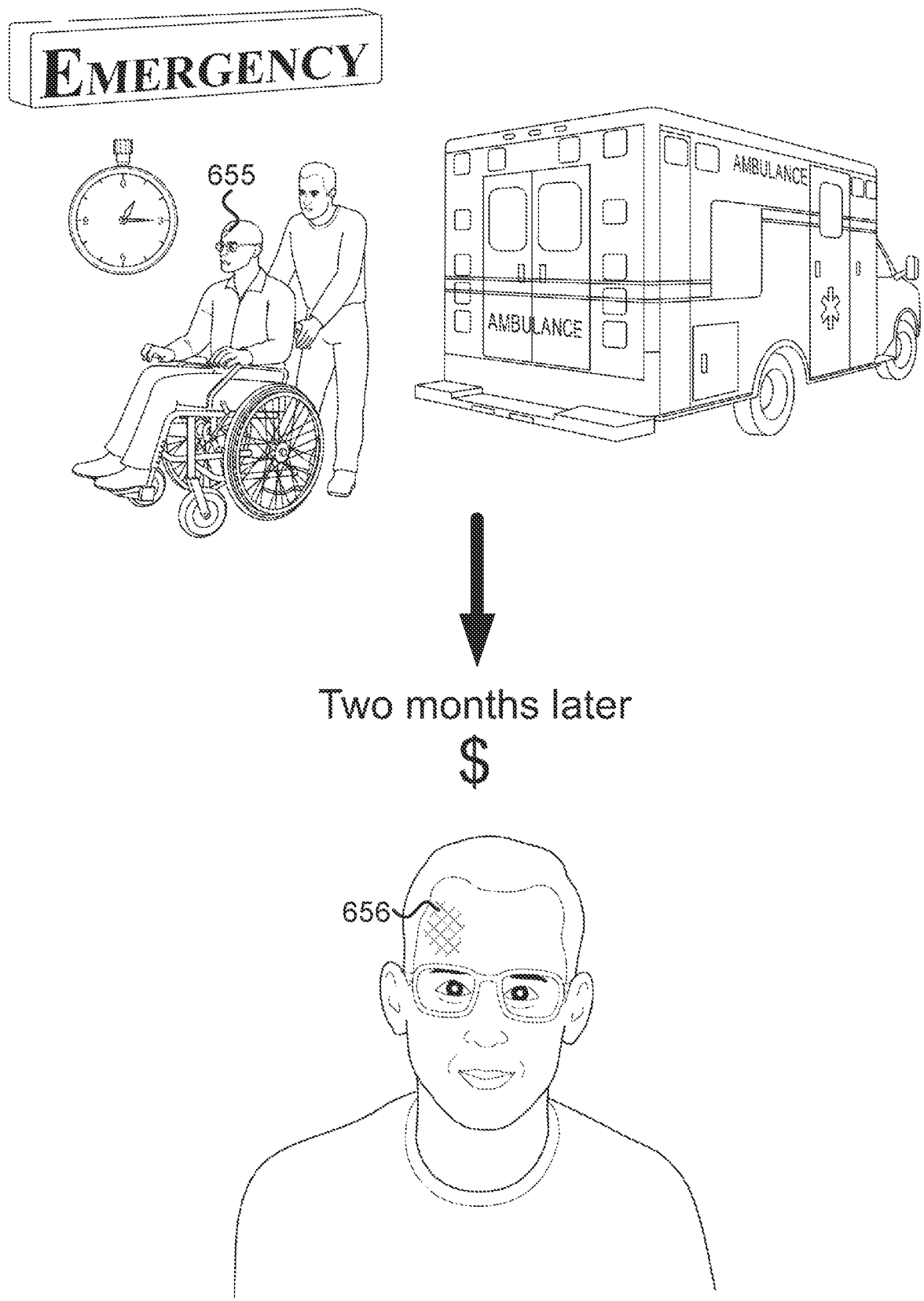
FIG. 84 and FIG. 85 illustrate the difference between a timely intervention in the event of a stroke and intervention that comes too late.
Figure 85:
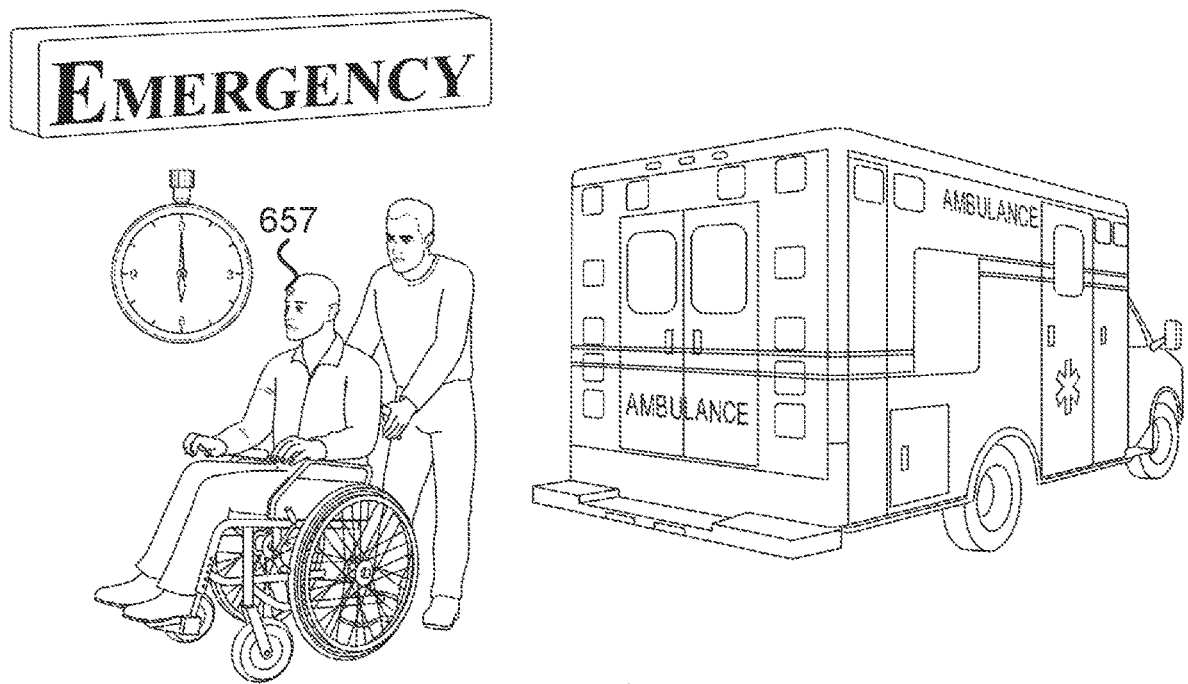
Figure 85:
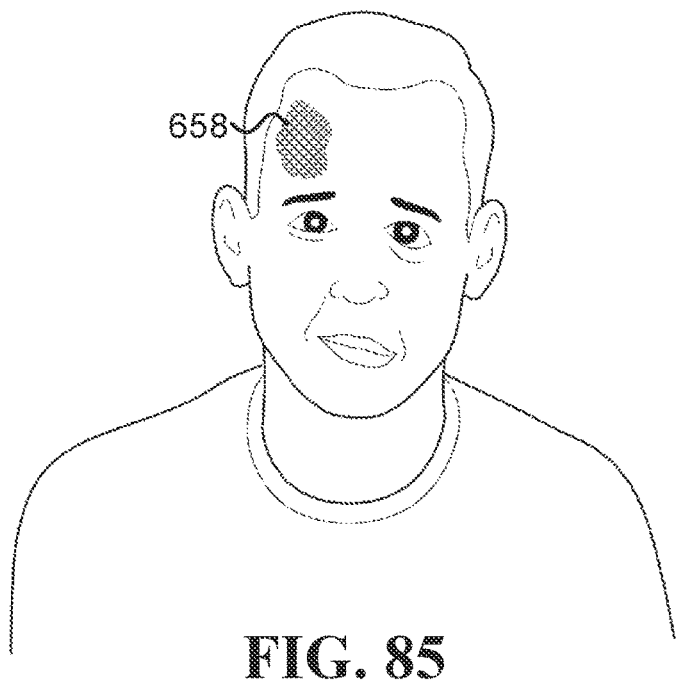

Early detection of a stroke, e.g., using one or more of the approaches described above, can be essential for minimizing the stroke-related damage. With strokes, it is certainly the case that time is of the essence. Early administration of treatment (e.g., within a few hours) can in many cases lead to minimal long term stroke-related damage. However, following a certain window of time (e.g., six hours since the start of the stroke), severe and irreversible long term damage may occur; impacting both quality of life and cost of care. FIG. 84 and FIG. 85 illustrate the difference between a timely intervention and intervention that comes too late. In FIG. 88, a patient arrives a short while (about an hour and fifteen minutes) after beginning of a stroke. This patient has moderate stroke damage (denoted by reference numeral 655). Intervention at this early stage is mostly successful, and after two months the patient has only slight long term damage (denoted by reference numeral 656), which involves a relatively small impact on the quality of life and a relatively low cost in terms of future medical expenses. FIG. 85 illustrates a case in which the patient arrives too late (e.g., six hours after the start of the stroke). In this scenario, the patient already has more severe stroke damage (denoted by reference numeral 657). Intervention at this late stage is mostly unsuccessful. Two months later, there is severe long term stroke-related damage, which involves a relatively large impact on the quality of life and a relatively high cost in terms of future medical expenses.

In addition to detecting a stroke, some embodiments may be used to detect an occurrence of a migraine attack. In one embodiment, the first and second regions are located above the user's eye level, and the computer is further configured to detect occurrence of a migraine attack based on asymmetry between $TH_{R1}$ and $TH_{L1}$. In another embodiment, the first and second regions are located above the user's eye level. The computer is further configured to generate feature values based on $TH_{R1}$ and $TH_{L1}$, and to utilize a model to calculate, based on the feature values, a value indicative of whether the user is experiencing a migraine attack or whether a migraine attack is imminent Optionally, the model if generated based on previous $TH_{R1}$ and $TH_{L1}$ of the user taken while the user had a migraine attack or taken 30 minutes or less before the user had a migraine attack.

In some embodiments, a system configured to detect a stroke based on asymmetric changes to blood flow includes at least first and second devices and a computer. The first and second devices are located to the right and to the left of the vertical symmetry axis that divides the face of a user, respectively; the first and second devices are configured to measure first and second signals ($S_{BF1}$ and $S_{BF2}$, respectively) indicative of blood flow in regions to right and to the left of the vertical symmetry axis. The computer detects whether the user has suffered a stroke based on an asymmetric change to blood flow, which is recognizable in $S_{BF1}$ and $S_{BF2}$. Optionally, the system includes a frame configured to be worn on a user's head, and the first and second devices are head-mounted devices that are physically coupled to the right and left sides of the frame, respectively.

The first and second devices may be devices of various types. Optionally, the first and second devices are the same type of device. Alternatively, the first and second devices may be different types of devices. The following are some examples of various types of devices that can be used in embodiments described herein in order to measure a signal indicative of blood flow in a region of the body of the user.

In one embodiment, the first and second devices comprise first and second cameras, respectively. The first and second cameras are based on sensors comprising at least 3×3 pixels configured to detect electromagnetic radiation having wavelengths in at least a portion of the range of 200 nm to 1200 nm. Optionally, the asymmetric changes to blood flow lead to asymmetric facial skin color changes to the face of the user. Optionally, the system includes first and second active light sources configured to illuminate the first and second regions, respectively. In one example, the first and second devices and first and second active light sources are head-mounted, and the first and second active light sources are configured to illuminate the first and second regions with electromagnetic radiation having wavelengths in at least a portion of the range of 800 nm to 1200 nm.

In addition to the first and second cameras mentioned above, some embodiments may include first and second outward-facing cameras that take images of the environment to the right and left of the user's head, respectively. Optionally, the computer utilizes the images to detect whether the user has suffered a stroke. Optionally, the images of the environment are indicative of illumination towards the face, images taken by the inward-facing cameras are indicative of reflections from the face. Thus, the images of the environment may be used to account, at least in part, for variations in ambient light that may cause errors in detections of blood flow.

In another embodiment, the first and second devices function as imaging photoplethysmography devices, and/or the first and second devices function as pulse oximeters.

There are various types of devices that may be used in embodiments described herein, and ways in which the devices may be attached to the user and/or located the user's proximity. In one example, the first and second device may be head-mounted devices, such as devices physically coupled to a frame worn on the user's head (e.g., a frame of smartglasses, such as augmented reality glasses, virtual reality glasses, or mixed reality glasses). In another example, the first and second devices are embedded in a garment worn by the user (e.g., a smart shirt) or some other wearable accessory (e.g., a necklace, bracelets, etc.). In yet another, the first and second devices may be located in headrests of a chair in which the user sits. In still another example, the first and second devices are attached to walls (e.g., of a vehicle cabin in which the user sits or a room in which the user spends time). In yet another example, the first and second devices may be coupled to robotic arms. Optionally, the robotic arms may be used to move and/or orient the devices in order to account for the user's movements, which may enable the first and second devices to measure the same regions on the user's head despite the user's movement.

The first and second devices may be utilized to measure various regions on the right and left sides of the user's head. In one embodiment, the regions on the right and left sides include portions of the right and left temples, respectively. In another embodiment, the regions on the right and left sides include portions of the right and left sides of the forehead, respectively. Optionally, the center of the region on the right is at least 3 cm from the center of the region on the left. In still another embodiment, the regions on the right and left sides include portions of the right and left cheeks, respectively. In still another embodiment, the regions on the right and left sides include areas behind the right and left ears, respectively. Optionally, the areas behind the right and left ears are below the hairline and cover at least a portion of the mastoid process in their respective sides of the head.

Figure 86A:
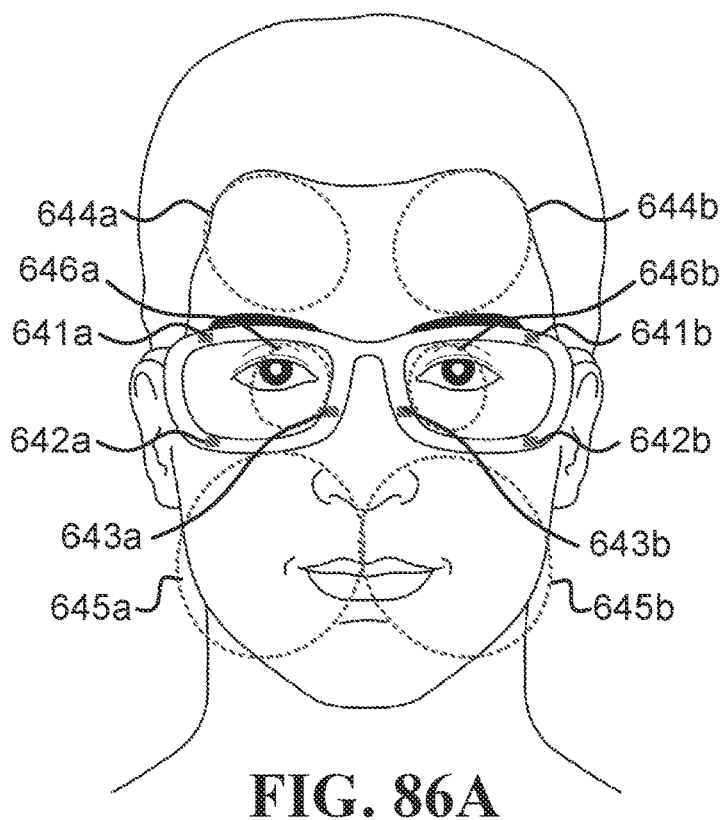
FIG. 86A illustrates one embodiment of a system that includes multiple pairs of right and left cameras and locations on the face that they may be used to measure.

FIG. 86A illustrates an embodiment of a system that includes multiple pairs of right and left cameras, and locations on the face that they may be used to measure. The cameras illustrated in the figure are coupled to a frame worn by the user, which may be, for example, any of the cameras mentioned herein. The illustrated example include: (i) cameras 641a and 641b that are coupled to the right and left sides of the top of the frame, respectively, which measure ROIs 644a and 644b on the right and left of the forehead, respectively; (ii) cameras 642a and 642b that are coupled to the right and left sides of the bottom of the frame, respectively, which measure ROIs 645a and 645b on the right and left cheeks, respectively; and (iii) cameras 643a and 643b that are coupled to the frame near the right and left sides of the nose, respectively, which measure ROIs 646a and 646b in the right and left periorbital regions, respectively.

Figure 86B:
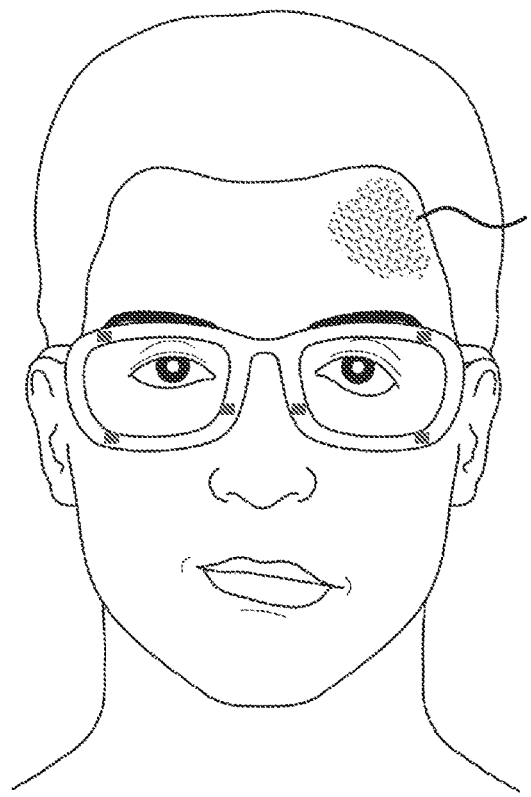
FIG. 86B illustrates a stroke sign that involves decreased blood flow in the forehead.
Figure 86C:
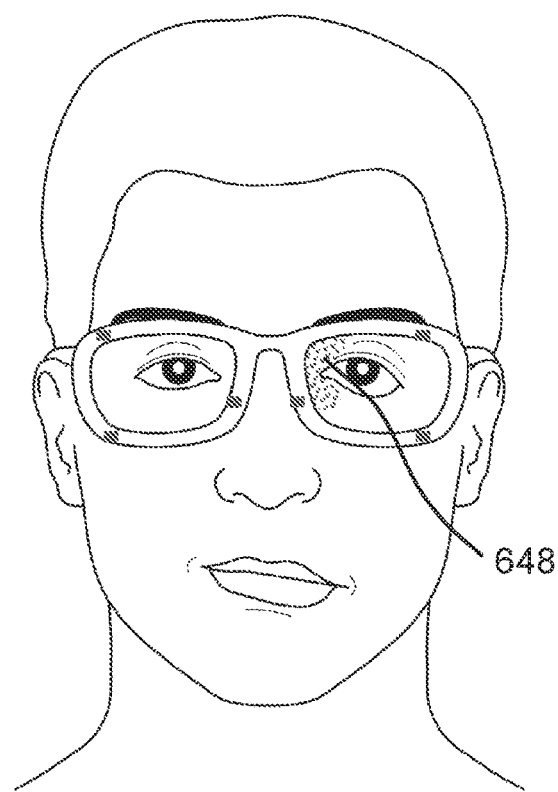
FIG. 86C illustrates a stroke sign that involves decreased blood flow in a periorbital region.

FIG. 86B illustrates a stroke sign 647, which involves decreased blood flow in the forehead, and may be detected using the system illustrated in FIG. 86A. Another stroke sign that may be detected by the system illustrated in FIG. 86C is stroke sign 648, which involves decreased temperature in the periorbital region.

Figure 87A:
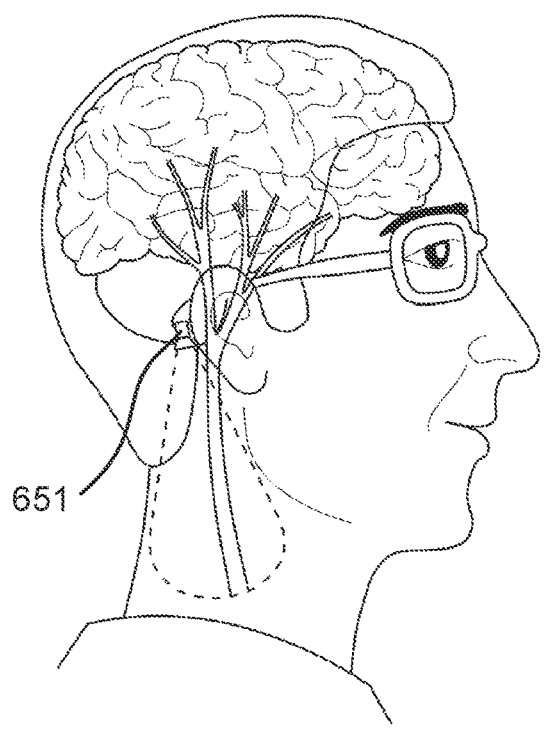
FIG. 87A and FIG. 87B illustrate embodiments of a system with a head-mounted camera located behind the ear.
Figure 87B:
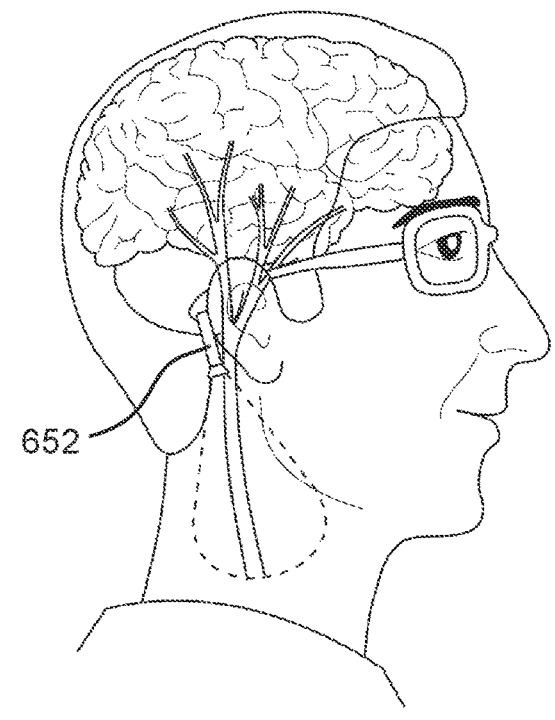

FIG. 87A illustrates a system in which the first and second devices are head-mounted cameras that are located behind the ears. The figure illustrates cameras 651, which may be a downward-facing video camera that takes images that include portions of the side of the neck. FIG. 87B illustrates a variant of the system illustrated in FIG. 87A in which camera 652 is a downward-facing camera that includes an extender body which enables the camera to move beyond the hairline in order to obtain unobstructed images of the side of the neck.

Figure 87C:
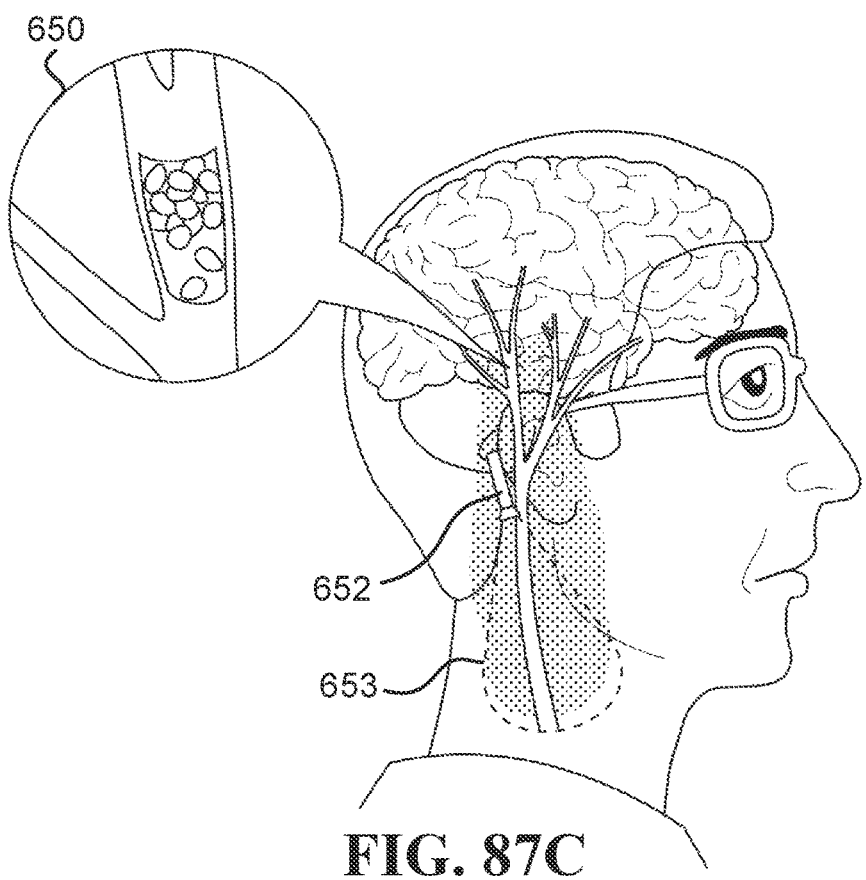
FIG. 87C illustrates an ischemic stroke that restricts the blood flow to the side of the head, which may be detected by embodiments described herein.

FIG. 87C illustrates ischemic stroke 650, which restricts the blood flow to the side of the head (illustrated as patch 653), which may be detected based on measurements of device 652 in order to alert about the user having suffered from a stroke.

Various types of values, which are indicative of blood flow (and taken by the first or second devices), can be determined based on a signal, which is denoted $S_{BF}$ in the discussion below. $S_{BF}$ may be, for example, aforementioned $S_{BF1}$ or $S_{BF2}$. Propagation of a cardiac pulse wave can lead to changes in the blood flow, with increased blood flow as a result of blood pumped during the systole, and lower blood flow at other times (e.g., during diastole). The changes in blood flow often manifest as changes to values in $S_{BF}$. For example, higher blood flow may correspond to increased intensity of certain colors of pixels (when $S_{BF}$ includes images), temperatures of pixels (when $S_{BF}$ includes thermal images), or increased absorption of certain wavelengths (when $S_{BF}$ includes measurements of a photoplethysmography device).

In some embodiments, calculating a statistic of $S_{BF}$ may provide an indication of the extent of the blood flow. For example, the statistic may be an average value (e.g., average pixel values), which is a calculated over a period, such as ten seconds, thirty seconds, or a minute. For example, in an embodiment in which the devices are cameras and $S_{BF}$ includes images, the average hue of pixels in the images can be indicative of the blood flow (e.g., a redder hue may correspond to more intense blood flow). In an embodiment in which the devices are thermal sensors and $S_{BF}$ includes thermal images, the average temperature of pixels in the thermal images can be indicative of the blood flow (e.g., a higher average temperature may correspond to more intense blood flow).

In other embodiments, analysis of propagation of cardiac pulse waves, as manifested in the values of $S_{BF}$, can be used to provide indications of the extent of blood flow. When $S_{BF}$ includes multiple pixels values (e.g., images or thermal images), propagation of a pulse wave typically involves an increase in pixel values that correspond to a period of a high blood flow during the pulse wave (e.g., when blood flow is driven by a systole) followed by a decrease in pixel values that correspond to a period of a lower blood flow during the pulse wave (e.g., decreasing towards a diastolic trough). The speed at which the pulse wave propagates along a segment of the images of $S_{BF}$ is indicative of the speed of blood flow in the segment depicted in the images. For example, the speed at which a peak (e.g., corresponding to the systole) is seen to propagate in the images is directly correlated with the blood flow.

Another parameter indicative of blood flow that can be derived from analysis of a propagation of a pulse wave, as it is manifested in values of $S_{BF}$, is the amplitude of the signal. For example, signals that display a periodic increase and decrease in values of $S_{BF}$, which corresponds to the heart rate, can be analyzed to determine the difference in values (e.g., difference in color, temperature, or intensity) between the peak and the trough observed in the values of $S_{BF}$ during the transition of a pulse wave. In some embodiments, the amplitude of the signal (e.g., the difference between the value at the peak and the value at the trough) is correlated with the blood flow. In one example, the higher the amplitude of the signal, the higher the blood flow.

Another parameter indicative of blood flow that can be derived from analysis of a propagation of a pulse wave, as it is manifested in values of $S_{BF}$, is the extent to which pixels in images (or thermal images) display a periodic change to their values that reaches a certain threshold. For example, the area on the face in which the periodic facial skin color changes (which correspond to the cardiac pulse) reach a certain threshold is correlated with the blood flow. The higher the blood flow, the larger the area.

The extent of Blood flow (e.g., the speed at which the blood flows) is correlated with the times at which a pulse wave is detected at different locations of the body. Typically, the farther a location from the heart, the later the pulse wave is detected (e.g., detection of a pulse wave may correspond to the time at which a systolic peak is observed). This phenomenon can be utilized, in some embodiments, to calculate values indicative of blood flow based on the difference in times at which pulse waves are detected at different locations. For example, analysis of one or more $S_{BF}$ signals, which include values that are indicative of propagation of a pulse wave at various locations, can determine the difference in time ($\Delta t$) between detection of a pulse wave at different locations. The value of $\Delta t$ is typically correlated with the blood flow: the higher the blood flow, the smaller $\Delta t$ is expected to be.

The computer is configured, in some embodiments, to detect whether the user has suffered a stroke based on an asymmetric change to blood flow, which is recognizable in $S_{BF1}$ and $S_{BF2}$.

Herein, sentences of the form "asymmetric change to blood flow recognizable in $S_{BF1}$ and $S_{BF2}$" refer to effects of blood flow that may be identified and/or utilized by the computer, which are usually not recognized by the naked eye (in the case of images), but are recognizable algorithmically when the signal values are analyzed. For example, blood flow may cause facial skin color changes (FSCC) that corresponds to different concentrations of oxidized hemoglobin due to varying blood pressure caused by the cardiac pulse Similar blood flow dependent effects may be viewed with other types of signals (e.g., slight changes in cutaneous temperatures due to the flow of blood.

When the blood flow on both sides of the head and/or body are monitored, asymmetric changes may be recognized. These changes are typically different from symmetric changes that can be caused by factors such as physical activity (which typically effects the blood flow on both sides in the same way). An asymmetric change to the blood flow can mean that one side has been affected by an event, such as a stroke, which does not influence the other side. In one example, the asymmetric change to blood flow comprises a change in blood flow velocity on left side of the face that is 10% greater or 10% lower than a change in blood flow velocity on one right side of the face. In another example, the asymmetric change to blood flow comprises a change in the volume of blood the flows during a certain period in the left side of the face that is 10% greater or 10% lower than the volume of blood that flows during the certain period in the right side of the face. In yet another example, the asymmetric change to blood flow comprises a change in the direction of the blood flow on one side of the face (e.g., as a result of a stroke), which is not observed at the symmetric location on the other side of the face.

In some embodiments, the computer detects whether the user has suffered a stroke based on a comparison between values belonging to a current set of $S_{BF1}$ and $S_{BF2}$ and values belonging to a previous set of $S_{BF1}$ and $S_{BF2}$ of the user. Optionally, the previous set was measured at least fifteen minutes before the current set, at least one hour before the current set, or at least one day before the current set. Optionally, the previous set serves to establish baseline blood flow values for both regions when the user was assumed not to be effected by a stroke.

In one embodiment, the computer uses a machine learning model to detect whether the user has suffered a stroke. Optionally, the computer is configured to: generate feature values based on data comprising a current set of $S_{BF1}$ and $S_{BF2}$ and a previous set of $S_{BF1}$ and $S_{BF2}$ of the user, and utilize the model to calculate, based on the feature values, a value indicative of whether the user has suffered a stroke. Optionally, the previous set was measured at least one hour before the current set. Optionally, at least some of the feature values are indicative of changes to the blood flow in each of the first and second regions between the time the current set was measured and when the previous set was measured.

In one embodiment, the model was generated based on data comprising "after" sets of $S_{BF1}$ and $S_{BF2}$ of other users and corresponding "before" sets of $S_{BF1}$ and $S_{BF2}$ of the other users. In these embodiments, the "after" sets were measured after the other users had suffered from a stroke (and the "before" sets were measured before they suffered from the stroke). Thus, training samples generated based on this data can reflect some of the types of asymmetric changes to blood flow that characterize suffering from a stroke.

In the event that a stroke is detected, the computer may prompt the user to take a FAST test (or portions thereof), as described above. In another example, the computer may suggest to the user to take images of the retinas. In this example, the computer is further configured to compare the images of the retinas with previously taken images of the retinas of the user, and to detect whether the user has suffered a stroke based on the comparison. Optionally, the comparison can take into account diameter of retinal arteries, swelling and blurring of the boundaries of the optic disk.

Blood flow usually exhibits typical patterns in the user's body. When a blood flow pattern changes, this usually happens in a predictable way (e.g., increase in blood flow due to physical activity, certain emotional responses, etc.). When a person's blood flow changes in an atypical way, this may indicate an occurrence of a certain medical incident, such as a stroke. Therefore, atypical blood flow patterns should be detected in order to investigate their cause.

In some embodiments, a system configured to detect an atypical blood flow pattern in the head of a user includes one or more head-mounted devices and a computer. The one or more head-mounted devices are configured to measure at least three signals ($S_{BF1}$, $S_{BF2}$ and $S_{BF3}$, respectively), indicative of blood flow in at least three corresponding regions of interest on the head ($ROI_1$, $ROI_2$, and $ROI_3$, respectively) of a user. Optionally, the centers of $ROI_1$, $ROI_2$ and $ROI_3$ are at least 1 cm away from each other. Optionally, the one or more head-mounted devices do not occlude $ROI_1$, $ROI_2$ and $ROI_3$.

There are various types of devices the one or more head-mounted devices may be. Optionally, each of the one or more head-mounted devices are the same type of device. Alternatively, when the one or more head-mounted devices are a plurality of devices, the plurality of devices may be of different types of devices. The following are some examples of various types of devices that can be used in embodiments described herein in order to measure a signal indicative of blood flow in a region of the body of the user.

In one embodiment, the one or more head-mounted devices include a camera that is based on a sensor comprising at least 3×3 pixels configured to detect electromagnetic radiation having wavelengths in at least a portion of the range of 200 nm to 1200 nm. Optionally, the system includes one or more light sources configured to $ROI_1$, $ROI_2$ and $ROI_3$. Optionally, the one or more light sources are configured to illuminate $ROI_1$, $ROI_2$ and $ROI_3$ with electromagnetic radiation having wavelengths in at least a portion of the range of 800 nm to 1200 nm.

In another embodiment, the one or more head-mounted devices include a device that functions as an imaging photoplethysmography device and/or a device that functions as a pulse oximeter.

The computer is configured, in one embodiment, to generate a blood flow pattern based on a current set of $S_{BF1}$, $S_{BF2}$ and $S_{BF3}$. The computer is also configured to calculate, based on a set of previous blood flow patterns of the user, a value indicative of the extent to which the blood flow pattern is atypical. Optionally, the set of previous blood flow patterns were generated based on sets of $S_{BF1}$, $S_{BF2}$ and $S_{BF3}$ measured at least one day prior to when the current set was measured. That is, the previous sets of blood flow patterns were generated based on data the comprises $S_{BF1}$, $S_{BF2}$ and $S_{BF3}$ measured at least one day before $S_{BF1}$, $S_{BF2}$ and $S_{BF3}$ in the current set. Optionally, the previous sets of blood flow patterns were generated based on data that was measured when the user was not known to be in an atypical condition (e.g., the user was considered healthy at the time).

In some embodiments, the value indicative of the extent to which the blood flow pattern is atypical is compared to a threshold. If the value reaches the threshold, the computer may take different actions. In one embodiment, responsive to the value reaching the threshold, the computer issues an alert. For example, the computer may send a message to a predetermined recipient (e.g., emergency services or a caregiver). In another example, the computer may command a user interface to generate an alert (e.g., a beeping sound, a text message, or vibrations. In another embodiment, responsive to the value reaching the threshold, the computer may prompt the user to perform a test, using an electronic device, to determine whether the user has suffered a stroke. For example, the user may be prompted to perform a FAST test (or portions thereof), as described elsewhere in this disclosure.

There are various ways in which a blood flow pattern may be generated based on $S_{BF1}$, $S_{BF2}$ and $S_{BF3}$. In one embodiment, $S_{BF1}$, $S_{BF2}$ and $S_{BF3}$ themselves may constitute the pattern. Optionally, the blood flow pattern comprises a time series that is indicative of blood flow at each of $ROI_1$, $ROI_2$, and $ROI_3$. In one example, the blood flow pattern may be a time series of the raw (unprocessed) values of $S_{BF1}$, $S_{BF2}$ and $S_{BF3}$ (e.g., a time series of values measured by the one or more head-mounted devices). In another example, blood flow pattern may be a time series of processed values, such as various statistics of $S_{BF1}$, $S_{BF2}$ and $S_{BF3}$ at different points of time (e.g., average pixel intensity for images taken by a camera at different points of time).

In another embodiment, the blood flow pattern may include statistics of the values of $S_{BF1}$, $S_{BF2}$ and $S_{BF3}$, such as values representing the average blood flow during the period $S_{BF1}$, $S_{BF2}$ and $S_{BF3}$ were measured. Values in a blood flow pattern, such as the statistics of the values of $S_{BF1}$, $S_{BF2}$ and $S_{BF3}$ may be of various types of values. The following are some examples of types of values that may be used in a "blood flow pattern". In one example, the blood flow pattern includes one or more values that describe the intensity of blood flow at each of $ROI_1$, $ROI_2$, and/or $ROI_3$. In another example, the blood flow pattern includes one or more values that describe the amplitude of changes to measurement values at $ROI_1$, $ROI_2$, and/or $ROI_3$, such as the amplitude of periodic changes (which correspond to the heart rate) to color, temperature, and/or absorbance at certain wavelengths. In yet another example, the blood flow pattern includes one or more values that describe the speed at which a pulse wave propagates through $ROI_1$, $ROI_2$, and/or $ROI_3$. In still another example, the blood flow pattern includes one or more values that describe the direction at which a pulse wave propagates in $ROI_1$, $ROI_2$, and/or $ROI_3$.

There are various ways in which the computer may utilize the previous blood flow patterns in order to determine the extent to which the blood flow pattern is atypical.

In one embodiment, the computer calculates the value indicative of the extent to which the blood flow pattern is atypical by calculating distances between the blood flow pattern and each of the previous blood flow patterns, and determining a minimal value among the distances. The larger this minimal value, the more atypical the blood flow pattern may be considered (due to its difference from all previous blood flow patterns considered). In one example, in which blood flow patterns include time series data, the distances may be calculated by finding the extent of similarity between the blood flow pattern and each of the previous blood flow patterns (e.g., using methods described in in Wang, Xiaoyue, et al. "Experimental comparison of representation methods and distance measures for time series data", Data Mining and Knowledge Discovery 26.2 (2013): 275-309). In another example, distances between blood flow patterns that include dimensional data, such as blood flow patterns that may be represented as vectors of values, may be calculated using various similarity metrics known in the art such as Euclidean distances or vector dot products.

In another embodiment, the computer calculates, based on the previous sets of $S_{BF1}$, $S_{BF2}$ and $S_{BF3}$, parameters of a probability density function (pdf) for blood flow patterns. For example, each blood flow pattern may be represented as a vector of values and the pdf may be a multivariate distribution (e.g., a multivariate Gaussian) whose parameters are calculated based on vectors of values representing the previous blood flow patterns. Given a vector of values representing the blood flow pattern, the probability of the vector of values is calculated based on the parameters of the pdf. Optionally, if the probability is below a threshold, the blood flow pattern may be considered atypical. Optionally, the threshold is determined based on probabilities calculated for the vectors of values representing the previous blood flow patterns, such the at least a certain proportion of the vectors have a probability that reaches the threshold. For example, the certain proportion may be at least 75%, at least 90%, at least 99%, or 100%.

In yet another embodiment, the computer calculates the value indicative of the extent to which the blood flow pattern is atypical using a model of a one-class classifier generated based on the set of previous blood flow patterns.

In still another embodiment, the computer calculates feature values and utilizes a model to calculate, based on the feature values, the value indicative of the extent to which the blood flow pattern is atypical. Optionally, one or more of the feature values are generated based on the blood flow pattern, and at least one of the feature values is generated based on the previous blood flow patterns. Optionally, feature values generated based on a blood flow pattern include one or more of the values described in examples given above as examples of values in a blood flow pattern. Optionally, one or more of the feature values describe differences between values representing the blood flow pattern, and values representing the previous blood flow patterns. The model is generated based on samples, with each sample comprising: (i) feature values calculated based on a blood flow pattern of a certain user, from among a plurality of users, and previous blood flow patterns of the certain user, and (ii) a label indicative of an extent to which the blood flow pattern of the certain user is atypical. Additional details regarding generating the model can be found herein in the discussion regarding machine learning approaches that may be used to detect a physiological response.

In some embodiments, the computer may use additional inputs to determine whether the blood flow pattern is an atypical blood flow pattern. In one example, the computer may receive measurements of various physiological signals (e.g., heart rate, respiration, or brain activity) and use these measurements to generate at least some of the feature values. In another example, the computer may receive an indication of a state of the user and to generate one or more of the feature values based on the indication. Optionally, the state of the user is indicative of at least one of the following: an extent of physical activity of the user, and consuming a certain substance by the user (e.g., alcohol or a drug).

The physiological and emotional state of a person can often be associated with certain cortical activity. Various phenomena, which may be considered abnormal states, such as anger or displaying symptomatic behavior of Attention Deficit Disorder (ADD) or Attention Deficit Hyperactivity Disorder (ADHD), are often associated with certain atypical cortical activity. This atypical cortical activity can change the blood flow patterns on the face, and especially on the forehead area. Thus, there is a need for a way to detect such changes in blood flow in real world day-to-day situations. Preferably, in order to be comfortable and more aesthetically acceptable, these measurements should be taken without involving direct physical contact with the forehead or occluding it.

In some embodiments, a system configured to detect an attack characterized by an atypical blood flow pattern includes the one or more head-mounted devices (described above) and a computer. The one or more head-mounted devices are configured to measure at least three signals ($S_{BF1}$, $S_{BF2}$ and $S_{BF3}$, respectively), indicative of blood flow in at least three corresponding regions of interest on the head ($ROI_1$, $ROI_2$, and $ROI_3$, respectively) of a user. Optionally, the centers of $ROI_1$, $ROI_2$ and $ROI_3$ are at least 1 cm away from each other. Optionally, the one or more head-mounted devices do not occlude $ROI_1$, $ROI_2$ and $ROI_3$. Optionally, $ROI_1$, $ROI_2$ and $ROI_3$ are on the same side of the face. Alternatively, $ROI_1$, $ROI_2$ and $ROI_3$ are on all on the same side of the face. For example, $ROI_1$ may be on the left side of the face, and $ROI_2$ on the right side of the face.

The computer is configured, in one embodiment, to calculate a value, based on $S_{BF1}$, $S_{BF2}$, and $S_{BF3}$, indicative of whether the user is in a normal or abnormal state.

In one embodiment, the state of the user is determined by comparing a blood flow pattern generated based on $S_{BF1}$, $S_{BF2}$, and $S_{BF3}$ to reference blood flow patterns of the user that include at least one reference blood flow pattern that corresponds to the normal state and at least one reference blood flow pattern that corresponds to the abnormal state. Optionally, a reference blood flow pattern is determined from previous $S_{BF1}$, $S_{BF2}$, and $S_{BF3}$ of the user, taken while the user was in a certain state corresponding to the reference blood flow pattern (e.g., normal or abnormal states). Optionally, if the similarity reaches a threshold, the user is considered to be in the state to which the reference blood flow pattern corresponds.

In another embodiment, the computer determines that the user is in a certain state (e.g., normal or abnormal) by generating feature values (at least some of which are generated based on $S_{BF1}$, $S_{BF2}$, and $S_{BF3}$) and utilizing a model to calculate, based on the feature values, the value indicative of whether the user is in a normal or abnormal state. Optionally, the model is trained based on samples, each comprising feature values generated based on previous $S_{BF1}$, $S_{BF2}$, and $S_{BF3}$ of the user, taken while the user was in the certain state.

In yet another embodiment, $S_{BF1}$, $S_{BF2}$, and $S_{BF3}$ comprise time series data, and the computer calculates the value indicative of whether the user is in a normal or abnormal state based on comparing the time series to at least first and second reference time series, each generated based on previously taken $S_{BF1}$, $S_{BF2}$, and $S_{BF3}$ of the user; the first reference time series is based on previous $S_{BF1}$, $S_{BF2}$, and $S_{BF3}$ taken while the user was in a normal state, and the second reference time series is based on previous $S_{BF1}$, $S_{BF2}$, and $S_{BF3}$ taken while the user was in an abnormal state. Optionally, the time series data and/or the first and second reference time series includes data taken over at least a certain period of time (e.g., at least ten seconds, at least one minute, or at least ten minutes).

Being in a normal/abnormal state may correspond to different behavioral and/or physiological responses. In one embodiment, the abnormal state involves the user displaying symptoms of one or more of the following: an anger attack, Attention Deficit Disorder (ADD), and Attention Deficit Hyperactivity Disorder (ADHD). In this embodiment, being in the normal state refers to usual behavior of the user that does not involve displaying said symptoms. In another embodiment, when the user is in the abnormal state, the user will display within a predetermined duration (e.g., shorter than an hour), with a probability above a predetermined threshold, symptoms of one or more of the following: anger, ADD, and ADHD. In this embodiment, when the user is in the normal state, the user will display the symptoms within the predetermined duration with a probability below the predetermined threshold. In yet another embodiment, when the user is in the abnormal state the user suffers from a headache and/or migraine (or an onset of a migraine attack will occur is a short time such as less than one hour), and when the user is in the normal state, the user does not suffer from a headache and/or a migraine. In still another embodiment, the abnormal state refers to times in which the user has a higher level of concentration compared to the normal state that refers to time in which the user has a usual level of concentration. Although the blood flow patterns of the forehead are usually specific to the user, they are usually repetitive, and thus the system may able to learn some blood flow patterns of the user that correspond to various states.

Determining the user's state based on $S_{BF1}$, $S_{BF2}$, and $S_{BF3}$ (and optionally other sources of data) may be done using a machine learning-based model. Optionally, the model is trained based on samples comprising feature values generated based on previous $S_{BF1}$, $S_{BF2}$, and $S_{BF3}$ taken when the user was in a known state (e.g., for different times it was known whether the user was in the normal or abnormal state). Optionally, the user may provide indications about his/her state at the time, such as by entering values via an app when having a headache, migraine, or an anger attack. Additionally or alternatively, an observer of the user, which may be another person or a software agent, may provide the indications about the user's state. For example, a parent may determine that certain behavior patterns of a child correspond to displaying symptomatic behavior of ADHD. In another example, indications of the state of the user may be determined based on measurements of physiological signals of the user, such as measurements of the heart rate, heart rate variability, breathing rate, galvanic skin response, and/or brain activity (e.g., using EEG). Optionally, the various indications described above are used to generate labels for the samples generated based on the previous $S_{BF1}$, $S_{BF2}$, and $S_{BF3}$.

In some embodiments, one or more of the feature values in the samples may be based on other sources of data (different from $S_{BF1}$, $S_{BF2}$, and $S_{BF3}$)—These may include additional physiological measurements of the user and/or measurements of the environment in which the user was while $S_{BF1}$, $S_{BF2}$, and $S_{BF3}$ were taken. In one example, at least some of the feature values used in samples include additional physiological measurements indicative of one or more of the following signals of the user: heart rate, heart rate variability, brainwave activity, galvanic skin response, muscle activity, and extent of movement. In another example, at least some of the feature values used in samples include measurements of the environment that are indicative of one or more of the following values of the environment in which the user was in: temperature, humidity level, noise level, air quality, wind speed, and infrared radiation level.

Given a set of samples comprising feature values generated based on $S_{BF1}$, $S_{BF2}$, and $S_{BF3}$ (and optionally the other sources of data) and labels generated based on the indications, the model can be trained using various machine learning-based training algorithms. Optionally, the model is utilized by a classifier that classifies the user's state (e.g., normal/abnormal) based on feature values generated based on $S_{BF1}$, $S_{BF2}$, and $S_{BF3}$ (and optionally the other sources).

The model may include various types of parameters, depending on the type of training algorithm utilized to generate the model. For example, the model may include parameters of one or more of the following: a regression model, a support vector machine, a neural network, a graphical model, a decision tree, a random forest, and other models of other types of machine learning classification and/or prediction approaches.

In some embodiments, the model is trained utilizing deep learning algorithms. Optionally, the model includes parameters describing multiple hidden layers of a neural network. Optionally, the model includes a convolution neural network (CNN), which is useful for identifying certain patterns in images, such as patterns of color changes on the forehead. Optionally, the model may be utilized to identify a progression of a state of the user (e.g., a gradual forming of a certain blood flow pattern on the forehead). In such cases, the model may include parameters that describe an architecture that supports a capability of retaining state information. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to generate a model suitable for identifying the state of the user in real-world day-to-day situations, in some embodiments, the samples used to train the model are based on $S_{BF1}$, $S_{BF2}$, and $S_{BF3}$ (and optionally the other sources of data) taken while the user was in different situations, locations, and/or conducting different activities. In a first example, the model may be trained based on a first set of previous $S_{BF1}$, $S_{BF2}$, and $S_{BF3}$ taken while the user was indoors and in the normal state, a second set of previous $S_{BF1}$, $S_{BF2}$, and $S_{BF3}$ taken while the user was indoors and in the abnormal state, a third set of previous $S_{BF1}$, $S_{BF2}$, and $S_{BF3}$ taken while the user was outdoors and in the normal state, and a fourth set of previous $S_{BF1}$, $S_{BF2}$, and $S_{BF3}$ taken while the user was outdoors and in the abnormal state. In a second example, the model may be trained based on a first set of previous $S_{BF1}$, $S_{BF2}$, and $S_{BF3}$ taken while the user was sitting and in the normal state, a second set of previous $S_{BF1}$, $S_{BF2}$, and $S_{BF3}$ taken while the user was sitting and in the abnormal state, a third set of previous $S_{BF1}$, $S_{BF2}$, and $S_{BF3}$ taken while the user was standing and/or moving around and in the normal state, and a fourth set of previous $S_{BF1}$, $S_{BF2}$, and $S_{BF3}$ taken while the user was standing and/or moving around and in the abnormal state. Usually the movements while standing and/or moving around, and especially when walking or running, are greater compared to the movement while sitting; therefore, a model trained on samples taken during both sitting and standing and/or moving around is expected to perform better compared to a model trained on samples taken only while sitting.

Having the ability to determine the state of the user can be advantageous when it comes to scheduling tasks for the user and/or making recommendations for the user, which suits the user's state. In one embodiment, responsive to determining that the user is in the normal state, the computer prioritizes a first activity over a second activity, and responsive to determining that the user is in the abnormal state, the computer prioritizes the second activity over the first activity. Optionally, accomplishing each of the first and second activities requires at least a minute of the user's attention, and the second activity is more suitable for the abnormal state than the first activity. Optionally, and the first activity is more suitable for the normal state than the second activity. Optionally, prioritizing the first and second activities is performed by a calendar management program, a project management program, and/or a "to do" list program. Optionally, prioritizing a certain activity over another means one or more of the following: suggesting the certain activity before suggesting the other activity, suggesting the certain activity more frequently than the other activity (in the context of the specific state), allotting more time for the certain activity than for the other activity, and giving a more prominent reminder for the certain activity than for the other activity (e.g., an auditory indication vs. a mention in a calendar program that is visible only if the calendar program is opened).

Such state-dependent prioritization may be implemented in various scenarios. In one example, the normal state refers to a normal concentration level, the abnormal state refers to a lower than normal concentration level, and the first activity requires a high attention level from the user compared to the second activity. For instance, the first and second activities may relate to different topics of a self-learning program for school; when identifying that the user is in the normal concentration state, a math class is prioritized higher than a sports lesson; and when identifying that the user is in the lower concentration state, the math class is prioritized lower than the sports lesson. In another example, the normal state refers to a normal anger level, the abnormal state refers to a higher than normal anger level, and the first activity involves more interactions of the user with other humans compared to the second activity. In still another example, the normal state refers to a normal fear level, the abnormal state refers to a panic attack, and the second activity is expected to have a more relaxing effect on the user compared to the first activity.

Passively taken sensor based measurements may be used, in some embodiments, in order to detect whether a user exhibits stroke signs. However, in some scenarios, sensors that may be used to detect stroke signs may provide inaccurate signals that can lead to a high rate of false alarms. Detecting whether a user exhibits stroke signs can also be done by an app that prompts the user to perform one or more activities involved in a FAST test, and analyzing the user's actions while performing the one or more activities. However, apps for detecting stroke signs are often not used because the person suffering from a stroke is not aware of the incident (and thus does not initiate a test). Thus, the combination of the two approaches can increase the rate at which stroke signs may be detected based on possibly inaccurate measurements, by having the sensor measurements serve as a trigger to activate an app to prompt the user to perform the one or more activities involved in the FAST test.

In one embodiment, a system configured detect stroke signs includes at least first, second, and third sensors, and a computer. The first and second sensors configured to take first and second measurements ($M_R$ and $M_L$, respectively) of regions belonging to the right and left sides of a user's body. Optionally, $M_R$ and $M_L$ are indicative of blood flow in the regions on the right and left sides of the user's body, respectively. The following are examples of various types of sensors that may be used, in some embodiments, as the first and second sensors.

In one example, the first and second sensors are electroencephalography (EEG) electrodes that measure brain activity and are positioned on the right and left sides of the head, respectively. Optionally, the first and second sensors are EEG electrodes implanted under the user's scalp. In another example, the first and second sensors are electromyography (EMG) sensors implanted in the left and right sides of the user's body, respectively. Alternatively, the first and second sensors may be EMG sensors attached to the surface of the user's body. In yet another example, the first and second sensors may be ultrasound sensors. Optionally, the ultrasound sensors are positioned such that they are in contact with the surface of the right and left sides of the user's body respectively. In still another example, the first and second sensors are photoplethysmogram (PPG) sensors that provide measurements indicative of the blood flow on the right and left sides of the user's body, respectively. In yet another example, the first and second sensors comprise cameras based on a sensor comprising at least 3×3 pixels configured to detect electromagnetic radiation having wavelengths in at least a portion of the range of 200 nm to 1200 nm. In yet another example, the first and second sensors are thermistors in contact with the right and left sides of the user's body. For example, the first and second sensors may be embedded in one or more of the following: a clothing item worn by the user, gloves, or a scarf. And in still another example, the first and second sensors are thermal cameras each comprising at least 3×3 pixels configured to detect electromagnetic radiation having wavelengths above 2500 nm.

The computer calculates, based on $M_R$ and $M_L$, a value indicative of a risk that the user has suffered from a stroke. Responsive to determining that the value reaches a threshold, the computer may instruct the user, via a user interface, to perform the predetermined activity. The computer may then detect whether the user exhibits stroke signs based on measurements ($M_A$) of a third sensor, which were taken while the user performed the predetermined activity. Optionally, the computer utilizes $M_R$ and $M_L$ along with $M_A$ in order to make a more accurate detection of stroke signs. Optionally, detection based on $M_R$, $M_L$, and $M_A$ is more accurate than detection based on $M_R$ alone $M_L$.

Calculating the value indicative of the risk that the user has suffered from a stroke may be done in different ways in different embodiments. In one embodiment, the value indicative of the risk is indicative difference between of extents of physiological changes in the right and left sides of the body, which are calculated based on $M_R$ and $M_L$, respectively. For example, the value may be indicative of a difference in blood flow between the right and left sides of the body, a difference in the temperature between the right and left sides, and/or a difference in skin color and/or extent of changes to skin color between the right and left sides. Optionally, when the difference reaches the threshold, this means that the user is at a risk of having suffered a stroke that is sufficiently high to warrant an additional test that involves performing the predetermined activity and measuring the user with the third sensor.

In another embodiment, the computer generates feature values based on $M_R$ and $M_L$ and utilizes a model to calculate, based on the feature values, the value indicative of the risk that the user has suffered from a stroke. Optionally, the model is generated based on previous $M_R$ and $M_L$ of multiple users. For example, the model may be generated based on data that comprises $M_R$ and $M_L$ of users who were healthy at the time the measurements were taken, and also based on $M_R$ and $M_L$ of users who suffered from a stroke while the measurements were taken.

There are various predetermined activities the computer may prompt the user to perform in order to detect whether the user exhibits stroke signs. These activities may be measured using different sensors. The following are examples of combinations of activities, and sensors that may be used to take the measurements $M_A$ of the user while the user performs the activities.

In one embodiment, performing the predetermined activity comprises smiling Optionally, in this embodiment, the third sensor is a camera. For example, the camera may be a camera embedded in a cell phone (or some other device) held by the user or some other person. In another example, the camera may be coupled to a frame worn on the user's head. In this embodiment, $M_A$ include images of the user's face that capture the user's facial expressions while the user was instructed to smile. The computer may detect the stroke signs based on analysis of images of the user which are indicative of one side of the face drooping. Optionally, the analysis involves comparing $M_A$ to previously taken images of the user's face.

In another embodiment, performing the predetermined activity comprises raising both arms. Optionally, in this embodiment, the third sensor is an inertial measurement unit (IMU). For example, the IMU may be embedded in a cell phone, a smart watch, or another device on worn or held by the user (e.g., on the hand, wrist, or arm). In this embodiment, the computer detects the stroke signs based on analysis of measurements of movements of the user (taken by the IMU) which are indicative of one arm drifting downward.

In yet another embodiment, performing the predetermined activity comprises walking Optionally, in this embodiment, the third sensor is an inertial measurement unit (IMU). For example, the IMU may be coupled to a frame worn on the user's head or in a device carried by the user (e.g., a smartphone or a smartwatch). In this embodiment, computer detects the stroke signs based on analysis measurements of movements of the user (taken by the IMU) which are indicative of imbalance of the user.

In still another embodiment, performing the predetermined activity comprises repeating a phrase. Optionally, in this embodiment, the third sensor is a microphone. For example, the microphone may belong to a device carried or worn by the user (e.g., a smartphone, a smartwatch, or microphone embedded in a head-mounted display). In this embodiment, computer detects the stroke signs based on analysis of a recording of voice of the user which is indicative of the user's speech being slurry. Optionally, the analysis of the recording of the user's voice is done based on a comparison with previous recordings of the user's voice.

In some embodiments, the computer may conduct tests to determine whether the user's brain function has been affected. For example, the computer may prompt the user to perform various tasks using an app that can test for memory and cognitive skills, such as answering trivia questions, solving puzzles, etc.

In some embodiments, following the user's performance of the predetermined activity and analysis of $M_A$, results of the analysis may be used to improve the accuracy of the calculation of the risk. For example, responsive to determining, based on specific $M_A$, that the user does not exhibit stroke signs after measuring specific $M_R$ and $M_L$ values (which indicated that there is sufficient risk), the computer is configured to adjust the threshold based on the specific $M_R$ and $M_L$ values. In another example, the computer may utilize the specific $M_R$ and $M_L$ to retrain a model used to calculate the risk. In this example, the specific $M_R$ and $M_L$ can constitute an example of a false positive that is used to adjust the model parameters.

One of the signs to having a stroke is sudden loss of balance or coordination. It is easier to identify loss of balance or coordination from measurements taken by a head-mounted IMU compared to measurements taken by an IMU inside a wrist band or a phone in the hand. The reason is that the movements of the head include much less noise compared to movements of a hand that is used to manipulate items. Therefore, a head-mounted IMU can be more beneficial for identifying loss of balance or coordination than a wrist-mounted IMU.

In one embodiment, a system configured to detect a medical condition, which involves a loss of at least one of balance and coordination, includes at least a head-mounted inertial measurement unit (IMU) and a computer. Some examples of medical conditions that involve loss of balance and/or coordination include a stroke and a spell of dizziness. The IMU is configured to measure movements of the head of a user wearing the IMU, and a computer. Optionally, the IMU comprises at least one of the following elements: an accelerometer, a gyroscope, and a magnetometer. Optionally, the IMU is coupled to a frame worn on the user's head. The computer is configured to detect the medical condition based on measurements of the IMU ($M_{current}$) and previous measurements of movements of the head of the user wearing the IMU ($M_{previous}$). Optionally, at least some of $M_{previous}$ were taken while the user did not have the medical condition. Optionally, the computer is further configured to alert a predetermined recipient (e.g., a caregiver or emergency services) responsive to detecting the medical condition.

There are various ways in which the medical condition may be detected based on $M_{current}$ and $M_{previous}$. In one embodiment, the computer is configured to detect the medical condition by calculating a difference between movement characteristics determined based on $M_{current}$ and typical movement characteristics of the user calculated based on $M_{previous}$. Optionally, if the difference reaches a threshold, the user is considered to have the medical condition. In another embodiment, the computer is configured to detect the medical condition by generating feature values and utilizing a model to calculate a value, based on the feature values, which is indicative of whether the user has the medical condition. Optionally, one or more of the feature values are calculated based on $M_{current}$ and the model is generated based $M_{previous}$ of the user. In yet another embodiment, the computer is configured to detect the medical condition by generating feature values and utilizing a model to calculate a value, based on the feature values, which is indicative of whether the user has the medical condition. Optionally, one or more of the feature values are calculated based on movements of the head of one or more other users wearing an IMU.

The user's movement characteristics may be affected by various factors, as discussed below. Thus, receiving an indication of such factors that influence movement and balance can help improve accuracy of detecting the medical condition based on $M_{current}$ and $M_{previous}$. In some embodiments, the computer is further configured to receive an indication of a situation in which the user is in while $M_{current}$ are taken, and to utilize the indication to detect the medical condition.

In one embodiment, the situation comprises being under influence of a medication, and the indication of the situation is received from at least one of: a pill dispenser, a sensor-enabled pill, and a user tracking application. Examples of user tracking applications include: (i) software that requires a user to log events, such as consumption of a certain item, usage of a certain item, having a certain experience, and/or being in a certain situation, (ii) an image analysis software that receives images taken by the user or a third party nearby the user, and infers the situation from the images using image processing techniques. Examples of sources for the image include: smartglasses with outfacing camera, augmented reality devices, mobile phones, and webcams.

In another one embodiment, the situation comprises being under influence of at least one of alcohol and caffeine, and the indication of the situation is received from at least one of: a refrigerator, a pantry, a serving robot, and a user tracking application; and wherein the indication indicates that the user took an alcoholic beverage. In yet another embodiment, the situation comprises being under a certain stress level, and the indication of the situation is received from a sensor that measures a physiological signal of the user, such as a thermal sensor, a heart rate sensor, a sensor of galvanic skin response, or an EEG sensor. In still another embodiment, the situation is selected from a group comprising: being inside a moving vehicle, and being on a static floor; and the indication of the situation is received from a positioning system. Examples of positioning systems include: GPS, wireless positioning systems, image processing to infer position.

Typically having a stroke will influence brain activity, which can be detected through electroencephalography (EEG). However, this signal may at times be noisy and insufficient to reliably detect a stroke. Thus, additional tests may be needed. In one embodiment, a system configured to detect stroke signs based on electroencephalography (EEG) includes at least a sensor configured to take measurements ($M_A$) of the user, and a computer. The computer is configured to: receive EEG signals of the user, and to utilize a model to calculate, based on the EEG signals, a value indicative of a risk that the user has suffered from a stroke. The value indicative of the risk is compared by the computer to a threshold, and responsive to determining that the value reaches a threshold, the computer instructs the user, via a user interface, to perform a predetermined activity. The computer then detects whether the user has stroke signs based on $M_A$ taken while the user performed the predetermined activity. Optionally, the computer utilizes the EEG signals along with $M_A$ in order to make a more accurate detection of stroke signs. Optionally, detection based on the EEG signals and $M_A$ is more accurate than detection based on the EEG signals alone.

Calculating the value indicative of the risk that the user has suffered from a stroke may be done in different ways in different embodiments. In one embodiment, the value indicative of the risk is indicative difference between of extents of electrical potential changes in the right and left sides of the brain, which are calculated based on EEG signals from electrodes on the right and left sides of the head. Optionally, when the difference reaches the threshold, this means that the user is at a risk of having suffered a stroke that is sufficiently high to warrant an additional test that involves performing the predetermined activity and measuring the user with the third sensor.

In another embodiment, the computer generates feature values based on the EEG signals and utilizes a model to calculate, based on the feature values, the value indicative of the risk that the user has suffered from a stroke. Optionally, the model is generated based on previous EEG signals of multiple users. For example, the model may be generated based on data that comprises EEG signals of users who were healthy at the time the measurements were taken, and also based on EEG signals of users who suffered from a stroke while the measurements were taken.

There are various predetermined activities the computer may prompt the user to perform in order to detect whether the user exhibits stroke signs. These activities may be measured using different sensors. Examples of combinations of activities, and sensors that may be used to take the measurements $M_A$ of the user while the user performs the activities are given above (e.g., smiling, raising hands, walking, and speaking a phrase).

In some embodiments, following the user's performance of the predetermined activity and analysis of $M_A$ results of the analysis may be used to improve the accuracy of the calculation of the risk. For example, responsive to determining, based on specific $M_A$, that the user does not exhibit stroke signs after measuring specific EEG signals values (which indicated that there is sufficient risk), the computer is configured to adjust the threshold based on the specific EEG signals. In another example, the computer may utilize the specific EEG signals to retrain a model used to calculate the risk. In this example, the specific EEG signals can constitute an example of a false positive that is used to adjust the model parameters.

FIG. 88A and FIG. 88B are schematic illustrations of possible embodiments for computers (400, 410) that are able to realize one or more of the embodiments discussed herein that include a "computer". The computer (400, 410) may be implemented in various ways, such as, but not limited to, a microcontroller, a computer on a chip, a system-on-chip (SoC), a system-on-module (SoM), a processor with its required peripherals, a server computer, a client computer, a personal computer, a cloud computer, a network device, a handheld device (e.g., a smartphone), an head-mounted system (such as smartglasses, an augmented reality system, a virtual reality system, and/or a smart-helmet), a computing device embedded in a wearable device (e.g., a smartwatch or a computer embedded in clothing), a computing device implanted in the human body, and/or any other computer form capable of executing a set of computer instructions. Further, references to a computer or a processor include any collection of one or more computers and/or processors (which may be at different locations) that individually or jointly execute one or more sets of computer instructions. This means that the singular term "computer" is intended to imply one or more computers, which jointly perform the functions attributed to "the computer". In particular, some functions attributed to the computer may be performed by a computer on a wearable device (e.g., smartglasses) and/or a computer of the user (e.g., smartphone), while other functions may be performed on a remote computer, such as a cloud-based server.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI}$" may be interpreted as "calculating based on the values of $TH_{ROI}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements ($\Delta T$), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 20° above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A doorway system, comprising:
a doorway that facilitates passage from an inside to an outside, and/or from the outside to the inside;
a barrier, disposed in the doorway, configured to move between an opened position and a closed position based on commands sent by a computer; wherein, when in the closed position, the barrier restricts passage through the doorway, and when in the opened position, the barrier does not restrict the passage through the doorway;
one or more sensors configured to measure: a first signal indicating that a first user is on the outside of the doorway, and a second signal indicating that a second user is on the inside of the doorway; and
the computer is configured to:
receive, from a first device carried and/or worn by the first user, a first indication indicative of health status of the first user;
receive, from a second device carried and/or worn by the second user, a second indication indicative of health status of the second user:
determine, based on the first and second indications, that both the first and second users are healthy; and
command the barrier to move to the opened position and/or remain in the opened position, based on the determination that both the first and second users are healthy.

2. The doorway of claim 1, wherein the computer is further configured to determine, based on a third signal and a third indication, that a third user located on the outside is not healthy, and command the barrier to move to the closed position and/or remain in the closed position based on the determination that the third user is not healthy.

3. The doorway of claim 1, wherein the computer is further configured to command the barrier to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

4. The doorway of claim 1, wherein the computer is further configured to command the barrier to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

5. The doorway of claim 1, wherein the first indication does not comprise information identifying the first user.

6. The doorway of claim 1, wherein the second indication does not comprise information identifying the second user.

7. The doorway of claim 1, wherein the barrier is a door that belongs to a vehicle, and commanding the barrier to move to the opened position and/or remain in the opened position comprises commanding the door to unlock and/or move to a position that enables the first user to enter a passenger cabin of the vehicle.

8. The doorway of claim 1, wherein the barrier is an entrance door to a room and/or building, and commanding the barrier to move to the opened position and/or remain in the opened position comprises commanding the entrance door to unlock and/or move to a position that enables the first user to enter the interior of the room and/or building.

9. The doorway of claim 1, wherein the barrier is a turnstile or a revolving door belonging to a gate, and commanding the barrier to move to the opened position and/or remain in the opened position comprises enabling the turnstile or the revolving door to revolve and/or revolving the turnstile or the revolving door, enabling the first user to pass through the gate.

10. The doorway of claim 1, wherein the one or more sensors comprise a camera aimed to the outside, the first signal comprises images of the outside, and detecting the first user is outside comprises identifying presence of a person in the images.

11. The doorway of claim 1, wherein the one or more sensors comprise a thermal sensor aimed to the outside, the first signal comprises thermal measurements of the outside, and detecting the first user is outside comprises identifying a thermal signature corresponding to a person in the thermal measurements.

12. The doorway of claim 1, wherein the one or more sensors comprise a pressure sensor disposed in a surface on the outside, the first signal comprises values indicative of pressure applied to the pressure sensor, and detecting the first user is outside comprises identifying the values reflect application of a pressure corresponding to a weight of a person.

13. A method for controlling a doorway, comprising:
receiving a first signal indicative of whether there is a first user on an outside of a doorway; wherein the doorway facilitates passage from an inside to the outside, and/or from the outside to the inside and the doorway comprises a barrier configured to move between an opened position and a closed position; and
wherein, when in the closed position, the barrier restricts passage through the doorway, and when in the opened position, the barrier does not restrict passage through the doorway;
detecting based on the first signal that the first user is on the outside;
receiving, from a first device carried and/or worn by the first user, a first indication indicative of health status of the first user;
receiving a second signal indicating that a second user is on the inside of the doorway;
receiving, from a second device carried and/or worn by the second user, a second indication indicative of health status of the second user;
determining, based on the first and second indications, that both the first and second users are healthy; and
commanding the barrier to move to the opened position and/or remain in the opened position, based on the determination that both the first and second users are healthy.

14. The method of claim 13, further comprising determining, based on a third signal and a third indication, that a third user located on the outside is not healthy, and commanding the barrier to move to the closed position and/or remain in the closed position based on the determination that the third user is not healthy.

15. The method of claim 13, further comprising commanding the barrier to move to the closed position and/or remain in the closed position, responsive to detecting, based on the first signal, that a plurality of users are on the outside, and not receiving, for each user from among the plurality of the users, an indication indicating said user is healthy, which is sent by a device carried and/or worn by said user.

16. The method of claim 13, further comprising commanding the barrier to move to the closed position and/or remain in the closed position, responsive to: detecting, based on the second signal, that a plurality of users are on the inside, and not receiving, for each user from among the plurality of the users, an indication indicating that said user is healthy, which is sent by a device carried and/or worn by said user.

17. The method of claim 13, further comprising: transmitting a request for the first indication indicating the first user is healthy, responsive to detecting that the first user is on the outside.

18. A non-transitory computer readable medium storing one or more computer programs configured to cause a processor based system to execute steps comprising:
receiving a first signal indicative of whether there is a first user on an outside of a doorway; wherein the doorway facilitates passage from an inside to the outside, and/or from the outside to the inside and the doorway comprises a barrier configured to move between an opened position and a closed position; and wherein, when in the closed position, the barrier restricts passage through the doorway, and when in the opened position, the barrier does not restrict passage through the doorway;
detecting based on the first signal that the first user is on the outside;
receiving, from a first device carried and/or worn by the first user, a first indication indicative of health status of the first user;
receiving a second signal indicative indicating that a second user is on the inside of the doorway;
receiving, from a second device carried and/or worn by the second user, a second indication indicative of health status of the second user;
determining, based on the first and second indications, that both the first and second users are healthy; and
commanding the barrier to move to the opened position and/or remain in the opened position, based on the determination that both the first and second users are healthy.

19. The non-transitory computer readable medium of claim 18, further comprising instructions for executing steps comprising: determining, based on a third signal and a third indication, that a third user located on the outside is not healthy, and commanding the barrier to move to the closed position and/or remain in the closed position based on the determination that the third user is not healthy.

* * * * *